US012569564B2

(12) United States Patent
Chen

(10) Patent No.: US 12,569,564 B2
(45) Date of Patent: Mar. 10, 2026

(54) SPIROCYCLIC MDM2 MODULATOR AND USES THEREOF

(71) Applicant: Newave Pharmaceutical Inc., Pleasanton, CA (US)

(72) Inventor: Yi Chen, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 409 days.

(21) Appl. No.: 18/272,709

(22) PCT Filed: Jan. 21, 2022

(86) PCT No.: PCT/US2022/013215

§ 371 (c)(1),
(2) Date: Jul. 17, 2023

(87) PCT Pub. No.: WO2022/159644

PCT Pub. Date: Jul. 28, 2022

(65) Prior Publication Data

US 2025/0073340 A1 Mar. 6, 2025

Related U.S. Application Data

(60) Provisional application No. 63/277,543, filed on Nov. 9, 2021, provisional application No. 63/218,398, filed on Jul. 5, 2021, provisional application No. 63/140,833, filed on Jan. 23, 2021.

(51) Int. Cl.
*A61K 47/55* (2017.01)
*A61P 35/00* (2006.01)

(52) U.S. Cl.
CPC .............. *A61K 47/55* (2017.08); *A61P 35/00* (2018.01)

(58) Field of Classification Search
CPC ................................ A61K 47/55; A61P 35/00
See application file for complete search history.

(56) References Cited

U.S. PATENT DOCUMENTS

2015/0291562 A1 10/2015 Crew et al.

FOREIGN PATENT DOCUMENTS

WO 2011/067185 A1 6/2011
WO 2011/153509 A1 12/2011
WO 2012/065022 A2 5/2012
WO 2017/176957 A1 10/2017

OTHER PUBLICATIONS

CAS Registry No. 2197190-00-2 (which entered STN on Mar. 23, 2018). (Year: 2018).*
STN Accession No. 1697698552, (2'R, 3R, 4'S, 5'R _-6-chloro-4'-(3-chloro-2-fluorophenyl)-2'-(cyclopentylmethyl)-N-(4-hydroxycyclohexyl)-1,2-dihydrospiro[indole-3,3'-pyrrolidine]-5'-carboximidic acid. 1 page, Apr. 19, 2021.
International Search Report and Written Opinion for Application No. PCT/US2022/013215, dated Jun. 7, 2022, 16 pages.
International Search Report and Written Opinion for Application No. PCT/US2023/023234, dated Aug. 16, 2023, 7 pages.
U.S. Appl. No. 18/865,919, filed Nov. 14, 2024, Pending.

* cited by examiner

*Primary Examiner* — Kamal A Saeed
*Assistant Examiner* — Quincy McKoy
(74) *Attorney, Agent, or Firm* — McCarter & English, LLP; Yu Lu; Zhongyu Wang

(57) ABSTRACT

The disclosure includes compounds of Formula (I), wherein each of Z, $R_0$, $R_1$, $R_2$, $R_3$, $R_4$, $R_5$, $R_6$, R, $L_1$, $L_2$, $L_3$, $L_4$, $L_5$, $L_6$, $Q_1$, $Q_2$, W, m, n, r, and s, are defined herein. Also disclosed is a method for treating a neoplastic disease, autoimmune disease, and inflammatory disorder with these compounds.

(I)

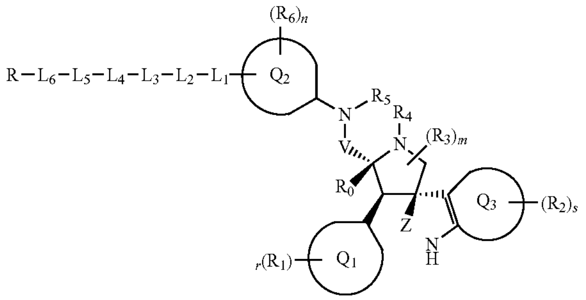

7 Claims, No Drawings

SPIROCYCLIC MDM2 MODULATOR AND USES THEREOF

REFERENCE TO RELATED APPLICATIONS

This patent application is a U.S. national stage application, filed under 35 U.S.C. § 371 (c), of International Application No. PCT/US2022/013215, filed on Jan. 21, 2022, which claims priority to U.S. Provisional Patent Application Nos. 63/140,833, filed on Jan. 23, 2021; 63/218,398, filed on Jul. 5, 2021; and 63/277,543, filed on Nov. 9, 2021, the. The entire contents of each of the above-referenced applications are hereby incorporated herein by reference.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Phthalimide-based drugs, e.g., thalidomide or lenalidomide, bind to protein-degradation machinery, e.g., cereblon (CRBN; part of an ubiquitin E3 ligase complex). This may promote the recruitment of two transcription factors (IKZF1 and IKZF3) that are essential to disease progression, resulting in drug-induced ubiquitylation and degradation by the proteasome. See, e.g., Ito et al., Science 327: 1345-1350 (2010) and Winter et al., Science 345: 1376-1381 (2015).

A high-affinity VHL ligand, see Bondeson et al., Nat. Chem. Biol. 11:611-617 (2015), may recruit a target protein to an E3 ubiquitin ligase, resulting in drug induced ubiquitination and degradation. See, e.g., van Hagen et al, Nucleic Acids Research 38: 1922-1931 (2010); Buckley et al, J. Am. Chem. Soc. 734:4465-4468 (2012); Buckley et al, Angew, Chem. Int. Ed. Engl. 57: 11463-11467 (2012); Lipkowitz and Weissman, Nat Rev Cancer 11:629-643 (2011); and Zengerle et al, ACS Chem. Biol. 70:1770-1777 (2015).

Although MDM2 inhibitor have made a significant contribution to the art, there is a strong need for continuing search in this field of art for improved pharmaceuticals.

SUMMARY OF THE INVENTION

The present invention relates to a class of MDM2 inhibitors and degraders. Thus, the compounds of the present invention may be useful in treating the cancer patient. The compounds of the present invention may also be useful in treating patients with diseases such as autoimmune disease, or inflammatory disorders.

In one aspect, this invention relates to a compound of Formula (0), or an N-oxide thereof, or a pharmaceutically acceptable salt, solvate, polymorph, tautomer, stereoisomer, an isotopic form, or a prodrug of said compound of Formula (0) or N-oxide thereof:

Formula (0)

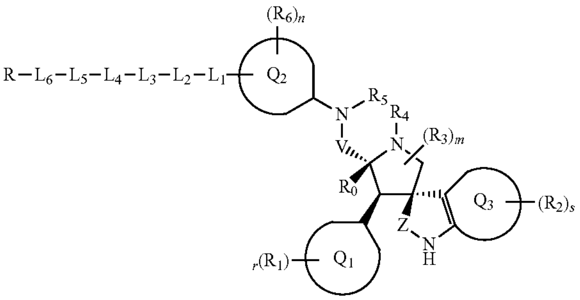

wherein

Z is $CH_2$, $—SO_2—$, or $—P(O)(R_a)—$; or Z is C(O) when $R_0$ is not H;

V is C(O), $P(O)(R_a)$, or $—SO_2—$;

R is H or a small molecule (e.g., molecular weight less than about 1,500 Da, 1,200 Da, 900 Da, 500 Da or less) E3 ubiquitin ligase binding moiety that binds an E3 ubiquitin ligase;

each of $L_1$, $L_2$, $L_3$, $L_4$, $L_5$, and $L_6$, independently, is absent, a bond, $(CR_aR_b)_p$, $N(R_a)$, O, S, C(O), $S(O_2)$, $—O(CR_aR_b)_p—$, $—N(R_a)(CR_aR_b)_p—$, OC(O), C(O)O, $OSO_2$, $S(O_2)O$, C(O)S, SC(O), C(O)C(O), $C(O)N(R_a)$, $N(R_a)C(O)$, $S(O_2)N(R_a)$, $N(R_a)S(O_2)$, OC(O)O, OC(O)S, $OC(O)N(R_a)$, $N(R_a)C(O)O$, $N(R_a)C(O)S$, $N(R_a)C(O)N(R_a)$, $(CR_aR_b)_pN(R_a)(CR_aR_b)_q$, $(CR_aR_b)_pN(R_a)C(O)(CR_aR_b)_q$, $OC(O)N(R_b)(CR_aR_b)_{p+1}N(R_b)(CR_aR_b)_q$, $(CR_aR_b)_pC(O)N(R_a)(CR_aR_b)_q$, bivalent alkyl, bivalent alkenyl, bivalent alkynyl, bivalent cycloalkyl, bivalent cycloalkenyl, bivalent heterocycloalkyl, bivalent heterocycloalkenyl, bivalent spiro-heterocyclic, bivalent fused-heterocyclic, bivalent bridged-heterocyclic, bivalent aryl, or bivalent heteroaryl, in which said bivalent alkyl, bivalent cycloalkyl, bivalent cycloalkenyl, bivalent heterocycloalkyl, bivalent heterocycloalkenyl, bivalent spiro-heterocyclic, bivalent fused-heterocyclic, bivalent bridged-heterocyclic, bivalent aryl, or bivalent heteroaryl is optionally substituted with one or more $R_d$;

each of $R_0$, $R_1$, $R_2$, $R_3$, $R_4$, $R_5$, and $R_6$, independently, is H, D, alkyl, spiroalkyl, alkenyl, alkynyl, cycloalkyl, cycloalkenyl, heterocycloalkyl, heterocycloalkenyl, spiroheterocyclic, fused-heterocyclic, bridged-heterocyclic, aryl, heteroaryl, halo, nitro, oxo, cyano, —$OR_a$, —$SR_a$, -alkyl-$R_a$, -alkyl-O—P(O)($R_a$)($R_b$), -alkyl-OC(O)N($R_a$)($R_b$), —NH$(CH_2)_pR_a$, —C(O)$R_a$, —S(O)$R_a$, —$SO_2R_a$, —C(O)O$R_a$, —OC(O)$R_a$, —$NR_bR_c$, —C(O)N($R_b$)$R_c$, —N($R_b$)C(O)$R_c$, in which said alkyl, spiroalkyl, alkenyl, alkynyl, cycloalkyl, cycloalkenyl, heterocycloalkyl, heterocycloalkenyl, spiroheterocyclic, fused-heterocyclic, bridged-heterocyclic, aryl, or heteroaryl is optionally substituted with one or more $R_d$;

each of $Q_1$, $Q_2$, and $Q_3$, independently, is cycloalkyl, cycloalkenyl, heterocycloalkyl, heterocycloalkenyl, spiro-heterocyclic, fused-heterocyclic, bridged-heterocyclic, aryl, or heteroaryl;

each $R_a$, $R_b$, $R_c$ and $R_d$, independently, is H, D, alkyl, spiroalkyl, alkenyl, alkynyl, halo, cyano, amine, nitro, hydroxy, =O, -alkyl-O—P(O)(OH)(OH), C(O)NHOH, C(O)OH, C(O)$NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, spiro-heterocyclic, fused-heterocyclic, bridged-heterocyclic, aryl, or heteroaryl, in which said alkyl, alkoxy, alkoxyalkyl, cycloalkyl, cycloalkenyl, heterocycloalkyl, heterocycloalkenyl, spiro-heterocyclic, fused-heterocyclic, bridged-heterocyclic, aryl, or heteroaryl is optionally substituted with one or more $R_e$;

each $R_e$ is independently H, D, alkyl, spiroalkyl, alkenyl, alkynyl, halo, cyano, amine, nitro, hydroxy, =O, -alkyl-O—P(O)(OH)(OH), C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, spiro-heterocyclic, fused-heterocyclic, bridged-heterocyclic, aryl, or heteroaryl, in which said alkyl, alkoxy, alkoxyalkyl, cycloalkyl, cycloalkenyl, heterocycloalkyl, heterocycloalkenyl, spiro-heterocyclic, fused-heterocyclic, bridged-heterocyclic, aryl, or heteroaryl is optionally substituted with one or more $R_f$; and each $R_f$ is independently H, D, alkyl, spiroalkyl, alkenyl, alkynyl, halo, cyano, amine, nitro, hydroxy, =O, -alkyl-O—P(O)(OH)(OH), C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, spiro-heterocyclic, fused-heterocyclic, bridged-heterocyclic, aryl, or heteroaryl; two of $R_1$ groups, taken together with the atom to which they are attached, may optionally form a cycloalkyl, heterocycloalkyl, heterocycloalkenyl, aryl, or heteroaryl, each optionally substituted with one or more $R_d$;

two of $R_2$ groups, taken together with the atom to which they are attached, may optionally form a cycloalkyl, heterocycloalkyl, heterocycloalkenyl, aryl, or heteroaryl, each optionally substituted with one or more $R_d$;

two of $R_3$ groups, taken together with the atom to which they are attached, may optionally form a cycloalkyl, heterocycloalkyl, heterocycloalkenyl, aryl, or heteroaryl, each optionally substituted with one or more $R_d$;

two of $R_6$ groups, taken together with the atom to which they are attached, may optionally form a cycloalkyl, heterocycloalkyl, heterocycloalkenyl, aryl, or heteroaryl, each optionally substituted with one or more $R_d$;

$R_3$ and $R_4$ groups, taken together with the atom to which they are attached, may optionally form a cycloalkyl, heterocycloalkyl, heterocycloalkenyl, aryl, or heteroaryl, each optionally substituted with one or more $R_d$;

$R_4$ and $R_5$ groups, taken together with the atom to which they are attached, may optionally form a cycloalkyl, heterocycloalkyl, heterocycloalkenyl, aryl, or heteroaryl, each optionally substituted with one or more $R_d$; and $R_5$ and $R_6$ groups, taken together with the atom to which they are attached, may optionally form a cycloalkyl, heterocycloalkyl, heterocycloalkenyl, aryl, or heteroaryl, each optionally substituted with one or more $R_d$;

two of $R_d$ groups, taken together with the atom to which they are attached, may optionally form a cycloalkyl, heterocycloalkyl, heterocycloalkenyl, aryl, or heteroaryl, each optionally substituted with one or more $R_e$;

two of $R_e$ groups, taken together with the atom to which they are attached, may optionally form a cycloalkyl, heterocycloalkyl, heterocycloalkenyl, aryl, or heteroaryl, each optionally substituted with one or more $R_f$; and each of m, n, r, and s, independently, is 0, 1, 2, or 3;

each of p and q, independently, is 0, 1, 2, 3, or 4.

In one aspect, this invention relates to a compound of Formula (I), or an N-oxide thereof, or a pharmaceutically acceptable salt, solvate, polymorph, tautomer, stereoisomer, an isotopic form, or a prodrug of said compound of Formula (I) or N-oxide thereof:

Formula (I)

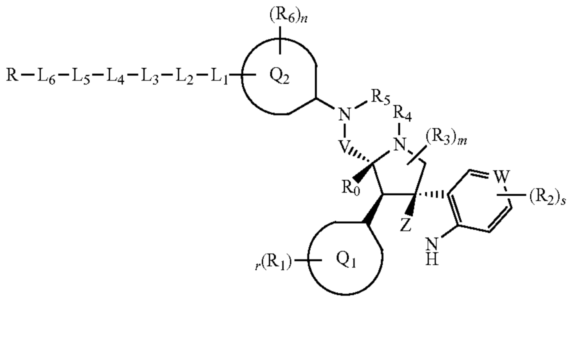

wherein

Z is $CH_2$, —$SO_2$—, or —P(O)($R_a$)—; or Z is C(O) when $R_0$ is not H;

V is C(O), P(O)($R_a$), or —$SO_2$—;

W is C($R_a$) or N;

R is H or a small molecule (e.g., molecular weight less than about 1,500 Da, 1,200 Da, 900 Da, 500 Da or less) E3 ubiquitin ligase binding moiety that binds an E3 ubiquitin ligase;

each of $L_1$, $L_2$, $L_3$, $L_4$, $L_5$, and $L_6$, independently, is absent, a bond, $(CR_aR_b)_p$, N($R_a$), O, S, C(O), S($O_2$), —O$(CR_aR_b)_p$—, —N($R_a$)$(CR_aR_b)_p$—, OC(O), C(O)O, $OSO_2$, S($O_2$)O, C(O)S, SC(O), C(O)C(O), C(O)N($R_a$), N($R_a$)C(O), S($O_2$)N($R_a$), N($R_a$)S($O_2$), OC(O)O, OC(O)S, OC(O)N($R_a$), N($R_a$)C(O)O, N($R_a$)C(O)S, $N(R_a)C(O)N(R_a)$, $(CR_aR_b)_pN(R_a)(CR_aR_b)_q$, $(CR_aR_b)_p N(R_a)C(O)(CR_aR_b)_q$, $OC(O)N(R_b)(CR_aR_b)_{p+1}N(R_b)(CR_aR_b)_q$, $(CR_aR_b)_pC(O)N(R_a)(CR_aR_b)_q$, bivalent alkyl, bivalent alkenyl, bivalent alkynyl, bivalent cycloalkyl, bivalent cycloalkenyl, bivalent heterocycloalkyl, bivalent heterocycloalkenyl, bivalent spiroheterocyclic, bivalent fused-heterocyclic, bivalent bridged-heterocyclic, bivalent aryl, or bivalent heteroaryl, in which said bivalent alkyl, bivalent cycloalkyl, bivalent cycloalkenyl, bivalent heterocycloalkyl, bivalent heterocycloalkenyl, bivalent spiro-heterocyclic, bivalent fused-heterocyclic, bivalent bridged-heterocyclic, bivalent aryl, or bivalent heteroaryl is optionally substituted with one or more $R_d$;

each of $R_0$, $R_1$, $R_2$, $R_3$, $R_4$, $R_5$, and $R_6$, independently, is H, D, alkyl, spiroalkyl, alkenyl, alkynyl, cycloalkyl, cycloalkenyl, heterocycloalkyl, heterocycloalkenyl, spiroheterocyclic, fused-heterocyclic, bridged-heterocyclic, aryl, heteroaryl, halo, nitro, oxo, cyano, $—OR_a$, $—SR_a$, -alkyl-$R_a$, -alkyl-O—$P(O)(R_a)(R_b)$, -alkyl-OC(O)$N(R_a)(R_b)$, $—NH(CH_2)_pR_a$, $—C(O)R_a$, $—S(O)R_a$, $—SO_2R_a$, $—C(O)OR_a$, $—OC(O)R_a$, $—NR_bR_c$, $—C(O)N(R_b)R_c$, $—N(R_b)C(O)R_c$, in which said alkyl, spiroalkyl, alkenyl, alkynyl, cycloalkyl, cycloalkenyl, heterocycloalkyl, heterocycloalkenyl, spiro-heterocyclic, fused-heterocyclic, bridged-heterocyclic, aryl, or heteroaryl is optionally substituted with one or more $R_d$;

each of $Q_1$ and $Q_2$, independently, is cycloalkyl, cycloalkenyl, heterocycloalkyl, heterocycloalkenyl, spiro-heterocyclic, fused-heterocyclic, bridged-heterocyclic, aryl, or heteroaryl;

each $R_a$, $R_b$, $R_c$ and $R_d$, independently, is H, D, alkyl, alkenyl, alkynyl, spiroalkyl, halo, cyano, amine, nitro, hydroxy, =O, -alkyl-O—P(O)(OH)(OH), C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, spiro-heterocyclic, fused-heterocyclic, bridged-heterocyclic, aryl, or heteroaryl, in which said alkyl, alkoxy, alkoxyalkyl, cycloalkyl, cycloalkenyl, heterocycloalkyl, heterocycloalkenyl, spiro-heterocyclic, fused-heterocyclic, bridged-heterocyclic, aryl, or heteroaryl is optionally substituted with one or more $R_e$;

each $R_e$ is independently H, D, alkyl, alkenyl, alkynyl, spiroalkyl, halo, cyano, amine, nitro, hydroxy, =O, -alkyl-O—P(O)(OH)(OH), C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, spiro-heterocyclic, fused-heterocyclic, bridged-heterocyclic, aryl, or heteroaryl, in which said alkyl, alkoxy, alkoxyalkyl, cycloalkyl, cycloalkenyl, heterocycloalkyl, heterocycloalkenyl, spiro-heterocyclic, fused-heterocyclic, bridged-heterocyclic, aryl, or heteroaryl is optionally substituted with one or more $R_f$; and each $R_f$ is independently H, D, alkyl, alkenyl, alkynyl, spiroalkyl, halo, cyano, amine, nitro, hydroxy, =O, -alkyl-O—P(O)(OH)(OH), C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, spiro-heterocyclic, fused-heterocyclic, bridged-heterocyclic, aryl, or heteroaryl; two of $R_1$ groups, taken together with the atom to which they are attached, may optionally form a cycloalkyl, heterocycloalkyl, heterocycloalkenyl, aryl, or heteroaryl, each optionally substituted with one or more $R_d$;

two of $R_2$ groups, taken together with the atom to which they are attached, may optionally form a cycloalkyl, heterocycloalkyl, heterocycloalkenyl, aryl, or heteroaryl, each optionally substituted with one or more $R_d$;

two of $R_3$ groups, taken together with the atom to which they are attached, may optionally form a cycloalkyl, heterocycloalkyl, heterocycloalkenyl, aryl, or heteroaryl, each optionally substituted with one or more $R_d$;

two of $R_6$ groups, taken together with the atom to which they are attached, may optionally form a cycloalkyl, heterocycloalkyl, heterocycloalkenyl, aryl, or heteroaryl, each optionally substituted with one or more $R_d$;

$R_3$ and $R_4$ groups, taken together with the atom to which they are attached, may optionally form a cycloalkyl, heterocycloalkyl, heterocycloalkenyl, aryl, or heteroaryl, each optionally substituted with one or more $R_d$;

$R_4$ and $R_5$ groups, taken together with the atom to which they are attached, may optionally form a cycloalkyl, heterocycloalkyl, heterocycloalkenyl, aryl, or heteroaryl, each optionally substituted with one or more $R_d$; and $R_5$ and $R_6$ groups, taken together with the atom to which they are attached, may optionally form a cycloalkyl, heterocycloalkyl, heterocycloalkenyl, aryl, or heteroaryl, each optionally substituted with one or more $R_d$;

two of $R_d$ groups, taken together with the atom to which they are attached, may optionally form a cycloalkyl, heterocycloalkyl, heterocycloalkenyl, aryl, or heteroaryl, each optionally substituted with one or more $R_e$;

two of $R_e$ groups, taken together with the atom to which they are attached, may optionally form a cycloalkyl, heterocycloalkyl, heterocycloalkenyl, aryl, or heteroaryl, each optionally substituted with one or more $R_f$; and each of m, n, r, and s, independently, is 0, 1, 2, or 3;

each of p and q, independently, is 0, 1, 2, 3, or 4.

In one embodiment, the compound is represented by Formula (II):

Formula (II)

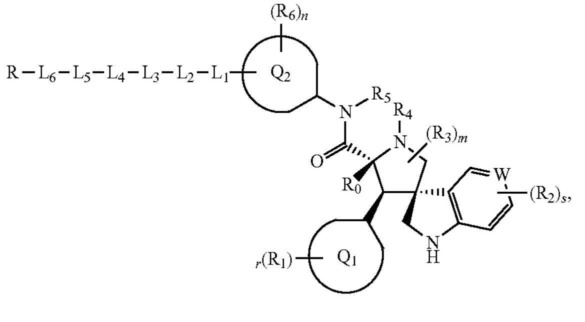

wherein the groups are as defined in Formula (I).

In one embodiment, the compound is represented by Formula (III):

Formula (III)

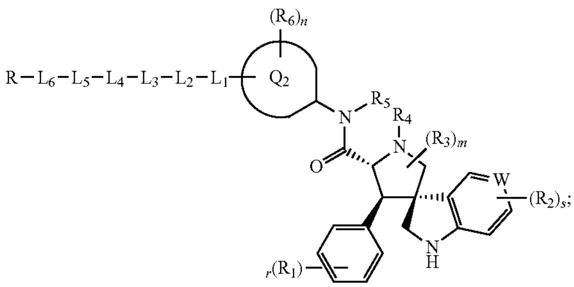

wherein the groups are as defined in Formula (I).

In preferred embodiments, the compound is represented by Formula (IV):

Formula (IV)

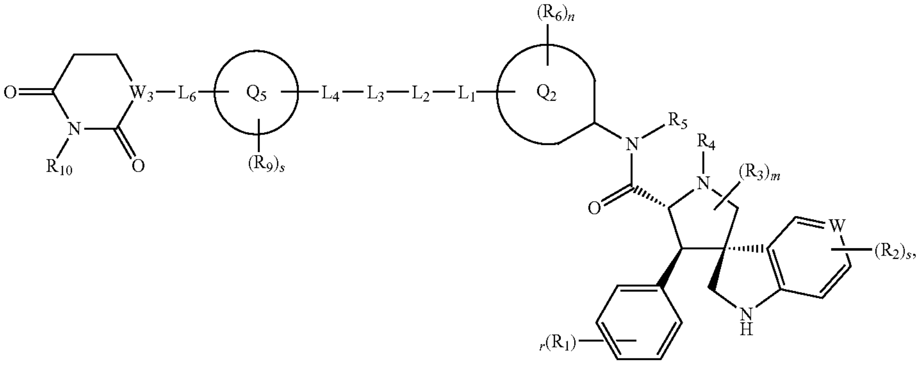

wherein $R_{10}$ is H, D, -alkyl-O—P(O)($R_a$)($R_b$), or -alkyl-OC(O)—$R_a$;

$W_3$ is N or CH;

$L_6$ is absent, NH, CONH, or O;

$Q_5$ is absent, cycloalkyl, cycloalkenyl, heterocycloalkyl, heterocycloalkenyl, spiro-heterocyclic, fused-heterocyclic, bridged-heterocyclic, aryl, or heteroaryl;

$R_9$ is absent, H, D, alkyl, spiroalkyl, alkenyl, alkynyl, cycloalkyl, cycloalkenyl, heterocycloalkyl, heterocycloalkenyl, spiro-heterocyclic, fused-heterocyclic, bridged-heterocyclic, aryl, heteroaryl, halo, oxo, cyano, —$OR_a$, —$SR_a$, -alkyl-$R_a$, -alkyl-O—P(O)($R_a$)($R_b$), -alkyl-OC(O)N($R_a$)($R_b$), —NH$(CH_2)_pR_a$, —C(O)$R_a$, —S(O)$R_a$, —$SO_2R_a$, —C(O)O$R_a$, —OC(O)$R_a$, —$NR_bR_c$, —C(O)N($R_b$)$R_c$, —N($R_b$)C(O)$R_c$, in which said alkyl, spiroalkyl, alkenyl, alkynyl, cycloalkyl, cycloalkenyl, heterocycloalkyl, heterocycloalkenyl, spiro-heterocyclic, fused-heterocyclic, bridged-heterocyclic, aryl, or heteroaryl is optionally substituted with one or more $R_d$;

$R_9$ and $L_4$ groups, taken together with the atom to which they are attached, may optionally form a cycloalkyl, heterocycloalkyl, heterocycloalkenyl, aryl, or heteroaryl, each optionally substituted with one or more $R_d$; and s is 0, 1, 2, 3, or 4;

wherein the remaining groups are as defined in Formula (I).

In one embodiment, the compound is represented by Formula (V):

Formula (V)

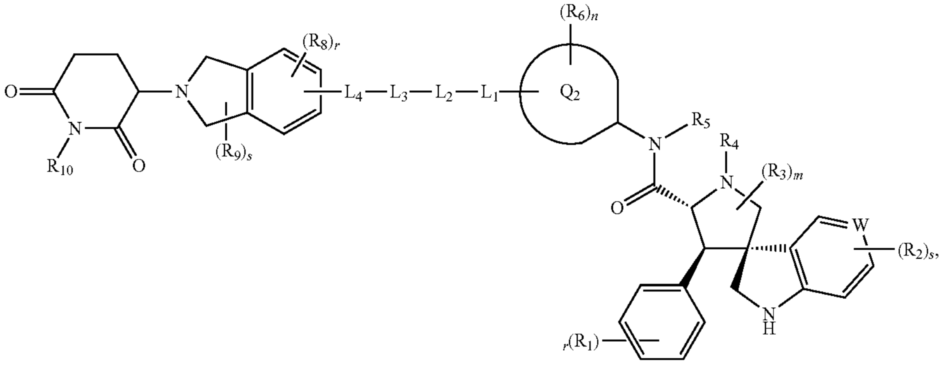

wherein $R_s$ is absent, H, D, alkyl, alkenyl, alkynyl, cycloalkyl, cycloalkenyl, heterocycloalkyl, heterocycloalkenyl, spiro-heterocyclic, fused-heterocyclic, bridged-heterocyclic, aryl, heteroaryl, halo, oxo, cyano, —$OR_a$, —$SR_a$, -alkyl-$R_a$, -alkyl-O—$P(O)(R_a)(R_b)$, -alkyl-$OC(O)N(R_a)(R_b)$, —$NH(CH_2)_pR_a$, —$C(O)R_a$, —$S(O)R_a$, —$SO_2R_a$, —$C(O)OR_a$, —$OC(O)R_a$, —$NR_bR_c$, —$C(O)N(R_b)R_c$, —$N(R_b)C(O)R_c$, in which said alkyl, spiroalkyl, alkenyl, alkynyl, cycloalkyl, cycloalkenyl, heterocycloalkyl, heterocycloalkenyl, spiro-heterocyclic, fused-heterocyclic, bridged-heterocyclic, aryl, or heteroaryl is optionally substituted with one or more $R_d$;

$R_8$ and $L_4$ groups, taken together with the atom to which they are attached, may optionally form a cycloalkyl, heterocycloalkyl, heterocycloalkenyl, aryl, or heteroaryl, each optionally substituted with one or more $R_d$; and r is 0, 1, 2, 3, or 4;

wherein the remaining groups are as defined in Formula (I).

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a neoplastic disease, autoimmune disease, and inflammatory disorders, therapeutic uses thereof, and use of the compounds for the manufacture of a medicament for treating the disease/disorder.

This invention also relates to a method of treating a neoplastic disease, by administering to a subject in need thereof an effective amount of one or more of the compounds, modifications, and/or salts, and compositions thereof described above.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following: List 1

(2'S,3S,4'S,5'R)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide, (2S,3S,4S,5R)—N-(4-carbamoyl-2-methoxyphenyl)-6'-chloro-4-(3-chloro-2-fluorophenyl)-2-neopentyl-1',2'-dihydrospiro[pyrrolidine-3,3'-pyrrolo[3,2-c]pyridine]-5-carboxamide, (2S,3S,4S,5R)—N-(4-carbamoyl-2-methoxyphenyl)-4-(3-chloro-2-fluorophenyl)-6'-ethyl-2-neopentyl-1',2'-dihydrospiro[pyrrolidine-3,3'-pyrrolo[3,2-c]pyridine]-5-carboxamide, (2S,3S,4S,5R)—N-(4-carbamoyl-2-methoxyphenyl)-4-(3-chloro-2-fluorophenyl)-6'-isopropyl-2-neopentyl-1',2'-dihydrospiro[pyrrolidine-3,3'-pyrrolo[3,2-c]pyridine]-5-carboxamide, (2'S,3R,4'S,5'R)—N-(4-carbamoyl-2-methoxyphenyl)-6-chloro-4'-(3-chloro-2-fluorophenyl)-2'-neopentyl-1H-spiro[benzo[c]isothiazole-3,3'-pyrrolidine]-5'-carboxamide 2,2-dioxide, (2R,2'S,3R,4'S,5'R)—N-(4-carbamoyl-2-methoxyphenyl)-6-chloro-4'-(3-chloro-2-fluorophenyl)-2-methyl-2'-neopentyl-1H-spiro[benzo[d][1,2]azaphosphole-3,3'-pyrrolidine]-5'-carboxamide 2-oxide, (2'S,3S,4'S,5'R)—N-(4-carbamoyl-2-methoxyphenyl)-4'-(3-chloro-2-fluorophenyl)-6-ethyl-2'-neopentylspiro[indoline-3,3'-pyrrolidine]-5'-carboxamide, (2'S,3S,4'S,5'R)—N-(4-carbamoyl-2-methoxyphenyl)-4'-(3-chloro-2-fluorophenyl)-6-isopropyl-2'-neopentylspiro[indoline-3,3'-pyrrolidine]-5'-carboxamide, (2'S,3S,4'S,5'R)—N-(4-carbamoyl-2-methoxyphenyl)-6-chloro-4'-(2-chloro-3-fluoropyridin-4-yl)-2'-neopentylspiro[indoline-3,3'-pyrrolidine]-5'-carboxamide, (2'S,3S,4'S,5'R)—N-(4-carbamoyl-2-methoxyphenyl)-6-chloro-4'-(3-chloro-2-fluorophenyl)-5'-methyl-2'-neopentylspiro[indoline-3,3'-pyrrolidine]-5'-carboxamide, (2'S,3S,4'S,5'R)—N-(4-carbamoyl-2-methoxyphenyl)-6-chloro-4'-(3-chloro-2-fluorophenyl)-5'-methyl-2'-neopentylspiro[indoline-3,3'-pyrrolidine]-5'-carboxamide, (2S,3S,4S,5R)—N-(4-carbamoyl-2-methoxyphenyl)-6'-chloro-4-(3-chloro-2-fluorophenyl)-5-isopropyl-2-neopentyl-1',2'-dihydrospiro[pyrrolidine-3,3'-pyrrolo[3,2-c]pyridine]-5-carboxamide, (3'S,4'S,5'R)—N-(4-carbamoyl-2-methoxyphenyl)-6"-chloro-4'-(3-chloro-2-fluorophenyl)-1'-ethyldispiro[cyclohexane-1,2'-pyrrolidine-3',3-indoline]-5'-carboxamide, 4-(((2'S,3S,4'S,5'S)-6-chloro-4'-(3-chloro-2-fluorophenyl)-2'-neopentylspiro[indoline-3,3'-pyrrolidine])-5'-sulfonamido)-3-methoxybenzamide, 4-((((2'S,3S,4'S,5'S)-6-chloro-4'-(3-chloro-2-fluorophenyl)-2'-neopentylspiro[indoline-3,3'-pyrrolidin]-5'-yl)(methyl)phosphoryl)amino)-3-methoxybenzamide, (2'S,3S,4'S,5'R)-6-chloro-4'-(3-chloro-2-fluorophenyl)-N-(2-methoxy-4-(methylsulfonyl)phenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(dimethylphosphoryl)-2-methoxyphenyl)-2'-neopentylspiro[indoline-3,3'-pyrrolidine]-5'-carboxamide, (2S,3S,4S,5R)—N-(4-carbamoyl-2-methoxyphenyl)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carboxamide, (2R,3S,4R,5S)—N2-(4-carbamoyl-2-methoxyphenyl)-3-(3-chloro-2-fluorophenyl)-4-(4-chlorophenyl)-5-neopentylpyrrolidine-2,4-dicarboxamide, (2R,3S,4R,5S)—N-(4-carbamoyl-2-methoxyphenyl)-3-(3-chloro-2-fluorophenyl)-4-(4-chlorophenyl)-4-(methylsulfonyl)-5-neopentylpyrrolidine-2-carboxamide, (2'S,3R,3'R,8a'S)—N-(4-carbamoyl-2-methoxyphenyl)-6-chloro-2'-(3-chloro-2-fluorophenyl)-7',7'-dimethyl-2-oxo-2',3',6',7',8',8a'-hexahydro-5'H-spiro[indoline-3,1'-indolizine]-3'-carboxamide, 4-((2S,3R,4S,5R)-6'-chloro-4-(3-chloro-2-fluorophenyl)-5-methyl-2-neopentyl-2'-oxo-1',2'-dihydrospiro[pyrrolidine-3,3'-pyrrolo[3,2-c]pyridine]-5-carboxamido)-3-methoxybenzoic acid, (2R,2'S,3R,4'S,5'R)—N-(4-carbamoyl-2-methoxyphenyl)-6-chloro-4'-(3-chloro-2-fluorophenyl)-2-methyl-2'-neopentyl-1H-spiro[benzo[d][1,2]azaphosphole-3,3'-pyrrolidine]-5'-carboxamide 2-oxide, (2'S,3S,4'S,5'R)—N-(4-carbamoyl-2-methoxyphenyl)-6-chloro-4'-(3-chloro-2-fluorophenyl)-5'-methyl-2'-neopentylspiro[indoline-3,3'-pyrrolidine]-5'-carboxamide, 4-((2'S,3S,4'S,5'R)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carboxamide, (S)-4-((2'S,3S,4'S,5'R)-6-chloro-4'-(3-chloro-2-fluorophenyl)-2'-neopentylspiro[indoline-3,3'-pyrrolidine]-5'-carbonyl)-2-methyl-3,4-dihydro-2H-benzo[b][1,4]oxazine-7-carboxamide, (R)-4-((2'S,3S,4'S,5'R)-6-chloro-4'-(3-chloro-2-fluorophenyl)-2'-neopentylspiro[indoline-3,3'-pyrrolidine]-5'-carbonyl)-2-methyl-3,4-dihydro-2H-benzo[b][1,4]oxazine-7-carboxamide, List 2

(2'S,3S,4'S,5'R)-6-chloro-4'-(3-chloro-2-fluorophenyl)-N-(4-(4-((2-(2,6-dioxopiperidin-3-yl)-1-oxoisoindolin-4-yl)ethynyl)piperidin-2-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(3-(3-((2-(2,6-dioxopiperidin-3-yl)-1-oxoisoindolin-4-yl)ethynyl)morpholino)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(2-((2-(2,6-dioxopiperidin-3-yl)-1-oxoisoindolin-4-yl)ethynyl)tetrahydro-2H-pyran-4-yl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-4-(4-(2-(2,6-dioxopiperidin-3-yl)-1-oxoisoindolin-4-yl)-2-methylbut-3-yn-2-yl)-2-methylpiperazin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-1-(4-(2-(2,6-dioxopiperidin-3-yl)-1-oxoisoindolin-4-yl)-2-methylbut-3-yn-2-yl)piperidin-3-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-((1S,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((1R,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-4-((1R,2R)-2-((2-(2,6-dioxopiperidin-3-yl)-1-oxoisoindolin-4-yl)ethynyl)cyclopropyl)morpholin-2-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2R)-2-((1R,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((1R,2R)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((1S,2S)-2-((2-(2,6-dioxopiperidin-3-yl)-1-oxoisoindolin-4-yl)ethynyl)cyclopropyl)-6-azaspiro[3.5]nonan-6-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((1S,2S)-2-((2-(2,6-dioxopiperidin-3-yl)-1-oxoisoindolin-4-yl)ethynyl)cyclopropyl)-5-azaspiro[3.5]nonan-5-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(1-(3-((2-(2,6-dioxopiperidin-3-yl)-1-oxoisoindolin-4-yl)ethynyl)cyclobutyl)piperidin-4-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-1-(3-((2-(2,6-dioxopiperidin-3-yl)-1-oxoisoindolin-4-yl)ethynyl)cyclobutyl)piperidin-3-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-4-(3-((2-(2,6-dioxopiperidin-3-yl)-1-oxoisoindolin-4-yl)ethynyl)cyclobutyl)morpholin-2-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-1-(3-((2-(2,6-dioxopiperidin-3-yl)-1-oxoisoindolin-4-yl)ethynyl)cyclobutyl)piperidin-2-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-(((1R,2R)-2-(2-(2,6-dioxopiperidin-3-yl)-1-oxoisoindolin-4-yl)cyclopropyl)ethynyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(3-(((1S,2S)-2-(2-(2,6-dioxopiperidin-3-yl)-1-oxoisoindolin-4-yl)cyclopropyl)ethynyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-2-(((1S,2S)-2-(2-(2,6-dioxopiperidin-3-yl)-1- oxoisoindolin-4-yl)cyclopropyl)ethynyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S)-1-(((1S,2S)-2-(2-(2,6-dioxopiperidin-3-yl)-1-oxoisoindolin-4-yl)cyclopropyl)ethynyl)-6-azaspiro[2.5]octan-6-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3R)-1-(((1R,2R)-2-(2-(2,6-dioxopiperidin-3-yl)-1-oxoisoindolin-4-yl)cyclopropyl)ethynyl)-5-azaspiro[2.5]octan-5-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(((1S,2R)-2-(2-(2,6-dioxopiperidin-3-yl)-1-oxoisoindolin-4-yl)cyclopropyl)ethynyl)-7-azaspiro[3.5]nonan-7-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(((1S,2R)-2-(2-(2,6-dioxopiperidin-3-yl)-1-oxoisoindolin-4-yl)cyclopropyl)ethynyl)-6-azaspiro[3.5]nonan-6-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(((1S,2R)-2-(2-(2,6-dioxopiperidin-3-yl)-1-oxoisoindolin-4-yl)cyclopropyl)ethynyl)-5-azaspiro[3.5]nonan-5-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(3-(2-(2,6-dioxopiperidin-3-yl)-1-oxoisoindolin-4-yl)azetidin-1-yl)-7-azaspiro[3.5]nonan-7-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(3-(2-(2,6-dioxopiperidin-3-yl)-1-oxoisoindolin-4-yl)azetidin-1-yl)-6-azaspiro[3.5]nonan-6-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(3-(2-(2,6-dioxopiperidin-3-yl)-1-oxoisoindolin-4-yl)azetidin-1-yl)-5-azaspiro[3.5]nonan-5-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(5-(1-(2-(2,6-dioxopiperidin-3-yl)-1-oxoisoindolin-4-yl)azetidin-3-yl)hexahydropyrrolo[3,4-c]pyrrol-2(1H)-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(5-(1-(2-(2,6-dioxopiperidin-3-yl)-1-oxoisoindolin-4-yl)azetidin-3-yl)hexahydropyrrolo[3,4-b]pyrrol-1(2H)-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((6S)-2-((2S)-2-(2-(2,6-dioxopiperidin-3-yl)-1-oxoisoindolin-5-yl)pyrrolidin-1-yl)-6-methyl-7-azaspiro[3.5]nonan-7-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-1-(3-((2S)-2-(2-(2,6-dioxopiperidin-3-yl)-1-oxoisoindolin-5-yl)pyrrolidin-1-yl)cyclobutyl)piperidin-3-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2-((2S)-2-(2-(2,6-dioxopiperidin-3-yl)-1-oxoisoindolin-5-yl)pyrrolidin-1-yl)-7-azaspiro[3.5]nonan-7-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-3-((2-((S)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-3-((2-((R)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-3-((2-((S)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-3-((2-((R)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((3S)-3-((2-(2,6-dioxopiperidin-3-yl)-1-oxoisoindolin-4-yl)ethynyl)morpholino)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((3R)-3-((2-(2,6-dioxopiperidin-3-yl)-1-oxoisoindolin-4-yl)ethynyl)morpholino)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-((3S)-3-((2-(2,6-dioxopiperidin-3-yl)-1-oxoisoindolin-4-yl)ethynyl)morpholino)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-((3R)-3-((2-(2,6-dioxopiperidin-3-yl)-1-oxoisoindolin-4-yl)ethynyl)morpholino)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-((1R,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-((1S,2R)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((1R,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((1S,2R)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-((1R,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-((1S,2R)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2R)-2-((1R,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2R)-2-((1S,2R)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-2-((1R,2S)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-2-((1S,2R)-2-((2-(2,6-dioxopiperidin-3-yl)-1-oxoisoindolin-4-yl)ethynyl)cyclopropyl)piperidin-1-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((1S,2R)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((1R,2S)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((1S,2S)-2-((2-(2,6-dioxopiperidin-3-yl)-1-oxoisoindolin-4-yl)ethynyl)cyclopropyl)-6-azaspiro[3.5]nonan-6-yl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((1S,2S)-2-((2-(2,6-dioxopiperidin-3-yl)-1-oxoisoindolin-4-yl)ethynyl)cyclopropyl)-5-azaspiro[3.5]nonan-5-yl)-2-methoxyphenyl)-2'-neopentylspiro[indoline-3,3'-pyrrolidine]-5'-carboxamide, List 3

(2'S,3S,4'S,5'R)-6-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2-((2-(2,6-dioxopiperidin-3-yl)-1-oxoisoindolin-4-yl)ethynyl)tetrahydro-2H-pyran-4-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(3-((2-(2,6-dioxopiperidin-3-yl)-1-oxoisoindolin-4-yl)ethynyl)tetrahydro-2H-pyran-4-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2-((2-(2,6-dioxopiperidin-3-yl)-1-oxoisoindolin-4-yl)ethynyl)-7-azaspiro[3.5]nonan-7-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1S)-1-((2-(2,6-dioxopiperidin-3-yl)-1-oxoisoindolin-4-yl)ethynyl)-6-azaspiro[2.5]octan-6-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((4-(4-(2-(2,6-dioxopiperidin-3-yl)-1-oxoisoindolin-4-yl)-2-methylbut-3-yn-2-yl)piperazin-1-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((4-((2-(2,6-dioxopiperidin-3-yl)-1-oxoisoindolin-4-yl)ethynyl)piperidin-1-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((5-(2-((R)-2,6-dioxopiperidin-3-yl)-1-oxoisoindolin-4-yl)pent-4-yn-1-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((5-(2-((S)-2,6-dioxopiperidin-3-yl)-1-oxoisoindolin-4-yl)pent-4-yn-1-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(2-methoxy-4-((5-(2-(1-methyl-2,6-dioxopiperidin-3-yl)-1-oxoisoindolin-4-yl)pent-4-yn-1-yl)carbamoyl)phenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-((2-(2,6-dioxopiperidin-3-yl)-1-oxoisoindolin-4-yl)ethynyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1S,3R)-3-((2-(2,6-dioxopiperidin-3-yl)-1-oxoisoindolin-4-yl)ethynyl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1R,3S)-3-((2-(2,6-dioxopiperidin-3-yl)-1-oxoisoindolin-4-yl)ethynyl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1R,3R)-3-((2-(2,6-dioxopiperidin-3-yl)-1-oxoisoindolin-4-yl)ethynyl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1S,3S)-3-((2-(2,6-dioxopiperidin-3-yl)-1-oxoisoindolin-4-yl)ethynyl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-2-(4-(2-((R)-2,6-dioxopiperidin-3-yl)-1-oxoisoindolin-4-yl)but-3-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-2-(4-(2-((S)-2,6-dioxopiperidin-3-yl)-1-oxoisoindolin-4-yl)but-3-yn-1-yl)piperidine-1-carbonyl)-2- methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-2-(4-(2-((R)-2,6-dioxopiperidin-3-yl)-1-oxoisoindolin-4-yl)but-3-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-2-(4-(2-((S)-2,6-dioxopiperidin-3-yl)-1-oxoisoindolin-4-yl)but-3-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1R,2S)-2-(3-(2-(2,6-dioxopiperidin-3-yl)-1-oxoisoindolin-4-yl)prop-2-yn-1-yl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1S,2R)-2-(3-(2-(2,6-dioxopiperidin-3-yl)-1-oxoisoindolin-4-yl)prop-2-yn-1-yl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-((2-(2,6-dioxopiperidin-3-yl)-1-oxoisoindolin-4-yl)ethynyl)-7-azaspiro[3.5]nonane-7-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((((1R,2S)-2-((2-(2,6-dioxopiperidin-3-yl)-1-oxoisoindolin-4-yl)ethynyl)cyclohexyl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((((1S,2S)-2-((2-(2,6-dioxopiperidin-3-yl)-1-oxoisoindolin-4-yl)ethynyl)cyclohexyl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((((1S,2R)-2-((2-(2,6-dioxopiperidin-3-yl)-1-oxoisoindolin-4-yl)ethynyl)cyclohexyl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((((1R,2R)-2-((2-(2,6-dioxopiperidin-3-yl)-1-oxoisoindolin-4-yl)ethynyl)cyclohexyl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2R)-2-((2-(2,6-dioxopiperidin-3-yl)-1-oxoisoindolin-4-yl)buta-1,3-diyn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-2-((2-(2,6-dioxopiperidin-3-yl)-1-oxoisoindolin-4-yl)buta-1,3-diyn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((5-(2-(2,6-dioxopiperidin-3-yl)-1-oxoisoindolin-4-yl)penta-2,4-diyn-1-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((5-(2-(2,6-dioxopiperidin-3-yl)-1-oxoisoindolin-4-yl)penta-2,4-diyn-1-yl)(isopropyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3-((2-(2,6-dioxopiperidin-3-yl)-1-oxoisoindolin-4-yl)ethynyl)bicyclo[1.1.1]pentan-1-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((2-(2,6-dioxopiperidin-3-yl)-1-oxoisoindolin-4-yl)ethynyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-((2-(2,6-dioxopiperidin-3-yl)-1-oxoisoindolin-4-yl)ethynyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((2-(2,6-dioxopiperidin-3-yl)-1-oxoisoindolin-4-yl)ethynyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-((2-(2,6-dioxopiperidin-3-yl)-1-oxoisoindolin-4-yl)ethynyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-((2-(2,6-dioxopiperidin-3-yl)-1-oxoisoindolin-4-yl)ethynyl)pyrrolidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-((2-(2,6-dioxopiperidin-3-yl)-1-oxoisoindolin-4-yl)ethynyl)pyrrolidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-(3-(2-(2,6-dioxopiperidin-3-yl)-1-oxoisoindolin-4-yl)prop-2-yn-1-yl)piperazine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((3S)-1-(3-(2-(2,6-dioxopiperidin-3-yl)-1-oxoisoindolin-4-yl)prop-2-yn-1-yl)piperidin-3-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((3R)-1-(3-(2-(2,6-dioxopiperidin-3-yl)-1-oxoisoindolin-4-yl)prop-2-yn-1-yl)piperidin-3-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((4S)-4-((2-(2,6-dioxopiperidin-3-yl)-1-oxoisoindolin-4-yl)ethynyl)azepane-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((4R)-4-((2-(2,6-dioxopiperidin-3-yl)-1-oxoisoindolin-4-yl)ethynyl)azepane-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((7S)-7-((2-(2,6-dioxopiperidin-3-yl)-1-oxoisoindolin-4-yl)ethynyl)-1,4-oxazepane-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((7R)-7-((2-(2,6-dioxopiperidin-3-yl)-1-oxoisoindolin-4-yl)ethynyl)-1,4-oxazepane-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-3-(3-(2-((S)-2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-3-(3-(2-((S)-2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-2-(3-(2-(2,6-dioxopiperidin-3-yl)-1-oxoisoindolin-4-yl)prop-2-yn-1-yl)morpholine-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((3S)-3-(3-(2-(2,6-dioxopiperidin-3-yl)-1-oxoisoindolin-4-yl)prop-2-yn-1-yl)piperidin-1-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((2S)-2-(3-(2-(2,6-dioxopiperidin-3-yl)-1-oxoisoindolin-4-yl)prop-2-yn-1-yl)morpholino)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((5-((2-(2,6-dioxopiperidin-3-yl)-1-oxoisoindolin-4-yl)ethynyl)pyridin-3-yl)carbamoyl)-2-methoxyphenyl)-2'-neopentylspiro[indoline-3,3'-pyrrolidine]-5'-carboxamide, (S)-3-(4-(3-((S)-1-(4-((2'S,3S,4'S,5'R)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carbonyl)piperidin-3-yl)prop-1-yn-1-yl)-1-oxoisoindolin-2-yl)piperidine-2,6-dione, (2'S,3S,4'S,5'R)-6-chloro-4'-(3-chloro-2-fluorophenyl)-N-(4-((3S)-3-(3-(2-(2,6-dioxopiperidin-3-yl)-6-fluoro-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-3-(3-(2-((S)-2,6-dioxopiperidin-3-yl)-1,3-dioxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-(3-(2-(2,6-dioxopiperidin-3-yl)-5-fluoro-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-(3-(2-(2,6-dioxopiperidin-3-yl)-5-morpholino-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3R)-3-(3-(2-(2,6-dioxopiperidin-3-yl)-1-oxoisoindolin-4-yl)prop-2-yn-1-yl)pyrrolidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-(3-(2-(2,6-dioxopiperidin-3-yl)-1-oxoisoindolin-4-yl)prop-2-yn-1-yl)azepane-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((6S)-6-(3-(2-(2,6-dioxopiperidin-3-yl)-1-oxoisoindolin-4-yl)prop-2-yn-1-yl)-1,4-oxazepane-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(5-(3-(2-(2,6-dioxopiperidin-3-yl)-1-oxoisoindolin-4-yl)prop-2-yn-1-yl)-4-methyl-1,2,3,6-tetrahydropyridine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-3-(3-(2-((R)-2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((6S)-6-(3-(2-(2,6-dioxopiperidin-3-yl)-1-oxoisoindolin-4-yl)prop-2-yn-1-yl)-2,2-dimethylmorpholine-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-2-(3-(2-(2,6-dioxopiperidin-3-yl)-1-oxoisoindolin-4-yl)prop-2-yn-1-yl)-5,5-dimethylmorpholine-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-(1-((2-(2,6-dioxopiperidin-3-yl)-1-oxoisoindolin-4-yl)ethynyl)cyclobutyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3S)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3R)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3S)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3R)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1R,3R)-1-((2-((S)-2,6-dioxopiperidin-3-yl)-1-oxoisoindolin-4-yl)ethynyl)-5-azaspiro[2.5]octan-5-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3S)-1-((2-((S)-2,6-dioxopiperidin-3-yl)-1-oxoisoindolin-4-yl)ethynyl)-4-oxa-7-azaspiro[2.5]octane-7-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1R,3S)-1-((2-((S)-2,6-dioxopiperidin-3-yl)-1-oxoisoindolin-4-yl)ethynyl)-4-oxa-7-azaspiro[2.5]octan-7-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1S,3R,4S)-1-((2-(2,6-dioxopiperidin-3-yl)-1-oxoisoindolin-4-yl)ethynyl)spiro[2.5]octan-4-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3S)-1-((2-((R)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3R)-1-((2-((R)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3S)-1-((2-((R)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3R)-1-((2-((R)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R)-1-((2-((S)-2,6-dioxopiperidin-3-yl)-1-oxoisoindolin-4-yl)ethynyl)-5-azaspiro[2.4]heptane-5-carbonyl)-2-methoxyphenyl)-2'-neopentylspiro[indo line-3,3'-pyrrolidine]-5'-carboxamide, (2'S,3S,4'S,5'R)-6-chloro-4'-(3-chloro-2-fluorophenyl)-N-(4-((1S)-1-((2-((S)-2,6-dioxopiperidin-3-yl)-1-oxoisoindolin-4-yl)ethynyl)-5-azaspiro[2.4]heptane-5-carbonyl)-2-methoxyphenyl)-2'-neopentylspiro[indo line-3,3'-pyrrolidine]-5'-carboxamide, (2'S,3S,4'S,5'R)-6-chloro-4'-(3-chloro-2-fluorophenyl)-N-(4-((1R)-1-((2-((R)-2,6-dioxopiperidin-3-yl)-1-oxoisoindolin-4-yl)ethynyl)-5-azaspiro[2.4]heptane-5-carbonyl)-2-methoxyphenyl)-2'-neopentylspiro[indo line-3,3'-pyrrolidine]-5'-carboxamide, (2'S,3S,4'S,5'R)-6-chloro-4'-(3-chloro-2-fluorophenyl)-N-(4-((1S)-1-((2-((R)-2,6-dioxopiperidin-3-yl)-1-oxoisoindolin-4-yl)ethynyl)-5-azaspiro[2.4]heptane-5-carbonyl)-2-methoxyphenyl)-2'-neopentylspiro[indo line-3,3'-pyrrolidine]-5'-carboxamide, (2'S,3S,4'S,5'R)-6-chloro-4'-(3-chloro-2-fluorophenyl)-N-(4-((1S)-1-((2-((S)-2,6-dioxopiperidin-3-yl)-1-oxoisoindolin-4-yl)ethynyl)-6-azaspiro[2.6]nonane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R)-1-((2-((S)-2,6-dioxopiperidin-3-yl)-1-oxoisoindolin-4-yl)ethynyl)-6-azaspiro[2.6]nonane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S)-1-((2-((R)-2,6-dioxopiperidin-3-yl)-1-oxoisoindolin-4-yl)ethynyl)-6-azaspiro[2.6]nonane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R)-1-((2-((R)-2,6-dioxopiperidin-3-yl)-1-oxoisoindolin-4-yl)ethynyl)-6-azaspiro[2.6]nonane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S)-1-((2-((R)-2,6-dioxopiperidin-3-yl)-1-oxoisoindolin-4-yl)ethynyl)-4-oxa-7-azaspiro[2.6]nonane-7-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(3-((2-(2,6-dioxopiperidin-3-yl)-1-oxoisoindolin-4-yl)ethynyl)tetrahydro-2H-pyran-4-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3S)-3-(4-((2-(2,6-dioxopiperidin-3-yl)-1-oxoisoindolin-4-yl)ethynyl)-6,6-dimethyl-5,6-dihydro-2H-pyran-3-yl)morpholine-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((3S,4R)-3-(3-(2-(2,6-dioxopiperidin-3-yl)-1-oxoisoindolin-4-yl)prop-2-yn-1-yl)tetrahydro-2H-pyran-4-yl)(isopropyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((5-(3-(2-(2,6-dioxopiperidin-3-yl)-1-oxoisoindolin-4-yl)prop-2-yn-1-yl)-2,2-dimethyl-3,6-dihydro-2H-pyran-4-yl)(isopropyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1R,2S)-2-(3-(2-(2,6-dioxopiperidin-3-yl)-1-oxoisoindolin-4-yl)prop-2-yn-1-yl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1S,2R)-2-(3-(2-(2,6-dioxopiperidin-3-yl)-1-oxoisoindolin-4-yl)prop-2-yn-1-yl)cyclohexyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2-(3-(2-(2,6-dioxopiperidin-3-yl)-1-oxoisoindolin-4-yl)prop-2-yn-1-yl)cyclohex-1-en-1-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1-((2-(2,6-dioxopiperidin-3-yl)-1-oxoisoindolin-4-yl)buta-1,3-diyn-1-yl)cyclopropyl)(isopropyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1-((2-(2,6-dioxopiperidin-3-yl)-1-oxoisoindolin-4-yl)buta-1,3-diyn-1-yl)cyclopropyl)(oxetan-3-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((2-((2-(2,6-dioxopiperidin-3-yl)-1-oxoisoindolin-4-yl)ethynyl)-4,4-dimethylcyclohex-1-en-1-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((2-((2-(2,6-dioxopiperidin-3-yl)-1-oxoisoindolin-4-yl)ethynyl)-5,5-dimethylcyclohex-1-en-1-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((4-((2-(2,6-dioxopiperidin-3-yl)-1-oxoisoindolin-4-yl)ethynyl)-6,6-dimethyl-5,6-dihydro-2H-pyran-3-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((5-((2-(2,6-dioxopiperidin-3-yl)-1-oxoisoindolin-4-yl)ethynyl)-2,2-dimethyl-3,6-dihydro-2H-pyran-4-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((5-((2-(2,6-dioxopiperidin-3-yl)-1-oxoisoindolin-4-yl)ethynyl)-2,3,6,7-tetrahydrooxepin-4-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((4-((2-(2,6-dioxopiperidin-3-yl)-1-oxoisoindolin-4-yl)ethynyl)pyridin-3-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((((3S,4S)-4-((2-(2,6-dioxopiperidin-3-yl)-1-oxoisoindolin-4-yl)ethynyl)tetrahydro-2H-pyran-3-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((((3S,4S)-4-((2-(2,6-dioxopiperidin-3-yl)-1-oxoisoindolin-4-yl)ethynyl)-1-(oxetan-3-yl)piperidin-3-yl)methyl)carbamoyl)-2-methoxyphenyl)-2'-neopentylspiro[indoline-3,3'-pyrrolidine]-5'-carboxamide, 3-(4-((5-((1-((2'S,3S,4'S,5'R)-6-chloro-4'-(3-chloro-2-fluorophenyl)-2'-neopentylspiro[indoline-3,3'-pyrrolidine]-5'-carbonyl)-6-oxo-1,2,3,6,8,9-hexahydro-7H-[1,4]oxazino[3,2-g]isoquinolin-7-yl)methyl)-2,2-dimethyl-3,6-dihydro-2H-pyran-4-yl)ethynyl)-1-oxoisoindolin-2-yl)piperidine-2,6-dione, 3-(4-((5-((4-((2'S,3S,4'S,5'R)-6-chloro-4'-(3-chloro-2-fluorophenyl)-2'-neopentylspiro[indoline-3,3'-pyrrolidine]-5'-carbonyl)-7-oxo-2,3,4,7,9,10-hexahydro-8H-[1,4]oxazino[2,3-f]isoquinolin-8-yl)methyl)-2,2-dimethyl-3,6-dihydro-2H-pyran-4-yl)ethynyl)-1-oxoisoindolin-2-yl)piperidine-2,6-dione, List 4

(2'S,3S,4'S,5'R)-6-chloro-4'-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R)-1-((2-(2,6-dioxopiperidin-3-yl)-1-oxoisoindolin-4-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-1-((2-((R)-2,6-dioxopiperidin-3-yl)-1-oxoisoindolin-4-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-1-((2-((R)-2,6-dioxopiperidin-3-yl)-1-oxoisoindolin-4-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((S)-1-((2-((S)-2,6-dioxopiperidin-3-yl)-1-oxoisoindolin-4-yl)ethynyl)-6-azaspiro[2.5]octan-6-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((R)-1-((2-((S)-2,6-dioxopiperidin-3-yl)-1-oxoisoindolin-4-yl)ethynyl)-6-azaspiro[2.5]octan-6-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,5R)-1-((2-((R)-2,6-dioxopiperidin-3-yl)-1-oxoisoindolin-4-yl)ethynyl)-5-methyl-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3S)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3S)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3R)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3R)-1-((2-((S)-2,6-dioxopiperidin-3-yl)-1-oxoisoindolin-4-yl)ethynyl)-5-azaspiro[2.5]octane-5-carbonyl)-2-methoxyphenyl)-2'-neopentylspiro[indoline-3,3'-pyrrolidine]-5'-carboxamide, ((S)-3-(4-(((R)-6-((4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxyphenyl)sulfonyl)-6-azaspiro[2.5]octan-1-yl)ethynyl)-1-oxoisoindolin-2-yl)-2,6-dioxopiperidin-1-yl)methyl dihydrogen phosphate, ((2'S,3S,4'S,5'R)-6-chloro-4'-(3-chloro-2-fluorophenyl)-5'-((4-(((R)-1-((2-((S)-2,6-dioxopiperidin-3-yl)-1-oxoisoindolin-4-yl)ethynyl)-6-azaspiro[2.5]octan-6-yl)sulfonyl)-2-methoxyphenyl)carbamoyl)-2'-neopentylspiro[indoline-3,3'-pyrrolidin]-1-yl)methyl dihydrogen phosphate, ((S)-3-(4-(((R)-6-((4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxyphenyl)sulfonyl)-6-azaspiro[2.5]octan-1-yl)ethynyl)-1-oxoisoindolin-2-yl)-2,6-dioxopiperidin-1-yl)methyl phosphate, disodium, ((S)-3-(4-(((R)-6-((4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxyphenyl)sulfonyl)-6-azaspiro[2.5]octan-1-yl)ethynyl)-1-oxoisoindolin-2-yl)-2,6-dioxopiperidin-1-yl)methyl phosphate, calcium (II), ((S)-3-(4-(((R)-6-((4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxyphenyl)sulfonyl)-6-azaspiro[2.5]octan-1-yl)ethynyl)-1-oxoisoindolin-2-yl)-2,6-dioxopiperidin-1-yl)methyl methyl(3-((phosphonooxy)methyl)pyridin-2-yl)carbamate, (2-(((((S)-3-(4-(((R)-6-((4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxyphenyl)sulfonyl)-6-azaspiro[2.5]octan-1-yl)ethynyl)-1-oxoisoindolin-2-yl)-2,6-dioxopiperidin-1-yl)methoxy)carbonyl)(methyl)amino)pyridin-3-yl)methyl phosphate, disodium, (2-(((((S)-3-(4-(((R)-6-((4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxyphenyl)sulfonyl)-6-azaspiro[2.5]octan-1-yl)ethynyl)-1-oxoisoindolin-2-yl)-2,6-dioxopiperidin-1-yl)methoxy)carbonyl)(methyl)amino)pyridin-3-yl)methyl phosphate, calcium (II), (2-(((((R)-3-(4-(((R)-6-((4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxyphenyl)sulfonyl)-6-azaspiro[2.5]octan-1-yl)ethynyl)-1-oxoisoindolin-2-yl)-2,6-dioxopiperidin-1-yl)methoxy)carbonyl)(2-(phosphonatooxy)ethyl)amino)pyridin-3-yl)methyl phosphate, sodium, (2'S,3S,4'S,5'R)-6-chloro-4'-(3-chloro-2-fluorophenyl)-N-(4-((S)-1-((2-((S)-2,6-dioxopiperidin-3-yl)-1,3-dioxoisoindolin-4-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((S)-1-((2-((S)-2,6-dioxopiperidin-3-yl)-1-oxoisoindolin-4-yl)ethynyl)-6-azaspiro[2.5]octan-6-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((S)-1-((2-((S)-2,6-dioxopiperidin-3-yl)-1,3-dioxoisoindolin-4-yl)ethynyl)-6-azaspiro[2.5]octan-6-yl)sulfonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-(2-(2,6-dioxopiperidin-3-yl)-1-oxoisoindolin-5-yl)piperazine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(5-(2-(2,6-dioxopiperidin-3-yl)-1-oxoisoindolin-5-yl)octahydropyrrolto[3,4-c]pyrrole-2-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-(4-(2-(2,6-dioxopiperidin-3-yl)-1-oxoisoindolin-5-yl)piperazin-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(4-(2-(2,6-dioxopiperidin-3-yl)-1-oxoisoindolin-5-yl)piperazin-1-yl)-7-azaspiro[3.5]nonane-7-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1-(2-(2,6-dioxopiperidin-3-yl)-1-oxoisoindolin-5-yl)piperidin-4-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((7-(2-(2,6-dioxopiperidin-3-yl)-1-oxoisoindolin-5-yl)-7-azaspiro[3.5]nonan-2-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3-(4-(2-(2,6-dioxopiperidin-3-yl)-1-oxoisoindolin-5-yl)piperazin-1-yl)cyclobutyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3-(4-(2-(2,6-dioxopiperidin-3-yl)-1-oxoisoindolin-5-yl)piperazin-1-yl)bicyclo[1.1.1]pentan-1-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((1-(2-(2,6-dioxopiperidin-3-yl)-1-oxoisoindolin-5-yl)piperidin-4-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(((7-(2-(2,6-dioxopiperidin-3-yl)-1-oxoisoindolin-5-yl)-7-azaspiro[3.5]nonan-2-yl)methyl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((8-(2-(2,6-dioxopiperidin-3-yl)-1-oxoisoindolin-5-yl)-5-oxa-8-azaspiro[3.5]nonan-2-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((5-(2-(2,6-dioxopiperidin-3-yl)-1-oxoisoindolin-5-yl)-8-oxa-5-azaspiro[3.5]nonan-2-yl)carbamoyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((4aS,8aS)-7-(2-(2,6-dioxopiperidin-3-yl)-1-oxoisoindolin-5-yl)decahydro-1,7-naphthyridine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((4aR,8aR)-6-(2-(2,6-dioxopiperidin-3-yl)-1-oxoisoindolin-5-yl)decahydro-2,6-naphthyridine-2-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((4aR,8aS)-7-(2-(2,6-dioxopiperidin-3-yl)-1-oxoisoindolin-5-yl)decahydro-2,7-naphthyridine-2-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-(2-(2,6-dioxopiperidin-3-yl)-1-oxoisoindolin-5-yl)piperazine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3aR,6aS)-5-(2-(2,6-dioxopiperidin-3-yl)-1-oxoisoindolin-5-yl)octahydropyrrolto[3,4-c]pyrrole-2-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((3aR,6aR)-5-(2-(2,6-dioxopiperidin-3-yl)-1-oxoisoindolin-5-yl)octahydropyrrolto[3,4-c]pyrrole-2-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-(4-(2-(2,6-dioxopiperidin-3-yl)-1-oxoisoindolin-5-yl)piperazin-1-yl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(2-(4-(2-(2,6-dioxopiperidin-3-yl)-1-oxoisoindolin-5-yl)piperazin-1-yl)-7-azaspiro[3.5]nonane-7-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-(4-((2-(2,6-dioxopiperidin-3-yl)-1-oxoisoindolin-5-yl)ethynyl)piperidine-1-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2R)-2-((2-(2,6-dioxopiperidin-3-yl)-1-oxoisoindolin-5-yl)ethynyl)morpholine-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((2S)-2-((2-(2,6-dioxopiperidin-3-yl)-1-oxoisoindolin-5-yl)ethynyl)morpholine-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((7S)-7-((2-(2,6-dioxopiperidin-3-yl)-1-oxoisoindolin-5-yl)ethynyl)-1,4-oxazepane-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((7R)-7-((2-(2,6-dioxopiperidin-3-yl)-1-oxoisoindolin-5-yl)ethynyl)-1,4-oxazepane-4-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((S)-1-((2-((S)-2,6-dioxopiperidin-3-yl)-1-oxoisoindolin-5-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((R)-1-((2-((S)-2,6-dioxopiperidin-3-yl)-1-oxoisoindolin-5-yl)ethynyl)-6-azaspiro[2.5]octane-6-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3R)-1-((2-(2,6-dioxopiperidin-3-yl)-1-oxoisoindolin-5-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1S,3S)-1-((2-(2,6-dioxopiperidin-3-yl)-1-oxoisoindolin-5-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3R)-1-((2-(2,6-dioxopiperidin-3-yl)-1-oxoisoindolin-5-yl)ethynyl)-5-azaspiro[2.5]octane-5-carbonyl)-2-methoxyphenyl)-2'-neopentylspiro[indoline-3,3'-pyrrolidine]-5'-carboxamide, (2'S,3S,4'S,5'R)-6-chloro-4'-(3-chloro-2-fluorophenyl)-N-(4-((1R,3S)-1-((2-(2,6-dioxopiperidin-3-yl)-1-oxoisoindolin-5-yl)ethynyl)-5-azaspiro[2.5]octane-5-carbonyl)-2-methoxyphenyl)-2'-neopentylspiro[indoline-3,3'-pyrrolidine]-5'-carboxamide, List 5:

(2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-(methoxy-d3)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-(trifluoromethoxy)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-isopropoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-1H-indazol-7-yl)-2-neopentyl-6'-(trifluoromethyl)-1',2'-dihydrospiro[pyrrolidine-3,3'-pyrrolo[3,2-c]pyridine]-5-carboxamide, 4-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-2-((S)-2,6-dioxopiperidin-3-yl)isoindoline-1,3-dione, ((S)-3-(4-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)-2,6-dioxopiperidin-1-yl-3-d)methyl dihydrogen phosphate, (S)-3-(4-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione-3-d, ((S)-3-(4-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)-2,6-dioxopiperidin-1-yl)methyl dihydrogen phosphate, ((3'S,4'S,5'R)-4'-(3-chloro-2-fluorophenyl)-5'-((R)-7-((S)-3-(3-(2-((S)-2,6-dioxopiperidin-3-yl)-1-oxoisoindolin-4-yl)prop-2-yn-1-yl)piperidine-1-carbonyl)-2-methyl-3,4-dihydro-2H-benzo[b][1,4]oxazine-4-carbonyl)-4,4-dimethyl-6"-(trifluoromethyl)-1",2"-dihydrodispiro[cyclohexane-1,2'-pyrrolidine-3',3-pyrrolo[3,2-c]pyridin]-1'-yl)methyl dihydrogen phosphate, ((3'S,4'S,5'R)-4'-(3-chloro-2-fluorophenyl)-5'-((R)-7-((S)-3-(3-(2-((S)-2,6-dioxopiperidin-3-yl)-1-oxoisoindolin-4-yl)prop-2-yn-1-yl)piperidine-1-carbonyl)-2-methyl-3,4-dihydro-2H-benzo[b][1,4]oxazine-4-carbonyl)-4,4-dimethyl-6"-(trifluoromethyl)dispiro[cyclohexane-1,2'-pyrrolidine-3',3-pyrrolo[3,2-c]pyridin]-1"(2"H)-yl)methyl dihydrogen phosphate, (3'S,4'S,5'R)-4'-(3-chloro-2-fluorophenyl)-N-(4-((S)-3-(3-(2-((R)-2,6-dioxopiperidin-3-yl)-1-oxoisoindolin-4-yl)

prop-2-yn-1-yl)piperidine-1-carbonyl)-2-methoxyphenyl)-6"-(trifluoromethyl)-1",2"-dihydrodispiro[cyclohexane-1,2'-pyrrolidine-3',3-pyrrolo[3,2-c]pyridine]-5'-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (R)-3-(4-(3-((S)-1-((R)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (R)-3-(4-(3-((S)-1-((S)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (R)-3-(4-(3-((S)-1-((R)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (R)-3-(4-(3-((S)-1-((S)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (R)-3-(4-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (R)-3-(4-(3-((S)-1-((S)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (R)-3-(4-(3-((S)-1-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (R)-3-(4-(3-((S)-1-((S)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-methyl-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-ethyl-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-methoxy-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-6'-cyclopropyl-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-isopropyl-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-(methoxy-d3)-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-2-neopentyl-6'-(trifluoromethoxy)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-methyl-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-ethyl-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-methoxy-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-6'-cyclopropyl-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-isopropyl-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-6'-(methoxy-d3)-2-neopentyl-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-3-(3-(2-((R)-2,6-dioxopiperidin-3-yl)-1-oxoisoindolin-4-yl)prop-2-yn-1-yl)piperidine-1-carbonyl)-2-methoxyphenyl)-2-neopentyl-6'-(trifluoromethoxy)-1',2'-dihydrospiro[pyrrolidine-3,3'-pyrrolo[3,2-c]pyridine]-5-carboxamide, (S)-3-(4-(3-((S)-1-(4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((R)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((R)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-3,3,6"-trimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-6"-ethyl-3,3-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-6"-methoxy-3,3-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-6"-cyclopropyl-3,3-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-6"-isopropyl-3,3-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-6"-(methoxy-d3)-3,3-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(4-(3-((S)-1-((S)-4-((1S,3'S,4'S,5'R)-4'-(3-chloro-2-fluorophenyl)-3,3-dimethyl-6"-(trifluoromethoxy)-1",2"-dihydrodispiro[cyclohexane-1,2'-pyrrolidine-3',3"-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-(methoxy-d3)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-(trifluoromethoxy)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-isopropoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-1H-indazol-7-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-2-(3-(2-((S)-2,6-dioxopiperidin-3-yl)-1-oxoisoindolin-4-yl)prop-2-yn-1-yl)morpholine-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((R)-2-(3-(2-((S)-2,6-dioxopiperidin-3-yl)-1-oxoisoindolin-4-yl)prop-2-yn-1-yl)morpholine-4-carbonyl)-2-methoxyphenyl)-2-neopentyl-6'-(trifluoromethyl)-1,2'-dihydrospiro[pyrrolidine-3,3'-pyrrolo[3,2-c]pyridine]-5-carboxamide, List 6:

(2S,3S,4S,5R)-4-(3-chloro-2-fluorophenyl)-N-(4-(((S)-1-((2-((S)-2,6-dioxopiperidin-3-yl)-1-oxoisoindolin-4-yl)ethynyl)-6-azaspiro[2.5]octan-6-yl)sulfonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(3-((S)-1-((2-((S)-2,6-dioxopiperidin-3-yl)-1-oxoisoindolin-4-yl)ethynyl)-6-azaspiro[2.5]octane-6-carbonyl)bicyclo[1.1.1]

pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1S,4R)-4-((S)-1-((2-((S)-2,6-dioxopiperidin-3-yl)-1-oxoisoindolin-4-yl)ethynyl)-6-azaspiro[2.5]octane-6-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-((S)-1-((2-((S)-2,6-dioxopiperidin-3-yl)-1-oxoisoindolin-4-yl)ethynyl)-6-azaspiro[2.5]octane-6-carbonyl)tetrahydro-2H-pyran-3-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(trifluoromethoxy)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-isopropoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(2-hydroxypropan-2-yl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)—N-(2-(2-aminopropan-2-yl)-4-((S)-1-((2-((S)-2,6-dioxopiperidin-3-yl)-1-oxoisoindolin-4-yl)ethynyl)-6-azaspiro[2.5]octane-6-carbonyl)phenyl)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(2-(2-cyanopropan-2-yl)-4-((S)-1-((2-((S)-2,6-dioxopiperidin-3-yl)-1-oxoisoindolin-4-yl)ethynyl)-6-azaspiro[2.5]octane-6-carbonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(methylsulfonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-((trifluoromethyl)sulfonyl)phenyl)-2-neopentyl-6'-(trifluoromethyl)-1',2'-dihydrospiro[pyrrolidine-3,3'-pyrrolo[3,2-c]pyridine]-5-carboxamide, (3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-1'-ethyl-6"-(trifluoromethyl)-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-1'-ethyl-4,4-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-1'-ethyl-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-6"-(trifluoromethyl)-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(trifluoromethoxy)phenyl)-2-neopentyl-6'-(trifluoromethyl)-1',2'-dihydrosproo[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-isopropoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)phenyl)-2-neopentyl-6'-(trifluoromethyl)-1',2'-dihydrospiro[pyrrolidine-3,3'-pyrrolo[3,2-c]pyri dine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(2-hydroxypropan-2-yl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)—N-(2-(2-aminopropan-2-yl)-4-((S)-1-((2-((S)-2,6-dioxopiperidin-3-yl)-1-oxoisoindolin-4-yl)ethynyl)-6-azaspiro[2.5]octane-6-carbonyl)phenyl)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(2-(2-cyanopropan-2-yl)-4-((S)-1-((2-((S)-2,6-dioxopiperidin-3-yl)-1-oxoisoindolin-4-yl)ethynyl)-6-azaspiro[2.5]octane-6-carbonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(methylsulfonyl)phenyl)-2-neopentyl-6'-(trifluoromethyl)-1',2'-dihydrospiro[pyrrolidine-3,3'-pyrrolo[3,2-c]pyridine]-5-carboxamide, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-6"-ethyl-4,4-dimethyl-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-6"-methoxy-4,4-dimethyl-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-4,4-dimethyl-6"-(trifluoromethoxy)-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-4,4,6"-trimethyl-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-6"-cyclopropyl-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-4,4-dimethyl-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-6"-isopropyl-4,4-dimethyl-1",2"-dihydrodispiro[cyclohexane-1,2'-pyrrolidine-3',3-pyrrolo[3,2-c]pyridine]-5'-carboxamide, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-6"-(methoxy-d3)-4,4-dimethyl-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)phenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(2-hydroxypropan-2-yl)phenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)—N-(2-(2-aminopropan-2-yl)-4-((S)-1-((2-((S)-2,6-dioxopiperidin-3-yl)-1-oxoisoindolin-4-yl)ethynyl)-6-azaspiro[2.5]octane-6-carbonyl)phenyl)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(2-(2-cyanopropan-2-yl)-4-((S)-1-((2-((S)-2,6-dioxopiperidin-3-yl)-1-oxoisoindolin-4-yl)ethynyl)-6-azaspiro[2.5]octane-6-carbonyl)phenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(methylsulfonyl)phenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(trifluoromethoxy)phenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-isopropoxyphenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-(trifluoromethyl)phenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(2-cyano-4-((S)-1-((2-((S)-2,6-dioxopiperidin-3-yl)-1-oxoisoindolin-4-yl)ethynyl)-6-azaspiro[2.5]octane-6-carbonyl)phenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methylphenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-isopropylphenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (1S,3'S,4'S,5'R)-4'-(3-chloro-2-fluorophenyl)-N-((2S,11a'R)-2-((2-((S)-2,6-dioxopiperidin-3-yl)-1-oxoisoindolin-4-yl)ethynyl)-6'-oxo-1',3',4',6',11',11a'-hexahydrospiro[cyclopropane-1,2'-pyrido[1,2-b]isoquinolin]-9'-yl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (2S,3S,4S,5R)-4-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (S)-3-(4-(((R)-6-(4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((S)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-6"-(trifluoromethyl)-1",2"-dihydrodispiro[cyclohexane-1,2'-pyrrolidine-3',3-pyrrolo[3,2-c]pyridine]-5'-carboxamide, (S)-3-(4-(((R)-6-(4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((S)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carboxamide, (S)-3-(4-(((R)-6-(4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((S)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (1S,3'S,4'S,5'R)-4'-(3-chloro-2-fluorophenyl)-N-(4-((R)-1-((2-((S)-2,6-dioxopiperidin-3-yl)-1-oxoisoindolin-4-yl)ethynyl)-6-azaspiro[2.5]octane-6-carbonyl)-2-methoxyphenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (S)-3-(4-(((R)-6-(4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((S)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (S)-3-(4-(((S)-6-(4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((R)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((S)-4-((2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-6"-(trifluoromethyl)-1",2"-dihydrodispiro[cyclohexane-1,2'-pyrrolidine-3',3-pyrrolo[3,2-c]pyridine]-5'-carboxamide, (S)-3-(4-(((S)-6-(4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((R)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((S)-4-((3'S,4'S,5'R)-4'-(3-chloro-2-fluorophenyl)-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carboxamide, (S)-3-(4-(((S)-6-(4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((S)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (1S,3'S,4'S,5'R)-4'-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carboxamide, (S)-3-(4-(((S)-6-(4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((S)-6-((S)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-(((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazin-7-yl)sulfonyl)-6-azaspiro[2.5]octan-1-yl)ethynyl)-1-oxoisoindolin-2-yl)piperidine-2,6-dione, (S)-3-(4-(((S)-6-(((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazin-7-yl)sulfonyl)-6-azaspiro[2.5]octan-1-yl)ethynyl)-1-oxoisoindolin-2-yl)piperidine-2,6-dione, 4-(((R)-6-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-2-((S)-2,6-dioxopiperidin-3-yl)isoindoline-1,3-dione, 4-(((R)-6-(((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazin-7-yl)sulfonyl)-6-azaspiro[2.5]octan-1-yl)ethynyl)-2-((S)-2,6-dioxopiperidin-3-yl)isoindoline-1,3-dione, 4-(((S)-6-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-2-((S)-2,6-dioxopiperidin-3-yl)isoindoline-1,3-dione, 4-(((S)-6-(((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazin-7-yl)sulfonyl)-6-azaspiro[2.5]octan-1-yl)ethynyl)-2-((S)-2,6-dioxopiperidin-3-yl)isoindoline-1,3-dione, (S)-3-(4-(((R)-6-((R)-4-((3'S,4'S,5'R)-4'-(3-chloro-2-fluorophenyl)-4,4,6"-trimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-6"-ethyl-4,4-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-6"-methoxy-4,4-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-6"-cyclopropyl-4,4-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-6"-isopropyl-4,4-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-6"-(methoxy-d3)-4,4-dimethyl-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, (S)-3-(4-(((R)-6-((R)-4-((3'S,4'S,5'R)-4'-(3-chloro-2-fluorophenyl)-4,4-dimethyl-6"-(trifluoromethoxy)-1",2"-dihydrodispiro[cyclohexane-1,2'-pyrrolidine-3',3-pyrrolo[3,2- c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, ((S)-3-(4-(((R)-6-(((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazin-7-yl)sulfonyl)-6-azaspiro[2.5]octan-1-yl)ethynyl)-1-oxoisoindolin-2-yl)-2,6-dioxopiperidin-1-yl)methyl dihydrogen phosphate, ((S)-3-(4-(((R)-6-(((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazin-7-yl)sulfonyl)-6-azaspiro[2.5]octan-1-yl)ethynyl)-1-oxoisoindolin-2-yl)-2,6-dioxopiperidin-1-yl)methyl methyl(3-((phosphonooxy)methyl)pyridin-2-yl)carbamate, (2S,3S,4S,5R)-4-(3-chloro-2-fluorophenyl)-N-(3-((1S)-1-((2-(2,6-dioxopiperidin-3-yl)-1-oxoisoindolin-4-yl)ethynyl)-6-azaspiro[2.5]octane-6-carbonyl)bicyclo[1.1.1]pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1S,4R)-4-((1S)-1-((2-(2,6-dioxopiperidin-3-yl)-1-oxoisoindolin-4-yl)ethynyl)-6-azaspiro[2.5]octane-6-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-((1S)-1-((2-(2,6-dioxopiperidin-3-yl)-1-oxoisoindolin-4-yl)ethynyl)-6-azaspiro[2.5]octane-6-carbonyl)tetrahydro-2H-pyran-3-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)-2-(trifluoromethoxy)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)-2-isopropoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)-2-(2-hydroxypropan-2-yl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)—N-(2-(2-aminopropan-2-yl)-4-((1S)-1-((2-(2,6-dioxopiperidin-3-yl)-1-oxoisoindolin-4-yl)ethynyl)-6-azaspiro[2.5]octane-6-carbonyl)phenyl)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(2-(2-cyanopropan-2-yl)-4-((1S)-1-((2-(2,6-dioxopiperidin-3-yl)-1-oxoisoindolin-4-yl)ethynyl)-6-azaspiro[2.5]octane-6-carbonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)-2-(methylsulfonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)-2-((trifluoromethyl)sulfonyl)phenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, List 7

(2S,3S,4S,5R)-4-(3-chloro-2-fluorophenyl)-N-(4-((R)-7-((2-((S)-2,6-dioxopiperidin-3-yl)-1-oxoisoindolin-4-yl)ethynyl)-1,4-oxazepane-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-7-((2-((S)-2,6-dioxopiperidin-3-yl)-1-oxoisoindolin-4-yl)ethynyl)-1,4-oxazepane-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((7R)-7-((2-(2,6-dioxopiperidin-3-yl)-1-oxoisoindolin-4-yl)ethynyl)-1,4-oxazepane-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((7S)-7-((2-(2,6-dioxopiperidin-3-yl)-1-oxoisoindolin-4-yl)ethynyl)-1,4-oxazepane-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, List 8

(2S,3S,4S,5R)-4-(3-chloro-2-fluorophenyl)-N-(4-((1S,3S)-1-((2-(2,6-dioxopiperidin-3-yl)-1-oxoisoindolin-4-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3R)-1-((2-(2,6-dioxopiperidin-3-yl)-1-oxoisoindolin-4-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3S)-1-((2-(2,6-dioxopiperidin-3-yl)-1-oxoisoindolin-4-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3R)-1-((2-(2,6-dioxopiperidin-3-yl)-1-oxoisoindolin-4-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3S,4R)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3R,4R)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3S,4R)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3R,4R)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3S,4S)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3R,4S)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3S,4S)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3R,4S)-1-((2-(2,6-dioxopiperidin-3-yl)-1-oxoisoindolin-4-yl)ethynyl)-4-methyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3S)-1-((2-(2,6-dioxopiperidin-3-yl)-1-oxoisoindolin-4-yl)ethynyl)-6,6-dimethyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3R)-1-((2-(2,6-dioxopiperidin-3-yl)-1-oxoisoindolin-4-yl)ethynyl)-6,6-dimethyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3S)-1-((2-(2,6-dioxopiperidin-3-yl)-1-oxoisoindolin-4-yl)ethynyl)-6,6-dimethyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3R)-1-((2-(2,6-dioxopiperidin-3-yl)-1-oxoisoindolin-4-yl)ethynyl)-6,6-dimethyl-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(3-((1S,3S)-1-((2-(2,6-dioxopiperidin-3-yl)-1-oxoisoindolin-4-yl)ethynyl)-5-azaspiro[2.5]octane-5-carbonyl)bicyclo[1.1.1]pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(3-((1S,3R)-1-((2-(2,6-dioxopiperidin-3-yl)-1-oxoisoindolin-4-yl)ethynyl)-5-azaspiro[2.5]octane-5-carbonyl)bicyclo[1.1.1]pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(3-((1R,3S)-1-((2-(2,6-dioxopiperidin-3-yl)-1-oxoisoindolin-4-yl)ethynyl)-5-azaspiro[2.5]octane-5-carbonyl)bicyclo[1.1.1]pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(3-((1R,3R)-1-((2-(2,6-dioxopiperidin-3-yl)-1-oxoisoindolin-4-yl)ethynyl)-5-azaspiro[2.5]octane-5-carbonyl)bicyclo[1.1.1]pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3S)-1-((2-(2,6-dioxopiperidin-3-yl)-1-oxoisoindolin-4-yl)ethynyl)-5-azaspiro[2.5]octane-5-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3R)-1-((2-(2,6-dioxopiperidin-3-yl)-1-oxoisoindolin-4-yl)ethynyl)-5-azaspiro[2.5]octane-5-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3S)-1-((2-(2,6-dioxopiperidin-3-yl)-1-oxoisoindolin-4-yl)ethynyl)-5-azaspiro[2.5]octane-5-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3R)-1-((2-(2,6-dioxopiperidin-3-yl)-1-oxoisoindolin-4-yl)ethynyl)-5-azaspiro[2.5]octane-5-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1S,4R)-4-((1S,3S)-1-((2-(2,6-dioxopiperidin-3-yl)-1-oxoisoindolin-4-yl)ethynyl)-5-azaspiro[2.5]octane-5-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1R,4R)-4-((1S,3R)-1-((2-(2,6-dioxopiperidin-3-yl)-1-oxoisoindolin-4-yl)ethynyl)-5-azaspiro[2.5]octane-5-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1S,4R)-4-((1R,3S)-1-((2-(2,6-dioxopiperidin-3-yl)-1-oxoisoindolin-4-yl)ethynyl)-5-azaspiro[2.5]octane-5-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1R,4R)-4-((1R,3R)-1-((2-(2,6-dioxopiperidin-3-yl)-1-oxoisoindolin-4-yl)ethynyl)-5-azaspiro[2.5]octane-5-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-((1S,3S)-1-((2-(2,6-dioxopiperidin-3-yl)-1-oxoisoindolin-4-yl)ethynyl)-5-azaspiro[2.5]octane-5-carbonyl)tetrahydro-2H-pyran-3-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-((1S,3R)-1-((2-(2,6-dioxopiperidin-3-yl)-1-oxoisoindolin-4-yl)ethynyl)-5-azaspiro[2.5]octane-5-carbonyl)tetrahydro-2H-pyran-3-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-((1R,3S)-1-((2-(2,6-dioxopiperidin-3-yl)-1-oxoisoindolin-4-yl)ethynyl)-5-azaspiro[2.5]octane-5-carbonyl)tetrahydro-2H-pyran-3-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-((1R,3R)-1-((2-(2,6-dioxopiperidin-3-yl)-1-oxoisoindolin-4-yl)ethynyl)-5-azaspiro[2.5]octane-5-carbonyl)tetrahydro-2H-pyran-3-yl)-2-neopentyl-6'-(trifluoromethyl)-1',2'-dihydrospiro[pyrrolidine-3,3'-pyrrolo[3,2-c]pyridine]-5-carboxamide, List 9

(S)-3-(5-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-1-oxoisoindolin-2-yl)piperidine-2,6-dione, (S)-3-(5-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-6-fluoro-1-oxoisoindolin-2-yl)piperidine-2,6-dione, 5-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3"-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-2-((S)-2,6-dioxopiperidin-3-yl)isoindoline-1,3-dione, 5-(3-((S)-1-((R)-4-((3'S,4'S,5'R)-4'-(3-chloro-2-fluorophenyl)-4,4-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)piperidin-3-yl)prop-1-yn-1-yl)-2-((S)-2,6-dioxopiperidin-3-yl)-6-fluoroisoindoline-1,3-dione, (S)-3-(5-(((R)-6-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-1-oxoisoindolin-2-yl)piperidine-2,6-dione, 5-(((R)-6-((R)-4-((1S,3'S,4'S,5'R)-4'-(3-chloro-2-fluorophenyl)-3,3-dimethyl-6"-(trifluoromethyl)-1",2"-dihydrodispiro[cyclohexane-1,2'-pyrrolidine-3',3-pyrrolo[3,2-c]pyridine]-5'-carbonyl)-2-methyl-3,4-dihydro-2H-benzo[b][1,4]oxazine-7-carbonyl)-6-azaspiro[2.5]octan-1-yl)ethynyl)-2-((S)-2,6-dioxopiperidin-3-yl)isoindoline-1,3-dione, (2S,3S,4S,5R)-4-(3-chloro-2-fluorophenyl)-N-(4-(4-(2-(2,6-dioxopiperidin-3-yl)-1-oxoisoindolin-5-yl)piperazine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3R)-3-(2-(2,6-dioxopiperidin-3-yl)-1-oxoisoindolin-5-yl)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(2-(2,6-dioxopiperidin-3-yl)-1-oxoisoindolin-5-yl)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(7-(2-(2,6-dioxopiperidin-3-yl)-1-oxoisoindolin-5-yl)-2,7-diazaspiro[3.5]nonane-2-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(8-(2-(2,6-dioxopiperidin-3-yl)-1-oxoisoindolin-5-yl)-2,8-diazaspiro[4.5]decane-2-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(9-(2-(2,6-dioxopiperidin-3-yl)-1-oxoisoindolin-5-yl)-3,9-diazaspiro[5.5]undecane-3-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-(4-(2-(2,6-dioxopiperidin-3-yl)-1-oxoisoindolin-5-yl)piperazin-1-yl)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(2-(4-(2-(2,6-dioxopiperidin-3-yl)-1-oxoisoindolin-5-yl)piperazin-1-yl)-7-azaspiro[3.5]nonane-7-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aR,6aR)-5-(2-(2,6-dioxopiperidin-3-yl)-1-oxoisoindolin-5-yl)octahydropyrrolto[3,4-c]pyrrole-2-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aS,6aS)-5-(2-(2,6-dioxopiperidin-3-yl)-1-oxoisoindolin-5-yl)octahydropyrrolto[3,4-c]pyrrole-2-carbonyl)-2- methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aR,6aS)-5-(2-(2,6-dioxopiperidin-3-yl)-1-oxoisoindolin-5-yl)octahydropyrrolto[3,4-c]pyrrole-2-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aR,6aS)-5-(2-(2,6-dioxopiperidin-3-yl)-1-oxoisoindolin-5-yl)octahydropyrrolto[3,4-c]pyrrole-2-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-((2-(2,6-dioxopiperidin-3-yl)-1-oxoisoindolin-5-yl)methyl)piperazine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-((2-(2,6-dioxopiperidin-3-yl)-1-oxoisoindolin-5-yl)amino)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3R)-3-((2-(2,6-dioxopiperidin-3-yl)-1-oxoisoindolin-5-yl)amino)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-((4-(2-(2,6-dioxopiperidin-3-yl)-1-oxoisoindolin-5-yl)piperazin-1-yl)methyl)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(3-((2-(2,6-dioxopiperidin-3-yl)-1-oxoisoindolin-5-yl)ethynyl)azetidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-((2-(2,6-dioxopiperidin-3-yl)-1-oxoisoindolin-5-yl)ethynyl)piperidine-1-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(9-((2-(2,6-dioxopiperidin-3-yl)-1-oxoisoindolin-5-yl)ethynyl)-3-azaspiro[5.5]undecane-3-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(2-((2-(2,6-dioxopiperidin-3-yl)-1-oxoisoindolin-5-yl)ethynyl)-7-azaspiro[3.5]nonane-7-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((2R)-2-((2-(2,6-dioxopiperidin-3-yl)-1-oxoisoindolin-5-yl)ethynyl)morpholine-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((2S)-2-((2-(2,6-dioxopiperidin-3-yl)-1-oxoisoindolin-5-yl)ethynyl)morpholine-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((7S)-7-((2-(2,6-dioxopiperidin-3-yl)-1-oxoisoindolin-5-yl)ethynyl)-1,4-oxazepane-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((7R)-7-((2-(2,6-dioxopiperidin-3-yl)-1-oxoisoindolin-5-yl)ethynyl)-1,4-oxazepane-4-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-5-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R)-1-((2-(2,6-dioxopiperidin-3-yl)-1-oxoisoindolin-5-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3S)-1-((2-(2,6-dioxopiperidin-3-yl)-1-oxoisoindolin-5-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3S)-1-((2-(2,6-dioxopiperidin-3-yl)-1-oxoisoindolin-5-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S,3R)-1-((2-(2,6-dioxopiperidin-3-yl)-1-oxoisoindolin-5-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1R,3R)-1-((2-(2,6-dioxopiperidin-3-yl)-1-oxoisoindolin-5-yl)ethynyl)-5-azaspiro[2.5]octane-5-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1r,4R)-4-(4-(2-(2,6-dioxopiperidin-3-yl)-1-oxoisoindolin-5-yl)piperazine-1-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1r,4R)-4-(4-(4-(2-(2,6-dioxopiperidin-3-yl)-1-oxoisoindolin-5-yl)piperazin-1-yl)piperidine-1-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1r,4R)-4-(2-(4-(2-(2,6-dioxopiperidin-3-yl)-1-oxoisoindolin-5-yl)piperazin-1-yl)-7-azaspiro[3.5]nonane-7-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1r,4R)-4-(4-((2-(2,6-dioxopiperidin-3-yl)-1-oxoisoindolin-5-yl)ethynyl)piperidine-1-carbonyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-(4-((2-(2,6-dioxopiperidin-3-yl)-1-oxoisoindolin-5-yl)ethynyl)piperidine-1-carbonyl)tetrahydro-2H-pyran-3- yl)-2-neopentyl-6'-(trifluoromethyl)-1',2'-dihydrospiro [pyrrolidine-3,3'-pyrrolo[3,2-c]pyridine]-5-carboxamide, (2S,3S,4S,5R)-4-(3-chloro-2-fluorophenyl)-N-(4-(4-((2-(2,6-dioxopiperidin-3-yl)-1-oxoisoindolin-5-yl)ethynyl)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(3-(4-((2-(2,6-dioxopiperidin-3-yl)-1-oxoisoindolin-5-yl)ethynyl)piperidine-1-carbonyl)bicyclo[1.1.1]pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((1r,4R)-4-((4-((2-(2,6-dioxopiperidin-3-yl)-1-oxoisoindolin-5-yl)ethynyl)piperidin-1-yl)methyl)cyclohexyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((4-((2-(2,6-dioxopiperidin-3-yl)-1-oxoisoindolin-5-yl)ethynyl)piperidin-1-yl)methyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(3-((4-((2-(2,6-dioxopiperidin-3-yl)-1-oxoisoindolin-5-yl)ethynyl)piperidin-1-yl)methyl)bicyclo[1.1.1]pentan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-((3R,6S)-6-((4-((2-(2,6-dioxopiperidin-3-yl)-1-oxoisoindolin-5-yl)ethynyl)piperidin-1-yl)methyl)tetrahydro-2H-pyran-3-yl)-2-neopentyl-6'-(trifluoromethyl)-1',2'-dihydrospiro [pyrrolidine-3,3'-pyrrolo[3,2-c]pyridine]-5-carboxamide, (2S,3S,4S,5R)-4-(3-chloro-2-fluorophenyl)-N-(4-((S)-2-(3-(2-((S)-2,6-dioxopiperidin-3-yl)-1-oxoisoindolin-5-yl)prop-2-yn-1-yl)morpholine-4-carbonyl)-2-methoxyphenyl)-2-neopentyl-6'-(trifluoromethyl)-1',2'-dihydrospiro [pyrrolidine-3,3'-pyrrolo[3,2-c]pyridine]-5-carboxamide, (2S,3S,4S,5R)-4-(3-chloro-2-fluorophenyl)-N-(4-((R)-2-(3-(2-((S)-2,6-dioxopiperidin-3-yl)-1-oxoisoindolin-5-yl)prop-2-yn-1-yl)morpholine-4-carbonyl)-2-methoxyphenyl)-2-neopentyl-6'-(trifluoromethyl)-1',2'-dihydrospiro [pyrrolidine-3,3'-pyrrolo[3,2-c]pyridine]-5-carboxamide List 10

(2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-N-methyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-N-isopropyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-cyclopropyl-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-1-methyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-N,1-dimethyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-N-isopropyl-1-methyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-cyclopropyl-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-1-methyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-1-ethyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-1-ethyl-N-methyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-1-ethyl-N-isopropyl-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-cyclopropyl-N-(4-((1S)-1-((2-(2,6-dioxopiperidin-3-yl)-1-oxoisoindolin-4-yl)ethynyl)-6-azaspiro[2.5]octane-6-carbonyl)bicyclo[2.2.2]octan-1-yl)-1-ethyl-2-neopentyl-6'-(trifluoromethyl)-1',2'-dihydrospiro[pyrrolidine-3,3'-pyrrolo[3,2-c]pyridine]-5-carboxamide, List 11

(2S,3S,4S,5R)-4-(3-chloro-2-fluorophenyl)-N-(4-(4-(2-(2,6-dioxopiperidin-3-yl)-1-oxoisoindolin-5-yl)piperazine-1-carbonyl)bicyclo[2.2.2]octan-1-yl)-2-neopentyl-6'-(trifluoromethyl)-1',2'-dihydrospiro[pyrrolidine-3,3'-pyrrolo [3,2-c]pyridine]-5-carboxamide, (2S,3S,4S,5R)-4-(3-chloro-2-fluorophenyl)-N-(4-(3-(2-(2,6-dioxopiperidin-3-yl)-1-oxoisoindolin-5-yl)azetidine-1-carbonyl)bicyclo[2.2.2]octan-1-yl)-2-neopentyl-6'-(trifluoromethyl)-1',2'-dihydrospiro[pyrrolidine-3,3'-pyrrolo [3,2-c]pyridine]-5-carboxamide, (2S,3S,4S,5R)-4-(3-chloro-2-fluorophenyl)-N-(4-((3S)-3-(2-(2,6-dioxopiperidin-3-yl)-1-oxoisoindolin-5-yl)pyrrolidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3R)-3-(2-(2,6-dioxopiperidin-3-yl)-1-oxoisoindolin-5-yl)pyrrolidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3R)-3-(2-(2,6-dioxopiperidin-3-yl)-1-oxoisoindolin-5-yl)piperidine-1-carbonyl)bicyclo[2.2.2]octan-1-yl)-2-neopentyl- 6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-(2-(2,6-dioxopiperidin-3-yl)-1-oxoisoindolin-5-yl)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-(2-(2,6-dioxopiperidin-3-yl)-1-oxoisoindolin-5-yl)-1,4-diazepane-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(2-(2-(2,6-dioxopiperidin-3-yl)-1-oxoisoindolin-5-yl)-2,7-diazaspiro[3.5]nonane-7-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(7-(2-(2,6-dioxopiperidin-3-yl)-1-oxoisoindolin-5-yl)-2,7-diazaspiro[3.5]nonane-2-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(8-(2-(2,6-dioxopiperidin-3-yl)-1-oxoisoindolin-5-yl)-2,8-diazaspiro[4.5]decane-2-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(9-(2-(2,6-dioxopiperidin-3-yl)-1-oxoisoindolin-5-yl)-3,9-diazaspiro[5.5]undecane-3-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-((2-(2,6-dioxopiperidin-3-yl)-1-oxoisoindolin-5-yl)amino)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3S)-3-((2-(2,6-dioxopiperidin-3-yl)-1-oxoisoindolin-5-yl)oxy)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3R)-3-((2-(2,6-dioxopiperidin-3-yl)-1-oxoisoindolin-5-yl)amino)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-(1-(2-(2,6-dioxopiperidin-3-yl)-1-oxoisoindolin-5-yl)piperidin-4-yl)piperazine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3R)-3-((2-(2,6-dioxopiperidin-3-yl)-1-oxoisoindolin-5-yl)oxy)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-(4-(2-(2,6-dioxopiperidin-3-yl)-1-oxoisoindolin-5-yl)piperazin-1-yl)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aR,6aR)-5-(2-(2,6-dioxopiperidin-3-yl)-1-oxoisoindolin-5-yl)octahydropyrrolo[3,4-c]pyrrole-2-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aR,6aS)-5-(2-(2,6-dioxopiperidin-3-yl)-1-oxoisoindolin-5-yl)octahydropyrrolo[3,4-c]pyrrole-2-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aS,6aS)-5-(2-(2,6-dioxopiperidin-3-yl)-1-oxoisoindolin-5-yl)octahydropyrrolo[3,4-c]pyrrole-2-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((3aR,6aS)-5-(2-(2,6-dioxopiperidin-3-yl)-1-oxoisoindolin-5-yl)octahydropyrrolo[3,4-c]pyrrole-2-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-((2-(2,6-dioxopiperidin-3-yl)-1-oxoisoindolin-5-yl)methyl)piperazine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-((4-(2-(2,6-dioxopiperidin-3-yl)-1-oxoisoindolin-5-yl)piperazin-1-yl)methyl)piperidine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(2-(4-(2-(2,6-dioxopiperidin-3-yl)-1-oxoisoindolin-5-yl)piperazin-1-yl)-7-azaspiro[3.5]nonane-7-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-(4-(7-(2-(2,6-dioxopiperidin-3-yl)-1-oxoisoindolin-5-yl)-7-azaspiro[3.5]nonan-2-yl)piperazine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide, List 12

(2S,3S,4S,5R)-4-(3-chloro-2-fluorophenyl)-N-(4-((1S)-1-((3-((2,6-dioxopiperidin-3-yl)amino)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((4-((2,6-dioxopiperidin-3-yl)amino)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((3-((2,6-dioxopiperidin-3-yl)oxy)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((4-((2,6-dioxopiperidin-3-yl)oxy)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((3-(2,6-dioxopiperidin-3-yl)phenyl)ethynyl)-6-azaspiro

[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((4-(2,6-dioxopiperidin-3-yl)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((3-(2,4-dioxotetrahydropyrimidin-1(2H)-yl)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((S)-1-((4-(2,4-dioxotetrahydropyrimidin-1(2H)-yl)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((4-((2,6-dioxopiperidin-3-yl)carbamoyl)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((3-((2,6-dioxopiperidin-3-yl)carbamoyl)phenyl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((3-(2,6-dioxopiperidin-3-yl)-1-methyl-2-oxo-2,3-dihydro-1H-benzo[d]imidazol-5-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((1-(2,6-dioxopiperidin-3-yl)-3-methyl-2-oxo-2,3-dihydro-1H-benzo[d]imidazol-5-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((3-(2,6-dioxopiperidin-3-yl)-1-methyl-1H-indazol-5-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((3-(2,6-dioxopiperidin-3-yl)-1-methyl-1H-indazol-6-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((1-(2,6-dioxopiperidin-3-yl)-2-methyl-3-oxo-2,3-dihydro-1H-indazol-6-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide, (2S,3S,4S,5R)-4-(3-chloro-2-fluorophenyl)-N-(4-((1S)-1-((1-(2,6-dioxopiperidin-3-yl)-2-methyl-3-oxo-2,3-dihydro-1H-indazol-5-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates.

Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Deuterium-enriched compounds: deuterium (D or $^{2}H$) is a stable, non-radioactive isotope of hydrogen and has an atomic weight of 2.0144. Hydrogen naturally occurs as a mixture of the isotopes $^{X}H$ (hydrogen or protium), D ($^{2}H$ or deuterium), and T ($^{3}H$ or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as ($C_{1-4}$) alkyl halides, e.g., methyl, ethyl, iso-propyl and tert-butyl chlorides, bromides and iodides; di-($C_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se).

Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Spiroalkyl refers to a compound comprising two saturated cyclic alkyl rings sharing only one common atom (also known as a spiro atom), with no heteroatom and no unsaturated bonds on any of the rings. In one embodiment, the spiroalkyl is bicyclic. In another embodiment, the spiroalikyl has more than two cycles. In certain embodiments, the spiroalkyl compound is a polyspiro compound connected by two or more spiroatoms making up three or more rings. In certain embodiments, one of the rings of the bicyclic spiroalkyl has 3, 4, 5, 6, 7, or 8 atoms, including the common spito atom. In one embodiment, the spiroalkyl is a 5 to 20 membered, 5 to 14 membered, 7 to 10 membered, or 5 to 10 membered polycyclic spiroalkyl group. Representative examples of spiroalkyl include, but are not limited to the following groups:

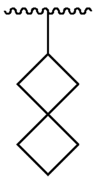
,
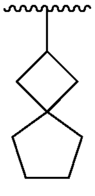
,
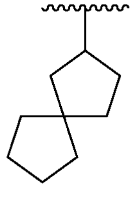
, and

-continued

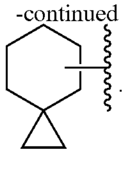

The term “fused cycloalkyl” refers to a fused ring which contains carbon atoms and is formed by two or more rings sharing two adjacent atoms. The term “4 to 10 membered fused cycloalkyl” refers to a fused ring which contains 4 to 10 ring carbon atoms and is formed by two or more rings sharing two adjacent atoms.

The term “bridged cycloalkyl” refers to a cyclic structure which contains carbon atoms and is formed by two rings sharing two atoms which are not adjacent to each other. The term 7 to 10 membered bridged cycloalkyl” refers to a cyclic structure which contains 7 to 12 carbon atoms and is formed by two rings sharing two atoms which are not adjacent to each other.

Spiroheterocyclyl or spiro-heterocyclic refers to a compound comprising two non-saturated rings sharing only one common atom (also known as a spiro atom), with at least one heteroatom on one of the two rings, such as a polycyclic heterocyclyl group with rings connected through one common carbon atom. The common atom can be carbon (C), silicon, or nitrogen (such as a positively charged quaternary nitrogen atom). The heteroatoms can comprise nitrogen, quaternary nitrogen, oxidized nitrogen (e.g., NO), oxygen, silicon, and sulfur, including sulfoxide and sulfone, and the remaining ring atoms are C. In addition, one or more of the rings may contain one or more double bonds. In one embodiment, the spiro heterocyclyl is bicyclic, with heteroatom(s) on either one or both cycles. In certain embodiments, one of the rings of the bicyclic spiro heterocyclyl has 3, 4, 5, 6, 7, or 8 atoms, including the common spito atom. In certain embodiments, the spiro heterocyclic compound is a polyspiro compound connected by two or more spiroatoms making up three or more rings. In one embodiment, the spiro heterocyclyl is a 5 to 20 membered, 5 to 14 membered, or 5 to 10 membered polycyclic heterocyclyl group. Representative examples of spiro heterocyclyl include, but are not limited to the following groups:

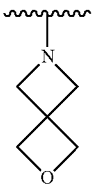
,
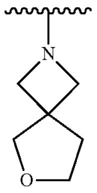
,
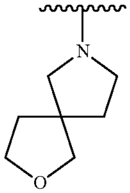
, and

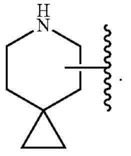

Fused heterocyclyl refers to a polycyclic heterocyclyl group, wherein each ring in the group shares an adjacent pair of atoms (such as carbon atoms) with another ring in the group, wherein one or more rings can contain one or more double bonds, and wherein said rings have one or more heteroatoms, which can be nitrogen, quaternary nitrogen, oxidized nitrogen (e.g., NO), oxygen, and sulfur, including sulfoxide and sulfone, and the remaining ring atoms are C. In certain embodiments, the fused heterocyclyl is bicyclic. In certain embodiments, the fused heterocyclyl contains more than two rings, at least two of which share an adjacent pair of atoms. In one embodiment, the fused heterocyclyl is a 5 to 20 membered, 5 to 16 membered, or 5 to 10 membered polycyclic heterocyclyl group. Representative examples of fused heterocyclyl include, but are not limited to the following groups:

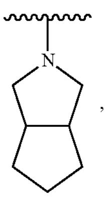
,
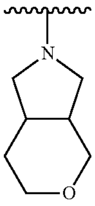
,
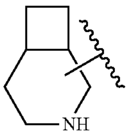
, and
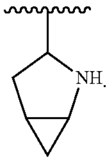

Bridged heterocyclyl refers to a compound having at least two rings sharing three or more common ring atoms, separating the two bridgehead atoms by a bridge containing at least one atom, wherein at least one ring atom is a heteroatom. The bridgehead atoms are the atoms from which three bonds radiate and where the rings meet. The rings of the bridged heterocyclyl can have one or more double bonds, and the ring heteroatom(s) can be nitrogen, quaternary nitrogen, oxidized nitrogen (e.g., NO), oxygen, and sulfur, including sulfoxide and sulfone as ring atoms, while the remaining ring atoms are C. In one embodiment, the bridged heterocyclyl is bicyclic. In one embodiment, the bridged heterocyclyl is a 5 to 20 membered, 5 to 16 membered, or 5 to 10 membered polycyclic heterocyclyl group. Representative examples of bridged heterocyclyl include, but are not limited to the following groups:

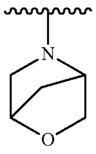
,
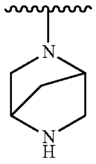
,
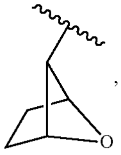
, and

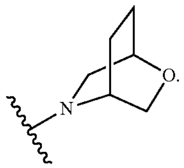

Alkyl, alkenyl, alkynyl, cycloalkyl, heterocycloalkyl, cycloalkenyl, heterocycloalkenyl, alkylamino, aryl, heteroaryl, spiroalkyl, fused cycloalkyl, bridged cycloalkyl, spiro heterocyclyl, fused heterocyclic, and bridged heterocyclyl, mentioned above include both substituted and unsubstituted moieties.

Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O═), thioxo (S═), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)$NR_aR_b$ where $R_a$ and $R_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH═O.

"Formimino" means the radical —HC═NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(═NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —$NO_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism).

Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), *Vinca* alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), antimicrotubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK (A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1 g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38 g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120 g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TA01, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F3171), ABL1(G250E), ABL1(H396P), ABL1 (M351T), ABL1(Q252H), ABL1(T3151), ABL1(Y253F), ALK (C1156Y), ALK(L1196M), ALK (F1174L), ALK (R1275Q), BRAF(V599E), BTK(E41K), CHK2(1157T), c-Kit(A829P), c-KIT(D816H), c-KIT(D816V), c-Kit (D820E), c-Kit(N822K), C-Kit (T6701), c-Kit(V559D), c-Kit(V559D/V654A), c-Kit(V559D/T6701), C-Kit (V560G), c-KIT(V654A), C-MET(D1228H), C-MET (D1228N), C-MET(F12001), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R, T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (12020T), LRRK2 (R1441C), p38a(T106M), PDGFRa(D842V), PDGFRa(T6741), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g.HSP90), poly-ADP (adenosine diphosphate)-ribose polymerase (PARP), hypoxia-inducible factors(HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), drug-antibody conjugate (e.g brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation.

Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, antimetabolites, topoisomerase inhibitors, anti-microtubule agents, kinase inhibitors, epigenetic agents, HSP90 inhibitors, PARP inhibitors, BCL-2 inhibitor, drug-antibody conjugate, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

In certain embodiments, the compounds of the invention are administered in combination with one or more anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate. Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates. The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

In certain embodiments, the compounds of the invention are administered in combination with one or more immunosuppressant agents.

In some embodiments, the immunosuppressant agent is glucocorticoid, methotrexate, cyclophosphamide, azathioprine, mercaptopurine, leflunomide, cyclosporine, tacrolimus, and mycophenolate mofetil, dactinomycin, anthracyclines, mitomycin C, bleomycin, or mithramycin, or fingolimod.

The invention further provides methods for the prevention or treatment of a neoplastic disease, autoimmune and/or inflammatory disease. In one embodiment, the invention relates to a method of treating a neoplastic disease, autoimmune and/or inflammatory disease in a subject in need of treatment comprising administering to said subject a therapeutically effective amount of a compound of the invention. In one embodiment, the invention further provides for the use of a compound of the invention in the manufacture of a medicament for halting or decreasing a neoplastic disease, autoimmune and/or inflammatory disease.

In one embodiment, the neoplastic disease is a B-cell malignancy includes but not limited to B-cell lymphoma, lymphoma (including Hodgkin's lymphoma and non-Hodgkin's lymphoma), hairy cell lymphoma, small lymphocytic lymphoma (SLL), mantle cell lymphoma (MCL), and diffuse large B-cell lymphoma (DLBCL), multiple myeloma, chronic and acute myelogenous leukemia and chronic and acute lymphocytic leukemia.

The autoimmune and/or inflammatory diseases that can be affected using compounds and compositions according to the invention include, but are not limited to allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barré syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

An approach to synthesize the intermediates

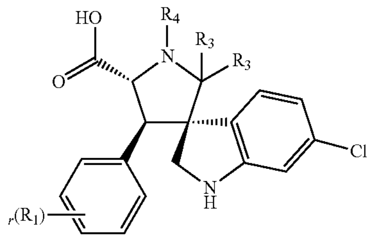

is described in Scheme A. $R_1$, $R_3$, $R_4$, and r, in general Scheme A is the same as those described in the Summary section above.

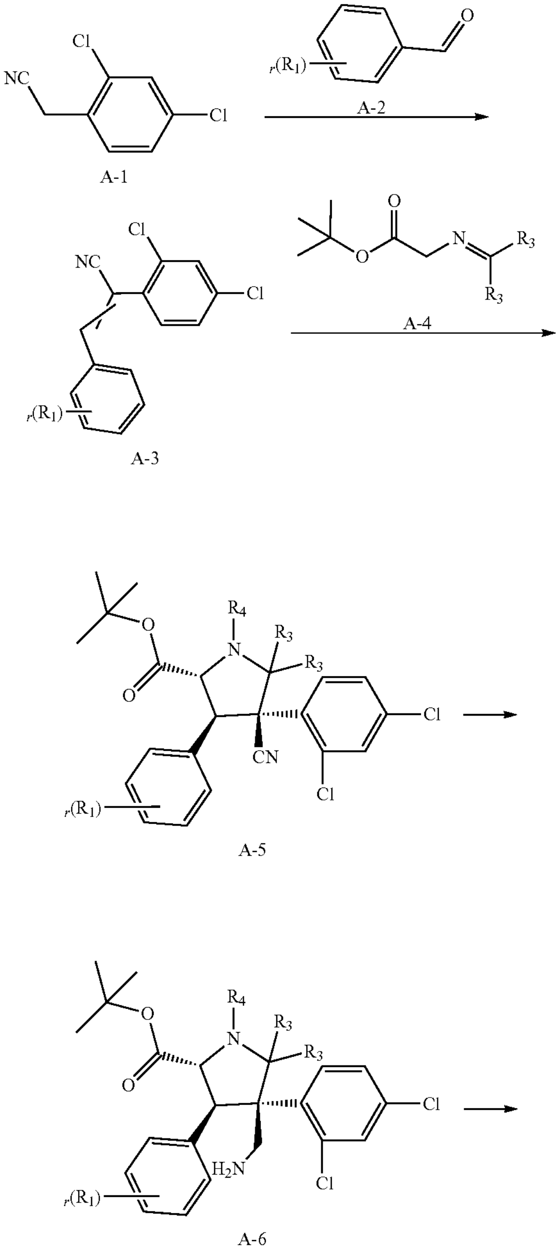

-continued

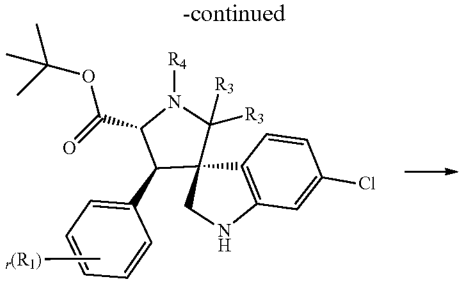

A-7

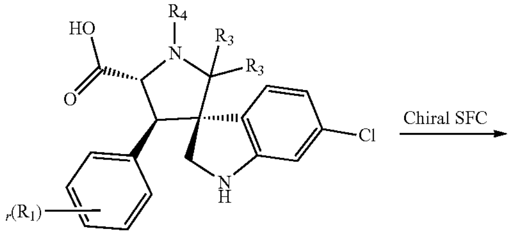

A-8

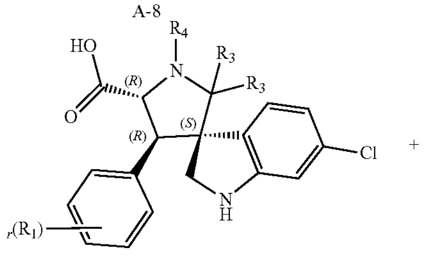

A-9

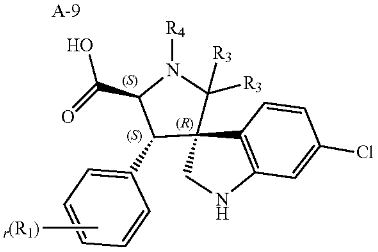

A-9A

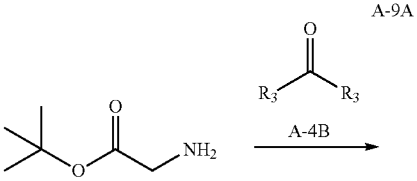

A-4A

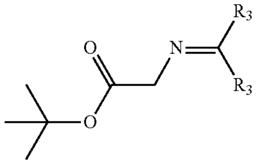

A-4

In Scheme A, the starting material A-1 can be prepared by conventional procedures using appropriate compounds and reagents. A-1 can react with A-2 to afford A-3, which can undergo an intermolecular [3+2]cyclization with A-4 derived from A-4A, to give A-5. After that, A-5 can be reduced to A-6, and then A-6 can go through an intramolecular coupling reaction to give A-7. A-7 can be transformed to A-8. Finally, A-9 can be obtained from A-8 by chiral separation.

Also, the target compounds can be synthesized by alternative methods but not limited to the above procedures.

An approach to synthesize the intermediates

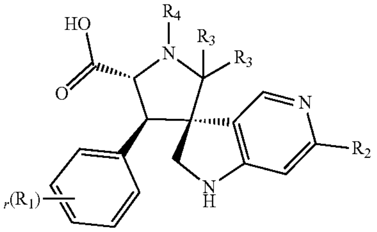

is described in Scheme B. $R_1$, $R_2$, $R_3$, $R_4$, and r, in general Scheme B is the same as those described in the Summary section above.

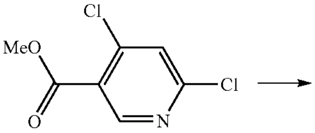

B-1

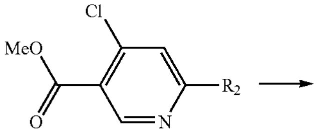

B-2

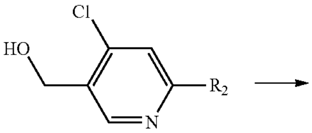

B-3

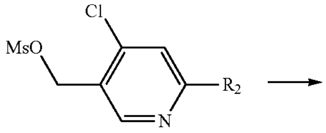

B-4

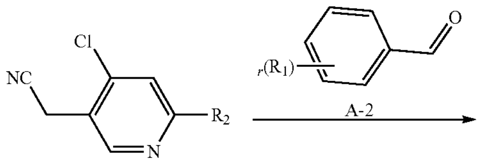

B-5

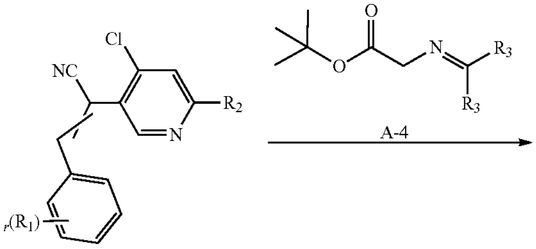

B-6

-continued

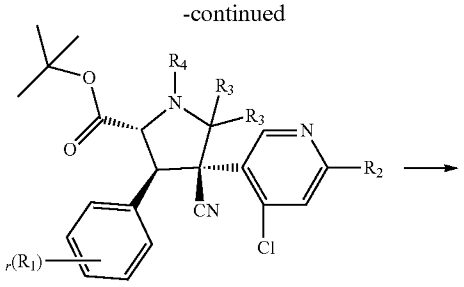

B-7

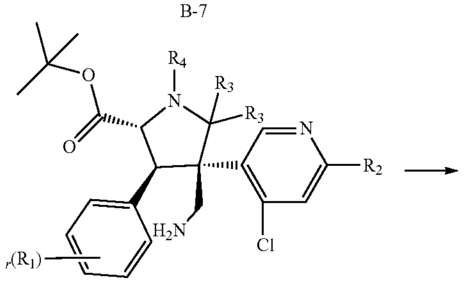

B-8

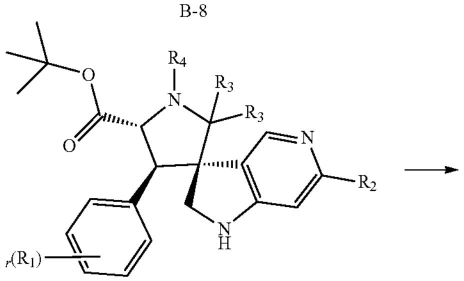

B-9

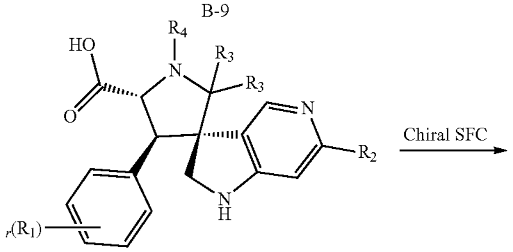

B-10

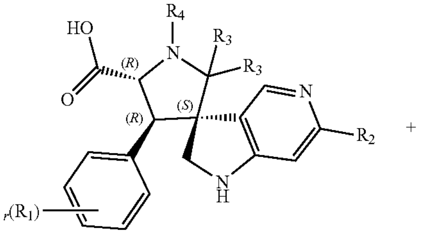

B-11

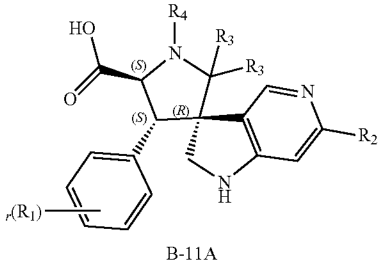

B-11A

In Scheme B, the starting material B-1 can be prepared by conventional procedures using appropriate compounds and reagents. The starting material B-1 is converted to B-2 by a coupling reaction, which can further be reduced to the alcohol intermediate B-3. After that, B-3 can go through a standard condition to yield B-4, which can subsequently be converted to B-5. Next, the cyanide B-5 can react with A-2 to afford B-6, which can under an intermolecular [3+2] cyclization with A-4 to give B-7. Next, B-7 is reduced to yield B-8, and the subsequent intramolecular coupling reaction to give B-9. B-9 can be hydrolyzed to B-10 under a suitable acid condition. Finally, B-11 can be obtained from B-10 by chiral separation.

Also, the target compounds can be synthesized by alternative methods but not limited to the above procedures.

The intermediate

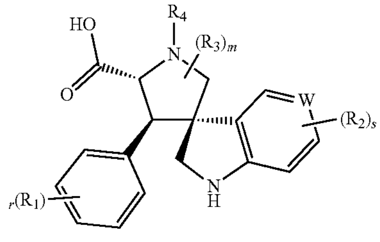

can be made by the method similar to Scheme A and B, by using different starting material and reagents, or by the standard organic reactions.

The intermediate

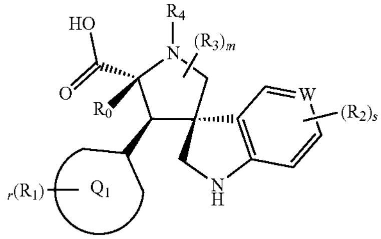

can be made by the method similar to Scheme A and B, by using different starting material and reagents, or by the standard organic reactions.

The intermediate

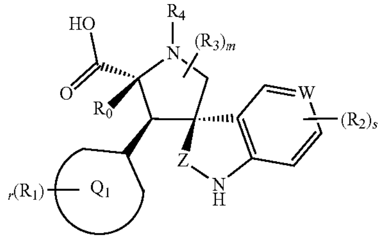

can be made by the method similar to Scheme A and B, by using different starting material and reagents, or by the standard organic reactions.

An approach to synthesize compounds of

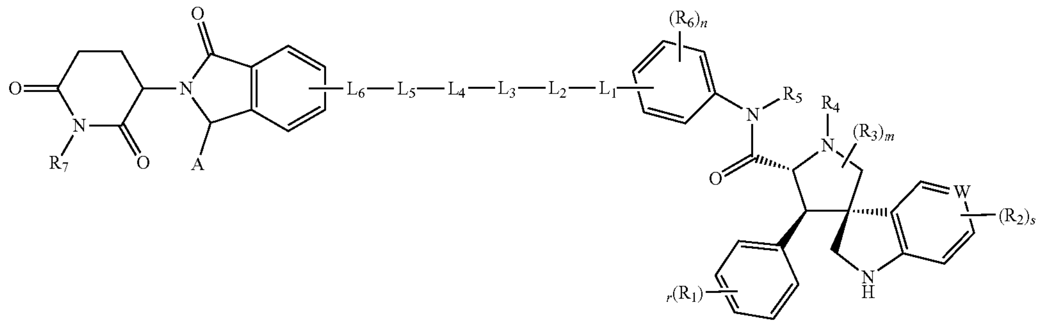

is described in Scheme 1. A, W, $R_1$, $R_2$, $R_3$, $R_4$, $R_5$, $R_6$, $R_7$, $L_1$, $L_2$, $L_3$, $L_4$, $L_5$, $L_6$, r, s, n, and m, in general Scheme 1 is the same as those described in the Summary section above.

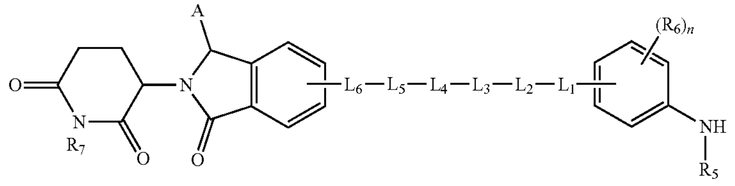

1-1

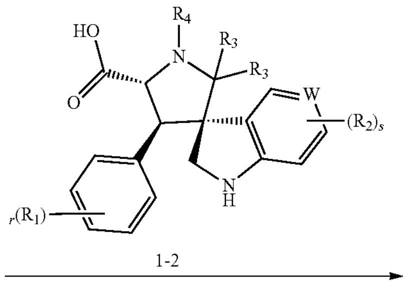

1-2

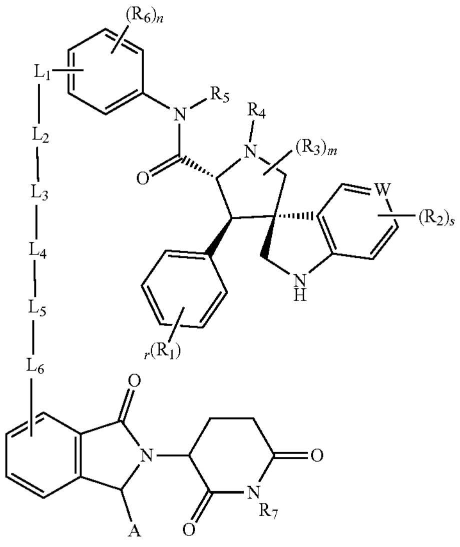

1-3

In Scheme 1, the starting material 1-1 can be prepared by standard organic reaction. The intermediate 1-2 can be prepared by the method similar to Scheme A and B, by using different starting material and reagents, or by the standard organic reactions. The amide coupling of 1-1 and 1-2 can afford the target compound 1-3.

The compounds

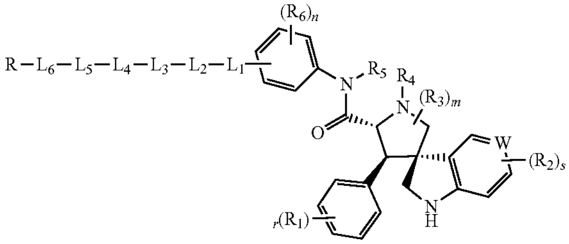

can be made by the method similar to Scheme 1, by using different starting material and reagents, or by the standard organic reactions.

The compounds

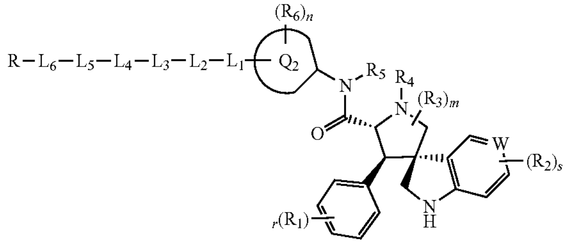

can be made by the method similar to Scheme 1, by using different starting material and reagents, or by the standard organic reactions.

The compounds

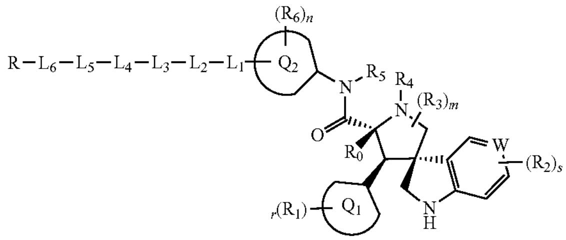

can be made by the method similar to Scheme 1, by using different starting material and reagents, or by the standard organic reactions.

The compounds

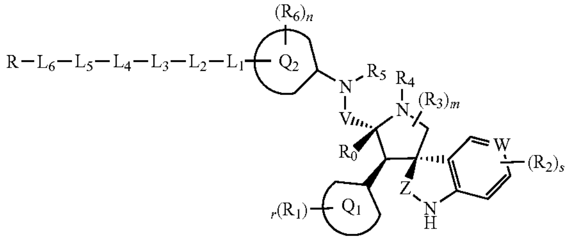

can be made by the method similar to Scheme 1, by using different starting material and reagents, or by the standard organic reactions.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1H$ spectra were obtained on XL400 (400 MHz) and are reported as ppm down field from $Me_4Si$ with number of protons, multiplicities, and coupling constants in Hertz indicated parenthetically. Where HPLC data are presented, analyses were performed using an Agilent 1100 system.

Where LC/MS data are presented, analyses were performed using an Applied Biosystems API-100 mass spectrometer and Shimadzu SCL-10A LC column:

Example INT-1: Preparation of tert-butyl 2-((3,3-dimethylbutylidene)amino)acetate

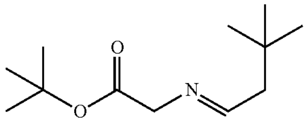

Synthesis of tert-butyl 2-((3,3-dimethylbutylidene) amino)acetate: Into a 2000-mL 3-necked round-bottom flask were placed tert-butyl 2-aminoacetate (70.0 g, 533.6 mmol, 1.0 eq), dichloromethane (700 mL), 3,3-dimethylbutanal (56.1 g, 560.3 mmol, 1.0 eq). The reaction mixture was stirred overnight at 25° C. The resulting mixture was concentrated under vacuum to give tert-butyl 2-((3,3-dimethylbutylidene)amino)acetate (135.0 g, crude) as light yellow oil. $^1$HNMR (300 MHz, DMSO-$d_6$) δ 7.71 (t, J=5.7 Hz, 1H), 4.04 (s, 2H), 2.10 (d, J=5.6 Hz, 2H), 1.41 (s, 9H), 0.95 (s, 9H).

Example INT-2: Preparation of 3-(3-chloro-2-fluorophenyl)-2-(2,4-dichlorophenyl) acrylonitrile Synthesis of 3-(3-chloro-2-fluorophenyl)-2-(2,4-dichlorophenyl) acrylonitrile: Into a 2000-mL 3-necked round-bottom flask were placed 2-(2,4-dichlorophenyl) acetonitrile (70.0 g, 376.3 mmol, 1.0 eq), methanol (700 mL), 3-chloro-2-fluorobenzaldehyde (59.7 g, 376.3 mmol, 1.0 eq). After that, sodium methanolate (30.5 g, 564.4 mmol, 1.5 eq) was added at 0° C. The reaction mixture was stirred for 3 hours at 50° C. The precipitated solids were collected by filtration and washed with methanol (2×300 mL). Finally, 3-(3-chloro-2-fluorophenyl)-2-(2,4-dichlorophenyl) acrylonitrile (110.0 g, 89%) was obtained as a light yellow solid. $^1$HNMR (400 MHz, Chloroform-d) δ 8.21 (ddd, J=8.0, 6.4, 1.8 Hz, 1H), 7.59-7.51 (m, 3H), 7.43 (d, J=8.4 Hz, 1H), 7.38 (dd, J=8.4, 2.2 Hz, 1H), 7.31-7.21 (m, 1H).

Example INT-3 (Method A): Preparation of (2'S,3S,4'S,5'R)-6-chloro-4'-(3-chloro-2-fluorophenyl)-2'-neopentylspiro[indoline-3,3'-pyrrolidine]-5'-carboxylic acid Synthesis of tert-butyl (2R,3S,4R,5S)-3-(3-chloro-2-fluorophenyl)-4-cyano-4-(2,4-dichlorophenyl)-5-neopentylpyrrolidine-2-carboxylate (racemate): Into a 2000-mL 3-necked round-bottom flask were placed 3-(3-chloro-2-fluorophenyl)-2-(2,4-dichlorophenyl) acrylonitrile (100.0 g, 306.2 mmol, 1.0 eq), tert-butyl 2-((3,3-dimethylbutylidene)amino) acetate (117.6 g, 551.2 mmol, 1.8 eq), 1,2-dichloroethane (1000 mL), AgF (46.6 g, 367.4 mmol, 1.2 eq), triethylamine (61.9 g, 612.4 mmol, 2.0 eq). The reaction mixture was stirred for 16 hours at 25° C. The resulting mixture was filtered and the filtrate was concentrated under vacuum. The crude residue was applied onto a silica gel column and eluted with ethyl acetate/petroleum ether=(0:1 to 1:3) to give tert-butyl (2R,3S,4R,5S and 2S,3R,4S,5R)-3-(3-chloro-2-fluorophenyl)-4-cyano-4-(2,4-dichlorophenyl)-5-neopentylpyrrolidine-2-carboxylate (racemate) (76.0 g, 46%) as a light yellow solid. LC-MS (ESI, m/z) M+1: 539/541. $^1$HNMR (300 MHz, Methanol-$d_4$) δ 7.75 (d, J=6.6 Hz, 1H), 7.70 (d, J=2.1 Hz, 1H), 7.56 (d, J=8.1 Hz, 1H), 7.51-7.44 (m, 1H), 7.42 (dd, J=8.4, 2.4 Hz, 1H), 7.28 (t, J=8.1 Hz, 1H), 5.35 (d, J=9.3 Hz, 1H), 5.0 (dd, J=8.7, 1.4 Hz, 2H), 4.80 (d, J=9.3 Hz, 1H), 1.89 (dd, J=15.0, 8.7 Hz, 1H), 1.48 (d, J=13.5 Hz, 1H), 1.38 (s, 9H), 0.95 (s, 9H).

Synthesis of tert-butyl (2R,3S,4S,5S and 2S,3R,4R,5R)-4-(aminomethyl)-3-(3-chloro-2-fluorophenyl)-4-(2,4-dichlorophenyl)-5-neopentylpyrrolidine-2-carboxylate (racemate): Into a 2000-mL round-bottom flask were placed tert-butyl (2R,3S,4R,5S)-3-(3-chloro-2-fluorophenyl)-4-cyano-4-(2,4-dichlorophenyl)-5-neopentylpyrrolidine-2-carboxylate (racemate) (28.0 g, 51.9 mmol, 1.0 eq), methanol (500 mL), acetic acid (125 mL), water (125 mL) and Raney-Ni (5.0 g). The reaction mixture was stirred at 50° C. under hydrogen (2 atm) for 48 hours. The resulting mixture was filtered, and the filtrate was concentrated under vacuum. Finally, tert-butyl (2R,3S,4S,5S and 2S,3R,4R,5R)-4-(aminomethyl)-3-(3-chloro-2-fluorophenyl)-4-(2,4-dichlorophenyl)-5-neopentylpyrrolidine-2-carboxylate (racemate) (20.0 g, 71%) was obtained as an off white solid. LC-MS (ESI, m/z) M+1: 543/545. $^1$HNMR (300 MHz, DMSO-$d_6$) δ 8.02 (s, 3H), 7.62 (d, J=2.4 Hz, 1H), 7.56-7.52 (m, 3H), 7.32 (d, J=8.4 Hz, 1H), 7.27 (t, J=7.8 Hz, 1H), 4.52 (d, J=12.0 Hz, 2H), 4.16 (d, J=8.4 Hz, 1H), 3.60-3.43 (m, 2H), 1.47 (dd, J=14.1, 10.2 Hz, 1H), 1.40-1.31 (m, 1H), 1.26 (s, 9H), 1.0 (s, 9H).

Synthesis of tert-butyl (2'S,3S,4'S,5'R)-6-chloro-4'-(3-chloro-2-fluorophenyl)-2'-neopentylspiro[indoline-3,3'-pyrrolidine]-5'-carboxylate (racemate): Into a 500 mL round-bottom flask and maintained under an inert atmosphere of nitrogen, were placed tert-butyl (2R,3S,4S,5S and 2S,3R,4R,5R)-4-(aminomethyl)-3-(3-chloro-2-fluorophenyl)-4-(2,4-dichlorophenyl)-5-neopentylpyrrolidine-2-carboxylate (racemate) (12.0 g, 22.1 mmol, 1.0 eq), methyl sulfoxide (240 mL), $K_3PO_4$ (18.7 g, 88.2 mmol, 4.0 eq), CuI (0.8 g, 13.2 mmol, 0.6 eq) and (1S,2S)—N,N'-dimethyl-1,2-diaminocyclohexane (1.3 g, 8.8 mmol, 0.4 eq). The reaction mixture was stirred for 2 hours at 100° C. The resulting mixture was diluted with water (300 mL) to give a suspension. After filtration, the filter cake was collected. The crude residue was applied onto a silica gel column and eluted with ethyl acetate/petroleum ether=(0:1 to 1:1) to give tert-butyl (2'S,3S,4'S,5'R)-6-chloro-4'-(3-chloro-2-fluorophenyl)-2'-neopentylspiro[indoline-3,3'-pyrrolidine]-5'-carboxylate (racemate) (6.0 g, 54%) as light yellow oil. LC-MS (ESI, m/z) M+1: 507/509. $^1$HNMR (400 MHz, Methanol-$d_4$) δ 7.36-7.31 (m, 1H), 7.28 (d, J=6.8 Hz, 1H), 7.12 (d, J=8.0 Hz, 2H), 6.65 (d, J=8.0 Hz, 1H), 6.41 (s, 1H), 4.12 (d, J=9.6 Hz, 1H), 3.99 (d, J=9.6 Hz, 1H), 3.60 (d, J=10.4 Hz, 1H), 3.50 (d, J=7.6 Hz, 1H), 3.47 (d, J=10.4 Hz, 1H), 1.41 (d, J=10.0 Hz, 2H), 1.33 (s, 9H), 0.88 (s, 9H).

Synthesis of (2'S,3S,4'S,5'R)-6-chloro-4'-(3-chloro-2-fluorophenyl)-2'-neopentylspiro[indoline-3,3'-pyrrolidine]-5'-carboxylic acid (racemate): Into a 250 mL round-bottom flask were placed tert-butyl (2'S,3S,4'S,5'R)-6-chloro-4'-(3-chloro-2-fluorophenyl)-2'-neopentylspiro[indoline-3,3'-pyrrolidine]-5'-carboxylate (racemate) (5.5 g, 10.8 mmol, 1.0 eq), trifluoroacetic acid (60 mL). The reaction mixture was stirred for 16 hours at 25° C. The resulting mixture was diluted with water (200 mL) and then extracted with ethyl acetate (2×100 mL). The combined organic phase was washed with brine (2×100 mL), dried over anhydrous sodium sulfate. After filtration, the filtrate was concentrated under vacuum. Finally, (2'S,3S,4'S,5'R)-6-chloro-4'-(3-chloro-2-fluorophenyl)-2'-neopentylspiro[indoline-3,3'-pyrrolidine]-5'-carboxylic acid (racemate) (4.7 g, crude) was obtained as light yellow solid. LC-MS (ESI, m/z) M+1: 451/453.

Example INT-3 (Method B): Preparation of (2'S,3S,4'S,5'R)-6-chloro-4'-(3-chloro-2-fluorophenyl)-2'-neopentylspiro[indoline-3,3'-pyrrolidine]-5'-carboxylic acid Synthesis of 2-(2-bromo-4-chlorophenyl)-3-(3-chloro-2-fluorophenyl) acrylonitrile: Into a 250-mL 3-necked round-bottom flask, were placed 2-(2-bromo-4-chlorophenyl)acetonitrile (10.0 g, 43.4 mmol, 1.0 eq), $CH_3OH$ (100 mL), 3-chloro-2-fluorobenzaldehyde (6.9 g, 43.4 mmol, 1.0 eq). After that, MeONa (3.5 g, 65.1 mmol, 1.5 eq) was added at 0° C. The reaction mixture was stirred for 3 hours at 50° C. The precipitated solids were collected by filtration and then washed with $CH_3OH$ (50 mL×2). Finally, 2-(2-bromo-4-chlorophenyl)-3-(3-chloro-2-fluorophenyl) acrylonitrile (13.0 g, 80%) was obtained as a light yellow oil. LC-MS (ESI, m/z) M+1: 370/372. $^1$HNMR (300 MHz, Chloroform-d) δ 8.04-7.94 (m, 2H), 7.88-7.72 (m, 1H), 7.72-7.61 (m, 3H), 7.41 (dt, J=31.2, 8.1 Hz, 1H).

Synthesis of tert-butyl 4-(2-bromo-4-chlorophenyl)-3-(3-chloro-2-fluorophenyl)-4-cyano-5-neopentylpyrrolidine-2-carboxylate: Into a 250-mL 3-necked round-bottom flask, were placed 2-(2-bromo-4-chlorophenyl)-3-(3-chloro-2-fluorophenyl) acrylonitrile (9.0 g, 24.4 mmol, 1.0 eq), tert-butyl 2-((3,3-dimethylbutylidene)amino)acetate (6.2 g, 29.3 mmol, 1.2 eq), 1,2-dichloroethane (90 mL), AgF (3.7 g, 29.3 mmol, 1.2 eq), triethylamine (4.9 g, 48.8 mmol, 2.0 eq). The reaction mixture was stirred for 16 hours at 25° C. The resulting mixture was filtered, the filtrate was concentrated under vacuum. The crude residue was applied onto a silica gel column and eluted with ethyl acetate/petroleum ether=(0:1 to 1:1). Finally, tert-butyl 4-(2-bromo-4-chlorophenyl)-3-(3-chloro-2-fluorophenyl)-4-cyano-5-neopentylpyrrolidine-2-carboxylate (5.0 g, crude) was obtained as an off white solid, which was directly used to the next step. LC-MS (ESI, m/z) M+1: 583/585.

Synthesis of tert-butyl (2R, 3S, 4R, 5S)-4-(2-bromo-4-chlorophenyl)-3-(3-chloro-2-fluorophenyl)-4-cyano-5-neopentylpyrrolidine-2-carboxylate(racemate): Into a 250-mL 3-necked round-bottom flask, were placed tert-butyl 4-(2-bromo-4-chlorophenyl)-3-(3-chloro-2-fluorophenyl)-4-cyano-5-neopentylpyrrolidine-2-carboxylate (crude product, 5.0 g, 1.0 eq), tetrahydrofuran (60 mL), LiOH (0.6 g, 25.7 mmol, 3.0 eq). The reaction mixture was stirred for 14 hours at 70° C. The resulting mixture was filtered, the filtrate was concentrated under vacuum. Finally, tert-butyl (2R, 3S, 4R, 5S)-4-(2-bromo-4-chlorophenyl)-3-(3-chloro-2-fluorophenyl)-4-cyano-5-neopentylpyrrolidine-2-carboxylate (racemate) (4.8 g, crude) was obtained as an off white solid. LC-MS (ESI, m/z) M+1: 583/585. $^1$HNMR (300 MHz, DMSO-$d_6$) δ 7.96 (d, J=2.4 Hz, 1H), 7.70 (t, J=6.6 Hz, 1H), 7.57-7.49 (m, 2H), 7.53-7.43 (m, 1H), 7.37-7.24 (m, 1H), 5.25 (d, −7.5 Hz, 1H), 4.68 (d, −9.0 Hz, 1H), 4.34 (d, −7.5 Hz, 1H), 1.52 (dd, J=14.1, 9.3 Hz, 1H), 1.32 (s, 9H), 1.24-1.16 (m, 1H), 0.89 (s, 9H).

Synthesis of tert-butyl (2R, 3S, 4R, 5S)-4-(aminomethyl)-4-(2-bromo-4-chlorophenyl)-3-(3-chloro-2-fluorophenyl)-5-neopentylpyrrolidine-2-carboxylate (racemate): Into a 250-mL 3-necked round-bottom flask, were placed tert-butyl (2R, 3S, 4R, 5S)-4-(2-bromo-4-chlorophenyl)-3-(3-chloro-2-fluorophenyl)-4-cyano-5-neopentylpyrrolidine-2-carboxylate (racemate) (4.8 g, 8.2 mmol, 1.0 eq) and $BH_3$(10 M in dimethyl sulfide, 50 mL). The reaction mixture was stirred for 1 hour at 50° C. The resulting mixture was diluted with tetrahydrofuran (500 mL), and then quenched by the addition of $CH_3OH$ (100 mL). The resulting solution was concentrated under vacuum. The crude residue was applied onto a silica gel column and eluted with ethyl acetate/petroleum ether=(1:0 to 10:1) to give tert-butyl (2R, 3S, 4R, 5S)-4-(aminomethyl)-4-(2-bromo-4-chlorophenyl)-3-(3-chloro-2-fluorophenyl)-5-neopentylpyrrolidine-2-carboxylate (racemate) (350 mg, 7%) as an off white solid. LC. MS (ESI, m/z) M+1: 587/589. $^1$HNMR (300 MHz, DMSO-$d_6$) δ 8.14 (br, 3H), 7.82 (s, 1H), 7.56 (br, 3H), 7.32-7.15 (m, 2H), 4.85 (br, 1H), 4.42-4.39 (m, 2H), 3.70 (br, 1H), 3.49 (br, 1H), 1.61-1.58 (m, 1H), 1.38 (d, J=14.1 Hz, 1H), 1.24 (s, 9H), 0.99 (s, 9H).

Synthesis of tert-butyl (2'S,3S,4'S,5'R)-6-chloro-4'-(3-chloro-2-fluorophenyl)-2'-neopentylspiro [indoline-3,3'-pyrrolidine]-5'-carboxylate (racemate): Into a 40 mL vial purged and maintained under an inert atmosphere of nitrogen, were placed tert-butyl (2R,3S, 4R, 5S and 2S, 3R, 4S, 5R)-4-(aminomethyl)-4-(2-bromo-4-chlorophenyl)-3-(3-chloro-2-fluorophenyl)-5-neopentylpyrrolidine-2-carboxylate (racemate) (300 mg, 0.5 mmol, 1.0 eq), toluene (12 mL), CuI (19 mg, 0.1 mmol, 0.2 eq), trans-1,2-diaminocyclohexane (12 mg, 0.1 mmol, 0.2 eq), $K_3PO_4$ (217 mg, 1.0 mmol, 2.0 eq). The reaction mixture was stirred for 16 hours at 100° C. Then the resulting solution was diluted with water (30 mL) and extracted with ethyl acetate (2×50 mL). The combined organic phase was washed with brine (2×50 mL), dried over anhydrous sodium sulfate. After filtration, the filtrate was concentrated under vacuum. The crude residue was applied onto a silica gel column and eluted with ethyl acetate/petroleum ether=(0:1 to 1:1) to give tert-butyl (2'S, 3S,4'S,5'R)-6-chloro-4'-(3-chloro-2-fluorophenyl)-2'-neopentylspiro[indoline-3,3'-pyrrolidine]-5'-carboxylate (racemate) (130 mg, 50%) as a light yellow oil. LC-MS (ESI, m/z) M+1: 507/509. $^1$HNMR (300 MHz, Methanol-$d_4$) δ 7.36-7.31 (m, 1H), 7.28 (d, J=6.6 Hz, 1H), 7.14-7.12 (m, 2H), 6.65 (d, J=7.8 Hz, 1H), 6.44 (s, 1H), 4.12 (d, J=9.6 Hz, 1H), 3.99 (d, J=9.6 Hz, 1H), 3.60 (d, J=10.5 Hz, 1H), 3.50 (d, J=7.5 Hz, 1H), 3.47 (d, J=10.5 Hz, 1H), 1.41 (d, J=10.2 Hz, 2H), 1.33 (s, 9H), 0.88 (s, 9H).

Synthesis of (2'S,3S,4'S,5'R)-6-chloro-4'-(3-chloro-2-fluorophenyl)-2'-neopentylspiro[indoline-3,3'-pyrrolidine]-5'-carboxylic acid (racemate): Into a 250 mL round-bottom flask were placed tert-butyl (2'S,3S,4'S,5'R)-6-chloro-4'-(3-chloro-2-fluorophenyl)-2'-neopentylspiro[indoline-3,3'-pyrrolidine]-5'-carboxylate (racemate) (5.5 g, 10.8 mmol, 1.0 eq), trifluoroacetic acid (60 mL). The reaction mixture was stirred for 16 hours at 25° C. The resulting mixture was diluted with water (200 mL) and then extracted with ethyl acetate (2×100 mL). The combined organic phase was washed with brine (2×100 mL), dried over anhydrous sodium sulfate. After filtration, the filtrate was concentrated under vacuum. Finally, (2'S,3S,4'S,5'R)-6-chloro-4'-(3-chloro-2-fluorophenyl)-2'-neopentylspiro[indoline-3,3'-pyrrolidine]-5'-carboxylic acid (racemate) (4.7 g, crude) was obtained as light yellow solid. LC-MS (ESI, m/z) M+1: 451/453.

Example INT-4: Preparation of tert-butyl (2S,3S,4S, 5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylate (racemate)

Synthesis of 4-chloro-6-(trifluoromethyl)pyridine-3-carboxylic acid: To a solution of 2,2,6,6-tetramethylpiperidine (33.7 g, 235.5 mmol, 3.0 eq) in tetrahydrofuran (300 mL) was added n-BuLi (2.5M in hexanes, 95 mL) dropwise at −78° C. Then the reaction mixture was stirred at −78° C.~−30° C. for 30 minutes. After that, the mixture was cooled to −78° C. and a solution of 6-(trifluoromethyl) pyridine-3-carboxylic acid (15.0 g, 78.5 mmol, 1.0 eq) in tetrahydrofuran (300 mL) was added dropwise at −78° C., and the mixture was stirred at −78° C.~−40° C. for another 1 hour. The mixture was cooled to −78° C. and a solution of hexachloroethane (38.1 g, 160.9 mmol, 2.1 eq) in tetrahydrofuran (100 mL) was added to the above solution dropwised. The reaction mixture was stirred at −78° C. for 3 hours. The resulting mixture was quenched by the addition of $NH_4Cl$ (aq.) (300 mL) at −78° C., acidified to pH 3-4 with HCl (1 M) and then extracted with ethyl acetate (2×300 mL). The combined organic phase was washed with brine (2×300 mL), dried over anhydrous sodium sulfate. After filtration, the filtrate was concentrated under vacuum. The crude residue was applied onto a silica gel column and eluted with ethyl acetate/petroleum ether=(1:0 to 20:1) to give 4-chloro-6-(trifluoromethyl)pyridine-3-carboxylic acid (10.0 g, 56%) as a light yellow solid. LC-MS (ESI, m/z) M−1: 224/226. $^1$HNMR (400 MHz, Methanol-$d_4$) δ 9.10 (d, J=17.2 Hz, 1H), 8.04 (s, 1H).

Synthesis of [4-chloro-6-(trifluoromethyl)pyridin-3-yl] methanol: Into a 500-mL 3-necked round-bottom flask, were placed 4-chloro-6-(trifluoromethyl)pyridine-3-carboxylic acid (10.0 g, 44.3 mmol, 1.0 eq), tetrahydrofuran (100 mL). After that, $BH_3$-tetrahydrofuran (1 M in tetrahydrofuran, 178 mL) was added at 0° C. The reaction mixture was stirred for 16 hours at 25° C. The resulting mixture was quenched by the addition of $NH_4Cl$ (aq.) (250 mL), and then extracted with ethyl acetate (2×200 mL). The combined organic phase was washed with brine (2×200 mL), dried over anhydrous sodium sulfate. After filtration, the filtrate was concentrated under vacuum to give [4-chloro-6-(trifluoromethyl)pyridin-3-yl]methanol (12.0 g, crude) as a light yellow oil. LC-MS (ESI, m/z) M+1: 212/214. $^1$HNMR (400 MHz, DMSO-$d_6$) δ 8.82 (s, 1H), 8.07 (s, 1H), 5.73 (t, J=5.6 Hz, 1H). 4.70 (d, J=5.6 Hz, 2H).

Synthesis of 4-chloro-5-(chloromethyl)-2-(trifluoromethyl)pyridine: [4-chloro-6-(trifluoromethyl)pyridin-3-yl] methanol (12.0 g, 56.7 mmol, 1.0 eq) was added to $SOCl_2$ (120 mL) slowly with ice bath, the reaction mixture was stirred for 16 hours at 85° C. The resulting mixture was concentrated and the residue was poured into water (200 mL). The resulting aqueous solution was adjusted to pH=7-8 with solid $NaHCO_3$, and then extracted with ethyl acetate (2×300 mL). The combined organic phase was washed with brine (2×300 mL), dried over anhydrous sodium sulfate. After filtration, the filtrate was concentrated under vacuum to give 4-chloro-5-(chloromethyl)-2-(trifluoromethyl)pyridine (13.0 g, crude) as a yellow oil.

Synthesis of 2-[4-chloro-6-(trifluoromethyl)pyridin-3-yl] acetonitrile: Into a 500-mL round-bottom flask were placed 4-chloro-5-(chloromethyl)-2-(trifluoromethyl)pyridine (13.0 g, 56.5 mmol, 1.0 eq), TBAF (29.6 g, 113.0 mmol, 2.0 eq), $CH_3CN$ (150 mL), TMSCN (11.2 g, 113.0 mmol, 2.0 eq). The reaction mixture was stirred for 2 hours at 25° C.

The resulting mixture was concentrated under vacuum. The residue was diluted with water (200 mL) and then extracted with ethyl acetate (2×200 mL). The combined organic phases was washed with brine (2×200 mL), dried over anhydrous sodium sulfate. After filtration, the filtrate was concentrated in vacuo. The crude residue was applied onto a silica gel column and eluted with ethyl acetate/petroleum ether=(0:1 to 1:3) to give 2-[4-chloro-6-(trifluoromethyl) pyridin-3-yl]acetonitrile (1.5 g, 12%) as a light yellow oil. LC-MS (ESI, m/z) M+1: 221/223. $^1$HNMR (300 MHz, Chloroform-d) δ 8.85 (s, 1H), 7.81 (s, 1H), 3.94 (s, 2H).

Synthesis of 3-(3-chloro-2-fluorophenyl)-2-(4-chloro-6-(trifluoromethyl)pyridin-3-yl)acrylonitrile: Into a 40 mL sealed tube, were placed 2-[4-chloro-6-(trifluoromethyl) pyridin-3-yl]acetonitrile (1.2 g, 5.4 mmol, 1.0 eq), $CH_3OH$ (12 mL), 3-chloro-2-fluorobenzaldehyde (0.9 g, 5.4 mmol, 1.0 eq) and piperidine (0.7 g, 8.2 mmol, 1.5 eq). The reaction mixture was stirred for 3 hours at 50° C. The resulting mixture was concentrated under vacuum. The residue was applied onto a silica gel column and eluted with ethyl acetate/petroleum ether=(0:1 to 1:5) to give 3-(3-chloro-2-fluorophenyl)-2-(4-chloro-6-(trifluoromethyl)pyridin-3-yl) acrylonitrile (800 mg, 41%) as a yellow solid. $^1$HNMR (300 MHz, DMSO-$d_6$) δ 9.0 (s, 1H), 8.36 (s, 1H), 8.10-8.03 (m, 1H), 7.99 (s, 1H), 7.88-7.81 (m, 1H), 7.49 (td, −7.8, 2.1 Hz, 1H).

Synthesis of tert-butyl (2R,3S,4R,5S)-3-(3-chloro-2-fluorophenyl)-4-[4-chloro-6-(trifluoromethyl) pyridin-3-yl]-4-cyano-5-(2,2-dimethylpropyl)pyrrolidine-2-carboxylate (racemate): Into a 50-mL round-bottom flask, were placed 3-(3-chloro-2-fluorophenyl)-2-(4-chloro-6-(trifluoromethyl)pyridin-3-yl)acrylonitrile (800 mg, 2.2 mmol, 1.0 eq), tert-butyl 2-((3,3-dimethylbutylidene)amino)acetate (709 mg, 3.3 mmol, 1.5 eq), AgF (337 mg, 2.6 mmol, 1.2 eq), triethylamine (448 mg, 4.4 mmol, 2.0 eq) and 1,2-dichloroethane (10 mL). The reaction mixture was stirred for 16 hours at 25° C. The resulting mixture was filtered and the filtrate was concentrated under vacuum. The residue was applied onto a silica gel column and eluted with ethyl acetate/petroleum ether=(0:1 to 1:3) to give tert-butyl (2R, 3S,4R,5S)-3-(3-chloro-2-fluorophenyl)-4-[4-chloro-6-(trifluoromethyl)pyridin-3-yl]-4-cyano-5-(2,2-dimethylpropyl) pyrrolidine-2-carboxylate (racemate) (400 mg, 31%) as an off white solid. LC-MS (ESI, m/z) M+1: 574/576. $^1$HNMR (400 MHz, DMSO-$d_6$) δ 8.74 (s, 1H), 8.34 (s, 1H), 7.75 (t, J=6.8 Hz, 1H), 7.56 (t, −7.2 Hz, 1H), 7.36 (t, −8.0 Hz, 1H), 5.03 (d, −7.0 Hz, 1H), 4.56 (t, −9.4 Hz, 1H), 4.37 (t, J=7.0 Hz, 1H), 3.63-3.54 (m, 1H), 1.54 (dd, J=14.2, 9.6 Hz, 1H), 1.34 (s, 9H), 1.29 (d, −7.8 Hz, 1H), 0.91 (s, 9H).

Synthesis of tert-butyl (2R,3S,4S,5S)-4-(aminomethyl)-3-(3-chloro-2-fluorophenyl)-4-[4-chloro-6-(trifluoromethyl)pyridin-3-yl]-5-(2,2-dimethylpropyl)pyrrolidine-2-carboxylate (racemate): Into a 50-mL round-bottom flask, were placed tert-butyl (2R,3S,4R,5S)-3-(3-chloro-2-fluorophenyl)-4-[4-chloro-6-(trifluoromethyl)pyridin-3-yl]-4-cyano-5-(2,2-dimethylpropyl)pyrrolidine-2-carboxylate (racemate) (400 mg, 0.7 mmol, 1.0 eq), $CH_3OH$ (9 mL), acetic acid (3 mL) and Raney-Ni (40 mg, 0.5 mmol, 0.7 eq). The reaction mixture was stirred at 25° C. under hydrogen (2 atm) for 24 hours. The resulting mixture was filtered and the filtrate was concentrated under vacuum. Finally, tert-butyl (2R,3S,4S,5S)-4-(aminomethyl)-3-(3-chloro-2-fluorophenyl)-4-[4-chloro-6-(trifluoromethyl)pyridin-3-yl]-5-(2,2-dimethylpropyl)pyrrolidine-2-carboxylate (racemate) (600 mg, crude) was obtained as a light green oil. LC-MS (ESI, m/z) M+1: 578/579.

Synthesis of tert-butyl (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylate (racemate): Into a 50 mL round-bottom flask were placed tert-butyl (2R,3S,4S,5S)-4-(aminomethyl)-3-(3-chloro-2-fluorophenyl)-4-[4-chloro-6-(trifluoromethyl)pyridin-3-yl]-5-(2,2-dimethylpropyl)pyrrolidine-2-carboxylate (racemate) (600 mg, 1.0 mmol, 1.0 eq), $CH_3CN$ (10 mL), $K_2CO_3$ (717 mg, 5.1 mmol, 5.0 eq). The reaction mixture was stirred for 16 hours at 25° C. The resulting mixture was filtered, the filtrate was concentrated under vacuum. The residue was diluted with water (50 mL) and extracted with ethyl acetate (50 mL). The organic phase was washed with brine (2×50 mL), dried over anhydrous sodium sulfate. After filtration, the filtrate was concentrated under vacuum. The crude residue was applied onto a silica gel column and eluted with ethyl acetate/petroleum ether=(0:1 to 1:0) to give tert-butyl (2S,3S,4S,5R)-4-(3-chloro-2-fluorophenyl)-2-(2,2-dimethylpropyl)-6'-(trifluoromethyl)-1',2'-dihydrospiro [pyrrolidine-3,3'-pyrrolo[3,2-c]pyridine]-5-carboxylate (racemate) (180 mg) as a light yellow solid. LC-MS (ESI, m/z) M+1: 542/543. $^1$HNMR (300 MHz, DMSO-$d_6$) δ 8.27 (s, 1H), 7.51-7.39 (m, 2H), 7.27-7.15 (m, 1H), 6.63 (d, J=15.0 Hz, 2H), 4.12 (s, 1H), 3.62 (d, J=12.0 Hz, 1H), 3.48-3.34 (m, 2H), 2.95 (s, 1H), 1.27 (s, 9H), 1.14 (d, J=13.8 Hz, 2H), 0.82 (s, 9H).

Example INT-5: Preparation of tert-butyl (2S,3S,4S,5R)-6'-chloro-4-(3-chloro-2-fluorophenyl)-2-neopentyl-1',2'-dihydrospiro[pyrrolidine-3,3'-pyrrolo[3,2-c]pyridine]-5-carboxylate Synthesis of 5-(bromomethyl)-2,4-dichloropyridine: Into a 500 mL 3-necked round-bottom flask were added 2,4-dichloro-5-methylpyridine (25.0 g, 154.3 mmol, 1.0 eq), chlorobenzene (250 mL), AIBN (2.5 g, 15.4 mmol, 0.1 eq) and NBS (30.1 g, 169.7 mmol, 1.1 eq) at 25° C. The reaction mixture was stirred for 16 hours at 130° C. The resulting mixture was concentrated under vacuum. The residue was diluted with water (100 mL), and extracted with ethyl acetate (3×100 mL). The combined organic layers were washed with brine (100 mL), dried over anhydrous sodium sulfate. After filtration, the filtrate was concentrated under vacuum. The crude residue was applied onto a silica gel column and eluted with ethyl acetate/petroleum ether=10:1 to give 5-(bromomethyl)-2,4-dichloropyridine (16.3 g, 43%) as white solid. LC-MS (ESI, m/z) M+1: 240/242.

Synthesis of 2-(4,6-dichloropyridin-3-yl)acetonitrile: Into a 500 mL 3-necked round-bottom flask were added 5-(bromomethyl)-2,4-dichloropyridine (16.3 g, 67.6 mmol, 1.0 eq), acetonitrile (160 mL) and LiOH·$H_2O$ (1.9 g, 81.2 mmol, 1.2 eq) at 25° C. To the above mixture was added TMSCN (8.1 g, 81.2 mmol, 1.2 eq) dropwise at 25° C. The reaction mixture was stirred for additional 2 hours at 25° C. The resulting mixture was diluted with water (200 mL) and extracted with ethyl acetate (3×100 mL). The combined organic layers were washed with brine (2×100 mL), dried over anhydrous sodium sulfate. After filtration, the filtrate was concentrated under vacuum. The crude residue was applied onto a silica gel column and eluted with ethyl acetate/petroleum ether=(10:1 to 3:1) to give 2-(4,6-dichloropyridin-3-yl)acetonitrile (12.0 g, 94%) as a white solid. LC-MS (ESI, m/z) M+1: 187/189. $^1$HNMR (300 MHz, DMSO-$d_6$) δ 8.53 (s, 1H), 7.93 (s, 1H), 4.16 (s, 2H).

Synthesis of 3-(3-chloro-2-fluorophenyl)-2-(4,6-dichloropyridin-3-yl)prop-2-enenitrile: Into a 500 mL 3-necked round-bottom flask were added 2-(4,6-dichloropyridin-3-yl)

acetonitrile (12.0 g, 64.2 mmol, 1.0 eq), 1,2-dichloroethane (200 mL), 3-chloro-2-fluorobenzaldehyde (11.2 g, 70.6 mmol, 1.1 eq) and $Cs_2Co_3$ (41.8 g, 128.3 mmol, 2.0 eq) at 25° C. The reaction mixture was stirred for 3 hours at 70° C. The resulting mixture was diluted with water (200 mL) and then extracted with dichloromethane (2×200 mL). The combined organic layers were washed with brine (300 mL), dried over anhydrous sodium sulfate. After filtration, the filtrate was concentrated under vacuum. The crude residue was applied onto a silica gel column and eluted with ethyl acetate/petroleum ether=(10:1 to 3:1) to give 3-(3-chloro-2-fluorophenyl)-2-(4,6-dichloropyridin-3-yl)prop-2-enenitrile (10.0 g, 47%) as a white solid. LC-MS (ESI, m/z) M+1: 327/329. $^1$HNMR (400 MHz, DMSO-$d_6$) δ 8.67 (s, 1H), 8.08-7.99 (m, 2H), 7.89 (s, 1H), 7.82 (t, J=7.5 Hz, 1H), 7.47 (t, J=8.0 Hz, 1H).

Synthesis of tert-butyl (2S,3S,4S,5R)-3-(3-chloro-2-fluorophenyl)-4-cyano-4-(4,6-dichloropyridin-3-yl)-5-(2,2-dimethylpropyl)pyrrolidine-2-carboxylate (racemate): Into a 500 mL round-bottom flask were added 3-(3-chloro-2-fluorophenyl)-2-(4,6-dichloropyridin-3-yl)prop-2-enenitrile (10.0 g, 30.5 mmol, 1.0 eq), 1,2-dichloroethane (200 mL), tert-butyl 2-[(3,3-dimethylbutylidene)amino]acetate (11.7 g, 55.0 mmol, 1.8 eq), trimethylamine (6.2 g, 61.1 mmol, 2.0 eq) and AgF (4.6 g, 36.6 mmol, 1.2 eq) at 25° C. The reaction mixture was stirred for 16 hours at 25° C. under nitrogen atmosphere. The resulting mixture was diluted with brine (200 mL) and then extracted with dichloromethane (2×200 mL). The combined organic layers were washed with brine (200 mL), dried over anhydrous sodium sulfate. After filtration, the filtrate was concentrated under vacuum. The crude residue was applied onto a silica gel column and eluted with ethyl acetate/petroleum ether=10:1 to give tert-butyl (2S,3S,4S,5R)-3-(3-chloro-2-fluorophenyl)-4-cyano-4-(4,6-dichloropyridin-3-yl)-5-(2,2-dimethylpropyl)pyrrolidine-2-carboxylate (racemate) (2.8 g, 17%) as a light yellow solid. LC-MS (ESI, m/z) M+1: 540/542. $^1$HNMR: (300 MHz, DMSO-$d_6$) δ 8.38 (s, 1H), 8.03 (s, 1H), 7.72 (t, J=7.2 Hz, 1H), 7.56 (td, J=7.5, 1.2 Hz, 1H), 7.35 (t, J=8.0 Hz, 1H), 4.99 (d, J=7.1 Hz, 1H), 4.47 (t, J=9.2 Hz, 1H), 4.34 (t, J=6.8 Hz, 1H), 3.58-3.46 (m, 1H), 1.51-1.47 (m, 1H), 1.34 (s, 9H), 1.24 (d, J=4.3 Hz, 1H), 0.90 (s, 9H).

Synthesis of tert-butyl (2S,3S,4S,5R)-4-(aminomethyl)-3-(3-chloro-2-fluorophenyl)-4-(4,6-dichloropyridin-3-yl)-5-(2,2-dimethylpropyl)pyrrolidine-2-carboxylate (racemate): Into a 250 mL 3-necked round-bottom flask were added methanol (30 mL), acetic acid (10 mL), Raney Ni (0.9 g, 15.5 mmol, 3.0 eq) and tert-butyl (2S,3S,4S,5R)-3-(3-chloro-2-fluorophenyl)-4-cyano-4-(4,6-dichloropyridin-3-yl)-5-(2,2-dimethylpropyl)pyrrolidine-2-carboxylate (racemate) (2.8 g, 5.2 mmol, 1.0 eq) at 25° C. The reaction mixture was stirred for 6 hours at 25° C. under hydrogen (3 atm) atmosphere. The resulting mixture was filtered and the filter cake was washed with methanol (60 mL). The filtrate was concentrated under vacuum to give tert-butyl (2S,3S,4S,5R)-4-(aminomethyl)-3-(3-chloro-2-fluorophenyl)-4-(4,6-dichloropyridin-3-yl)-5-(2,2-dimethylpropyl)pyrrolidine-2-carboxylate (racemate) (2.4 g, crude) as colorless oil. LC-MS (ESI, m/z) M+1: 544/546.

Synthesis of tert-butyl (2S,3S,4S,5R)-6'-chloro-4-(3-chloro-2-fluorophenyl)-2-neopentyl-1',2'-dihydrospiro[pyrrolidine-3,3'-pyrrolo[3,2-c]pyridine]-5-carboxylate (racemate): Into a 100 mL round-bottom flask were added tert-butyl (2S,3S,4S,5R)-4-(aminomethyl)-3-(3-chloro-2-fluorophenyl)-4-(4,6-dichloropyridin-3-yl)-5-(2,2-dimethylpropyl)pyrrolidine-2-carboxylate (racemate) (2.4 g, 4.4 mmol, 1.0 eq), acetonitrile (25 mL) and $K_2CO_3$ (1.2 g, 8.8 mmol, 2.0 eq) at 25° C. The reaction mixture was stirred for 3 hours at 70° C. The resulting mixture was diluted with water (30 mL) and extracted with ethyl acetate (3×30 mL). The combined organic layers were washed with brine (30 mL), dried over anhydrous sodium sulfate. After filtration, the filtrate was concentrated under vacuum. The crude residue was applied onto a silica gel column and eluted with ethyl acetate/petroleum ether=(10:1 to 1:1) to give tert-butyl (2S,3S,4S,5R)-6'-chloro-4-(3-chloro-2-fluorophenyl)-2-neopentyl-1',2'-dihydrospiro[pyrrolidine-3,3'-pyrrolo[3,2-c]pyridine]-5-carboxylate (racemate) (170 mg, 7%) as light yellow solid. LC-MS (ESI, m/z) M+1: 508/510. $^1$HNMR (300 MHz, DMSO-$d_6$) δ 7.92 (d, J=1.6 Hz, 1H), 7.44 (t, J=7.4 Hz, 2H), 7.20 (t, J=7.9 Hz, 1H), 6.88 (s, 1H), 6.56 (s, 1H), 6.21 (s, 1H), 4.07 (s, 2H), 3.57 (d, J=11.1 Hz, 1H), 3.36-3.34 (m, 1H), 2.90 (bs, 1H), 2.18 (s, 1H), 1.43-1.14 (m, 2H), 1.25 (s, 9H), 0.83 (s, 9H).

Example INT-6: Preparation of 3-(4-iodo-1-oxo-3H-isoindol-2-yl)piperidine-2,6-dione Synthesis of methyl 3-iodo-2-methylbenzoate: To a stirred mixture of 3-iodo-2-methylbenzoic acid (20.0 g, 76.3 mmol, 1.0 eq) in methanol (200 mL) was added thionyl chloride (27.2 g, 228.9 mmol, 3.0 eq) dropwise at 0° C. The reaction mixture was stirred for 3 hours at 80° C. The resulting mixture was neutralized to pH=7 with saturated $NaHCO_3$ (aq.) and then extracted with ethyl acetate (3×200 mL). The combined organic phase was washed with brine (200 mL), dried over anhydrous sodium sulfate. After filtration, the filtrate was concentrated under vacuum to give methyl 3-iodo-2-methylbenzoate (18.0 g, 85%) as yellow oil. $^1$HNMR (300 MHz, DMSO-$d_6$) δ 8.06 (dd, J=7.8, 1.2 Hz, 1H), 7.70 (dd, J=7.8, 1.5 Hz, 1H), 7.06 (td, J=7.8, 0.6 Hz, 1H), 3.84 (s, 3H), 2.55 (s, 3H).

Synthesis of 3-(4-iodo-1-oxo-3H-isoindol-2-yl)piperidine-2,6-dione: A mixture of methyl 3-iodo-2-methylbenzoate (18.0 g, 65.2 mmol, 1.0 eq), NBS (13.9 g, 78.2 mmol, 1.2 eq) and AIBN (1.1 g, 6.5 mmol, 0.1 eq) in $CCl_4$ (200 mL) was stirred for 14 hours at 80° C. The resulting mixture was concentrated under vacuum, and then diluted with dichloromethane (200 mL). The organic phase was washed with water (3×50 mL), brine (50 mL) and dried over anhydrous sodium sulfate. After filtration, the filtrate was concentrated under vacuum to give methyl 2-(bromomethyl)-3-iodobenzoate (16.0 g, 69%) as a brown solid.

Synthesis of 3-(4-iodo-1-oxo-3H-isoindol-2-yl)piperidine-2,6-dione: A mixture of methyl 2-(bromomethyl)-3-iodobenzoate (16.0 g, 45.1 mmol, 1.0 eq), 3-aminopiperidine-2,6-dione (8.7 g, 67.6 mmol, 1.5 eq) and triethylamine (13.7 g, 135.2 mmol, 3.0 eq) in acetonitrile (150 mL) was stirred for 14 hours at 80° C. The resulting mixture was concentrated under vacuum, diluted with ethyl acetate (100 mL) and water (100 mL). The precipitated solids were collected by filtration and washed with water (50 mL). Finally, 3-(4-iodo-1-oxo-3H-isoindol-2-yl)piperidine-2,6-dione (11.0 g, 66%) was obtained as a blue solid. $^1$HNMR (300 MHz, DMSO-$d_6$) δ 11.02 (bs, 1H), 7.88 (d, J=7.8 Hz, 1H), 7.78 (d, J=7.5 Hz, 1H), 7.52 (t, J=7.8 Hz, 1H), 5.16 (dd, J=13.2, 5.1 Hz, 1H), 4.43 (d, J=17.7 Hz, 1H), 4.27 (d, J=17.7 Hz, 1H), 2.93 (ddd, J=18.3, 13.5, 5.4 Hz, 1H), 2.66-2.52 (m, 1H), 2.44 (dd, J=13.5, 4.5 Hz, 1H), 2.11-1.96 (m, 1H).

Example INT-7: Preparation of 3-[2-(2,6-dioxopiperidin-3-yl)-1-oxo-3H-isoindol-4-yl]prop-2-ynal Synthesis of 3-[4-(3,3-diethoxyprop-1-yn-1-yl)-1-oxo-3H-isoindol-2-yl]piperidine-2,6-dione: Into a 100 mL round flask purged and maintained under an inert atmosphere of nitrogen, were placed 3-(4-iodo-1-oxo-3H-isoindol-2-yl)piperidine-2,6-dione (2.0 g, 5.4 mmol, 1.0 eq), 3,3-diethoxypropyne (830 mg, 6.4 mmol, 1.2 eq), $Pd(PPh_3)_4$ (620 mg, 0.5 mmol, 0.1 eq), CuI (100 mg, 0.5 mmol, 0.1 eq), triethylamine (1.6 g, 16.2 mmol, 3.0 eq) and N,N-dimethylformamide (20 mL). The reaction mixture was stirred for 2 hours at 70° C. The resulting mixture was diluted with water (150 mL) and extracted with ethyl acetate (2×100 mL). The combined organic phase was washed with brine (2×100 mL), dried over anhydrous sodium sulfate. After filtration, the filtrate was concentrated under vacuum. The crude residue was applied onto a silica gel column and eluted with ethyl acetate/petroleum ether=1:0 to give 3-[4-(3,3-diethoxyprop-1-yn-1-yl)-1-oxo-3H-isoindol-2-yl]piperidine-2,6-dione (1.8 g, 89.9%) as light yellow solid. LC-MS (ESI, m/z) M+1: 371. $^1$H NMR (300 MHz, DMSO-$d_6$) δ 11.01 (s, 1H), 7.79 (ddd, J=11.7, 7.5, 1.2 Hz, 2H), 7.68-7.51 (m, 2H), 5.60 (s, 1H), 5.15 (dd, J=13.2, 5.1 Hz, 1H), 4.51 (d, J=17.7 Hz, 1H), 4.36 (d, J=17.7 Hz, 1H), 3.77-3.55 (m, 4H), 3.01-2.83 (m, 2H), 2.63 (s, 1H), 2.11-1.97 (m, 1H), 1.19 (t, J=7.1 Hz, 6H).

Synthesis of 3-[2-(2,6-dioxopiperidin-3-yl)-1-oxo-3H-isoindol-4-yl]prop-2-ynal: Into a 50 mL round-bottom flask, were placed 3-[4-(3,3-diethoxyprop-1-yn-1-yl)-1-oxo-3H-isoindol-2-yl]piperidine-2,6-dione (1.6 g, 4.3 mmol, 1.0 eq) and formic acid (8 mL). Then the reaction mixture was stirred for 1 hour at 25° C. The precipitated solids were collected by filtration and washed with water (2×30 mL). Finally, 3-[2-(2,6-dioxopiperidin-3-yl)-1-oxo-3H-isoindol-4-yl]prop-2-ynal (600 mg, 46.9%) was obtained as brown yellow solid. LC-MS (ESI, m/z) M+1: 297.

Example INT-8: Preparation of Synthesis of tert-butyl 1-ethynyl-6-azaspiro[2.5]octane-6-carboxylate Synthesis of tert-butyl 4-(2-ethoxy-2-oxoethylidene)piperidine-1-carboxylate: To a stirred mixture of triethyl phosphonoacetate (21.9 g, 97.9 mmol, 1.3 eq) in tetrahydrofuran (150 mL) was added t-BuOK (10.9 g, 97.9 mmol, 1.3 eq) in portions at 0° C. The reaction mixture was stirred for 1 hour at 0° C. After that, to the above mixture was added tert-butyl 4-oxopiperidine-1-carboxylate (15.0 g, 75.3 mmol, 1.0 eq) at −50° C. The reaction mixture was stirred for additional 14 hours at 25° C. The resulting mixture was diluted with water (200 mL) and extracted with ethyl acetate (3×150 mL). The combined organic layers were washed with brine (100 mL), dried over anhydrous sodium sulfate. After filtration, the filtrate was concentrated under vacuum. The crude residue was applied onto a silica gel column and eluted with ethyl acetate/petroleum ether=(0:1 to 5:1) to give tert-butyl 4-(2-ethoxy-2-oxoethylidene)piperidine-1-carboxylate (10 g, 49%) as a brown oil. $^1$H NMR (400 MHz, Chloroform-d) δ 5.72 (t, J=1.6 Hz, 1H), 4.16 (q, J=7.2 Hz, 2H), 3.51-3.43 (m, 4H), 2.99-2.91 (m, 2H), 2.33-2.25 (m, 2H), 1.48 (S, 9H), 28 (t, J=7.2 Hz, 3H).

Synthesis of 6-tert-butyl 1-ethyl 6-azaspiro[2.5]octane-1,6-dicarboxylate: To a stirred mixture of trimethyl(oxo)-lambda6-sulfanylium iodide (16.3 g, 74.2 mmol, 2.0 eq) in methyl sulfoxide (150 mL) was added t-BuOK (8.3 g, 74.2 mmol, 2.0 eq) in portions at 25° C. The reaction mixture was stirred for 3 hours at 25° C. After that, to the above mixture was added tert-butyl 4-(2-ethoxy-2-oxoethylidene)piperidine-1-carboxylate (10.0 g, 37.1 mmol, 1.0 eq) at 25° C. The reaction mixture was stirred for additional 6 hours at 25° C. The resulting mixture was diluted with water (300 mL) and extracted with ethyl acetate (3×150 mL). The combined organic layers were washed with water (2×50 mL) and brine (50 mL), dried over anhydrous sodium sulfate. After filtration, the filtrate was concentrated under vacuum. The crude residue was applied onto a silica gel column and eluted with ethyl acetate/petroleum ether=(0:1 to 10:1) to give 6-tert-butyl 1-ethyl 6-azaspiro[2.5]octane-1,6-dicarboxylate (4.5 g, 43%) as a yellow oil. $^1$H NMR (300 MHz, Chloroform-d) δ 4.23-4.09 (m, 2H), 3.59-3.37 (m, 3H), 3.35-3.21 (m, 1H), 1.81-1.68 (m, 2H), 1.68-1.52 (m, 2H), 1.52-1.34 (m, 11H), 1.29 (t, J=7.2 Hz, 3H), 1.19 (t, J=5.1 Hz, 1H).

Synthesis of tert-butyl 1-(hydroxymethyl)-6-azaspiro[2.5]octane-6-carboxylate: To a stirred solution of 6-tert-butyl 1-ethyl 6-azaspiro[2.5]octane-1,6-dicarboxylate (4.5 g, 15.9 mmol, 1.0 eq) in tetrahydrofuran (50 mL) was added $LiAlH_4$ (1.8 g, 47.6 mmol, 3.0 eq) in portions at 0° C. under nitrogen atmosphere. The reaction mixture was stirred for 5 hours at 0° C. under nitrogen atmosphere. The reaction mixture was quenched by the addition of water (2 mL) and 15% NaOH (2 mL) and water (6 mL) at 0° C. The resulting mixture was filtered, and the filter cake was washed with tetrahydrofuran (3×10 mL). The filtrate was concentrated under vacuum to give tert-butyl 1-(hydroxymethyl)-6-azaspiro[2.5]octane-6-carboxylate (3.4 g, 89%) as a brown solid. $^1$H NMR (300 MHz, Chloroform-d) δ 3.81-3.46 (m, 4H), 3.40-3.25 (m, 2H), 1.74-1.54 (m, 2H), 1.47 (s, 11H), 1.29-1.15 (m, 1H), 0.99 (tdd, J=8.7, 6.6, 5.4 Hz, 1H), 0.58 (dd, J=8.7 Hz, 4.5 Hz, 1H), 0.30-0.21 (m, 1H).

Synthesis of tert-butyl 1-formyl-6-azaspiro[2.5]octane-6-carboxylate: To a stirred mixture of tert-butyl 1-(hydroxymethyl)-6-azaspiro[2.5]octane-6-carboxylate (3.4 g, 14.1 mmol, 1.0 eq) in dichloromethane (50 mL) was added Dess-Martin Periodinane (11.9 g, 28.2 mmol, 2.0 eq) in portions at 25° C. The reaction mixture was stirred for 4 hours at 25° C. The resulting mixture was filtered, the filter cake was washed with dichloromethane (3×10 mL). The filtrate was washed with $NaHCO_3$ (3×10 mL, aqueous), brine (10 mL), dried anhydrous sodium sulfate and then concentrated under vacuum. The crude residue was applied onto a silica gel column and eluted with ethyl acetate/petroleum ether=(0:1 to 3:1) to give tert-butyl 1-formyl-6-azaspiro[2.5]octane-6-carboxylate (1.8 g, 53%) as a brown solid. LC-MS (ESI, m/z) M+1-tBu: 184.

Synthesis of tert-butyl 1-ethynyl-6-azaspiro[2.5]octane-6-carboxylate: To a stirred mixture of tert-butyl 1-formyl-6-azaspiro[2.5]octane-6-carboxylate (1.8 g, 7.5 mmol, 1.0 eq) and dimethyl (1-diazo-2-oxopropyl)phosphonate (1.3 g, 9.8 mmol, 1.3 eq) in $CH_3OH$ (30 mL) was added $K_2CO_3$ (3.1 g, 22.6 mmol, 3.0 eq) at 25° C. The reaction mixture was stirred for 3 hours at 25° C. The resulting mixture was concentrated under vacuum. The crude residue was applied onto a silica gel column and eluted with ethyl acetate/petroleum ether=(0:1 to 3:1) to give tert-butyl 1-ethynyl-6-azaspiro[2.5]octane-6-carboxylate (1.3 g, 73%) as a yellow oil.

Example INT-9: Preparation of (1R)-1-ethynyl-6-(3-methoxy-4-nitrobenzoyl)-6-azaspiro[2.5]octane and (1S)-1-ethynyl-6-(3-methoxy-4-nitrobenzoyl)-6-azaspiro[2.5]octane Synthesis of 1-ethynyl-6-azaspiro[2.5]octane: To a stirred mixture of tert-butyl 1-ethynyl-6-azaspiro[2.5]octane-6-carboxylate (1.2 g, 5.1 mmol, 1.0 eq) and 2,6-dimethylpyridine (1.6 g, 15.3 mmol, 3.0 eq) in dichloromethane (20 mL) was added TMSI (2.0 g, 10.2 mmol, 2.0 eq) dropwise at 0° C. The reaction mixture was stirred for 2 hours at 0° C. The resulting mixture was concentrated under vacuum to give 1-ethynyl-6-azaspiro[2.5]octane (2.3 g, crude) as a brown solid.

Synthesis of 1-ethynyl-6-(3-methoxy-4-nitrobenzoyl)-6-azaspiro[2.5]octane: To a stirred mixture of 1-ethynyl-6-azaspiro[2.5]octane (2.3 g, crude), 3-methoxy-4-nitrobenzoic acid (3.4 g, 17.0 mmol, 1.0 eq), N-ethyl-N-isopropylpropan-2-amine (4.4 g, 34.0 mmol, 2.0 eq) in N,N-dimethylformamide (50 mL) was added HATU (9.7 g, 25.5 mmol, 1.5 eq) in portions at 25° C. The reaction mixture was stirred for 14 hours at 25° C. The resulting mixture was diluted with water (150 mL) and extracted with ethyl acetate (3×50 mL). The combined organic layers were washed with water (3×30 mL) and brine (30 mL), dried over anhydrous sodium sulfate. After filtration, the filtrate was concentrated under vacuum. The crude residue was applied onto a silica gel column and eluted with ethyl acetate/petroleum ether=(0:1 to 1:1) to give 1-ethynyl-6-(3-methoxy-4-nitrobenzoyl)-6-azaspiro[2.5]octane (1.1 g, 16%) as a yellow oil. LC-MS (ESI, m/z) M+1: 351.

Synthesis of (1R)-1-ethynyl-6-(3-methoxy-4-nitrobenzoyl)-6-azaspiro[2.5]octane and (1S)-1-ethynyl-6-(3-methoxy-4-nitrobenzoyl)-6-azaspiro[2.5]octane: 500 mg of 1-ethynyl-6-(3-methoxy-4-nitrobenzoyl)-6-azaspiro[2.5]octane was purified by Chiral-SFC using the following conditions: Column: CHIRAL ART Cellulose-SB, 3*25 cm, 5 μm; mobile phase A: $CO_2$; mobile phase B: $CH_3CH_3OH$—Preparative; Flow rate: 50 mL/min; Gradient: isocratic 40% B; Detect 220 nm. Finally, (1R)-1-ethynyl-6-(3-methoxy-4-nitrobenzoyl)-6-azaspiro[2.5]octane (200 mg) was obtained as a brown solid and (1S)-1-ethynyl-6-(3-methoxy-4-nitrobenzoyl)-6-azaspiro[2.5]octane (200 mg) was obtained as a brown solid. 8A, $T_R$=1.337 min in CHIRAL-SFC, Column: Amylose Neo 50*3.0 mm, 3.0 um. mobile phase A: $CO_2$; mobile phase B: IPA:Hex=1:1, Start Conc. of Pump B: 10% to 50% in 2.0 min, hold 1.0 min at 50%, Oven Temperature: 35° C. 8B, $T_R$=1.461 min in CHIRAL-SFC, Column: Amylose Neo 50*3.0 mm, 3.0 um. mobile phase A: $CO_2$; mobile phase B: IPA:Hex=1:1, Start Conc. of Pump B: 10% to 50% in 2.0 min, hold 1.0 min at 50%, Oven Temperature: 35° C.

Example INT-10: Preparation of 3-(4-{2-[(1S)-6-azaspiro[2.5]octan-1-yl]ethynyl}-1-oxo-3H-isoindol-2-yl)piperidine-2,6-dione Synthesis of tert-butyl (1R)-1-ethynyl-6-azaspiro[2.5]octane-6-carboxylate & (tert-butyl (1S)-1-ethynyl-6-azaspiro[2.5]octane-6-carboxylate: 8.0 g of tert-butyl 1-ethynyl-6-azaspiro[2.5]octane-6-carboxylate was purified by Chiral-Prep-SFC using the following conditions: Column: CHIRALPAK IG, 3*25 cm, 5 μm; Mobile Phase A: Hex—HPLC, Mobile Phase B: IPA—HPLC; Flow rate: 65 mL/min; Gradient: 5% B to 5% B in 10 min; Wave Length: 220 nm. Finally, tert-butyl (1R)-1-ethynyl-6-azaspiro[2.5]octane-6-carboxylate was obtained as a light yellow oil (3.5 g, 43.8%) and (tert-butyl (1S)-1-ethynyl-6-azaspiro[2.5]octane-6-carboxylate was obtained as a light yellow oil (2.7 g, 33.8%). 5A, $T_R$=2.227 min in CHIRAL-HPLC, Column: CHIRALPAK AD-3, 100*4.6 mm, 3 um AD30CS—V0006, mobile phase A: n-Hexane; mobile phase B: Ethanol, Start Conc. of Pump B: 2.0%, Oven Temperature: 25° C. 5B, $T_R$=2.642 min in CHIRAL-HPLC, Column: CHIRALPAK AD-3, 100*4.6 mm, 3 um AD30CS—V0006, mobile phase A: n-Hexane; mobile phase B: Ethanol, Start Conc. of Pump B: 2.0%, Oven Temperature: 25° C.

Synthesis of tert-butyl (1S)-1-{2-[2-(2,6-dioxopiperidin-3-yl)-1-oxo-3H-isoindol-4-yl]ethynyl}-6-azaspiro[2.5]octane-6-carboxylate: Into a 40-mL sealed-tube purged and maintained with an inert atmosphere of nitrogen, were placed tert-butyl (1S)-1-ethynyl-6-azaspiro[2.5]octane-6-carboxylate (800 mg, 3.4 mmol, 1.0 eq), 3-(4-iodo-1-oxo-3H-isoindol-2-yl)piperidine-2,6-dione (1.4 g, 3.7 mmol, 1.1 eq), CuI (65 mg, 0.3 mmol, 0.1 eq), $Pd(PPh_3)_4$ (393 mg, 0.3 mmol, 0.1 eq), $Et_3N$ (1.0 g, 10.2 mmol, 3.0 eq), DMF (10 mL). The resulting solution was stirred for 2 hours at 70° C. The resulting mixture was then quenched by the addition of water (100 mL) and then was extracted with ethyl acetate (2×100 mL). The combined organics were washed with brine (2×100 mL) and dried over anhydrous $Na_2SO_4$. After filtration, the filtrate was concentrated under vacuum. The crude residue was applied onto a silica gel column and eluted with ethyl acetate/petroleum ether=1:1 to give tert-butyl (1S)-1-{2-[2-(2,6-dioxopiperidin-3-yl)-1-oxo-3H-isoindol-4-yl]ethynyl}-6-azaspiro[2.5]octane-6-carboxylate as a light yellow solid (1.4 g, 86.2%). LC-MS (ESI, m/z) M+1: 478. $^1$HNMR (400 MHz, DMSO-$d_6$) δ 11.00 (d, J=2.6 Hz, 1H), 7.70 (d, J=7.6 Hz, 1H), 7.66-7.48 (m, 2H), 5.13 (dd, J=13.4, 5.2 Hz, 1H), 4.43 (dd, J=17.8, 8.8 Hz, 1H), 4.31 (dd, J=17.8, 3.0 Hz, 1H), 3.54-3.45 (m, 2H), 3.40-3.31 (m, 2H), 3.00-2.86 (m, 1H), 2.60 (dd, J=17.4, 3.8 Hz, 1H), 2.49-2.41 (m, 1H), 2.04 (dd, J=12.2, 6.0 Hz, 1H), 1.67-1.56 (m, 3H), 1.51-1.43 (m, 1H), 1.41 (s, 9H), 1.34-1.25 (m, 1H), 1.03 (dd, J=8.6, 4.2 Hz, 1H), 0.80-0.77 (m, 1H).

Synthesis of 3-(4-{2-[(1S)-6-azaspiro[2.5]octan-1-yl]ethynyl}-1-oxo-3H-isoindol-2-yl)piperidine-2,6-dione: Into a 100-mL round-bottom flask, were placed tert-butyl (1S)-1-{2-[2-(2,6-dioxopiperidin-3-yl)-1-oxo-3H-isoindol-4-yl]ethynyl}-6-azaspiro[2.5]octane-6-carboxylate (assumed) (1.3 g, 2.7 mmol, 1.0 eq), $CH_2Cl_2$ (15 mL), 2,6-dimethylpyridine (1.2 g, 10.9 mmol, 4.0 eq). After that, TMSI (1.6 g, 8.2 mmol, 3.0 eq) was added at 0° C. The resulting mixture was stirred for 2 hours at 25° C. The resulting mixture was concentrated under vacuum to give 3-(4-{2-[(1S)-6-azaspiro[2.5]octan-1-yl]ethynyl}-1-oxo-3H-isoindol-2-yl)piperidine-2,6-dione (assumed) as a yellow solid (1.6 g crude). LC-MS (ESI, m/z) M+1: 378.

Example INT-11: Preparation of (2S)-4-(3-methoxy-4-nitrobenzoyl)-2-(prop-2-yn-1-yl)morpholine & (2R)-4-(3-methoxy-4-nitrobenzoyl)-2-(prop-2-yn-1-yl)morpholine Synthesis of tert-butyl 2-formylmorpholine-4-carboxylate: Into a 500 mL 3-necked round-bottom flask and maintained with an inert atmosphere of nitrogen, were placed oxalic dichloride (17.5 g, 138.1 mmol, 2.0 eq), dichloromethane (150 mL). After that, methyl sulfoxide (27.0 g, 345.2 mmol, 5.0 eq) was added at −78° C. Then the mixture was stirred for 1 hour at −78° C. A solution of tert-butyl 2-(hydroxymethyl)morpholine-4-carboxylate (15.0 g, 69.0 mmol, 1.0 eq) in dichloromethane (50 mL) was added dropwise at −78° C., then the mixture was stirred for 30 minutes. This was followed by the addition of triethylamine (34.9 g, 345.2 mmol, 5.0 eq) at −78° C. The mixture was stirred at 25° C. for 1 hour. The resulting mixture was then quenched by the addition of water (300 mL) and then extracted with dichloromethane (2×200 mL). The combined organics were washed with brine (2×200 mL) and dried over anhydrous $Na_2SO_4$. After filtration, the filtrate was concentrated under vacuum. The crude residue was applied onto a silica gel column and eluted with ethyl acetate/petroleum ether=1:1 to give tert-butyl 2-formylmorpholine-4-carboxylate as a light yellow oil (12.0 g, 80.7%). LC-MS (ESI, m/z) M-(t-Bu)+41+1: 201. $^1$HNMR (400 MHz, DMSO-$d_6$) δ 9.57

(s, 1H), 4.07 (dd, J=8.8, 3.6 Hz, 1H), 3.90-3.85 (m, 1H), 3.80-3.66 (m, 2H), 3.58-3.52 (m, 1H), 3.12-3.01 (m, 2H), 1.41 (d, J=2.4 Hz, 9H).

Synthesis of tert-butyl 2-(2-methoxyethenyl)morpholine-4-carboxylate: Into a 500-mL 3-necked round-bottom flask purged and maintained with an inert atmosphere of nitrogen, were placed (methoxymethyl)triphenylphosphanium chloride (28.7 g, 83.6 mmol, 1.5 eq), tetrahydrofuran (120 mL). After that, t-BuOK (9.4 g, 83.6 mmol, 1.5 eq) was added at 0° C. After 30 minutes stirring, to the above mixture was added a solution of tert-butyl 2-formylmorpholine-4-carboxylate (12.0 g, 55.7 mmol, 1.0 eq) in tetrahydrofuran at −20° C. The resulting solution was allowed to stirring for an additional 6 hours at 25° C. The resulting mixture was then quenched by the addition of $NH_4Cl$ (aq.) (100 mL) and extracted with ethyl acetate (2×150 mL). The combined organics were washed with brine (2×150 mL) and dried over anhydrous $Na_2SO_4$. After filtration, the filtrate was concentrated under vacuum. The crude residue was applied onto a silica gel column and eluted with ethyl acetate/petroleum ether=1:1 to give tert-butyl 2-(2-methoxyethenyl)morpholine-4-carboxylate as a light yellow oil (4.5 g, 33.2%). LC-MS (ESI, m/z) M-(t-Bu)+41+1: 229. $^1$HNMR (300 MHz, DMSO-$d_6$) δ 6.68 (d, J=12.6 Hz, 1H), 6.12 (dd, J=6.3, 1.2 Hz, 1H), 4.72 (dd, J=12.6, 7.8 Hz, 1H), 4.31 (dd, J=7.8, 6.3 Hz, 1H), 4.16-4.09 (m, 1H), 3.87-3.74 (m, 1H), 3.79-3.62 (m, 1H), 3.60 (s, 3H), 3.42-3.32 (m, 2H), 1.41 (s, 9H).

Synthesis of tert-butyl 2-(2-oxoethyl)morpholine-4-carboxylate: Into a 100-mL round-bottom flask, were placed tert-butyl 2-(2-methoxyethenyl)morpholine-4-carboxylate (4.5 g, 18.5 mmol, 1.0 eq), formic acid (10 mL). The resulting solution was stirred for 1 hour at 25° C. The mixture was neutralized to pH=7-8 with $NaHCO_3$ (aq.) and then extracted with ethyl acetate (2×100 mL). The combined organics were washed with brine (2×100 mL) and dried over anhydrous $Na_2SO_4$. After filtration, the filtrate was concentrated under vacuum. The crude residue was applied onto a silica gel column and eluted with ethyl acetate/petroleum ether=1:3 to give tert-butyl 2-(2-oxoethyl)morpholine-4-carboxylate as a light yellow oil (2.5 g, 58.9%). LC-MS (ESI, m/z) M-(t-Bu)+41+1: 215. $^1$HNMR (300 MHz, DMSO-$d_6$) δ 9.68-9.52 (m, 1H), 4.24-4.08 (m, 1H), 3.95-3.65 (m, 4H), 3.48-3.37 (m, 1H), 2.89-2.80 (s, 1H), 2.63 (ddd, J=16.8, 4.5, 1.2 Hz, 1H), 2.50-2.42 (m, 1H), 1.41 (s, 9H).

Synthesis of tert-butyl 2-(prop-2-yn-1-yl)morpholine-4-carboxylate: Into a 100-mL round-bottom flask, were placed tert-butyl 2-(2-oxoethyl)morpholine-4-carboxylate (2.5 g, 10.9 mmol, 1.0 eq), MeOH (30 mL), $K_2CO_3$ (3.0 g, 21.8 mmol, 2.0 eq), seyferth-gilbert homologation (3.1 g, 16.4 mmol, 1.5 eq). The resulting solution was stirred for 2 hours at 25° C. The resulting mixture was then quenched by the addition of water (60 mL) and then extracted with ethyl acetate (2×60 mL). The combined organics were washed with brine (2×60 mL) and dried over anhydrous $Na_2SO_4$. After filtration, the filtrate was concentrated under vacuum. The crude residue was applied onto a silica gel column and eluted with ethyl acetate/petroleum ether=1:3 to give tert-butyl 2-(prop-2-yn-1-yl)morpholine-4-carboxylate as a light yellow oil (2.0 g, 81.4%). LC-MS (ESI, m/z) M-(t-Bu)+41+1: 211. $^1$HNMR (400 MHz, DMSO-$d_6$) δ 3.91 (d, J=13.2 Hz, 1H), 3.80 (ddd, J=11.6, 3.8, 1.6 Hz, 1H), 3.74-3.65 (m, 1H), 3.44-3.36 (m, 3H), 2.88 (t, J=2.8 Hz, 1H), 2.62 (br, 1H), 2.38 (td, J=6.6, 2.8 Hz, 2H), 1.41 (s, 9H).

Synthesis of 2-(prop-2-yn-1-yl)morpholine hydrochloride: Into a 100-mL round-bottom flask, were placed tert-butyl 2-(prop-2-yn-1-yl)morpholine-4-carboxylate (1.8 g, 8.0 mmol, 1.0 eq), dichloromethane (20 mL), HCl(gas) in 1,4-dioxane (20 mL). The resulting solution was stirred for 1 hour at 25° C. The resulting mixture was concentrated under vacuum to give 2-(prop-2-yn-1-yl)morpholine hydrochloride as a light yellow oil (1.2 g crude). LC-MS (ESI, m/z) M+1: 126.

Synthesis of 4-(3-methoxy-4-nitrobenzoyl)-2-(prop-2-yn-1-yl)morpholine: Into a 50-mL round-bottom flask, were placed 2-(prop-2-yn-1-yl)morpholine hydrochloride (1.1 g, 6.8 mmol, 1.0 eq), 3-methoxy-4-nitrobenzoic acid (1.3 g, 6.8 mmol, 1.0 eq), HATU (2.6 g, 6.8 mmol, 1.0 eq), DIEA (2.6 g, 20.4 mmol, 3.0 eq), N,N-Dimethylformamide (11 mL). The resulting solution was stirred for 2 hours at 25° C. The resulting mixture was then quenched by the addition of water (100 mL) and then extracted with ethyl acetate (2×100 mL). The combined organics were washed with brine (2×100 ml) and dried over anhydrous $Na_2SO_4$. After filtration, the filtrate was concentrated under vacuum. The crude residue was applied onto a silica gel column and eluted with ethyl acetate/petroleum ether=1:0 to give 4-(3-methoxy-4-nitrobenzoyl)-2-(prop-2-yn-1-yl)morpholine as a light yellow oil (1.8 g, 86.9%). LC-MS (ESI, m/z) M+1: 305. $^1$HNMR (300 MHz, DMSO-$d_6$) δ 7.95 (d, J=8.1 Hz, 1H), 7.40 (d, J=1.5 Hz, 1H), 7.14 (dd, J=8.1, 1.5 Hz, 1H), 4.50 (d, J=13.2 Hz, 1H), 4.28 (d, J=13.5 Hz, 1H), 3.96 (s, 3H), 3.75 (d, J=11.7 Hz, 1H), 3.66-3.44 (m, 1H), 3.35-3.11 (m, 1H), 3.11-2.62 (m, 4H), 2.34 (s, 1H).

Synthesis of (2S)-4-(3-methoxy-4-nitrobenzoyl)-2-(prop-2-yn-1-yl)morpholine & (2R)-4-(3-methoxy-4-nitrobenzoyl)-2-(prop-2-yn-1-yl)morpholine: 700 mg of 4-(3-methoxy-4-nitrobenzoyl)-2-(prop-2-yn-1-yl)morpholine was purified by Chiral-Prep-SFC using the following conditions: Column: (R, R)-WHELK-O1-Kromasil, 2.11*25 cm, 5 μm; Mobile Phase A: $CO_2$, Mobile Phase B: IPA; Flow rate: 55 mL/min; Gradient: isocratic 30% B; Wave Length: 220 nm. Finally, (2S)-4-(3-methoxy-4-nitrobenzoyl)-2-(prop-2-yn-1-yl)morpholine was obtained as a light yellow oil (300 mg) and (2R)-4-(3-methoxy-4-nitrobenzoyl)-2-(prop-2-yn-1-yl)morpholine was obtained as a light yellow oil (310 mg). 6A, $T_R$=1.556 min in CHIRAL-SFC, Column: 3:(R,R)-WHELK-O1 50×4.6 mm 3.5 um phase A: $CO_2$; mobile phase B: IPA (50% Hex), Start Conc. of Pump B: 10.0% in 4 min, Oven Temperature: 35° C. 6B, $T_R$=1.685 min in CHIRAL-SFC, Column: 3: (R,R)-WHELK-O1 50×4.6 mm 3.5 um phase A: $CO_2$; mobile phase B: IPA (50% Hex), Start Conc. of Pump B: 10.0% in 4 min, Oven Temperature: 35° C.

Example INT-12: Preparation of 3-(5-iodo-1-oxoisoindolin-2-yl)piperidine-2,6-dione Synthesis of methyl 2-(bromomethyl)-4-iodobenzoate: Into a 500-mL round-bottom flask, were placed methyl 4-iodo-2-methylbenzoate (24.0 g, 86.9 mmol, 1.0 eq), NBS (20.1 g, 113.0 mmol, 1.3 eq), AIBN (8.6 g, 52.2 mmol, 0.6 eq), $CCl_4$ (250 mL). The reaction mixture was stirred for 14 hours at 80° C. The resulting mixture was then quenched by the addition of water (100 mL) and then extracted with dichloromethane (2×100 mL). The combined organics were washed with brine (2×100 mL) and dried over anhydrous $Na_2SO_4$. After filtration, the filtrate was concentrated under vacuum to give methyl 2-(bromomethyl)-4-iodobenzoate as a dark blue solid (26.0 g crude).

Synthesis of 3-(5-iodo-1-oxoisoindolin-2-yl)piperidine-2,6-dione: Into a 1000-mL round-bottom flask, were placed methyl 2-(bromomethyl)-4-iodobenzoate (26.0 g, 73.2 mmol, 1.0 eq), 3-aminopiperidine-2,6-dione (14.1 g, 109.9 mmol, 1.5 eq), $Et_3N$ (22.2 g, 219.7 mmol, 3.0 eq), $CH_3CN$ (300 mL). The resulting solution was stirred for 14 hours at 80° C. The resulting mixture was then quenched by the addition of water (100 mL) and then extracted with ethyl acetate (2×100 mL). The combined organics were washed with brine (2×100 mL) and dried over anhydrous $Na_2SO_4$. After filtration, the resulting mixture was concentrated under vacuum. The crude residue was applied onto a silica gel column and eluted with ethyl acetate/petroleum ether=1:0 to give 3-(5-iodo-1-oxoisoindolin-2-yl)piperidine-2,6-dione as a dark blue solid (5.4 g, 19.9%). LC-MS (ESI, m/z) M+1: 370. $^1$HNMR (300 MHz, DMSO-$d_6$) δ 11.00 (s, 1H), 8.07 (s, 1H), 7.89 (d, J=7.8 Hz, 1H), 7.52 (d, J=9.0 Hz, 1H), 5.11 (dd, J=13.5, 5.1 Hz, 1H), 4.45 (d, J=17.7 Hz, 1H), 4.32 (d, J=17.4 Hz, 1H), 2.99-2.79 (m, 1H), 2.60 (d, J=17.7 Hz, 1H), 2.45-2.28 (m, 1H), 2.02 (d, J=8.7 Hz, 1H).

Example INT-13: Preparation of (7R)-7-ethynyl-4-(3-methoxy-4-nitrobenzoyl)-1,4-oxazepane & (7S)-7-ethynyl-4-(3-methoxy-4-nitrobenzoyl)-1,4-oxazepane Synthesis of 4-(benzyloxy)-3-hydroxybutanenitrile: Into a 1 L 3-necked round-bottom flask, were added 2-[(benzyloxy)methyl]oxirane (30.0 g, 182.7 mmol, 1.0 eq), DMF (300 mL), water (60 mL), KCN (23.8 g, 365.4 mmol, 2.0 eq) at 25° C. The resulting mixture was stirred for 14 hours at 25° C. The resulting mixture was diluted with EtOAc (300 mL), and then washed with water (3×100 mL) and brine (100 mL). The organic layer was dried over anhydrous $Na_2SO_4$. After filtration, the filtrate was concentrated under vacuum. The crude residue was applied onto a silica gel column and eluted with ethyl acetate/petroleum ether=1:3 to give 4-(benzyloxy)-3-hydroxybutanenitrile as a white oil (18.0 g, 51.5%). $^1$HNMR (300 MHz, DMSO-$d_6$) δ 7.36-7.23 (m, 5H), 4.52 (s, 2H), 4.10-3.72 (m, 2H), 3.45 (dd, J=9.9, 5.4 Hz, 1H), 3.36 (dd, J=9.9, 6.0 Hz, 1H), 2.70-2.58 (m, 2H).

Synthesis of 4-amino-1-(benzyloxy)butan-2-ol: Into a 500 mL 3-necked round-bottom flask, were added 4-(benzyloxy)-3-hydroxybutanenitrile (18.0 g, 94.1 mmol, 1.0 eq), THE (200 mL). After that, $LiAlH_4$ (5.4 g, 141.2 mmol, 1.5 eq) was added in portions at 0° C. The resulting mixture was stirred for additional 30 min at 0° C. The reaction was quenched by the addition of water (5.4 mL), 15% NaOH (5.4 mL), water (16.2 mL) at 0° C. The resulting mixture was filtered, and the filtrate was concentrated under vacuum to give 4-amino-1-(benzyloxy)butan-2-ol as a brown oil (14.1 g crude).

Synthesis of N-[4-(benzyloxy)-3-hydroxybutyl]-2-chloroacetamide: Into a 500 mL round-bottom flask, were added 4-amino-1-(benzyloxy)butan-2-ol (14.1 g, crude), dichloromethane (200 mL), TEA (4.4 g, 43.1 mmol, 1.5 eq) at 25° C. After that, chloroacetyl chloride (3.9 g, 34.4 mmol, 1.2 eq) was added dropwise. The resulting mixture was stirred for 4 hours at 25° C. The reaction mixture was quenched with water (3 mL), and then concentrated under vacuum. The residue was purified by reverse flash chromatography using the following conditions: column, C18 silica gel; mobile phase, $CH_3CN$ in water (0.1% TFA), 30% to 70% gradient in 10 min; detector, UV 220 nm. Finally, N-[4-(benzyloxy)-3-hydroxybutyl]-2-chloroacetamide was obtained as a white oil (3.2 g, 32.9%). $^1$HNMR (300 MHz, DMSO-$d_6$) δ 8.19 (d, J=6.3 Hz, 1H), 7.47-7.18 (m, 5H), 4.67 (bs, 1H), 4.49 (s, 2H), 4.03 (s, 2H), 3.74-3.60 (m, 1H), 3.41-3.25 (m, 2H), 3.25-3.08 (m, 2H), 1.75-1.43 (m, 2H).

Synthesis of 7-[(benzyloxy)methyl]-1,4-oxazepan-3-one: Into a 500 mL round-bottom flask, were added N-[4-(benzyloxy)-3-hydroxybutyl]-2-chloroacetamide (3.2 g, 11.7 mmol, 1.0 eq), NaOH (1.4 g, 35.3 mmol, 3.0 eq), dichloromethane (200 mL). The resulting mixture was stirred for 2 days at 25° C. The reaction mixture was washed with aq. $NH_4Cl$ (100 mL) and brine (100 mL), and then dried over anhydrous $Na_2SO_4$. After filtration, the filtrate was concentrated under vacuum. The residue was purified by reverse flash chromatography using the following conditions: column, C18 silica gel; mobile phase, $CH_3CN$ in water (0.1% TFA), 20% to 50% gradient in 10 min; detector, UV 220 nm. Finally, 7-[(benzyloxy)methyl]-1,4-oxazepan-3-one was obtained as a white solid (1.1 g, 39.7%). LC-MS (ESI, m/z) M+1: 236.

Synthesis of 7-[(benzyloxy)methyl]-1,4-oxazepane: Into a 50 mL round-bottom flask, were added 7-[(benzyloxy)methyl]-1,4-oxazepan-3-one (1.1 g, 4.7 mmol, 1.0 eq), THE (20 mL). After that, $LiAlH_4$ (0.5 g, 14.1 mmol, 3.0 eq) was added in portions at 0° C. The resulting mixture was stirred for 2 hours at 25° C. The reaction was quenched by the addition of water (0.5 mL), 15% NaOH (0.5 mL), water (1.5 mL) at 0° C. The resulting mixture was filtered, and then the filtrate was concentrated under vacuum to give 7-[(benzyloxy)methyl]-1,4-oxazepane as a brown oil (1.1 g crude). LC-MS (ESI, m/z) M+1: 222.

Synthesis of tert-butyl 7-[(benzyloxy)methyl]-1,4-oxazepane-4-carboxylate: Into a 50 mL round-bottom flask, were added 7-[(benzyloxy)methyl]-1,4-oxazepane (1.1 g, crude), dichloromethane (15 mL), TEA (0.9 g, 9.0 mmol, 2.0 eq) and $Boc_2O$ (1.3 g, 5.8 mmol, 1.3 eq) at 25° C. The reaction mixture was stirred for 14 hours at 25° C. The resulting mixture was concentrated under vacuum. The crude residue was applied onto a silica gel column and eluted with ethyl acetate/petroleum ether=1:5 to give tert-butyl 7-[(benzyloxy)methyl]-1,4-oxazepane-4-carboxylate as a brown oil (500 mg, 34.4%).

Synthesis of tert-butyl 7-(hydroxymethyl)-1,4-oxazepane-4-carboxylate: Into a 50 mL pressure tank reactor, were added tert-butyl 7-[(benzyloxy)methyl]-1,4-oxazepane-4-carboxylate (500 mg, 1.6 mmol, 1.0 eq), Pd/C (100 mg) and MeOH (15 mL) at 25° C. The resulting mixture was stirred for 2 days at 30° C. under $H_2$ atmosphere. The resulting mixture was filtered, the filter cake was washed with MeOH (3×30 mL). The filtrate was concentrated under vacuum. Finally, tert-butyl 7-(hydroxymethyl)-1,4-oxazepane-4-carboxylate was obtained as a brown oil (300 mg, 83.4%). LC-MS (ESI, m/z) M+1: 232.

Synthesis of tert-butyl 7-formyl-1,4-oxazepane-4-carboxylate: Into a 50 mL round-bottom flask, were added tert-butyl 7-(hydroxymethyl)-1,4-oxazepane-4-carboxylate (270 mg, 1.2 mmol, 1.0 eq), dichloromethane (10 mL) and Dess-Martin reagent (990 mg, 2.3 mmol, 2.0 eq) at 25° C. The reaction mixture was stirred for 2 hours at 25° C. The resulting mixture was diluted with dichloromethane (50 mL) and then washed with water (10 mL) and aq. $NaHCO_3$ (10 mL). The organic phase was dried over anhydrous $Na_2SO_4$. After filtration, the filtrate was concentrated under vacuum. The crude residue was applied onto a silica gel column and eluted with ethyl acetate/petroleum ether=1:3 to give tert-butyl 7-formyl-1,4-oxazepane-4-carboxylate as a brown oil (220 mg, 82.2%). LC-MS (ESI, m/z) M+1: 230.

Synthesis of tert-butyl 7-ethynyl-1,4-oxazepane-4-carboxylate: Into a 50 mL round-bottom flask, were added tert-butyl 7-formyl-1,4-oxazepane-4-carboxylate (220 mg, 1.0 mmol, 1.0 eq), dimethyl (1-diazo-2-oxopropyl)phosphonate (184 mg, 1.0 mmol, 1.1 eq), $K_2CO_3$ (265 mg, 1.9 mmol, 2.0 eq) and MeOH (10 mL) at 25° C. The resulting mixture was stirred for 2 hours at 25° C. The resulting mixture was then quenched by the addition of water (0.5 mL). The resulting mixture was filtered, the filter cake was washed with MeOH (3×10 mL). The filtrate was concentrated under vacuum. The crude residue was applied onto a silica gel column and eluted with ethyl acetate/petroleum ether=1:5 to give tert-butyl 7-ethynyl-1,4-oxazepane-4-carboxylate as a white solid (120 mg, 55.5%). $^1$HNMR (300 MHz, Chloroform-d) δ 4.47 (ddd, J=8.1, 4.2, 2.1 Hz, 1H), 4.04 (ddd, J=12.9, 5.4, 3.3 Hz, 1H), 3.74-3.43 (m, 5H), 2.55 (d, J=2.1 Hz, 1H), 2.30-2.04 (m, 2H), 1.57 (s, 9H).

Synthesis of 7-ethynyl-1,4-oxazepane hydrochloride: Into a 50-mL round-bottom flask, were placed tert-butyl 7-ethynyl-1,4-oxazepane-4-carboxylate (110 mg, 0.5 mmol, 1.0 eq), $CH_2Cl_2$ (2 mL), HCl (gas) in 1,4-dioxane (2 mL). The resulting mixture was stirred for 2 hours at 25° C. The resulting mixture was concentrated under vacuum to give 7-ethynyl-1,4-oxazepane hydrochloride as a yellow solid (80 mg crude).

Synthesis of 7-ethynyl-4-(3-methoxy-4-nitrobenzoyl)-1,4-oxazepane: Into an 8-mL sealed tube, were placed 7-ethynyl-1,4-oxazepane hydrochloride (70 mg, 0.4 mmol, 1.0 eq), 3-methoxy-4-nitrobenzoic acid (85 mg, 0.4 mmol, 1.0 eq), TCFH (182 mg, 0.6 mmol, 1.5 eq), NMI (124 mg, 1.5 mmol, 3.5 eq), $CH_3CN$ (2 mL). The resulting solution was stirred for 2 hours at 25° C. The resulting mixture was then quenched by the addition of water (30 mL) and then extracted with ethyl acetate (2×30 mL). The combined organic layers were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:1 to give 7-ethynyl-4-(3-methoxy-4-nitrobenzoyl)-1,4-oxazepane as a yellow solid (100 mg, 75.9%). LC-MS (ESI, m/z) M+1: 305. $^1$HNMR (300 MHz, Chloroform-d) δ 7.89 (dd, J=8.1, 3.0 Hz, 1H), 7.16 (d, J=6.0 Hz, 1H), 7.05 (dd, J=11.7, 8.1 Hz, 1H), 4.65 (s, 1H), 4.01 (s, 3H), 3.95-3.81 (m, 1H), 3.79-3.57 (m, 2H), 3.54-3.47 (m, 2H), 2.66-2.55 (m, 1H), 2.43-2.32 (m, 1H), 2.25-2.10 (m, 1H), 1.90-1.82 (m, 1H).

Synthesis of (7R)-7-ethynyl-4-(3-methoxy-4-nitrobenzoyl)-1,4-oxazepane & (7S)-7-ethynyl-4-(3-methoxy-4-nitrobenzoyl)-1,4-oxazepane: 100 mg of 7-ethynyl-4-(3-methoxy-4-nitrobenzoyl)-1,4-oxazepane (100 mg, 0.3 mmol, 1.0 eq) was purified by Chiral-Prep-SFC using the following conditions: Column: CHIRAL ART Amylose-C NEO, 3*25 cm, 5 μm; Mobile Phase A: MeOH—HPLC, Mobile Phase B: EtOH—HPLC; Flow rate: 35 mL/min; Gradient: 50% B to 50% B in 15 min; Wave Length: 220/254 nm. Finally, (7R)-7-ethynyl-4-(3-methoxy-4-nitrobenzoyl)-1,4-oxazepane was obtained as an off-white solid (46 mg, 46.0%) and (7S)-7-ethynyl-4-(3-methoxy-4-nitrobenzoyl)-1,4-oxazepane was obtained as an off-white solid (46 mg, 46.0%). A, $T_R$=2.645 min in CHIRAL-HPLC, Column: CHIRALPAK AD-3, 100*4.6 mm, 3 um AD30CS—VC006. Mobile Phase B: EtOH/MeOH=1/1. Conc. of Pump B: 100.0%. Oven Temperature: 25° C. B, $T_R$=3.731 min in CHIRAL-HPLC, Column: CHIRALPAK AD-3, 100*4.6 mm, 3 um AD30CS—VC006. Mobile Phase B: EtOH/MeOH=1/1. Conc. of Pump B: 100.0%. Oven Temperature: 25° C.

Example INT-14: Preparation of (1-ethynyl-5-azaspiro[2.5]octan-5-yl)(3-methoxy-4-nitrophenyl) methanone Synthesis of tert-butyl 3-methylidenepiperidine-1-carboxylate: Into a 3 L 4-necked round-bottom flask, were placed methyltriphenylphosphaniumbromide (365.7 g, 1023.8 mmol, 1.2 eq), THE (1.7 L). After that, n-BuLi (65.6 g, 1023.8 mmol, 1.2 eq) was added at 0° C. The resulting mixture was stirred for 1 hour at 0° C., and then tert-butyl 3-oxopiperidine-1-carboxylate (170.0 g, 853.2 mmol, 1.0 eq) was added at −50° C. The resulting mixture was stirred for 1 hour at 0° C. The resulting mixture was quenched by the addition of water (500 mL) and then extracted with ethyl acetate (2×1000 mL). The combined organic layers were washed with brine (2×1000 mL). The mixture was dried over anhydrous $Na_2SO_4$. After filtration, the filtrate was concentrated under vacuum. The crude residue was applied onto a silica gel column and eluted with ethyl acetate/petroleum ether=1:5 to give tert-butyl 3-methylidenepiperidine-1-carboxylate as a light yellow oil (76.0 g, 45.2%). LC-MS (ESI, m/z) M+1: 198. $^1$HNMR (300 MHz, DMSO-$d_6$) δ 4.82-4.69 (m, 2H), 3.81 (s, 2H), 3.44-3.31 (m, 2H), 2.23 (tt, J=6.0, 1.2 Hz, 2H), 1.63-1.46 (m, 2H), 1.39 (s, 9H).

Synthesis of 5-tert-butyl 1-ethyl 5-azaspiro[2.5]octane-1,5-dicarboxylate: Into a 3 L 4-necked round-bottom flask, were placed tert-butyl 3-methylidenepiperidine-1-carboxylate (90.0 g, 456.2 mmol, 1.0 eq), toluene (900 mL), $CuSO_4$ (7.3 g, 45.6 mmol, 0.1 eq). After that, ethyl diazoacetate (104.1 g, 912.4 mmol, 2.0 eq) was added at 80° C. under nitrogen atmosphere. The resulting mixture was stirred for 16 hours at 30° C. The resulting mixture was then quenched by the addition of water (500 mL) and then extracted with ethyl acetate (2×800 mL). The combined organic layers were washed with brine (2×800 mL) and dried over anhydrous $Na_2SO_4$. After filtration, the filtrate was concentrated under vacuum. The crude residue was applied onto a silica gel column and eluted with ethyl acetate/petroleum ether=1:5 to give 5-tert-butyl 1-ethyl 5-azaspiro[2.5]octane-1,5-dicarboxylate as a light yellow oil (15.0 g, 11.6%). LC-MS (ESI, m/z) M+1: 284. $^1$HNMR (300 MHz, DMSO-$d_6$) δ 4.12-4.04 (m, 2H), 3.43 (s, 2H), 2.85 (dd, J=11.4, 6.3 Hz, 2H), 2.36 (dd, J=11.1, 6.3 Hz, 2H), 1.99 (s, 2H), 1.47-1.29 (m, 9H), 1.25-1.13 (m, 3H), 1.11-1.00 (m, 2H), 0.99-0.86 (m, 1H).

Synthesis of tert-butyl 1-(hydroxymethyl)-5-azaspiro[2.5]octane-5-carboxylate: Into a 1000 mL 3-necked round-bottom flask, were placed 5-tert-butyl 1-ethyl 5-azaspiro[2.5]octane-1,5-dicarboxylate (15.0 g, 52.9 mmol, 1.0 eq), THE (180 mL). After that, $LiAlH_4$ (4.0 g, 105.9 mmol, 2.0 eq) was added at 0° C. under nitrogen atmosphere. The resulting mixture was stirred for 1 hour at 0° C. The reaction mixture was quenched by the addition of water (4 mL), 15% NaOH (4 mL) and water (12 mL) at 0° C. The resulting solution was stirred for 20 minutes and dried over anhydrous magnesium sulfate. After filtration, the filtrate was concentrated under vacuum to give tert-butyl 1-(hydroxymethyl)-5-azaspiro[2.5]octane-5-carboxylate as a light yellow solid (2.9 g crude). LC-MS (ESI, m/z) M+1: 242. $^1$HNMR (400 MHz, DMSO-$d_6$) δ 4.40 (s, 1H), 3.45 (t, J=7.0 Hz, 2H), 3.40 (d, J=6.4 Hz, 2H), 3.34-3.19 (m, 2H), 2.10-2.06 (d, J=6.2 Hz, 1H), 1.94 (t, J=6.4 Hz, 1H), 1.74-1.68 (m, 1H), 1.63-1.54 (m, 1H), 1.41 (d, J=17.2 Hz, 9H), 1.01-0.76 (m, 1H), 0.57-0.37 (m, 1H), 0.09 (t, J=5.0 Hz, 1H).

Synthesis of tert-butyl 1-formyl-5-azaspiro[2.5]octane-5-carboxylate: Into a 250-mL 3-necked round-bottom flask, were placed tert-butyl 1-(hydroxymethyl)-5-azaspiro[2.5]octane-5-carboxylate (2.9 g, 12.0 mmol, 1.0 eq), dichloromethane (40 mL). After that, PCC (5.2 g, 24.0 mmol, 2.0 eq) was added at 0° C. The resulting mixture was stirred for 2 hours at 0° C. The resulting mixture was then quenched by the addition of water (50 mL) and then extracted with ethyl acetate (2×60 mL). The combined organic layers were washed with brine (2×60 mL) and dried over anhydrous $Na_2SO_4$. After filtration, the filtrate was concentrated under vacuum. The crude residue was applied onto a silica gel column and eluted with ethyl acetate/petroleum ether=1:3 to give tert-butyl 1-formyl-5-azaspiro[2.5]octane-5-carboxylate as a brown solid (800 mg, 27.8%). LC-MS (ESI, m/z) M+1-tBu: 140. $^1$HNMR (300 MHz, DMSO-$d_6$) δ 9.31 (d, J=5.4 Hz, 1H), 3.56-3.45 (m, 1H), 3.26-3.04 (m, 2H), 1.90-1.64 (m, 3H), 1.54 (ddd, J=13.5, 7.2, 3.6 Hz, 1H), 1.40 (s, 9H), 1.41-1.33 (m, 2H), 1.16-0.77 (m, 2H).

Synthesis of tert-butyl 1-ethynyl-5-azaspiro[2.5]octane-5-carboxylate: Into a 100-mL round-bottom flask, were placed tert-butyl 1-formyl-5-azaspiro[2.5]octane-5-carboxylate (800 mg, 3.3 mmol, 1.0 eq), $CH_3OH$ (10 mL), $K_2CO_3$ (924 mg, 6.7 mmol, 2.0 eq). After that, dimethyl (1-diazo-2-oxopropyl)phosphonate (963 mg, 5.0 mmol, 1.5 eq) was added at 0° C. The resulting mixture was stirred for 1 hour at 25° C. The reaction mixture was quenched by the addition of water (10 mL) and then extracted with ethyl acetate (2×50 mL). The combined organic layers were washed with brine (2×50 mL) and dried over anhydrous $Na_2SO_4$. After filtration, the filtrate was concentrated under vacuum. The crude residue was applied onto a silica gel column and eluted with ethyl acetate/petroleum ether=1:3 to give tert-butyl 1-ethynyl-5-azaspiro[2.5]octane-5-carboxylate as a light yellow oil (540 mg, 68.6%). LC-MS (ESI, m/z) M+1-tBu: 136. $^1$HNMR (300 MHz, DMSO-$d_6$) δ 3.55-3.47 (m, 1H), 3.20-3.09 (m, 3H), 2.70 (d, J=2.1 Hz, 1H), 1.68-1.50 (m, 4H), 1.39 (s, 9H), 1.39-1.30 (m, 1H), 0.97-0.82 (m, 1H), 0.51 (t, J=4.8 Hz, 1H).

Synthesis of 1-ethynyl-5-azaspiro[2.5]octane: Into a 100-mL round-bottom flask, were placed tert-butyl 1-ethynyl-5-azaspiro[2.5]octane-5-carboxylate (250 mg, 1.1 mmol, 1.0 eq), 2,6-dimethylpyridine (342 mg, 3.2 mmol, 3.0 eq), dichloromethane (5 mL). After that, TMSI (425 mg, 2.1 mmol, 2.0 eq) was added at 0° C. The reaction mixture was stirred for 2 hours at 0° C. The resulting mixture was concentrated under vacuum to give 1-ethynyl-5-azaspiro[2.5]octane as a brown solid (600 mg crude).

Synthesis of (1-ethynyl-5-azaspiro[2.5]octan-5-yl)(3-methoxy-4-nitrophenyl)methanone: Into a 50-mL round-bottom flask, were placed 1-ethynyl-5-azaspiro[2.5]octane (600 mg crude), 3-methoxy-4-nitrobenzoic acid (225 mg, 1.1 mmol, 1.1 eq), DIEA (268 mg, 2.1 mmol, 2.0 eq), DMF (2 mL), HATU (433 mg, 1.1 mmol, 1.1 eq). The reaction mixture was stirred for 2 hours at 25° C. The resulting mixture was quenched by the addition of water (50 mL) and then extracted with ethyl acetate (3×50 mL). The combined organic layers were washed with brine (3×50 mL) and dried over anhydrous $Na_2SO_4$. After filtration, the filtrate was concentrated under vacuum. The crude residue was applied onto a silica gel column and eluted with ethyl acetate/petroleum ether=1:0 to give (1-ethynyl-5-azaspiro[2.5]octan-5-yl)(3-methoxy-4-nitrophenyl)methanone as a light yellow solid (200 mg, 61.4%). LC-MS (ESI, m/z) M+1: 315. $^1$HNMR (400 MHz, DMSO-$d_6$) δ 7.93 (dd, J=12.8, 8.0 Hz, 1H), 7.28 (d, J=11.8 Hz, 1H), 7.05 (dd, J=17.2, 8.2 Hz, 1H), 3.95 (d, J=5.0 Hz, 3H), 3.86-3.78 (m, 1H), 3.60-3.38 (m, 1H), 3.17-2.98 (m, 1H), 2.74 (d, J=5.6 Hz, 1H), 1.68 (s, 2H), 1.60 (s, 1H), 1.48 (s, 1H), 1.30-1.21 (m, 1H), 1.07-0.99 (m, 1H), 0.78-0.73 (m, 1H), 0.65-0.48 (m, 1H).

Example 1: Preparation of (2'S,3S,4'S,5'R)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide Synthesis of (2'S,3S,4'S,5'R)-6-chloro-4'-(3-chloro-2-fluorophenyl)-2'-neopentylspiro[indoline-3,3'-pyrrolidine]-5'-carboxylic acid (racemate): Into an 8 mL vial were placed tert-butyl (2'S,3S,4'S,5'R)-6-chloro-4'-(3-chloro-2-fluorophenyl)-2'-neopentylspiro[indoline-3,3'-pyrrolidine]-5'-carboxylate (racemate) (120 mg, 0.2 mmol, 1.0 eq) and trifluoroacetic acid (2 mL). The reaction mixture was stirred for 16 hours at 25° C. The resulting mixture was diluted with water (20 mL) and extracted with ethyl acetate (2×20 mL). The combined organic phase was washed with brine (220 mL), dried over anhydrous sodium sulfate. After filtration, the filtrate was concentrated under vacuum to give (2'S,3S,4'S,5'R)-6-chloro-4'-(3-chloro-2-fluorophenyl)-2'-neopentylspiro[indoline-3,3'-pyrrolidine]-5'-carboxylic acid (racemate) (100 mg, crude) as a light yellow oil. LC. MS (ESI, m/z) M+1: 451/453.

Synthesis of (2'S,3S,4'S,5'R)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide (racemate): Into an 8 mL vial were placed (2'S,3S,4'S,5'R)-6-chloro-4'-(3-chloro-2-fluorophenyl)-2'-neopentylspiro[indoline-3,3'-pyrrolidine]-5'-carboxylic acid (racemate) (90 mg, 0.2 mmol, 1.0 eq), N,N-dimethylformamide (2 mL), HATU (91 mg, 0.2 mmol, 1.2 eq), DIEA (103 mg, 0.8 mmol, 4.0 eq), 4-amino-3-methoxybenzamide (40 mg, 0.2 mmol, 1.2 eq). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3{\cdot}H_2O$) and $CH_3CN$ (70% Phase B up to 90% in 12 min); Detector, UV 254/220 nm. Finally, (2'S,3S,4'S,5'R)—N-(4-carbamoyl-2-methoxyphenyl)-6-chloro-4'-(3-chloro-2-fluorophenyl)-2'-neopentylspiro [indoline-3,3'-pyrrolidine]-5'-carboxamide (racemate) (23 mg, 19%) was obtained as a white solid. LC-MS (ESI, m/z) M+1: 599/601.

Synthesis of (2'S,3S,4'S,5'R)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide: 23 mg of (2'S,3S,4'S,5'R)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide (racemate) was purified by Chiral-Prep-HPLC using the following conditions: Column: CHIRAL ART Cellulose-SC, 3*25 cm, 5 μm; mobile phase A: n-Hexane; mobile phase B: Ethanol; Flow rate: 35 mL/min; Gradient: 50% B to 50% B in 12 min; Detector, 254 nm. Finally, (2'S,3S,4'S,5'R)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide (4 mg) was obtained as a white solid. LC-MS (ESI, m/z) M+1: 599/601. $T_R$=2.597 min in CHIRAL-HPLC, Column: YMC Cellulose-SC, 100*4.6 mm, 3 um. mobile phase A: n-Hexane (0.1% DEA); mobile phase B: Ethanol, Pump Mode: Binary gradient, Conc. of Pump B: 50.0% in 7 min, Oven Temperature: 25° C. $^1$HNMR (400 MHz, Methanol-$d_4$) δ 8.38 (d, J=8.4 Hz, 1H), 7.59 (d, J=2.0 Hz, 1H), 7.50 (dd, J=8.4, 2.0 Hz, 1H), 7.38-7.23 (m, 2H), 7.18 (dd, J=8.0, 1.6 Hz, 1H), 7.18-7.05 (m, 1H), 6.63 (dd, J=8.0, 2.0 Hz, 1H), 6.43 (d, J=2.0 Hz, 1H), 4.45 (d, J=9.6 Hz, 1H), 4.13 (d, J=9.6 Hz, 1H), 3.98 (s, 3H), 3.60 (d, J=10.4 Hz, 1H), 3.38 (d, J=10.4 Hz, 1H), 3.27 (t, J=5.6 Hz, 1H), 1.46-1.28 (m, 2H), 1.0 (s, 9H).

Example 2: Preparation of Synthesis of (2'R,3R,4'R,5'S)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide Synthesis of (2'R,3R,4'R,5'S)—N-(4-carbamoyl-2-methoxyphenyl)-6-chloro-4'-(3-chloro-2-fluorophenyl)-2'- neopentylspiro[indoline-3,3'-pyrrolidine]-5'-carboxamide: 23 mg of (2'S,3S,4'S,5'R)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide (racemate) was purified by Chiral-Prep-HPLC using the following conditions: Column: CHIRAL ART Cellulose-SC, 3*25 cm, 5 μm; mobile phase A: n-Hexane; mobile phase B: Ethanol; Flow rate: 35 mL/min; Gradient: 50% B to 50% B in 12 min; Detector, 254 nm. Finally, (2'R,3R,4'R,5'S)—N-(4-carbamoyl-2-methoxyphenyl)-6-chloro-4'-(3-chloro-2-fluorophenyl)-2'-neopentylspiro[indoline-3,3'-pyrrolidine]-5'-carboxamide (3 mg) was obtained as a white solid. LC-MS (ESI, m/z) M+1: 599/601. $T_R$=3.548 min in CHIRAL-HPLC, Column: YMC Cellulose-SC, 100*4.6 mm, 3 um. mobile phase A: n-Hexane (0.1% DEA); mobile phase B: Ethanol, Pump Mode: Binary gradient, Conc. of Pump B: 50.0% in 7 min, Oven Temperature: 25° C. $^1$HNMR (400 MHz, Methanol-$d_4$) δ 8.38 (d, –8.4 Hz, 1H), 7.59 (d, –2.0 Hz, 1H), 7.50 (dd, J=8.4, 2.0 Hz, 1H), 7.38-7.24 (m, 2H), 7.18 (dd, J=8.0, 1.6 Hz, 1H), 7.11 (dd, –8.4, 7.2 Hz, 1H), 6.63 (dd, J=8.0, 2.0 Hz, 1H), 6.43 (d, J=2.0 Hz, 1H), 4.45 (d, J=9.6 Hz, 1H), 4.13 (d, J=9.6 Hz, 1H), 3.98 (s, 3H), 3.60 (d, J=10.4 Hz, 1H), 3.38 (d, J=10.4 Hz, 1H), 3.29-3.25 (m, 1H), 1.46-1.38 (m, 2H), 1.0 (s, 9H).

Example 3: Preparation of 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoic acid Synthesis of 6-chloro-3-[(3-chloro-2-fluorophenyl)methylidene]-1H-indol-2-one: Into a 1000 mL round-bottom flask were placed 6-chloro-1,3-dihydroindol-2-one (150.0 g, 895.0 mmol, 1.0 eq), EtOH (500 ml), 3-chloro-2-fluorobenzaldehyde (149.0 g, 939.7 mmol, 1.0 eq) and piperazine (15.4 g, 179.0 mmol, 0.2 eq). The reaction mixture was stirred for 3 hours at 80° C. The resulting solution was stirred for an additional 14 hours at 25° C. The solids were collected by filtration. Finally, 6-chloro-3-[(3-chloro-2-fluorophenyl)methylidene]-1H-indol-2-one (200.0 g, 72%) was obtained as a yellow solid. LC-MS (ESI, m/z) M+1: 308/310.

Synthesis of tert-butyl (2'S,3R,4'S,5'R)-6-chloro-4'-(3-chloro-2-fluorophenyl)-2'-(2,2-dimethylpropyl)-2-oxo-1H-spiro[indole-3,3'-pyrrolidine]-5'-carboxylate (racemate): Into a 3-L round-bottom flask were placed 6-chloro-3-[(3-chloro-2-fluorophenyl)methylidene]-1H-indol-2-one (150.0 g, 486.8 mmol, 1.0 eq), DABCO (87.3 g, 778.8 mmol, 1.6 eq), LiCl (30.9 g, 730.2 mmol, 1.5 eq) and tetrahydrofuran (1.5 L). The reaction mixture was stirred for 30 mins at 40° C. After that, Tert-butyl 2-[(3,3-dimethylbutylidene)amino] acetate (135.0 g, 632.8 mmol, 1.3 eq) was added and the reaction mixture was stirred for 14 hours at 40° C. The resulting mixture was quenched by the addition of water (1 L) at 0° C., and then extracted with ethyl acetate (3×1 L). The combined organic layers were washed with water (2×300 mL) and brine (300 mL), dried over anhydrous sodium sulfate. After filtration, the filtrate was concentrated under vacuum. The crude residue was applied onto a silica gel column and eluted with ethyl acetate/petroleum ether=(0:10 to 10:1) to give tert-butyl (2'S,3R,4'S,5'R)-6-chloro-4'-(3-chloro-2-fluorophenyl)-2'-(2,2-dimethylpropyl)-2-oxo-1H-spiro[indole-3,3'-pyrrolidine]-5'-carboxylate (racemate) (130 g, crude) as a white solid.

Synthesis of (2'R,3R,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylate (racemate): Into a 1-L round-bottom flask, were placed tert-butyl (2'S,3R,4'S,5'R)-6-chloro-4'-(3-chloro-2-fluorophenyl)-2'-(2,2-dimethylpropyl)-2-oxo-1H-spiro[indole-3,3'-pyrrolidine]-5'-carboxylate (racemate) (25 g, crude), $BH_3$-tetrahydrofuran (1 M) (250.0 mL). The reaction mixture was stirred for 16 hours at 50° C. The reaction was then quenched by the addition of $CH_3OH$ (50 mL) and then concentrated under vacuum. The residue was applied onto a silica gel column and eluted with ethyl acetate/petroleum ether=1:10 to give (2'R,3R,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylate (racemate) (1.3, crude) as a white solid.

Synthesis of (2'R,3R,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (racemate): A 50-mL round-bottom flask were placed (2'R,3R,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylate (racemate) (500 mg, 0.1 mmol, 1.0 eq), DCM (5 mL) and TFA (2.50 mL). The reaction mixture was stirred for 2 hours at 25° C. The resulting mixture was concentrated in vacuum and then diluted with DCM (10 mL). The resulting solution was washed with $NaHCO_3$(aqueous), dried over anhydrous sodium sulfate. After filtration, the filtrate was concentrated under vacuum. The crude residue was applied onto a silica gel column and eluted with dichloromethane/methanol=(10:0 to 10:1) to give (2'R,3R,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (racemate) (300 mg, 67%) as a yellow solid. LC-MS (ESI, m/z) M+1: 451/453.

Synthesis of methyl 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoate (racemate): Into a 5-mL vial were placed (2'R,3R,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (racemate) (200 mg, 0.4 mmol, 1.0 eq), methyl 4-amino-3-methoxybenzoate (120 mg, 0.6 mmol, 1.5 eq), DCM (5 mL), N-ethyl-N-isopropylpropan-2-amine (114 mg, 0.8 mmol, 2.0 eq), HATU (252 mg, 0.6 mmol, 1.5 eq). The reaction mixture was stirred for 14 hours at 25° C. The resulting mixture was concentrated. The residue was purified by Prep-TLC (dichloromethane) to give methyl 4-[(2'R,3R,4'S,5'R and 2'S,3S,4'R,5'S)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoate (racemate) (115 mg) as a light brown solid. LC-MS (ESI, m/z) M+1: 614/616.

Synthesis of methyl 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoate and methyl 4-((2'S,3S,4'R,5'S)-6-chloro-4'-(3-chloro-2-fluorophenyl)-2'-neopentylspiro[indoline-3,3'-pyrrolidine]-5'-carboxamido)-3-methoxybenzoate: The crude product methyl 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoate (racemate) (116 mg) was was purified by Chiral-SFC using the following conditions: Column: CHIRAL ART Cellulose-SB, 3*25 cm, 5 μm; mobile phase A: $CO_2$; mobile phase B: $CH_3CH_3OH$—Preparative; Flow rate: 50 mL/min; Gradient: isocratic 40% B; Detect 220 nm. Finally, methyl 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoate (24 mg, 19%) was obtained as a white solid. And methyl 4-((2'S,3S,4'R,5'S)-

6-chloro-4'-(3-chloro-2-fluorophenyl)-2'-neopentylspiro[indoline-3,3'-pyrrolidine]-5'-carboxamido)-3-methoxybenzoate (24 mg, 19%) was obtained as a white solid. 7A, $T_R$=2.310 min in CHIRAL-HPLC, CHIRALPAK ID-3, 50*4.6 mm, 3 um ID3000-TE003, mobile phase A: n-Hexane (0.1% DEA); mobile phase B: Ethanol, Start Conc. of Pump B: 20% in 6 min, Oven Temperature: 35° C. 7B, $T_R$=3.270 min in CHIRAL-HPLC, CHIRALPAK ID-3, 50*4.6 mm, 3 um ID3000-TE003, mobile phase A: n-Hexane (0.1% DEA); mobile phase B: Ethanol, Start Conc. of Pump B: 20% in 6 min, Oven Temperature: 35° C.

Synthesis of 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoic acid: Into an 8 mL vial were placed methyl 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoate (24 mg, 0.1 mmol, 1.0 eq), MeOH (1 mL), water (0.3 mL), NaOH (6 mg, 0.4 mmol, 4.0 eq). The reaction mixture was stirred for 14 hours at 25° C. The pH value of the solution was adjusted to 6 with HOAc. The solids were collected by filtration. Finally, 4-[(2'R,3R,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoic acid (3.4 mg, 15%) was obtained as a white solid. LC-MS (ESI, m/z) M+1: 600/602. $^1$HNMR (300 MHz, DMSO-$d_6$) δ 10.82 (s, 1H), 8.17 (d, J=8.1 Hz, 1H), 7.61-7.52 (m, 2H), 7.47 (dd, J=8.1, 1.5 Hz, 2H), 7.29 (t, J=7.8 Hz, 1H), 6.41 (d, J=2.1 Hz, 1H), 6.16 (dd, J=8.1, 2.1 Hz, 1H), 5.78 (s, 1H), 5.51 (d, J=8.1 Hz, 1H), 4.40-4.30 (m, 1H), 4.06 (d, J=6.9 Hz, 1H), 3.92 (s, 3H), 3.60-3.53 (m, 2H), 2.98 (d, J=9.9 Hz, 1H), 1.81 (s, 4H), 0.94 (s, 9H).

Example 4: Preparation of 4-((2'S,3S,4'R,5'S)-6-chloro-4'-(3-chloro-2-fluorophenyl)-2'-neopentylspiro[indoline-3,3'-pyrrolidine]-5'-carboxamido)-3-methoxybenzoic acid Synthesis of 4-((2'S,3S,4'R,5'S)-6-chloro-4'-(3-chloro-2-fluorophenyl)-2'-neopentylspiro[indoline-3,3'-pyrrolidine]-5'-carboxamido)-3-methoxybenzoic acid: Into an 8 mL vial were placed methyl 4-[(2'S,4'R,5'S)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoate (23 mg, 0.1 mmol, 1.0 eq), MeOH (1 mL), water (0.3 mL), NaOH (6 mg, 0.4 mmol, 4.0 eq). The reaction mixture was stirred for 14 hours at 25° C. The pH value of the solution was adjusted to 6 with HOAc. The solids were collected by filtration. Finally, 4-((2'S,3S,4'R,5'S)-6-chloro-4'-(3-chloro-2-fluorophenyl)-2'-neopentylspiro[indoline-3,3'-pyrrolidine]-5'-carboxamido)-3-methoxybenzoic acid (4.1 mg, 17%) was obtained as a white solid. LC-MS (ESI, m/z) M+1: 600/602. $^1$HNMR (300 MHz, DMSO-$d_6$) δ 10.82 (s, 1H), 8.17 (d, J=8.1 Hz, 1H), 7.61-7.52 (m, 2H), 7.47 (dd, J=8.1, 1.5 Hz, 2H), 7.29 (t, J=7.8 Hz, 1H), 6.41 (d, J=2.1 Hz, 1H), 6.16 (dd, J=8.1, 2.1 Hz, 1H), 5.78 (s, 1H), 5.51 (d, J=8.1 Hz, 1H), 4.40-4.30 (m, 1H), 4.06 (d, J=6.9 Hz, 1H), 3.92 (s, 3H), 3.60-3.53 (m, 2H), 2.98 (d, J=9.9 Hz, 1H), 1.81 (s, 4H), 0.94 (s, 9H).

Example 5: Preparation of Synthesis of (2'S,3R,3'R,8'aS)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide Synthesis of 3,3-dimethylpentane-1,5-diol: Into a 1 L 3-necked round-bottom flask purged under an inert atmosphere of nitrogen were placed tetrahydrofuran (400 mL). After that, $LiAlH_4$ (27.0 g, 711.6 mmol, 3.0 eq) was added in portions at 0° C. To the above solution was added 3,3-dimethylpentanedioic acid (38.0 g, 237.2 mmol, 1.0 eq) dropwise with stirring at 0° C. The reaction mixture was stirred for 14 hours at 25° C. The resulting mixture was then quenched by the addition of water (27 mL), 15% NaOH (27 mL) and water (70 mL). After filtration, the filtrate was dried over anhydrous sodium sulfate, filtered and concentrated under vacuum. Finally, 3,3-dimethylpentane-1,5-diol (24 g, 76%) was obtained as a colorless oil. $^1$HNMR (300 MHz, Chloroform-d) (td, J=7.2, 1.5 Hz, 4H), 2.42 (d, J=1.5 Hz, 2H), 1.59 (td, J=7.2, 1.5 Hz, 4H), 0.96 (d, J=1.5 Hz, 6H).

Synthesis of 5-[(tert-butyldimethylsilyl)oxy]-3,3-dimethylpentan-1-ol: Into a 1-L 3-necked round-bottom flask purged under an inert atmosphere of nitrogen were placed 3,3-dimethylpentane-1,5-diol (15.0 g, 113.4 mmol, 1.0 eq), dichloromethane (200 mL), DIEA (29.3 g, 226.9 mmol, 2.0 eq). After that, t-butyldimethylchlorosilane (17.1 g, 113.4 mmol, 1.0 eq) was added dropwise with stirring at 0° C. The reaction mixture was stirred for 2 hours at 25° C. The resulting mixture was concentrated. The crude residue was applied onto a silica gel column and eluted with ethyl acetate/petroleum ether=(0:1 to 10:1). Finally, 5-[(tert-butyldimethylsilyl)oxy]-3,3-dimethylpentan-1-ol (12.0 g, 43%) was obtained as colorless oil. $^1$HNMR (300 MHz, Chloroform-d) δ 3.73 (td, J=7.2, 3.6 Hz, 4H), 1.76 (s, 1H), 1.57 (q, J=6.76 Hz, 4H), 0.96 (s, 6H), 0.92 (s, 9H), 0.09 (d, J=1.2 Hz, 6H).

Synthesis of 5-[(tert-butyldimethylsilyl)oxy]-3,3-dimethylpentanal: Into a 500-mL round-bottom flask were placed 5-[(tert-butyldimethylsilyl)oxy]-3,3-dimethylpentan-1-ol (11.0 g, 44.6 mmol, 1.0 eq), dichloromethane (200 mL). After that, PCC (19.2 g, 89.2 mmol, 2.0 eq) was added in portions at 0° C. The reaction mixture was stirred for 2 hours at 25° C. The resulting mixture was diluted with dichloromethane (100 mL) and then washed with $NaHCO_3$ (3×10 mL) and brine (10 mL). The organic phase was dried over anhydrous sodium sulfate. After filtration, the filtrate was concentrated under vacuum. The crude residue was applied onto a silica gel column and eluted with ethyl acetate/petroleum ether=(0:1 to 1:10) to give 5-[(tert-butyldimethylsilyl)oxy]-3,3-dimethylpentanal (4.5 g, 41%) as off-colorless oil. $^1$HNMR (300 MHz, Chloroform-d) δ 9.87 (t, J=3.0 Hz, 1H), 3.74 (t, J=6.6 Hz, 2H), 2.34 (d, J=3.0 Hz, 2H), 1.63 (t, J=6.6 Hz, 2H), 1.10 (s, 6H), 0.92 (s, 9H), 0.07 (s, 6H).

Synthesis of tert-butyl(2'S,3R,4'S,5'R)-2'-(4-((tert-butyldimethylsilyl)oxy)-2,2-dimethylbutyl)-6-chloro-4'-(3-chlor-2-fluorophenyl)-2-oxospiro[indoline-3,3'-pyrrolidine]-5'-carboxylate (racemate): Into a 500-mL round-bottom flask were placed 6-chloro-3-(3-chloro-2-fluorobenzylidene)indolin-2-one (4 g, 13.0 mmol, 1.0 eq), 5-[(tert-butyldimethylsilyl)oxy]-3,3-dimethylpentana (4.1 g, 16.7 mmol, 1.3 eq), LiCl (1.1 g, 26.1 mmol, 2.0 eq), DABCO (2.9 g, 26.1 mmol, 2.0 eq) and tetrahydrofuran (100 mL). The reaction mixture was stirred for 14 hours at 40° C. The resulting mixture was diluted with ethyl acetate (100 mL), and then washed with water (3×30 mL) and brine (30 mL). The organic phase was dried anhydrous sodium sulfate. After filtration, the filtrate was concentrated under vacuum. The residue was purified by a flash column (silica gel, ethyl acetate/petroleum ether=0:1 to 1:10) to give tert-butyl(2'S,3R,4'S,5'R)-2'-(4-((tert-butyldimethylsilyl)oxy)-2,2-dimethylbutyl)-6-chloro-4'-(3-chloro-2-fluorophenyl)-2-oxospiro[indoline-3,3'-pyrrolidine]-5'-carboxylate (3.2 g, racemate) as off-colorless oil. $^1$HNMR (300 MHz, DMSO-$d_6$) δ 10.49 (s, 1H), 7.60-7.50 (m, 1H), 7.46 (d, J=8.1 Hz, 1H), 7.38 (t, J=7.5 Hz, 1H), 7.15 (t, J=7.8 Hz, 1H), 7.03 (dd, J=8.1, 2.1 Hz, 1H), 6.69 (d, J=2.1 Hz, 1H), 4.45 (d, J=9.3 Hz, 1H), 4.31 (d, J=9.3 Hz, 1H), 3.73 (d, J=9.3 Hz, 1H), 3.55-3.38 (m, 2H), 1.58-1.32 (m, 3H), 1.26 (s, 10H), 0.82 (d, J=1.8 Hz, 10H), 0.79 (s, 6H), 0.0 (s, 6H).

Synthesis of tert-butyl (3R,4'S)-6-chloro-4'-(3-chloro-2-fluorophenyl)-2'-(4-hydroxy-2,2-dimethylbutyl)-2-oxo-1H-spiro[indole-3,3'-pyrrolidine]-5'-carboxylate (racemate): Into a 50-mL round-bottom flask were placed tert-butyl(2'S,3R,4'S,5'R)-2'-(4-((tert-butyldimethylsilyl)oxy)-2,2-dimethylbutyl)-6-chloro-4'-(3-chloro-2-fluorophenyl)-2-oxospiro[indoline-3,3'-pyrrolidine]-5'-carboxylate (racemate) (3.2 g) and TBAF in tetrahydrofuran (1 M, 30 mL). The reaction mixture was stirred for 14 hours at 30° C. The resulting mixture was concentrated and diluted with dichloromethane (100 mL). The organic phase was washed with water (3×20 mL), dried over anhydrous sodium sulfate. After filtration, the filtrate was concentrated under vacuum. The crude residue was applied onto a silica gel column and eluted with ethyl acetate/petroleum ether=(0:1 to 1:10) to give tert-butyl (3R,4'S)-6-chloro-4'-(3-chloro-2-fluorophenyl)-2'-(4-hydroxy-2,2-dimethylbutyl)-2-oxo-1H-spiro[indole-3,3'-pyrrolidine]-5'-carboxylate (1 g, racemate) as a white solid. LC-MS (ESI, m/z) M+1: 551/553.

Synthesis of tert-butyl (2'S,3R,8'aS)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxylate (racemate): Into a 50-mL round-bottom flask were placed tert-butyl (3R,4'S)-6-chloro-4'-(3-chloro-2-fluorophenyl)-2'-(4-hydroxy-2,2-dimethylbutyl)-2-oxo-1H-spiro[indole-3,3'-pyrrolidine]-5'-carboxylate (racemate) (1.0 g, 1.8 mmol, 1.0 eq), $CCl_4$ (10 mL), $CH_3CN$ (10. mL), triethylamine (0.4 g, 3.6 mmol, 2.0 eq). After that, $Ph_3P$ (0.9 g, 3.6 mmol, 2.0 eq) was added at 0° C. The reaction mixture was stirred for 14 hours at 25° C. The resulting mixture was washed with water (3×5 mL). The organic phase was dried over anhydrous sodium sulfate. After filtration, the filtrate was concentrated under vacuum. The crude residue was applied onto a silica gel column and eluted with ethyl acetate/petroleum ether=(0:1 to 1:1) to give tert-butyl (2'S,3R,8'aS)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxylate (racemate) (450 mg) as a yellow solid.

Synthesis of (2'S,3R,8'aS)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxylic acid (racemate): Into a 50-mL round-bottom flask were placed tert-butyl (2'S,3R,8'aS)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxylate (racemate) (650 mg, 1.2 mmol, 1.0 eq), dichloromethane (10.0 mL), TFA (3.0 mL). The reaction mixture was stirred for 14 hours at 25° C. The resulting mixture was washed with $NaHCO_3$ (10 mL) and NaCl (10 mL). The organic phase was dried over anhydrous sodium sulfate. After filtration, the filtrate was concentrated under vacuum. The crude residue was applied onto a silica gel column and eluted with dichloromethane/methanol=(0:1 to 10:1) to give (2'S,3R,8'aS)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxylic acid (racemate) (420 mg) as a yellow solid. LC-MS (ESI, m/z) M+1: 477/479.

Synthesis of (2'S,3R,8'aS)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxylic acid (racemate): Into a 50-mL round-bottom flask were placed (2'S,3R,3'R,8'aS)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxylic acid (350 mg, 0.7 mmol, 1.0 eq), dichloromethane (10 mL), DIEA (283 mg, 2.2 mmol, 3.0 eq) and diphenylphosphinoyl chloride (346 mg, 1.4 mmol, 2.0 eq), 4-amino-3-methoxybenzamide (182 mg, 1.1 mmol, 1.5 eq). The reaction mixture was stirred for 14 hours at 25° C. The resulting mixture was washed with brine (10 mL), and dried over anhydrous sodium sulfate. After filtration, the filtrate was concentrated under vacuum. The crude residue was applied onto a silica gel column and eluted with ethyl acetate/petroleum ether=(0:1 to 1:0) to give (2'S,3R,3'R,8'aS)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide (racemate) (33 mg, 7%) of as a white solid. LC-MS (ESI, m/z) M+1: 625/627.

Synthesis of (2'S,3R,3'R,8'aS)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide: The crude product (33 mg) (2'S,3R,3'R,8'aS)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide (racemate) was purified by Chiral-SFC using the following conditions: Column: CHIRAL ART Cellulose-SB, 3*25 cm, 5 μm; mobile phase A: $CO_2$; mobile phase B: $CH_3CH_3OH$—Preparative; Flow rate: 50 mL/min; Gradient: isocratic 40% B; Detect 220 nm. Finally, (2'S,3R,3'R,8'aS)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide (6 mg) was obtained as a white solid. $T_R$=1.138 min in CHIRAL-SFC, Column: SB 100×4.6 mm, 3.0 um, mobile phase A: $CO_2$; mobile phase B: MeOH+30% DCM, Start Conc. of Pump B: 30% in 4 min, Oven Temperature: 35° C. LC-MS (ESI, m/z) M+1: 625/627. $^1$HNMR (300 MHz, Chloroform-d) δ 10.12 (bs, 1H), 8.40 (d, J=8.4 Hz, 1H), 7.67-7.40 (m, 3H), 7.33-7.30 (m, 1H), 7.24 (s, 1H), 7.13 (t, J=8.1 Hz, 1H), 6.81 (d, J=1.8 Hz, 1H), 6.68 (dd, J=8.1, 1.8 Hz, 1H), 6.23 (bs, 1H), 6.10-5.30 (m, 2H), 4.18 (d, J=7.8 Hz, 1H), 4.06 (s, 3H), 3.89 (d, J=7.8 Hz, 1H), 3.14 (d, J=11.4 Hz, 1H), 2.97 (d, J=11.4 Hz, 1H), 2.48 (t, J=11.7 Hz, 1H), 1.65-1.53 (m, 2H), 1.50-1.40 (m, 2H), 0.99 (s, 3H), 0.89 (s, 3H).

Example 6: Preparation of (2'R,3S,3'S,8'aR)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide Synthesis of (2'R,3S,3'S,8'aR)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide: The crude product (33 mg) (2'S,3R,3'R,8'aS)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'-carboxamide (racemate) was purified by Chiral-SFC using the following conditions: Column: CHIRAL ART Cellulose-SB, 3*25 cm, 5 μm; mobile phase A: $CO_2$; mobile phase B: $CH_3CH_3OH$ Preparative; Flow rate: 50 mL/min; Gradient: isocratic 40% B; Detect 220 nm. Finally, (2'R,3S,3'S,8'aR)—N-(4-carbamoyl-2-methoxyphenyl)-6-chloro-2'-(3-chloro-2-fluorophenyl)-7',7'-dimethyl-2-oxo-2',3',5',6',8',8'a-hexahydro-1H-spiro[indole-3,1'-indolizine]-3'- carboxamide (6 mg) was obtained as a white solid. $T_R$=1.737 min in CHIRAL-SFC, Column: SB 100×4.6 mm, 3.0 um, mobile phase A: $CO_2$; mobile phase B: MeOH+30% DCM, Start Conc. of Pump B: 30% in 4 min, Oven Temperature: 35° C. LC-MS (ESI, m/z) M+1: 625/627. $^1$HNMR (300 MHz, Chloroform-d) δ 10.12 (bs, 1H), 8.40 (d, J=8.4 Hz, 1H), 7.67-7.40 (m, 3H), 7.33-7.30 (m, 1H), 7.24 (s, 1H), 7.13 (t, J=8.1 Hz, 1H), 6.81 (d, J=1.8 Hz, 1H), 6.68 (dd, J=8.1, 1.8 Hz, 1H), 6.23 (bs, 1H), 6.10-5.30 (m, 2H), 4.18 (d, J=7.8 Hz, 1H), 4.06 (s, 3H), 3.89 (d, J=7.8 Hz, 1H), 3.14 (d, J=11.4 Hz, 1H), 2.97 (d, J=11.4 Hz, 1H), 2.48 (t, J=11.7 Hz, 1H), 1.65-1.53 (m, 2H), 1.50-1.40 (m, 2H), 0.99 (s, 3H), 0.89 (s, 3H).

Example 7: Preparation of (2'S,3S,4'S,5'R)—N-(4-carbamoyl-2-methoxyphenyl)-6-chloro-4'-(3-chloro-2-fluorophenyl)-2'-(2,2-dimethylpropyl)-5'-methyl-1,2-dihydrospiro[indole-3,3'-pyrrolidine]-5'-carboxamide Synthesis of tert-butyl 2-[(3,3-dimethylbutylidene)amino]propanoate: Into a 1000 mL 3-necked round-bottom flask were added tert-butyl 2-aminopropanoate hydrochloride (54.4 g, 299 mmol, 1.0 eq), dichloromethane (550 mL), trimethylamine (45.5 g, 449 mmol, 1.5 eq) at 25° C. The reaction mixture was stirred for 1 hour at 25° C. After that, 3,3-dimethylbutanal (30.0 g, 299 mmol, 1.0 eq) was added at 25° C. The reaction mixture was stirred overnight at 25° C. After filtration, the filter cake was washed with dichloromethane (2×100 mL). The filtrate was concentrated under vacuum. The crude residue was dissolved in ethyl acetate (500 mL), and then washed with brine (2×200 mL) and dried over anhydrous sodium sulfate. After filtration, the filtrate was concentrated under vacuum to give tert-butyl 2-[(3,3-dimethylbutylidene)amino]propanoate (62.0 g, 91%) as colorless oil. $^1$HNMR (300 MHz, Chloroform-d) δ 7.76 (ddd, J=6.0, 5.2, 0.8 Hz, 1H), 3.89-3.76 (m, 1H), 2.17-1.96 (m, 2H), 1.39 (s, 9H), 1.22 (d, J=6.7 Hz, 3H), 0.95 (s, 9H).

Synthesis of 3-(3-chloro-2-fluorophenyl)-2-(2,4-dichlorophenyl)prop-2-enenitrile: Into a 1000 mL 3-necked round-bottom flask were added 2-(2,4-dichlorophenyl)acetonitrile (100.0 g, 537 mmol, 1.0 eq), methanol (1000 mL) and 3-chloro-2-fluorobenzaldehyde (85.2 g, 537 mmol, 1.0 eq) at 25° C. After that, a solution of sodium methanolate (154.0 g, 855 mmol, 1.6 eq) in MeOH was added dropwise at 25° C. under nitrogen atmosphere. The reaction mixture was stirred for 3 hours at 50° C. The precipitated solids were collected by filtration and washed with methanol (2×100 mL). Finally, 3-(3-chloro-2-fluorophenyl)-2-(2,4-dichlorophenyl)prop-2-enenitrile (162.0 g, 92%) was obtained as a white solid. $^1$HNMR (300 MHz, Chloroform-d) δ 8.0 (t, J=7.3 Hz, 1H), 7.82 (d, J=2.2 Hz, 1H), 7.80-7.65 (m, 3H), 7.61 (dd, J=8.3, 2.1 Hz, 1H), 7.45 (t, J=8.0 Hz, 1H).

Synthesis of tert-butyl (2'S,3S,4'S,5'R)-3-(3-chloro-2-fluorophenyl)-4-cyano-4-(2,4-dichlorophenyl)-5-(2,2-dimethylpropyl)-2-methylpyrrolidine-2-carboxylate (racemate): Into a 500 mL 3-necked round-bottom flask were added 3-(3-chloro-2-fluorophenyl)-2-(2,4-dichlorophenyl)prop-2-enenitrile (20.0 g, 61 mmol, 1.0 eq), dichloromethane (200 mL) and tert-butyl 2-[(3,3-dimethylbutylidene)amino]propanoate (25.0 g, 110 mmol, 1.8 eq), trimethylamine (12.4 g, 122 mmol, 2.0 eq), AgF (9.3 g, 73 mmol, 1.2 eq) at 25° C. The reaction mixture was stirred for 16 hours at 25° C. under nitrogen atmosphere. The resulting mixture was diluted with water (500 mL) and then extracted with ethyl acetate (2×200 mL). The combined organic layers were washed with brine (2×200 mL), dried over anhydrous sodium sulfate. After filtration, the filtrate was concentrated under vacuum. The crude residue was applied onto a silica gel column and eluted with ethyl acetate/petroleum ether=10:1 to give tert-butyl (2'S,3S,4'S,5'R)-3-(3-chloro-2-fluorophenyl)-4-cyano-4-(2,4-dichlorophenyl)-5-(2,2-dimethylpropyl)-2-methylpyrrolidine-2-carboxylate (racemate) (5.0 g, 14%) as colorless oil. LC-MS (ESI, m/z) M+1: 553/555. $^1$HNMR (300 MHz, Chloroform-d) δ 7.86 (ddd, J=8.2, 6.6, 1.6 Hz, 1H), 7.72 (d, J=4.3 Hz, 1H), 7.71 (d, J=2.0 Hz, 1H), 7.53 (d, J=2.3 Hz, 1H), 7.50 (dd, J=4.6, 1.9 Hz, 1H), 7.28 (td, J=8.1, 1.2 Hz, 1H), 5.47 (s, 1H), 4.53 (t, J=8.3 Hz, 1H), 3.37 (d, J=7.9 Hz, 1H), 1.65-1.50 (m, 1H), 1.44 (s, 9H), 1.22 (d, J=2.7 Hz, 2H), 1.18 (d, J=6.8 Hz, 4H), 0.88 (s, 9H).

Synthesis of tert-butyl (2'S,3S,4'S,5'R)-4-(aminomethyl)-3-(3-chloro-2-fluorophenyl)-4-(2,4-dichlorophenyl)-5-(2,2-dimethylpropyl)-2-methylpyrrolidine-2-carboxylate (racemate): Into a 100 mL 3-necked round-bottom flask were added tert-butyl (2'S,3S,4'S,5'R)-3-(3-chloro-2-fluorophenyl)-4-cyano-4-(2,4-dichlorophenyl)-5-(2,2-dimethylpropyl)-2-methylpyrrolidine-2-carboxylate (racemate) (4.5 g, 8 mmol, 1.0 eq), tetrahydrofuran (45 mL) and 10 M $BH_3$-$Me_2S$ (10 mL) at 25° C. The reaction mixture was stirred for 12 hours at 25° C. The reaction was quenched by the addition of methanol (50 mL) at 25° C., and then stirred for an additional 1 hour at 25° C. The resulting mixture was diluted with water (100 mL) and extracted with ethyl acetate (3×100 mL). The combined organic layers were washed with brine (100 mL), dried over anhydrous sodium sulfate. After filtration, the filtrate was concentrated under vacuum. The crude residue was purified by reverse flash choursomatography using the following conditions: column, silica gel; mobile phase, acetonitrile in water, 10% to 80% gradient in 10 min; detector, UV 254 nm. Finally, tert-butyl (2'S,3S,4'S,5'R)-4-(aminomethyl)-3-(3-chloro-2-fluorophenyl)-4-(2,4-dichlorophenyl)-5-(2,2-dimethylpropyl)-2-methylpyrrolidine-2-carboxylate (racemate) (900 mg, 19%) was obtained as white solid. LC-MS (ESI, m/z) M+1: 557/559.

Synthesis of tert-butyl (2'S,3S,4'S,5'R)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylate (racemate): Into a 100 mL round-bottom flask were added tert-butyl (2'S,3S,4'S,5'R)-4-(aminomethyl)-3-(3-chloro-2-fluorophenyl)-4-(2,4-dichlorophenyl)-5-(2,2-dimethylpropyl)-2-methylpyrrolidine-2-carboxylate (racemate) (900 mg, 2 mmol, 1.0 eq), DMSO (18.0 mL), CuI (122 mg, 1 mmol, 0.5 eq), $K_3PO_4$ (685 mg, 3 mmol, 2.0 eq), trans-1,2-diaminocyclohexane (73 mg, 1 mmol, 0.5 eq) at 25° C. The reaction mixture was stirred for 3 hours at 100° C. under nitrogen atmosphere. The resulting mixture was diluted with water (50 mL) and then extracted with ethyl acetate (3×20 mL). The combined organic layers were washed with brine (20 mL), dried over anhydrous sodium sulfate. After filtration, the filtrate was concentrated under vacuum. The crude residue was purified by a flash column (silica gel, ethyl acetate/petroleum ether=1:1) to give tert-butyl (2'S,3S,4'S,5'R)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylate (racemate) (560 mg, 66%) as brown solid. LC-MS (ESI, m/z) M+1: 521/523. $^1$HNMR (300 MHz, Chloroform-d) δ 7.43 (t, J=7.5 Hz, 2H), 7.15 (t, J=8.0 Hz, 1H), 6.93 (d, J=7.9 Hz, 1H), 6.52 (dd, J=7.9, 1.9 Hz, 1H), 6.39 (d, J=2.0 Hz, 1H), 5.84 (s, 1H), 5.76 (s, 1H), 4.35 (s, 1H), 3.66-3.55 (m, 1H), 3.09 (s, 1H), 2.87 (s, 1H), 1.44 (s, 9H), 1.26 (d, J=5.0 Hz, 2H), 1.05 (s, 3H), 0.79 (s, 9H).

Synthesis of (2'S,3S,4'S,5'R)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylic acid and (2'R,3R,4'R,5'S)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylic acid: Into a 100 mL round-bottom flask were added tert-butyl (2'S,3S,4'S,5'R)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylate (racemate) (460 mg, 1 mmol, 1.0 eq) and TFA (6.0 mL) at 25° C. The reaction mixture was stirred for 12 hours at 25° C. The resulting mixture was concentrated under vacuum. The crude residue was dissolved in ethyl acetate (50 mL), and then washed with brine (3×20 mL) and dried over anhydrous sodium sulfate. After filtration, the filtrate was concentrated under vacuum. The crude residue was purified by a flash column (silica gel, dichloromethanel methanol=10:1). The crude product (350 mg) was further purified by Prep-SFC using the following conditions (Column: CHIRAL ART Cellulose-SC, 3*25 cm, 5 μm; Mobile Phase A: $CO_2$, Mobile Phase B: methanol—Preparative; Flow rate: 80 mL/min; Gradient: isocratic 25% B; Column Temperature (25° C.): 35; Back Pressure(bar): 100; Wave Length: 220 nm; RT1(min): 6; RT2(min): 8.4; Sample Solvent: methanol: dichloromethane=1: 1; Injection Volume: 6 mL; Number Of Runs: 10). Finally, (2'S,3S,4'S,5'R)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylic acid (60 mg, 14%) was obtained as a white solid. And (2'R,3R,4'R,5'S)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylic acid (62 mg, 15%) was obtained as white solid. LC-MS (ESI, m/z) M+1: 465/467.

Synthesis of (2'S,3S,4'S,5'R)—N-(4-carbamoyl-2-methoxyphenyl)-6-chloro-4'-(3-chloro-2-fluorophenyl)-2'-(2,2-dimethylpropyl)-5'-methyl-1,2-dihydrospiro[indole-3,3'-pyrrolidine]-5'-carboxamide: Into a 2 mL vial were added (2'S,3S,4'S,5'R)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylic acid (60 mg, 1 mmol, 1.0 eq), dichloromethane (2.0 mL), 4-amino-3-methoxybenzamide (25 mg, 0.1 mmol, 1.2 eq), DIEA (33 mg, 0.2 mmol, 2.0 eq), HATU (59 mg, 0.2 mmol, 2.0 eq) at 0° C. The reaction mixture was stirred for 1 hour at 0° C., and then stirred overnight at 25° C. The resulting mixture was diluted with water (10 mL) and extracted with dichloromethane (3×5 mL). The combined organic layers were washed with brine (5 mL), dried over anhydrous sodium sulfate. After filtration, the filtrate was concentrated under vacuum. The crude product was purified by Prep-HPLC using the following conditions (Column, X Bridge Shield RP18 OBD Column, 5 μm, 19*150 mm; mobile phase, water (0.05% $NH_3{\cdot}H_2O$) and acetonitrile (26% Phase B up to 50% in 7 min); Detector, UV 254/220 nm) to give (2'S,3S,4'S,5'R)—N-(4-carbamoyl-2-methoxyphenyl)-6-chloro-4'-(3-chloro-2-fluorophenyl)-2'-(2,2-dimethylpropyl)-5'-methyl-1,2-dihydrospiro[indole-3,3'-pyrrolidine]-5'-carboxamide (25 mg, 31%) as white solid. LC-MS (ESI, m/z) M+1: 613/615. $^1$HNMR (300 MHz, Chloroform-d) δ 10.62 (s, 1H), 8.61 (d, J=8.4 Hz, 1H), 7.56 (d, J=1.8 Hz, 1H), 7.39-7.27 (m, 2H), 7.28 (s, 3H), 7.24 (s, 1H), 7.07 (d, J=8.0 Hz, 2H), 6.67 (dd, J=8.0, 1.9 Hz, 1H), 6.49 (d, J=1.9 Hz, 1H), 4.59 (s, 1H), 3.94 (s, 3H), 3.68 (d, J=9.7 Hz, 1H), 3.51 (d, J=10.1 Hz, 1H), 3.03 (s, 1H), 2.07 (d, J=24.1 Hz, 1H), 1.68 (d, J=14.3 Hz, 1H), 1.46 (d, J=14.3 Hz, 1H) 1.41 (s, 3H), 0.94 (s, 9H).

Example 8: Preparation of (2'R,3R,4'R,5'S)—N-(4-carbamoyl-2-methoxyphenyl)-6-chloro-4'-(3-chloro-2-fluorophenyl)-2'-(2,2-dimethylpropyl)-5'-methyl-1,2-dihydrospiro[indole-3,3'-pyrrolidine]-5'-carboxamide Synthesis of (2'R,3R,4'R,5'S)—N-(4-carbamoyl-2-methoxyphenyl)-6-chloro-4'-(3-chloro-2-fluorophenyl)-2'-(2,2-dimethylpropyl)-5'-methyl-1,2-dihydrospiro[indole-3,3'-pyrrolidine]-5'-carboxamide: Into a 2 mL vial were added (2'R,3R,4'R,5'S)-6-chloro-4'-(3-chloro-2-fluorophenyl)-2'-(2,2-dimethylpropyl)-5'-methyl-1,2-dihydrospiro[indole-3,3'-pyrrolidine]-5'-carboxylic acid (62 mg, 0.1 mmol, 1.0 eq), dichloromethane (2.0 mL), 4-amino-3-methoxybenzamide (26 mg, 0.1 mmol, 1.2 eq), DIEA (34 mg, 0.2 mmol, 2.0 eq) and HATU (59 mg, 0.2 mmol, 2.0 eq) at 0° C. The reaction mixture was stirred for 1 hour at 0° C., and then stirred overnight at 25° C. The resulting mixture was diluted with water (10 mL) and extracted with dichloromethane (3×5 mL). The combined organic layers were washed with brine (5 mL), dried over anhydrous sodium sulfate. After filtration, the filtrate was concentrated under vacuum. The crude product was purified by Prep-HPLC using the following conditions (Column, X Bridge Shield RP18 OBD Column, 5 μm, 19*150 mm; mobile phase, water (0.05% $NH_3{\cdot}H_2O$) and acetonitrile (26% Phase B up to 50% in 7 min); Detector, UV 254/220 nm) to give (2'R,3R,4'R,5'S)—N-(4-carbamoyl-2-methoxyphenyl)-6-chloro-4'-(3-chloro-2-fluorophenyl)-2'-(2,2-dimethylpropyl)-5'-methyl-1,2-dihydrospiro[indole-3,3'-pyrrolidine]-5'-carboxamide (20 mg, 24%) as white solid. LC-MS (ESI, m/z) M+1: 613/615. $^1$HNMR (300 MHz, Chloroform-d) δ 10.63 (s, 1H), 8.62 (d, J=8.4 Hz, 1H), 7.56 (d, J=1.8 Hz, 1H), 7.39-7.28 (m, 2H), 7.28 (s, 1H), 7.23 (t, J=7.0 Hz, 1H), 7.06 (t, J=7.8 Hz, 2H), 6.67 (dd, J=8.0, 1.9 Hz, 1H), 6.49 (d, J=1.9 Hz, 1H), 6.07 (s, 1H), 5.53 (s, 1H), 4.59 (s, 1H), 3.95 (s, 3H), 3.68 (d, J=10.0 Hz, 1H), 3.51 (d, J=9.8 Hz, 1H), 3.03 (d, J=9.1 Hz, 1H), 1.68 (d, J=14.2 Hz, 1H), 1.59 (s, 1H), 1.41 (s, 3H), 1.34 (dd, J=14.3, 9.5 Hz, 1H), 0.94 (s, 9H).

Example 9: Preparation of (2S,3S,4S,5R)—N-(4-carbamoyl-2-methoxyphenyl)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxamide Synthesis of (2S,3S,4S,5R)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxylic acid (racemate): Into an 8 mL vial were added ethyl (2S,3S,4S,5R)-6'-chloro-4-(3-chloro-2-fluorophenyl)-2-(2-methylpropyl)-1',2'-dihydrospiro[pyrrolidine-3,3'-pyrrolo[3,2-c]pyridine]-5-carboxylate (racemate) (50 mg, crude) and TFA (1.0 mL) at 25° C. The reaction mixture was stirred for 12 hours at 25° C. The resulting mixture was concentrated under vacuum to give (2S,3S,4S,5R and 2R,3R,4R)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxylic (racemate) (32 mg) as colorless oil. LC-MS (ESI, m/z) M+1: 452/454.

Synthesis of (2S,3S,4S,5R)—N-(4-carbamoyl-2-methoxyphenyl)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxamide: Into an 8 mL vial were added (2S,3S,4S,5R)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxylic acid (racemate) (32 mg, 0.07 mmol, 1.0 eq), 4-amino-3-methoxybenzamide (12 mg, 0.07 mmol, 1.0 eq), dichloromethane (2.0 mL), DIEA (11 mg, 0.08 mmol, 1.2 eq) and HATU (32 mg, 0.08 mmol, 1.2 eq) at 25° C. The reaction mixture was stirred for 12 hours at 25° C. The resulting mixture was concentrated under vacuum. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3{\cdot}H_2O$) and acetonitrile (35% $CH_3CN$ up to 75% in 10 min); Detector, uv. The collected solution was concentrated under vacuum to remove acetonitrile and the resulting solution was dried by lyophilization. The residue was purified by Chiral-SFC using the following conditions: Column: CHIRAL ART Cellulose-SB, 3*25 cm, 5 μm; mobile phase A: $CO_2$; mobile phase B: methanol—Preparative; Flow rate: 80 mL/min; Gradient: isocratic 40% B; Detector, 220 nm. Finally, (2S,3S,4S,5R)—N-(4-carbamoyl-2-methoxyphenyl)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxamide (7 mg, 16%) was obtained as a white solid. $T_R$=1.366 min in CHIRAL-HPLC. Column: CHIRALPAK IG-3, 100*4.6 mm, 3 um IG30CS-UL011.mobile phase A: n-Hexane/DCM=1:1; mobile phase B: Ethanol (0.1% DEA), Start Conc. of Pump B: 50.0% in 4 min, Oven Temperature: 25° C. LC-MS (ESI, m/z) M+1: 600. $^1$HNMR (300 MHz, Methanol-$d_4$) δ 8.34-8.31 (m, 2H), 7.55-7.40 (m, 4H), 7.26 (t, J=7.8 Hz, 1H), 6.58 (s, 1H), 4.57 (d, J=9.9 Hz, 1H), 4.37 (d, J=9.9 Hz, 1H), 3.96 (br, 1H), 3.93 (s, 3H), 3.66 (dd, J=18.6, 10.7 Hz, 2H), 1.58 (dd, J=14.4, 9.4 Hz, 1H), 1.37-1.24 (m, 1H), 1.05 (s, 9H).

Example 10: Preparation of (2R,3R,4R,5S)—N-(4-carbamoyl-2-methoxyphenyl)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxamide Synthesis of (2R,3R,4R,5S)—N-(4-carbamoyl-2-methoxyphenyl)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxamide: Into an 8 mL vial were added (2S,3S,4S,5R)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxylic acid (racemate) (32 mg, 0.07 mmol, 1.0 eq),4-amino-3-methoxybenzamide (12 mg, 0.07 mmol, 1.0 eq), dichloromethane (2.0 mL), DIEA (11 mg, 0.08 mmol, 1.2 eq) and HATU (32 mg, 0.08 mmol, 1.2 eq) at 25° C. The reaction mixture was stirred for 12 hours at 25° C. The resulting mixture was concentrated under vacuum. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3{\cdot}H_2O$) and acetonitrile (35% $CH_3CN$ up to 75% in 10 min); Detector, uv. The collected solution was concentrated under vacuum to remove acetonitrile and the resulting solution was dried by lyophilization. The residue was purified by Chiral-SFC using the following conditions: Column: CHIRAL ART Cellulose-SB, 3*25 cm, 5 μm; mobile phase A: $CO_2$; mobile phase B: methanol—Preparative; Flow rate: 80 mL/min; Gradient: isocratic 40% B; Detector, 220 nm. Finally, (2R,3R,4R,5S)—N-(4-carbamoyl-2-methoxyphenyl)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxamide (8 mg, 18%) was obtained as white solid. $T_R$=2.094 min in CHIRAL-HPLC. Column: CHIRALPAK IG-3, 100*4.6 mm, 3 um IG30CS-UL011.mobile phase A: n-Hexane/DCM=1/1; mobile phase B: Ethanol (0.1% DEA), Start Conc. of Pump B: 50.0% in 4 min, Oven Temperature: 25° C. LC-MS (ESI, m/z) M+1: 600. $^1$HNMR (300 MHz, Methanol-$d_4$) δ 8.35-8.32 (m, 2H), 7.50-7.40 (m, 4H), 7.24 (t, J=7.8 Hz, 1H), 6.61 (s, 1H), 4.53 (s, 1H), 4.37 (d, J=9.6 Hz, 1H), 3.96 (br, 1H), 3.93 (s, 3H), 71 (d, J=12.3 Hz, 1H), 3.63 (s, 1H), 1.48 (t, J=12.3 Hz, 1H), 1.36-1.28 (m, 1H), 1.06 (s, 9H).

Example 11: Preparation of (2S,3S,4S,5R)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide Synthesis of (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (racemate): Into a 50 mL round-bottom flask were placed tert-butyl (2S,3S,4S,5R)-4-(3-chloro-2-fluorophenyl)-2-(2,2-dimethylpropyl)-6'-(trifluoromethyl)-1,2'-dihydrospiro[pyrrolidine-3,3'-pyrrolo[3,2-c]pyridine]-5-carboxylate (racemate) (160 mg, 0.3 mmol, 1.0 eq), trifluoroacetic acid (4 mL). The reaction mixture was stirred for 16 hours at 25° C. The resulting mixture was diluted with water (20 mL) and then extracted with ethyl acetate (2×20 mL). The combined organic phase was washed with brine (2×20 mL), dried over anhydrous sodium sulfate and concentrated under vacuum. Finally, (2S,3S,4S,5R)-4-(3-chloro-2-fluorophenyl)-2-(2,2-dimethylpropyl)-6'-(trifluoromethyl)-1,2'-dihydrospiro[pyrrolidine-3,3'-pyrrolo[3,2-c]pyridine]-5-carboxylic acid (racemate) (140 mg, crude) was obtained as a light yellow solid. LC-MS (ESI, m/z) M+1: 486/488. $^1$HNMR (400 MHz, Methanol-$d_4$) δ 8.60 (s, 1H), 7.59 (t, −7.0 Hz, 1H), 7.47 (t, J=7.6 Hz, 1H), 7.25 (t, J=8.0 Hz, 1H), 6.88 (s, 1H), 5.14 (d, J=11.4 Hz, 1H), 4.55 (d, J=11.4 Hz, 1H), 4.37 (d, −8.0 Hz, 1H), 4.03 (d, J=12.6 Hz, 1H), 3.87 (d, J=12.6 Hz, 1H), 1.96 (dd, −15.4, 8.6 Hz, 1H), 1.65 (d, J=15.4 Hz, 1H), 0.99 (s, 9H).

Synthesis of (2S,3S,4S,5R)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide (racemate): Into an 8 mL vial were placed (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (racemate) (130 mg, 0.3 mmol, 1.0 eq), 4-amino-3-methoxybenzamide (58 mg, 0.4 mmol, 1.3 eq), HATU (122 mg, 0.3 mmol, 1.2 eq), DIEA (104 mg, 0.8 mmol, 3.0 eq), N,N-dimethylformamide (3 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3{\cdot}H_2O$) and $CH_3CN$ (70% Phase B up to 80% in 12 min); Detector, UV 254/220 nm. Finally, (2S,3S,4S,5R)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide (racemate) (50 mg, 29%) was obtained as an off white solid. LC-MS (ESI, m/z) M+1: 634/636.

Synthesis of (2S,3S,4S,5R)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide: 50 mg of (2S,3S,4S,5R)—N-(4-carbamoyl-2-methoxyphenyl)-4-(3- chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide (racemate) was purified by Chiral-Prep-HPLC using the following conditions: Column: CHIRALPAK IG, 3*25 cm, 5 μm; Mobile Phase A: Hexane: dichloromethane=3:1—HPLC, Mobile Phase B: ethanol (0.1% $NH_3 \cdot H_2O$)—HPLC; Flow rate: 35 mL/min; Gradient: 50% B to 50% B in 8 min; Wave Length: 220/254 nm. Finally, (2S,3S,4S,5R)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide (20 mg) was obtained as an off white solid. LC-MS (ESI, m/z) M+1: 634/636. $T_R$=1.392 min in CHIRAL-HPLC, Column: CHIRALPAK IG-3, 100*4.6 mm, 3 um. mobile phase A: n-Hexane/DCM=5/1; mobile phase B: Ethanol (0.1% DEA), Pump Mode: Binary gradient, Conc. of Pump B: 50.0% in 5 min, Oven Temperature: 25° C. $^1$HNMR (400 MHz, DMSO-$d_6$) δ 10.68 (s, 1H), 8.43 (s, 1H), 8.34 (d, J=8.4 Hz, 1H), 7.91 (s, 1H), 7.57 (d, J=1.8 Hz, 1H), 7.50 (dd, J=8.4, 1.8 Hz, 1H), 7.49-7.38 (m, 2H), 7.27 (s, 1H), 7.23 (t, J=8.0 Hz, 1H), 6.61 (s, 2H), 4.36 (t, J=9.8 Hz, 1H), 4.28 (d, J=9.8 Hz, 1H), 3.90 (s, 3H), 3.82-3.71 (m, 1H), 3.67 (d, J=11.2 Hz, 1H), 3.46-3.36 (m, 2H), 1.38 (dd, J=14.2, 9.2 Hz, 1H), 1.12 (d, J=13.8 Hz, 1H), 0.94 (s, 9H).

Example 12: Preparation of (2R,3R,4R,5S)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide Synthesis of (2R,3R,4R,5S)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide: 50 mg of (2S,3S,4S,5R)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide (racemate) was purified by Chiral-Prep-HPLC using the following conditions: Column: CHIRALPAK IG, 3*25 cm, 5 μm; Mobile Phase A: Hexane: dichloromethane=3:1—HPLC, Mobile Phase B: ethanol (0.1% $NH_3 \cdot H_2O$)—HPLC; Flow rate: 35 mL/min; Gradient: 50% B to 50% B in 8 min; Wave Length: 220/254 nm. Finally, (2R,3R,4R,5S)—N-(4-carbamoyl-2-methoxyphenyl)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxamide (22 mg) was obtained as an off white solid. $T_R$=2.061 min in CHIRAL-HPLC, Column: CHIRALPAK IG-3, 100*4.6 mm, 3 um. mobile phase A: n-Hexane/DCM=5/1; mobile phase B: Ethanol (0.1% DEA), Pump Mode: Binary gradient, Conc. of Pump B: 50.0% in 5 min, Oven Temperature: 25° C. LC-MS (ESI, m/z) M+1: 634/636. $^1$HNMR (400 MHz, DMSO-$d_6$) δ 10.68 (s, 1H), 8.44 (d, J=1.4 Hz, 1H), 8.34 (d, J=8.4 Hz, 1H), 7.91 (s, 1H), 7.57 (d, J=2.0 Hz, 1H), 7.50 (dd, J=8.4, 1.8 Hz, 1H), 7.49-7.38 (m, 2H), 7.27 (s, 1H), 7.23 (t, J=7.8 Hz, 1H), 6.61 (s, 2H), 4.36 (t, J=9.8 Hz, 1H), 4.28 (d, J=9.8 Hz, 1H), 3.90 (s, 3H), 3.82-3.71 (m, 1H), 3.67 (d, J=11.2 Hz, 1H), 3.46-3.33 (m, 2H), 1.38 (dd, J=14.2, 9.4 Hz, 1H), 1.12 (d, J=14.0 Hz, 1H), 0.94 (s, 9H).

Example 13: Preparation of (2S,3S,4S,5R)—N-(4-carbamoyl-2-methoxyphenyl)-4-(3-chloro-2-fluorophenyl)-6'-cyclopropyl-2-(2,2-dimethylpropyl)-1',2'-dihydrospiro[pyrrolidine-3,3'-pyrrolo[3,2-c]pyridine]-5-carboxamide (racemate)

Synthesis of tert-butyl (2S,3S,4S,5R)-4-(3-chloro-2-fluorophenyl)-6'-cyclopropyl-2-(2,2-dimethylpropyl)-1',2'-dihydrospiro[pyrrolidine-3,3'-pyrrolo[3,2-c]pyridine]-5-carboxylate (racemate): Into an 8 mL vial were added tert-butyl (2S,3S,4S,5R)-6'-chloro-4-(3-chloro-2-fluorophenyl)-2-(2,2-dimethylpropyl)-1',2'-dihydrospiro[pyrrolidine-3,3'-pyrrolo[3,2-c]pyridine]-5-carboxylate (racemate) (115 mg, 0.2 mmol, 1.0 eq), dioxane (2.0 mL), cyclopropylboronic acid (39 mg, 0.4 mmol, 2.0 eq), $K_3PO_4$ (96 mg, 0.4 mmol, 2.0 eq) and Pd(dppf)$Cl_2 \cdot CH_2Cl_2$ (18 mg, 0.02 mmol, 0.1 eq) at 25° C. The reaction mixture was stirred for 12 hours at 100° C. under nitrogen atmosphere. The resulting mixture was diluted with water (4 mL) and then extracted with ethyl acetate (3×5 mL). The combined organic layers were washed with brine (5 mL), dried over anhydrous sodium sulfate. After filtration, the filtrate was concentrated under vacuum. The crude residue was applied onto a silica gel column and eluted with ethyl acetate/petroleum ether=1:1 to give tert-butyl (2S,3S,4S,5R and 2R,3R,4R)-4-(3-chloro-2-fluorophenyl)-6'-cyclopropyl-2-(2,2-dimethylpropyl)-1,2'-dihydrospiro[pyrrolidine-3,3'-pyrrolo[3,2-c]pyridine]-5-carboxylate (racemate) (35 mg, 30%) as white solid. LC-MS (ESI, m/z) M+1: 514/516.

Synthesis of (2S,3S,4S,5R)-4-(3-chloro-2-fluorophenyl)-6'-cyclopropyl-2-(2,2-dimethylpropyl)-1',2'-dihydrospiro[pyrrolidine-3,3'-pyrrolo[3,2-c]pyridine]-5-carboxylic acid (racemate): Into an 8 mL vial were added tert-butyl (2S,3S,4S,5R)-4-(3-chloro-2-fluorophenyl)-6'-cyclopropyl-2-(2,2-dimethylpropyl)-1',2'-dihydrospiro[pyrrolidine-3,3'-pyrrolo[3,2-c]pyridine]-5-carboxylate (racemate) (35 mg, 0.07 mmol, 1.0 eq) and 2,2,2-trifluoroacetic acid (1 mL) at 25° C. The reaction mixture was stirred for 12 hours at 25° C. The resulting mixture was concentrated under vacuum to give (2S,3S,4S,5R)-4-(3-chloro-2-fluorophenyl)-6'-cyclopropyl-2-(2,2-dimethylpropyl)-1',2'-dihydrospiro[pyrrolidine-3,3'-pyrrolo[3,2-c]pyridine]-5-carboxylic acid (racemate) (20 mg, 64%) as colorless oil. LC-MS (ESI, m/z) M+1: 458/560.

Synthesis of (2S,3S,4S,5R)—N-(4-carbamoyl-2-methoxyphenyl)-4-(3-chloro-2-fluorophenyl)-6'-cyclopropyl-2-(2,2-dimethylpropyl)-1',2'-dihydrospiro[pyrrolidine-3,3'-pyrrolo[3,2-c]pyridine]-5-carboxamide (racemate): Into an 8 mL vial were added (2S,3S,4S,5R)-4-(3-chloro-2-fluorophenyl)-6'-cyclopropyl-2-(2,2-dimethylpropyl)-1',2'-dihydrospiro[pyrrolidine-3,3'-pyrrolo[3,2-c]pyridine]-5-carboxylic acid (racemate) (20 mg, 0.04 mmol, 1.0 eq), dichloromethane (1.0 mL), 4-amino-3-methoxybenzamide (11 mg, 0.06 mmol, 1.5 eq), DIEA (11 mg, 0.08 mmol, 2.0 eq) and HATU (20 mg, 0.05 mmol, 1.2 eq) at 25° C. The reaction mixture was stirred for 12 hours at 25° C. The resulting mixture was concentrated under vacuum. The crude residue was purified with Prep-TLC (acetate/petroleum ether=1:2), and then further purified by reverse flash chousomatography using the following conditions: column, silica gel; mobile phase, acetonitrile in water, 10% to 60% gradient in 10 min; detector, UV 254 nm. Finally, (2S,3S,4S,5R)—N-(4-carbamoyl-2-methoxyphenyl)-4-(3-chloro-2-fluorophenyl)-6'-cyclopropyl-2-(2,2-dimethylpropyl)-1,2'-dihydrospiro[pyrrolidine-3,3'-pyrrolo[3,2-c]pyridine]-5-carboxamide (racemate) (1.8 mg, 6%) was obtained as white solid. LC-MS (ESI, m/z) M+1: 606/608. $^1$HNMR (300 MHz, $CD_3OD$-d) δ 8.38 (d, J=8.4 Hz, 1H), 8.23 (s, 1H), 7.59 (d, J=1.9 Hz, 1H), 7.55-7.46 (m, 2H), 7.42 (t, J=7.3 Hz, 1H), 7.24 (t, J=8.0 Hz, 1H), 6.17 (s, 1H), 5.36 (t, J=4.7 Hz, 1H), 4.48 (d, J=9.7 Hz, 1H), 4.35 (d, J=9.8 Hz, 1H), 3.90 (d, J=12.2 Hz, 1H), 3.76-3.61 (m, 1H), 2.10-1.99 (m, 1H), 1.66-1.54 (m, 5H), 1.38 (s, 9H), 1.08 (s, 9H).

Example 14: Preparation of 4-((2'S,3S,4'S,5'R)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carboxamide Synthesis of tert-butyl (2'S,3S,4'S,5'R)-6-chloro-4'-(3-chloro-2-fluorophenyl)-2'-neopentylspiro[indoline-3,3'-pyrrolidine]-5'-carboxylate and (2'R,3R,4'R,5'S)-6-chloro-4'-(3-chloro-2-fluorophenyl)-2'-neopentylspiro[indoline-3,3'-pyrrolidine]-5'-carboxylate: 5.0 g of tert-butyl (2'S,3S,4'S,5'R)-6-chloro-4'-(3-chloro-2-fluorophenyl)-2'-neopentylspiro[indoline-3,3'-pyrrolidine]-5'-carboxylate (racemate) was purified by Chiral-SFC using the following conditions: Column: CHIRAL ART Cellulose-SC, 3*25 cm, 5 μm; Mobile Phase A: $CO_2$, Mobile Phase B: $CH_3OH$ (0.1%2M $NH_3$—$CH_3OH$); Flow rate: 80 mL/min; Gradient: isocratic 20% B Detector, 220 nm. Finally, tert-butyl (2'S,3S,4'S,5'R)-6-chloro-4'-(3-chloro-2-fluorophenyl)-2'-neopentylspiro[indoline-3,3'-pyrrolidine]-5'-carboxylate (2.2 g) was obtained as a light brown solid. And (2'R,3R,4'R,5'S)-6-chloro-4'-(3-chloro-2-fluorophenyl)-2'-neopentylspiro[indoline-3,3'-pyrrolidine]-5'-carboxylate (2.1 g) was obtained as a light brown solid. LC-MS (ESI, m/z) M+1: 507/509. A, $T_R$=1.210 min in CHIRAL-SFC, Column: SC 100×4.6 mm 3.0 um. mobile phase A: $CO_2$; mobile phase B: $CH_3OH$ (20 mM $NH_3$), Start Conc. of Pump B: 10.0% in 4 min, Oven Temperature: 35° C. B, $T_R$=0.780 min in CHIRAL-SFC, Column: SC 100×4.6 mm 3.0 um. mobile phase A: $CO_2$; mobile phase B: $CH_3OH$ (20 mM $NH_3$), Start Conc. of Pump B: 10.0% in 4 min, Oven Temperature: 35° C.

Synthesis of 3,4-dihydro-2H-benzo[b][1,4]oxazine-7-carboxamide: Into a 40 mL vial were placed methyl 3,4-dihydro-2H-benzo[b][1,4]oxazine-7-carboxylate (1.0 g, 10.3 mmol, 1.0 eq), $NH_3 \cdot H_2O$ (10 mL). The reaction mixture was stirred for 16 hours at 100° C. The resulting mixture was diluted with water (100 mL), and extracted with ethyl acetate (2×100 mL). The combined organic phase was washed with brine (2×100 mL) and dried over anhydrous sodium sulfate. After filtration, the filtrate was concentrated under vacuum. Finally, 3,4-dihydro-2H-benzo[b][1,4]oxazine-7-carboxamide (400 mg, crude) was obtained as a light brown solid. LC-MS (ESI, m/z) M+1: 179. $^1$HNMR (400 MHz, DMSO-$d_6$) δ 7.53 (s, 1H), 7.30-7.18 (m, 2H), 6.87 (s, 1H), 6.53 (d, J=8.2 Hz, 1H), 6.31 (s, 1H), 4.15-4.06 (m, 2H), 3.30 (d, J=2.8 Hz, 2H).

Synthesis of 4-((2'S,3S,4'S,5'R)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carboxamide: Into a 40 mL round-bottom flask and maintained under an inert atmosphere of nitrogen, were placed tert-butyl (2'S,3S,4'S,5'R)-6-chloro-4'-(3-chloro-2-fluorophenyl)-2'-neopentylspiro[indoline-3,3'-pyrrolidine]-5'-carboxylate (150 mg, 0.3 mmol, 1.0 eq), dichloromethane (5 mL), 3,4-dihydro-2H-benzo[b][1,4]oxazine-7-carboxamide (63 g, 0.4 mmol, 1.2 eq). After that, trimethylaluminium (2 M in toluene, 1 mL, 1.8 mmol, 6.0 eq) was added at 0° C. Then the reaction mixture was stirred for 6 hours at 25° C. The resulting mixture was diluted with water (50 mL) and extracted with ethyl acetate (2×50 mL). The combined organic phase was washed with brine (2×50 mL), dried over anhydrous sodium sulfate. After filtration, the filtrate was concentrated under vacuum. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (40% Phase B up to 60% in 7 min); Detector, UV 254/220 nm. Finally, 4-((2'S,3S,4'S,5'R)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carboxamide (10 mg, 6%) was obtained as a white solid. LC-MS (ESI, m/z) M+1: 611. $^1$HNMR (300 MHz, DMSO-$d_6$) δ 7.88 (s, 1H), 7.44-7.31 (m, 3H), 7.28 (s, 2H), 7.23-7.07 (m, 2H), 6.59 (dd, J=7.8, 1.8 Hz, 1H), 6.33 (d, J=1.8 Hz, 1H), 5.52 (s, 1H), 4.68 (s, 2H), 4.35 (d, J=10.2 Hz, 1H), 4.26-4.15 (m, 2H), 3.72 (s, 1H), 3.49 (d, J=10.2 Hz, 1H), 3.13 (d, J=10.5 Hz, 2H), 1.22 (d, J=10.5 Hz, 4H), 0.76 (s, 9H).

Example 15: Preparation of 4-((2'R,3R,4'R,5'S)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carboxamide Synthesis of 4-((2'R,3R,4'R,5'S)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carboxamide: Into a 40 mL round-bottom flask and maintained under an inert atmosphere of nitrogen, were placed (2'R,3R,4'R,5'S)-6-chloro-4'-(3-chloro-2-fluorophenyl)-2'-neopentylspiro[indoline-3,3'-pyrrolidine]-5'-carboxylate (150 mg, 0.3 mmol, 1.0 eq), dichloromethane (5 mL), 3,4-dihydro-2H-benzo[b][1,4]oxazine-7-carboxamide (63 g, 0.4 mmol, 1.2 eq). After that, trimethylaluminium (2 M in toluene, 1 mL, 1.8 mmol, 6.0 eq) was added at 0° C. Then the reaction mixture was stirred for 6 hours at 25° C. The resulting mixture was diluted with water (50 mL), extracted with ethyl acetate (2×50 mL). The combined organic phase was washed with brine (2×50 mL), and dried over anhydrous sodium sulfate. After filtration, the filtrate was concentrated under vacuum. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (40% Phase B up to 60% in 7 min); Detector, UV 254/220 nm. Finally, 4-((2'R,3R,4'R,5'S)-6-chloro-4'-(3-chloro-2-fluorophenyl)-2'-neopentylspiro[indoline-3,3'-pyrrolidine]-5'-carbonyl)-3,4-dihydro-2H-benzo[b][1,4]oxazine-7-carboxamide (10 mg, 6%) was obtained as a white solid. LC-MS (ESI, m/z) M+1: 611. $^1$HNMR (300 MHz, DMSO-$d_6$) δ 7.87 (s, 1H), 7.44-7.31 (m, 3H), 7.28 (s, 2H), 7.23-7.08 (m, 2H), 6.59 (dd, J=7.9, 1.9 Hz, 1H), 6.33 (d, J=1.9 Hz, 1H), 5.52 (s, 1H), 4.68 (s, 2H), 4.37-4.33 (m, 1H), 4.21 (d, J=13.4 Hz, 2H), 3.71 (s, 1H), 3.48 (d, J=10.5 Hz, 1H), 3.13 (d, J=10.8 Hz, 2H), 1.22 (d, J=10.6 Hz, 4H), 0.76 (s, 9H).

Example 16: Preparation of (2'S,3S,4'S,5'R)-6-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)-2-methoxyphenyl)-2'-neopentylspiro[indoline-3,3'-pyrrolidine]-5'-carboxamide (racemate)

Synthesis of methyl 3-bromo-2-(bromomethyl)benzoate: Into a 500 mL round-bottom flask were added methyl 3-bromo-2-methylbenzoate (20.0 g, 87.7 mmol, 1.0 eq) and $CCl_4$ (200 mL) and NBS (18.7 g, 105.2 mmol, 1.2 eq) and BPO (2.1 g, 8.7 mmol, 0.1 eq). The reaction mixture was stirred overnight at 100° C. The resulting mixture was quenched by the addition of water (300 mL), and then extracted with dichloromethane (3×300 mL). The resulting mixture was concentrated under vacuum. The crude residue was applied onto a silica gel column and eluted with ethyl acetate/petroleum ether=(1:0 to 10:1) to give methyl 3-bromo-2-(bromomethyl)benzoate (17.0 g, 63%) as a brown oil. $^1$HNMR: (300 MHz, DMSO-$d_6$) δ 7.88 (ddd, J=15.9, 7.8, 1.2 Hz, 2H), 7.40 (t, J=7.8 Hz, 1H), 5.03 (s, 2H), 3.89 (s, 3H).

Synthesis of 3-(1-oxo-3H-isoindol-2-yl)piperidine-2,6-dione: Into a 250 mL round-bottom flask were added methyl 3-bromo-2-(bromomethyl)benzoate (7.6 g, 23.0 mmol, 1.0 eq) and 3-aminopiperidine-2,6-dione (5.0 g, 28.0 mmol, 1.2 eq) and acetonitrile (100 mL) and DIEA (3.3 g, 30.6 mml, 1.3 eq). The reaction mixture was stirred overnight at 80° C. The reaction was quenched with water (100 mL). The resulting mixture was filtered, the filter cake was washed with acetonitrile (3×200 mL) and water (3×200 mL). Finally, 3-(1-oxo-3H-isoindol-2-yl)piperidine-2,6-dione (4.0 g, 50%) was obtained as a grey solid. LC-MS (ESI, m/z) M−1: 321/323.

Synthesis of tert-butyl N-{5-[2-(2,6-dioxopiperidin-3-yl)-1-oxo-3H-isoindol-4-yl]pent-4-yn-1-yl}carbamate: Into a solution of 3-(4-bromo-1-oxo-3H-isoindol-2-yl)piperidine-2,6-dione (2.0 g, 6.2 mmol, 1.0 eq) and tert-butyl N-(pent-4-yn-1-yl)carbamate (2.2 g, 12.4 mmol, 2.0 eq) in N,N-dimethylformamide (20 mL) and triethylamine (1.8 g, 18.6 mmol, 3.0 eq) were added CuI (236 mg, 1.2 mmol, 0.2 eq) and $Pd(PPh_3)_2Cl_2$ (436 mg, 0.6 mmol, 0.1 eq). The reaction mixture was stirred for 3 hours at 70° C. under a nitrogen atmosphere. The resulting mixture was filtered. The filtrate was diluted with ethyl acetate (100 mL) and then washed with water (3×100 mL), dried over anhydrous sodium sulfate. After filtration, the filtrate was concentrated under vacuum. The residue was applied onto a silica gel column and eluted with petroleum ether/ethyl acetate=(1:0 to 1:1) to give tert-butyl N-{5-[2-(2,6-dioxopiperidin-3-yl)-1-oxo-3H-isoindol-4-yl]pent-4-yn-1-yl}carbamate (2.2 g, 84%) as a brown solid. LC-MS (ESI, m/z) M−1: 424.

Synthesis of 3-[4-(5-aminopent-1-yn-1-yl)-1-oxo-3H-isoindol-2-yl]piperidine-2,6-dione: Into a 50 mL 3-necked round-bottom flask were added tert-butyl N-{5-[2-(2,6-dioxopiperidin-3-yl)-1-oxo-3H-isoindol-4-yl]pent-4-yn-1-yl}carbamate (1.0 g, 2.3 mmol, 1.0 eq) and DCM (15 mL). After that, to the above mixture was added TFA (15 mL) dropwise at 0° C. The reaction mixture was stirred for 3 hours at 25° C. The resulting mixture was neutralized to pH=7 with saturated $NaHCO_3$(aq.) and then extracted with dichloromethane (3×60 mL). The combined organic phase was dried over anhydrous sodium sulfate. After filtration, the filtrate was concentrated under vacuum to give 3-[4-(5-aminopent-1-yn-1-yl)-1-oxo-3H-isoindol-2-yl]piperidine-2,6-dione (750 mg, 98%) as a grey solid. LC-MS (ESI, m/z) M+1: 326.2.

Synthesis of N-(5-(2-(2,6-dioxopiperidin-3-yl)-1-oxoisoindolin-4-yl)pent-4-yn-1-yl)-3-methoxy-4-nitrobenzamide: Into a 20 mL sealed tube, were placed 3-[4-(5-aminopent-1-yn-1-yl)-1-oxo-3H-isoindol-2-yl]piperidine-2,6-dione (300 mg, 0.9 mmol, 1.0 eq), 3-methoxy-4-nitrobenzoic acid (218.1 mg, 1.1 mmol, 1.2 eq), HATU (421 mg, 1.1 mmol, 1.2 eq), DIEA (358 mg, 2.7 mmol, 3.0 eq), N,N-dimethylformamide (5 mL). The reaction mixture was stirred for 2 hours at 25° C. The reaction was then quenched by the addition of water (50 mL) and then extracted with ethyl acetate (2×50 mL). The combined organic phase was washed with brine (2×50 mL), dried over anhydrous sodium sulfate. After filtration, the filtrate was concentrated under vacuum.

The crude residue was applied onto a silica gel column and eluted with ethyl acetate/petroleum ether=(0:1 to 1:0). Finally, N-(5-(2-(2,6-dioxopiperidin-3-yl)-1-oxoisoindolin-4-yl) pent-4-yn-1-yl)-3-methoxy-4-nitrobenzamide (380 mg, 82%) was obtained as a yellow solid. LC-MS (ESI, m/z)

M+1: 505. $^1$HNMR (400 MHz, DMSO-$d_6$) δ 11.0 (s, 1H), 8.81 (t, J=5.6 Hz, 1H), 7.94 (d, J=8.2 Hz, 1H), 7.71 (dd, J=4.8, 3.0 Hz, 2H), 7.62 (d, J=7.6 Hz, 1H), 7.59-7.47 (m, 2H), 5.16 (dd, J=13.2, 5.2 Hz, 1H), 4.49 (d, J=17.8 Hz, 1H), 4.35 (d, J=17.8 Hz, 1H), 3.98 (s, 3H), 3.48 (q, J=6.6 Hz, 2H), 2.64-2.54 (m, 2H), 1.87 (p, J=7.0 Hz, 2H), 1.25 (d, J=6.8 Hz, 4H).

Synthesis of 4-amino-N-(5-(2-(2,6-dioxopiperidin-3-yl)-1-oxoisoindolin-4-yl)pent-4-yn-1-yl)-3-methoxybenzamide: Into a 20 mL sealed tube were placed N-(5-(2-(2,6-dioxopiperidin-3-yl)-1-oxoisoindolin-4-yl)pent-4-yn-1-yl)-3-methoxy-4-nitrobenzamide (330 mg, 0.6 mmol, 1.0 eq), Fe (146 mg, 2.6 mmol, 4.0 eq), $NH_4Cl$ (278 mg, 5.2 mmol, 8.0 eq), ethanol (6 mL), water (2 mL). The reaction mixture was stirred for 2 hours at 50° C. The resulting mixture was filtered, the filtrate was concentrated under vacuum. The crude residue was applied onto a silica gel column and eluted with ethyl acetate/petroleum ether=20:1 to give 4-amino-N-(5-(2-(2,6-dioxopiperidin-3-yl)-1-oxoisoindolin-4-yl) pent-4-yn-1-yl)-3-methoxybenzamide (240 mg, 77%) as light yellow solid. LC-MS (ESI, m/z) M+1: 475.

Synthesis of (2'S,3S,4'S,5'R)-6-chloro-4'-(3-chloro-2-fluorophenyl)-N-(4-((5-(2-(2,6-dioxopiperidin-3-yl)-1-oxoisoindolin-4-yl)pent-4-yn-1-yl)carbamoyl)-2-methoxyphenyl)-2'-neopentylspiro[indoline-3,3'-pyrrolidine]-5'-carboxamide (racemate): Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (200 mg, 0.4 mmol, 1.0 eq), 4-amino-N-(5-(2-(2,6-dioxopiperidin-3-yl)-1-oxoisoindolin-4-yl)pent-4-yn-1-yl)-3-methoxybenzamide (231 mg, 0.5 mmol, 1.1 eq), HATU (185 mg, 0.5 mmol, 1.1 eq), DIEA (114.5 mg, 0.7 mmol, 2.0 eq), N,N-dimethylformamide (4 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (80% Phase B up to 90% in 7 min); Detector, UV 254/220 nm. Finally, (2'S,3S,4'S,5'R)-6-chloro-4'-(3-chloro-2-fluorophenyl)-N-(4-((5-(2-(2,6-dioxopiperidin-3-yl)-1-oxoisoindolin-4-yl) pent-4-yn-1-yl) carbamoyl)-2-methoxyphenyl)-2'-neopentylspiro[indoline-3,3'-pyrrolidine]-5'-carboxamide (racemate) (120 mg) was obtained as a white solid. LC-MS (ESI, m/z) M+1: 907/909. $^1$HNMR (400 MHz, DMSO-$d_6$) δ 10.99 (s, 1H), 10.67 (d, J=2.4 Hz, 1H), 8.47 (s, 1H), 8.32 (d, J=8.4 Hz, 1H), 7.71 (dt, −7.6, 1.6 Hz, 1H), 7.62 (dt, −7.6, 1.3 Hz, 1H), 7.57-7.37 (m, 4H), 7.43-7.20 (m, 2H), 7.23-7.17 (m, 1H), 6.57-6.47 (m, 1H), 6.31 (d, J=1.9 Hz, 1H), 5.52 (s, 1H), 5.21-5.06 (m, 1H), 4.48 (dd, J=17.8, 9.6 Hz, 1H), 4.40-4.25 (m, 2H), 4.25-4.08 (m, 1H), 3.88 (d, −5.4 Hz, 3H), 3.71 (t, J=11.1 Hz, 1H), 3.53 (d, J=10.5 Hz, 1H), 3.49-3.40 (m, 2H), 3.20 (d, J=9.8 Hz, 2H), 2.91 (s, 1H), 2.57 (t, J=6.6 Hz, 2H), 2.02 (d, J=13.6 Hz, 1H), 1.85 (t, −6.9 Hz, 2H), 1.35 (dd, J=14.2, 9.4 Hz, 1H), 1.24 (s, 3H), 0.92 (s, 9H).

Example 17: Preparation of (2'S,3S,4'S,5'R)-6-chloro-4'-(3-chloro-2-fluorophenyl)-N-(4-((5-(2-((R)-2,6-dioxopiperidin-3-yl)-1-oxoisoindolin-4-yl) pent-4-yn-1-yl)carbamoyl)-2-methoxyphenyl)-2'-neopentylspiro[indoline-3,3'-pyrrolidine]-5'-carboxamide Synthesis of (2'S,3S,4'S,5'R)-6-chloro-4'-(3-chloro-2-fluorophenyl)-N-(4-((5-(2-((R)-2,6-dioxopiperidin-3-yl)-1-oxoisoindolin-4-yl)pent-4-yn-1-yl)carbamoyl)-2-methoxyphenyl)-2'-neopentylspiro[indoline-3,3'-pyrrolidine]-5'- carboxamide: 30 mg of (2'S,3S,4'S,5'R)-6-chloro-4'-(3-chloro-2-fluorophenyl)-N-(4-((5-(2-(2,6-dioxopiperidin-3-yl)-1-oxoisoindolin-4-yl) pent-4-yn-1-yl) carbamoyl)-2-methoxyphenyl)-2'-neopentylspiro[indoline-3,3'-pyrrolidine]-5'-carboxamide (racemate) was purified by Chiral-Prep-HPLC using the following conditions: Column: CHIRAL ART Cellulose-SC, 3*25 cm, 5 μm; mobile Phase A: Hexane: dichloromethane=1:1—HPLC, Mobile Phase B: ethanol—HPLC; Flow rate: 30 mL/min; Gradient: 50% B to 50% B in 26 min; Detector, 254 nm. Finally, (2'S,3S,4'S, 5'R)-6-chloro-4'-(3-chloro-2-fluorophenyl)-N-(4-((5-(2-((R)-2,6-dioxopiperidin-3-yl)-1-oxoisoindolin-4-yl) pent-4-yn-1-yl) carbamoyl)-2-methoxyphenyl)-2'-neopentylspiro [indoline-3,3'-pyrrolidine]-5'-carboxamide (10 mg) was obtained as a white solid. LC-MS (ESI, m/z) M+1: 907/909. $T_R$=2.348 min in CHIRAL-HPLC, Column: YMC Cellulose-SC, 100*4.6 mm, 3 um. mobile phase A: n-Hexane/DCM=1/1; mobile phase B: Ethanol, Pump Mode: Binary gradient, Conc. of Pump B: 50.0% in 5 min, Oven Temperature: 25° C. $^1$HNMR (400 MHz, DMSO-$d_6$) δ 10.99 (s, 1H), 10.66 (s, 1H), 8.46 (t, J=5.8 Hz, 1H), 8.32 (d, −8.4 Hz, 1H), 7.70 (d, J=7.5 Hz, 1H), 7.62 (d, −7.5 Hz, 1H), 7.52 (d, −7.6 Hz, 1H), 7.52-7.39 (m, 3H), 7.39-7.29 (m, 2H), 7.20 (t, −7.9 Hz, 1H), 6.51 (dd, J=8.0, 1.9 Hz, 1H), 6.31 (d, −1.9 Hz, 1H), 5.52 (s, 1H), 5.15 (dd, J=13.2, 5.1 Hz, 1H), 4.46 (d, J=17.9 Hz, 1H), 4.37-4.26 (m, 2H), 4.13 (d, J=9.5 Hz, 1H), 3.87 (s, 3H), 3.70 (t, J=11.2 Hz, 1H), 3.53 (d, J=10.5 Hz, 1H), 3.44 (d, −6.8 Hz, 2H), 3.19 (t, J=9.7 Hz, 2H), 2.97-2.84 (m, 1H), 2.57 (q, −7.8, 6.9 Hz, 4H), 2.07-1.99 (m, 1H), 1.89-1.81 (m, 2H), 1.35 (dd, J=14.3, 9.4 Hz, 1H), 1.26-1.17 (m, 1H), 0.92 (s, 9H).

Example 18: Preparation of (2'S,3S,4'S,5'R)-6-chloro-4'-(3-chloro-2-fluorophenyl)-N-(4-((5-(2-((S)-2,6-dioxopiperidin-3-yl)-1-oxoisoindolin-4-yl) pent-4-yn-1-yl)carbamoyl)-2-methoxyphenyl)-2'-neopentylspiro[indoline-3,3'-pyrrolidine]-5'-carboxamide Synthesis of (2'S,3S,4'S,5'R)-6-chloro-4'-(3-chloro-2-fluorophenyl)-N-(4-((5-(2-((S)-2,6-dioxopiperidin-3-yl)-1-oxoisoindolin-4-yl)pent-4-yn-1-yl)carbamoyl)-2-methoxyphenyl)-2'-neopentylspiro[indoline-3,3'-pyrrolidine]-5'-carboxamide: 30 mg of (2'S,3S,4'S,5'R)-6-chloro-4'-(3-chloro-2-fluorophenyl)-N-(4-((5-(2-(2,6-dioxopiperidin-3-yl)-1-oxoisoindolin-4-yl) pent-4-yn-1-yl) carbamoyl)-2-methoxyphenyl)-2'-neopentylspiro[indoline-3,3'-pyrrolidine]-5'-carboxamide (racemate) was purified by Chiral-Prep-HPLC using the following conditions: Column: CHIRAL ART Cellulose-SC, 3*25 cm, 5 μm; mobile Phase A: Hexane: dichloromethane=1:1—HPLC, Mobile Phase B: ethanol—HPLC; Flow rate: 30 mL/min; Gradient: 50% B to 50% B in 26 min; Detector, 254 nm. Finally, (2'S,3S,4'S, 5'R)-6-chloro-4'-(3-chloro-2-fluorophenyl)-N-(4-((5-(2-((S)-2,6-dioxopiperidin-3-yl)-1-oxoisoindolin-4-yl) pent-4-yn-1-yl)carbamoyl)-2-methoxyphenyl)-2'-neopentylspiro [indoline-3,3'-pyrrolidine]-5'-carboxamide (9 mg) was obtained as a white solid. LC-MS (ESI, m/z) M+1: 907/909. $T_R$=2.997 min in CHIRAL-HPLC, Column: YMC Cellulose-SC, 100*4.6 mm, 3 um. mobile phase A: n-Hexane/DCM=1/1; mobile phase B: Ethanol, Pump Mode: Binary gradient, Conc. of Pump B: 50.0% in 5 min, Oven Temperature: 25° C. $^1$HNMR (400 MHz, DMSO-$d_6$) δ 10.99 (s, 1H), 10.67 (s, 1H), 8.47 (t, −5.7 Hz, 1H), 8.32 (d, −8.4 Hz, 1H), 7.71 (d, J=7.5 Hz, 1H), 7.62 (d, −7.6 Hz, 1H), 7.56-7.43 (m, 3H), 7.47-7.40 (m, 1H), 7.43-7.32 (m, 1H), 7.35-7.27 (m, 1H), 7.20 (t, J=7.9 Hz, 1H), 6.51 (dd, −8.0, 1.9 Hz, 1H), 6.31 (d, J=1.9 Hz, 1H), 5.52 (s, 1H), 5.15 (dd, J=13.3, 5.1 Hz, 1H), 4.49 (d, J=17.8 Hz, 1H), 4.38-4.26 (m, 2H), 4.12 (d, J=9.5 Hz, 1H), 3.89 (s, 3H), 3.71 (t, J=11.2 Hz, 1H), 3.53 (d, J=10.5 Hz, 1H), 3.44 (q, −6.7 Hz, 2H), 3.18 (t, J=11.0 Hz, 2H), 2.99-2.86 (m, 1H), 2.57 (q, −7.4, 6.7 Hz, 3H), 2.02 (d, J=12.5 Hz, 1H), 1.85 (p, −7.0 Hz, 2H), 1.35 (dd, J=14.3, 9.3 Hz, 1H), 1.26-1.16 (m, 2H), 0.92 (s, 9H).

Example 19: Preparation of (2'S,3S,4'S,5'R)-6-chloro-4'-(3-chloro-2-fluorophenyl)-2'-(2,2-dimethylpropyl)-N-[2-methoxy-4-({5-[2-(1-methyl-2,6-dioxopiperidin-3-yl)-1-oxo-3H-isoindol-4-yl]pent-4-yn-1-yl}carbamoyl)phenyl]-1,2-dihydrospiro[indole-3,3'-pyrrolidine]-5'-carboxamide Synthesis of 3-(4-iodo-1-oxo-3H-isoindol-2-yl)-1-methylpiperidine-2,6-dione: Into a 100 mL round-bottom flask, were placed 3-(4-iodo-1-oxo-3H-isoindol-2-yl)piperidine-2,6-dione (1.5 g, 4.1 mmol, 1.0 eq), N,N-dimethylformamide (20 mL), $CH_3I$ (1.2 g, 8.1 mmol, 2.0 eq). After that, DBU (1.2 g, 8.1 mmol, 2.0 eq) was added at 0° C. The reaction mixture was stirred for 2 hours at 25° C. The resulting mixture was concentrated under vacuum. The residue was diluted with water (100 mL) and extracted with ethyl acetate (2×80 mL). The combined organic phase was washed with brine (2×80 mL), dried over anhydrous sodium sulfate. After filtration, the filtrate was concentrated under vacuum. The crude residue was applied onto a silica gel column and eluted with ethyl acetate/petroleum ether=(0:1 to 1:1) to give 3-(4-iodo-1-oxo-3H-isoindol-2-yl)-1-methylpiperidine-2,6-dione (1.1 g, 71%) as a purple solid. LC-MS (ESI, m/z) M+1: 385. $^1$HNMR (400 MHz, DMSO-$d_6$) δ 8.04 (dd, J=7.4, 2.0 Hz, 1H), 7.78 (dd, J=7.6, 3.4 Hz, 1H), 7.36 (t, J=7.8 Hz, 1H), 5.30-5.12 (m, 1H), 4.34-4.23 (m, 1H), 4.15 (d, J=17.4 Hz, 1H), 3.02 (s, 3H), 2.98 (dd, J=12.8, 4.6 Hz, 1H), 2.79 (dd, J=4.6, 2.4 Hz, 1H), 2.45 (dd, J=13.2, 4.6 Hz, 1H), 2.10-1.97 (m, 1H).

Synthesis of tert-butyl N-{5-[2-(1-methyl-2,6-dioxopiperidin-3-yl)-1-oxo-3H-isoindol-4-yl]pent-4-yn-1-yl}carbamate: Into a 40 mL sealed tube purged and maintained under an inert atmosphere of nitrogen, were placed 3-(4-iodo-1-oxo-3H-isoindol-2-yl)-1-methylpiperidine-2,6-dione (1.0 g, 2.6 mmol, 1.0 eq), tert-butyl N-(pent-4-yn-1-yl)carbamate (0.6 g, 3.1 mmol, 1.2 eq), CuI (0.1 g, 0.3 mmol, 0.1 eq), $Pd(PPh_3)_4$ (300 mg, 0.3 mmol, 0.1 eq), triethylamine (0.8 g, 7.8 mmol, 3.0 eq), N,N-dimethylformamide (10 mL). The reaction mixture was stirred for 2 hours at 70° C. The resulting mixture was diluted with water (50 mL), and extracted with ethyl acetate (2×100 mL). The combined organic phase was washed with brine (2×100 mL), dried over anhydrous sodium sulfate. After filtration, the filtrate was concentrated under vacuum. The crude residue was applied onto a silica gel column and eluted with ethyl acetate/petroleum ether=(0:1 to 1:0) to give tert-butyl N-{5-[2-(1-methyl-2,6-dioxopiperidin-3-yl)-1-oxo-3H-isoindol-4-yl]pent-4-yn-1-yl}carbamate (1.0 g, 87%) as light yellow solid. LC-MS (ESI, m/z) M+1: 440. $^1$HNMR (400 MHz, DMSO-$d_6$) δ 7.73 (dd, J=7.6, 1.1 Hz, 1H), 7.65 (dd, J=7.8, 1.1 Hz, 1H), 7.54 (d, J=7.6 Hz, 1H), 6.88 (t, J=5.8 Hz, 1H), 5.24 (dd, J=13.6, 5.2 Hz, 1H), 4.49 (d, J=17.8 Hz, 1H), 4.33 (d, J=17.8 Hz, 1H), 3.17-3.01 (m, J=8.0, 7.2 Hz, 2H), 3.01 (s, 3H), 2.76 (ddd, J=17.6, 4.6, 2.2 Hz, 1H), 2.48 (t, J=7.0 Hz, 3H), 2.10-1.97 (m, 1H), 1.67 (p, J=7.0 Hz, 3H), 1.36 (s, 9H).

Synthesis of 3-[4-(5-aminopent-1-yn-1-yl)-1-oxo-3H-isoindol-2-yl]-1-methylpiperidine-2,6-dione hydrochloride: Into a 100 mL round-bottom flask were placed tert-butyl N-{5-[2-(1-methyl-2,6-dioxopiperidin-3-yl)-1-oxo-3H-isoindol-4-yl]pent-4-yn-1-yl}carbamate (900 mg, 2.1 mmol, 1.0 eq), HCl (gas) in 1,4-dioxane (9 mL), dichloromethane (9 mL). The reaction mixture was stirred for 1 hour at 25° C. The resulting mixture was concentrated under vacuum to give 3-[4-(5-aminopent-1-yn-1-yl)-1-oxo-3H-isoindol-2-yl]-1-methylpiperidine-2,6-dione hydrochloride (700 mg, crude) as a light yellow solid. LC-MS (ESI, m/z) M+1: 340.

Synthesis of 3-methoxy-N-{5-[2-(1-methyl-2,6-dioxopiperidin-3-yl)-1-oxo-3H-isoindol-4-yl]pent-4-yn-1-yl}-4-nitrobenzamide: Into a 40 mL sealed tube, were placed 3-[4-(5-aminopent-1-yn-1-yl)-1-oxo-3H-isoindol-2-yl]-1-methylpiperidine-2,6-dione hydrochloride (600 mg, 1.6 mmol, 1.0 eq), 3-methoxy-4-nitrobenzoic acid (378 mg, 1.9 mmol, 1.2 eq), HATU (729 mg, 1.9 mmol, 1.2 eq), DIEA (619 mg, 4.8 mmol, 3.0 eq) and N,N-dimethylformamide (10 mL). The reaction mixture was stirred for 2 hours at 25° C. The resulting mixture was diluted with water (50 mL) and extracted with ethyl acetate (2×50 mL). The combined organic phase was washed with brine (2×50 mL) and dried over anhydrous sodium sulfate. After filtration, the filtrate was concentrated under vacuum. The crude residue was applied onto a silica gel column and eluted with ethyl acetate/petroleum ether=(0:1 to 1:0) to give 3-methoxy-N-{5-[2-(1-methyl-2,6-dioxopiperidin-3-yl)-1-oxo-3H-isoindol-4-yl]pent-4-yn-1-yl}-4-nitrobenzamide (550 mg, 66%) as an off white solid. LC-MS (ESI, m/z) M+1: 519. $^1$HNMR (400 MHz, DMSO-$d_6$) δ 8.80 (t, −5.6 Hz, 1H), 7.94 (d, −8.4 Hz, 1H), 7.74-7.68 (m, 2H), 7.65-7.60 (m, 1H), 7.55-7.50 (m, 2H), 5.23 (dd, J=13.4, 5.2 Hz, 1H), 4.48 (d, J=17.8 Hz, 1H), 4.34 (d, J=17.8 Hz, 1H), 3.98 (s, 3H), 3.47 (q, J=6.6 Hz, 2H), 2.99 (s, 3H), 2.80-2.67 (m, 1H), 2.58 (t, −7.0 Hz, 2H), 2.47-2.43 (m, 1H), 2.08-1.97 (m, 1H), 1.89-1.82 (m, 2H), 1.26-1.14 (m, 1H).

Synthesis of 4-amino-3-methoxy-N-{5-[2-(1-methyl-2,6-dioxopiperidin-3-yl)-1-oxo-3H-isoindol-4-yl]pent-4-yn-1-yl}benzamide: Into a 20 mL sealed tube were placed 3-methoxy-N-{5-[2-(1-methyl-2,6-dioxopiperidin-3-yl)-1-oxo-3H-isoindol-4-yl]pent-4-yn-1-yl}-4-nitrobenzamide (500 mg, 0.9 mmol, 1.0 eq), Fe (215 mg, 3.8 mmol, 4.0 eq), $NH_4Cl$ (155 mg, 2.9 mmol, 3.0 eq), ethanol (9 mL), water (3 mL). The reaction mixture was stirred for 2 hours at 50° C. The resulting mixture was filtered, the filtrate was concentrated under vacuum. The crude residue was applied onto a silica gel column and eluted with dichloromethane/methanol=20:1 to give 4-amino-3-methoxy-N-{5-[2-(1-methyl-2,6-dioxopiperidin-3-yl)-1-oxo-3H-isoindol-4-yl]pent-4-yn-1-yl}benzamide (300 mg, 64%) as a light yellow solid. LC-MS (ESI, m/z) M+1: 489. $^1$HNMR (400 MHz, DMSO-$d_6$) δ 8.12 (t, −5.6 Hz, 1H), 7.73 (dd, J=7.6, 1.1 Hz, 1H), 7.64 (dd, −7.6, 1.1 Hz, 1H), 7.53 (t, J=7.6 Hz, 1H), 7.35-7.23 (m, 2H), 6.60 (d, J=8.2 Hz, 1H), 5.22 (dd, J=13.6, 5.0 Hz, 1H), 5.22 (s, 2H), 4.49 (d, J=18.0 Hz, 1H), 4.35 (d, J=17.8 Hz, 1H), 3.80 (s, 3H), 3.39 (q, −6.6 Hz, 2H), 3.0 (s, 3H), 2.80-2.67 (m, 1H), 2.55 (d, J=7.0 Hz, 2H), 2.08-1.99 (m, 1H), 2.0 (s, 1H), 1.85-1.81 (m, 2H), 1.18 (t, J=7.2 Hz, 1H).

Synthesis of (2'S,3S,4'S,5'R)-6-chloro-4'-(3-chloro-2-fluorophenyl)-2'-(2,2-dimethylpropyl)-N-[2-methoxy-4-({5-[2-(1-methyl-2,6-dioxopiperidin-3-yl)-1-oxo-3H-isoindol-4-yl]pent-4-yn-1-yl}carbamoyl)phenyl]-1,2-dihydrospiro[indole-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 4-amino-3-methoxy-N-{5-[2-(1-methyl-2,6-dioxopiperidin-3-yl)-1-oxo-3H-isoindol-4-yl]pent-4-yn-1-yl}benzamide (39 mg, 0.1 mmol, 1.2 eq), HATU (28 mg, 0.1 mmol, 1.1 eq), DIEA (17 mg, 0.1 mmol, 2.0 eq), N,N-dimethylformamide (2 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (70% Phase B up to 85% in 7 min); Detector, UV 254/220 nm. Finally, (2'S,3S,4'S,5'R)-6-chloro-4'-(3-chloro-2-fluorophenyl)-2'-(2,2-dimethylpropyl)-N-[2-methoxy-4-({5-[2-(1-methyl-2,6-dioxopiperidin-3-yl)-1-oxo-3H-isoindol-4-yl]pent-4-yn-1-yl}carbamoyl) phenyl]-1,2-dihydrospiro[indole-3,3'-pyrrolidine]-5'-carboxamide (20 mg, 33%) was obtained as an off white solid. LC-MS (ESI, m/z) M+1: 921/923. $^1$HNMR (400 MHz, DMSO-$d_6$) δ 10.66 (d, J=3.2 Hz, 1H), 8.45 (d, J=4.4 Hz, 1H), 8.32 (d, J=8.4 Hz, 1H), 7.72 (dd, J=7.4, 2.4 Hz, 1H), 7.63 (d, J=7.6 Hz, 1H), 7.56-7.47 (m, 2H), 7.43 (t, J=9.4 Hz, 2H), 7.33 (dt, J=15.6, 7.2 Hz, 2H), 7.20 (t, J=8.0 Hz, 1H), 6.51 (dd, J=8.0, 2.0 Hz, 1H), 6.31 (d, J=2.0 Hz, 1H), 5.52 (s, 1H), 5.22 (dd, J=13.4, 5.2 Hz, 1H), 4.46 (dd, J=17.8, 12.4 Hz, 1H), 4.38-4.26 (m, 2H), 4.13 (dd, J=9.6, 4.8 Hz, 1H), 3.88 (d, J=6.6 Hz, 3H), 3.71 (t, J=11.2 Hz, 1H), 3.53 (d, J=10.6 Hz, 1H), 3.44 (d, J=7.0 Hz, 2H), 3.20 (d, J=10.2 Hz, 2H), 2.99 (s, 3H), 2.73 (d, J=17.0 Hz, 1H), 2.56 (t, −6.8 Hz, 3H), 2.10-1.97 (m, 1H), 1.85 (q, J=7.0 Hz, 3H), 1.35 (dd, J=14.2, 9.4 Hz, 1H), 1.21 (d, J=14.2 Hz, 1H), 0.94-0.90 (m, 9H).

Example 20: Preparation of (2'S,3S,4'S,5'R)-6-chloro-4'-(3-chloro-2-fluorophenyl)-2'-(2,2-dimethylpropyl)-N-[4-(4-{2-[2-(2,6-dioxopiperidin-3-yl)-1-oxo-3H-isoindol-4-yl]ethynyl}piperidine-1-carbonyl)-2-methoxyphenyl]-1,2-dihydrospiro[indole-3,3'-pyrrolidine]-5'-carboxamide Synthesis of tert-butyl 4-{2-[2-(2,6-dioxopiperidin-3-yl)-1-oxo-3H-isoindol-4-yl]ethynyl}piperidine-1-carboxylate: To a stirred mixture of tert-butyl 4-ethynylpiperidine-1-carboxylate (950 mg, 4.5 mmol, 1.0 eq) and 3-(4-iodo-1-oxo-3H-isoindol-2-yl)piperidine-2,6-dione (1680 mg, 4.5 mmol, 1.0 eq) in N,N-dimethylformamide (20 mL), DIEA (4 mL) were added $Pd(PPh_3)_4$ (524 mg, 0.5 mmol, 0.1 eq) and CuI (86 mg, 0.5 mmol, 0.1 eq) in portions at 25° C. under nitrogen atmosphere. The reaction mixture was stirred for 6 hours at 25° C. The resulting mixture was diluted with water (60 mL) and then extracted with ethyl acetate (3×50 mL). The combined organic layers were washed with water (3×20 mL), dried over anhydrous sodium sulfate. After filtration, the filtrate was concentrated under vacuum. The crude residue was applied onto a silica gel column and eluted with ethyl acetate/petroleum ether=(0:1 to 1:1) to give tert-butyl 4-{2-[2-(2,6-dioxopiperidin-3-yl)-1-oxo-3H-isoindol-4-yl]ethynyl}piperidine-1-carboxylate (1.1 g, 53%) as a brown solid. LC. MS (ESI, m/z) M+1-tBu: 396.

Synthesis of 3-{1-oxo-4-[2-(piperidin-4-yl)ethynyl]-3H-isoindol-2-yl}piperidine-2,6-dione: A mixture of tert-butyl 4-{2-[2-(2,6-dioxopiperidin-3-yl)-1-oxo-3H-isoindol-4-yl]ethynyl}piperidine-1-carboxylate (500 mg, 1.1 mmol, 1.0 eq) and HCl in 1,4-dioxane (4 M, 5 mL) was stirred for 4 hours at 25° C. The resulting mixture was concentrated under vacuum to give 3-{1-oxo-4-[2-(piperidin-4-yl)ethynyl]-3H-isoindol-2-yl}piperidine-2,6-dione (350 mg, 90%) as a white solid. LC-MS (ESI, m/z) M+1: 352.

Synthesis of 3-(4-{2-[1-(3-methoxy-4-nitrobenzoyl)piperidin-4-yl]ethynyl}-1-oxo-3H-isoindol-2-yl)piperidine-2,6-dione: To a stirred mixture of 3-{1-oxo-4-[2-(piperidin-4-yl)ethynyl]-3H-isoindol-2-yl}piperidine-2,6-dione (350 mg, 1.0 mmol, 1.0 eq) and 3-methoxy-4-nitrobenzoic acid (196 mg, 1.0 mmol, 1.0 eq) in dichloromethane (10 mL) were added DIEA (386.1 mg, 3.0 mmol, 3.0 eq) and HATU (568 mg, 1.5 mmol, 1.5 eq) in portions at 25° C. The reaction mixture was stirred for 2 hours at 25° C. The resulting mixture was concentrated under vacuum. The residue was purified by a flash column (silica gel, ethyl acetate/petroleum ether=0:1 to 1:0) to give 3-(4-{2-[1-(3-methoxy-4-nitrobenzoyl)piperidin-4-yl]ethynyl}-1-oxo-3H-isoindol-2-yl)piperidine-2,6-dione (450 mg, 85%) as a white solid. $^1$HNMR (300 MHz, DMSO-$d_6$) δ 11.01 (s, 1H), 7.94 (d, J=8.1 Hz, 1H), 7.73 (dd, J=7.5, 1.1 Hz, 1H), 7.71-7.64 (m, 1H), 7.56-7.48 (m, 1H), 7.38 (d, J=1.5 Hz, 1H), 7.12 (dd, J=8.1, 1.5 Hz, 1H), 5.15 (dd, J=13.2, 5.1 Hz, 1H), 4.47 (d, J=17.7 Hz, 1H), 4.33 (d, J=17.7 Hz, 1H), 3.96 (s, 3H), 3.75-3.57 (m, 3H), 3.55-3.40 (m, 2H), 3.23-3.02 (m, 4H), 2.20-1.98 (m, 2H), 1.72-1.40 (m, 2H).

Synthesis of 3-(4-{2-[1-(4-amino-3-methoxybenzoyl)piperidin-4-yl]ethynyl}-1-oxo-3H-isoindol-2-yl)piperidine-2,6-dione: To a stirred mixture of 3-(4-{2-[1-(3-methoxy-4-nitrobenzoyl)piperidin-4-yl]ethynyl}-1-oxo-3H-isoindol-2-yl)piperidine-2,6-dione (450 mg, 0.8 mmol, 1.0 eq) and $NH_4Cl$ (363 mg, 6.8 mmol, 8.0 eq) in EtOH (6 mL) and water (2 mL) were added Fe (284 mg, 5.0 mmol, 6.0 eq) in portions at 25° C. The reaction mixture was stirred for 2 hours at 50° C. The resulting mixture was filtered, the filter cake was washed with EtOH (3×10 mL). The filtrate was concentrated under vacuum. The residue was purified by a flash column (silica gel, dichloromethane/$CH_3OH$=10:0 to 10:1) to give 3-(4-{2-[1-(4-amino-3-methoxybenzoyl)piperidin-4-yl]ethynyl}-1-oxo-3H-isoindol-2-yl)piperidine-2,6-dione (300 mg, 70%) as a brown solid. LC-MS (ESI, m/z) M+1: 501.

Synthesis of (2'S,3S,4'S,5'R)-6-chloro-4'-(3-chloro-2-fluorophenyl)-2'-(2,2-dimethylpropyl)-N-[4-(4-{2-[2-(2,6-dioxopiperidin-3-yl)-1-oxo-3H-isoindol-4-yl]ethynyl}piperidine-1-carbonyl)-2-methoxyphenyl]-1,2-dihydrospiro[indole-3,3'-pyrrolidine]-5'-carboxamide: To a stirred mixture of 3-(4-{2-[1-(4-amino-3-methoxybenzoyl)piperidin-4-yl]ethynyl}-1-oxo-3H-isoindol-2-yl)piperidine-2,6-dione (30 mg, 0.06 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (27 mg, 0.1 mmol, 1.0 eq) and N-ethyl-N-isopropylpropan-2-amine (23 mg, 0.2 mmol, 3.0 eq) in N,N-dimethylformamide (5 mL) was added HATU (34 mg, 0.1 mmol, 1.5 eq) in portions at 25° C. The reaction mixture was stirred for 4 hours at 25° C. The crude product was purified by Prep HPLC using the following conditions: Column, Xbridge RP18; mobile phase, 0.05% $NH_3 \cdot H_2O$ in water and $CH_3CN$ (30% $CH_3CN$ up to 75% in 5 min); Detector, UV 254 nm. Finally, (2'S,3S,4'S,5'R)-6-chloro-4'-(3-chloro-2-fluorophenyl)-2'-(2,2-dimethylpropyl)-N-[4-(4-{2-[2-(2,6-dioxopiperidin-3-yl)-1-oxo-3H-isoindol-4-yl]ethynyl}piperidine-1-carbonyl)-2-methoxyphenyl]-1,2-dihydrospiro[indole-3,3'-pyrrolidine]-5'-carboxamide (11 mg, 20%) was obtained as a white solid. LC-MS (ESI, m/z) M+1: 933. $^1$HNMR (300 MHz, DMSO-$d_6$) δ 11.02 (bs, 1H), 10.63 (s, 1H), 8.33 (d, J=8.1 Hz, 1H), 7.73 (d, J=7.5 Hz, 1H), 7.71-7.62 (m, 1H), 7.54 (t, J=7.5 Hz, 1H), 7.42 (t, J=7.5 Hz, 1H), 7.35 (t, J=7.2 Hz, 1H), 7.26 (d, J=8.0 Hz, 1H), 7.20 (t, J=7.8 Hz, 1H), 7.10 (d, J=1.8 Hz, 1H), 7.01-6.93 (m, 1H), 6.51 (dd, J=7.9, 1.8 Hz, 1H), 6.31 (d, J=1.8 Hz, 1H), 5.53 (s, 1H), 5.14 (dd, J=13.2, 5.1 Hz, 1H), 4.47 (d, J=18.0 Hz, 1H), 4.35 (d, J=10.8 Hz, 1H), 4.32-4.23 (m, 1H), 4.10 (d, J=9.3 Hz, 1H), 3.87 (s, 3H), 3.72 (t, J=11.1 Hz, 1H), 3.53 (d, J=10.5 Hz, 1H), 3.18 (d, J=11.1 Hz, 2H), 3.09-2.82 (m, 2H), 2.66-2.60 (m, 2H), 2.50-2.38 (m, 2H) 2.10-1.82 (m, 3H), 1.70-1.58 (m, 2H), 1.40-1.24 (m, 4H), 0.91 (s, 9H).

Example 21: Preparation of (2'S,3S,4'S,5'R)-6-chloro-4'-(3-chloro-2-fluorophenyl)-2'-(2,2-dimethylpropyl)-N-{4-[(3-{2-[2-(2,6-dioxopiperidin-3-yl)-1-oxo-3H-isoindol-4-yl]ethynyl}bicyclo[1.1.1]pentan-1-yl)carbamoyl]-2-methoxyphenyl}-1,2-dihydrospiro[indole-3,3'-pyrrolidine]-5'-carboxamide Synthesis of tert-butyl N-[3-(hydroxymethyl)bicyclo[1.1.1]pentan-1-yl]carbamate: Into a 1000 mL 3-necked round-bottom flask, were placed tetrahydrofuran (300 mL), methyl 3-[(tert-butoxycarbonyl)amino]bicyclo[1.1.1]pentane-1-carboxylate (5.0 g, 207.2 mmol, 1.0 eq). After that, $LiBH_4$ (18.0 g, 828.9 mmol, 4.0 eq) was added in several batches at 0° C. The reaction mixture was stirred for 6 hours at 25° C. The resulting mixture was then quenched by the addition of water (500 mL), and then extracted with ethyl acetate (3×400 mL). The combined organic layers were dried over anhydrous sodium sulfate, filtered and concentrated under vacuum. The crude residue was applied onto a silica gel column and eluted with ethyl acetate/petroleum ether=1:1 to give tert-butyl N-[3-(hydroxymethyl)bicyclo[1.1.1]pentan-1-yl]carbamate (4 g, 81%) as a white solid. $^1$HNMR (400 MHz, DMSO-$d_6$) δ 7.38 (bs, 1H), 4.44 (t, J=5.6 Hz, 1H), 3.43 (d, J=5.5 Hz, 2H), 1.74 (s, 6H), 1.37 (s, 9H).

Synthesis of tert-butyl N-[3-formylbicyclo[1.1.1]pentan-1-yl]carbamate: Into a 1000 mL 3-necked round-bottom flask, were placed dichoromethane (300 mL), tert-butyl N-[3-(hydroxymethyl)bicyclo[1.1.1]pentan-1-yl]carbamate (4.0 g, 187.6 mmol, 1.0 eq). After that, Dess-martin periodinane (9.5 g, 225.1 mmol, 1.2 eq) was added in several batches at 0° C. The reaction mixture was stirred for 16 hours at 25° C. The resulting mixture was then quenched by the addition of water (300 mL), and then extracted with dichloromethane (3×400 mL). The combined organic layers were dried over anhydrous sodium sulfate, filtered and concentrated under vacuum. The crude residue was applied onto a silica gel column and eluted with ethyl acetate/petroleum ether=1:1 to give of tert-butyl N-[3-formylbicyclo[1.1.1]pentan-1-yl]carbamate (3.0 g, 68%) as a white solid. $^1$HNMR (400 MHz, DMSO-$d_6$) δ 9.60 (s, 1H), 7.53 (d, J=72.0 Hz, 1H), 2.11 (d, J=15.0 Hz, 5H), 2.05-1.67 (m, 1H), 1.38 (s, 9H).

Synthesis of tert-butyl N-[3-ethynylbicyclo[1.1.1]pentan-1-yl]carbamate: Into a 1000 mL 3-necked round-bottom flask, were placed methanol (300 mL), tert-butyl N-[3-formylbicyclo[1.1.1]pentan-1-yl]carbamate (3.0 g, 142.0 mmol, 1.0 eq), $K_2CO_3$ (5.8 g, 426.0 mmol, 3.0 eq). After that, seyferth-gilbert homologation (4.9 g, 213.0 mmol, 1.5 eq) was added dropwise with stirring at 0° C. The reaction mixture was stirred for 2 hours at 25° C. The resulting mixture was then quenched by the addition of water (500 mL), and then extracted with ethyl acetate (3×300 mL). The organic layers combined and dried over anhydrous sodium sulfate. After filtration, the filtrate was concentrated under vacuum. The crude residue was applied onto a silica gel column and eluted with ethyl acetate/petroleum ether=1:1 to give tert-butyl N-[3-ethynylbicyclo[1.1.1]pentan-1-yl]carbamate (1.6 g, 50%) as a white solid. $^1$HNMR (400 MHz, DMSO-$d_6$) δ 7.59 (bs, 1H), 3.09 (s, 1H), 1.94-2.31 (s, 6H), 1.37 (s, 9H).

Synthesis of 3-ethynylbicyclo[1.1.1]pentan-1-amine: Into a 100 mL round-bottom flask were added tert-butyl N-{3-ethynylbicyclo[1.1.1]pentan-1-yl}carbamate (1.0 g, 4.8 mmol, 1.0 eq) and 4 M HCl in dioxane at 25° C. The reaction mixture was stirred for 6 hours at 25° C. The resulting mixture was concentrated under vacuum to give 3-ethynylbicyclo[1.1.1]pentan-1-amine (450 mg, 87%) as a white solid. $^1$HNMR (300 MHz, DMSO-$d_6$) δ 9.0 (bs, 2H), 3.25 (s, 1H), 2.25 (s, 6H).

Synthesis of N-{3-ethynylbicyclo[1.1.1]pentan-1-yl}-3-methoxy-4-nitrobenzamide: Into a 20 mL vial were added 3-ethynylbicyclo[1.1.1]pentan-1-amine (400 mg, 3.7 mmol, 1.0 eq), 3-methoxy-4-nitrobenzoic acid (736 mg, 3.7 mmol, 1.0 eq), HATU (1.5 g, 4.1 mmol, 1.1 eq), DIEA (1.4 g, 11.2 mmol, 3.0 eq) and N,N-dimethyl formamide (5 mL) at 25° C. The reaction mixture was stirred for 2 hours at 25° C. The resulting mixture was quenched with water (5 mL) and then extracted with ethyl acetate (3×5 mL). The combined organic layers were washed with brine (2×5 mL), dried over anhydrous sodium sulfate. After filtration, the filtrate was concentrated under vacuum. The crude residue was applied onto a silica gel column and eluted with ethyl acetate/petroleum ether=1:1 to give N-{3-ethynylbicyclo[1.1.1]pentan-1-yl}-3-methoxy-4-nitrobenzamide (600 mg, 56%) as a yellow solid. $^1$HNMR (300 MHz, DMSO-$d_6$) δ 9.34 (bs, 1H), 7.95 (d, J=8.4 Hz, 1H), 7.69 (d, J=1.6 Hz, 1H), 7.52 (dd, J=8.4, 1.6 Hz, 1H), 3.98 (s, 3H), 3.17 (s, 1H), 2.19-2.37 (m, 6H).

Synthesis of N-(3-{2-[2-(2,6-dioxopiperidin-3-yl)-1-oxo-3H-isoindol-4-yl]ethynyl}bicyclo[1.1.1]pentan-1-yl)-3-methoxy-4-nitrobenzamide: Into an 8 mL vial were added N-{3-ethynylbicyclo[1.1.1]pentan-1-yl}-3-methoxy-4-nitrobenzamide (300 mg, 1.1 mmol, 1.0 eq), $Pd(PPh_3)_4$ (121 mg, 0.1 mmol, 0.1 eq), CuI (20 mg, 0.1 mmol, 0.1 eq) and N,N-dimethyl formamide (5 mL) under nitrogen atmosphere. The reaction mixture was stirred for 2 hours at 25° C. under nitrogen atmosphere. The reaction was quenched with water (5 mL) and extracted with ethyl acetate (3×5 mL). The combined organic layers were washed with brine (2×5 mL), dried over anhydrous sodium sulfate. After filtration, the filtrate was concentrated under vacuum. The crude residue was applied onto a silica gel column and eluted with dichloromethane/methanol=10:1 to give N-(3-{2-[2-(2,6-dioxopiperidin-3-yl)-1-oxo-3H-isoindol-4-yl]ethynyl}bicyclo[1.1.1]pentan-1-yl)-3-methoxy-4-nitrobenzamide (200 mg, 36%) as a light yellow solid. $^1$HNMR (400 MHz, DMSO-$d_6$) δ 11.01 (bs, 1H), 9.40 (bs, 1H), 7.96 (d, J=8.4 Hz, 1H), 7.75 (dd, J=7.6, 1.0 Hz, 1H), 7.73-7.67 (m, 2H), 7.55 (ddd, J=7.6, 4.3, 2.6 Hz, 2H), 5.16 (dd, J=13.2, 5.1 Hz, 1H), 4.51-4.46 (m, 1H), 4.34 (d, J=17.8 Hz, 1H), 3.99 (s, 3H), 2.92 (ddd, J=17.7, 13.5, 5.4 Hz, 1H), 2.77-2.54 (m, 2H), 2.45 (s, 6H), 2.10-1.89 (m, 1H).

Synthesis of 4-amino-N-(3-{2-[2-(2,6-dioxopiperidin-3-yl)-1-oxo-3H-isoindol-4-yl]ethynyl}bicyclo[1.1.1]pentan-1-yl)-3-methoxybenzamide: Into an 8 mL vial were added N-(3-{2-[2-(2,6-dioxopiperidin-3-yl)-1-oxo-3H-isoindol-4-yl]ethynyl}bicyclo[1.1.1]pentan-1-yl)-3-methoxy-4-nitrobenzamide (100 mg, 0.2 mmol, 1.0 eq), Fe (85 mg, 1.5 mmol, 8.0 eq), $NH_4Cl$ (81 mg, 1.5 mmol, 8.0 eq) and ethanol (2 mL) and water (1 mL) at 25° C. The reaction mixture was stirred for 2 hours at 25° C. After filtration, the filtrate was concentrated under vacuum. The residue was diluted with water (3 mL) and then extracted with dichloromethane (3×2 mL). The combined organic layers were washed with brine (2 mL), dried over anhydrous sodium sulfate. After filtration, the filtrate was concentrated under vacuum. The crude residue was purified by Prep-TLC (dichloromethane/methyl ethanol=10:1) to give 4-amino-N-(3-{2-[2-(2,6-dioxopiperidin-3-yl)-1-oxo-3H-isoindol-4-yl]ethynyl}bicyclo[1.1.1]pentan-1-yl)-3-methoxybenzamide (55 mg, 58%) as a light yellow solid. LC-MS: (ESI, m/z): M+1: 499.

Synthesis of (2'S,3S,4'S,5'R)-6-chloro-4'-(3-chloro-2-fluorophenyl)-2'-(2,2-dimethylpropyl)-N-{4-[(3-{2-[2-(2,6-dioxopiperidin-3-yl)-1-oxo-3H-isoindol-4-yl]ethynyl}bicyclo[1.1.1]pentan-1-yl)carbamoyl]-2-methoxyphenyl}-1,2-dihydrospiro[indole-3,3'-pyrrolidine]-5'-carboxamide: Into an 8 mL vial were added 4-amino-N-(3-{2-[2-(2,6-dioxopiperidin-3-yl)-1-oxo-3H-isoindol-4-yl]ethynyl}bicyclo[1.1.1]pentan-1-yl)-3-methoxybenzamide (50 mg, 0.10 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (45 mg, 0.1 mmol, 1.0 eq), NMI (25 mg, 0.3 mmol, 3.0 eq), TCFH (37 mg, 0.1 mmol, 1.3 eq), DMAP (2 mg, 0.01 mmol, 0.1 eq) and $CH_3CN$ (2 mL) at 25° C. The reaction mixture was stirred for 2 hours at 45° C. The resulting mixture was quenched with water (2 mL) and then extracted with ethyl acetate (3×2 mL). The combined organic layers were washed with brine (2 mL), dried over anhydrous sodium sulfate. After filtration, the filtrate was concentrated under vacuum. The crude residue was purified by reverse flash choursomatography using the following conditions: column, C18 silica gel; mobile phase, methanol in water, 10% to 50% gradient in 10 min; detector, UV 254 nm to give (2'S,3S,4'S,5'R)-6-chloro-4'-(3-chloro-2-fluorophenyl)-2'-(2,2-dimethylpropyl)-N-{4-[(3-{2-[2-(2,6-dioxopiperidin-3-yl)-1-oxo-3H-isoindol-4-yl]ethynyl}bicyclo[1.1.1]pentan-1-yl)carbamoyl]-2-methoxyphenyl}-1,2-dihydrospiro[indole-3,3'-pyrrolidine]-5'-carboxamide (5 mg, 5%) as a white solid. LC-MS: (ESI, m/z): M+1: 931. $^1$HNMR (300 MHz, DMSO-$d_6$) δ 11.01 (bs, 1H), 10.69 (bs, 1H), 9.05 (s, 1H), 8.34 (d, J=8.4 Hz, 1H), 7.79-7.65 (m, 2H), 7.60-7.50 (m, 2H), 7.50-7.38 (m, 2H), 7.37-7.26 (m, 2H), 7.20 (t, J=8.0 Hz, 1H), 6.51 (dd, J=7.9, 1.9 Hz, 1H), 6.31 (d, J=1.9 Hz, 1H), 5.52 (s, 1H), 5.16 (dd, J=13.3, 5.1 Hz, 1H), 4.48 (d, J=17.9 Hz, 1H), 4.32 (dd, J=18.3, 8.2 Hz, 2H), 4.12 (d, J=9.7 Hz, 1H), 3.90 (s, 3H), 3.80-3.60 (m, 3H), 3.53 (d, J=10.2 Hz, 2H), 3.20 (d, J=10.5 Hz, 2H), 2.90 (d, J=13.3 Hz, 2H), 2.60 (d, J=17.7 Hz, 2H), 2.0 (d, J=5.2 Hz, 1H), 1.45-1.27 (m, 1H), 1.23 (d, J=6.7 Hz, 1H), 1.21-1.17 (m, 2H), 0.91 (s, 9H).

Example 22: Preparation of (2'S,3S,4'S,5'R)-6-chloro-4'-(3-chloro-2-fluorophenyl)-N-(4-(2-((1S,2R)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide Synthesis of tert-butyl 2-(methoxymethylene)-7-azaspiro[3.5]nonane-7-carboxylate: Into a 1000 mL round-bottom flask purged and maintained under an inert atmosphere of nitrogen, were placed (methoxymethyl) triphenylphosphanium chloride (55.9 g, 162.9 mmol, 1.3 eq), toluene (500 mL), t-BuOK (18.3 g, 162.9 mmol, 1.3 eq). The reaction mixture was stirred for 20 mins at 25° C. After that, a solution of tert-butyl 2-oxo-7-azaspiro[3.5]nonane-7-carboxylate (30.0 g, 125.4 mmol, 1.0 eq) in 100 mL toluene was added dropwised. The reaction mixture was stirred for 4 hours at 70° C. The resulting mixture was then quenched by the addition of $NH_4Cl$ (aq.) (500 mL) and then extracted with ethyl acetate (2×500 mL). The combined organic phase was washed with brine (2×500 mL), dried over anhydrous sodium sulfate. After filtration, the filtrate was concentrated under vacuum. The crude residue was applied onto a silica gel column and eluted with ethyl acetate/petroleum ether=(0:1 to 1:3) to give tert-butyl 2-(methoxymethylidene)-7- azaspiro[3.5]nonane-7-carboxylate (18.0 g, 54%) as a light yellow oil. LC-MS (ESI, m/z) M-56(t-Bu)+41+1: 253. $^1$HNMR (400 MHz, DMSO-$d_6$) δ 5.94-5.91 (m 1H), 3.47 (d, J=2.0 Hz, 3H), 3.23 (t, J=5.6 Hz, 4H), 2.34 (t, J=2.6 Hz, 2H), 2.30 (t, J=2.2 Hz, 2H), 1.49-1.42 (m, 4H), 1.39 (d, J=2.0 Hz, 9H).

Synthesis of tert-butyl 2-formyl-7-azaspiro[3.5]nonane-7-carboxylate: Into a 2000-mL round-bottom flask were placed tert-butyl 2-(methoxymethylidene)-7-azaspiro[3.5]nonane-7-carboxylate (18.0 g, 67.3 mmol, 1.0 eq), $CH_3CN$ (640 mL), water (160 mL), trifluoroacetic acid (15.4 g, 134.6 mmol, 2.0 eq). The reaction mixture was stirred for 2 hours at 25° C. The resulting mixture was then quenched by the addition of $NaHCO_3$ (aq.) (300 mL), and then extracted with ethyl acetate (2×300 mL). The combined organic phase was washed with brine (2×300 mL), dried over anhydrous sodium sulfate. After filtration, the filtrate was concentrated under vacuum. The crude residue was applied onto a silica gel column and eluted with ethyl acetate/petroleum ether=(0:1 to 1:3) to give tert-butyl 2-formyl-7-azaspiro[3.5]nonane-7-carboxylate (15.0 g, 88%) as a light yellow oil. LC-MS (ESI, m/z) M-56(t-Bu)+41+1: 239. $^1$HNMR (400 MHz, DMSO-$d_6$) δ 9.68 (d, J=1.7 Hz, 1H), 3.30-3.13 (m, 5H), 1.94 (dd, −8.8, 2.8 Hz, 4H), 1.57-1.50 (m, 2H), 1.39 (s, 9H), 1.37-1.31 (m, 2H).

Synthesis of tert-butyl 2-(3-ethoxy-3-oxoprop-1-en-1-yl)-7-azaspiro[3.5]nonane-7-carboxylate: Into a 500-mL round-bottom flask were placed triethyl phosphonoacetate (17.3 g, 76.9 mmol, 1.3 eq), N,N-dimethylformamide (75 mL), tetrahydrofuran (75 mL). After that, NaH (2.8 g, 118.5 mmol, 2.0 eq) was added at 0° C. The reaction mixture was stirred for 20 mins at 0° C., and then to the above mixture was added tert-butyl 2-formyl-7-azaspiro[3.5]nonane-7-carboxylate (15.0 g, 59.2 mmol, 1.0 eq). The reaction mixture was stirred for 3 hours at 25° C. The resulting mixture was then quenched by the addition of $NH_4Cl$ (aq.) (300 mL) and extracted with ethyl acetate (2×300 mL). The combined organic phase was washed with brine (2×300 mL), dried over anhydrous sodium sulfate. After filtration, the filtrate was concentrated under vacuum. The crude residue was applied onto a silica gel column and eluted with ethyl acetate/petroleum ether=(0:1 to 1:3) to give tert-butyl 2-(3-ethoxy-3-oxoprop-1-en-1-yl)-7-azaspiro[3.5]nonane-7-carboxylate (14.0 g, 73%) as a light yellow oil. LC-MS (ESI, m/z) M-56(t-Bu)+41+1: 309. $^1$HNMR (400 MHz, Chloroform-d) δ 7.06 (dd, −15.6, 6.8 Hz, 1H), 5.75 (dd, J=15.6, 1.6 Hz, 1H), 4.25-4.19 (m, 2H), 3.42-3.24 (m, 4H), 3.11-3.15 (m, 1H), 2.15-2.02 (m, 3H), 1.80-1.69 (m, 2H), 1.64-1.58 (m, 2H), 1.48 (d, −5.7 Hz, 1H), 1.46 (s, 9H), 1.30 (t, −7.2 Hz, 3H).

Synthesis of tert-butyl 2-((1R,2S and 1S,2R)-2-(ethoxycarbonyl)cyclopropyl)-7-azaspiro[3.5]nonane-7-carboxylate (racemate): Into a 100 mL round-bottom flask purged and maintained under an inert atmosphere of nitrogen, were placed boron trifluoride methyldiphenylsulfanium fluoride (4.6 g, 16.1 mmol, 1.3 eq), tetrahydrofuran (40 mL). After that, NaHMDS (2M in tetrahydrofuran, 10 mL, 1.6 eq) was added at 0° C. The reaction mixture was stirred for 30 mins at 0° C., and to the above mixture was added tert-butyl (E)-2-(3-ethoxy-3-oxoprop-1-en-1-yl)-7-azaspiro[3.5]nonane-7-carboxylate (4.0 g, 12.4 mmol, 1.0 eq). The reaction mixture was stirred for 2 hours at 25° C. The resulting mixture was then quenched by the addition of $NH_4Cl$ (aq.) (40 mL) and extracted with ethyl acetate (2×40 mL). The combined organic phase was washed with brine (2×40 mL) and dried over anhydrous sodium. After filtration, the filtrate was concentrated under vacuum. The crude residue was applied onto a silica gel column and eluted with ethyl acetate/petroleum ether=(0:1 to 1:3) to give tert-butyl 2-((1R,2S and 1S,2R)-2-(ethoxycarbonyl) cyclopropyl)-7-azaspiro[3.5]nonane-7-carboxylate (racemate) (2.0 g, 48%) as a light yellow oil. LC-MS (ESI, m/z) M-56(t-Bu)+41+1: 323.

Synthesis of tert-butyl 2-((1R,2S and 1S,2R)-2-(hydroxymethyl)cyclopropyl)-7-azaspiro[3.5]nonane-7-carboxylate (racemate): Into a 100 mL 3-necked round-bottom flask, were placed tert-butyl 2-((1R,2S and 1S,2R)-2-(ethoxycarbonyl)cyclopropyl)-7-azaspiro[3.5]nonane-7-carboxylate (racemate) (2.0 g, 5.9 mmol, 1.0 eq), tetrahydrofuran (20.0 mL). After that, $LiAlH_4$ (0.5 g, 11.8 mmol, 2.0 eq) was added at 0° C. The reaction mixture was stirred for 1 hour at 0° C. The resulting mixture was then quenched by the addition of 1 mL of water, 1 mL of 15% NaOH, 3 mL of water. After filtration, the filtrate was concentrated under vacuum to give tert-butyl 2-((1R,2S and 1S,2R)-2-(hydroxymethyl)cyclopropyl)-7-azaspiro[3.5]nonane-7-carboxylate (racemate) (1.6 g, crude) as a light yellow oil. LC-MS (ESI, m/z) M-56(t. Bu)+41+1: 281. $^1$HNMR (300 MHz, DMSO-d6) δ 4.37 (dt, J=6.3, 5.4 Hz, 1H), 3.30-3.12 (m, 5H), 2.10-1.90 (m, 1H), 1.87-1.74 (m, 2H), 1.48-1.41 (m, 3H), 1.38 (s, 11H), 1.35 (d, −6.0 Hz, 2H), 0.74-0.60 (m, 2H), 0.31-0.14 (m, 2H).

Synthesis of tert-butyl 2-((1R,2S and 1S,2R)-2-formylcyclopropyl)-7-azaspiro[3.5]nonane-7-carboxylate (racemate): Into a 100 mL 3-necked round-bottom flask, were placed tert-butyl 2-((1R,2S and 1S,2R)-2-(hydroxymethyl) cyclopropyl)-7-azaspiro[3.5]nonane-7-carboxylate (racemate) (1.6 g, 5.4 mmol, 1.0 eq), dichloromethane (30 mL). After that, PCC (2.3 g, 10.8 mmol, 2.0 eq) was added at 0° C. The reaction mixture was stirred for 1 hour at 25° C. The resulting mixture was filtered, the filter cake was washed with dichloromethane (2×50 mL). The filtrate was concentrated under vacuum. The residue was purified by a flash column (silica gel, ethyl acetate/petroleum ether=0:1 to 1:1) to give tert-butyl 2-((1R,2S)-2-formylcyclopropyl)-7-azaspiro[3.5]nonane-7-carboxylate (racemate) (1.4 g, 88%) as a light yellow oil. LC-MS (ESI, m/z) M-56(t. Bu)+41+1: 279. $^1$HNMR (300 MHz, DMSO-d6) δ 8.87 (d, −5.7 Hz, 1H), 3.30-3.21 (m, 2H), 3.17 (dd, J=6.6, 4.5 Hz, 2H), 2.16-2.11 (m, 1H), 1.86 (td, −8.7, 2.5 Hz, 2H), 1.60 (tdd, −7.2, 5.1, 2.7 Hz, 2H), 1.51-1.33 (m, 5H), 1.32 (s, 10H), 1.30-1.11 (m, 1H), 1.01-0.78 (m, 1H).

Synthesis of tert-butyl 2-((1R,2S and 1S,2R)-2-ethynylcyclopropyl)-7-azaspiro[3.5]nonane-7-carboxylate (racemate): Into a 100 mL round-bottom flask were placed tert-butyl 2-((1R,2S and 1S,2R)-2-formylcyclopropyl)-7-azaspiro[3.5]nonane-7-carboxylate (racemate) (1.4 g, 4.7 mmol, 1.0 eq), MeOH (30 mL), $K_2CO_3$ (1.3 g, 9.5 mmol, 2.0 eq), seyferth-gilbert homologation (1.4 g, 7.1 mmol, 1.5 eq). The reaction mixture was stirred for 2 hours at 25° C. The resulting mixture was then quenched by the addition of water (50 mL) and then extracted with ethyl acetate (2×50 mL). The combined organic phase was washed with brine (2×50 mL), dried over anhydrous sodium sulfate. After filtration, the filtrate was concentrated under vacuum. The residue was purified by a flash column (silica gel, ethyl acetate/petroleum ether=0:1 to 1:3) to give tert-butyl 2-((1R, 2S and 1S,2R)-2-ethynylcyclopropyl)-7-azaspiro[3.5]nonane-7-carboxylate (racemate) (1.1 g, 80%) as a light yellow oil. LC-MS (ESI, m/z) M-56(t-Bu)+41+1: 275.

Synthesis of 2-((1R,2S and 1S,2R)-2-ethynylcyclopropyl)-7-azaspiro[3.5]nonane (racemate): Into a 100 mL round-bottom flask were placed tert-butyl 2-((1R,2S)-2-ethynylcyclopropyl)-7-azaspiro[3.5]nonane-7-carboxylate (racemate) (1.1 g, 3.8 mmol, 1.0 eq), dichloromethane (20 mL), 2,6-dimethylpyridine (1.2 g, 11.4 mmol, 3.0 eq). After that, TMSI (2.3 g, 11.4 mmol, 3.0 eq) was added at 0° C. The reaction mixture was stirred for 1 hour at 0° C. The resulting mixture was then quenched by the addition of water (30 mL) and then extracted with dichloromethane (2×30 mL). The combined organic phase was washed with brine (2×30 mL), dried over anhydrous sodium sulfate. After filtration, the filtrate was concentrated under vacuum. Finally, 2-((1R,2S and 1S,2R)-2-ethynylcyclopropyl)-7-azaspiro[3.5]nonane (racemate) (1.3 g, crude) was obtained as a light yellow solid. LC-MS (ESI, m/z) M+1: 189.

Synthesis of 2-((1R,2S and 1S,2R)-2-ethynylcyclopropyl)-7-(3-methoxy-4-nitrophenyl)-7-azaspiro[3.5]nonane (racemate): Into a 50-mL round-bottom flask were placed 2-((1R,2S)-2-ethynylcyclopropyl)-7-azaspiro[3.5]nonane (racemate) (1.3 g, 6.8 mmol, 1.0 eq), 4-fluoro-2-methoxy-1-nitrobenzene (1.2 g, 6.8 mmol, 1.0 eq), DIEA (1.8 g, 13.7 mmol, 2.0 eq), N,N-dimethylformamide (15 mL). The reaction mixture was stirred for 2 hours at 80° C. The resulting mixture was diluted with water (50 mL) and then extracted with ethyl acetate (2×50 mL). The combined organic phase was washed with brine (2×50 mL), dried over anhydrous sodium sulfate. After filtration, the filtrate was concentrated under vacuum. The residue was purified by a flash column (silica gel, ethyl acetate/petroleum ether=0:1 to 1:3) to give 2-((1R,2S)-2-ethynylcyclopropyl)-7-(3-methoxy-4-nitrophenyl)-7-azaspiro[3.5]nonane (racemate) (900 mg, 38%) as a light yellow solid. LC-MS (ESI, m/z) M+1: 341. $^1$HNMR (400 MHz, DMSO-$d_6$) δ 7.86 (d, J=9.4 Hz, 1H), 6.58 (dd, J=9.5, 2.5 Hz, 1H), 6.49 (d, J=2.5 Hz, 1H), 3.90 (s, 3H), 3.46-3.38 (m, 2H), 3.37-3.32 (m, 2H), 2.59 (d, J=2.1 Hz, 1H), 2.06-2.01 (m, 1H), 1.95-1.82 (m, 2H), 1.69-1.55 (m, 2H), 1.59-1.50 (m, 2H), 1.52-1.45 (m, 1H), 1.48-1.33 (m, 1H), 1.23-1.12 (m, 1H), 1.11-0.97 (m, 1H), 0.6-0.72 (m, 1H), 0.65-0.61 (m, 1H).

Synthesis of 2-((1S,2R)-2-ethynylcyclopropyl)-7-(3-methoxy-4-nitrophenyl)-7-azaspiro[3.5]nonane and 2-((1R,2S)-2-ethynylcyclopropyl)-7-(3-methoxy-4-nitrophenyl)-7-azaspiro[3.5]nonane: 500 mg of 2-((1R,2S and 1S,2R)-2-ethynylcyclopropyl)-7-(3-methoxy-4-nitrophenyl)-7-azaspiro[3.5]nonane (racemate) was purified by Chiral-Prep-HPLC using the following conditions: CHIRALPAK IG, 5*15 cm, 10 μm; Mobile Phase A: $CO_2$, Mobile Phase B: $CH_3CN$; Flow rate: 100 mL/min; Gradient: isocratic 50% B; Detector, 220 nm. Finally, 2-((1S,2R)-2-ethynylcyclopropyl)-7-(3-methoxy-4-nitrophenyl)-7-azaspiro[3.5]nonane (210 mg) was obtained as a yellow solid. And 2-((1R,2S)-2-ethynylcyclopropyl)-7-(3-methoxy-4-nitrophenyl)-7-azaspiro[3.5]nonane (200 mg) was obtained as a yellow solid. LC-MS (ESI, m/z) M+1: 341. A, $T_R$=1.349 min in CHIRAL-SFC, Column: IG 100×4.6 mm 3.0 um. mobile phase A: $CO_2$; mobile phase B: $CH_3CN$, Start Conc. of Pump B: 50.0% in 4 min, Oven Temperature: 35° C. B, $T_R$=1.854 min in CHIRAL-SFC, Column: IG 100×4.6 mm 3.0 um. mobile phase A: $CO_2$; mobile phase B: $CH_3CN$, Start Conc. of Pump B: 50.0% in 4 min, Oven Temperature: 35° C.

Synthesis of 3-(4-(((1R,2S)-2-(7-(3-methoxy-4-nitrophenyl)-7-azaspiro[3.5]nonan-2-yl)cyclopropyl)ethynyl)-1-oxoisoindolin-2-yl)piperidine-2,6-dione: Into a 20 mL sealed tube purged and maintained under an inert atmosphere of nitrogen, were placed 2-((1S,2R)-2-ethynylcyclopropyl)-7-(3-methoxy-4-nitrophenyl)-7-azaspiro[3.5]nonane (180 mg, 0.5 mmol, 1.0 eq), 3-(4-iodo-1-oxo-3H-isoindol-2-yl)piperidine-2,6-dione (196 mg, 0.5 mmol, 1.0 eq), CuI (11 mg, 0.1 mmol, 0.1 eq), triethylamine (161 mg, 1.6 mmol, 3.0 eq), $Pd(PPh_3)_4$(61 mg, 0.1 mmol, 0.1 eq), N,N-dimethylformamide (3 mL). The reaction mixture was stirred for 2 hours at 70° C. The resulting mixture was diluted with water (30 mL) and then extracted with ethyl acetate (2×30 mL). The combined organic phase was washed with brine (2×30 mL), dried over anhydrous sodium sulfate. After filtration, the filtrate was concentrated under vacuum. The residue was purified by a flash column (silica gel, ethyl acetate/petroleum ether=0:1-1:0) to give 3-(4-(((1R,2S)-2-(7-(3-methoxy-4-nitrophenyl)-7-azaspiro[3.5]nonan-2-yl)cyclopropyl)ethynyl)-1-oxoisoindolin-2-yl)piperidine-2,6-dione (230 mg, 75%) as a yellow solid. LC-MS (ESI, m/z) M+1: 583.

Synthesis of 3-(4-(((1R,2S)-2-(7-(4-amino-3-methoxyphenyl)-7-azaspiro[3.5]nonan-2-yl)cyclopropyl)ethynyl)-1-oxoisoindolin-2-yl)piperidine-2,6-dione: Into a 20 mL sealed tube were placed 3-(4-(((1R,2S)-2-(7-(3-methoxy-4-nitrophenyl)-7-azaspiro[3.5]nonan-2-yl)cyclopropyl)ethynyl)-1-oxoisoindolin-2-yl)piperidine-2,6-dione (200 mg, 0.3 mmol, 1.0 eq), Fe (77 mg, 1.4 mmol, 4.0 eq), $NH_4Cl$ (147 mg, 2.7 mmol, 8.0 eq), ethanol (3 mL), water (1 mL). The reaction mixture was stirred for 2 hours at 50° C. The resulting mixture was filtered, the filtrate was concentrated under vacuum. The residue was purified by a flash column (silica gel, dichloromethane/methanol=20:1) to give 3-(4-(((1R,2S)-2-(7-(4-amino-3-methoxyphenyl)-7-azaspiro[3.5]nonan-2-yl)cyclopropyl)ethynyl)-1-oxoisoindolin-2-yl)piperidine-2,6-dione (140 mg 73.80%) as a light yellow solid. LC-MS (ESI, m/z) M+1: 553.

Synthesis of (2'S,3S,4'S,5'R)-6-chloro-4'-(3-chloro-2-fluorophenyl)-N-(4-(2-((1S,2R)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (50 mg, 0.1 mmol, 1.0 eq), 3-(4-(((1R,2S)-2-(7-(4-amino-3-methoxyphenyl)-7-azaspiro[3.5]nonan-2-yl)cyclopropyl)ethynyl)-1-oxoisoindolin-2-yl)piperidine-2,6-dione (74 mg, 0.1 mmol, 1.2 eq), HATU (46 mg, 0.1 mmol, 1.1 eq), DIEA (29 mg, 0.2 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (86% Phase B up to 94% in 7 min); Detector, UV 254 nm. Finally, (2'S,3S,4'S,5'R)-6-chloro-4'-(3-chloro-2-fluorophenyl)-N-(4-(2-((1S,2R)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide (30 mg, 28%) was obtained as a white solid. LC-MS (ESI, m/z) M+1: 985/987. $^1$HNMR (400 MHz, DMSO-$d_6$) δ 11.0 (s, 1H), 10.28 (s, 1H), 8.08 (d, J=8.7 Hz, 1H), 7.69 (dd, J=7.5, 1.2 Hz, 1H), 7.61 (dd, J=7.5, 1.2 Hz, 1H), 7.50 (t, J=7.5 Hz, 1H), 7.46-7.35 (m, 1H), 7.33 (t, J=7.2 Hz, 1H), 7.28-7.14 (m, 2H), 6.63 (d, J=2.4 Hz, 1H), 6.51 (dd, J=7.8, 1.8 Hz, 1H), 6.43 (dd, J=9.0, 2.4 Hz, 1H), 6.31 (d, J=1.8 Hz, 1H), 5.55-5.48 (m, 1H), 5.14 (dd, J=13.2, 5.1 Hz, 1H), 4.47-4.42 (m, 1H), 4.35-4.16 (m, 2H), 4.05 (d, J=9.3 Hz, 1H), 3.81 (s, 3H), 3.64 (t, J=11.1 Hz, 1H), 3.52 (d, J=10.5 Hz, 1H), 3.17 (d, J=9.6 Hz, 1H), 3.07 (s, 4H), 3.02-2.84 (m, 3H), 2.63 (s, 1H), 2.57 (s, 1H), 2.11 (dd, J=13.2, 5.7 Hz, 1H), 2.05-1.82 (m, 3H), 1.66 (s, 2H), 1.58 (s, 2H), 1.56-1.13 (m, 6H), 1.01-0.92 (m, 1H), 0.90 (s, 9H).

Example 23: Preparation of (2'S,3S,4'S,5'R)-6-chloro-4'-(3-chloro-2-fluorophenyl)-N-(4-(2-((1R,2S)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide Synthesis of 3-(4-(((1S,2R)-2-(7-(3-methoxy-4-nitrophenyl)-7-azaspiro[3.5]nonan-2-yl)cyclopropyl)ethynyl)-1-oxoisoindolin-2-yl)piperidine-2,6-dione: Into a 20 mL sealed tube purged and maintained under an inert atmosphere of nitrogen, were placed 2-((1R,2S)-2-ethynylcyclopropyl)-7-(3-methoxy-4-nitrophenyl)-7-azaspiro[3.5]nonane (170 mg, 0.5 mmol, 1.0 eq), 3-(4-iodo-1-oxo-3H-isoindol-2-yl)piperidine-2,6-dione (185 mg, 0.5 mmol, 1.0 eq), triethylamine (152 mg, 1.5 mmol, 3.0 eq), CuI (10 mg, 0.1 mmol, 0.1 eq), $Pd(PPh_3)_4$(58 mg, 0.1 mmol, 0.1 eq), N,N-dimethylformamide (3 mL). The reaction mixture was stirred for 2 hours at 70° C. The resulting mixture was diluted with water (30 mL) and then extracted with ethyl acetate (2×30 mL). The combined organic phase was washed with brine (2×30 mL), dried over anhydrous sodium sulfate. After filtration, the filtrate was concentrated under vacuum. The residue was purified by a flash column (silica gel, ethyl acetate/petroleum ether=0:1 to 1:0) to give 3-(4-(((1S,2R)-2-(7-(3-methoxy-4-nitrophenyl)-7-azaspiro[3.5]nonan-2-yl)cyclopropyl)ethynyl)-1-oxoisoindolin-2-yl)piperidine-2,6-dione (210 mg, 73%) as a yellow solid. LC-MS (ESI, m/z) M+1: 583.

Synthesis of 3-(4-(((1S,2R)-2-(7-(4-amino-3-methoxyphenyl)-7-azaspiro[3.5]nonan-2-yl)cyclopropyl)ethynyl)-1-oxoisoindolin-2-yl)piperidine-2,6-dione: Into a 20 mL sealed tube were placed 3-(4-(((1S,2R)-2-(7-(3-methoxy-4-nitrophenyl)-7-azaspiro[3.5]nonan-2-yl)cyclopropyl)ethynyl)-1-oxoisoindolin-2-yl)piperidine-2,6-dione (180 mg, 0.3 mmol, 1.0 eq), Fe (69 mg, 1.2 mmol, 4.0 eq), $NH_4Cl$ (132 mg, 2.4 mmol, 8.0 eq), ethanol (3 mL), water (1 mL). The reaction mixture was stirred for 2 hours at 50° C. The resulting mixture was filtered, and the filtrate was concentrated under vacuum. The residue was purified by a flash column (silica gel, dichloromethane/methanol=20:1) to give 3-(4-(((1S,2R)-2-(7-(4-amino-3-methoxyphenyl)-7-azaspiro[3.5]nonan-2-yl)cyclopropyl) ethynyl)-1-oxoisoindolin-2-yl)piperidine-2,6-dione (120 mg, 70%) as a light yellow solid. LC-MS (ESI, m/z) M+1: 553.

Synthesis of (2'S,3S,4'S,5'R)-6-chloro-4'-(3-chloro-2-fluorophenyl)-N-(4-(2-((1R,2S)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (50 mg, 0.1 mmol, 1.0 eq), 3-(4-(((1S,2R)-2-(7-(4-amino-3-methoxyphenyl)-7-azaspiro[3.5]nonan-2-yl)cyclopropyl) ethynyl)-1-oxoisoindolin-2-yl)piperidine-2,6-dione (74 mg, 0.1 mmol, 1.2 eq), HATU (46 mg, 0.1 mmol, 1.1 eq), DIEA (29 mg, 0.2 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (86% Phase B up to 94% in 7 min); Detector, UV 254 nm. Finally, (2'S,3S,4'S,5'R)-6-chloro-4'-(3-chloro-2-fluorophenyl)-N-(4-(2-((1R,2S)-2-((2-(2,6-dioxopiperidin-3-yl)-1-oxoisoindolin-4-yl)ethynyl)cyclopropyl)-7-azaspiro[3.5]nonan-7-yl)-2-methoxyphenyl)-2'-neopentylspiro[indoline-3,3'-pyrrolidine]-5'-carboxamide (25 mg, 23%) was obtained as a white solid. LC-MS (ESI, m/z) M+1: 985/987. $^1$HNMR (300 MHz, DMSO-$d_6$) δ 11.0 (s, 1H), 10.27 (s, 1H), 8.08 (d, J=8.7 Hz, 1H), 7.69 (dd, J=7.5, 1.2 Hz, 1H), 7.61 (dd, J=7.5, 1.2 Hz, 1H), 7.50 (t, J=7.5 Hz, 1H), 7.46-7.35 (m, 1H), 7.33 (t, J=7.2 Hz, 1H), 7.28-7.14 (m, 2H), 6.63 (d, J=2.4 Hz, 1H), 6.51 (dd, J=7.8, 1.8 Hz, 1H), 6.43 (dd, J=8.7, 2.4 Hz, 1H), 6.31 (d, J=2.0 Hz, 1H), 5.52 (s, 1H), 5.14 (dd, J=13.2, 5.1 Hz, 1H), 4.46-4.42 (m, 1H), 4.35-4.16 (m, 2H), 4.05 (d, J=9.3 Hz, 1H), 3.81 (s, 3H), 3.64 (t, J=11.1 Hz, 1H), 3.52 (d, J=10.2 Hz, 1H), 3.17 (d, J=9.3 Hz, 1H), 3.07 (s, 1H), 3.01-2.84 (m, 4H), 2.63 (s, 1H), 2.57 (s, 1H), 2.11 (dd, J=13.2, 5.7 Hz, 1H), 2.05-1.82 (m, 2H), 1.66 (s, 2H), 1.58 (s, 2H), 1.56-1.45 (m, 1H), 1.35 (dt, J=15.3, 7.8 Hz, 4H), 1.27-1.14 (m, 2H), 0.96 (t, J=6.3 Hz, 1H), 0.90 (s, 9H).

Example 24: Preparation of (2'S,3S,4'S,5'R)-6-chloro-4'-(3-chloro-2-fluorophenyl)-N-(4-((3R)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide Synthesis of tert-butyl 3-(2-methoxyvinyl)piperidine-1-carboxylate: Into a 250-mL round-bottom flask purged and maintained under an inert atmosphere of nitrogen, were placed (methoxymethyl)triphenylphosphanium chloride (10.8 g, 31.6 mmol, 1.5 eq), tetrahydrofuran (45 mL). After that, t-BuOK (3.5 g, 31.6 mmol, 1.5 eq) was added at 0° C. After stirring at 0° C. for 0.5 hour, to the above solution was added a solution of tert-butyl 3-formylpiperidine-1-carboxylate (4.5 g, 21.1 mmol, 1.0 eq) in tetrahydrofuran at −20° C. The reaction mixture was stirred for an additional 16 hours at 25° C. The resulting mixture was then quenched by the addition of $NH_4Cl$ (aq.) (50 mL) and then extracted with ethyl acetate (2×100 mL). The combined organic phase was washed with brine (2×100 mL), dried over anhydrous sodium sulfate. After filtration, the filtrate was concentrated under vacuum. The residue was purified by a flash column (silica gel, ethyl acetate/petroleum ether=0:1 to 1:5) to give tert-butyl 3-(2-methoxyvinyl)piperidine-1-carboxylate (3.5 g, 69%) as a light yellow oil. LC-MS (ESI, m/z) M+1: 242. $^1$HNMR (400 MHz, DMSO-$d_6$) δ 6.43 (d, J=12.8 Hz, 1H), 4.60 (dd, J=12.8, 8.0 Hz, 1H), 3.84-3.70 (m, 3H), 3.43 (s, 3H), 2.80-2.65 (m, 1H), 1.99 (dtt, J=10.6, 7.0, 4.0 Hz, 1H), 1.76-1.65 (m, 1H), 1.63-1.59 (m, 1H), 1.39 (s, 9H), 1.29-1.25 (m, 2H).

Synthesis of tert-butyl 3-(2-oxoethyl)piperidine-1-carboxylate: Into a 50-mL round-bottom flask were placed tert-butyl 3-(2-methoxyvinyl)piperidine-1-carboxylate (3.5 g, 14.5 mmol, 1.0 eq), formic acid (7 mL). The reaction mixture was stirred for 1 hour at 25° C. The resulting mixture was then quenched by the addition of $NaHCO_3$(aq.) (100 mL) and then extracted with ethyl acetate (2×100 mL). The combined organic phase was washed with brine (2×100 mL), dried over anhydrous sodium sulfate. After filtration, the filtrate was concentrated under vacuum. The residue was purified by a flash column (silica gel, ethyl acetate/petroleum ether=0:1 to 1:4) to give tert-butyl 3-(2-oxoethyl) piperidine-1-carboxylate (2.5 g, 76%) as a light yellow oil. LC-MS (ESI, m/z) M+1: 228. $^1$HNMR (400 MHz, DMSO-$d_6$) δ 9.67 (t, J=1.7 Hz, 1H), 3.86-3.60 (m, 3H), 2.83 (ddd, J=13.4, 10.6, 3.2 Hz, 1H), 2.44-2.26 (m, 2H), 1.94 (dtd, J=10.2, 6.6, 3.4 Hz, 1H), 1.73 (dd, J=13.0, 4.4 Hz, 1H), 1.57 (dt, J=13.2, 4.1 Hz, 1H), 1.39 (s, 9H), 1.38-1.26 (m, 1H), 1.20-1.12 (m, 1H).

Synthesis of tert-butyl 3-(prop-2-yn-1-yl)piperidine-1-carboxylate: Into a 100 mL round-bottom flask were placed tert-butyl 3-(2-oxoethyl)piperidine-1-carboxylate (2.5 g, 10.9 mmol, 1.0 eq), $CH_3OH$ (30 mL), $K_2CO_3$ (3.0 g, 21.9 mmol, 2.0 eq), seyferth-gilbert homologation (3.2 g, 16.5 mmol, 1.5 eq). The reaction mixture was stirred for 2 hours at 25° C. The resulting mixture was then quenched by the addition of water (100 mL) and then extracted with ethyl acetate (2×100 mL). The combined organic phase was washed with brine (2×100 mL), dried over anhydrous sodium sulfate. After filtration, the filtrate was concentrated under vacuum. The residue was purified by a flash column (silica gel, ethyl acetate/petroleum ether=0:1 to 1:4) to give tert-butyl 3-(prop-2-yn-1-yl) piperidine-1-carboxylate (2.1 g, 85%) as a light yellow oil. LC-MS (ESI, m/z) M-(t-Bu)+41+1: 209. $^1$HNMR (400 MHz, DMSO-$d_6$) δ 4.0-3.68 (m, 3H), 2.83 (t, J=2.8 Hz, 1H), 2.74 (ddd, J=13.8, 11.4, 3.2 Hz, 1H), 2.10 (dt, J=7.2, 2.8 Hz, 2H), 1.84-1.75 (m, 1H), 1.58-1.52 (m, 1H), 1.40 (s, 9H), 1.36-1.20 (m, 1H), 1.22-1.12 (m, 1H).

Synthesis of 3-(prop-2-yn-1-yl)piperidine hydrochloride: Into a 100 mL round-bottom flask were placed tert-butyl 3-(prop-2-yn-1-yl)piperidine-1-carboxylate (2.1 g, 9.4 mmol, 1.0 eq), dichloromethane (21 mL), HCl (gas) in 1,4-dioxane (21 mL). The reaction mixture was stirred for 1 hour at 25° C. The resulting mixture was concentrated under vacuum to give 3-(prop-2-yn-1-yl)piperidine hydrochloride (1.2 g, crude) as an off white solid. LC-MS (ESI, m/z) M+1: 160.

Synthesis of (3-methoxy-4-nitrophenyl)(3-(prop-2-yn-1-yl)piperidin-1-yl)methanone: Into a 50-mL round flask, were placed 3-(prop-2-yn-1-yl)piperidine hydrochloride (1.0 g, 8.1 mmol, 1.0 eq), 3-methoxy-4-nitrobenzoic acid (1.6 g, 8.1 mmol, 1.0 eq), HATU (3.4 g, 8.9 mmol, 1.1 eq), DIEA (3.2 g, 24.3 mmol, 3.0 eq), N,N-dimethylformamide (10 mL). The reaction mixture was stirred for 2 hours at 25° C. The resulting mixture was then quenched by the addition of water (50 mL) and extracted with ethyl acetate (2×50 mL). The combined organic phase was washed with brine (2×50 mL), dried over anhydrous sodium sulfate. After filtration, the filtrate was concentrated under vacuum. The residue was purified by a flash column (silica gel, ethyl acetate/petroleum ether=0:1 to 1:1) to give (3-methoxy-4-nitrophenyl)(3-(prop-2-yn-1-yl)piperidin-1-yl)methanone (1.2 g, 49%) as a light yellow oil. LC-MS (ESI, m/z) M+1: 303. $^1$HNMR (400 MHz, DMSO-$d_6$) δ 7.93 (d, −8.2 Hz, 1H), 7.35 (d, J=1.4 Hz, 1H), 7.09 (dd, −8.1, 1.5 Hz, 1H), 4.55-4.36 (m, 1H), 3.95 (s, 3H), 3.62-3.45 (m, 2H), 2.89-2.78 (m, 1H), 2.75-2.59 (m, 1H), 2.22 (d, −6.6 Hz, 1H), 2.06 (s, 1H), 1.89-1.86 (m, 1H), 1.72 (br, 2H), 1.51 (dt, J=38.5, 12.7 Hz, 1H), 1.32 (t, J=11.6 Hz, 1H).

Synthesis of (R)-(3-methoxy-4-nitrophenyl) (3-(prop-2-yn-1-yl)piperidin-1-yl)methanone and (S)-(3-methoxy-4-nitrophenyl)(3-(prop-2-yn-1-yl)piperidin-1-yl)methanone:

500 mg of (3-methoxy-4-nitrophenyl) (3-(prop-2-yn-1-yl) piperidin-1-yl)methanone was purified by Chiral-Prep-HPLC using the following conditions: (R, R)-WHELK-O1-Kromasil, 2.11*25 cm, 5 μm; Mobile Phase A: $CO_2$, Mobile Phase B: IPA (0.5% 2M $NH_3$-MeOH); Flow rate: 55 mL/min; Gradient: isocratic 20% B; Detector, 220 nm. Finally, (R)-(3-methoxy-4-nitrophenyl) (3-(prop-2-yn-1-yl) piperidin-1-yl)methanone (200 mg) was obtained as a light yellow solid. And (S)-(3-methoxy-4-nitrophenyl) (3-(prop-2-yn-1-yl)piperidin-1-yl)methanone (210 mg) was obtained as a light yellow solid. LC-MS (ESI, m/z) M+1: 303. 5A, $T_R$=1.801 min in CHIRAL-SFC, Column: (R,R)-WHELK-O1 50×4.6 mm 3.5 um. mobile phase A: $CO_2$; mobile phase B: IPA (20 mM NH3), Start Conc. of Pump B: 15.0% in 4 min, Oven Temperature: 35° C. 5B, $T_R$=2.027 min in CHIRAL-SFC, Column: (R, R)-WHELK-O1 50×4.6 mm 3.5 um. mobile phase A: $CO_2$; mobile phase B: IPA (20 mM NH3), Start Conc. of Pump B: 15.0% in 4 min, Oven Temperature: 35° C.

Synthesis of 3-(4-(3-((R)-1-(3-methoxy-4-nitrobenzoyl) piperidin-3-yl)prop-1-yn-1-yl)-1-oxoisoindolin-2-yl)piperidine-2,6-dione: Into a 20 mL sealed tube purged and maintained under an inert atmosphere of nitrogen, were placed (R)-(3-methoxy-4-nitrophenyl)(3-(prop-2-yn-1-yl)piperidin-1-yl)methanone (188 mg, 0.6 mmol, 1.0 eq), 3-(4-iodo-1-oxo-3H-isoindol-2-yl)piperidine-2,6-dione (230 mg, 0.6 mmol, 1.0 eq), CuI (12 mg, 0.1 mmol, 0.1 eq), triethylamine (189 mg, 1.8 mmol, 3.0 eq), $Pd(PPh_3)_4$ (72 mg, 0.1 mmol, 0.1 eq), N,N-dimethylformamide (3 mL). The reaction mixture was stirred for 2 hours at 70° C. The resulting mixture was diluted with water (30 mL) and then extracted with ethyl acetate (2×30 mL). The combined organic phase was washed with brine (2×30 mL), dried over anhydrous sodium sulfate and filtered. The filtrate was concentrated under vacuum. The residue was purified by a flash column (silica gel, ethyl acetate/petroleum ether=0:1 to 1:0). Finally, 3-(4-(3-((R)-1-(3-methoxy-4-nitrobenzoyl) piperidin-3-yl) prop-1-yn-1-yl)-1-oxoisoindolin-2-yl) piperidine-2,6-dione (250 mg, 74%) was obtained as a light yellow solid. LC-MS (ESI, m/z) M+1: 545.

Synthesis of 3-(4-(3-((R)-1-(4-amino-3-methoxybenzoyl) piperidin-3-yl)prop-1-yn-1-yl)-1-oxoisoindolin-2-yl)piperidine-2,6-dione: Into a 20 mL sealed tube were placed 3-(4-(3-((R)-1-(3-methoxy-4-nitrobenzoyl) piperidin-3-yl) prop-1-yn-1-yl)-1-oxoisoindolin-2-yl)piperidine-2,6-dione (240 mg, 0.4 mmol, 1.0 eq), Fe (99 mg, 1.7 mmol, 4.0 eq), $NH_4Cl$ (189 mg, 3.5 mmol, 8.0 eq), ethanol (6 mL) and water (2 mL). The reaction mixture was stirred for 2 hours at 50° C. The resulting mixture was filtered, and the filtrate was concentrated under vacuum. The residue was purified by a flash column (silica gel, dichloromethane/methanol=20:1) to give 3-(4-(3-((R)-1-(4-amino-3-methoxybenzoyl)piperidin-3-yl)prop-1-yn-1-yl)-1-oxoisoindolin-2-yl) piperidine-2,6-dione (200 mg, 88%) as a light yellow solid. LC-MS (ESI, m/z) M+1: 515.

Synthesis of (2'S,3S,4'S,5'R)-6-chloro-4'-(3-chloro-2-fluorophenyl)-N-(4-((3R)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide: Into an 8-mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 3-(4-(3-((R)-1-(4-amino-3-methoxybenzoyl) piperidin-3-yl) prop-1-yn-1-yl)-1-oxoisoindolin-2-yl) piperidine-2,6-dione (51 mg, 0.1 mmol, 1.5 eq), HATU (28 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (85% Phase B up to 95% in 7 min); Detector, UV 254/220 nm. Finally, (2'S,3S,4'S,5'R)-6-chloro-4'-(3-chloro-2-fluorophenyl)-N-(4-((3R)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide (20 mg, 32%) was obtained as a white solid. LC-MS (ESI, m/z) M+1: 947/949. $^1$HNMR (400 MHz, DMSO-$d_6$) δ 10.95 (s, 1H), 10.57 (br, 1H), 8.28 (br, 1H), 7.73 (d, J=8.0 Hz, 1H), 7.50 (s, 2H), 7.43 (t, J=7.5 Hz, 1H), 7.37 (s, 2H), 7.24 (dt, J=21.2, 7.4 Hz, 2H), 7.06 (s, 1H), 6.95 (d, −8.2 Hz, 1H), 6.52 (d, −7.9 Hz, 1H), 6.32 (d, J=1.7 Hz, 1H), 5.53 (s, 1H), 5.13 (s, 1H), 4.34-4.24 (m, 3H), 4.08 (d, −9.5 Hz, 1H), 3.84 (s, 4H), 3.68 (s, 2H), 3.54 (d, J=10.6 Hz, 1H), 3.20 (d, J=10.4 Hz, 1H), 3.14 (s, 1H), 3.0 (s, 1H), 2.86 (d, J=19.3 Hz, 2H), 1.99 (d, −7.6 Hz, 1H), 1.99-1.95 (m, 2H), 1.82 (br, 1H), 1.71-1.67 (m, 1H), 1.49 (d, J=10.9 Hz, 1H), 1.36 (dd, J=14.0, 9.3 Hz, 3H), 1.27-1.16 (m, 2H), 0.90 (s, 10H).

Example 25: Preparation of (2'S,3S,4'S,5'R)-6-chloro-4'-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide Synthesis of 3-(4-(3-((S)-1-(3-methoxy-4-nitrobenzoyl) piperidin-3-yl)prop-1-yn-1-yl)-1-oxoisoindolin-2-yl)piperidine-2,6-dione: Into a 20 mL sealed tube purged and maintained under an inert atmosphere of nitrogen, were placed (S)-(3-methoxy-4-nitrophenyl)(3-(prop-2-yn-1-yl)piperidin-1-yl)methanone (200 mg, 0.7 mmol, 1.0 eq), 3-(4-iodo-1-oxo-3H-isoindol-2-yl)piperidine-2,6-dione (245 mg, 0.7 mmol, 1.0 eq), triethylamine (201 mg, 1.9 mmol, 3.0 eq), CuI (13 mg, 0.1 mmol, 0.1 eq), $Pd(PPh_3)_4$ (76 mg, 0.1 mmol, 0.1 eq), N,N-dimethylformamide (4 mL). The reaction mixture was stirred for 2 hours at 70° C. The resulting mixture was diluted with water (30 mL) and then extracted with ethyl acetate (2×30 mL). The combined organic phase was washed with brine (2×30 mL), dried over anhydrous sodium sulfate. After filtration, the filtrate was concentrated under vacuum. The residue was purified by a flash column (silica gel, ethyl acetate/petroleum ether=0:1 to 1:0) to give 3-(4-(3-((S)-1-(3-methoxy-4-nitrobenzoyl) piperidin-3-yl)prop-1-yn-1-yl)-1-oxoisoindolin-2-yl)piperidine-2,6-dione (270 mg, 75%) as a light yellow solid. LC-MS (ESI, m/z) M+1: 545.

Synthesis of 3-(4-(3-((S)-1-(4-amino-3-methoxybenzoyl) piperidin-3-yl)prop-1-yn-1-yl)-1-oxoisoindolin-2-yl)piperidine-2,6-dione: Into a 20 mL sealed tube were placed 3-(4-(3-((S)-1-(3-methoxy-4-nitrobenzoyl) piperidin-3-yl) prop-1-yn-1-yl)-1-oxoisoindolin-2-yl)piperidine-2,6-dione (260 mg, 0.5 mmol, 1.0 eq), Fe (107 mg, 1.9 mmol, 4.0 eq), $NH_4Cl$ (204 mg, 3.8 mmol, 8.0 eq), ethanol (6 mL), water (2 mL). The reaction mixture was stirred for 2 hours at 50° C. The resulting mixture was filtered, and the filtrate was concentrated under vacuum. The residue was purified by a flash column (silica gel, dichloromethane/methanol=20:1) to give 3-(4-(3-((S)-1-(4-amino-3-methoxybenzoyl)piperidin-3-yl)prop-1-yn-1-yl)-1-oxoisoindolin-2-yl)piperidine-2,6-dione (210 mg, 85%) as a light yellow solid. LC-MS (ESI, m/z) M+1: 515.

Synthesis of (2'S,3S,4'S,5'R)-6-chloro-4'-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 3-(4-(3-((S)-1-(4-amino-3-methoxybenzoyl) piperidin-3-yl) prop-1-yn-1-yl)-1-oxoisoindolin-2-yl)piperidine-2,6-dione (51 mg, 0.1 mmol, 1.5 eq), HATU (28 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (85% Phase B up to 95% in 7 min); Detector, UV 254/220 nm. Finally, (2'S,3S,4'S,5'R)-6-chloro-4'-(3-chloro-2-fluorophenyl)-N-(4-((3S)-3-(3-(2-(2,6-dioxopiperidin-3-yl)-1-oxoisoindolin-4-yl)prop-2-yn-1-yl)piperidine-1-carbonyl)-2-methoxyphenyl)-2'-neopentylspiro[indoline-3,3'-pyrrolidine]-5'-carboxamide (20 mg, 32%) was obtained as a white solid. LC-MS (ESI, m/z) M+1: 947/949. $^1$HNMR (400 MHz, DMSO-$d_6$) δ 10.96 (s, 1H), 10.57 (br, 1H), 8.30-8.27 (m, 1H), 7.77-7.70 (m, 1H), 7.45-7.37 (m, 4H), 7.31-7.20 (m, 2H), 7.06-7.02 (m, 1H), 6.94 (d, J=8.0 Hz, 1H), 6.52 (s, 1H), 6.34-6.29 (m, 1H), 5.53 (s, 1H), 5.13 (br, 1H), 4.57-4.27 (m, 5H), 3.84-3.55 (m, 6H), 3.23-3.11 (m, 2H), 2.92-2.88 (m, 3H), 2.79-2.74 (m, 1H), 1.99 (d, J=7.6 Hz, 1H), 1.99-1.95 (m, 2H), 1.82 (s, 1H), 1.68 (br, 1H), 1.49 (d, J=10.9 Hz, 1H), 1.36 (dd, J=14.0, 9.3 Hz, 2H), 1.27-1.16 (m, 2H), 0.90 (s, 9H).

Example 26: Preparation of (2'S,3S,4'S,5'R)-6-chloro-4'-(3-chloro-2-fluorophenyl)-2'-(2,2-dimethylpropyl)-N-(4-{4-[(1S,2R)-2-{2-[2-(2,6-dioxopiperidin-3-yl)-1-oxo-3H-isoindol-4-yl]ethynyl}cyclopropyl]piperidin-1-yl}-2-methoxyphenyl)-1,2-dihydrospiro[indole-3,3'-pyrrolidine]-5'-carboxamide Synthesis of tert-butyl 4-[3-ethoxy-3-oxoprop-1-en-1-yl] piperidine-1-carboxylate: To a stirred solution of triethyl phosphonoacetate (15.8 g, 70.3 mmol, 1.0 eq) in tetrahydrofuran was added NaH (2.8 g, 70.3 mmol, 1.0 eq) dropwise at 0° C. under $N_2$ atmosphere. The reaction mixture was stirred for 30 min at 0° C. After that, to the above mixture was added tert-butyl 4-formylpiperidine-1-carboxylate (15 g, 70.3 mmol, 1.0 eq). The reaction mixture was stirred for 14 hours at 25° C. The resulting mixture was quenched by the addition of water (5 mL) at 0° C. and then concentrated under vacuum. The residue was diluted with dichloromethane (200 mL), washed with water (50 mL) and dried over anhydrous sodium sulfate. After filtration, the filtrate was concentrated under vacuum. The crude residue was purified by a flash column (silica gel, ethyl acetate/petroleum ether=0:1 to 10:1) to give tert-butyl 4-[3-ethoxy-3-oxoprop-1-en-1-yl]piperidine-1-carboxylate (14.0 g, 70%) as a yellow oil. $^1$HNMR (300 MHz, DMSO-$d_6$) δ 6.85 (dd, J=15.9, 6.6 Hz, 1H), 5.89-5.73 (m, 1H), 4.11 (q, J=7.2 Hz, 2H), 3.95 (d, J=13.2 Hz, 2H), 2.75 (s, 2H), 2.43-2.27 (m, 1H), 1.74-1.58 (m, 2H), 1.40 (s, 9H), 1.30-1.11 (m, 5H).

Synthesis tert-butyl 4-[(1S,2R and 1R,2S)-2-(ethoxycarbonyl)cyclopropyl]piperidine-1-carboxylate: To a stirred solution of trimethyl(oxo)-lambda6-sulfanylium iodide (32.6 g, 148.2 mmol, 3.0 eq) in DMSO (300 mL) was added NaH (5.9 g, 148.3 mmol, 3.0 eq 60%) in portions at 0° C. The reaction mixture was stirred for 30 min at 25° C. After that, to the above mixture was added tert-butyl 4-[(1E)-3-ethoxy-3-oxoprop-1-en-1-yl]piperidine-1-carboxylate (14.0 g, 49.4 mmol, 1.0 eq) at 25° C. The reaction mixture was stirred for additional 14 hours at 25° C. The resulting mixture was diluted with water (500 mL) and extracted with ethyl acetate (3×100 mL). The combined organic layers were washed with water (3×50 mL) and NaCl (aq. 50 mL), dried over anhydrous sodium sulfate. After filtration, the filtrate was concentrated under vacuum. The residue was purified by a flash column (silica gel, ethyl acetate/petroleum ether=0:1 to 10:1) to give tert-butyl 4-[(1S,2R and 1R,2S)-2-(ethoxycarbonyl)cyclopropyl]piperidine-1-carboxylate (racemate) (1.7 g, 11%) as a yellow oil. $^1$HNMR (300 MHz, DMSO-d6) δ 4.04 (qd, J=7.8, 1.8 Hz, 2H), 3.92 (d, J=13.2 Hz, 2H), 2.80-2.53 (m, 2H), 1.68-1.57 (m, 2H), 1.56-1.43 (m, 1H), 1.39 (s, 9H), 1.23-1.12 (m, 5H), 1.12-0.76 (m, 4H).

Synthesis of tert-butyl 4-[(1S,2R and 1R,2S)-2-(hydroxymethyl)cyclopropyl]piperidine-1-carboxylate: To a stirred mixture of tert-butyl 4-[(1S,2R and 1R,2S)-2-(ethoxycarbonyl)cyclopropyl]piperidine-1-carboxylate (racemate) (1.7 g, 5.7 mmol, 1.0 eq) in tetrahydrofuran (20 mL) was added $LiAlH_4$ (0.7 g, 17.1 mmol, 3.0 eq) at 0° C. The reaction mixture was stirred for 2 hours at 0° C. The resulting mixture was quenched with water (0.7 mL), 15% NaOH (0.7 mL) and water (2.0 mL). The resulting mixture was filtered, and the filter cake was washed with tetrahydrofuran (3×15 mL). The filtrate was dried with anhydrous sodium sulfate and concentrated under vacuum to give tert-butyl 4-[(1S,2R and 1R,2S)-2-(hydroxymethyl)cyclopropyl]piperidine-1-carboxylate (racemate) (1.3 g, 89%) as a colorless oil. $^1$HNMR (300 MHz, DMSO-$d_6$) δ 4.37 (t, J=5.7 Hz, 1H), 4.02-3.77 (m, 2H), 3.32-3.12 (m, 2H), 2.70-2.63 (m, 2H), 1.64 (t, J=11.4 Hz, 2H), 1.39 (s, 9H), 1.16-1.04 (m, 3H), 0.83-0.66 (m, 2H), 0.50-0.35 (m, 1H), 0.33-0.17 (m, 1H).

Synthesis of tert-butyl 4-[(1S,2R and 1R,2S)-2-formylcyclopropyl]piperidine-1-carboxylate: A mixture of tert-butyl 4-[(1S,2R and 1R,2S)-2-(hydroxymethyl)cyclopropyl]piperidine-1-carboxylate (racemate) (1.2 g, 4.7 mmol, 1.0 eq) and PCC (1.5 g, 7.1 mmol, 1.5 eq) in dichloromethane (20 mL) was stirred for 2 hours at 25° C. The resulting mixture was filtered, the filter cake was washed with dichloromethane (3×10 mL). The filtrate was washed with water (3×10 mL) and dried over anhydrous sodium sulfate. After filtration, the filtrate was concentrated under vacuum. The residue was purified by a flash column (silica gel, ethyl acetate/petroleum ether=0:1 to 3:1) to give tert-butyl 4-[(1S,2R and 1R,2S)-2-formylcyclopropyl]piperidine-1-carboxylate (racemate) (900 mg, 76%) as a brown solid. $^1$HNMR (300 MHz, DMSO-$d_6$) δ 8.86 (d, J=6.0 Hz, 1H), 3.92 (d, J=13.8 Hz, 2H), 2.75-2.50 (m, 2H), 1.76-1.57 (m, 3H), 1.39 (s, 11H), 1.28-1.05 (m, 4H).

Synthesis of 4-[(1S,2R and 1R,2S)-2-ethynylcyclopropyl] piperidine-1-carboxylate: To a stirred solution of tert-butyl 4-[(1S,2R and 1R,2S)-2-formylcyclopropyl]piperidine-1-carboxylate (racemate) (900 mg, 3.6 mmol, 1.0 eq) and $K_2CO_3$ (1472 mg, 10.7 mmol, 3.0 eq) in $CH_3OH$ (20 mL) was added seyferth-gilbert homologation (1023 mg, 5.3 mmol, 1.5 eq) in portions at 25° C. The reaction mixture was stirred for 2 hours. The resulting mixture was quenched with water (0.5 mL), and then the precipitated solids were collected by filtration. The residue was purified by a flash column (silica gel, ethyl acetate/petroleum ether=0:1 to 10:1) to give tert-butyl 4-[(1S,2R)-2-ethynylcyclopropyl] piperidine-1-carboxylate (racemate) (600 mg, 68%) as a brown solid.

Synthesis of 4-[(1S,2R and 1R,2S)-2-ethynylcyclopropyl] piperidine: To a stirred mixture of tert-butyl 4-[(1S,2R and 1R,2S)-2-ethynylcyclopropyl]piperidine-1-carboxylate (racemate) (600 mg, 2.4 mmol, 1.0 eq) and 2,6-dimethylpyridine (773 mg, 7.2 mmol, 3.0 eq) in dichloromethane (15 mL) was added TMSI (963 mg, 4.8 mmol, 2.0 eq) dropwises at 0° C. The reaction mixture was stirred at 0° C. for 2 hours. The reaction was quenched with water (0.2 mL). The resulting mixture was concentrated under vacuum to give 4-[(1S,2R and 1R,2S)-2-ethynylcyclopropyl]piperidine (racemate) (1.5 g, crude) as a brown solid.

Synthesis of 4-[(1S,2R and 1R,2S)-2-ethynylcyclopropyl]-1-(3-methoxy-4-nitrophenyl)piperidine: To a stirred mixture 4-[(1S,2R and 1R,2S)-2-ethynylcyclopropyl]piperidine (racemate) (1.5 g, 10.0 mmol, 1.0 eq) and $K_2CO_3$ (4.2 g, 30.1 mmol, 3.0 eq) in N,N-dimethylformamide (20 mL) was added 4-fluoro-2-methoxy-1-nitrobenzene (1.7 g, 10.1 mmol, 1.0 eq). The reaction mixture was stirred for 14 hours at 80° C. The resulting mixture was diluted with water (60 mL) and extracted with ethyl acetate (3×20 mL). The combined organic layers were washed with water (2×10 mL), dried over anhydrous sodium sulfate. After filtration, the filtrate was concentrated under vacuum. The residue was purified by a flash column (silica gel, ethyl acetate/petroleum ether=0:1 to 1:1) to give 4-[(1S,2R and 1R,2S)-2-ethynylcyclopropyl]-1-(3-methoxy-4-nitrophenyl)piperidine (racemate) (630 mg, 25%) as a yellow solid. $^1$HNMR (300 MHz, DMSO-$d_6$) δ 7.88 (d, J=9.3 Hz, 1H), 6.59 (dd, J=9.3, 2.4 Hz, 1H), 6.49 (d, J=2.4 Hz, 1H), 4.04 (d, J=13.2 Hz, 2H), 3.91 (s, 3H), 2.96-2.80 (m, 2H), 2.59 (d, J=2.1 Hz, 1H), 1.80 (d, J=13.2 Hz, 1H), 1.7-1.40 (m, 2H), 1.50-1.36 (m, 2H), 1.02-0.88 (m, 2H), 0.80-0.65 (m, 2H).

Synthesis of 4-[(1S,2R)-2-ethynylcyclopropyl]-1-(3-methoxy-4-nitrophenyl)piperidine and 4-[(1R,2S)-2-ethynylcyclopropyl]-1-(3-methoxy-4-nitrophenyl)piperidine: 500 mg of 4-[(1S,2R and 1R,2S)-2-ethynylcyclopropyl]-1-(3-methoxy-4-nitrophenyl)piperidine (500 mg) (racemate) was purified by Chiral-SFC using the following conditions: Column: CHIRAL ART Cellulose-SB, 3*25 cm, 5 μm; mobile phase A: $CO_2$; mobile phase B: ethanol—Preparative; Flow rate: 50 mL/min; Gradient: isocratic 40% B; Detector, 220 nm. Finally, 4-[(1S,2R)-2-ethynylcyclopropyl]-1-(3-methoxy-4-nitrophenyl)piperidine (220 mg) was obtained as a yellow solid. And 4-[(1R,2S)-2-ethynylcyclopropyl]-1-(3-methoxy-4-nitrophenyl)piperidine (220 mg) was obtained as a yellow solid. 8A, $T_R$=2.391 min in CHIRAL-SFC, Column: YMC Cellulose-SB, 100*4.6 mm, 3 μm 121AB00077. mobile phase A: n-Hexane (0.1% DEA); mobile phase B: Ethanol/MeOH=1/1, Start Conc. of Pump B: 50.0% in 5 min, Oven Temperature: 35° C. 8B, $T_R$=2.692 min in CHIRAL-SFC, Column: YMC Cellulose-SB, 100*4.6 mm, 3 μm 121AB00077. mobile phase A: n-Hexane (0.1% DEA); mobile phase B: Ethanol/MeOH=1/1, Start Conc. of Pump B: 50.0% in 5 min, Oven Temperature: 35° C.

Synthesis of 3-(4-{2-[(1R,2S)-2-[1-(3-methoxy-4-nitrophenyl)piperidin-4-yl]cyclopropyl]ethynyl}-1-oxo-3H-isoindol-2-yl)piperidine-2,6-dione: To a stirred solution of 4-[(1S,2R)-2-ethynylcyclopropyl]-1-(3-methoxy-4-nitrophenyl)piperidine (160 mg, 0.5 mmol, 1.0 eq) and 3-(4-iodo-1-oxo-3H-isoindol-2-yl)piperidine-2,6-dione (197 mg, 0.5 mmol, 1.0 eq) in N,N-dimethylformamide (5 mL) and DIEA (1 mL) was added CuI (10 mg, 0.1 mmol, 0.1 eq) and $Pd(PPh_3)_4$(60 mg, 0.1 mmol, 0.1 eq) at 25° C. under argon atmosphere. The reaction mixture was stirred for 4 hours at 25° C. under nitrogen atmosphere. The resulting mixture was diluted with water (20 mL) and then extracted with ethyl acetate (3×15 mL). The combined organic layers were washed with water (2×10 mL) and brine (10 mL), dried over anhydrous sodium sulfate. After filtration, the filtrate was concentrated under vacuum. The residue was purified by a flash column (silica gel, dichloromethane/$CH_3OH$=100:0 to 100:5) to give 3-(4-{2-[(1R,2S)-2-[1-(3-methoxy-4-nitrophenyl)piperidin-4-yl]cyclopropyl]ethynyl}-1-oxo-3H-isoindol-2-yl)piperidine-2,6-dione (360 mg, 76%) as a brown solid. LC-MS (ESI, m/z) M+1: 543.

Synthesis of 3-(4-{2-[(1R,2S)-2-[1-(4-amino-3-methoxyphenyl)piperidin-4-yl]cyclopropyl]ethynyl}-1-oxo-3H-isoindol-2-yl)piperidine-2,6-dione: To a stirred mixture of 3-(4-{2-[(1R,2S)-2-[1-(3-methoxy-4-nitrophenyl)piperidin-4-yl]cyclopropyl]ethynyl}-1-oxo-3H-isoindol-2-yl)piperidine-2,6-dione (360 mg, 0.7 mmol, 1.0 eq) and $NH_4Cl$ (284 mg, 5.3 mmol, 8.0 eq) in ethanol (5 mL) and water (1 mL) was added Fe (222 mg, 4.0 mmol, 6 eq) in portions at 25° C. The reaction mixture was stirred for 3 hours at 50° C. The resulting mixture was filtered, and the filter cake was washed with ethanol (3×10 mL). The residue was purified by a flash column (silica gel, dichloromethane/$CH_3OH$=100:0 to 100:5) to give 3-(4-{2-[(1R,2S)-2-[1-(4-amino-3-methoxyphenyl)piperidin-4-yl]cyclopropyl]ethynyl}-1-oxo-3H-isoindol-2-yl)piperidine-2,6-dione (210 mg, 62%) as a yellow solid. LC-MS (ESI, m/z) M+1: 513.

Synthesis of (2'S,3S,4'S,5'R)-6-chloro-4'-(3-chloro-2-fluorophenyl)-2'-(2,2-dimethylpropyl)-N-(4-{4-[(1S,2R)-2-{2-[2-(2,6-dioxopiperidin-3-yl)-1-oxo-3H-isoindol-4-yl]ethynyl}cyclopropyl]piperidin-1-yl}-2-methoxyphenyl)-1,2-dihydrospiro[indole-3,3'-pyrrolidine]-5'-carboxamide: To a stirred mixture of 3-(4-{2-[(1R,2S)-2-[1-(4-amino-3-methoxyphenyl)piperidin-4-yl]cyclopropyl]ethynyl}-1-oxo-3H-isoindol-2-yl)piperidine-2,6-dione (100 mg, 0.1 mmol, 1.0 eq), DIEA (49 mg, 0.4 mmol, 3.0 eq) and (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (57 mg, 0.1 mmol, 1.0 eq) in N,N-dimethylformamide (5 mL) was added HATU (72 mg, 0.2 mmol, 1.5 eq) in portions at 25° C. The reaction mixture was stirred for 4 hours at 25° C. The crude product was purified by Prep-HPLC using the following conditions: Column, X-bridge RP18; mobile phase, 0.05% $NH_3 \cdot H_2O$ in water and $CH_3CN$ (30% $CH_3CN$ up to 75% in 5 min); Detector, UV 254 nm. Finally, (2'S,3S,4'S,5'R)-6-chloro-4'-(3-chloro-2-fluorophenyl)-2'-(2,2-dimethylpropyl)-N-(4-{4-[(1S,2R)-2-{2-[2-(2,6-dioxopiperidin-3-yl)-1-oxo-3H-isoindol-4-yl]ethynyl}cyclopropyl]piperidin-1-yl}-2-methoxyphenyl)-1,2-dihydrospiro[indole-3,3'-pyrrolidine]-5'-carboxamide (25 mg, 21%) was obtained as a white solid. LC-MS (ESI, m/z) M+1: 945/947. $^1$HNMR (300 MHz, DMSO-$d_6$) δ 11.0 (s, 1H), 10.28 (s, 1H), 8.09 (d, J=8.7 Hz, 1H), 7.68 (dd, J=7.5, 1.2 Hz, 1H), 7.61 (dd, −7.5, 1.2 Hz, 1H), 7.50 (t, J=7.5 Hz, 1H), 7.45-7.28 (m, 2H), 7.27-7.14 (m, 2H), 6.64 (d, J=2.4 Hz, 1H), 6.51 (dd, −7.8, 1.8 Hz, 1H), 6.44 (dd, −9.0, 2.4 Hz, 1H), 6.31 (d, −1.8 Hz, 1H), 5.52 (s, 1H), 5.14 (dd, J=13.2, 5.1 Hz, 1H), 4.43 (d, J=18.0 Hz, 1H), 4.34-4.16 (m, 2H), 4.05 (d, −9.3 Hz, 1H), 3.82 (s, 3H), 3.66 (d, J=11.4 Hz, 3H), 3.52 (d, J=10.5 Hz, 1H), 3.20-3.04 (m, 2H), 3.01-2.83 (m, 1H), 2.10-1.95 (m, 2H), 1.84 (d, J=12.3 Hz, 1H), 1.75 (d, J=12.6 Hz, 1H), 1.48-1.20 (m, 6H), 0.90 (s, 11H)

Example 27: Preparation of (2'S,3S,4'S,5'R)-6-chloro-4'-(3-chloro-2-fluorophenyl)-2'-(2,2-dimethylpropyl)-N-(4-{4-[(1R,2S)-2-{2-[2-(2,6-dioxopiperidin-3-yl)-1-oxo-3H-isoindol-4-yl]ethynyl}cyclopropyl]piperidin-1-yl}-2-methoxyphenyl)-1,2-dihydrospiro[indole-3,3'-pyrrolidine]-5'-carboxamide Synthesis of 3-(4-{2-[(1S,2R)-2-[1-(3-methoxy-4-nitrophenyl)piperidin-4-yl]cyclopropyl]ethynyl}-1-oxo-3H-isoindol-2-yl)piperidine-2,6-dione: To a stirred solution of 4-[(1R,2S)-2-ethynylcyclopropyl]-1-(3-methoxy-4-nitrophenyl)piperidine (160 mg, 0.5 mmol, 1.0 eq) and 3-(4-iodo-1-oxo-3H-isoindol-2-yl)piperidine-2,6-dione (197 mg, 0.5 mmol, 1.0 eq) in N,N-dimethylformamide (5 mL) and ethyl acetate (1 mL) was added CuI (10 mg, 0.1 mmol, 0.1 eq) and $Pd(PPh_3)_4$ (60 mg, 0.1 mmol, 0.1 eq) at 25° C. under argon atmosphere. The reaction mixture was stirred for 4 hours at 25° C. under nitrogen atmosphere. The resulting mixture was diluted with water (20 mL) and then extracted with ethyl acetate (3×15 mL). The combined organic layers were washed with water (2×10 mL) and brine (10 mL), dried over anhydrous sodium sulfate. After filtration, the filtrate was concentrated under vacuum. The residue was purified by a flash column (silica gel, dichloromethane/$CH_3OH$=100:0 to 100:5) to give 3-(4-{2-[(1S,2R)-2-[1-(3-methoxy-4-nitrophenyl)piperidin-4-yl]cyclopropyl]ethynyl}-1-oxo-3H-isoindol-2-yl)piperidine-2,6-dione (360 mg, 76%) as a brown solid. LC-MS (ESI, m/z) M+1: 543.

Synthesis of 3-(4-{2-[(1S,2R)-2-[1-(4-amino-3-methoxyphenyl)piperidin-4-yl]cyclopropyl]ethynyl}-1-oxo-3H-isoindol-2-yl)piperidine-2,6-dione: To a stirred mixture of 3-(4-{2-[(1S,2R)-2-[1-(3-methoxy-4-nitrophenyl)piperidin-4-yl]cyclopropyl]ethynyl}-1-oxo-3H-isoindol-2-yl)piperidine-2,6-dione (360 mg, 0.7 mmol, 1.0 eq) and $NH_4Cl$ (284 mg, 5.3 mmol, 8.0 eq) in ethanol (5 mL) and water (1 mL) was added Fe (222 mg, 4.0 mmol, 6 eq) in portions at 25° C. The reaction mixture was stirred for 3 hours at 50° C. The resulting mixture was filtered, and the filter cake was washed with ethanol (3×10 mL). The residue was purified by a flash column (silica gel, dichloromethane/$CH_3OH$=100:0 to 100:5) to give 3-(4-{2-[(1S,2R)-2-[1-(4-amino-3-methoxyphenyl)piperidin-4-yl]cyclopropyl]ethynyl}-1-oxo-3H-isoindol-2-yl)piperidine-2,6-dione (210 mg, 62%) as a yellow solid.

Synthesis of (2'S,3S,4'S,5'R)-6-chloro-4'-(3-chloro-2-fluorophenyl)-2'-(2,2-dimethylpropyl)-N-(4-{4-[(1R,2S)-2-{2-[2-(2,6-dioxopiperidin-3-yl)-1-oxo-3H-isoindol-4-yl]ethynyl}cyclopropyl]piperidin-1-yl}-2-methoxyphenyl)-1,2-dihydrospiro[indole-3,3'-pyrrolidine]-5'-carboxamide: To a stirred mixture of 3-(4-{2-[(1S,2R)-2-[1-(4-amino-3-methoxyphenyl)piperidin-4-yl]cyclopropyl]ethynyl}-1-oxo-3H-isoindol-2-yl)piperidine-2,6-dione (100 mg, 0.127 mmol, 1.0 eq), DIEA (49 mg, 0.4 mmol, 3.0 eq) and (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (57 mg, 0.1 mmol, 1.0 eq) in N,N-dimethylformamide (5 mL) was added HATU (72 mg, 0.2 mmol, 1.5 eq) in portions at 25° C. The reaction mixture was stirred for 4 hours at 25° C. The crude product was purified by Prep-HPLC using the following conditions: Column, X-bridge RP18; mobile phase, 0.05% $NH_3 \cdot H_2O$ in water and $CH_3CN$ (30% $CH_3CN$ up to 75% in 5 min); Detector, UV 254 nm. Finally, (2'S,3S,4'S,5'R)-6-chloro-4'-(3-chloro-2-fluorophenyl)-2'-(2,2-dimethylpropyl)-N-(4-{4-[(1R,2S)-2-{2-[2-(2,6-dioxopiperidin-3-yl)-1-oxo-3H-isoindol-4-yl]ethynyl}cyclopropyl]piperidin-1-yl}-2-methoxyphenyl)-1,2-dihydrospiro[indole-3,3'-pyrrolidine]-5'-carboxamide (25 mg, 21%) was obtained as a white solid. LC-MS (ESI, m/z) M+1: 945/947. $^1$HNMR (300 MHz, DMSO-$d_6$) δ 11.0 (s, 1H), 10.28 (s, 1H), 8.09 (d, J=8.7 Hz, 1H), 7.68 (dd, J=7.5, 1.2 Hz, 1H), 7.61 (dd, −7.5, 1.2 Hz, 1H), 7.50 (t, J=7.5 Hz, 1H), 7.45-7.28 (m, 2H), 7.27-7.14 (m, 2H), 6.64 (d, J=2.4 Hz, 1H), 6.51 (dd, −7.8, 1.8 Hz, 1H), 6.44 (dd, −9.0, 2.4 Hz, 1H), 6.31 (d, −1.8 Hz, 1H), 5.52 (s, 1H), 5.14 (dd, J=13.2, 5.1 Hz, 1H), 4.43 (d, J=18.0 Hz, 1H), 4.34-4.16 (m, 2H), 4.05 (d, −9.3 Hz, 1H), 3.82 (s, 3H), 3.66 (d, J=11.4 Hz, 3H), 3.52 (d, J=10.5 Hz, 1H), 3.20-3.04 (m, 2H), 3.01-2.83 (m, 1H), 2.10-1.95 (m, 2H), 1.84 (d, J=12.3 Hz, 1H), 1.75 (d, J=12.6 Hz, 1H), 1.48-1.20 (m, 6H), 0.90 (s, 11H).

Example 28: Preparation of (2'S,3S,4'S,5'R)-6-chloro-4'-(3-chloro-2-fluorophenyl)-N-(4-((R)-3-((2-((S)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide Synthesis of 3-ethynylpiperidine hydrochloride: Into a 100 mL round-bottom flask were placed tert-butyl 3-ethynylpiperidine-1-carboxylate (2.0 g, 9.6 mmol, 1.0 eq), dichloromethane (20 mL), HCl (gas) in 1,4-dioxane (20 mL). The reaction mixture was stirred for 1 hours at 25° C. The resulting mixture was concentrated under vacuum to give 3-ethynylpiperidine hydrochloride (1.2 g, crude) as an off white solid. LC-MS (ESI, m/z) M+1: 110.

Synthesis of 3-ethynyl-1-(3-methoxy-4-nitrophenyl)piperidine: Into a 50-mL round-bottom flask were placed 3-ethynylpiperidine hydrochloride (1.2 g, 10.9 mmol, 1.0 eq), 4-fluoro-2-methoxy-1-nitrobenzene (1.9 g, 10.9 mmol, 1.0 eq), DIEA (4.3 g, 32.9 mmol, 3.0 eq), N,N-dimethylformamide (12 mL). The reaction mixture was stirred for 2 hours at 80° C. The resulting mixture was diluted with water (50 mL) and then extracted with ethyl acetate (2×50 mL). The combined organic phase was washed with brine (2×50 mL), dried over anhydrous sodium sulfate and concentrated under vacuum. The residue was purified by a flash column (silica gel, ethyl acetate/petroleum ether=0:1 to 1:2) to give 3-ethynyl-1-(3-methoxy-4-nitrophenyl) piperidine (900 mg, 31%) as a yellow solid. LC-MS (ESI, m/z) M+1: 261. $^1$HNMR (400 MHz, DMSO-$d_6$) δ 7.87 (d, J=9.4 Hz, 1H), 6.60 (dd, J=9.6, 2.4 Hz, 1H), 6.52 (d, J=2.4 Hz, 1H), 3.91 (s, 3H), 3.87 (dd, J=13.2, 3.6 Hz, 1H), 3.71 (dt, J=13.4, 4.6 Hz, 1H), 3.30-3.21 (m, 2H), 2.99 (d, J=2.4 Hz, 1H), 2.66-2.56 (m, 1H), 1.96 (dd, J=12.8, 5.2 Hz, 1H), 1.76-1.72 (m, 1H), 1.72-1.58 (m, 1H), 1.55-1.51 (m, 1H).

Synthesis of (R)-3-ethynyl-1-(3-methoxy-4-nitrophenyl) piperidine and (S)-3-ethynyl-1-(3-methoxy-4-nitrophenyl) piperidine: 500 mg of 3-ethynyl-1-(3-methoxy-4-nitrophenyl) piperidine was purified by Chiral-Prep-HPLC using the following conditions: CHIRALPAK IG, 3*25 cm, 5 μm; Mobile Phase A: $CO_2$, Mobile Phase B: $CH_3OH$—Preparative; Flow rate: 80 mL/min; Gradient: isocratic 15% B; Detector, 220 nm. Finally, (R)-3-ethynyl-1-(3-methoxy-4-nitrophenyl) piperidine (190 mg) was obtained as a light yellow solid. And (S)-3-ethynyl-1-(3-methoxy-4-nitrophenyl) piperidine (210 mg) was obtained as a light yellow solid. LC-MS (ESI, m/z) M+1: 260. A, $T_R$=2.179 min in CHIRAL-SFC, Column: IG 100×4.6 mm 3.0 um. mobile phase A: $CO_2$; mobile phase B: $CH_3OH$, Start Conc. of Pump B: 20.0% in 4 min, Oven Temperature: 35° C. B, $T_R$=2.344 min in CHIRAL-SFC, Column: IG 100×4.6 mm 3.0 um. mobile phase A: $CO_2$; mobile phase B: $CH_3OH$, Start Conc. of Pump B: 20.0% in 4 min, Oven Temperature: 35° C.

Synthesis of 3-(4-(((R)-1-(3-methoxy-4-nitrophenyl)piperidin-3-yl)ethynyl)-1-oxoisoindolin-2-yl)piperidine-2,6-dione: Into a 20 mL sealed tube purged and maintained under an inert atmosphere of nitrogen, were placed (R)-3-ethynyl-1-(3-methoxy-4-nitrophenyl) piperidine (170 mg, 0.6 mmol, 1.0 eq), 3-(4-iodo-1-oxo-3H-isoindol-2-yl) piperidine-2,6-dione (242 mg, 0.6 mmol, 1.0 eq), CuI (12 mg, 0.1 mmol, 0.1 eq), $Pd(PPh_3)_4$(76 mg, 0.1 mmol, 0.1 eq), triethylamine (198 mg, 1.9 mmol, 3.0 eq), N,N-dimethylformamide (3 mL). The reaction mixture was stirred for 2 hours at 70° C. The resulting mixture was diluted with water (50 mL) and extracted with ethyl acetate (2×50 mL). The combined organic phase was washed with brine (2×50 mL), dried over anhydrous sodium sulfate. After filtration, the filtrate was concentrated under vacuum. The residue was purified by a flash column (silica gel, ethyl acetate/petroleum ether=0:1 to 1:0) to give 3-(4-(((R)-1-(3-methoxy-4-nitrophenyl) piperidin-3-yl) ethynyl)-1-oxoisoindolin-2-yl) piperidine-2,6-dione (250 mg, 76%) as a yellow solid. LC-MS (ESI, m/z) M+1: 503.

Synthesis of 3-(4-(((R)-1-(4-amino-3-methoxyphenyl)piperidin-3-yl)ethynyl)-1-oxoisoindolin-2-yl)piperidine-2,6-dione: Into a 20 mL sealed tube were placed 3-(4-(((R)-1-(3-methoxy-4-nitrophenyl)piperidin-3-yl)ethynyl)-1-oxoisoindolin-2-yl)piperidine-2,6-dione (240 mg, 0.5 mmol, 1.0 eq), Fe (107 mg, 1.9 mmol, 4.0 eq), $NH_4Cl$ (204 mg, 3.8 mmol, 8.0 eq), ethanol (6 mL) and water (2 mL). The reaction mixture was stirred for 2 hours at 50° C. The resulting mixture was filtered, the filtrate was concentrated under vacuum. The residue was purified by a flash column (silica gel, dichloromethane/methanol=20:1) to give 3-(4-(((R)-1-(4-amino-3-methoxyphenyl)piperidin-3-yl)ethynyl)-1-oxoisoindolin-2-yl)piperidine-2,6-dione (190 mg, 84%) as a light yellow solid. LC-MS (ESI, m/z) M+1: 473.

Synthesis of (2'S,3S,4'S,5'R)-6-chloro-4'-(3-chloro-2-fluorophenyl)-N-(4-((R)-3-((2-((S)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 3-(4-(((R)-1-(4-amino-3-methoxyphenyl) piperidin-3-yl) ethynyl)-1-oxoisoindolin-2-yl)piperidine-2,6-dione (47 mg, 0.1 mmol, 1.5 eq), HATU (28 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (85% Phase B up to 95% in 7 min); Detector, UV 254/220 nm. Finally, (2'S,3S,4'S,5'R)-6-chloro-4'-(3-chloro-2-fluorophenyl)-N-(4-((R)-3-((2-((S)-2,6-dioxopiperidin-3-yl)-1-oxoisoindolin-4-yl) ethynyl) piperidin-1-yl)-2-methoxyphenyl)-2'-neopentylspiro[indoline-3,3'-pyrrolidine]-5'-carboxamide (13 mg) was obtained as a white solid. LC-MS (ESI, m/z) M+1: 905/907. $^1$HNMR (400 MHz, DMSO-$d_6$) δ 10.97 (s, 1H), 10.27 (s, 1H), 8.09 (d, −8.8 Hz, 1H), 7.71 (d, J=7.6 Hz, 1H), 7.63 (d, −7.6 Hz, 1H), 7.52 (t, −7.6 Hz, 1H), 7.41 (t, J=7.2 Hz, 1H), 7.33 (t, −6.8 Hz, 1H), 7.26-7.15 (m, 2H), 6.68 (d, −2.4 Hz, 1H), 6.49 (ddd, −12.0, 8.4, 2.2 Hz, 2H), 6.30 (d, −2.0 Hz, 1H), 5.51 (s, 1H), 5.12 (dd, J=13.2, 5.2 Hz, 1H), 4.39 (d, J=18.0 Hz, 1H), 4.32-4.17 (m, 2H), 4.06 (d, J=9.4 Hz, 1H), 3.81 (s, 3H), 3.65-3.62 (m, 2H), 3.51 (d, J=10.6 Hz, 1H), 3.37 (d, J=12.8 Hz, 1H), 3.20-2.99 (m, 2H), 2.97-2.93 (m, 3H), 2.59 (s, 1H), 2.40-2.25 (m, 1H), 2.02-1.98 (m, 1H), 1.80 (s, 1H), 1.65-1.62 (m, 2H), 1.33 (dd, J=14.4, 9.6 Hz, 1H), 1.26-1.15 (m, 2H), 0.89 (s, 9H).

Example 29: Preparation of (2'S,3S,4'S,5'R)-6-chloro-4'-(3-chloro-2-fluorophenyl)-N-(4-((R)-3-((2-((R)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide Synthesis of (2'S,3S,4'S,5'R)-6-chloro-4'-(3-chloro-2-fluorophenyl)-N-(4-((R)-3-((2-((R)-2,6-dioxopiperidin-3-yl)-1-oxoisoindolin-4-yl)ethynyl)piperidin-1-yl)-2- methoxyphenyl)-2'-neopentylspiro[indoline-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 3-(4-(((R)-1-(4-amino-3-methoxyphenyl) piperidin-3-yl) ethynyl)-1-oxoisoindolin-2-yl)piperidine-2,6-dione (47 mg, 0.1 mmol, 1.5 eq), HATU (28 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 µm, 19*150 mm; mobile phase, water (0.05% $NH_3 \cdot H_2O$) and $CH_3CN$ (85% Phase B up to 95% in 7 min); Detector, UV 254/220 nm. Finally, (2'S,3S,4'S,5'R)-6-chloro-4'-(3-chloro-2-fluorophenyl)-N-(4—((R)-3-((2-((R)-2,6-dioxopiperidin-3-yl)-1-oxoisoindolin-4-yl) ethynyl) piperidin-1-yl)-2-methoxyphenyl)-2'-neopentylspiro[indoline-3,3'-pyrrolidine]-5'-carboxamide (13 mg) was obtained as a white solid. LC-MS (ESI, m/z) M+1: 905/907. $^1$HNMR (400 MHz, DMSO-$d_6$) δ 10.96 (s, 1H), 10.28 (s, 1H), 8.10 (d, J=8.8 Hz, 1H), 7.71 (d, J=7.4 Hz, 1H), 7.63 (d, J=7.4 Hz, 1H), 7.52 (t, J=7.6 Hz, 1H), 7.40 (t, J=7.6 Hz, 1H), 7.33 (t, J=7.2 Hz, 1H), 7.26-7.15 (m, 2H), 6.69 (d, J=2.6 Hz, 1H), 6.49 (ddd, J=9.2, 6.4, 2.2 Hz, 2H), 6.30 (d, J=2.0 Hz, 1H), 5.51 (s, 1H), 5.11 (dd, J=13.4, 5.2 Hz, 1H), 4.42 (d, J=18.0 Hz, 1H), 4.29 (d, J=18.0 Hz, 1H), 4.23 (t, J=9.6 Hz, 1H), 4.06 (d, J=9.4 Hz, 1H), 3.82 (s, 3H), 3.70-3.58 (m, 1H), 3.51 (d, J=10.4 Hz, 1H), 3.40 (d, J=12.0 Hz, 1H), 3.17 (d, J=9.6 Hz, 1H), 3.16-3.06 (m, 1H), 3.04-2.83 (m, 4H), 2.60 (s, 1H), 2.38 (dd, J=13.4, 4.6 Hz, 1H), 2.0 (dd, J=15.8, 8.8 Hz, 2H), 1.80 (s, 1H), 1.63 (t, −9.0 Hz, 2H), 1.33 (dd, J=14.4, 9.4 Hz, 1H), 1.26-1.15 (m, 2H), 0.90 (s, 9H).

Example 30: Preparation of (2'S,3S,4'S,5'R)-6-chloro-4'-(3-chloro-2-fluorophenyl)-N-(4-((S)-3-((2-((S)-2,6-dioxopiperidin-3-yl)-1-oxoisoindolin-4-yl) ethynyl)piperidin-1-yl)-2-methoxyphenyl)-2'-neopentylspiro[indoline-3,3'-pyrrolidine]-5'-carboxamide Synthesis of 3-(4-(((S)-1-(3-methoxy-4-nitrophenyl)piperidin-3-yl)ethynyl)-1-oxoisoindolin-2-yl)piperidine-2,6-dione: Into a 20 mL sealed tube purged and maintained under an inert atmosphere of nitrogen, were placed (S)-3-ethynyl-1-(3-methoxy-4-nitrophenyl) piperidine (200 mg, 0.8 mmol, 1.0 eq), 3-(4-iodo-1-oxo-3H-isoindol-2-yl)piperidine-2,6-dione (284 mg, 0.8 mmol, 1.0 eq), CuI (15 mg, 0.1 mmol, 0.1 eq), $Pd(PPh_3)_4$(89 mg, 0.1 mmol, 0.1 eq), triethylamine (233 mg, 2.3 mmol, 3.0 eq), N,N-dimethylformamide (4 mL). The reaction mixture was stirred for 2 hours at 70° C. The resulting mixture was diluted with water (50 mL) and extracted with ethyl acetate (2×50 mL). The combined organic phase was washed with brine (2×50 mL), dried over anhydrous sodium sulfate. After filtration, the filtrate was concentrated under vacuum. The residue was purified by a flash column (silica gel, ethyl acetate/petroleum ether=0:1 to 1:0) to give 3-(4-(((S)-1-(3-methoxy-4-nitrophenyl) piperidin-3-yl) ethynyl)-1-oxoisoindolin-2-yl) piperidine-2,6-dione (270 mg, 70%) as a light yellow solid. LC-MS (ESI, m/z) M+1: 503.

Synthesis of 3-(4-(((S)-1-(4-amino-3-methoxyphenyl)piperidin-3-yl)ethynyl)-1-oxoisoindolin-2-yl)piperidine-2,6-dione: Into a 20 mL sealed tube were placed 3-(4-(((S)-1-(3-methoxy-4-nitrophenyl) piperidin-3-yl)ethynyl)-1-oxoisoindolin-2-yl)piperidine-2,6-dione (250 mg, 0.5 mmol, 1.0 eq), Fe (111 mg, 1.9 mmol, 4.0 eq), $NH_4Cl$ (213 mg, 3.9 mmol, 8.0 eq), ethanol (6 mL) and water (2 mL). The reaction mixture was stirred for 2 hours at 50° C. The resulting mixture was filtered, the filtrate was concentrated under vacuum. The residue was purified by a flash column (silica gel, dichloromethane/methanol=20:1) to give 3-(4-(((S)-1-(4-amino-3-methoxyphenyl) piperidin-3-yl)ethynyl)-1-oxoisoindolin-2-yl)piperidine-2,6-dione (200 mg, 85%) as a light yellow solid. LC-MS (ESI, m/z) M+1: 475.

Synthesis of (2'S,3S,4'S,5'R)-6-chloro-4'-(3-chloro-2-fluorophenyl)-N-(4-((S)-3-((2-((S)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 3-(4-(((S)-1-(4-amino-3-methoxyphenyl)piperidin-3-yl) ethynyl)-1-oxoisoindolin-2-yl)piperidine-2,6-dione (47 mg, 0.1 mmol, 1.5 eq), HATU (29 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 µm, 19*150 mm; mobile phase, water (0.05% $NH_3 \cdot H_2O$) and $CH_3CN$ (85% Phase B up to 95% in 7 min); Detector, UV 254/220 nm. Finally, (2'S,3S,4'S,5'R)-6-chloro-4'-(3-chloro-2-fluorophenyl)-N-(4-((S)-3-((2-((S)-2,6-dioxopiperidin-3-yl)-1-oxoisoindolin-4-yl)ethynyl) piperidin-1-yl)-2-methoxyphenyl)-2'-neopentylspiro[indoline-3,3'-pyrrolidine]-5'-carboxamide (13 mg) was obtained as a white solid. LC-MS (ESI, m/z) M+1: 905/907. $^1$HNMR (400 MHz, DMSO-$d_6$) δ 10.96 (s, 1H), 10.27 (s, 1H), 8.09 (d, −8.8 Hz, 1H), 7.71 (d, J=7.6 Hz, 1H), 7.63 (d, −7.6 Hz, 1H), 7.52 (t, −7.6 Hz, 1H), 7.40 (t, J=7.4 Hz, 1H), 7.33 (t, −7.2 Hz, 1H), 7.27-7.14 (m, 2H), 6.68 (d, −2.4 Hz, 1H), 6.49 (ddd, −9.0, 6.2, 2.2 Hz, 2H), 6.30 (d, −2.0 Hz, 1H), 5.51 (d, J=2.4 Hz, 1H), 5.12 (dd, −13.4, 5.2 Hz, 1H), 4.42 (d, −18.0 Hz, 1H), 4.30 (s, 1H), 4.28-4.18 (m, 1H), 4.06 (d, J=9.4 Hz, 1H), 3.81 (s, 2H), 3.64 (d, J=11.4 Hz, 2H), 3.51 (d, J=10.6 Hz, 1H), 3.38 (d, J=12.8 Hz, 1H), 3.21-2.98 (m, 3H), 2.90 (s, 1H), 2.96-2.83 (m, 1H), 2.59 (s, 1H), 1.98 (dd, J=16.4, 9.6 Hz, 3H), 1.81-1.78 (m, 1H), 1.63 (t, J=9.0 Hz, 2H), 1.33 (dd, J=14.2, 9.4 Hz, 1H), 1.26-1.15 (m, 2H), 0.90 (s, 9H).

Example 31: Preparation of (2'S,3S,4'S,5'R)-6-chloro-4'-(3-chloro-2-fluorophenyl)-N-(4-((S)-3-((2-((R)-2,6-dioxopiperidin-3-yl)-1-oxoisoindolin-4-yl) ethynyl)piperidin-1-yl)-2-methoxyphenyl)-2'-neopentylspiro[indoline-3,3'-pyrrolidine]-5'-carboxamide Synthesis of (2'S,3S,4'S,5'R)-6-chloro-4'-(3-chloro-2-fluorophenyl)-N-(4-((S)-3-((2-((R)-2,6-dioxopiperidin-3-yl)-1-oxoisoindolin-4-yl)ethynyl)piperidin-1-yl)-2-methoxyphenyl)-2'-neopentylspiro[indoline-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 3-(4-(((S)-1-(4-amino-3-methoxyphenyl)piperidin-3-yl) ethynyl)-1-oxoisoindolin-2-yl)piperidine-2,6-dione (47 mg, 0.1 mmol, 1.5 eq), HATU (29 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 µm, 19*150 mm; mobile phase, water (0.05%

$NH_3 \cdot H_2O$) and $CH_3CN$ (85% Phase B up to 95% in 7 min); Detector, UV 254/220 nm. Finally, (2'S,3S,4'S,5'R)-6-chloro-4'-(3-chloro-2-fluorophenyl)-N-(4-((S)-3-((2-((R)-2,6-dioxopiperidin-3-yl)-1-oxoisoindolin-4-yl) ethynyl) piperidin-1-yl)-2-methoxyphenyl)-2'-neopentylspiro[indoline-3,3'-pyrrolidine]-5'-carboxamide (15 mg) was obtained as a white solid. LC-MS (ESI, m/z) M+1: 905/907. $^1$HNMR (400 MHz, DMSO-$d_6$) δ 10.96 (s, 1H), 10.28 (s, 1H), 8.10 (d, −8.8 Hz, 1H), 7.71 (d, J=7.6 Hz, 1H), 7.63 (d, −7.6 Hz, 1H), 7.52 (t, −7.6 Hz, 1H), 7.40 (t, J=7.6 Hz, 1H), 7.33 (t, −7.2 Hz, 1H), 7.27-7.14 (m, 2H), 6.69 (d, −2.4 Hz, 1H), 6.49 (td, −9.4, 8.6, 2.2 Hz, 2H), 6.30 (d, J=2.0 Hz, 1H), 5.51 (s, 1H), 5.11 (dd, −13.4, 5.1 Hz, 1H), 4.41 (d, J=17.8 Hz, 1H), 4.29 (d, J=18.0 Hz, 1H), 4.23 (t, J=9.6 Hz, 1H), 4.08 (d, J=9.4 Hz, 1H), 3.82 (s, 3H), 3.64 (d, J=11.6 Hz, 2H), 3.51 (d, J=10.4 Hz, 1H), 3.37 (s, 1H), 3.18-3.12 (m, 1H), 3.06-2.96 (m, 1H), 2.89 (dd, J=23.7, 8.0 Hz, 3H), 2.59 (s, 1H), 2.0 (d, J=13.7 Hz, 3H), 1.80 (s, 1H), 1.63 (t, J=9.2 Hz, 2H), 1.33 (dd, J=14.4, 9.4 Hz, 1H), 1.26-1.15 (m, 2H), 0.90 (s, 9H).

Example 32: Preparation of (2'S,3S,4'S,5'R)-6-chloro-4'-(3-chloro-2-fluorophenyl)-2'-(2,2-dimethylpropyl)-N-(4-{[(1S,3R)-3-{2-[2-(2,6-dioxopiperidin-3-yl)-1-oxo-3H-isoindol-4-yl] ethynyl}cyclohexyl]carbamoyl}-2-methoxyphenyl)-1,2-dihydrospiro[indole-3,3'-pyrrolidine]-5'-carboxamide Synthesis of 3-[(tert-butoxycarbonyl)amino]cyclohexane-1-carboxylic acid: Into a 500 mL 3-necked round-bottom flask were added 3-aminocyclohexane-1-carboxylic acid (20.0 g, 139.6 mmol, 1.0 eq), 1,4-dioxane (160 mL), water (80 mL), NaOH (16.8 g, 420.0 mmol, 3.0 eq) and $Boc_2O$ (45.7 g, 209.4 mmol, 1.50 eq) at 25° C. The reaction mixture was stirred for 12 hours at 25° C. The resulting mixture was diluted with water (200 mL) and then acidified to pH=5 with 2 M HCl (aq.). The resulting solution was extracted with ethyl acetate (3×200 mL). The combined organic layers were washed with brine (200 mL), dried over anhydrous sodium sulfate. After filtration, the filtrate was concentrated under vacuum to give 3-[(tert-butoxycarbonyl)amino]cyclohexane-1-carboxylic acid (34.0 g, crude) as white solid. LC-MS (ESI, m/z) M-56+ACN+1: 229.

Synthesis of tert-butyl N-{3-[methoxy(methyl)carbamoyl]cyclohexyl}carbamate: Into a 1000 mL 3-necked round-bottom flask were added 3-[(tert-butoxycarbonyl)amino] cyclohexane-1-carboxylic acid (34.0 g, 139.7 mmol, 1.0 eq), dichloromethane (400 mL), methoxy(methyl)amine hydrochloride (16.3 g, 167.7 mmol, 1.2 eq), trimethylamine (42.4 g, 419.2 mmol, 3.0 eq), EDCI (32.2 g, 167.7 mmol, 1.2 eq) and HOBT (22.6 g, 167.7 mmol, 1.2 eq) at 25° C. The reaction mixture was stirred for 3 hours at 25° C. The resulting mixture was diluted with water (400 mL) and then extracted with dichloromethane (2×200 mL). The combined organic layers were washed with brine (300 mL), dried over anhydrous sodium sulfate. After filtration, the filtrate was concentrated under vacuum to give tert-butyl N-{3-[methoxy(methyl)carbamoyl]cyclohexyl}carbamate (40.0 g, 99%) as white solid. LC-MS (ESI, m/z) M+1: 287. $^1$HNMR (400 MHz, DMSO-$d_6$) δ 6.76 (d, J=8.2 Hz, 1H), 3.67 (s, 3H), 3.35-3.22 (m, 1H), 3.08 (s, 3H), 2.72 (t, J=12.3 Hz, 1H), 1.99 (s, 1H), 1.74 (ddd, J=13.9, 6.3, 3.1 Hz, 2H), 1.67-1.50 (m, 1H), 1.37 (s, 9H), 1.22-1.10 (m, 3H), 1.11-0.99 (m, 1H).

Synthesis of tert-butyl N-(3-formylcyclohexyl)carbamate: Into a 1000 mL 3-necked round-bottom flask were added tert-butyl N-{3-[methoxy(methyl)carbamoyl] cyclohexyl}carbamate (40.0 g, 139.6 mmol, 1.0 eq) and tetrahydrofuran (0.5 L). After that, to the above mixture was added DIBAL-H (186 mL, 279.2 mmol, 2.0 eq) dropwise at −78° C. The reaction mixture was stirred for an additional 2 hours at −78° C. The resulting mixture was quenched by the addition of sat. $NH_4Cl$ (aq.) (200 mL) at −78° C. and then extracted with ethyl acetate (2×200 mL). The combined organic layers were washed with brine (300 mL), dried over anhydrous sodium sulfate. After filtration, the filtrate was concentrated under vacuum. The crude residue was purified by a flash column (silica gel, ethyl acetate/petroleum ether=10:1 to 1:1) to give tert-butyl N-(3-formylcyclohexyl) carbamate (12.0 g, 37%) as colorless oil.

Synthesis of tert-butyl N-(3-ethynylcyclohexyl)carbamate: Into a 250 mL 3-necked round-bottom flask were added tert-butyl N-(3-formylcyclohexyl)carbamate (12.0 g, 52.8 mmol, 1.0 eq), methanol (120 mL), $K_2CO_3$ (14.6 g, 105.6 mmol, 2.0 eq) and dimethyl (1-diazo-2-oxopropyl)phosphonate (15.2 g, 79.1 mmol, 1.5 eq) at 25° C. The reaction mixture was stirred for 3 hours at 25° C. The resulting mixture was diluted with water (200 mL) and then extracted with ethyl acetate (2×200 mL). The combined organic layers were washed with brine (200 mL), dried over anhydrous sodium sulfate. After filtration, the filtrate was concentrated under vacuum. The crude residue was purified by a flash column (silica gel, ethyl acetate/petroleum ether=3:1) to give tert-butyl N-(3-ethynylcyclohexyl)carbamate (6.3 g, 53%) as colorless oil. LC-MS (ESI, m/z) M-56+ACN+1: 209. $^1$HNMR (400 MHz, DMSO-$d_6$) δ 6.75 (d, J=8.0 Hz, 1H), 3.25-3.12 (m, 1H), 2.92-2.82 (m, 1H), 2.29 (td, J=11.7, 3.1 Hz, 1H), 1.94 (d, J=12.7 Hz, 1H), 1.84-1.75 (m, 1H), 1.75-1.61 (m, 1H), 1.38 (s, 9H), 1.29-0.96 (m, 4H).

Synthesis of 3-ethynylcyclohexan-1-amine hydrochloride: Into a 100 mL 3-necked round-bottom flask were added tert-butyl N-(3-ethynylcyclohexyl)carbamate (5.0 g, 22.4 mmol, 1.0 eq) and HCl (g) in methanol (16 mL, 67.2 mmol, 3.0 eq) at 25° C. The reaction mixture was stirred for 12 hours at 25° C. The resulting mixture was concentrated under vacuum to give 3-ethynylcyclohexan-1-amine hydrochloride (3.6 g, crude) as white solid. LC-MS (ESI, m/z) M-HCl+1: 124. $^1$HNMR (400 MHz, DMSO-$d_6$) δ 8.21 (s, 3H), 3.43 (s, 1H), 2.96 (d, J=2.3 Hz, 1H), 2.42-2.35 (m, 1H), 2.22-2.10 (m, 1H), 2.02-1.78 (m, 2H), 1.72 (dq, J=9.1, 3.1 Hz, 1H), 1.45-1.05 (m, 3H).

Synthesis of N-(3-ethynylcyclohexyl)-3-methoxy-4-nitrobenzamide: Into a 100 mL 3-necked round-bottom flask were added 3-ethynylcyclohexan-1-amine hydrochloride (3.6 g, 22.5 mmol, 1.0 eq), dichloromethane (50 mL), 3-methoxy-4-nitrobenzoic acid (4.4 g, 22.5 mmol, 1.0 eq), DIEA (8.7 g, 67.5 mmol, 3.0 eq) and HATU (10.2 g, 26.8 mmol, 1.2 eq) at 25° C. The reaction mixture was stirred for 3 h at 25° C. The resulting mixture was diluted with water (70 mL) and then extracted with dichloromethane (3×50 mL). The combined organic layers were washed with brine (100 mL), dried over anhydrous sodium sulfate. After filtration, the filtrate was concentrated under vacuum. The crude residue was purified by a flash column (silica gel, ethyl acetate/petroleum ether=10:1 to 1:1) to give N-(3-ethynylcyclohexyl)-3-methoxy-4-nitrobenzamide (5.0 g, 73%) as a white solid. LC-MS (ESI, m/z) M+1: 303. $^1$HNMR (400 MHz, DMSO-$d_6$) δ 8.50 (d, J=7.8 Hz, 1H), 7.96 (d, J=8.4 Hz, 1H), 7.69 (d, J=1.6 Hz, 1H), 7.54 (dd, J=8.4, 1.7 Hz, 1H), 3.99 (s, 3H), 3.80 (dtd, J=11.6, 7.6, 3.9 Hz, 1H), 3.32 (s, 1H), 2.90 (d, J=2.3 Hz, 1H), 2.42 (tdd, J=10.3, 7.3, 3.1 Hz, 1H), 2.08 (d, J=12.5 Hz, 1H), 1.86 (t, J=12.5 Hz, 2H), 1.52-1.15 (m, 4H).

Synthesis of 4-amino-N-[(1S,3R)-3-ethynylcyclohexyl]-3-methoxybenzamide and 4-amino-N. [(1R,3S)-3-ethynylcyclohexyl]-3-methoxybenzamide and 4-amino-N-[(1R,3R)-3-ethynylcyclohexyl]-3-methoxybenzamide and 4-amino-N-[(1S,3S)-3-ethynylcyclohexyl]-3-methoxybenzamide: Into a 100 mL 3-necked round-bottom flask were added N-(3-ethynylcyclohexyl)-3-methoxy-4-nitrobenzamide (2.0 g, 6.6 mmol, 1.0 eq), ethanol (20 mL), water (5 mL), Fe (1.5 g, 26.5 mmol, 4.0 eq) and $NH_4Cl$ (1.4 g, 26.5 mmol, 4.0 eq) at 25° C. The reaction mixture was stirred for 2 hours at 50° C. The resulting mixture was filtered, and the filter cake was washed with ethyl acetate (30 mL) and then the filtrate was concentrated under vacuum. The crude was purification by Prep-SFC with pressure. Column: CHIRAL-ART Cellulose-SB, 3*25 cm, 5 μm; Mobile Phase A: $CO_2$, Mobile Phase B: IPA; Flow rate: 80 mL/min; Gradient: isocratic 40% B; Column Temperature (° C.): 35; Back Pressure(bar): 100; Wave Length: 220 nm; RT1(min): 6.4; RT2(min): 9.5; Sample Solvent: MeOH-HPLC; Injection Volume: 3 mL; Number Of Runs: 20. Finally, 4-amino-N-[(1S,3R)-3-ethynylcyclohexyl]-3-methoxybenzamide (300 mg, 16%) was obtained as a white solid. 4-amino-N-[(1R,3S)-3-ethynylcyclohexyl]-3-methoxybenzamide (300 mg, 16.65%) was obtained as white solid. 4-amino-N-[(1R,3R)-3-ethynylcyclohexyl]-3-methoxybenzamide (200 mg, 11.10%) as white solid. And 4-amino-N-[(1S,3S)-3-ethynylcyclohexyl]-3-methoxybenzamide (250 mg, 13.88%) as white solid. LC-MS (ESI, m/z) M+1: 273. 4-amino-N-[(1S,3R)-3-ethynylcyclohexyl]-3-methoxybenzamide: $^1$HNMR (400 MHz, DMSO-$d_6$) δ 7.80 (d, J=7.9 Hz, 1H), 7.37-7.13 (m, 2H), 6.61 (d, J=8.6 Hz, 1H), 5.21 (s, 2H), 3.81 (s, 3H), 2.87 (d, J=2.3 Hz, 1H), 2.39 (td, J=11.8, 2.8 Hz, 1H), 2.02 (d, J=12.5 Hz, 1H), 1.93-1.63 (m, 3H), 1.45-1.09 (m, 4H). 4-amino-N-[(1R,3S)-3-ethynylcyclohexyl]-3-methoxybenzamide: $^1$HNMR (400 MHz, DMSO-$d_6$) δ 7.79 (d, J=7.9 Hz, 1H), 7.51-7.12 (m, 2H), 6.60 (d, J=8.6 Hz, 1H), 5.21 (s, 2H), 3.81 (s, 3H), 2.87 (d, J=2.3 Hz, 1H), 2.51 (p, J=1.9 Hz, 3H), 2.38 (dt, J=11.8, 6.6 Hz, 1H), 2.02 (d, J=12.6 Hz, 1H), 1.93-1.66 (m, 3H), 1.49-1.11 (m, 4H). 4-amino-N-[(1R,3R)-3-ethynylcyclohexyl]-3-methoxybenzamide: $^1$HNMR (400 MHz, DMSO-$d_6$) δ 7.74 (d, J=7.8 Hz, 1H), 7.29 (dd, J=4.2, 2.5 Hz, 2H), 6.60 (d, J=8.6 Hz, 1H), 5.21 (s, 2H), 4.11 (td, J=10.7, 10.2, 5.1 Hz, 1H), 3.81 (s, 3H), 3.33 (s, 1H), 2.95 (d, J=2.3 Hz, 1H), 2.51 (q, J=1.9 Hz, 4H), 1.88-1.51 (m, 6H), 1.49-1.14 (m, 1H). 4-amino-N-[(1S,3S)-3-ethynylcyclohexyl]-3-methoxybenzamide: $^1$HNMR (400 MHz, DMSO-$d_6$) δ 7.74 (d, J=7.9 Hz, 1H), 7.29 (dd, J=4.3, 2.5 Hz, 2H), 6.60 (d, J=8.6 Hz, 1H), 5.21 (s, 2H), 4.41-4.02 (m, 1H), 3.81 (s, 3H), 3.34 (s, 3H), 2.95 (d, J=2.3 Hz, 1H), 1.92-1.52 (m, 6H), 1.49-1.16 (m, 1H).

Synthesis of 4-amino-N-[(1S,3R)-3-{2-[2-(2,6-dioxopiperidin-3-yl)-1-oxo-3H-isoindol-4-yl]ethynyl}cyclohexyl]-3-methoxybenzamide: Into a 40 mL vial were added 4-amino-N-[(1S,3R)-3-ethynylcyclohexyl]-3-methoxybenzamide (200 mg, 1 mmol, 1.0 eq) and 3-(4-iodo-1-oxo-3H-isoindol-2-yl)piperidine-2,6-dione (136 mg, 0.4 mmol, 1.0 eq), N,N-dimethylformamide (4.0 mL), CuI (14 mg, 0.1 mmol, 0.2 eq), trimethylamine (111 mg, 1.2 mmol, 3.0 eq), $Pd(PPh_3)_4$(42 mg, 0.1 mmol, 0.2 eq) at 25° C. The reaction mixture was stirred for 2 hours at 70° C. under nitrogen atmosphere. The resulting mixture was diluted with water (5 mL) and then extracted with ethyl acetate (3×5 mL). The combined organic layers were washed with brine (5 mL), dried over anhydrous sodium sulfate. After filtration, the filtrate was concentrated under vacuum. The crude residue was purified by a flash column (silica gel, ethyl acetate/petroleum ether=10:1 to 1:1) to give 4-amino-N-[(1S,3R)-3-{2-[2-(2,6-dioxopiperidin-3-yl)-1-oxo-3H-isoindol-4-yl]ethynyl}cyclohexyl]-3-methoxybenzamide (300 mg, 79%) as white solid. LC-MS (ESI, m/z) M+1: 515.

Synthesis of (2'S,3S,4'S,5'R)-6-chloro-4'-(3-chloro-2-fluorophenyl)-2'-(2,2-dimethylpropyl)-N-(4-{[(1S,3R)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide: Into an 8 mL vial were added 4-amino-N-[(1S,3R)-3-{2-[2-(2,6-dioxopiperidin-3-yl)-1-oxo-3H-isoindol-4-yl]ethynyl}cyclohexyl]-3-methoxybenzamide (34 mg, 0.1 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), acetonitrile (2.0 mL), TCFH (28 mg, 0.1 mmol, 1.5 eq), NMI (11 mg, 0.1 mmol, 2.0 eq) at 25° C. The crude product was purified by Chiral-Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and acetonitrile (30% acetonitrile up to 78% in 8 min); Detector, UV 220 Finally, (2'S,3S,4'S,5'R)-6-chloro-4'-(3-chloro-2-fluorophenyl)-2'-(2,2-dimethylpropyl)-N-(4-{[(1S,3R)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide (30 mg, 47%) was obtained as white solid. LC-MS (ESI, m/z) M+1: 947/949. $^1$HNMR (400 MHz, DMSO-$d_6$) δ 8.33 (dd, J=8.4, 5.3 Hz, 1H), 7.75 (d, J=7.5 Hz, 1H), 7.61 (d, J=7.6 Hz, 1H), 7.54-7.45 (m, 2H), 7.42 (dt, J=8.5, 1.9 Hz, 1H), 7.30 (q, J=7.2, 6.8 Hz, 2H), 7.20 (d, J=8.0 Hz, 1H), 7.10 (t, J=7.9 Hz, 1H), 6.62 (dd, J=8.0, 1.9 Hz, 1H), 6.43 (d, J=1.9 Hz, 1H), 5.16 (dd, J=13.2, 5.2 Hz, 1H), 4.43 (d, J=8.2 Hz, 3H), 4.22-4.07 (m, 1H), 3.96 (s, 4H), 3.60 (d, J=10.4 Hz, 1H), 3.37 (d, J=10.5 Hz, 1H), 3.28 (d, J=5.3 Hz, 1H), 2.98-2.66 (m, 3H), 2.51 (qd, J=13.0, 4.8 Hz, 1H), 2.30 (d, J=12.4 Hz, 1H), 2.16 (d, J=12.5 Hz, 1H), 2.10-2.0 (m, 1H), 1.95 (t, J=11.8 Hz, 2H), 1.67-1.37 (m, 6H), 1.36-1.21 (m, 1H), 1.0 (s, 9H).

Example 33: Preparation of (2'S,3S,4'S,5'R)-6-chloro-4'-(3-chloro-2-fluorophenyl)-2'-(2,2-dimethylpropyl)-N-(4-{[(1R,3S)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide Synthesis of 4-amino-N-[(1R,3S)-3-{2-[2-(2,6-dioxopiperidin-3-yl)-1-oxo-3H-isoindol-4-yl]ethynyl}cyclohexyl]-3-methoxybenzamide: Into a 40 mL vial were added 4-amino-N-[(1R,3S)-3-ethynylcyclohexyl]-3-methoxybenzamide (200 mg, 0.4 mmol, 1.0 eq) and 3-(4-iodo-1-oxo-3H-isoindol-2-yl)piperidine-2,6-dione (136 mg, 0.4 mmol, 1.0 eq), N,N-dimethylformamide (4.0 mL), CuI (14 mg, 0.1 mmol, 0.2 eq), trimethylamine (111 mg, 1.2 mmol, 3.0 eq), $Pd(PPh_3)_4$(42 mg, 0.1 mmol, 0.2 eq) at 25° C. The reaction mixture was stirred for 2 hours at 70° C. under nitrogen atmosphere. The resulting mixture was diluted with water (5 mL) and then extracted with ethyl acetate (3×5 mL). The combined organic layers were washed with brine (5 mL), dried over anhydrous sodium sulfate. After filtration, the filtrate was concentrated under vacuum. The crude residue was purified by a flash column (silica gel, ethyl acetate/petroleum ether=10:1 to 1:1) to give 4-amino-N-[(1R,3S)-3-{2-[2-(2,6-dioxopiperidin-3-yl)-1-oxo-3H-isoindol-4-yl]ethynyl}cyclohexyl]-3-methoxybenzamide (300 mg, 79%) as white solid. LC-MS (ESI, m/z) M+1: 515.

Synthesis of (2'S,3S,4'S,5'R)-6-chloro-4'-(3-chloro-2-fluorophenyl)-2'-(2,2-dimethylpropyl)-N-(4-{[(1R,3S)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide: Into an 8 mL vial were added 4-amino-N-[(1R,3S)-3-{2-[2-(2,6-dioxopiperidin-3-yl)-1-oxo-3H-isoindol-4-yl]ethynyl}cyclohexyl]-3-methoxybenzamide (34 mg, 1 mmol, 1.0 eq) and (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (20 mg, 1 mmol, 1.0 eq), acetonitrile (2.0 mL), TCFH (28 mg, 1 mmol, 1.5 eq), NMI (11 mg, 1 mmol, 2.0 eq) at 25° C. The reaction mixture was stirred for 2 hours at 25° C. The resulting mixture was concentrated under vacuum. The crude product was purified by Chiral-Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and acetonitrile (30% acetonitrile up to 78% in 8 min); Detector, UV 220. Finally, (2'S,3S,4'S,5'R)-6-chloro-4'-(3-chloro-2-fluorophenyl)-2'-(2,2-dimethylpropyl)-N-(4-{[(1R,3S)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide (30 mg, 47%) was obtained as a white solid. LC-MS (ESI, m/z) M+1: 947/949. $^1$HNMR (300 MHz, Methanol-$d_4$) δ 8.40-8.29 (m, 1H), 7.75 (dd, J=7.5, 1.1 Hz, 1H), 7.61 (d, J=7.6 Hz, 1H), 7.56-7.46 (m, 2H), 7.43 (dd, J=8.4, 1.9 Hz, 1H), 7.31 (q, J=6.6 Hz, 2H), 7.25-7.15 (m, 1H), 7.10 (t, J=7.9 Hz, 1H), 6.62 (dd, J=8.0, 1.9 Hz, 1H), 6.43 (d, J=1.9 Hz, 1H), 5.16 (dd, J=13.2, 5.1 Hz, 1H), 4.56-4.37 (m, 3H), 4.13 (dd, J=9.6, 3.0 Hz, 1H), 3.95 (d, J=4.2 Hz, 4H), 3.60 (d, J=10.4 Hz, 1H), 3.38 (d, J=10.5 Hz, 1H), 3.27 (s, 2H), 2.93-2.73 (m, 3H), 2.63-2.42 (m, 1H), 2.32 (d, J=12.4 Hz, 1H), 2.23-1.89 (m, 4H), 1.76-1.28 (m, 7H), 1.0 (s, 9H).

Example 34: Preparation of (2'S,3S,4'S,5'R)-6-chloro-4'-(3-chloro-2-fluorophenyl)-2'-(2,2-dimethylpropyl)-N-(4-{[(1R,3R)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide Synthesis of 4-amino-N-[(1R,3R)-3-{2-[2-(2,6-dioxopiperidin-3-yl)-1-oxo-3H-isoindol-4-yl]ethynyl}cyclohexyl]-3-methoxybenzamide: Into a 40 mL vial were added 4-amino-N-[(1R,3R)-3-ethynylcyclohexyl]-3-methoxybenzamide (100 mg, 0.4 mmol, 1.0 eq) and 3-(4-iodo-1-oxo-3H-isoindol-2-yl)piperidine-2,6-dione (136 mg, 0.4 mmol, 1.0 eq), N,N-dimethylformamide (4.0 mL), CuI (14 mg, 0.1 mmol, 0.2 eq), trimethylamine (111 mg, 1.2 mmol, 3.0 eq), $Pd(PPh_3)_4$(42 mg, 0.1 mmol, 0.2 eq) at 25° C. The reaction mixture was stirred for 2 hours at 70° C. under nitrogen atmosphere. The resulting mixture was diluted with water (5 mL) and extracted with ethyl acetate (3×5 mL). The combined organic layers were washed with brine (5 mL), dried over anhydrous sodium sulfate. After filtration, the filtrate was concentrated under vacuum. The crude residue was purified by a flash column (silica gel, ethyl acetate/petroleum ether=10:1 to 1:1) to give 4-amino-N-[(1R,3R)-3-{2-[2-(2,6-dioxopiperidin-3-yl)-1-oxo-3H-isoindol-4-yl]ethynyl}cyclohexyl]-3-methoxybenzamide (150 mg, 79%) as white solid. LC-MS (ESI, m/z) M+1: 515.

Synthesis of (2'S,3S,4'S,5'R)-6-chloro-4'-(3-chloro-2-fluorophenyl)-2'-(2,2-dimethylpropyl)-N-(4-{[(1R,3R)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide: Into an 8 mL vial were added 4-amino-N-[(1R,3R)-3-{2-[2-(2,6-dioxopiperidin-3-yl)-1-oxo-3H-isoindol-4-yl]ethynyl}cyclohexyl]-3-methoxybenzamide (34 mg, 0.1 mmol, 1.0 eq) and (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), acetonitrile (2.0 mL), TCFH (28 mg, 0.1 mmol, 1.5 eq), NMI (11 mg, 0.1 mmol, 2.0 eq) at 25° C. The reaction mixture was stirred for 2 hours at 25° C. The resulting mixture was concentrated under vacuum. The crude product was purified by Chiral-Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and acetonitrile (30% acetonitrile up to 78% in 8 min); Detector, UV 220. Finally, (2'S,3S,4'S,5'R)-6-chloro-4'-(3-chloro-2-fluorophenyl)-2'-(2,2-dimethylpropyl)-N-(4-{[(1R,3R)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide (25 mg, 39%) was obtained as white solid. LC-MS (ESI, m/z) M+1: 947/949. $^1$HNMR (300 MHz, Methanol-$d_4$) δ 8.36 (d, J=8.4 Hz, 1H), 7.78 (d, J=7.6 Hz, 1H), 7.67 (d, J=7.5 Hz, 1H), 7.59-7.47 (m, 2H), 7.43 (dt, J=8.4, 2.2 Hz, 1H), 7.31 (q, J=7.2 Hz, 2H), 7.18 (dd, J=8.0, 1.7 Hz, 1H), 7.10 (t, J=8.0 Hz, 1H), 6.62 (dd, J=8.0, 1.9 Hz, 1H), 6.43 (d, J=1.8 Hz, 1H), 5.20 (dd, J=12.5, 5.3 Hz, 1H), 4.79-4.55 (m, 2H), 4.51-4.40 (m, 2H), 4.13 (d, J=9.6 Hz, 1H), 3.98 (s, 3H), 3.60 (d, J=10.4 Hz, 1H), 3.38 (d, J=10.4 Hz, 1H), 3.26 (d, J=5.3 Hz, 2H), 2.95-2.82 (m, 1H), 2.74 (dd, J=14.9, 5.0 Hz, 2H), 2.25-2.10 (m, 2H), 2.07-1.54 (m, 6H), 1.53-1.37 (m, 3H), 1.32 (s, 1H), 1.0 (s, 9H).

Example 35: Preparation of (2'S,3S,4'S,5'R)-6-chloro-4'-(3-chloro-2-fluorophenyl)-2'-(2,2-dimethylpropyl)-N-(4-{[(1S,3S)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide Synthesis of 4-amino-N-[(1S,3S)-3-{2-[2-(2,6-dioxopiperidin-3-yl)-1-oxo-3H-isoindol-4-yl]ethynyl}cyclohexyl]-3-methoxybenzamide: Into a 40 mL vial were added 4-amino-N-[(1S,3S)-3-ethynylcyclohexyl]-3-methoxybenzamide (100 mg, 0.4 mmol, 1.0 eq), 3-(4-iodo-1-oxo-3H-isoindol-2-yl)piperidine-2,6-dione (136 mg, 0.4 mmol, 1.0 eq), N,N-dimethylformamide (4.0 mL), CuI (14 mg, 0.1 mmol, 0.2 eq), trimethylamine (111 mg, 1.2 mmol, 3.0 eq), $Pd(PPh_3)_4$(42 mg, 0.1 mmol, 0.2 eq) at 25° C. The reaction mixture was stirred for 2 hours at 70° C. under nitrogen atmosphere. The resulting mixture was diluted with water (5 mL) and extracted with ethyl acetate (3×5 mL). The combined organic layers were washed with brine (5 mL), dried over anhydrous sodium sulfate. After filtration, the filtrate was concentrated under vacuum. The crude residue was purified by a flash column (silica gel, ethyl acetate/petroleum ether=10:1 to 1:1) to give 4-amino-N-[(1S,3S)-3-{2-[2-(2,6-dioxopiperidin-3-yl)-1-oxo-3H-isoindol-4-yl]ethynyl}cyclohexyl]-3-methoxybenzamide (150 mg, 79%) as white solid. LC-MS (ESI, m/z) M+1: 515.

Synthesis of (2'S,3S,4'S,5'R)-6-chloro-4'-(3-chloro-2-fluorophenyl)-2'-(2,2-dimethylpropyl)-N-(4-{[(1S,3S)-3-{2-[2-(2,6-dioxopiperidin-3-yl)-1-oxo-3H-isoindol-4-yl]

ethynyl}cyclohexyl]carbamoyl}-2-methoxyphenyl)-1,2-dihydrospiro[indole-3,3'-pyrrolidine]-5'-carboxamide: Into an 8 mL vial were added 4-amino-N-[(1S,3S)-3-{2-[2-(2,6-dioxopiperidin-3-yl)-1-oxo-3H-isoindol-4-yl]ethynyl}cyclohexyl]-3-methoxybenzamide (34 mg, 0.1 mmol, 1.0 eq) and (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), acetonitrile (2.0 mL), TCFH (28 mg, 0.1 mmol, 1.5 eq), NMI (11 mg, 0.1 mmol, 2.0 eq) at 25° C. The reaction mixture was stirred for 2 hours at 25° C. The resulting mixture was concentrated under vacuum. The crude product was purified by Chiral-Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and acetonitrile (30% acetonitrile up to 78% in 8 min); Detector, UV 220. Finally, (2'S,3S,4'S,5'R)-6-chloro-4'-(3-chloro-2-fluorophenyl)-2'-(2,2-dimethylpropyl)-N-(4-{[(1S,3S)-3-{2-[2-(2,6-dioxopiperidin-3-yl)-1-oxo-3H-isoindol-4-yl]ethynyl}cyclohexyl]carbamoyl}-2-methoxyphenyl)-1,2-dihydrospiro[indole-3,3'-pyrrolidine]-5'-carboxamide (25 mg, 39%) was obtained as a white solid. LC-MS (ESI, m/z) M+1: 947/949. $^1$HNMR (300 MHz, Methanol-$d_4$) δ 8.36 (d, J=8.4 Hz, 1H), 7.78 (dd, J=7.7, 1.1 Hz, 1H), 7.67 (dd, J=7.7, 1.1 Hz, 1H), 7.59-7.47 (m, 2H), 7.43 (dt, J=8.4, 2.2 Hz, 1H), 7.30 (q, J=7.3 Hz, 2H), 7.17 (dd, J=8.0, 1.6 Hz, 1H), 7.10 (t, J=7.9 Hz, 1H), 6.62 (dd, J=8.0, 1.9 Hz, 1H), 6.43 (d, J=1.9 Hz, 1H), 5.20 (dd, J=12.8, 5.1 Hz, 1H), 4.76-4.57 (m, 2H), 4.51-4.39 (m, 2H), 4.13 (d, J=9.6 Hz, 1H), 3.98 (s, 3H), 3.60 (d, J=10.5 Hz, 1H), 3.37 (d, J=10.4 Hz, 1H), 3.27 (d, J=5.7 Hz, 2H), 2.94-2.82 (m, 1H), 2.74 (d, J=14.8 Hz, 2H), 2.17 (t, J=12.6 Hz, 2H), 2.08-1.56 (m, 6H), 1.51-1.36 (m, 3H), 1.31 (s, 1H), 1.0 (s, 9H).

Example 36: Preparation of (2'S,3S,4'S,5'R)-6-chloro-4'-(3-chloro-2-fluorophenyl)-2'-(2,2-dimethylpropyl)-N-{4-[(2R)-2-(4-{2-[(3R)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide Synthesis of 3-(piperidin-2-yl)propan-1-ol (racemate): Into a 100 mL pressure tank reactor were added 2-pyridinepropanol (5.0 g, 36.5 mmol, 1.0 eq) and $PtO_2$ (1.0 g, 4.4 mmol, 0.1 eq) at 25° C. The reaction mixture was stirred for 14 hours at 50° C. under $H_2$ (20 atm). The resulting mixture was filtered, the filter cake was washed with ethanol (3×10 mL). The filtrate was concentrated under vacuum to give 3-(piperidin-2-yl)propan-1-ol (racemate) (4.5 g, 86%) as a green solid. LC-MS (ESI, m/z) M+1: 144.

Synthesis of tert-butyl 2-(3-hydroxypropyl)piperidine-1-carboxylate(racemate): To a stirred mixture of 3-(piperidin-2-yl)propan-1-ol (racemate) (4.5 g, 31.4 mmol, 1.0 eq) and triethylamine (9.5 g, 94.3 mmol, 3.0 eq) in $CH_3OH$ (100 mL) was added $Boc_2O$ (6.9 g, 31.4 mmol, 1.0 eq) dropwise at 25° C. The reaction mixture was stirred for 14 hours at 25° C. The resulting mixture was concentrated under vacuum. The crude residue was purified by a flash column (silica gel, dichloromethane/$CH_3OH$=100:0 to 100:10) to give tert-butyl 2-(3-hydroxypropyl)piperidine-1-carboxylate (racemate) (7.0 g, crude) as a brown oil.

Synthesis of tert-butyl 2-(3-oxopropyl)piperidine-1-carboxylate(racemate): To a stirred mixture of tert-butyl 2-(3-hydroxypropyl)piperidine-1-carboxylate (racemate) (5.0 g, crude) in dichloromethane (100 mL) was added PCC (6.6 g, 30.8 mmol, 1.5 eq) dropwise at 25° C. The reaction mixture was stirred for 4 hours at 25° C. The resulting mixture was filtered, the filter cake was washed with dichloromethane (3×10 mL). The filtrate was washed with water (3×10 mL) and $NaHCO_3$ (3×10 mL), dried over anhydrous sodium sulfate. After filtration, the filtrate was concentrated under vacuum. The residue was purified by a flash column (silica gel, ethyl acetate/petroleum ether=0:1 to 1:3) to give tert-butyl 2-(3-oxopropyl)piperidine-1-carboxylate (racemate) (1.5 g, 29%) as a yellow oil. $^1$HNMR (400 MHz, Chloroform-d) δ 9.81 (t, J=1.2 Hz, 1H), 4.27 (bs, 1H), 4.0 (d, J=13.6 Hz, 1H), 2.75 (t, J=13.2 Hz, 1H), 2.52-2.34 (m, 2H), 2.10 (dddd, J=14.4, 10.4, 8.4, 6.0 Hz, 1H), 1.84-1.53 (m, 7H), 1.47 (s, 9H).

Synthesis of tert-butyl 2-(but-3-yn-1-yl)piperidine-1-carboxylate(racemate): To a stirred mixture of tert-butyl 2-(3-oxopropyl)piperidine-1-carboxylate (1.4 g, 5.8 mmol, 1.0 eq) and $K_2CO_3$ (2.4 g, 17.4 mmol, 3.0 eq) in $CH_3OH$ (30 mL) were added seyferth-gilbert homologation (1.5 g, 7.5 mmol, 1.3 eq) dropwise at 25° C. The reaction mixture was stirred for 3 hours at 25° C. The reaction was quenched by the addition of water (1 mL). The residue was purified by a flash column (silica gel, ethyl acetate/petroleum ether=0:1 to 1:3) to give tert-butyl 2-(but-3-yn-1-yl)piperidine-1-carboxylate (racemate) (1.1 g, 80%) as a white solid. $^1$H NMR (300 MHz, Chloroform-d) δ4.39-4.26 (m, 1H), 4.02 (d, J=13.8 Hz, 1H), 2.77 (dd, J=13.8, 11.4 Hz, 1H), 2.10-1.90 (m, 2H), 1.74-1.51 (m, 8H), 1.48-1.41 (m, 10H).

Synthesis of 2-(but-3-yn-1-yl)piperidine hydrochloride (racemate): A mixture of tert-butyl 2-(but-3-yn-1-yl)piperidine-1-carboxylate (racemate) (1.1 g, 4.6 mmol, 1 eq) and HCl in 1,4-dioxane (2 M, 15 mL) was stirred for 4 hours at 25° C. The resulting mixture was concentrated under vacuum to give 2-(but-3-yn-1-yl)piperidine hydrochloride (racemate) (800 mg, 100%) as a white solid.

Synthesis of 2-(but-3-yn-1-yl)-1-(3-methoxy-4-nitrobenzoyl)piperidine(racemate): To a stirred mixture of 2-(but-3-yn-1-yl)piperidine hydrochloride (racemate) (800 mg, 4.6 mmol, 1 eq), N-ethyl-N-isopropylpropan-2-amine (1.8 g, 13.8 mmol, 3.0 eq) and 3-methoxy-4-nitrobenzoic acid (0.9 g, 4.6 mmol, 1.0 eq) in N,N-dimethylformamide (20 mL) was added HATU (2.6 g, 6.9 mmol, 1.5 eq) in portions at 25° C. The reaction mixture was stirred for 4 hours at 25° C. The resulting mixture was diluted with water (60 mL) and then extracted with ethyl acetate (3×30 mL). The combined organic layers were washed with water (3×10 mL) and brine (20 mL), dried over anhydrous sodium sulfate. After filtration, the filtrate was concentrated under vacuum. The residue was purified by a flash column (silica gel, ethyl acetate/petroleum ether=0:1 to 1:1) to give 2-(but-3-yn-1-yl)-1-(3-methoxy-4-nitrobenzoyl)piperidine (racemate) (1.1 g, 75%) as a yellow oil. LC-MS (ESI, m/z) M+1: 317.

Synthesis of (2R)-2-(but-3-yn-1-yl)-1-(3-methoxy-4-nitrobenzoyl)piperidine and (2S)-2-(but-3-yn-1-yl)-1-(3-methoxy-4-nitrobenzoyl)piperidine: 500 mg of 2-(but-3-yn-1-yl)-1-(3-methoxy-4-nitrobenzoyl)piperidine (racemate) was purified by Chiral-SFC using the following conditions: Column: CHIRAL ART Cellulose-SB, 3*25 cm, 5 μm; mobile phase A: $CO_2$; mobile phase B: EtOH—Preparative; Flow rate: 50 mL/min; Gradient: isocratic 40% B; Detect 220 nm. Finally, (2R)-2-(but-3-yn-1-yl)-1-(3-methoxy-4-nitrobenzoyl)piperidine (210 mg) was obtained as a brown solid. And (2S)-2-(but-3-yn-1-yl)-1-(3-methoxy-4-nitrobenzoyl)piperidine (200 mg) was obtained as a brown solid. 8A, $T_R$=2.117 min in CHIRAL-SFC, Column: 6:IG 100×4.6 mm 3.0 um. mobile phase A: $CO_2$; mobile phase B: IPA, Start Conc. of Pump B: 10.0% in 4 min, Oven Temperature: 35° C. 8B, $T_R$=2.440 min in CHIRAL-SFC, Column: 6:IG 100×4.6 mm 3.0 um. mobile phase A: $CO_2$; mobile phase B: IPA, Start Conc. of Pump B: 10.0% in 4 min, Oven Temperature: 35° C.

Synthesis of 3-(4-{4-[(2R)-1-(3-methoxy-4-nitrobenzoyl)piperidin-2-yl]but-1-yn-1-yl}-1-oxo-3H-isoindol-2-yl)piperidine-2,6-dione (assumed): To a stirred mixture of (2R)-2-(but-3-yn-1-yl)-1-(3-methoxy-4-nitrobenzoyl)piperidine (180 mg, 0.6 mmol, 1.0 eq) and 3-(4-iodo-1-oxo-3H-isoindol-2-yl)piperidine-2,6-dione (210 mg, 0.6 mmol, 1.0 eq) in N,N-dimethylformamide (6 mL) and triethylamine (2 mL) were added CuI (11 mg, 0.1 mmol, 0.1 eq) and $Pd(PPh_3)_4$ (66 mg, 0.1 mmol, 0.1 eq) in portions at 25° C. under nitrogen atmosphere. The reaction mixture was stirred for 14 hours at 25° C. The resulting mixture was diluted with water (20 mL) and then extracted with ethyl acetate (3×15 mL). The combined organic layers were washed with water (2×10 mL), dried over anhydrous sodium sulfate. After filtration, the filtrate was concentrated under vacuum. The residue was purified by a flash column (silica gel, dichloromethane/$CH_3OH$=100:0 to 100:5) to give 3-(4-{4-[(2R)-1-(3-methoxy-4-nitrobenzoyl)piperidin-2-yl]but-1-yn-1-yl}-1-oxo-3H-isoindol-2-yl)piperidine-2,6-dione (400 mg, 91%) as a brown solid. LC-MS (ESI, m/z) M+1: 559.

Synthesis of 3-(4-{4-[(2R)-1-(4-amino-3-methoxybenzoyl)piperidin-2-yl]but-1-yn-1-yl}-1-oxo-3H-isoindol-2-yl)piperidine-2,6-dione(assumed): To a stirred mixture of 3-(4-{4-[(2R)-1-(3-methoxy-4-nitrobenzoyl)piperidin-2-yl]but-1-yn-1-yl}-1-oxo-3H-isoindol-2-yl)piperidine-2,6-dione (400 mg, 0.7 mmol, 1 eq) and $NH_4Cl$ (306 mg, 5.7 mmol, 8.0 eq) in EtOH (10 mL) and water (2 mL) were added Fe (240 mg, 4.3 mmol, 6.0 eq) in portions at 25° C. The reaction mixture was stirred for 2 hours at 50° C. The resulting mixture was filtered, the collected filter cake was washed with ethanol (3×10 mL). The residue was purified by a flash column (silica gel, dichloromethane/$CH_3OH$=100:0 to 100:5) to give 3-(4-{4-[(2R)-1-(4-amino-3-methoxybenzoyl)piperidin-2-yl]but-1-yn-1-yl}-1-oxo-3H-isoindol-2-yl)piperidine-2,6-dione (200 mg, 53%) as a brown solid. LC-MS (ESI, m/z) M+1: 529.

Synthesis of (2'S,3S,4'S,5'R)-6-chloro-4'-(3-chloro-2-fluorophenyl)-2'-(2,2-dimethylpropyl)-N-{4-[(2R)-2-(4-{2-[(3R)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide: Into an 8 mL vial were added 3-(4-{4-[(2R)-1-(4-amino-3-methoxybenzoyl)piperidin-2-yl]but-1-yn-1-yl}-1-oxo-3H-isoindol-2-yl)piperidine-2,6-dione (76 mg, 0.1 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (52 mg, 0.1 mmol, 0.8 eq), NMI (35 mg, 0.4 mmol, 3.0 eq), TCFH (60 mg, 0.2 mmol, 1.5 eq) and $CH_3CN$ (3 mL) at 25° C. The reaction mixture was stirred for 2 hours at 25° C. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(2R)-2-(4-{2-[(3R)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide (17 mg, 12%) was obtained as a white solid. LC-MS (ESI, m/z) M+1: 961/963. $^1$H NMR (300 MHz, DMSO-$d_6$) δ 10.95 (bs, 1H), 10.21 (bs, 1H), 8.38-8.12 (m, 1H), 7.74 (d, J=7.2 Hz, 1H), 7.67-7.31 (m, 4H), 7.23 (q, J=8.1 Hz, 2H), 7.0 (s, 1H), 6.95-6.86 (m, 1H), 6.51 (dd, J=7.8, 1.8 Hz, 1H), 6.31 (d, J=1.8 Hz, 1H), 5.56-5.49 (m, 1H), 5.12 (dd, J=13.2, 5.1 Hz, 1H), 4.50-4.0 (m, 4H), 3.75 (s, 3H), 3.73-3.50 (m, 5H), 3.24-2.82 (m, 4H), 2.45-2.22 (m, 4H), 2.17-1.84 (m, 3H), 1.80-1.62 (m, 4H), 1.40-1.36 (m, 2H), 1.20 (t, J=12.0 Hz, 1H), 0.90 (s, 9H).

Example 37: Preparation of (2'S,3S,4'S,5'R)-6-chloro-4'-(3-chloro-2-fluorophenyl)-2'-(2,2-dimethylpropyl)-N-{4-[(2R)-2-(4-{2-[(3S)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide Synthesis of (2'S,3S,4'S,5'R)-6-chloro-4'-(3-chloro-2-fluorophenyl)-2'-(2,2-dimethylpropyl)-N-{4-[(2R)-2-(4-{2-[(3S)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide: Into an 8 mL vial were added 3-(4-{4-[(2R)-1-(4-amino-3-methoxybenzoyl)piperidin-2-yl]but-1-yn-1-yl}-1-oxo-3H-isoindol-2-yl)piperidine-2,6-dione (76 mg, 0.1 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (52 mg, 0.1 mmol, 0.8 eq), NMI (35 mg, 0.4 mmol, 3.0 eq), TCFH (60 mg, 0.2 mmol, 1.5 eq) and $CH_3CN$ (3 ml) at 25° C. The reaction mixture was stirred for 2 hours at 25° C. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(2R)-2-(4-{2-[(3S)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide (17 mg, 12%) was obtained as white solid. LC-MS (ESI, m/z) M+1: 961/963. $^1$H NMR (300 MHz, DMSO-$d_6$) δ 10.95 (bs, 1H), 10.21 (bs, 1H), 8.38-8.12 (m, 1H), 7.74 (d, J=7.2 Hz, 1H), 7.67-7.31 (m, 4H), 7.23 (q, J=8.1 Hz, 2H), 7.0 (s, 1H), 6.95-6.86 (m, 1H), 6.51 (dd, J=7.8, 1.8 Hz, 1H), 6.31 (d, J=1.8 Hz, 1H), 5.56-5.49 (m, 1H), 5.12 (dd, J=13.2, 5.1 Hz, 1H), 4.50-4.0 (m, 4H), 3.75 (s, 3H), 3.73-3.50 (m, 5H), 3.24-2.82 (m, 4H), 2.45-2.22 (m, 4H), 2.17-1.84 (m, 3H), 1.80-1.62 (m, 4H), 1.40-1.36 (m, 2H), 1.20 (t, J=12.0 Hz, 1H), 0.90 (s, 9H).

Example 38: Preparation of (2'S,3S,4'S,5'R)-6-chloro-4'-(3-chloro-2-fluorophenyl)-2'-(2,2-dimethylpropyl)-N-{4-[(2S)-2-(4-{2-[(3R)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide Synthesis of 3-(4-{4-[(2S)-1-(3-methoxy-4-nitrobenzoyl)piperidin-2-yl]but-1-yn-1-yl}-1-oxo-3H-isoindol-2-yl)piperidine-2,6-dione: To a stirred mixture of (2S)-2-(but-3-yn-1-yl)-1-(3-methoxy-4-nitrobenzoyl)piperidine (180 mg, 0.6 mmol, 1 eq) and 3-(4-iodo-1-oxo-3H-isoindol-2-yl)piperidine-2,6-dione (210 mg, 0.6 mmol, 1.0 eq) in N,N-dimethylformamide (6 mL) and triethylamine (2 mL) were added $Pd(PPh_3)_4$ (66 mg, 0.1 mmol, 0.1 eq) and CuI (11 mg, 0.1 mmol, 0.1 eq) in portions at 25° C. under nitrogen atmosphere.

The reaction mixture was stirred for 14 hours at 25° C. The resulting mixture was diluted with water (20 mL) and then extracted with ethyl acetate (3×15 mL). The combined organic layers were washed with water (2×10 mL), dried over anhydrous sodium sulfate. After filtration, the filtrate was concentrated under vacuum. The residue was purified by a flash column (silica gel, dichloromethane/$CH_3OH$=100:0 to 100:5) to give 3-(4-{4-[(2S)-1-(3-methoxy-4-nitrobenzoyl)piperidin-2-yl]but-1-yn-1-yl}-1-oxo-3H-isoindol-2-yl)piperidine-2,6-dione (370 mg, 86%) as a brown solid. LC-MS (ESI, m/z) M+1: 559.

Synthesis of 3-(4-{4-[(2S)-1-(4-amino-3-methoxybenzoyl)piperidin-2-yl]but-1-yn-1-yl}-1-oxo-3H-isoindol-2-yl) piperidine-2,6-dione: To a stirred mixture of 3-(4-{4-[(2S)-1-(3-methoxy-4-nitrobenzoyl)piperidin-2-yl]but-1-yn-1-yl}-1-oxo-3H-isoindol-2-yl)piperidine-2,6-dione (350 mg, 0.6 mmol, 1.0 eq) and $NH_4Cl$ (268 mg, 5.0 mmol, 8.0 eq) in EtOH (10 mL) and water (2 mL) were added Fe (210 mg, 3.8 mmol, 6.0 eq) in portions at 25° C. The reaction mixture was stirred for 2 hours at 50° C. The resulting mixture was filtered, the filter cake was washed with ethanol (3×10 mL). The filtrate was purified by a flash column (silica gel, dichloromethane/$CH_3OH$=100:0 to 100:5) to give 3-(4-{4-[(2S)-1-(4-amino-3-methoxybenzoyl)piperidin-2-yl]but-1-yn-1-yl}-1-oxo-3H-isoindol-2-yl)piperidine-2,6-dione (200 mg, 60%) as a brown solid.

Synthesis of (2'S,3S,4'S,5'R)-6-chloro-4'-(3-chloro-2-fluorophenyl)-2'-(2,2-dimethylpropyl)-N-{4-[(2S)-2-(4-{2-[(3R)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide: To an 8 mL vial were added 3-(4-{4-[(2S)-1-(4-amino-3-methoxybenzoyl)piperidin-2-yl]but-1-yn-1-yl}-1-oxo-3H-isoindol-2-yl)piperidine-2,6-dione (100 mg, 0.1 mmol, 1.0 eq 65%), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (50 mg, 0.1 mmol, 0.9 eq), TCFH (52 mg, 0.2 mmol, 1.5 eq), NMI (30 mg, 0.4 mmol, 3.0 eq) and $CH_3CN$ (3 mL) at 25° C. The reaction mixture was stirred for 2 hours at 25° C. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3·H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(2S)-2-(4-{2-[(3R)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide (15 mg, 13%) was obtained as white solid. LC-MS (ESI, m/z) M+1: 961/963. $^1H$ NMR (300 MHz, DMSO-$d_6$) δ 10.95 (bs, 1H), 10.21 (bs, 1H), 8.38-8.12 (m, 1H), 7.74 (d, J=7.2 Hz, 1H), 7.67-7.31 (m, 4H), 7.23 (q, J=8.1 Hz, 2H), 7.0 (s, 1H), 6.95-6.86 (m, 1H), 6.51 (dd, J=7.8, 1.8 Hz, 1H), 6.31 (d, J=1.8 Hz, 1H), 5.56-5.49 (m, 1H), 5.12 (dd, J=13.2, 5.1 Hz, 1H), 4.50-4.0 (m, 4H), 3.75 (s, 3H), 3.73-3.50 (m, 5H), 3.24-2.82 (m, 4H), 2.45-2.22 (m, 4H), 2.17-1.84 (m, 3H), 1.80-1.62 (m, 4H), 1.40-1.36 (m, 2H), 1.20 (t, J=12.0 Hz, 1H), 0.90 (s, 9H).

Example 39: Preparation of (2'S,3S,4'S,5'R)-6-chloro-4'-(3-chloro-2-fluorophenyl)-2'-(2,2-dimethylpropyl)-N-{4-[(2S)-2-(4-{2-[(3S)-2,6-dioxopiperidin-3-yl]-1-oxo-3H-isoindol-4-yl}but-3-yn-1-yl) piperidine-1-carbonyl]-2-methoxyphenyl}-1,2-dihydrospiro[indole-3,3'-pyrrolidine]-5'-carboxamide Synthesis of (2'S,3S,4'S,5'R)-6-chloro-4'-(3-chloro-2-fluorophenyl)-2'-(2,2-dimethylpropyl)-N-{4-[(2S)-2-(4-{2-[(3S)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide: To an 8 mL vial were added 3-(4-{4-[(2S)-1-(4-amino-3-methoxybenzoyl)piperidin-2-yl]but-1-yn-1-yl}-1-oxo-3H-isoindol-2-yl)piperidine-2,6-dione (100 mg, 0.1 mmol, 1.0 eq 65%), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (50 mg, 0.1 mmol, 0.9 eq), TCFH (52 mg, 0.2 mmol, 1.5 eq), NMI (30 mg, 0.4 mmol, 3.0 eq) and $CH_3CN$ (3 mL) at 25° C. The reaction mixture was stirred for 2 hours at 25° C. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3·H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(2S)-2-(4-{2-[(3S)-2,6-dioxopiperidin-3-yl]-1-oxo-3H-isoindol-4-yl}but-3-yn-1-yl)piperidine-1-carbonyl]-2-methoxyphenyl}-1,2-dihydrospiro[indole-3,3'-pyrrolidine]-5'-carboxamide (20 mg, 18%) was obtained as a white solid. LC-MS (ESI, m/z) M+1: 961/963. $^1H$ NMR (300 MHz, DMSO-$d_6$) δ 10.95 (bs, 1H), 10.21 (bs, 1H), 8.38-8.12 (m, 1H), 7.74 (d, J=7.2 Hz, 1H), 7.67-7.31 (m, 4H), 7.23 (q, J=8.1 Hz, 2H), 7.0 (s, 1H), 6.95-6.86 (m, 1H), 6.51 (dd, J=7.8, 1.8 Hz, 1H), 6.31 (d, J=1.8 Hz, 1H), 5.56-5.49 (m, 1H), 5.12 (dd, J=13.2, 5.1 Hz, 1H), 4.50-4.0 (m, 4H), 3.75 (s, 3H), 3.73-3.50 (m, 5H), 3.24-2.82 (m, 4H), 2.45-2.22 (m, 4H), 2.17-1.84 (m, 3H), 1.80-1.62 (m, 4H), 1.40-1.36 (m, 2H), 1.20 (t, J=12.0 Hz, 1H), 0.90 (s, 9H).

Example 40: Preparation of (2'S,3S,4'S,5'R)-6-chloro-4'-(3-chloro-2-fluorophenyl)-2'-(2,2-dimethylpropyl)-N-(4-{[(1S,2S)-2-{3-[2-(2,6-dioxopiperidin-3-yl)-1-oxo-3H-isoindol-4-yl]prop-2-yn-1-yl}cyclohexyl]carbamoyl}-2-methoxyphenyl)-1,2-dihydrospiro[indole-3,3'-pyrrolidine]-5'-carboxamide Synthesis of ethyl 7-hydroxyhept-2-enoate: Into a 1000 mL 3-necked round-bottom flask, dihydropyran (20.0 g, 237.7 mmol, 1.0 eq) was suspended in water (100 mL), HCl (1M, 2 mL) was added and the reaction was stirred at 25° C. for 3 h. After that, $K_2CO_3$ (39.4 g, 285.3 mmol, 1.2 eq), triethyl phosphonoacetate (63.9 g, 285.3 mmol, 1.2 eq) and methyl sulfoxide (80 mL) were added at 25° C. The reaction mixture was stirred at 50° C. for 16 hours. The resulting solution was extracted with ethyl acetate (2×200 mL). The combined organic phase was washed with brine (2×200 mL), dried over anhydrous sodium sulfate and concentrated under vacuum. The residue was purified by a flash column (silica gel, ethyl acetate/petroleum ether=0:1 to 1:3) to give ethyl 7-hydroxyhept-2-enoate (24.0 g, 58%) as a light yellow oil. $^1$HNMR (300 MHz, DMSO-$d_6$) δ 6.89 (dt, J=15.6, 7.1 Hz, 1H), 5.84 (dt, J=15.6, 1.5 Hz, 1H), 4.38 (t, J=5.1 Hz, 1H), 4.11 (q, J=7.1 Hz, 2H), 3.40 (qd, J=5.4, 5.1, 3.3 Hz, 2H), 2.20 (qd, J=7.1, 1.5 Hz, 2H), 1.54-1.35 (m, 4H), 1.21 (t, J=7.1 Hz, 3H).

Synthesis of ethyl 7-iodohept-2-enoate: Into a 1000 mL 3-necked round-bottom flask, were placed ethyl 7-hydroxyhept-2-enoate (24.0 g, 139.4 mmol, 1.0 eq), $CH_3CN$ (100 mL), ethyl ether (300 mL). After that, $PPh_3$ (54.8 g, 209.1 mmol, 1.5 eq), 1H-imidazole (14.2 g, 209.1 mmol, 1.5 eq), 12 (53.1 g, 209.1 mmol, 1.5 eq) were added at 0° C. Then the reaction mixture was stirred for 3 hours at 0° C. The resulting mixture was quenched by the addition of saturated Sodium thiosulfate solution (250 mL), and then extracted with ethyl ether (2×300 mL). The combined organic phase was washed with saturated Sodium thiosulfate solution (300 mL), water (300 mL), brine (300 mL) and then dried over anhydrous sodium sulfate. After filtration, the filtrate was concentrated under vacuum. The residue was purified by a flash column (silica gel, ethyl acetate/petroleum ether=0:1 to 1:3) to give ethyl 7-iodohept-2-enoate (26 g, 66%) as a light yellow oil. $^1$HNMR (300 MHz, DMSO-$d_6$) δ 6.88 (dt, J=15.6, 6.9 Hz, 1H), 5.87 (dt, J=15.6, 1.5 Hz, 1H), 4.11 (q, J=7.1 Hz, 2H), 3.29 (t, J=6.9 Hz, 2H), 2.23 (qd, J=7.1, 1.5 Hz, 2H), 1.77 (p, J=7.1 Hz, 2H), 1.51 (p, J=7.4 Hz, 2H), 1.21 (t, J=7.1 Hz, 3H).

Synthesis of ethyl 2-(2-nitrocyclohexyl)acetate: Into a 1000 mL 3-necked round-bottom flask, were placed ethyl 7-iodohept-2-enoate (26.0 g, 92.1 mmol, 1.0 eq), N,N-dimethylformamide (350 mL), $Cs_2CO_3$ (90.1 g, 276.5 mmol, 3.0 eq), $CH_3NO_2$ (28.1 g, 460.8 mmol, 5.0 eq). The reaction mixture was stirred for 16 hours at 25° C. The resulting mixture was diluted with water (700 mL), and then extracted with ethyl acetate (2×400 mL). The combined organic phase was washed with brine (2×400 mL), dried over anhydrous sodium sulfate. After filtration, the filtrate was concentrated under vacuum. The residue was purified by a flash column (silica gel, ethyl acetate/petroleum ether=0:1 to 1:3) to give ethyl 2-(2-nitrocyclohexyl)acetate (3.5 g, 18%) as a light yellow oil. $^1$HNMR (400 MHz, DMSO-$d_6$) δ 4.53 (td, J=10.8, 4.2 Hz, 1H), 4.10-4.03 (m, 2H), 2.33-2.14 (m, 4H), 1.84-1.55 (m, 4H), 1.40-1.24 (m, 2H), 1.18 (t, J=7.2 Hz, 4H).

Synthesis of ethyl 2-(2-aminocyclohexyl)acetate: Into a 250-mL round-bottom flask were placed ethyl 2-(2-nitrocyclohexyl)acetate (3.0 g, 13.9 mmol, 1.0 eq), Fe (3.1 g, 55.7 mmol, 4.0 eq), $NH_4Cl$ (5.9 g, 111.5 mmol, 8.0 eq), ethanol (60 mL), water (20 mL). The reaction mixture was stirred for 2 hours at 50° C. The resulting mixture was filtered, the filtrate was concentrated under vacuum. The residue was purified by a flash column (silica gel, dichloromethane/methanol=1:0 to 10:1) to give ethyl 2-(2-aminocyclohexyl)acetate (2.0 g, 77%) as an off white solid. $^1$HNMR (400 MHz, DMSO-$d_6$) δ 7.80 (br, 2H), 4.08 (q, J=7.2 Hz, 2H), 2.86-2.75 (m, 2H), 2.12 (dd, J=15.8, 9.6 Hz, 1H), 2.03-1.95 (m, 1H), 1.86-1.79 (m, 2H), 1.70 (d, J=9.4 Hz, 2H), 1.64-1.56 (m, 1H), 1.35-1.23 (m, 2H), 1.19 (t, J=7.2 Hz, 3H), 1.14-0.99 (m, 1H).

Synthesis of ethyl 2-{2-[(tert-butoxycarbonyl)amino]cyclohexyl}acetate: Into a 100 mL round-bottom flask were placed ethyl 2-(2-aminocyclohexyl)acetate (2.0 g, 10.8 mmol, 1.0 eq), dichloromethane (30 mL), triethylamine (2.7 g, 26.9 mmol, 2.5 eq), $(Boc)_2O$ (3.5 g, 16.2 mmol, 1.5 eq). The reaction mixture was stirred for 2 hours at 25° C. The resulting mixture was diluted with water (100 mL) and then extracted with dichloromethane (2×100 mL). The combined organic phase was washed with brine (2×100 mL), dried over anhydrous sodium sulfate and concentrated under vacuum. The residue was purified by a flash column (silica gel, ethyl acetate/petroleum ether=0:1 to 1:3) to give ethyl 2-{2-[(tert-butoxycarbonyl)amino]cyclohexyl}acetate (2.8 g, 91%) as an off white solid.

Synthesis of tert-butyl N-[2-(2-hydroxyethyl)cyclohexyl]carbamate: Into a 100 mL 3-necked round-bottom flask, were placed ethyl 2-{2-[(tert-butoxycarbonyl)amino]cyclohexyl}acetate (2.8 g, 9.8 mmol, 1.0 eq), tetrahydrofuran (40 mL). After that, $LiAlH_4$(740 mg, 19.6 mmol, 2.0 eq) was added at 0° C. The reaction mixture was stirred for 1 hour at 0° C. The resulting mixture was then quenched by the addition of 1.0 mL of water, 1.0 mL of 15% NaOH, 3.0 mL of water. After filtration, the filtrate was concentrated under vacuum. The residue was purified by a flash column (silica gel, ethyl acetate/petroleum ether=0:1 to 1:3) to give tert-butyl N-[2-(2-hydroxyethyl)cyclohexyl]carbamate (1.5 g, 63%) as a light yellow oil. $^1$HNMR (400 MHz, DMSO-$d_6$) δ 6.58 (d, J=9.2 Hz, 1H), 4.25 (s, 1H), 3.49-3.35 (m, 2H), 3.02-2.90 (m, 1H), 1.83-1.76 (m, 1H), 1.76-1.52 (m, 4H), 1.38 (s, 9H), 1.27-1.14 (m, 3H), 1.17-0.99 (m, 2H), 0.90 (qd, J=12.4, 11.8, 3.2 Hz, 1H).

Synthesis of tert-butyl N-[2-(2-oxoethyl)cyclohexyl]carbamate: Into a 100 mL round flask, were placed tert-butyl N-[2-(2-hydroxyethyl)cyclohexyl]carbamate (1.2 g, 4.9 mmol, 1.0 eq), dichloromethane (30 mL), Dess-Martin (4.2 g, 9.9 mmol, 2.0 eq). The reaction mixture was stirred for 2 hours at 25° C. The reaction was then quenched by the addition of water (50 mL), and then extracted with dichloromethane (2×50 mL). The organic phase was washed with brine (2×50 mL), dried over anhydrous sodium sulfate. After filtration, the filtrate was concentrated under vacuum. The residue was purified by a flash column (silica gel, ethyl acetate/petroleum ether=0:1 to 1:3) to give tert-butyl N-[2-(2-oxoethyl)cyclohexyl]carbamate (900 mg, 75%) as a light yellow oil.

Synthesis of tert-butyl N-[2-(prop-2-yn-1-yl)cyclohexyl]carbamate: Into a 50-mL round-bottom flask were placed tert-butyl N-[2-(2-oxoethyl)cyclohexyl]carbamate (900 mg, 3.7 mmol, 1.0 eq), $CH_3OH$ (15 mL), $K_2CO_3$ (1.0 g, 7.4 mmol, 2.0 eq), seyferth-gilbert homologation (1.1 g, 5.6 mmol, 1.5 eq). The reaction mixture was stirred for 2 hours at 25° C. The reaction was then quenched by the addition of water (50 mL) and then extracted with ethyl acetate (2×50 mL). The combined organic phase was washed with brine (2×50 mL), dried over anhydrous sodium sulfate. After filtration, the filtrate was concentrated under vacuum. The residue was purified by a flash column (silica gel, ethyl acetate/petroleum ether=0:1 to 1:3) to give tert-butyl N-[2-(prop-2-yn-1-yl)cyclohexyl]carbamate (600 mg, 68%) as a light yellow oil. $^1$HNMR (400 MHz, DMSO-$d_6$) δ 6.70 (d, J=8.9 Hz, 1H), 3.02 (qd, J=10.3, 9.9, 3.7 Hz, 1H), 2.73 (t, J=2.7 Hz, 1H), 2.29 (dt, J=16.8, 3.2 Hz, 1H), 1.99-1.91 (m, 2H), 1.74 (d, J=11.6 Hz, 1H), 1.64 (s, 2H), 1.38 (s, 9H), 1.36 (s, 1H), 1.27-0.99 (m, 4H).

Synthesis of 2-(prop-2-yn-1-yl)cyclohexan-1-amine hydrochloride: Into a 50-mL round-bottom flask were placed tert-butyl N-[2-(prop-2-yn-1-yl)cyclohexyl]carbamate (600 mg, 2.5 mmol, 1.0 eq), dichloromethane (6 mL), HCl (gas) in 1,4-dioxane (6 mL). The reaction mixture was stirred for 1 hour at 25° C. The resulting mixture was concentrated under vacuum to give 2-(prop-2-yn-1-yl)cyclohexan-1-amine hydrochloride (350 mg, crude) as an off white solid.

Synthesis of 2-methoxy-4-nitro-N-[2-(prop-2-yn-1-yl)cyclohexyl]benzamide: Into a 50-mL round flask, were placed 2-(prop-2-yn-1-yl)cyclohexan-1-amine hydrochloride (350 mg, 2.0 mmol, 1.0 eq), 3-methoxy-4-nitrobenzoic acid (477 mg, 2.4 mmol, 1.2 eq), HATU (920 mg, 2.4 mmol, 1.2 eq), DIEA (781 mg, 6.0 mmol, 3.0 eq), N,N-dimethylformamide (4 mL). The reaction mixture was stirred for 2 hours at 25° C. The reaction was then quenched by the addition of water (50 mL) and then extracted with ethyl acetate (2×50 mL). The combined organic phase was washed with brine (2×50 mL), and dried over anhydrous sodium sulfate. After filtration, the filtrate was concentrated under vacuum. The residue was purified by a flash column (silica gel, ethyl acetate/petroleum ether=0:1 to 1:1) to give 2-methoxy-4-nitro-N-[2-(prop-2-yn-1-yl)cyclohexyl]benzamide (510 mg, 80%) as a off white solid. LC-MS (ESI, m/z) M+1: 317. $^1$HNMR (300 MHz, DMSO-$d_6$) δ 8.47 (d, J=8.7 Hz, 1H), 7.96 (d, J=8.4 Hz, 1H), 7.70 (d, J=1.5 Hz, 1H), 7.56 (dd, J=8.4, 1.5 Hz, 1H), 4.0 (s, 3H), 3.80-3.53 (m, 1H), 2.76 (t, J=2.7 Hz, 1H), 2.34 (dt, J=16.5, 3.3 Hz, 1H), 2.09-2.05 (m, 1H), 1.91-1.81 (m, 1H), 1.74-1.59 (m, 4H), 1.3-1.27 (m, 2H), 1.19 (d, J=8.4 Hz, 2H).

Synthesis of 2-methoxy-4-nitro-N-[(1S,2S)-2-(prop-2-yn-1-yl)cyclohexyl]benzamide and 2-methoxy-4-nitro-N-[(1R,2R)-2-(prop-2-yn-1-yl)cyclohexyl]benzamide: 500 mg of 2-methoxy-4-nitro-N-[2-(prop-2-yn-1-yl)cyclohexyl]benzamide was purified by Chiral-Prep-SFC using the following conditions:Column: Lux 5 um Cellulose-4, 3*25 cm, 10 μm; Mobile Phase A: $CO_2$, Mobile Phase B: isopropanol (0.5%2M $NH_3$—$CH_3OH$); Flow rate: 100 mL/min; Gradient: isocratic 15% B; Wave Length: 220 nm. Finally, 2-methoxy-4-nitro-N-[(1S,2S)-2-(prop-2-yn-1-yl)cyclohexyl]benzamide (200 mg) was obtained as an off white solid. And 2-methoxy-4-nitro-N-[(1R,2R)-2-(prop-2-yn-1-yl)cyclohexyl]benzamide (210 mg) was obtained as an off white solid. 10A, $T_R$=1.514 min in CHIRAL-SFC, Column: Lux-4 100×4.6 mm 3.0 um. mobile phase A: $CO_2$; mobile phase B: IPA (20 mM $NH_3$), Start Conc. of Pump B: 10.0% in 4 min, Oven Temperature: 35° C. 10B, $T_R$=1.640 min in CHIRAL-SFC, Column: Lux-4 100×4.6 mm 3.0 um. mobile phase A: $CO_2$; mobile phase B: IPA (20 mM $NH_3$), Start Conc. of Pump B: 10.0% in 4 min, Oven Temperature: 35° C.

Synthesis of N-[(1S,2S)-2-{3-[2-(2,6-dioxopiperidin-3-yl)-1-oxo-3H-isoindol-4-yl]prop-2-yn-1-yl}cyclohexyl]-3-methoxy-4-nitrobenzamide: Into a 20 mL sealed tube purged and maintained under an inert atmosphere of nitrogen, were placed 2-methoxy-4-nitro-N-[(1S,2S)-2-(prop-2-yn-1-yl)cyclohexyl]benzamide (180 mg, 0.6 mmol, 1.0 eq), 3-(4-iodo-1-oxo-3H-isoindol-2-yl)piperidine-2,6-dione (211 mg, 0.6 mmol, 1.0 eq), $Pd(PPh_3)_4$(66 mg, 0.1 mmol, 0.1 eq), CuI (11 mg, 0.1 mmol, 0.1 eq), triethylamine (173 mg, 1.7 mmol, 3.0 eq), N,N-dimethylformamide (3 mL). The reaction mixture was stirred for 2 hours at 70° C. The resulting mixture was diluted with water (30 mL), and then extracted with ethyl acetate (2×30 mL). The combined organic phase was washed with brine (2×30 mL), dried over anhydrous sodium sulfate. After filtration, the filtrate was concentrated under vacuum. The residue was purified by a flash column (silica gel, ethyl acetate/petroleum ether=0:1 to 1:0) to give N-[(1S,2S)-2-{3-[2-(2,6-dioxopiperidin-3-yl)-1-oxo-3H-isoindol-4-yl]prop-2-yn-1-yl}cyclohexyl]-3-methoxy-4-nitrobenzamide (260 mg, 82%) as a light yellow solid. LC-MS (ESI, m/z) M+1: 559.

Synthesis of 4-amino-N-[(1S,2S)-2-{3-[2-(2,6-dioxopiperidin-3-yl)-1-oxo-3H-isoindol-4-yl]prop-2-yn-1-yl}cyclohexyl]-3-methoxybenzamide: Into a 20 mL sealed tube were placed N-[(1S,2S)-2-{3-[2-(2,6-dioxopiperidin-3-yl)-1-oxo-3H-isoindol-4-yl]prop-2-yn-1-yl}cyclohexyl]-3-methoxy-4-nitrobenzamide (240 mg, 0.4 mmol, 1.0 eq), Fe (96 mg, 1.7 mmol, 4.0 eq), $NH_4Cl$ (184 mg, 3.4 mmol, 8.0 eq), ethanol (6 mL), water (2 mL). The reaction mixture was stirred for 2 hours at 50° C. The resulting mixture was filtered, and the filtrate was concentrated under vacuum. The residue was purified by a flash column (silica gel, dichloromethane/methanol=1:0 to 20:1) to give 4-amino-N-[(1S,2S)-2-{3-[2-(2,6-dioxopiperidin-3-yl)-1-oxo-3H-isoindol-4-yl]prop-2-yn-1-yl}cyclohexyl]-3-methoxybenzamide (180 mg, 79%) as a light yellow solid. LC-MS (ESI, m/z) M+1: 529.

Synthesis of (2'S,3S,4'S,5'R)-6-chloro-4'-(3-chloro-2-fluorophenyl)-2'-(2,2-dimethylpropyl)-N-(4-{[(1S,2S)-2-{3-[2-(2,6-dioxopiperidin-3-yl)-1-oxo-3H-isoindol-4-yl]prop-2-yn-1-yl}cyclohexyl]carbamoyl}-2-methoxyphenyl)-1,2-dihydrospiro[indole-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 4-amino-N-[(1S,2S)-2-{3-[2-(2,6-dioxopiperidin-3-yl)-1-oxo-3H-isoindol-4-yl]prop-2-yn-1-yl}cyclohexyl]-3-methoxybenzamide (46 mg, 0.1 mmol, 1.3 eq), HATU (29 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3·H_2O$) and $CH_3CN$ (86% Phase B up to 94% in 7 min); Detector, UV 254/220 nm. Finally, (2'S,3S,4'S,5'R)-6-chloro-4'-(3-chloro-2-fluorophenyl)-2'-(2,2-dimethylpropyl)-N-(4-{[(1S,2S)-2-{3-[2-(2,6-dioxopiperidin-3-yl)-1-oxo-3H-isoindol-4-yl]prop-2-yn-1-yl}cyclohexyl]carbamoyl}-2-methoxyphenyl)-1,2-dihydrospiro[indole-3,3'-pyrrolidine]-5'-carboxamide (10 mg, 15%) was obtained as a white solid. LC-MS (ESI, m/z) M+1: 961/963. $^1$HNMR (300 MHz, DMSO-$d_6$) δ 11.0 (d, −4.5 Hz, 1H), 10.65 (d, −8.1 Hz, 1H), 8.31 (t, J=8.1 Hz, 1H), 8.17 (d, J=7.2 Hz, 1H), 7.72-7.63 (m, 1H), 7.58 (dd, −6.6, 3.0 Hz, 1H), 7.51 (d, J=2.4 Hz, 1H), 7.47 (t, J=5.1 Hz, 2H), 7.34 (ddd, J=27.9, 18.9, 9.6 Hz, 3H), 7.20 (t, J=7.8 Hz, 1H), 6.56-6.47 (m, 1H), 6.31 (d, J=1.8 Hz, 1H), 5.52 (s, 1H), 5.17-5.06 (m, 2H), 4.28 (d, J=13.5 Hz, 3H), 4.24-4.08 (m, 2H), 3.84 (d, J=17.7 Hz, 3H), 3.71 (s, 2H), 3.53 (d, J=10.5 Hz, 2H), 3.20 (d, J=10.2 Hz, 2H), 2.91-2.84 (m, 1H), 2.06-1.98 (m, 2H), 1.84-1.74 (m, 3H), 1.4-1.29 (m, 5H), 1.27-1.15 (m, 2H), 0.92 (s, 9H).

Example 41: Preparation of (2'S,3S,4'S,5'R)-6-chloro-4'-(3-chloro-2-fluorophenyl)-2'-(2,2-dimethylpropyl)-N-(4-{[(1R,2R)-2-{3-[2-(2,6-dioxopiperidin-3-yl)-1-oxo-3H-isoindol-4-yl]prop-2-yn-1-yl}cyclohexyl]carbamoyl}-2-methoxyphenyl)-1,2-dihydrospiro[indole-3,3'-pyrrolidine]-5'-carboxamide Synthesis of N-[(1R,2R)-2-{3-[2-(2,6-dioxopiperidin-3-yl)-1-oxo-3H-isoindol-4-yl]prop-2-yn-1-yl}cyclohexyl]-3-methoxy-4-nitrobenzamide: Into a 20 mL sealed tube purged and maintained under an inert atmosphere of nitrogen, were placed 2-methoxy-4-nitro-N-[(1R,2R)-2-(prop-2-yn-1-yl)cyclohexyl]benzamide (190 mg, 0.6 mmol, 1.0 eq), 3-(4-iodo-1-oxo-3H-isoindol-2-yl)piperidine-2,6-dione (222 mg, 0.6 mmol, 1.0 eq), $Pd(PPh_3)_4$(69 mg, 0.1 mmol, 0.1 eq), CuI (11 mg, 0.1 mmol, 0.1 eq), triethylamine (182 mg, 1.8 mmol, 3.0 eq), N,N-dimethylformamide (3 mL). The reaction mixture was stirred for 2 hours at 70° C. The resulting mixture was diluted with water (30 mL) and then extracted with ethyl acetate (2×30 mL) and washed with brine (2×30 mL). The organic phase was dried over anhydrous sodium sulfate, filtered and the filtrate was concentrated under vacuum. The residue was purified by a flash column (silica gel, ethyl acetate/petroleum ether=0:1 to 1:0) to give N-[(1R,2R)-2-{3-[2-(2,6-dioxopiperidin-3-yl)-1-oxo-3H-isoindol-4-yl]prop-2-yn-1-yl}cyclohexyl]-3-methoxy-4-nitrobenzamide (260 mg, 77%) as a light yellow solid. LC-MS (ESI, m/z) M+1: 559.

Synthesis of 4-amino-N-[(1R,2R)-2-{3-[2-(2,6-dioxopiperidin-3-yl)-1-oxo-3H-isoindol-4-yl]prop-2-yn-1-yl}cyclohexyl]-3-methoxybenzamide: Into a 20 mL sealed tube were placed N-[(1R,2R)-2-{3-[2-(2,6-dioxopiperidin-3-yl)-1-oxo-3H-isoindol-4-yl]prop-2-yn-1-yl}cyclohexyl]-3-methoxy-4-nitrobenzamide (250 mg, 0.5 mmol, 1.0 eq), Fe (100 mg, 1.8 mmol, 4.0 eq), $NH_4Cl$ (192 mg, 3.6 mmol, 8.0 eq), ethanol (6 mL), water (2 mL). The reaction mixture was stirred for 2 hours at 50° C. The resulting mixture was filtered, and the filtrate was concentrated under vacuum. The residue was purified by a flash column (silica gel, dichloromethane/methanol=1:0 to 20:1) to give 4-amino-N-[(1R, 2R)-2-{3-[2-(2,6-dioxopiperidin-3-yl)-1-oxo-3H-isoindol-4-yl]prop-2-yn-1-yl}cyclohexyl]-3-methoxybenzamide (180 mg, 76%) as a light yellow solid. LC-MS (ESI, m/z) M+1: 529.

Synthesis of (2'S,3S,4'S,5'R)-6-chloro-4'-(3-chloro-2-fluorophenyl)-2'-(2,2-dimethylpropyl)-N-(4-{[(1R,2R)-2-{3-[2-(2,6-dioxopiperidin-3-yl)-1-oxo-3H-isoindol-4-yl] prop-2-yn-1-yl}cyclohexyl]carbamoyl}-2-methoxyphenyl)-1,2-dihydrospiro[indole-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 4-amino-N-[(1R,2R)-2-{3-[2-(2,6-dioxopiperidin-3-yl)-1-oxo-3H-isoindol-4-yl]prop-2-yn-1-yl}cyclohexyl]-3-methoxybenzamide (46 mg, 0.1 mmol, 1.0 eq), HATU (27 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (86% Phase B up to 94% in 7 min); Detector, UV 254/220 nm. Finally, (2'S,3S,4'S,5'R)-6-chloro-4'-(3-chloro-2-fluorophenyl)-2'-(2,2-dimethylpropyl)-N-(4-{[(1R,2R)-2-{3-[2-(2,6-dioxopiperidin-3-yl)-1-oxo-3H-isoindol-4-yl]prop-2-yn-1-yl}cyclohexyl] carbamoyl}-2-methoxyphenyl)-1,2-dihydrospiro[indole-3, 3'-pyrrolidine]-5'-carboxamide (10 mg, 16%) was obtained as a white solid. LC-MS (ESI, m/z) M+1: 961/963. $^1$HNMR (300 MHz, DMSO-$d_6$) δ 11.0 (s, 1H), 10.65 (s, 1H), 8.29 (dd, J=10.5, 8.4 Hz, 1H), 8.17 (t, J=8.7 Hz, 1H), 7.72-7.64 (m, 1H), 7.63-7.54 (m, 1H), 7.59-7.38 (m, 4H), 7.33 (t, J=7.8 Hz, 2H), 7.20 (t, J=7.8 Hz, 1H), 6.51 (dd, J=7.8, 1.8 Hz, 1H), 6.31 (d, J=1.8 Hz, 1H), 5.53 (s, 1H), 5.12 (dd, J=13.2, 5.4 Hz, 1H), 4.44-4.31 (m, 1H), 4.31 (s, 1H), 4.25 (d, J=13.5 Hz, 2H), 4.20-4.08 (m, 2H), 3.86 (d, J=3.9 Hz, 3H), 3.71 (t, J=11.1 Hz, 2H), 3.53 (d, J=10.8 Hz, 2H), 3.19 (d, J=10.5 Hz, 2H), 2.97-2.82 (m, 1H), 2.05-1.98 (m, 2H), 1.88-1.81 (m, 2H), 1.78-1.70 (m, 3H), 1.42-1.26 (m, 2H), 1.25-1.14 (m, 2H), 0.92 (d, J=1.8 Hz, 9H).

Example 42: Preparation of (2'S,3S,4'S,5'R)-6-chloro-4'-(3-chloro-2-fluorophenyl)-N-(4-(2-((2-(2,6-dioxopiperidin-3-yl)-1-oxoisoindolin-4-yl)ethynyl)-7-azaspiro[3.5]nonane-7-carbonyl)-2-methoxyphenyl)-2'-neopentylspiro[indoline-3,3'-pyrrolidine]-5'-carboxamide Synthesis of tert-butyl 2-(methoxymethylidene)-7-azaspiro[3.5]nonane-7-carboxylate: Into a 500 mL round-bottom flask were added (methoxymethyl)triphenylphosphanium (16.7 g, 54.3 mmol, 1.3 eq), tert-butoxypotassium (6.1 g, 54.3 mmol, 1.3 eq), toluene (150 mL) at 25° C. The reaction mixture was stirred for 20 mins at 25° C. After that, to the above mixture was added a solution of tert-butyl 2-oxo-7-azaspiro[3.5]nonane-7-carboxylate (10.0 g, 41.8 mmol, 1.0 eq) in 50 mL toluene at 25° C. The reaction mixture was stirred for 4 hours at 70° C. The resulting mixture was quenched with sat. $NH_4Cl$ at 0° C., and then extracted with ethyl acetate (3×50 mL). The combined organic layers were washed with brine (50 mL), dried over anhydrous sodium sulfate. After filtration, the filtrate was concentrated under vacuum. The crude residue was purified by silica gel column choursomatography and eluted with petroleum ether/ethyl acetate=3:1 to give tert-butyl 2-(methoxymethylidene)-7-azaspiro[3.5]nonane-7-carboxylate (9.1 g, 81%) as a colorless liquid. $^1$HNMR (400 MHz, DMSO-$d_6$) δ 5.91-5.92 (m, J=2.5 Hz, 1H), 3.47 (s, 3H), 3.23 (t, J=5.6 Hz, 4H), 2.32 (dt, J=18.1, 2.4 Hz, 4H), 1.49-1.42 (m, 4H), 1.39 (s, 9H).

Synthesis of tert-butyl 2-formyl-7-azaspiro[3.5]nonane-7-carboxylate: A solution of tert-butyl 2-(methoxymethylidene)-7-azaspiro[3.5]nonane-7-carboxylate (9.0 g, 33.7 mmol, 1.0 eq) in $CH_3CN$ (320.0 g, 7.8 mol) and water (80 g, 4.4 mol) was treated with trifluoroacetic acid (2.8 g, 24.6 mmol, 0.7 eq) for 4 hours at 25° C. The resulting mixture was quenched with sat. sodium hyposulfite at 25° C., and then extracted with ethyl acetate (3×30 mL). The combined organic layers were washed with brine (30 mL), dried over anhydrous sodium sulfate. After filtration, the filtrate was concentrated under vacuum. The crude residue was purified by silica gel column chousomatography and eluted with petroleum ether/ethyl acetate=5:1 to give tert-butyl 2-formyl-7-azaspiro[3.5]nonane-7-carboxylate (8.3 g, 97%) as a light yellow liquid. $^1$HNMR (400 MHz, DMSO-$d_6$) δ 9.68 (d, J=1.6 Hz, 1H), 3.29-3.22 (m, 2H), 3.19-3.15 (m, 3H), 1.97-1.89 (m, 4H), 1.56-1.49 (m, 2H), 1.39 (s, 9H), 1.37-1.32 (m, 2H).

Synthesis of tert-butyl 2-ethynyl-7-azaspiro[3.5]nonane-7-carboxylate: To a stirred mixture of tert-butyl 2-formyl-7-azaspiro[3.5]nonane-7-carboxylate (2 g, 7.9 mmol, 1.0 eq) and $K_2CO_3$ (2.2 g, 15.8 mmol, 2.0 eq) in methanol (20 mL) was added seyferth-gilbert homologation (2.3 g, 11.8 mmol, 1.5 eq) in portions at 0° C. The reaction mixture was stirred for 2 hours at 25° C. The resulting mixture was quenched with water (10 mL) and then extracted with ethyl acetate (3×10 mL). The combined organic layers were washed with brine (10 mL), dried over anhydrous sodium sulfate. After filtration, the filtrate was concentrated under vacuum. The crude residue was purified by silica gel column chousomatography, eluted with petroleum ether/ethyl acetate=5:1) to give tert-butyl 2-ethynyl-7-azaspiro[3.5]nonane-7-carboxylate (1.8 g, 91%) as a Brown yellow oil. $^1$HNMR (300 MHz, DMSO-$d_6$) δ 3.28-3.13 (m, 4H), 3.06-3.0 (m, 1H), 3.0-2.92 (m, 1H), 2.13 (td, J=9.1, 2.2 Hz, 2H), 1.87-1.69 (m, 2H), 1.51-1.42 (m, 4H), 1.38 (s, 9H).

Synthesis of 2-ethynyl-7-azaspiro[3.5]nonane: Into a 50 mL round-bottom flask were added tert-butyl 2-ethynyl-7-azaspiro[3.5]nonane-7-carboxylate (1.8 g) and HCl (gas) in 1,4-dioxane (20 mL) at 25° C. The reaction mixture was stirred for 2 hours at 25° C. The resulting mixture was concentrated under vacuum to give 2-ethynyl-7-azaspiro [3.5]nonane (1.1 g, 93%) as white solid. $^1$HNMR (300 MHz, DMSO-$d_6$) δ 8.91 (bs, 1H), 3.39-3.30 (m, 1H), 3.03 (d, J=2.4 Hz, 1H), 2.97-2.82 (m, 4H), 2.18 (td, –9.1, 2.3 Hz, 2H), 1.89-1.77 (m, 2H), 1.73 (dt, J=7.3, 2.9 Hz, 4H).

Synthesis of 2-ethynyl-7-(3-methoxy-4-nitrobenzoyl)-7-azaspiro[3.5]nonane: To a stirred mixture of 2-ethynyl-7-azaspiro[3.5]nonane (1.0 g, 6.7 mmol, 1.0 eq) and 3-methoxy-4-nitrobenzoic acid (1.5 g, 7.4 mmol, 1.1 eq), DIEA (0.5 g, 7.4 mmol, 1.1 eq) in dimethyl formamide (10 mL) was added HATU (7.6 g, 20.1 mmol, 3.0 eq) in portions at 0° C. The reaction mixture was stirred for 2 hours at 25° C. The resulting mixture was quenched with water (10 mL) at 25° C. The resulting mixture was extracted with ethyl acetate (3×10 mL). The combined organic layers were washed with brine (10 mL), dried over anhydrous sodium sulfate. After filtration, the filtrate was concentrated under vacuum. The crude residue was purified by silica gel column chousomatography and eluted with petroleum ether/ethyl acetate=2:1 to give 2-ethynyl-7-(3-methoxy-4-nitrobenzoyl)-7-azaspiro[3.5]nonane (2.1 g, 95%) as a light yellow solid. LC-MS: (ESI, m/z): M+1: 370.

Synthesis of 3-(4-{2-[7-(3-methoxy-4-nitrobenzoyl)-7-azaspiro[3.5]nonan-2-yl]ethynyl}-1-oxo-3H-isoindol-2-yl) piperidine-2,6-dione: Into a 20 mL vial were added 2-ethynyl-7-(3-methoxy-4-nitrobenzoyl)-7-azaspiro[3.5]nonane (500 mg, 1.5 mmol, 1.0 eq) and 3-(4-iodo-1-oxo-3H-isoindol-2-yl)piperidine-2,6-dione (620 mg, 1.7 mmol, 1.1 eq), $Pd(PPh_3)_4$ (176 mg, 0.2 mmol, 0.1 eq), CuI (29 mg, 0.2 mmol, 0.1 eq), triethylamine (462 mg, 4.6 mmol, 3.0 eq), dimethyl formamide (8 mL) at 25° C. The reaction mixture was stirred for 2 hours at 70° C. under nitrogen atmosphere. The resulting mixture was diluted with water (5 mL) and then extracted with ethyl acetate (3×5 mL). The combined organic layers were washed with brine (5 mL), dried over anhydrous sodium sulfate. After filtration, the filtrate was concentrated under vacuum. The crude residue was purified by silica gel column chousomatography and eluted with petroleum ether/ethyl acetate=2:1 to give 3-(4-{2-[7-(3-methoxy-4-nitrobenzoyl)-7-azaspiro[3.5]nonan-2-yl]ethynyl}-1-oxo-3H-isoindol-2-yl)piperidine-2,6-dione (360 mg, 41%) as a light yellow solid. LC-MS: (ESI, m/z): M+1: 571.

Synthesis of 3-(4-{2-[7-(4-amino-3-methoxybenzoyl)-7-azaspiro[3.5]nonan-2-yl]ethynyl}-1-oxo-3H-isoindol-2-yl) piperidine-2,6-dione: Into a 20 mL vial were added 3-(4-{2-[7-(3-methoxy-4-nitrobenzoyl)-7-azaspiro[3.5]nonan-2-yl]ethynyl}-1-oxo-3H-isoindol-2-yl)piperidine-2,6-dione (360 mg, 0.6 mmol, 1.0 eq), Fe (211 mg, 3.8 mmol, 6.0 eq), $NH_4Cl$ (270 mg, 5.0 mmol, 8.0 eq), ethanol (6 mL) and water (2 mL) at 25° C. The reaction mixture was stirred for 2 hours at 50° C. The precipitated solids were collected by filtration and washed with $CH_3OH$ (3×5 mL). After filtration, the filtrate was concentrated under vacuum. The resulting mixture was diluted with $CH_2Cl_2$ (3×5 mL) and then washed with brine (5 mL) and dried over anhydrous sodium sulfate. After filtration, the filtrate was concentrated under vacuum. The crude residue was purified by silica gel column chousomatography and eluted with petroleum ether/ethyl acetate=1:1 to give 3-(4-{2-[7-(4-amino-3-methoxybenzoyl)-7-azaspiro[3.5]nonan-2-yl]ethynyl}-1-oxo-3H-isoindol-2-yl)piperidine-2,6-dione (180 mg, 53%) as a light yellow solid. LC-MS: (ESI, m/z): M+1: 541.

Synthesis of (2'S,3S,4'S,5'R)-6-chloro-4'-(3-chloro-2-fluorophenyl)-2'-(2,2-dimethylpropyl)-N-[4-(2-{2-[2-(2,6-dioxopiperidin-3-yl)-1-oxo-3H-isoindol-4-yl]ethynyl}-7-azaspiro[3.5]nonane-7-carbonyl)-2-methoxyphenyl]-1,2-dihydrospiro[indole-3,3'-pyrrolidine]-5'-carboxamide: Into an 8 mL vial were added 3-(4-{2-[7-(4-amino-3-methoxybenzoyl)-7-azaspiro[3.5]nonan-2-yl]ethynyl}-1-oxo-3H-isoindol-2-yl)piperidine-2,6-dione (36 mg, 0.07 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), N,N-dimethyl formamide (2 mL) and NMI (16 mg, 0.2 mmol, 2.9 eq), TCFH (24 mg, 0.1 mmol, 1.3 eq) at 25° C. The reaction mixture was stirred for 2 hours at 25° C. The resulting mixture was quenched with water (2 mL) and then extracted with ethyl acetate (3×2 mL). The combined organic layers were washed with brine (2 mL), dried over anhydrous sodium sulfate. After filtration, the filtrate was concentrated under vacuum. The crude residue was purified by Prep-TLC ($CH_3CN$/water=5:1) to give (2'S,3S,4'S,5'R)-6-chloro-4'-(3-chloro-2-fluorophenyl)-2'-(2,2-dimethylpropyl)-N-[4-(2-{2-[2-(2,6-dioxopiperidin-3-yl)-1-oxo-3H-isoindol-4-yl] ethynyl}-7-azaspiro[3.5]nonane-7-carbonyl)-2-methoxyphenyl]-1,2-dihydrospiro[indole-3,3'-pyrrolidine]-5'-carboxamide (20 mg, 31%) as a white solid. LC-MS: (ESI, m/z): M+1: 973. $^1$HNMR (400 MHz, DMSO-$d_6$) δ 10.99 (bs, 1H), 10.62 (s, 1H), 8.31 (d, J=8.1 Hz, 1H), 7.71 (d, J=7.5 Hz, 1H), 7.64 (d, J=7.6 Hz, 1H), 7.52 (t, J=7.6 Hz, 1H), 7.42 (d, J=7.6 Hz, 1H), 7.35 (t, J=7.2 Hz, 1H), 7.22 (dt, J=15.8, 8.0 Hz, 2H), 7.05 (d, J=1.8 Hz, 1H), 6.92 (d, J=8.3 Hz, 1H), 6.51 (dd, J=7.9, 1.9 Hz, 1H), 6.31 (d, J=2.0 Hz, 1H), 5.52 (s, 1H), 5.13 (dd, J=13.3, 5.1 Hz, 1H), 4.45 (d, J=17.8 Hz, 1H), 4.31 (dd, J=18.8, 9.5 Hz, 2H), 4.09 (d, J=9.5 Hz, 1H), 3.7-3.3(m, 8H), 3.86 (s, 3H), 2.60 (d, J=17.5 Hz, 2H), 2.30 (t, J=10.2 Hz, 2H), 1.99 (t, J=10.3 Hz, 3H), 1.62 (s, 4H), 1.35 (dd, J=14.2, 9.4 Hz, 1H), 1.27-1.12 (m, 2H), 0.91 (s, 9H).

Example 43: Preparation of (2'S,3S,4'S,5'R)-6-chloro-4'-(3-chloro-2-fluorophenyl)-2'-(2,2-dimethylpropyl)-N-{4-[(1R)-1-{2-[2-(2,6-dioxopiperidin-3-yl)-1-oxo-3H-isoindol-4-yl]ethynyl}-6-azaspiro[2.5] octane-6-carbonyl]-2-methoxyphenyl}-1,2-dihydrospiro[indole-3,3'-pyrrolidine]-5'-carboxamide Synthesis of 3-(4-{2-[(1R)-6-(3-methoxy-4-nitrobenzoyl)-6-azaspiro[2.5]octan-1-yl]ethynyl}-1-oxo-3H-isoindol-2-yl)piperidine-2,6-dione(assumed): To a stirred mixture of (1R)-1-ethynyl-6-(3-methoxy-4-nitrobenzoyl)-6-azaspiro[2.5]octane (100 mg, 0.3 mmol, 1.0 eq) and 3-(4-iodo-1-oxo-3H-isoindol-2-yl)piperidine-2,6-dione (118 mg, 0.3 mmol, 1.0 eq) in N,N-dimethylformamide (4 mL) and triethylamine (1 mL) were added CuI (6 mg, 0.1 mmol, 0.1 eq) and $Pd(PPh_3)_4$(36.8 mg, 0.1 mmol, 0.1 eq) in portions at 25° C. under nitrogen atmosphere. The reaction mixture was stirred for 14 hours at 25° C. The resulting mixture was diluted with water (20 mL) and then extracted with ethyl acetate (3×15 mL). The combined organic layers were washed with water (2×10 mL), dried over anhydrous sodium sulfate and concentrated in vacuo. The residue was purified by a flash column (silica gel, dichloromethane/$CH_3OH$=100:0 to 100:5) to give 3-(4-{2-[(1R)-6-(3-methoxy-4-nitrobenzoyl)-6-azaspiro[2.5]octan-1-yl]ethynyl}-1-oxo-3H-isoindol-2-yl)piperidine-2,6-dione (130 mg, 73%) as a brown solid. LC-MS (ESI, m/z) M+1: 557.

Synthesis of 3-(4-{2-[(1R)-6-(4-amino-3-methoxybenzoyl)-6-azaspiro[2.5]octan-1-yl]ethynyl}-1-oxo-3H-isoindol-2-yl)piperidine-2,6-dione: To a stirred mixture of 3-(4-{2-[(1R)-6-(3-methoxy-4-nitrobenzoyl)-6-azaspiro[2.5] octan-1-yl]ethynyl}-1-oxo-3H-isoindol-2-yl)piperidine-2,6-dione (130 mg, 0.2 mmol, 1.0 eq) and $NH_4Cl$ (100 mg, 1.9 mmol, 8.0 eq) in ethanol (4 mL) and water (1 mL) were added Fe (78 mg, 1.4 mmol, 6.0 eq) in portions at 25° C. The reaction mixture was stirred for 2 hours at 25° C. The resulting mixture was filtered, the filter cake was washed with ethanol (3×10 mL) and the filtrate was concentrated under vacuum. The residue was purified by a flash column (silica gel, dichloromethane/$CH_3OH$=100:0 to 100:5) to give 3-(4-{2-[(1R)-6-(4-amino-3-methoxybenzoyl)-6-azaspiro[2.5]octan-1-yl]ethynyl}-1-oxo-3H-isoindol-2-yl) piperidine-2,6-dione (100 mg, 81%) as a brown solid. $^1$HNMR (300 MHz, DMSO-$d_6$) δ 10.99 (s 1H), 7.69 (d, J=7.5 Hz, 1H), 7.67-7.59 (m, 1H), 7.51 (t, J=7.5 Hz, 1H), 6.86 (d, J=1.8 Hz, 1H), 6.81 (dd, J=8.0, 1.8 Hz, 1H), 6.61 (d, J=8.0 Hz, 1H), 5.20-5.10 (m, 3H), 4.43 (dd, J=17.7, 7.0 Hz, 1H), 4.30 (d, J=17.7 Hz, 1H), 3.78 (s, 3H), 3.75-3.45 (m, 4H), 2.99-2.82 (m, 1H), 2.60-2.50 (m, 2H), 2.45-2.40 (m, 3H), 2.11-1.96 (m, 1H), 1.68-1.58 (m, 3H), 1.55-1.40 (m, 3H), 1.07 (dd, J=8.4, 4.2 Hz, 1H), 0.90-0.84 (m, 1H).

Synthesis of (2'S,3S,4'S,5'R)-6-chloro-4'-(3-chloro-2-fluorophenyl)-2'-(2,2-dimethylpropyl)-N-{4-[(1R)-1-{2-[2-(2,6-dioxopiperidin-3-yl)-1-oxo-3H-isoindol-4-yl]ethynyl}-

6-azaspiro[2.5]octane-6-carbonyl]-2-methoxyphenyl}-1,2-dihydrospiro[indole-3,3'-pyrrolidine]-5'-carboxamide: To an 8 mL vial were added 3-(4-{2-[(1R)-6-(4-amino-3-methoxybenzoyl)-6-azaspiro[2.5]octan-1-yl]ethynyl}-1-oxo-3H-isoindol-2-yl)piperidine-2,6-dione (50 mg, 0.1 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (43 mg, 0.1 mmol, 1.0 eq), NMI (23 mg, 0.3 mmol, 3.0 eq), TCFH (40 mg, 0.1 mmol, 1.5 eq) and $CH_3CN$ (4 mL) at 25° C. The reaction mixture was stirred for 2 hours at 25° C. The crude product was purified by Prep-HPLC using the following conditions (Prep-HPLC-003): Column, SunFire Prep C18 OBD Column, 19150 mm, 5 μm 10 nm; mobile phase, water (0.05% $NH_3 \cdot H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(1R)-1-{2-[2-(2,6-dioxopiperidin-3-yl)-1-oxo-3H-isoindol-4-yl]ethynyl}-6-azaspiro[2.5]octane-6-carbonyl]-2-methoxyphenyl}-1,2-dihydrospiro[indole-3,3'-pyrrolidine]-5'-carboxamide (15 mg, 16%) was obtained as a white solid. LC-MS (ESI, m/z) M+1: 959/961. $^1$HNMR (300 MHz, DMSO-$d_6$) δ 10.98 (bs, 1H), 10.63 (d, J=4.8 Hz, 1H), 8.33 (d, J=8.1 Hz, 1H), 7.66 (dd, J=18.3, 7.5 Hz, 2H), 7.56-7.14 (m, 6H), 7.11 (d, J=1.5 Hz, 1H), 6.98 (d, J=8.1 Hz, 1H), 6.51 (dt, J=7.8, 1.8 Hz, 1H), 6.31 (d, J=1.8 Hz, 1H), 5.53 (d, J=2.1 Hz, 1H), 5.17-5.07 (m, 1H), 4.50-4.35 (m, 1H), 4.35-4.24 (m, 2H), 4.15-4.06 (m, 1H), 3.87 (s, 3H), 3.72-3.53 (m, 4H), 3.18 (d, J=10.5 Hz, 2H), 3.30-2.80 (m, 1H), 2.60-2.56 (m, 1H), 2.10-1.90 (m, 1H), 1.82-1.51 (m, 3H), 1.35 (dd, J=14.4, 9.3 Hz, 2H), 1.27-1.15 (m, 2H), 1.09 (s, 1H), 0.91 (s, 9H), 0.83 (s, 1H).

Example 44: Preparation of (2'S,3S,4'S,5'R)-6-chloro-4'-(3-chloro-2-fluorophenyl)-2'-(2,2-dimethylpropyl)-N—{4-[(1S)-1-{2-[2-(2,6-dioxopiperidin-3-yl)-1-oxo-3H-isoindol-4-yl]ethynyl}-6-azaspiro[2.5]octane-6-carbonyl]-2-methoxyphenyl}-1,2-dihydrospiro[indole-3,3'-pyrrolidine]-5'-carboxamide Synthesis of 3-(4-{2-[(1S)-6-(3-methoxy-4-nitrobenzoyl)-6-azaspiro[2.5]octan-1-yl]ethynyl}-1-oxo-3H-isoindol-2-yl)piperidine-2,6-dione: To a stirred mixture of (1S)-1-ethynyl-6-(3-methoxy-4-nitrobenzoyl)-6-azaspiro[2.5]octane (100 mg, 0.3 mmol, 1 eq) and 3-(4-iodo-1-oxo-3H-isoindol-2-yl)piperidine-2,6-dione (118 mg, 0.3 mmol, 1 eq) in N,N-dimethylformamide (4 mL) and triethylamine (1 mL) were added CuI (6 mg, 0.1 mmol, 0.1 eq) and $Pd(PPh_3)_4$ (37 mg, 0.1 mmol, 0.1 eq) in portions at 25° C. under nitrogen atmosphere. The reaction mixture was stirred for 14 hours at 25° C. The resulting mixture was diluted with water (20 mL) and then extracted with ethyl acetate (3×15 mL). The combined organic layers were washed with water (2×10 mL), dried over anhydrous sodium sulfate. After filtration, The residue was purified by a flash column (silica gel, dichloromethane/$CH_3OH$=100:0 to 100:5) to give 3-(4-{2-[(1S)-6-(3-methoxy-4-nitrobenzoyl)-6-azaspiro[2.5]octan-1-yl]ethynyl}-1-oxo-3H-isoindol-2-yl)piperidine-2,6-dione (130 mg, 73%) as a yellow solid. LC-MS (ESI, m/z) M+1: 557.

Synthesis of 3-(4-{2-[(1S)-6-(4-amino-3-methoxybenzoyl)-6-azaspiro[2.5]octan-1-yl]ethynyl}-1-oxo-3H-isoindol-2-yl)piperidine-2,6-dione: To a stirred mixture of 3-(4-{2-[(1S)-6-(3-methoxy-4-nitrobenzoyl)-6-azaspiro[2.5]octan-1-yl]ethynyl}-1-oxo-3H-isoindol-2-yl)piperidine-2,6-dione (130 mg, 0.23 mmol, 1.0 eq) and $NH_4Cl$ (100 mg, 1.9 mmol, 8.0 eq) in ethanol (4 mL) and water (1 mL) were added Fe (78 mg, 1.4 mmol, 6.0 eq) in portions at 25° C. The reaction mixture was stirred for 2 hours at ° C. The resulting mixture was filtered, the filter cake was washed with EtOH (3×10 mL). The filtrate was concentrated under vacuum. The residue was purified by a flash column (silica gel, dichloromethane/$CH_3OH$=100:0 to 100:5) to give 3-(4-{2-[(1S)-6-(4-amino-3-methoxybenzoyl)-6-azaspiro[2.5]octan-1-yl]ethynyl}-1-oxo-3H-isoindol-2-yl)piperidine-2,6-dione (100 mg, 81%) as a brown solid. LC-MS (ESI, m/z) M+1: 527.

Synthesis of (2'S,3S,4'S,5'R)-6-chloro-4'-(3-chloro-2-fluorophenyl)-2'-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]-2-methoxyphenyl}-1,2-dihydrospiro[indole-3,3'-pyrrolidine]-5'-carboxamide: To an 8 mL vial were were added 3-(4-{2-[(1S)-6-(4-amino-3-methoxybenzoyl)-6-azaspiro[2.5]octan-1-yl]ethynyl}-1-oxo-3H-isoindol-2-yl)piperidine-2,6-dione (50 mg, 0.1 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (43 mg, 0.1 mmol, 1.0 eq), NMI (23 mg, 0.3 mmol, 3.0 eq), TCFH (40 mg, 0.1 mmol, 1.5 eq) and $CH_3CN$ (4 mL) at 25° C. The reaction mixture was stirred for 2 hours at 25° C. The crude product was purified by Prep-HPLC using the following conditions (Prep-HPLC-003): Column, SunFire Prep C18 OBD Column, 19150 mm, 5 μm 10 nm; mobile phase, water (0.05% $NH_3 \cdot H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]-2-methoxyphenyl}-1,2-dihydrospiro[indole-3,3'-pyrrolidine]-5'-carboxamide (22 mg, 24%) was obtained as a white solid. LC-MS (ESI, m/z) M+1: 959/961. $^1$HNMR (300 MHz, DMSO-$d_6$) δ 10.98 (bs, 1H), 10.63 (d, J=4.8 Hz, 1H), 8.33 (d, J=8.1 Hz, 1H), 7.66 (dd, J=18.3, 7.5 Hz, 2H), 7.56-7.14 (m, 6H), 7.11 (d, J=1.5 Hz, 1H), 6.98 (d, J=8.1 Hz, 1H), 6.51 (dt, J=7.8, 1.8 Hz, 1H), 6.31 (d, J=1.8 Hz, 1H), 5.53 (d, J=2.1 Hz, 1H), 5.17-5.07 (m, 1H), 4.50-4.35 (m, 1H), 4.35-4.24 (m, 2H), 4.15-4.06 (m, 1H), 3.87 (s, 3H), 3.72-3.53 (m, 4H), 3.18 (d, J=10.5 Hz, 2H), 3.30-2.80 (m, 1H), 2.60-2.56 (m, 1H), 2.10-1.90 (m, 1H), 1.82-1.51 (m, 3H), 1.35 (dd, J=14.4, 9.3 Hz, 2H), 1.27-1.15 (m, 2H), 1.09 (s, 1H), 0.91 (s, 9H), 0.83 (s, 1H).

Example 45: Preparation of (2'S,3S,4'S,5'R)-6-chloro-4'-(3-chloro-2-fluorophenyl)-2'-(2,2-dimethylpropyl)-N-[4-({5-[2-(2,6-dioxopiperidin-3-yl)-1-oxo-3H-isoindol-4-yl]penta-2,4-diyn-1-yl}carbamoyl)-2-methoxyphenyl]-1,2-dihydrospiro[indole-3,3'-pyrrolidine]-5'-carboxamide Synthesis of tert-butyl N-[5-(trimethylsilyl)penta-2,4-diyn-1-yl]carbamate: A solution of CuI (8.5 g, 44.8 mmol, 1.1 eq) and TMEDA (9.5 g, 81.5 mmol, 2.0 eq) in dichloromethane (10 mL) was stirred for 15 min at 25° C. under argon atmosphere. After that, to the above solution was added a solution of trimethylsilylacetylene (4.0 g, 40.7 mmol, 1.0 eq) and tert-butyl N-(prop-2-yn-1-yl)carbamate (12.6 g, 81.5 mmol, 2.0 eq) in dichloromethane (10 mL) at 25° C. under oxygen atmosphere. The reaction mixture was stirred for 6 hours at 25° C. under oxygen atmosphere. The resulting mixture was filtered, the filter cake was washed with dichloromethane (310 mL). The filtrate was washed with water (3×10 mL), brine (10 mL) and then dried over anhydrous sodium sulfate. After filtration, the filtrate was concentrated under vacuum. The residue was purified by a flash column (silica gel, ethyl acetate/petroleum ether=0:1 to 1:5) to give tert-butyl N-[5-(trimethylsilyl)penta-2,4-diyn-1-yl]carbamate (2.1 g, 80%) as a brown oil. $^1$HNMR (300 MHz, DMSO-$d_6$) 7.37 (t, J=5.7 Hz, 1H), 3.85 (d, J=5.7 Hz, 2H), 1.39 (s, 9H), 0.18 (s, 9H).

Synthesis of (5-aminopenta-1,3-diyn-1-yl)trimethylsilane: A mixture of tert-butyl N-[5-(trimethylsilyl)penta-2,4-diyn-1-yl]carbamate (2.1 g, 80%) and HCl (4 M) in 1,4-dioxane (20 mL) was stirred for 14 hours at 25° C. The resulting mixture was concentrated under vacuum to give (5-aminopenta-1,3-diyn-1-yl)trimethylsilane (1.0 g, crude) as a brown solid.

Synthesis of 3-methoxy-4-nitro-N-[5-(trimethylsilyl) penta-2,4-diyn-1-yl]benzamide: To a stirred mixture of (5-aminopenta-1,3-diyn-1-yl)trimethylsilane (1.0 g, crude), 3-methoxy-4-nitrobenzoic acid (1.3 g, 6.6 mmol, 1.0 eq) and N-ethyl-N-isopropylpropan-2-amine (3.4 g, 26.4 mmol, 4.0 eq) in N,N-dimethylformamide (15 mL) was added HATU (3.3 g, 8.6 mmol, 1.3 eq) in portions at 25° C. The reaction mixture was stirred for 4 hours at 25° C. The resulting mixture was diluted with water (30 mL) and then extracted with ethyl acetate (3×15 mL). The combined organic layers were washed with water (3×10 mL) and brine (10 mL), dried over anhydrous sodium sulfate. After filtration, the filtrate was concentrated under vacuum. The residue was purified by a flash column (silica gel, ethyl acetate/petroleum ether=0:1 to 1:1) to give 3-methoxy-4-nitro-N-[5-(trimethylsilyl)penta-2,4-diyn-1-yl]benzamide (450 mg, 21%) as a brown solid. $^1$HNMR (300 MHz, DMSO-$d_6$) 9.29 (t, J=5.4 Hz, 1H), 7.98 (d, J=8.4 Hz, 1H), 7.74 (d, J=1.8 Hz, 1H), 7.56 (dd, J=8.4, 1.8 Hz, 1H), 4.25 (d, J=5.4 Hz, 2H), 4.0 (s, 3H), 0.18 (s, 9H).

Synthesis of N-{5-[2-(2,6-dioxopiperidin-3-yl)-1-oxo-3H-isoindol-4-yl]penta-2,4-diyn-1-yl}-3-methoxy-4-nitrobenzamide: A mixture of 3-(4-iodo-1-oxo-3H-isoindol-2-yl)piperidine-2,6-dione (336 mg, 0.9 mmol, 1.0 eq), $Pd(PPh_3)_4$ (105 mg, 0.1 mmol, 0.1 eq), $K_2CO_3$ (1004 mg, 7.3 mmol, 8.0 eq) and silver chloride (26 mg, 0.2 mmol, 0.2 eq) in N,N-dimethylformamide (10 mL) was stirred for 15 min at 25° C. under nitrogen atmosphere. To the above mixture was added 3-methoxy-4-nitro-N-[5-(trimethylsilyl)penta-2,4-diyn-1-yl]benzamide (300 mg, 0.9 mmol, 1.0 eq) and $CH_3OH$ (233 mg, 7.3 mmol, 8.0 eq) in portions at 25° C. The reaction mixture was stirred for additional 3 hours at 25° C. The resulting mixture was diluted with water (20 mL) and then extracted with ethyl acetate (3×10 mL). The combined organic layers were washed with water (3×10 mL) and brine (10 mL), dried over anhydrous sodium sulfate. After filtration, the filtrate was concentrated under vacuum. The residue was purified by reverse flash chousromatography using the following conditions: column, C18 silica gel; mobile phase A: water (0.05% TFA) and mobile phase B:$CH_3CN$, 20% to 70% gradient in 10 min; detector, UV 220 nm. Finally, N-{5-[2-(2,6-dioxopiperidin-3-yl)-1-oxo-3H-isoindol-4-yl]penta-2,4-diyn-1-yl}-3-methoxy-4-nitrobenzamide (230 mg, 28%) was obtained as a brown solid.

Synthesis of 4-amino-N-{5-[2-(2,6-dioxopiperidin-3-yl)-1-oxo-3H-isoindol-4-yl]penta-2,4-diyn-1-yl}-3-methoxy-benzamide: To a stirred mixture of N-{5-[2-(2,6-dioxopiperidin-3-yl)-1-oxo-3H-isoindol-4-yl]penta-2,4-diyn-1-yl}-3-methoxy-4-nitrobenzamide (200 mg, 0.2 mmol, 1.0 eq) and $NH_4Cl$ (94 mg, 1.6 mmol, 8.0 eq) in ethanol (4 mL) and water (1 mL) were added Fe (74 mg, 1.2 mmol, 6.0 eq) in portions at 25° C. The reaction mixture was stirred for 2 hours at 50° C. The resulting mixture was filtered, the filter cake was washed with ethanol (3×5 mL). The filtrate was concentrated under vacuum. The residue was purified by a flash column (silica gel, dichloromethane/$CH_3OH$=100:0 to 100:5) to give 4-amino-N-{5-[2-(2,6-dioxopiperidin-3-yl)-1-oxo-3H-isoindol-4-yl]penta-2,4-diyn-1-yl}-3-methoxy-benzamide (70 mg, 68%) as a brown solid. LC-MS (ESI, m/z) M+1: 471.

Synthesis of (2'S,3S,4'S,5'R)-6-chloro-4'-(3-chloro-2-fluorophenyl)-2'-(2,2-dimethylpropyl)-N-[4-({5-[2-(2,6-dioxopiperidin-3-yl)-1-oxo-3H-isoindol-4-yl]penta-2,4-diyn-1-yl}carbamoyl)-2-methoxyphenyl]-1,2-dihydrospiro [indole-3,3'-pyrrolidine]-5'-carboxamide: To an 8 mL vial were added 4-amino-N-{5-[2-(2,6-dioxopiperidin-3-yl)-1-oxo-3H-isoindol-4-yl]penta-2,4-diyn-1-yl}-3-methoxybenzamide (60 mg, 0.1 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (57 mg, 0.1 mmol, 1.0 eq), HATU (73 mg, 0.2 mmol, 1.5 eq), N-ethyl-N-isopropylpropan-2-amine (50 mg, 0.3 mmol, 3.0 eq) and N,N-dimethylformamide (5 mL) at 25° C. The reaction mixture was stirred for 2 hours at 25° C. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-[4-({5-[2-(2,6-dioxopiperidin-3-yl)-1-oxo-3H-isoindol-4-yl]penta-2,4-diyn-1-yl}carbamoyl)-2-methoxyphenyl]-1,2-dihydrospiro[indole-3,3'-pyrrolidine]-5'-carboxamide (6 mg, 5%) was obtained as white solid. LC-MS (ESI, m/z) M+1: 903/905. $^1$HNMR (300 MHz, DMSO-$d_6$) 10.99 (s, 1H), 10.71 (s, 1H), 9.01 (t, J=5.4 Hz, 1H), 8.37 (d, J=8.4 Hz, 1H), 7.83 (d, J=7.8 Hz, 2H), 7.64-7.51 (m, 2H), 7.47 (d, J=11.3 Hz, 1H), 7.43-7.31 (m, 2H), 7.30-7.25 (m, 1H), 7.20 (t, J=7.8 Hz, 1H), 6.51 (dd, J=7.8, 1.8 Hz, 1H), 6.31 (d, J=1.8 Hz, 1H), 5.52 (s, 1H), 5.14 (dd, J=13.2, 5.1 Hz, 1H), 4.56 (d, J=18.0 Hz, 1H), 4.40 (s, 1H), 4.37-4.27 (m, 3H), 4.12 (d, J=9.6 Hz, 1H), 3.91 (s, 3H), 3.72 (t, J=11.1 Hz, 1H), 3.53 (d, J=10.2 Hz, 1H), 3.25-3.15 (m, 2H), 3.0-2.84 (m, 1H), 2.68-2.55 (m, 2H), 2.04-1.95 (m, 2H), 1.41-1.30 (m, 1H), 0.92 (s, 9H).

Example 46: Preparation of (2'S,3S,4'S,5'R)-6-chloro-4'-(3-chloro-2-fluorophenyl)-2'-(2,2-dimethylpropyl)-N-{4-[(2R)-2-{4-[2-(2,6-dioxopiperidin-3-yl)-1-oxo-3H-isoindol-4-yl]buta-1,3-diyn-1-yl}piperidine-1-carbonyl]-2-methoxyphenyl}-1,2-dihydrospiro[indole-3,3'-pyrrolidine]-5'-carboxamide Synthesis of tert-butyl 2-ethynylpiperidine-1-carboxylate: To a stirred mixture of tert-butyl 2-formylpiperidine-1-carboxylate (10.0 g, 46.9 mmol, 1.0 eq) in $CH_3OH$ (100 mL) was added seyferth-gilbert homologation (11.7 g, 60.9 mmol, 1.3 eq) at 25° C. The reaction mixture was stirred for 6 hours at 25° C. The resulting mixture was quenched by the addition of water (1 mL), and then concentrated under vacuum. The residue was purified by a flash column (silica gel, ethyl acetate/petroleum ether=0:1 to 5:1) to give tert-butyl 2-ethynylpiperidine-1-carboxylate (9.5 g, 97%) as a yellow oil.

Synthesis of tert-butyl 2-[4-(trimethylsilyl)buta-1,3-diyn-1-yl]piperidine-1-carboxylate: A solution of CuI (9.0 g, 47.3 mmol, 1.1 eq) and TMEDA (10.0 g, 86.0 mmol, 2.0 eq) in dichloromethane (20 mL) was stirred for 15 min at 25° C. under argon atmosphere. To a stirred solution of tert-butyl 2-ethynylpiperidine-1-carboxylate (9.0 g, 43.0 mmol, 1.0 eq) and trimethylsilylacetylene (8.5 g, 86.0 mmol, 2.0 eq) in dichloromethane (90 mL) were added a mixture of CuI and TMEDA in portions at 25° C. under oxygen atmosphere.

The reaction mixture was stirred for 4 hours at 25° C. under oxygen atmosphere. The resulting mixture was filtered, the filter cake was washed with dichloromethane (3×10 mL). The filtrate was washed with water (3×10 mL) and brine (10 mL). The combined organic phase was dried anhydrous sodium sulfate, filtered and concentrated under vacuum. The residue was purified by a flash column (silica gel, ethyl acetate/petroleum ether=0:1 to 10:1) to give tert-butyl 2-[4-(trimethylsilyl)buta-1,3-diyn-1-yl]piperidine-1-carboxylate (4.2 g, crude) as a yellow solid.

Synthesis of 2-[4-(trimethylsilyl)buta-1,3-diyn-1-yl]piperidine: Into a 50 mL round-bottom flask were added tert-butyl 2-[4-(trimethylsilyl)buta-1,3-diyn-1-yl]piperidine-1-carboxylate (2 g, crude) and HCl in 1,4-dioxane (4 M, 20 mL) at 25° C. The reaction mixture was stirred for 14 hours at 25° C. The resulting mixture was concentrated under vacuum to give 2-[4-(trimethylsilyl)buta-1,3-diyn-1-yl]piperidine (1.3 g, crude) as a white solid. LC-MS (ESI, m/z) M+1: 206.

Synthesis of 1-(3-methoxy-4-nitrobenzoyl)-2-[4-(trimethylsilyl)buta-1,3-diyn-1-yl]piperidine: To a stirred mixture of 2-[4-(trimethylsilyl)buta-1,3-diyn-1-yl]piperidine (1.1 g, crude), 3-methoxy-4-nitrobenzoic acid (1.0 g, 5.4 mmol, 1.0 eq), DIEA (2.1 g, 16.1 mmol, 3.0 eq) in N,N-dimethylformamide (15 mL) was added HATU (2.6 g, 6.9 mmol, 1.3 eq) in portions at 25° C. The reaction mixture was stirred for 14 hours at 25° C. The resulting mixture was diluted with water (50 mL), and then extracted with ethyl acetate (3×20 mL). The combined organic layers were washed with water (3×10 mL) and brine (10 mL), dried over anhydrous sodium sulfate. After filtration, the filtrate was concentrated under vacuum. The residue was purified by a flash column (silica gel, ethyl acetate/petroleum ether=0:1 to 1:1) to give 1-(3-methoxy-4-nitrobenzoyl)-2-[4-(trimethylsilyl)buta-1,3-diyn-1-yl]piperidine (1.0 g, 49%) as a yellow solid.

Synthesis of 2-(buta-1,3-diyn-1-yl)-1-(3-methoxy-4-nitrobenzoyl)piperidine: To a stirred mixture of 1-(3-methoxy-4-nitrobenzoyl)-2-[4-(trimethylsilyl)buta-1,3-diyn-1-yl]piperidine (950 mg, 2.5 mmol, 1.0 eq) and $CH_3OH$ (15 mL) was added $K_2CO_3$ (1024 mg, 7.5 mmol, 3.0 eq) in portions at 25° C. The reaction mixture was stirred for 4 hours at 25° C. The resulting mixture was filtered, the filter cake was washed with $CH_3OH$ (3×10 mL). The filtrate was concentrated under vacuum. The residue was purified by a flash column (silica gel, ethyl acetate/petroleum ether=0:1 to 3:1) to give 2-(buta-1,3-diyn-1-yl)-1-(3-methoxy-4-nitrobenzoyl)piperidine (600 mg, 78%) as an off white solid. $^1$HNMR (300 MHz, DMSO-$d_6$) δ 7.96 (d, J=8.1 Hz, 1H), 7.37 (d, J=1.5 Hz, 1H), 7.11 (dd, J=8.1, 1.5 Hz, 1H), 4.02 (s, 3H), 3.77-3.70 (m, 1H), 3.50-3.40 (m, 1H), 3.35-3.30 (m, 1H), 2.0 (s, 1H), 2.0.1.30 (m, 6H).

Synthesis of (2R)-2-(buta-1,3-diyn-1-yl)-1-(3-methoxy-4-nitrobenzoyl)piperidine and (2S)-2-(buta-1,3-diyn-1-yl)-1-(3-methoxy-4-nitrobenzoyl)piperidine: 500 mg of 2-(buta-1,3-diyn-1-yl)-1-(3-methoxy-4-nitrobenzoyl)piperidine was purified by Chiral-SFC using the following conditions: Column: CHIRAL ART Cellulose-SB, 3*25 cm, 5 μm; mobile phase A: $CO_2$; mobile phase B: ethanol—Preparative; Flow rate: 50 mL/min; Gradient: isocratic 40% B; Detect 220 nm. Finally, (2R)-2-(buta-1,3-diyn-1-yl)-1-(3-methoxy-4-nitrobenzoyl)piperidine (200 mg, 40%) was obtained as a yellow solid and (2S)-2-(buta-1,3-diyn-1-yl)-1-(3-methoxy-4-nitrobenzoyl)piperidine (200 mg, 40%) was obtained as a yellow solid. 7A, $T_R$=1.793 min in CHIRAL-SFC, Column: 6:IG 100×4.6 mm 3.0 um. mobile phase A: $CO_2$; mobile phase B: $CH_3OH$, Start Conc. of Pump B: 10.0% in 4 min, Oven Temperature: 35° C. 7B, $T_R$=2.028 min in CHIRAL-SFC, Column: 6:IG 100×4.6 mm 3.0 um. mobile phase A: $CO_2$; mobile phase B: $CH_3OH$, Start Conc. of Pump B: 10.0% in 4 min, Oven Temperature: 35° C.

Synthesis of 3-(4-(((R)-1-(3-methoxy-4-nitrobenzoyl)piperidin-2-yl)buta-1,3-diyn-1-yl)-1-oxoisoindolin-2-yl)piperidine-2,6-dione: To a stirred mixture of (2R)-2-(buta-1,3-diyn-1-yl)-1-(3-methoxy-4-nitrobenzoyl)piperidine (180 mg, 0.6 mmol, 1.0 eq) and 3-(4-iodo-1-oxoisoindolin-2-yl)piperidine-2,6-dione (213 mg, 0.6 mmol, 1.0 eq) in N,N-dimethylformamide (4 mL) and triethylamine (1 mL) were added CuI (11 mg, 0.1 mmol, 0.1 eq) and $Pd(PPh_3)_4$(67 mg, 0.1 mmol, 0.1 eq) in portions at 25° C. under nitrogen atmosphere. The reaction mixture was stirred for 14 hours at 25° C. The resulting mixture was diluted with water (20 mL) and then extracted with ethyl acetate (3×15 mL). The combined organic layers were washed with water (2×10 mL) and brine (10 mL), dried over anhydrous sodium sulfate. After filtration, the filtrate was concentrated under vacuum.

The residue was purified by a flash column (silica gel, dichloromethane/$CH_3OH$=100:0 to 100:5) to give 3-(4-(((R)-1-(3-methoxy-4-nitrobenzoyl)piperidin-2-yl)buta-1,3-diyn-1-yl)-1-oxoisoindolin-2-yl)piperidine-2,6-dione (140 mg, 24%) as a brown solid. LC-MS (ESI, m/z) M+1: 555.

Synthesis of 3-(4-{4-[(2R)-1-(4-amino-3-methoxybenzoyl)piperidin-2-yl]buta-1,3-diyn-1-yl}-1-oxo-3H-isoindol-2-yl)piperidine-2,6-dione: To a stirred mixture of 3-(4-(((R)-1-(3-methoxy-4-nitrobenzoyl)piperidin-2-yl)buta-1,3-diyn-1-yl)-1-oxoisoindolin-2-yl)piperidine-2,6-dione (130 mg, 0.2 mmol, 1.0 eq) and Fe (76 mg, 1.4 mmol, 6.0 eq) in ethanol (4 mL) and water (1 mL) were added $NH_4Cl$ (100 mg, 1.9 mmol, 8.0 eq) in portions at 25° C. The reaction mixture was stirred for 2 hours at 50° C. The resulting mixture was filtered, the filter cake was washed with ethanol (3×10 mL). The filtrate was concentrated under vacuum. The residue was purified by a flash column (silica gel, dichloromethane/$CH_3OH$=100:0 to 100:5) to give 3-(4-{4-[(2R)-1-(4-amino-3-methoxybenzoyl)piperidin-2-yl]buta-1,3-diyn-1-yl}-1-oxo-3H-isoindol-2-yl)piperidine-2,6-dione (120 mg, 54%) as a brown solid. LC-MS (ESI, m/z) M+1: 525.

Synthesis of (2'S,3S,4'S,5'R)-6-chloro-4'-(3-chloro-2-fluorophenyl)-2'-(2,2-dimethylpropyl)-N-{4-[(2R)-2-{4-[2-(2,6-dioxopiperidin-3-yl)-1-oxo-3H-isoindol-4-yl]buta-1,3-diyn-1-yl}piperidine-1-carbonyl]-2-methoxyphenyl}-1,2-dihydrospiro[indole-3,3'-pyrrolidine]-5'-carboxamide: To an 8 mL vial were added 3-(4-{4-[(2R)-1-(4-amino-3-methoxybenzoyl)piperidin-2-yl]buta-1,3-diyn-1-yl}-1-oxo-3H-isoindol-2-yl)piperidine-2,6-dione (80 mg, 0.2 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (69 mg, 0.2 mmol, 1.0 eq), TCFH (64 mg, 0.2 mmol, 1.5 eq), NMI (38 mg, 0.6 mmol, 3.0 eq) and $CH_3CN$ (4 mL) at 25° C. The reaction mixture was stirred for 2 hours at 25° C. The crude product was purified by Prep-HPLC using the following conditions (Prep-HPLC-003): Column, SunFire Prep C18 OBD Column, 19 150 mm, 5 μm 10 nm; mobile phase, water (0.05% $NH_3 \cdot H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(2R)-2-{4-[2-(2,6-dioxopiperidin-3-yl)-1-oxo-3H-isoindol-4-yl]buta-1,3-diyn-1-yl}piperidine-1-carbonyl]-2-methoxyphenyl}-1,2-dihydrospiro[indole-3,3'-pyrrolidine]-5'-carboxamide (15 mg, 10%) was obtained as a white solid. LC-MS (ESI, m/z) M+1: 957/959. $^1$HNMR (300 MHz, Chloroform-d) δ 8.40-8.06 (m, 2H), 7.92 (d, J=7.6 Hz, 1H), 7.71 (d, J=7.7 Hz, 1H), 7.57-7.30 (m, 3H), 7.21-6.90 (m, 4H), 6.74 (d, J=8.7 Hz, 1H), 6.51 (d, J=1.8 Hz, 1H), 5.30-5.20 (m, 1H), 4.60 (d, J=16.8 Hz, 1H), 4.44 (d, J=16.8 Hz, 1H), 4.30-4.14 (m, 1H), 3.56 (d, J=114.2 Hz, 7H), 3.03-2.84 (m, 2H), 2.51-2.37 (m, 1H), 2.32-2.19 (m, 1H), 2.07-1.65 (m, 5H), 1.28 (s, 6H), 0.98 (s, 9H).

Example 47: Preparation of (2'S,3S,4'S,5'R)-6-chloro-4'-(3-chloro-2-fluorophenyl)-2'-(2,2-dimethylpropyl)-N-{4-[(2S)-2-{4-[2-(2,6-dioxopiperidin-3-yl)-1-oxo-3H-isoindol-4-yl]buta-1,3-diyn-1-yl}piperidine-1-carbonyl]-2-methoxyphenyl}-1,2-dihydrospiro[indole-3,3'-pyrrolidine]-5'-carboxamide Synthesis of 3-(4-{4-[(2S)-1-(3-methoxy-4-nitrobenzoyl)piperidin-2-yl]buta-1,3-diyn-1-yl}-1-oxo-3H-isoindol-2-yl)piperidine-2,6-dione: To a stirred mixture of (2S)-2-(buta-1,3-diyn-1-yl)-1-(3-methoxy-4-nitrobenzoyl)piperidine (180 mg, 0.6 mmol, 1.0 eq) and 3-(4-iodo-1-oxo-3H-isoindol-2-yl)piperidine-2,6-dione (213 mg, 0.6 mmol, 1.0 eq) in N,N-dimethylformamide (4 mL) and triethylamine (1 mL) were added CuI (11 mg, 0.1 mmol, 0.1 eq) and $Pd(PPh_3)_4$ (67 mg, 0.1 mmol, 0.1 eq) in portions at 25° C. under nitrogen atmosphere. The reaction mixture was stirred for 14 hours at 25° C. The resulting mixture was diluted with water (20 mL) and then extracted with ethyl acetate (3×15 mL). The combined organic layers were washed with water (2×10 mL) and brine (10 mL), dried over anhydrous sodium sulfate. After filtration, the filtrate was concentrated under vacuum. The residue was purified by a flash column (silica gel, dichloromethane/$CH_3OH$=100:0 to 100:5) to give 3-(4-{4-[(2S)-1-(3-methoxy-4-nitrobenzoyl)piperidin-2-yl]buta-1,3-diyn-1-yl}-1-oxo-3H-isoindol-2-yl)piperidine-2,6-dione (170 mg, crude) as a brown solid. LC-MS (ESI, m/z) M+1: 555.

Synthesis of 3-(4-{4-[(2S)-1-(4-amino-3-methoxybenzoyl)piperidin-2-yl]buta-1,3-diyn-1-yl}-1-oxo-3H-isoindol-2-yl)piperidine-2,6-dione: To a stirred mixture of 3-(4-{4-[(2S)-1-(3-methoxy-4-nitrobenzoyl)piperidin-2-yl]buta-1,3-diyn-1-yl}-1-oxo-3H-isoindol-2-yl)piperidine-2,6-dione (170 mg, 0.3 mmol, 1.0 eq) and Fe (103 mg, 1.8 mmol, 6.0 eq), ethanol (4 mL) and water (1 mL) were added $NH_4Cl$ (131 mg, 2.5 mmol, 8.0 eq) in portions at 25° C. The reaction mixture was stirred for 2 hours at 50° C. The resulting mixture was filtered, the filter cake was washed with ethanol (3×10 mL). The filtrate was concentrated under vacuum. The residue was purified by a flash column (silica gel, dichloromethane/$CH_3OH$=100:0 to 100:5) to give 3-(4-{4-[(2S)-1-(4-amino-3-methoxybenzoyl)piperidin-2-yl]buta-1,3-diyn-1-yl}-1-oxo-3H-isoindol-2-yl)piperidine-2,6-dione (110 mg, 43%) as a brown solid. LC-MS (ESI, m/z) M+1: 525.

Synthesis of (2'S,3S,4'S,5'R)-6-chloro-4'-(3-chloro-2-fluorophenyl)-2'-(2,2-dimethylpropyl)-N-{4-[(2S)-2-{4-[2-(2,6-dioxopiperidin-3-yl)-1-oxo-3H-isoindol-4-yl]buta-1,3-diyn-1-yl}piperidine-1-carbonyl]-2-methoxyphenyl}-1,2-dihydrospiro[indole-3,3'-pyrrolidine]-5'-carboxamide: Into an 8 mL vial were added 3-(4-{4-[(2S)-1-(4-amino-3-methoxybenzoyl)piperidin-2-yl]buta-1,3-diyn-1-yl}-1-oxo-3H-isoindol-2-yl)piperidine-2,6-dione (80 mg, 0.2 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (69 mg, 0.2 mmol, 1.0 eq), TCFH (56 mg, 0.2 mmol, 1.3 eq), NMI (25 mg, 0.3 mmol, 2.0 eq) and $CH_3CN$ (4 mL) at 25° C. The reaction mixture was stirred for 2 hours at 25° C. The crude product was purified by Prep-HPLC using the following conditions (Prep-HPLC-003): Column, SunFire Prep C18 OBD Column, 19 150 mm, 5 μm 10 nm; mobile phase, water (0.05% $NH_3 \cdot H_2O$) and $CH_3CN$ (30% $CH_3CN$ up to 78% in 8 min); Detector, UV 220 nm. Finally, (2'S,3S,4'S,5'R)-6-chloro-4'-(3-chloro-2-fluorophenyl)-2'-(2,2-dimethylpropyl)-N-{4-[(2S)-2-{4-[2-(2,6-dioxopiperidin-3-yl)-1-oxo-3H-isoindol-4-yl]buta-1,3-diyn-1-yl}piperidine-1-carbonyl]-2-methoxyphenyl}-1,2-dihydrospiro[indole-3,3'-pyrrolidine]-5'-carboxamide (16 mg, 11%) was obtained as a white solid. LC-MS (ESI, m/z) M+1: 957/959. $^1$HNMR (300 MHz, Chloroform-d) δ 8.40-8.06 (m, 2H), 7.92 (d, J=7.6 Hz, 1H), 7.71 (d, J=7.7 Hz, 1H), 7.57-7.30 (m, 3H), 7.21-6.90 (m, 4H), 6.74 (d, J=8.7 Hz, 1H), 6.51 (d, J=1.8 Hz, 1H), 5.30-5.20 (m, 1H), 4.60 (d, J=16.8 Hz, 1H), 4.44 (d, J=16.8 Hz, 1H), 4.30-4.14 (m, 1H), 3.56 (d, J=114.2 Hz, 7H), 3.03-2.84 (m, 2H), 2.51-2.37 (m, 1H), 2.32-2.19 (m, 1H), 2.07-1.65 (m, 5H), 1.28 (s, 6H), 0.98 (s, 9H).

Example 48: Preparation of (2'S,3S,4'S,5'R)-6-chloro-4'-(3-chloro-2-fluorophenyl)-2'-(2,2-dimethylpropyl)-N-{4-[(3R)-3-{2-[2-(2,6-dioxopiperidin-3-yl)-1-oxo-3H-isoindol-4-yl]ethynyl}pyrrolidine-1-carbonyl]-2-methoxyphenyl}-1,2-dihydrospiro[indole-3,3'-pyrrolidine]-5'-carboxamide Synthesis of tert-butyl 3-ethynylpyrrolidine-1-carboxylate: Into a 250 mL round-bottom flask were added tert-butyl 3-formylpyrrolidine-1-carboxylate (4.0 g, 20.1 mmol, 1.0 eq), $K_2CO_3$ (5.6 g, 40.2 mmol, 2.0 eq), MeOH (50 mL) and seyferth-gilbert homologation (5.8 g, 30.1 mmol, 1.5 eq) at 0° C. The reaction mixture was stirred for 2 hours at 25° C. The resulting mixture was quenched by the addition of water (30 mL) at 0° C., and then extracted with EtOAc (3×30 mL). The combined organic layers were washed with brine (30 mL), dried over anhydrous sodium sulfate. After filtration, the filtrate was concentrated under vacuum. The crude residue was purified by a flash column (silica gel, petroleum ether: ethyl acetate=3:1) to give tert-butyl 3-ethynylpyrrolidine-1-carboxylate (3.8 g, 97.0%) as a colorless oil. $^1$HNMR (300 MHz, DMSO-$d_6$) δ 3.66 (d, J=11.8 Hz, 1H), 3.49 (t, J=8.6 Hz, 1H), 3.34 (ddd, J=10.5, 7.7, 5.3 Hz, 1H), 3.29-3.19 (m, 1H), 3.13 (t, J=8.4 Hz, 1H), 3.02 (d, J=1.8 Hz, 2H), 2.18-1.99 (m, 1H), 1.82 (q, J=11.3, 9.7 Hz, 1H), 1.40 (s, 10H).

Synthesis of 3-ethynylpyrrolidine: Into a 50 mL round-bottom flask were added tert-butyl 3-ethynylpyrrolidine-1-carboxylate (1.8 g, 9.2 mmol, 1.0 eq) and 4 M HCl in 1,4-dioxane (10 mL) at 25° C. The reaction mixture was stirred for 1 hour at 25° C. The resulting mixture was concentrated under vacuum to give 3-ethynylpyrrolidine (1.2 g, 96.0%). $^1$HNMR (300 MHz, DMSO-$d_6$) δ 3.72 (d, J=10.9 Hz, 1H), 3.50-3.34 (m, 1H), 3.34-3.22 (m, 1H), 3.20-3.07 (m, 3H), 2.99 (dq, J=13.1, 6.4 Hz, 1H), 2.20 (dtd, J=12.6, 7.0, 5.6 Hz, 1H), 1.86 (dq, J=12.6, 7.9 Hz, 1H).

Synthesis of 3-ethynyl-1-(3-methoxy-4-nitrobenzoyl)pyrrolidine: Into a 50 mL round-bottom flask were added 3-ethynylpyrrolidine (1.0 g, 10.5 mmol, 1.0 eq), HATU (4.4 g, 11.6 mmol, 1.1 eq), DIEA (4.1 g, 31.5 mmol, 3.0 eq) and N,N-dimethylformamide (10 mL) at 25° C. The reaction mixture was stirred for 2 hours at 25° C. The reaction was quenched with water (5 mL), and then extracted with EtOAc (3×5 mL). The combined organic layers were washed with brine (5 mL), dried over anhydrous sodium sulfate. After filtration, the filtrate was concentrated under vacuum. The crude residue was purified by a flash column (silica gel, petroleum ether: ethyl acetate=1:1) to give 3-ethynyl-1-(3-methoxy-4-nitrobenzoyl)pyrrolidine (1.3 g, 45.0%) as a yellow solid. $^1$HNMR (300 MHz, DMSO-$d_6$) δ 8.10-7.86

(m, 1H), 7.43 (d, J=1.5 Hz, 1H), 7.21 (ddd, J=8.2, 2.7, 1.5 Hz, 1H), 3.96 (s, 3H), 3.80 (dd, J=11.6, 7.3 Hz, 1H), 3.68-3.57 (m, 1H), 3.55-3.45 (m, 1H), 3.45-3.34 (m, 2H), 3.08 (dd, J=14.4, 1.8 Hz, 1H), 2.18 (ddt, J=18.4, 12.1, 6.1 Hz, 1H), 1.91 (td, J=12.8, 7.7 Hz, 1H).

Synthesis of 4-[(3R)-3-ethynylpyrrolidine-1-carbonyl]-2-methoxyaniline (assumed): Into a 40 mL vial were added 3-ethynyl-1-(3-methoxy-4-nitrobenzoyl)pyrrolidine (400 mg, 1 mmol, 1.0 eq) and EtOH (6 mL), water (2 mL), Fe (325 mg, 5.8 mmol, 4.0 eq), $NH_4Cl$ (624 mg, 11.6 mmol, 8.0 eq). The reaction mixture was stirred for 2 hours at 50° C. The resulting mixture was filtered, the filter cake was washed with MeOH (3×10 mL) and the filtrate was concentrated under vacuum. The crude residue was purified by Prep-SFC: Column: CHIRAL ART Amylose-C NEO, 3*25 cm, 5 μm; Mobile Phase A: $CO_2$, Mobile Phase B: IPA: HEX=1: 1(0.1.0% 2 M $NH_3$·MeOH); Flow rate: 80 mL/min; Gradient: isocratic 40.0% B; Column Temperature (° C.): 35; Back Pressure(bar): 100; Wave Length: 220 nm; RT1 (min): 10.7; $RT_2$(min): 15.88; Sample Solvent: IPA; Injection Volume: 9 mL; Number Of Runs: 5. Finally, 4-[(3R)-3-ethynylpyrrolidine-1-carbonyl]-2-methoxyaniline (100 mg, 28.0%) was obtained as a light yellow solid. LC-MS (ESI, m/z) M+1: 245.

Synthesis of 3-(4-{2-[(3R)-1-(4-amino-3-methoxybenzoyl)pyrrolidin-3-yl]ethynyl}-1-oxo-3H-isoindol-2-yl)piperidine-2,6-dione: Into an 8 mL vial were added 4-[(3R)-3-ethynylpyrrolidine-1-carbonyl]-2-methoxyaniline (100 mg, 0.4 mmol, 1.0 eq) and N,N-dimethylformamide (3 mL), DIEA (124 mg, 1.2 mmol, 3.0 eq) and 3-(4-iodo-1-oxo-3H-isoindol-2-yl)piperidine-2,6-dione (166 mg, 0.4 mmol, 1.1 eq), CuI (15 mg, 0.1 mmol, 0.2 eq), $Pd(PPh_3)_4$(47 mg, 0.04 mmol, 0.1 eq) under nitrogen atmosphere. The reaction mixture was stirred for 2 hours at 70° C. under nitrogen atmosphere. The resulting mixture was quenched with water (5 mL) and then extracted with DCM (3×6 mL). The combined organic layers were dried over anhydrous sodium sulfate. After filtration, the filtrate was concentrated under vacuum. The crude residue was purified by silica gel column choursomatography and eluted with dichloromethane/methanol=10:1 to give 3-(4-{2-[(3R)-1-(4-amino-3-methoxybenzoyl)pyrrolidin-3-yl]ethynyl}-1-oxo-3H-isoindol-2-yl)piperidine-2,6-dione (110 mg, 55.0%) as a light yellow solid. LC-MS (ESI, m/z) M+1: 487.

Synthesis of (2'S,3S,4'S,5'R)-6-chloro-4'-(3-chloro-2-fluorophenyl)-2'-(2,2-dimethylpropyl)-N-{4-[(3R)-3-{2-[2-(2,6-dioxopiperidin-3-yl)-1-oxo-3H-isoindol-4-yl]ethynyl}pyrrolidine-1-carbonyl]-2-methoxyphenyl}-1,2-dihydrospiro[indole-3,3'-pyrrolidine]-5'-carboxamide: Into an 8 mL vial were added 3-(4-{2-[(3R)-1-(4-amino-3-methoxybenzoyl)pyrrolidin-3-yl]ethynyl}-1-oxo-3H-isoindol-2-yl)piperidine-2,6-dione (60 mg, 0.1 mmol, 1.0 eq) and N,N-dimethylformamide (4 mL), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (61 mg, 0.1 mmol, 1.1 eq) and HATU (52 mg, 0.1 mmol, 1.1 eq) and DIEA (32 mg, 0.2 mmol, 2.0 eq). The reaction mixture was stirred for 4 hours at 25° C. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and $CH_3CN$ (35.0% $CH_3CN$ up to 75.0% in 10 min). Finally, (2'S,3S,4'S,5'R)-6-chloro-4'-(3-chloro-2-fluorophenyl)-2'-(2,2-dimethylpropyl)-N-{4-[(3R)-3-{2-[2-(2,6-dioxopiperidin-3-yl)-1-oxo-3H-isoindol-4-yl]ethynyl}pyrrolidine-1-carbonyl]-2-methoxyphenyl}-1,2-dihydrospiro[indole-3,3'-pyrrolidine]-5'-carboxamide (20 mg, 17.6%) was obtained as a white solid. LC-MS (ESI, m/z) M+1: 919/921. $^1$HNMR (300 MHz, DMSO-$d_6$) δ 11.0 (s, 1H), 10.66 (s, 1H), 8.38-8.29 (m, 1H), 7.78-7.72 (m, 1H), 7.71-7.58 (s, 1H), 7.56-7.47 (m, 1H), 7.45-7.38 (m, 1H), 7.36-7.29 (m, 1H), 7.28-7.24 (m, 1H), 7.23-7.17 (m, 2H), 7.16-7.11 (m, 1H), 6.51 (dd, J=7.8, 1.8 Hz, 1H), 6.31 (d, J=1.8 Hz, 1H), 5.53 (s, 1H), 5.19-5.09 (m, 1H), 4.32 (dd, J=20.7, 11.4 Hz, 2H), 4.11 (d, J=9.3 Hz, 1H), 3.87 (s, 3H), 3.73 (t, J=11.2 Hz, 1H), 3.62-3.48 (m, 3H), 3.18 (d, J=10.5 Hz, 2H), 3.0-2.85 (m, 1H), 2.63 (s, 1H), 1.99 (s, 1H), 1.46 (s, 1H), 1.42-1.28 (m, 2H), 1.24 (s, 6H), 0.91 (s, 9H).

Example 49: Preparation of ((2'S,3S,4'S,5'R)-6-chloro-4'-(3-chloro-2-fluorophenyl)-2'-(2,2-dimethylpropyl)-N-{4-[(3S)-3-{2-[2-(2,6-dioxopiperidin-3-yl)-1-oxo-3H-isoindol-4-yl]ethynyl}pyrrolidine-1-carbonyl]-2-methoxyphenyl}-1,2-dihydrospiro[indole-3,3'-pyrrolidine]-5'-carboxamide Synthesis of 4-[(3s)-3-ethynylpyrrolidine-1-carbonyl]-2-methoxyaniline: Into a 40 mL vial were added 3-ethynyl-1-(3-methoxy-4-nitrobenzoyl)pyrrolidine (400 mg, 1.4 mmol, 1.0 eq) and EtOH (6 mL), water (2 mL), Fe (325 mg, 5.8 mmol, 4.0 eq), $NH_4Cl$ (624 mg, 11.6 mmol, 8.0 eq). The reaction mixture was stirred for 2 hours at 50° C. The resulting mixture was filtered, the filter cake was washed with MeOH (3×10 mL) and the filtrate was concentrated under vacuum. The crude residue was purified by Prep-SFC: Column: CHIRAL ART Amylose-C NEO, 3*25 cm, 5 μm; Mobile Phase A: $CO_2$, Mobile Phase B: IPA: HEX=1: 1(0.1.0%2M $NH_3$·MeOH); Flow rate: 80 mL/min; Gradient: isocratic 40.0% B; Column Temperature (° C.): 35; Back Pressure(bar): 100; Wave Length: 220 nm; RT1(min): 10.7; $RT_2$(min): 15.88; Sample Solvent: IPA; Injection Volume: 9 mL; Number Of Runs: 5. Finally, 4-[(3S-3-ethynylpyrrolidine-1-carbonyl]-2-methoxyaniline (100 mg, 28.0%) was obtained as a light yellow solid. LC-MS (ESI, m/z) M+1: 245.

Synthesis of (2'S,3S,4'S,5'R)-6-chloro-4'-(3-chloro-2-fluorophenyl)-2'-(2,2-dimethylpropyl)-N-{4-[(3R)-3-{2-[2-(2,6-dioxopiperidin-3-yl)-1-oxo-3H-isoindol-4-yl]ethynyl}pyrrolidine-1-carbonyl]-2-methoxyphenyl}-1,2-dihydrospiro[indole-3,3'-pyrrolidine]-5'-carboxamide: Into an 8 mL vial were added 4-[(3R)-3-ethynylpyrrolidine-1-carbonyl]-2-methoxyaniline (100 mg, 0.4 mmol, 1.0 eq) and N,N-dimethylformamide (3 mL), DIEA (124 mg, 1.2 mmol, 3.0 eq) and 3-(4-iodo-1-oxo-3H-isoindol-2-yl)piperidine-2,6-dione (166 mg, 0.4 mmol, 1.1 eq), CuI (15 mg, 0.1 mmol, 0.2 eq), $Pd(PPh_3)_4$ (47 mg, 0.04 mmol, 0.1 eq) under nitrogen atmosphere. The reaction mixture was stirred for 2 hours at 70° C. under nitrogen atmosphere. The resulting mixture was quenched with water (5 mL) and extracted with DCM (3×6 mL). The combined organic layers were dried over anhydrous sodium sulfate. After filtration, the filtrate was concentrated under vacuum. The crude residue was purified by silica gel column choursomatography, eluted with dichloromethanel methanol=10:1 to give 3-(4-{2-[(3S)-1-(4-amino-3-methoxybenzoyl)pyrrolidin-3-yl]ethynyl}-1-oxo-3H-isoindol-2-yl)piperidine-2,6-dione (120 mg, 60%) as a light yellow solid. LC-MS (ESI, m/z) M+1: 487.

Synthesis of (2'S,3S,4'S,5'R)-6-chloro-4'-(3-chloro-2-fluorophenyl)-2'-(2,2-dimethylpropyl)-N-{4-[(3S)-3-{2-[2-(2,6-dioxopiperidin-3-yl)-1-oxo-3H-isoindol-4-yl]ethynyl}pyrrolidine-1-carbonyl]-2-methoxyphenyl}-1,2-dihydrospiro[indole-3,3'-pyrrolidine]-5'-carboxamide: Into an 8 mL vial were added 3-(4-{2-[(3S)-1-(4-amino-3-methoxybenzoyl)pyrrolidin-3-yl]ethynyl}-1-oxo-3H-isoindol-2-yl)piperidine-2,6-dione (60 mg, 0.1 mmol, 1.0 eq) and (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (61 mg, 0.1 mmol, 1.1 eq), N,N-dimethylformamide (4 mL), HATU (52 mg, 0.1 mmol, 1.1 eq) and DIEA (31 mg, 0.2 mmol, 2.0 eq). The reaction mixture was stirred for 4 hours at 25° C. The crude product was purified by Prep-HPLC using the following conditions (Prep-HPLC-003): Column, SunFire Prep C18 OBD Column, 19*150 mm, 5 μm 10 nm; mobile phase, water (0.05% $NH_3 \cdot H_2O$) and $CH_3CN$ (35.0% $CH_3CN$ up to 75.0% in 10 min). Finally, (2'S,3S,4'S,5'R)-6-chloro-4'-(3-chloro-2-fluorophenyl)-2'-(2,2-dimethylpropyl)-N-{4-[(3S)-3-{2-[2-(2,6-dioxopiperidin-3-yl)-1-oxo-3H-isoindol-4-yl]ethynyl}pyrrolidine-1-carbonyl]-2-methoxyphenyl}-1,2-dihydrospiro[indole-3,3'-pyrrolidine]-5'-carboxamide (19 mg, 16.7%) was obtained as a white solid. LC-MS (ESI, m/z) M+1: 919/921. $^1$HNMR (300 MHz, DMSO-$d_6$) δ 11.0 (s, 1H), 10.66 (s, 1H), 8.38-8.29 (m, 1H), 7.78-7.72 (m, 1H), 7.71-7.58 (s, 1H), 7.56-7.47 (m, 1H), 7.45-7.38 (m, 1H), 7.36-7.29 (m, 1H), 7.28-7.24 (m, 1H), 7.23-7.17 (m, 2H), 7.16-7.11 (m, 1H), 6.51 (dd, J=7.8, 1.8 Hz, 1H), 6.31 (d, J=1.8 Hz, 1H), 5.53 (s, 1H), 5.19-5.09 (m, 1H), 4.32 (dd, J=20.7, 11.4 Hz, 2H), 4.11 (d, J=9.3 Hz, 1H), 3.87 (s, 3H), 3.73 (t, J=11.2 Hz, 1H), 3.62-3.48 (m, 3H), 3.18 (d, J=10.5 Hz, 2H), 3.0-2.85 (m, 1H), 2.63 (s, 1H), 1.99 (s, 1H), 1.46 (s, 1H), 1.42-1.28 (m, 2H), 1.24 (s, 6H), 0.91 (s, 9H).

Example 50: Preparation of (2'S,3S,4'S,5'R)-6-chloro-4'-(3-chloro-2-fluorophenyl)-2'-(2,2-dimethylpropyl)-N-(4-{[(3R)-1-{3-[2-(2,6-dioxopiperidin-3-yl)-1-oxo-3H-isoindol-4-yl]prop-2-yn-1-yl}piperidin-3-yl]carbamoyl}-2-methoxyphenyl)-1,2-dihydrospiro[indole-3,3'-pyrrolidine]-5'-carboxamide Synthesis of tert-butyl (3R)-3-(3-methoxy-4-nitrobenzamido)piperidine-1-carboxylate: Into a 50 mL round flask, were placed tert-butyl (3R)-3-aminopiperidine-1-carboxylate (1.0 g, 5.0 mmol, 1.0 eq), 3-methoxy-4-nitrobenzoic acid (980 mg, 5.0 mmol, 1.0 eq), HATU (2.1 g, 5.5 mmol, 1.1 eq), DIEA (1.3 g, 10.0 mmol, 2.0 eq), N,N-dimethylformamide (10 mL). The reaction mixture was stirred for 2 hours at 25° C. The resulting mixture was then quenched by the addition of water (100 mL) and then extracted with ethyl acetate (2×100 mL). The combined organic layers combined, washed with brine (2×100 mL) and dried over anhydrous sodium sulfate. After filtration, the filtrate was concentrated under vacuum. The crude residue was purified by a flash column (silica gel, ethyl acetate/petroleum ether=1:0) to give tert-butyl (3R)-3-(3-methoxy-4-nitrobenzamido)piperidine-1-carboxylate (1.5 g, 79.2%) as light yellow oil. LC-MS (ESI, m/z) M+1: 380.

Synthesis of 3-methoxy-4-nitro-N-[(3R)-piperidin-3-yl]benzamide hydrochloride: Into a 100 mL round-bottom flask were placed tert-butyl (3R)-3-(3-methoxy-4-nitrobenzamido)piperidine-1-carboxylate (1.4 g, 3.7 mmol, 1.0 eq), dichloromethane (15 mL), HCl (gas) in 1,4-dioxane (15 mL). The reaction mixture was stirred for 1 hour at 25° C. The resulting mixture was concentrated under vacuum to give 3-methoxy-4-nitro-N-[(3R)-piperidin-3-yl]benzamide hydrochloride (900 mg, crude) as light yellow solid. LC-MS (ESI, m/z) M+1: 280.

Synthesis of N-[(3R)-1-{3-[2-(2,6-dioxopiperidin-3-yl)-1-oxo-3H-isoindol-4-yl]prop-2-yn-1-yl}piperidin-3-yl]-3-methoxy-4-nitrobenzamide: Into a 20 mL sealed tube was added 3-[2-(2,6-dioxopiperidin-3-yl)-1-oxo-3H-isoindol-4-yl]prop-2-ynal (200 mg, 0.7 mmol, 1.0 eq), 3-methoxy-4-nitro-N-[(3R)-piperidin-3-yl]benzamide hydrochloride (256 mg, 0.8 mmol, 1.2 eq), EtOH (3 mL), $NaBH_3CN$ (212 mg, 3.4 mmol, 5.0 eq) and $ZnCl_2$ (552 mg, 4.1 mmol, 6.0 eq). The reaction mixture was stirred for 4 hours at 25° C. The resulting mixture was then quenched by the addition of water (30 mL) and then extracted with dichloromethane/methanol (10:1, 2×50 mL). The combined organic phase was washed with brine (2×50 mL), dried over anhydrous sodium sulfate. After filtration, the filtrate was concentrated under vacuum. The crude residue was purified by a flash column (silica gel, dichloromethane/methanol=10:1) to give N-[(3R)-1-{3-[2-(2,6-dioxopiperidin-3-yl)-1-oxo-3H-isoindol-4-yl]prop-2-yn-1-yl}piperidin-3-yl]-3-methoxy-4-nitrobenzamide (110 mg, 29.1%) as light yellow solid. LC-MS (ESI, m/z) M+1: 560.

Synthesis of 4-amino-N-[(3R)-1-{3-[2-(2,6-dioxopiperidin-3-yl)-1-oxo-3H-isoindol-4-yl]prop-2-yn-1-yl}piperidin-3-yl]-3-methoxybenzamide: Into a 20 mL sealed tube were placed N-[(3R)-1-{3-[2-(2,6-dioxopiperidin-3-yl)-1-oxo-3H-isoindol-4-yl]prop-2-yn-1-yl}piperidin-3-yl]-3-methoxy-4-nitrobenzamide (100 mg, 0.2 mmol, 1.0 eq), Fe (40 mg, 0.7 mmol, 4.0 eq), $NH_4Cl$ (76 mg, 1.4 mmol, 8.0 eq), EtOH (3 mL), water (1 mL). The reaction mixture was stirred for 2 hours at 50° C. The resulting mixture was filtered, the filtrate was concentrated under vacuum. The crude residue was purified by a flash column (silica gel, dichloromethane/methanol=10:1) to give 4-amino-N-[(3R)-1-{3-[2-(2,6-dioxopiperidin-3-yl)-1-oxo-3H-isoindol-4-yl]prop-2-yn-1-yl}piperidin-3-yl]-3-methoxybenzamide (60 mg, 63.4%) as light yellow solid. LC-MS (ESI, m/z) M+1: 530.

Synthesis of (2'S,3S,4'S,5'R)-6-chloro-4'-(3-chloro-2-fluorophenyl)-2'-(2,2-dimethylpropyl)-N-(4-{[(3R)-1-{3-[2-(2,6-dioxopiperidin-3-yl)-1-oxo-3H-isoindol-4-yl]prop-2-yn-1-yl}piperidin-3-yl]carbamoyl}-2-methoxyphenyl)-1,2-dihydrospiro[indole-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (30 mg, 0.1 mmol, 1.0 eq), 4-amino-N-[(3R)-1-{3-[2-(2,6-dioxopiperidin-3-yl)-1-oxo-3H-isoindol-4-yl]prop-2-yn-1-yl}piperidin-3-yl]-3-methoxybenzamide (42 mg, 0.1 mmol, 1.2 eq), HATU (28 mg, 0.1 mmol, 1.1 eq), DIEA (17 mg, 0.1 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (60% Phase B up to 80% in 7 min); Detector, UV 254/220 nm. Finally, (2'S,3S,4'S,5'R)-6-chloro-4'-(3-chloro-2-fluorophenyl)-2'-(2,2-dimethylpropyl)-N-(4-{[(3R)-1-{3-[2-(2,6-dioxopiperidin-3-yl)-1-oxo-3H-isoindol-4-yl]prop-2-yn-1-yl}piperidin-3-yl]carbamoyl}-2-methoxyphenyl)-1,2-dihydrospiro[indole-3,3'-pyrrolidine]-5'-carboxamide (10 mg, 15.6%) was obtained as a white solid. LC-MS (ESI, m/z) M+1: 962/964. $^1$HNMR (300 MHz, DMSO-$d_6$) δ 10.99 (d, J=6.5 Hz, 1H), 10.68 (s, 1H), 8.33 (d, J=8.3 Hz, 1H), 8.12 (d, J=7.9 Hz, 1H), 7.73 (dd, J=15.1, 7.5 Hz, 2H), 7.61-7.50 (m, 2H), 7.44 (dd, −17.7, 8.1 Hz, 2H), 7.37-7.25 (m, 2H), 7.22-7.16 (m, 1H), 6.51 (dd, −8.0, 2.0 Hz, 1H), 6.31 (d, −1.9 Hz, 1H), 5.52 (s, 1H), 5.17-5.09 (m, 1H), 4.55-4.43 (m, 1H), 4.39-4.27 (m, 2H), 4.12 (d, −9.2 Hz, 1H), 4.02-3.95 (m, 1H), 3.89 (s, 3H), 3.73-3.62 (m, 3H), 3.53 (d, −10.0 Hz, 1H), 3.19 (d, J=10.0 Hz, 2H), 2.99-2.90 (m, 2H), 2.84-2.74 (m, 1H), 2.29-2.15

(m, 2H), 2.04-1.95 (m, 2H), 1.84-1.72 (m, 2H), 1.35-1.28 (m, 2H), 1.31-1.20 (m, 3H), 0.91 (s, 9H).

Example 51: Preparation of (2'S,3S,4'S,5'R)-6-chloro-4'-(3-chloro-2-fluorophenyl)-2'-(2,2-dimethylpropyl)-N-[4-(4-{3-[2-(2,6-dioxopiperidin-3-yl)-1-oxo-3H-isoindol-4-yl]prop-2-yn-1-yl}piperazine-1-carbonyl)-2-methoxyphenyl]-1,2-dihydrospiro[indole-3,3'-pyrrolidine]-5'-carboxamide Synthesis of tert-butyl 4-(3-methoxy-4-nitrobenzoyl)piperazine-1-carboxylate: Into a 50 mL round flask were placed tert-butyl piperazine-1-carboxylate (1.0 g, 5.4 mmol, 1.0 eq), 3-methoxy-4-nitrobenzoic acid (1.1 g, 5.4 mmol, 1.0 eq), HATU (2.3 g, 5.9 mmol, 1.1 eq), DIEA (1.4 g, 10.7 mmol, 2.0 eq), N,N-dimethylformamide (10 mL). The reaction mixture was stirred for 2 hours at 25° C. The reaction was then quenched by the addition of water (100 mL) and then extracted with ethyl acetate (2×100 mL). The combined organic phase was washed with brine (2×100 mL), dried over anhydrous sodium sulfate. After filtration, the filtrate was concentrated under vacuum. The crude residue was purified by a flash column (silica gel, ethyl acetate/petroleum ether=1:0) to give tert-butyl 4-(3-methoxy-4-nitrobenzoyl)piperazine-1-carboxylate (1.4 g, 71.4%) as light yellow oil. LC-MS (ESI, m/z) M+1: 366.

Synthesis of 1-(3-methoxy-4-nitrobenzoyl)piperazine hydrochloride: Into a 100 mL round-bottom flask were placed tert-butyl 4-(3-methoxy-4-nitrobenzoyl)piperazine-1-carboxylate (1.2 g, 3.3 mmol, 1.0 eq), dichloromethane (15 mL), HCl (gas) in 1,4-dioxane (15 mL). The reaction mixture was stirred for 1 hour at 25° C. The resulting mixture was concentrated under vacuum to give 1-(3-methoxy-4-nitrobenzoyl)piperazine hydrochloride (800 mg, crude) as light yellow solid. LC-MS (ESI, m/z) M+1: 266.

Synthesis of 3-(4-(3-(4-(3-methoxy-4-nitrobenzoyl)piperazin-1-yl)prop-1-yn-1-yl)-1-oxoisoindolin-2-yl)piperidine-2,6-dione: Into a 20 mL sealed tube was added 3-[2-(2,6-dioxopiperidin-3-yl)-1-oxo-3H-isoindol-4-yl]prop-2-ynal (200 mg, 0.7 mmol, 1.0 eq), 1-(3-methoxy-4-nitrobenzoyl)piperazine hydrochloride (244 mg, 0.8 mmol, 1.2 eq), dichloromethane (4 mL), $NaBH(OAc)_3$ (429 mg, 2.0 mmol, 3.0 eq) and acetic acid (203 mg, 3.4 mmol, 5.0 eq). The reaction mixture was stirred for 4 hours at 25° C. The reaction was then quenched by the addition of water (30 mL) and then extracted with dichloromethane/methanol (10:1, 2×50 mL). The combined organic layer was washed with brine (2×50 mL), dried over anhydrous sodium sulfate. After filtration, the filtrate was concentrated under vacuum. The crude residue was purified by a flash column (silica gel, dichloromethane/methanol=10:1) to give 3-(4-(3-(4-(3-methoxy-4-nitrobenzoyl)piperazin-1-yl)prop-1-yn-1-yl)-1-oxoisoindolin-2-yl)piperidine-2,6-dione (200 mg, 54.3%) as light yellow solid. LC-MS (ESI, m/z) M+1: 546.

Synthesis of 3-(4-(3-(4-(4-amino-3-methoxybenzoyl)piperazin-1-yl)prop-1-yn-1-yl)-1-oxoisoindolin-2-yl)piperidine-2,6-dione: Into a 20 mL sealed tube were placed 3-(4-(3-(4-(3-methoxy-4-nitrobenzoyl)piperazin-1-yl)prop-1-yn-1-yl)-1-oxoisoindolin-2-yl)piperidine-2,6-dione (180 mg, 0.3 mmol, 1.0 eq), Fe (74 mg, 1.3 mmol, 4.0 eq), $NH_4Cl$ (141 mg, 2.6 mmol, 8.0 eq), EtOH (6 mL) and water (2 mL). The reaction mixture was stirred for 2 hours at 50° C. The resulting mixture was filtered, the filtrate was concentrated under vacuum. The crude residue was purified by a flash column (silica gel, dichloromethane/methanol=10:1) to give 3-(4-(3-(4-(4-amino-3-methoxybenzoyl)piperazin-1-yl)prop-1-yn-1-yl)-1-oxoisoindolin-2-yl)piperidine-2,6-dione (130 mg, 76.4%) as light yellow solid. LC-MS (ESI, m/z) M+1: 516.

Synthesis of (2'S,3S,4'S,5'R)-6-chloro-4'-(3-chloro-2-fluorophenyl)-2'-(2,2-dimethylpropyl)-N-[4-(4-{3-[2-(2,6-dioxopiperidin-3-yl)-1-oxo-3H-isoindol-4-yl]prop-2-yn-1-yl}piperazine-1-carbonyl)-2-methoxyphenyl]-1,2-dihydrospiro[indole-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (50 mg, 0.1 mmol, 1.0 eq), 3-(4-(3-(4-(4-amino-3-methoxybenzoyl)piperazin-1-yl)prop-1-yn-1-yl)-1-oxoisoindolin-2-yl)piperidine-2,6-dione (69 mg, 0.1 mmol, 1.2 eq), HATU (46 mg, 0.1 mmol, 1.1 eq), DIEA (29 mg, 0.2 mmol, 2.0 eq) and N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (50% Phase B up to 65% in 7 min); Detector, UV 254/220 nm. Finally, (2'S,3S,4'S,5'R)-6-chloro-4'-(3-chloro-2-fluorophenyl)-2'-(2,2-dimethylpropyl)-N-[4-(4-{3-[2-(2,6-dioxopiperidin-3-yl)-1-oxo-3H-isoindol-4-yl]prop-2-yn-1-yl}piperazine-1-carbonyl)-2-methoxyphenyl]-1,2-dihydrospiro[indole-3,3'-pyrrolidine]-5'-carboxamide (15 mg, 14.3%) was obtained as white solid. LC-MS (ESI, m/z) M+1: 948/950. $^1$HNMR (300 MHz, DMSO-$d_6$) δ 10.98 (s, 1H), 10.63 (s, 1H), 8.33 (d, −8.2 Hz, 1H), 7.80-7.67 (m, 2H), 7.55 (t, −7.6 Hz, 1H), 7.44-7.40 (m, 1H), 7.34 (t, −7.1 Hz, 1H), 7.29-7.14 (m, 2H), 7.08 (s, 1H), 6.96 (d, −7.8 Hz, 1H), 6.51 (dd, J=7.9, 1.9 Hz, 1H), 6.31 (d, −1.9 Hz, 1H), 5.52 (s, 1H), 5.13 (dd, J=13.2, 5.1 Hz, 1H), 4.49 (d, J=17.7 Hz, 1H), 4.37-4.27 (m, 2H), 4.10 (d, −9.4 Hz, 1H), 3.86 (s, 3H), 3.75-3.50 (m, 5H), 3.22-3.07 (m, 2H), 2.97-2.72 (m, 1H), 2.62-2.53 (m, 4H), 2.07-1.96 (m, 2H), 1.43-1.30 (m, 2H), 1.28-1.19 (m, 4H), 0.91 (s, 9H).

Example 52: Preparation of (2'S,3S,4'S,5'R)-6-chloro-4'-(3-chloro-2-fluorophenyl)-2'-(2,2-dimethylpropyl)-N-(4-{[(3S)-1-{3-[2-(2,6-dioxopiperidin-3-yl)-1-oxo-3H-isoindol-4-yl]prop-2-yn-1-yl}piperidin-3-yl]carbamoyl}-2-methoxyphenyl)-1,2-dihydrospiro[indole-3,3'-pyrrolidine]-5'-carboxamide Synthesis of tert-butyl (3S)-3-(3-methoxy-4-nitrobenzamido)piperidine-1-carboxylate: Into a 50 mL round-bottom flask were placed tert-butyl (3S)-3-aminopiperidine-1-carboxylate (1.0 g, 5.0 mmol, 1.0 eq), 3-methoxy-4-nitrobenzoic acid (980 mg, 5.0 mmol, 1.0 eq), HATU (2.1 g, 5.5 mmol, 1.1 eq), DIEA (1.3 g, 10.0 mmol, 2.0 eq), N,N-dimethylformamide (10 mL). The reaction mixture was stirred for 2 hours at 25° C. The resulting mixture was diluted with water (100 mL) and then extracted with ethyl acetate (2×100 mL). The combined organic layer was washed with brine (2×100 mL), dried over anhydrous sodium sulfate. After filtration, the filtrate was concentrated under vacuum. The crude residue was purified by a flash column (silica gel, ethyl acetate/petroleum ether=1:0) to give tert-butyl (3S)-3-(3-methoxy-4-nitrobenzamido)piperidine-1-carboxylate (1.5 g, 79.2%) as light yellow oil. LC-MS (ESI, m/z) M+1: 380. $^1$HNMR (300 MHz, DMSO-$d_6$) δ 8.52 (d, J=7.5 Hz, 1H), 7.97 (d, J=8.4 Hz, 1H), 7.69 (d, J=1.5 Hz, 1H), 7.56 (dd, J=8.4, 1.5 Hz, 1H), 3.99 (s, 3H), 3.88-3.72 (m, 4H), 2.81 (t, J=12.6 Hz, 1H), 1.92 (dd, J=9.9, 5.1 Hz, 2H), 1.80-1.70 (m, 1H), 1.64-1.45 (m, 1H), 1.39 (s, 9H).

Synthesis of 3-methoxy-4-nitro-N-[(3S)-piperidin-3-yl]benzamide hydrochloride: Into a 100 mL round-bottom flask were placed tert-butyl (3S)-3-(3-methoxy-4-nitrobenzamido)piperidine-1-carboxylate (1.3 g, 3.4 mmol, 1.0 eq), dichloromethane (15 mL), HCl (gas) in 1,4-dioxane (15 mL). The reaction mixture was stirred for 1 hour at 25° C. The resulting mixture was concentrated under vacuum to give 3-methoxy-4-nitro-N-[(3S)-piperidin-3-yl]benzamide hydrochloride (850 mg, crude) as off white solid. LC-MS (ESI, m/z) M+1: 280.

Synthesis of N-[(3S)-1-{3-[2-(2,6-dioxopiperidin-3-yl)-1-oxo-3H-isoindol-4-yl]prop-2-yn-1-yl}piperidin-3-yl]-3-methoxy-4-nitrobenzamide: Into a 20 mL sealed tube were placed 3-[2-(2,6-dioxopiperidin-3-yl)-1-oxo-3H-isoindol-4-yl]prop-2-ynal (400 mg, 1.4 mmol, 1.0 eq), 3-methoxy-4-nitro-N-[(3S)-piperidin-3-yl]benzamide hydrochloride (512 mg, 1.6 mmol, 1.2 eq), EtOH (6 mL), $NaBH_3CN$ (424 mg, 6.7 mmol, 5.0 eq) and $ZnCl_2$ (1.1 g, 8.1 mmol, 6.0 eq). The reaction mixture was stirred for 4 hours at 25° C. The resulting mixture was then quenched by the addition of water (30 mL) and then extracted with dichloromethane/methanol (10:1, 2×50 mL). The combined organic layer was washed with brine (2×50 mL), dried over anhydrous sodium sulfate. After filtration, the filtrate was concentrated under vacuum. The crude residue was purified by a flash column (silica gel, dichloromethane/methanol=10:1) to give N-[(3S)-1-{3-[2-(2,6-dioxopiperidin-3-yl)-1-oxo-3H-isoindol-4-yl]prop-2-yn-1-yl}piperidin-3-yl]-3-methoxy-4-nitrobenzamide (210 mg, 27.8%) as light yellow solid. LC-MS (ESI, m/z) M+1: 560.

Synthesis of 4-amino-N-[(3S)-1-{3-[2-(2,6-dioxopiperidin-3-yl)-1-oxo-3H-isoindol-4-yl]prop-2-yn-1-yl}piperidin-3-yl]-3-methoxybenzamide: Into a 20 mL sealed tube were placed N-[(3S)-1-{3-[2-(2,6-dioxopiperidin-3-yl)-1-oxo-3H-isoindol-4-yl]prop-2-yn-1-yl}piperidin-3-yl]-3-methoxy-4-nitrobenzamide (210 mg, 0.4 mmol, 1.0 eq), Fe (84 mg, 1.5 mmol, 4.0 eq), $NH_4Cl$ (161 mg, 3.0 mmol, 8.0 eq), EtOH (3 mL), water (1 mL). The reaction mixture was stirred for 2 hours at 50° C. The resulting mixture was filtered, the filtrate was concentrated under vacuum. The crude residue was purified by a flash column (silica gel, dichloromethane/methanol=10:1) to give 4-amino-N-[(3S)-1-{3-[2-(2,6-dioxopiperidin-3-yl)-1-oxo-3H-isoindol-4-yl]prop-2-yn-1-yl}piperidin-3-yl]-3-methoxybenzamide (150 mg, 75.5%) as light yellow solid. LC-MS (ESI, m/z) M+1: 530.

Synthesis of (2'S,3S,4'S,5'R)-6-chloro-4'-(3-chloro-2-fluorophenyl)-2'-(2,2-dimethylpropyl)-N-(4-{[(3S)-1-{3-[2-(2,6-dioxopiperidin-3-yl)-1-oxo-3H-isoindol-4-yl]prop-2-yn-1-yl}piperidin-3-yl]carbamoyl}-2-methoxyphenyl)-1,2-dihydrospiro[indole-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (60 mg, 0.1 mmol, 1.0 eq), 4-amino-N-[(3S)-1-{3-[2-(2,6-dioxopiperidin-3-yl)-1-oxo-3H-isoindol-4-yl]prop-2-yn-1-yl}piperidin-3-yl]-3-methoxybenzamide (84 mg, 0.2 mmol, 1.2 eq), HATU (56 mg, 0.1 mmol, 1.1 eq), DIEA (34 mg, 0.3 mmol, 2.0 eq), N,N-dimethylformamide (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3{\cdot}H_2O$) and $CH_3CN$ (60% Phase B up to 80% in 7 min); Detector, UV 254/220 nm. Finally, (2'S,3S,4'S,5'R)-6-chloro-4'-(3-chloro-2-fluorophenyl)-2'-(2,2-dimethylpropyl)-N-(4-{[(3S)-1-{3-[2-(2,6-dioxopiperidin-3-yl)-1-oxo-3H-isoindol-4-yl]prop-2-yn-1-yl}piperidin-3-yl]carbamoyl}-2-methoxyphenyl)-1,2-dihydrospiro[indole-3,3'-pyrrolidine]-5'-carboxamide (10 mg, 7.8%) was obtained as a white solid. LC-MS (ESI, m/z) M+1: 962/964. $^1$H NMR (400 MHz, DMSO-$d_6$) δ 10.98 (d, J=7.8 Hz, 1H), 10.68 (s, 1H), 8.33 (d, J=8.4 Hz, 1H), 8.15-8.09 (m, 1H), 7.75 (d, J=7.6 Hz, 1H), 7.70 (d, J=7.6 Hz, 1H), 7.60-7.38 (m, 4H), 7.34 (t, J=7.2 Hz, 1H), 7.29 (dd, J=8.2, 1.6 Hz, 1H), 7.20 (t, J=8.0 Hz, 1H), 6.51 (dd, J=8.0, 2.0 Hz, 1H), 6.31 (d, −2.0 Hz, 1H), 5.52 (s, 1H), 5.19-5.07 (m, 1H), 4.49 (dd, J=17.8, 5.6 Hz, 1H), 4.41-4.26 (m, 2H), 4.12 (d, −9.6 Hz, 1H), 4.04-3.92 (m, 1H), 3.89 (s, 3H), 3.73-3.65 (m, 3H), 3.53 (d, J=10.4 Hz, 1H), 3.22-3.13 (m, 2H), 2.99-2.75 (m, 2H), 2.26-2.14 (m, 2H), 2.05-1.98 (m, 1H), 1.87-1.71 (m, 2H), 1.80-1.71 (m, 1H), 1.65-1.53 (m, 1H), 1.39-1.31 (m, 2H), 1.27-1.16 (m, 2H), 0.91 (s, 9H).

Example 54: Preparation of (2'S,3S,4'S,5'R)-6-chloro-4'-(3-chloro-2-fluorophenyl)-2'-(2,2-dimethylpropyl)-N-{4-[(1R)-1-(2-{2-[(3S)-2,6-dioxopiperidin-3-yl]-1-oxo-3H-isoindol-4-yl}ethynyl)-6-azaspiro[2.5]octane-6-carbonyl]-2-methoxyphenyl}-1,2-dihydrospiro[indole-3,3'-pyrrolidine]-5'-carboxamide Synthesis of tert-butyl (4S)-4-carbamoyl-4-(4-{2-[(1R)-6-(3-methoxy-4-nitrobenzoyl)-6-azaspiro[2.5]octan-1-yl]ethynyl}-1-oxo-3H-isoindol-2-yl)butanoate: To a stirred mixture of (1R)-1-ethynyl-6-(3-methoxy-4-nitrobenzoyl)-6-azaspiro[2.5]octane (100 mg, 0.3 mmol, 1.0 eq) and tert-butyl (4S)-4-carbamoyl-4-(4-iodo-1-oxo-3H-isoindol-2-yl)butanoate (141 mg, 0.3 mmol, 1.0 eq) in N,N-dimethylformamide (4 mL) and triethylamine (1 mL) were added CuI (18 mg, 0.1 mmol, 0.3 eq) and $Pd(PPh_3)_4$(37 mg, 0.03 mmol, 0.1 eq) in portions at 25° C. under nitrogen atmosphere. The reaction mixture was stirred for 4 hours at 25° C. The resulting mixture was diluted with water (20 mL) and then extracted with ethyl acetate (3×15 mL). The combined organic layers were washed with water (2×10 mL), dried over anhydrous sodium sulfate. After filtration, The crude residue was purified by a flash column (silica gel, ethyl acetate/petroleum ether=0:1 to 1:0) to give tert-butyl (4S)-4-carbamoyl-4-(4-{2-[(1R)-6-(3-methoxy-4-nitrobenzoyl)-6-azaspiro[2.5]octan-1-yl]ethynyl}-1-oxo-3H-isoindol-2-yl)butanoate (100 mg, 49.8%) as a white solid. LC-MS (ESI, m/z) M+1: 631.

Synthesis of (3S)-3-(4-{2-[(1R)-6-(3-methoxy-4-nitrobenzoyl)-6-azaspiro[2.5]octan-1-yl]ethynyl}-1-oxo-3H-isoindol-2-yl)piperidine-2,6-dione: A mixture of tert-butyl (4S)-4-carbamoyl-4-(4-{2-[(1R)-6-(3-methoxy-4-nitrobenzoyl)-6-azaspiro[2.5]octan-1-yl]ethynyl}-1-oxo-3H-isoindol-2-yl)butanoate (100 mg, 0.16 mmol, 1.0 eq) and benzenesulfonic acid (75 mg, 0.5 mmol, 3.0 eq) in $CH_3CN$ (4 mL) was stirred for 4 hours at 80° C. The resulting mixture was concentrated under vacuum. The crude residue was purified by Prep-TLC (EA) to give (3S)-3-(4-{2-[(1R)-6-(3-methoxy-4-nitrobenzoyl)-6-azaspiro[2.5]octan-1-yl]ethynyl}-1-oxo-3H-isoindol-2-yl)piperidine-2,6-dione (60 mg, 68.0%) as a white solid. LC-MS (ESI, m/z) M+1: 557.

Synthesis of (3S)-3-(4-{2-[(1R)-6-(4-amino-3-methoxybenzoyl)-6-azaspiro[2.5]octan-1-yl]ethynyl}-1-oxo-3H-isoindol-2-yl)piperidine-2,6-dione: To a stirred mixture of (3S)-3-(4-{2-[(1R)-6-(3-methoxy-4-nitrobenzoyl)-6-azaspiro[2.5]octan-1-yl]ethynyl}-1-oxo-3H-isoindol-2-yl)piperidine-2,6-dione (50 mg, 0.1 mmol, 1.0 eq) in ethanol (2 mL) and water (0.5 mL) were added Fe (30 mg, 0.6 mmol, 6.0 eq) and $NH_4Cl$ (38 mg, 0.8 mmol, 8.0 eq) in portions at 25° C. The reaction mixture was stirred for 2 hours at 50° C. The resulting mixture was filtered, the filter cake was washed with ethanol (3×10 mL). The filtrate was concentrated under vacuum. The crude residue was purified by a flash column (silica gel, dichloromethane/$CH_3OH$=100:0 to 100:5) to give (3S)-3-(4-{2-[(1R)-6-(4-amino-3-methoxybenzoyl)-6-azaspiro[2.5]octan-1-yl]ethynyl}-1-oxo-3H-isoindol-2-yl)piperidine-2,6-dione (40 mg, 85.1%) as a white solid. LC-MS (ESI, m/z) M+1: 527.

Synthesis of (2'S,3S,4'S,5'R)-6-chloro-4'-(3-chloro-2-fluorophenyl)-2'-(2,2-dimethylpropyl)-N-{4-[(1R)-1-(2-{2-[(3S)-2,6-dioxopiperidin-3-yl]-1-oxo-3H-isoindol-4-yl}ethynyl)-6-azaspiro[2.5]octane-6-carbonyl]-2-methoxyphenyl}-1,2-dihydrospiro[indole-3,3'-pyrrolidine]-5'-carboxamide: Into an 8 mL vial were added (3S)-3-(4-{2-[(1R)-6-(4-amino-3-methoxybenzoyl)-6-azaspiro[2.5]octan-1-yl]ethynyl}-1-oxo-3H-isoindol-2-yl)piperidine-2,6-dione (30 mg, 0.06 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (26 mg, 0.06 mmol, 1.0 eq), NMI (12 mg, 0.14 mmol, 2.5 eq), TCFH (24 mg, 0.09 mmol, 1.5 eq) and $CH_3CN$ (2 mL) at 25° C. The reaction mixture was stirred for 2 hours at 25° C. The resulting mixture was concentrated under vacuum. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (50% Phase B up to 65% in 7 min); Detector, UV 220 nm. Finally, (2'S,3S,4'S,5'R)-6-chloro-4'-(3-chloro-2-fluorophenyl)-2'-(2,2-dimethylpropyl)-N-{4-[(1R)-1-(2-{2-[(3S)-2,6-dioxopiperidin-3-yl]-1-oxo-3H-isoindol-4-yl}ethynyl)-6-azaspiro[2.5]octane-6-carbonyl]-2-methoxyphenyl}-1,2-dihydrospiro[indole-3,3'-pyrrolidine]-5'-carboxamide (8 mg, 14.6%) was obtained as a white solid. LC-MS (ESI, m/z) M+1: 959/961. $^1$HNMR (300 MHz, Methanol-$d_4$) δ 8.38 (d, J=8.4 Hz, 1H), 7.75 (d, J=7.5 Hz, 1H), 7.62 (d, J=7.5 Hz, 1H), 7.51 (t, J=7.8 Hz, 1H), 7.38-7.25 (m, 2H), 7.19 (d, J=8.1 Hz, 1H), 7.16-7.06 (m, 2H), 7.04 (dd, J=8.1, 1.8 Hz, 1H), 6.63 (dd, J=8.1, 1.8 Hz, 1H), 6.43 (d, J=1.8 Hz, 1H), 5.21-5.11 (m, 1H), 4.58-4.33 (m, 3H), 4.27-4.07 (m, 2H), 3.95 (s, 3H), 3.80-3.48 (m, 4H), 3.45-3.35 (m, 2H), 3.06-2.70 (m, 2H), 2.30-2.15 (m, 1H), 1.93-1.60 (m, 4H), 1.42-1.28 (m, 4H), 1.17-1.08 (m, 1H), 1.0 (s, 9H), 0.92-0.83 (m, 1H). $T_R$=6.237 min in CHIRAL-HPLC, Column: YMC Cellulose-SB, 100*4.6 mm, 3 um. mobile phase A: water/0.05% TFA; mobile phase B: ACN, Start Conc. of Pump B: 50.0%, Oven Temperature: 30° C.

Example 55: Preparation of (2'S,3S,4'S,5'R)-6-chloro-4'-(3-chloro-2-fluorophenyl)-2'-(2,2-dimethylpropyl)-N-[4-(3-{2-[2-(2,6-dioxopiperidin-3-yl)-1-oxo-3H-isoindol-4-yl]ethynyl}azetidine-1-carbonyl)-2-methoxyphenyl]-1,2-dihydrospiro[indole-3,3'-pyrrolidine]-5'-carboxamide Synthesis of tert-butyl 3-{2-[2-(2,6-dioxopiperidin-3-yl)-1-oxo-3H-isoindol-4-yl]ethynyl}azetidine-1-carboxylate: To a stirred mixture of tert-butyl 3-ethynylazetidine-1-carboxylate (1.0 g, 5.5 mmol, 1.0 eq) and 3-(4-iodo-1-oxo-3H-isoindol-2-yl)piperidine-2,6-dione (2.5 g, 6.6 mmol, 1.2 eq) in Dimethyl Formamide (20 mL) and triethylamine (5 mL) was added CuI (0.3 g, 1.6 mmol, 0.3 eq) and $Pd(PPh_3)_4$ (0.6 g, 0.6 mmol, 0.1 eq) in portions at 25° C. under nitrogen atmosphere. The reaction mixture was stirred for 14 hours at 25° C. under nitrogen atmosphere. The resulting mixture was diluted with water (60 mL) and then extracted with ethyl acetate (3×50 mL). The combined organic layers were washed with water (3×30 mL) and brine (30 mL), dried over anhydrous sodium sulfate. After filtration, the filtrate was concentrated under vacuum. The crude residue was purified by a flash column (silica gel, ethyl acetate/petroleum ether=3:1) to give tert-butyl 3-{2-[2-(2,6-dioxopiperidin-3-yl)-1-oxo-3H-isoindol-4-yl]ethynyl}azetidine-1-carboxylate (1.2 g, 51.3%) as a brown solid. LC. MS (ESI, m/z) M+1: 368.

Synthesis of 3-{4-[2-(azetidin-3-yl)ethynyl]-1-oxo-3H-isoindol-2-yl}piperidine-2,6-dione: Into an 8 mL sealed tube were added tert-butyl N-{4-[2-(2,6-dioxopiperidin-3-yl)-1-oxo-3H-isoindol-4-yl]but-3-yn-1-yl}carbamate (0.5 g, 1.2 mmol, 1.0 eq) and HCl in dioxane (4 M, 5 mL) at 25° C. The reaction mixture was stirred for 14 hours. The resulting mixture was concentrated under vacuum. The crude product mixture was directly used in the next step without further purification. LC-MS (ESI, m/z) M+1: 371.

Synthesis of 3-(4-{2-[1-(3-methoxy-4-nitrobenzoyl)azetidin-3-yl]ethynyl}-1-oxo-3H-isoindol-2-yl)piperidine-2,6-dione: Into a 50 mL round flask were placed 3-{4-[2-(azetidin-3-yl)ethynyl]-1-oxo-3H-isoindol-2-yl}piperidine-2,6-dione (330 mg, 1.0 mmol, 1.0 eq), 3-methoxy-4-nitrobenzoic acid (201 mg, 1.0 mmol, 1.0 eq), HATU (582 mg, 1.5 mmol, 1.1 eq), DIEA (527 mg, 4.0 mmol, 2.0 eq) and dichloromethane (10 mL). The reaction mixture was stirred for 14 hours at 25° C. The resulting mixture was concentrated under vacuum. The crude residue was purified by a flash column (silica gel, ethyl acetate/petroleum ether=1:1) to give 3-(4-{2-[1-(3-methoxy-4-nitrobenzoyl)azetidin-3-yl]ethynyl}-1-oxo-3H-isoindol-2-yl)piperidine-2,6-dione (250 mg, 48.7%) as a brown solid. LC-MS (ESI, m/z) M+1: 503.

Synthesis of 3-(4-{2-[1-(4-amino-3-methoxybenzoyl)azetidin-3-yl]ethynyl}-1-oxo-3H-isoindol-2-yl)piperidine-2,6-dione: Into an 8 mL sealed tube were added 3-(4-{2-[1-(3-methoxy-4-nitrobenzoyl)azetidin-3-yl]ethynyl}-1-oxo-3H-isoindol-2-yl)piperidine-2,6-dione (250 mg, 0.5 mmol, 1.0 eq), Fe (166 mg, 3.0 mmol, 6.0 eq), $NH_4Cl$ (213 mg, 4.0 mmol, 8.0 eq), EtOH (4 mL) and water (1 mL) at 25° C. The reaction mixture was stirred for 4 hours at 25° C. The resulting mixture was filtered, the filter cake was washed with EtOH (5 mL). The filtrate was concentrated under vacuum. The crude residue was purified by a flash column (silica gel, ethyl acetate/petroleum ether=10:1) to give 3-(4-((1-(4-amino-3-methoxybenzoyl)azetidin-3-yl)ethynyl)-1-oxoisoindolin-2-yl)piperidine-2,6-dione (170 mg, 72.3%) as a brown solid. LC-MS (ESI, m/z) M+1: 473.

Synthesis of (2'S,3S,4'S,5'R)-6-chloro-4'-(3-chloro-2-fluorophenyl)-2'-(2,2-dimethylpropyl)-N-[4-(3-{2-[2-(2,6-dioxopiperidin-3-yl)-1-oxo-3H-isoindol-4-yl]ethynyl}azetidine-1-carbonyl)-2-methoxyphenyl]-1,2-dihydrospiro[indole-3,3'-pyrrolidine]-5'-carboxamide: Into a 20 mL sealed tube were added 3-(4-{2-[1-(4-amino-3-methoxybenzoyl)azetidin-3-yl]ethynyl}-1-oxo-3H-isoindol-2-yl)piperidine-2,6-dione (50 mg, 0.1 mmol, 1.0 eq), (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (48 mg, 0.1 mmol, 1.0 eq), N,N,N',N'-Tetramethylchloroformamidinium hexafluorophosphate (45 mg, 0.2 mmol, 1.5 eq), 1-Methylimidazole (26 mg, 0.3 mmol, 3.0 eq) and $CH_3CN$ (5 mL) at 25° C. The reaction mixture was stirred for 14 hours at 25° C. The resulting mixture was dried under vacuum. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (50% Phase B up to 65% in 7 min); Detector, UV 254/220 nm. Finally, (2'S,3S,4'S,5'R)-6-chloro-4'-(3-chloro-2-fluorophenyl)-2'-(2,2-dimethylpropyl)-N-[4-(3-{2-[2-(2,6-dioxopiperidin-3-yl)-1-oxo-3H-isoindol-4-yl]ethynyl}azetidine-1-carbonyl)-2-methoxyphenyl]-1,2-dihydrospiro[indole-3,3'-pyrrolidine]-5'-carboxamide (20 mg, 20.8%) was obtained as a white solid. LC-MS (ESI, m/z) M+1: 905/907. $^1$HNMR (300 MHz, DMSO-$d_6$) δ 10.99 (s, 1H), 10.69 (s, 1H), 8.35 (d, J=8.4 Hz, 1H), 7.73 (dd, J=13.8, 7.5 Hz, 2H), 7.55 (t, J=7.8 Hz, 1H), 7.47-7.35 (m, 2H), 7.31-7.4 (m, 2H), 7.21-7.32 (m, 3H), 6.55-6.46 (m, 1H), 6.30 (d, J=1.8 Hz, 1H), 5.51 (s, 1H), 5.14 (dd, J=13.2, 5.1 Hz, 1H), 4.63 (bs, 1H), 4.51-4.61 (m, 2H), 4.42-4.24 (m, 3H), 4.10 (d, J=9.3 Hz, 2H), 3.89 (s, 3H), 3.74 (d, J=11.4 Hz, 1H), 3.16 (t, J=10.8 Hz, 3H), 2.62 (s, 1H), 2.02-1.91 (m, 1H), 1.42-1.28 (m, 2H), 1.19-1.23 (m, J=14.1 Hz, 2H), 0.90 (s, 9H).

Example 56: Preparation of (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide Synthesis of (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid: Into a 50 mL round-bottom flask were placed tert-butyl (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylate (300 mg, 0.6 mmol, 1.0 eq), trifluoroacetic acid (6 mL). The reaction mixture was stirred for 16 hours at 25° C. The resulting mixture was diluted with water (50 mL) and then extracted with ethyl acetate (2×50 mL). The combined organic phase was washed with water (2×50 mL), brine (2×50 mL) and dried over anhydrous sodium sulfate. After filtration, the filtrate was concentrated under vacuum. Finally, (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (200 mg crude) was obtained as an off white solid. LC-MS (ESI, m/z) M+1: 486/488. $^1$HNMR (400 MHz, Methanol-$d_4$) δ 8.60 (s, 1H), 7.59 (t, −7.0 Hz, 1H), 7.47 (t, −7.6 Hz, 1H), 7.25 (t, −8.0 Hz, 1H), 6.88 (s, 1H), 5.14 (d, J=11.4 Hz, 1H), 4.55 (d, J=11.4 Hz, 1H), 4.37 (d, −8.0 Hz, 1H), 4.03 (d, −12.6 Hz, 1H), 3.87 (d, J=12.6 Hz, 1H), 1.96 (dd, J=15.4, 8.6 Hz, 1H), 1.65 (d, J=15.4 Hz, 1H), 0.99 (s, 9H).

Synthesis of tert-butyl (4S)-4-carbamoyl-4-(4-{2-[(1S)-6-(3-methoxy-4-nitrobenzoyl)-6-azaspiro[2.5]octan-1-yl]ethynyl}-1-oxo-3H-isoindol-2-yl)butanoate: To a stirred mixture of (1S)-1-ethynyl-6-(3-methoxy-4-nitrobenzoyl)-6-azaspiro[2.5]octane (280 mg, 0.9 mmol, 1.0 eq) and tert-butyl (4S)-4-carbamoyl-4-(4-iodo-1-oxo-3H-isoindol-2-yl)butanoate (475 mg, 1.1 mmol, 1.2 eq) in N,N-dimethylformamide (4 mL) and triethylamine (1 mL) were added CuI (51 mg, 0.3 mmol, 0.3 eq) and $Pd(PPh_3)_4$(102 mg, 0.1 mmol, 0.1 eq) in portions at 25° C. under nitrogen atmosphere. The reaction mixture was stirred for 4 hours at 25° C. The resulting mixture was diluted with water (20 mL) and then extracted with ethyl acetate (3×15 mL). The combined organic layers were washed with water (2×10 mL), dried over anhydrous sodium sulfate. After filtration, The crude residue was purified by a flash column (silica gel, ethyl acetate/petroleum ether=1:0) to give tert-butyl (4S)-4-carbamoyl-4-(4-{2-[(1S)-6-(3-methoxy-4-nitrobenzoyl)-6-azaspiro[2.5]octan-1-yl]ethynyl}-1-oxo-3H-isoindol-2-yl)butanoate (300 mg, 53.5%) as a white solid. LC-MS (ESI, m/z) M+1: 631.

Synthesis of (3S)-3-(4-{2-[(1S)-6-(3-methoxy-4-nitrobenzoyl)-6-azaspiro[2.5]octan-1-yl]ethynyl}-1-oxo-3H-isoindol-2-yl)piperidine-2,6-dione: A mixture of tert-butyl (4S)-4-carbamoyl-4-(4-{2-[(1S)-6-(3-methoxy-4-nitrobenzoyl)-6-azaspiro[2.5]octan-1-yl]ethynyl}-1-oxo-3H-isoindol-2-yl)butanoate (280 mg, 0.4 mmol, 1.0 eq) and benzenesulfonic acid (210 mg, 1.3 mmol, 3.0 eq) in $CH_3CN$ (10 mL) was stirred for 4 hours at 80° C. The resulting mixture was concentrated under vacuum. The crude residue was purified by Prep-TLC (EA) to give (3S)-3-(4-{2-[(1S)-6-(3-methoxy-4-nitrobenzoyl)-6-azaspiro[2.5]octan-1-yl]ethynyl}-1-oxo-3H-isoindol-2-yl)piperidine-2,6-dione (140 mg, 56.6%) as a white solid. LC-MS (ESI, m/z) M+1: 557.

Synthesis of (3S)-3-(4-{2-[(1S)-6-(4-amino-3-methoxybenzoyl)-6-azaspiro[2.5]octan-1-yl]ethynyl}-1-oxo-3H-isoindol-2-yl)piperidine-2,6-dione: To a stirred mixture of (3S)-3-(4-{2-[(1S)-6-(3-methoxy-4-nitrobenzoyl)-6-azaspiro[2.5]octan-1-yl]ethynyl}-1-oxo-3H-isoindol-2-yl)piperidine-2,6-dione (130 mg, 0.2 mmol, 1.0 eq) and $NH_4Cl$ (100 mg, 1.9 mmol, 8.0 eq) in ethanol (4 mL) and water (1 mL) were added Fe (78 mg, 1.4 mmol, 6.0 eq) in portions at 25° C. The reaction mixture was stirred for 2 hours at 50° C. The resulting mixture was filtered, the filter cake was washed with ethanol (3×10 mL). The filtrate was concentrated under vacuum. The crude residue was purified by a flash column (silica gel, dichloromethane/$CH_3OH$=100:5) to give (3S)-3-(4-{2-[(1S)-6-(4-amino-3-methoxybenzoyl)-6-azaspiro[2.5]octan-1-yl]ethynyl}-1-oxo-3H-isoindol-2-yl)piperidine-2,6-dione (80 mg, 65%) as a white solid. LC-MS (ESI, m/z) M+1: 527.

Synthesis of 2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide: Into an 8 mL vial were added (S)-3-(4-(((S)-6-(4-amino-3-methoxybenzoyl)-6-azaspiro[2.5]octan-1-yl)ethynyl)-1-oxoisoindolin-2-yl)piperidine-2,6-dione (20 mg, 0.03 mmol, 1.0 eq), (2S,3S,4S,5R)-4-(3-chloro-2-fluorophenyl)-2-neopentyl-6'-(trifluoromethyl)-1',2'-dihydrospiro[pyrrolidine-3,3'-pyrrolo[3,2-c]pyridine]-5-carboxylic acid (24 mg, 0.05 mmol, 1.3 eq), NMI (9.3 mg, 0.11 mmol, 3.0 eq), TCFH (15.9 mg, 0.05 mmol, 1.5 eq) and $CH_3CN$ (4 mL) at 25° C. The reaction mixture was stirred for 2 hours at 25° C. The resulting mixture was concentrated under vacuum. The crude residue was purified by Prep-TLC (EA:DCM=10:1) to give (2S,3S,4S,5R)-4-(3-chloro-2-fluorophenyl)-N-(4-((1S)-1-((2-(2,6-dioxopiperidin-3-yl)-1-oxoisoindolin-4-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide (24 mg, 31.35%, racemate) as a white solid.

The racemate was further purified by Chiral-SFC using the following conditions: Column: CHIRAL ART Cellulose-SB, 3*25 cm, 5 μm; mobile phase A: n-Hexane: DCM=1:1; mobile phase B: $CH_3CH_2OH$ (0.2% DIEA)—Preparative; Flow rate: 50 mL/min; Gradient: isocratic 30% B; Detect 220 nm. Finally, (2S,3S,4S,5R)-4-(3-chloro-2-fluorophenyl)-N-(4-((S)-1-((2-((S)-2,6-dioxopiperidin-3-yl)-1-oxoisoindolin-4-yl)ethynyl)-6-azaspiro[2.5]octane-6-carbonyl)-2-methoxyphenyl)-2-neopentyl-6'-(trifluoromethyl)-1',2'-dihydrospiro[pyrrolidine-3,3'-pyrrolo[3,2-c]pyridine]-5-carboxamide (2.5 mg, 0.56%) was obtained as a white solid.

LC-MS (ESI, m/z) M+1: 994/996. $^1$HNMR (300 MHz, Chloroform-d) δ 8.35 (m, 1H), 7.82 (d, J=7.5 Hz, 2H), 7.57 (m, J=7.5 Hz, 3H), 7.45 (t, J=7.8 Hz, 1H), 7.06-6.94 (m, 3H), 6.73 (s, 1H), 6.5-6.28 (m, 1H), 5.48-5.60 (m, 1H) 5.10-5.20 (m, 1H), 4.62-4.01 (m, 4H), 3.77-3.52 (m, 10H), 3.32-2.5 (m, 4H), 2.01-1.91 (m, 1H), 1.21-0.80 (m, 19H). $T_R$=2.675 min in CHIRAL-HPLC, Column: YMC Cellulose-SB, 100*4.6 mm, 3 μm 121AB00077. mobile phase A: n-Hexane/DCM=1/1; mobile phase B: EtOH (0.2% DEA), Start Conc. of Pump B: 30.0%, Oven Temperature: 25° C.

Example 57: Preparation of (2'S,3S,4'S,5'R)-6-chloro-4'-(3-chloro-2-fluorophenyl)-2'-(2,2-dimethylpropyl)-N-[4-(8-{2-[2-(2,6-dioxopiperidin-3-yl)-1-oxo-3H-isoindol-4-yl]ethynyl}-2,3-dihydro-1,4-benzoxazine-4-carbonyl)-2-methoxyphenyl]-1,2-dihydrospiro[indole-3,3'-pyrrolidine]-5'-carboxamide Synthesis of 3-amino-2-hydroxybenzoate: Into a 250-mL sealed tube were placed methyl 2-hydroxy-3-nitrobenzoate (7.0 g, 35.5 mmol, 1.0 eq), Fe (7.9 g, 142.1 mmol, 4.0 eq), $NH_4Cl$ (15.2 g, 284.1 mmol, 8.0 eq), EtOH (60 mL), water (20 mL). The reaction mixture was stirred for 2 hours at 50° C. The resulting mixture was filtered, and the filtrate was concentrated under vacuum. The crude residue was purified by a flash column (silica gel, ethyl acetate/petroleum ether=1:1) to give methyl 3-amino-2-hydroxybenzoate (5.8 g crude) as off white solid. LC-MS (ESI, m/z) M+1: 168. $^1$HNMR (300 MHz, DMSO-$d_6$) δ 10.61 (s, 1H), 7.02 (dd, J=8.1, 1.5 Hz, 1H), 6.87 (dd, J=7.8, 1.5 Hz, 1H), 6.69 (t, J=7.8 Hz, 1H), 4.96 (s, 2H), 3.89 (s, 3H).

Synthesis of methyl 3-oxo-2,4-dihydro-1,4-benzoxazine-8-carboxylate: Into a 250-mL 3-necked round-bottom flask, were placed methyl 3-amino-2-hydroxybenzoate (5.5 g, 32.9 mmol, 1.0 eq), N,N-dimethylformamide (60 mL). After that, chloroacetyl chloride (4.1 g, 36.2 mmol, 1.1 eq) was added at 0° C. The reaction mixture was stirred for 20 minutes at 25° C., and then to the above reaction mixture was added $K_2CO_3$ (21.8 g, 157.9 mmol, 4.8 eq). The reaction mixture was stirred for 16 hours at 25° C. The reaction was then quenched by the addition of water (200 mL) and then extracted with ethyl acetate (2×300 mL). The combined organic phase was washed with water (2×300 mL) and brine (2×300 mL), dried over anhydrous sodium sulfate.

After filtration, the filtrate was concentrated under vacuum to give methyl 3-oxo-2,4-dihydro-1,4-benzoxazine-8-carboxylate (6.0 g crude) as off white solid. LC-MS (ESI, m/z) M+1: 208. $^1$HNMR (300 MHz, DMSO-$d_6$) δ 10.86 (s, 1H), 7.38-7.26 (m, 1H), 7.09 (dd, J=7.8, 1.8 Hz, 1H), 7.02 (t, J=7.8 Hz, 1H), 4.65 (s, 2H), 3.80 (s, 3H).

Synthesis of methyl 3,4-dihydro-2H-1,4-benzoxazine-8-carboxylate: Into a 250-mL 3-necked round-bottom flask, were placed tert-butyl methyl 3-oxo-2,4-dihydro-1,4-benzoxazine-8-carboxylate (5.5 g, 26.5 mmol, 1.0 eq), tetrahydrofuran (60 mL), $BH_3$ (2 M in dimethyl sulfide, 26 mL). The reaction mixture was stirred for 2 hours at 70° C. The resulting solution was quenched by the addition of MeOH (20 mL), and then concentrated under vacuum. The crude residue was purified by a flash column (silica gel, ethyl acetate/petroleum ether=1:1) to give methyl 3,4-dihydro-2H-1,4-benzoxazine-8-carboxylate (4.5 g, 87.7%) as light yellow oil. LC-MS (ESI, m/z) M+1: 194. $^1$HNMR (400 MHz, DMSO-$d_6$) δ 6.82 (dd, J=6.8, 2.8 Hz, 1H), 6.77-6.66 (m, 2H), 4.19-4.12 (m, 2H), 3.75 (s, 3H), 3.30 (td, J=4.4, 2.6 Hz, 2H).

Synthesis of 4-tert-butyl 8-methyl 2,3-dihydro-1,4-benzoxazine-4,8-dicarboxylate: Into a 250-mL 3-necked round-bottom flask, were placed methyl 3,4-dihydro-2H-1,4-benzoxazine-8-carboxylate (3.0 g, 15.5 mmol, 1.0 eq), dichloromethane (40 mL), $Boc_2O$ (6.8 g, 31.1 mmol, 2.0 eq), triethylamine (6.3 g, 62.1 mmol, 4.0 eq), DMAP (600 mg, 4.6 mmol, 0.3 eq). The reaction mixture was stirred for 16 hours at 25° C. The resulting mixture was diluted with water (80 mL) and then extracted with ethyl acetate (2×60 mL). The combined organic phase was washed with brine (2×60 mL), dried over anhydrous sodium sulfate. After filtration, the filtrate was concentrated under vacuum. The crude residue was purified by a flash column (silica gel, ethyl acetate/petroleum ether=1:1) to give 4-tert-butyl 8-methyl 2,3-dihydro-1,4-benzoxazine-4,8-dicarboxylate (2.6 g, 57.1%) as light yellow oil. LC-MS (ESI, m/z) M+1: 294. $^1$HNMR (400 MHz, DMSO-$d_6$) δ 7.89 (d, J=8.4 Hz, 1H), 7.34 (dd, J=7.8, 1.8 Hz, 1H), 6.93 (t, J=8.0 Hz, 1H), 4.31-4.24 (m, 2H), 3.82-3.80 (m, 2H), 3.78 (s, 3H), 1.49 (s, 9H).

Synthesis of tert-butyl 8-(hydroxymethyl)-2,3-dihydro-1,4-benzoxazine-4-carboxylate: Into a 100 mL 3-necked round-bottom flask, were placed 4-tert-butyl 8-methyl 2,3-dihydro-1,4-benzoxazine-4,8-dicarboxylate (2.5 g, 8.5 mmol, 1.0 eq), tetrahydrofuran (30 mL). After that, $LiAlH_4$ (600 mg, 17.0 mmol, 2.0 eq) was added at 0° C. The reaction mixture was stirred for 1 hour at 0° C. The resulting mixture was then quenched by the addition of water (1 mL), 15% NaOH (1 mL), water (3 mL). After filtration, the filtrate was concentrated under vacuum to give tert-butyl 8-(hydroxymethyl)-2,3-dihydro-1,4-benzoxazine-4-carboxylate (2.2 g crude) as off white solid. LC-MS (ESI, m/z) M+1: 266. $^1$HNMR (300 MHz, DMSO-$d_6$) δ 7.59 (d, J=8.4 Hz, 1H), 7.09 (dd, J=7.5, 1.5 Hz, 1H), 6.84 (t, J=7.8 Hz, 1H), 4.97 (t, J=5.7 Hz, 1H), 4.46 (d, J=5.7 Hz, 2H), 4.27-4.18 (m, 2H), 3.82-3.73 (m, 2H), 1.48 (s, 9H).

Synthesis of tert-butyl 8-formyl-2,3-dihydro-1,4-benzoxazine-4-carboxylate: Into a 100 mL round flask, were placed tert-butyl 8-(hydroxymethyl)-2,3-dihydro-1,4-benzoxazine-4-carboxylate (2.0 g, 7.5 mmol, 1.0 eq), dichloromethane (30 mL). After that, PCC (3.3 g, 15.1 mmol, 2.0 eq) was added at 0° C. The reaction mixture was stirred for 2 hours at 25° C. The resulting mixture was then quenched by the addition of water (100 mL) and then extracted with dichloromethane (2×100 mL). The combined organic phase was washed with brine (2×100 mL), dried over anhydrous sodium sulfate. After filtration, the filtrate was concentrated under vacuum.

The crude residue was purified by a flash column (silica gel, ethyl acetate/petroleum ether=1:1) to give tert-butyl 8-formyl-2,3-dihydro-1,4-benzoxazine-4-carboxylate (1.6 g, 80.6%) as off white solid. LC-MS (ESI, m/z) M+1: 264. $^1$HNMR (400 MHz, DMSO-$d_6$) δ 10.32 (s, 1H), 8.02 (d, J=8.2 Hz, 1H), 7.42 (dd, J=7.8, 1.6 Hz, 1H), 7.05-6.97 (m, 1H), 4.39 (dd, J=5.2, 4.0 Hz, 2H), 3.87 (dd, J=5.2, 4.0 Hz, 2H), 1.50 (s, 9H).

Synthesis of tert-butyl 8-ethynyl-2,3-dihydro-1,4-benzoxazine-4-carboxylate: Into a 100 mL round-bottom flask were placed tert-butyl 8-formyl-2,3-dihydro-1,4-benzoxazine-4-carboxylate (1.5 g, 5.7 mmol, 1.0 eq), MeOH (30 mL), $K_2CO_3$ (1.6 g, 11.4 mmol, 2.0 eq), seyferth-gilbert homologation (1.6 g, 8.5 mmol, 1.5 eq). The reaction mixture was stirred for 2 hours at 25° C. The resulting mixture was quenched by the addition of water (50 mL) and then extracted with ethyl acetate (2×60 mL). The combined organic phase was washed with brine (2×60 mL), dried over anhydrous sodium sulfate. After filtration, the filtrate was concentrated under vacuum. The crude residue was purified by a flash column (silica gel, ethyl acetate/petroleum ether=1:3) to give tert-butyl 8-ethynyl-2,3-dihydro-1,4-benzoxazine-4-carboxylate (1.3 g, 88.0%) as off white solid. LC-MS (ESI, m/z) M+1: 260. $^1$HNMR (400 MHz, DMSO-$d_6$) δ 7.75 (d, J=8.4 Hz, 1H), 7.12 (dd, J=7.6, 1.6 Hz, 1H), 6.85 (dd, J=8.4, 7.6 Hz, 1H), 4.29 (dd, J=5.2, 4.0 Hz, 2H), 4.23 (s, 1H), 3.80 (dd, J=5.2, 4.0 Hz, 2H), 1.49 (s, 9H).

Synthesis of tert-butyl 8-{2-[2-(2,6-dioxopiperidin-3-yl)-1-oxo-3H-isoindol-4-yl]ethynyl}-2,3-dihydro-1,4-benzoxazine-4-carboxylate: Into a 100 mL round flask purged and maintained under an inert atmosphere of nitrogen, were placed tert-butyl 8-ethynyl-2,3-dihydro-1,4-benzoxazine-4-carboxylate (1.2 g, 4.6 mmol, 1.0 eq), 3-(4-iodo-1-oxo-3H-isoindol-2-yl)piperidine-2,6-dione (2.1 g, 5.5 mmol, 1.2 eq), $Pd(PPh_3)_4$ (500 mg, 0.5 mmol, 0.1 eq), CuI (100 mg, 0.5 mmol, 0.1 eq), triethylamine (1.4 g, 13.9 mmol, 3.0 eq), N,N-dimethylformamide (15 mL). The reaction mixture was stirred for 2 hours at 70° C. The resulting mixture was diluted with water (100 mL) and then extracted with ethyl acetate (2×100 mL). The combined organic phase was washed with brine (2×100 mL), dried over anhydrous sodium sulfate. After filtration, the filtrate was concentrated under vacuum. The crude residue was purified by a flash column (silica gel, ethyl acetate/petroleum ether=1:1) to give tert-butyl 8-{2-[2-(2,6-dioxopiperidin-3-yl)-1-oxo-3H-isoindol-4-yl]ethynyl}-2,3-dihydro-1,4-benzoxazine-4-carboxylate (1.3 g, 56.0%) as brown solid. LC-MS (ESI, m/z) M+1: 502. $^1$HNMR (400 MHz, DMSO-$d_6$) δ 11.02 (s, 1H), 7.82 (d, −8.4 Hz, 1H), 7.77 (td, −7.8, 1.0 Hz, 2H), 7.67-7.47 (m, 1H), 7.28 (dd, −7.6, 1.6 Hz, 1H), 6.93 (t, −8.0 Hz, 1H), 5.18 (dd, J=13.4, 5.2 Hz, 1H), 4.55 (d, J=18.0 Hz, 1H), 4.41 (d, J=18.0 Hz, 1H), 4.40-4.31 (m, 2H), 3.88-3.81 (m, 2H), 3.0-2.87 (m, 1H), 2.66-2.57 (m, 1H), 2.47-2.43 (m, 1H), 2.10-1.97 (m, 1H), 1.50 (s, 9H).

Synthesis of 3-{4-[2-(3,4-dihydro-2H-1,4-benzoxazin-8-yl)ethynyl]-1-oxo-3H-isoindol-2-yl}piperidine-2,6-dione: Into a 100 mL round flask, were placed tert-butyl 8-{2-[2-(2,6-dioxopiperidin-3-yl)-1-oxo-3H-isoindol-4-yl]ethynyl}-2,3-dihydro-1,4-benzoxazine-4-carboxylate (1.0 g, 2.0 mmol, 1.0 eq), dichloromethane (15 mL) and $ZnBr_2$ (4.5 g, 19.9 mmol, 10.0 eq). The reaction mixture was stirred for 3 hours at 25° C. The resulting mixture was concentrated under vacuum. The resulting mixture was diluted with water (100 mL), and then extracted with ethyl acetate (2×100 mL). The combined organic phase was washed with brine (2×50 mL), dried over anhydrous sodium sulfate. After filtration, the filtrate was concentrated under vacuum to give 3-{4-[2-(3,4-dihydro-2H-1,4-benzoxazin-8-yl)ethynyl]-1-oxo-3H-isoindol-2-yl}piperidine-2,6-dione (800 mg crude) as brown solid. LC-MS (ESI, m/z) M+1: 402.

Synthesis of 3-(4-{2-[4-(3-methoxy-4-nitrobenzoyl)-2,3-dihydro-1,4-benzoxazin-8-yl]ethynyl}-1-oxo-3H-isoindol-2-yl)piperidine-2,6-dione: Into a 50-mL round flask, were placed 3-{4-[2-(3,4-dihydro-2H-1,4-benzoxazin-8-yl)ethynyl]-1-oxo-3H-isoindol-2-yl}piperidine-2,6-dione (800 mg, 2.0 mmol, 1.0 eq), 3-methoxy-4-nitrobenzoic acid (472 mg, 2.4 mmol, 1.2 eq), TCFH (839 mg, 3.0 mmol, 1.5 eq), NMI (409 mg, 5.0 mmol, 2.5 eq), $CH_3CN$ (8 mL). The reaction mixture was stirred for 2 hours at 25° C. The precipitated solids were collected by filtration, washed with $CH_3CN$ (2×20 mL) and then dried on rotary evaporator. Finally, 3-(4-{2-[4-(3-methoxy-4-nitrobenzoyl)-2,3-dihydro-1,4-benzoxazin-8-yl]ethynyl}-1-oxo-3H-isoindol-2-yl)piperidine-2,6-dione (600 mg crude) was obtained as brown solid. LC-MS (ESI, m/z) M+1: 581.

Synthesis of 3-(4-{2-[4-(4-amino-3-methoxybenzoyl)-2,3-dihydro-1,4-benzoxazin-8-yl]ethynyl}-1-oxo-3H-isoindol-2-yl)piperidine-2,6-dione: Into a 40 mL sealed tube were placed 3-(4-{2-[4-(3-methoxy-4-nitrobenzoyl)-2,3-dihydro-1,4-benzoxazin-8-yl]ethynyl}-1-oxo-3H-isoindol-2-yl)piperidine-2,6-dione (500 mg, 0.9 mmol, 1.0 eq), Fe (193 mg, 3.4 mmol, 4.0 eq), $NH_4Cl$ (369 mg, 6.9 mmol, 8.0 eq), EtOH (6 mL) and water (2 mL). The reaction mixture was stirred for 2 hours at 50° C. The resulting mixture was filtered, the filtrate was concentrated under vacuum. The crude residue was purified by a flash column (silica gel, dichloromethane/methanol=20:1) to give 3-(4-{2-[4-(4-amino-3-methoxybenzoyl)-2,3-dihydro-1,4-benzoxazin-8-yl]ethynyl}-1-oxo-3H-isoindol-2-yl)piperidine-2,6-dione (350 mg, 73.8%) as light yellow solid. LC-MS (ESI, m/z) M+1: 551.

Synthesis of (2'S,3S,4'S,5'R)-6-chloro-4'-(3-chloro-2-fluorophenyl)-2'-(2,2-dimethylpropyl)-N-[4-(8-{2-[2-(2,6-dioxopiperidin-3-yl)-1-oxo-3H-isoindol-4-yl]ethynyl}-2,3-dihydro-1,4-benzoxazine-4-carbonyl)-2-methoxyphenyl]-1,2-dihydrospiro[indole-3,3'-pyrrolidine]-5'-carboxamide: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (50 mg, 0.1 mmol, 1.0 eq), 3-(4-{2-[4-(4-amino-3-methoxybenzoyl)-2,3-dihydro-1,4-benzoxazin-8-yl]ethynyl}-1-oxo-3H-isoindol-2-yl)piperidine-2,6-dione (73 mg, 0.1 mmol, 1.2 eq), TCFH (47 mg, 0.2 mmol, 1.5 eq), NMI (23 mg, 0.3 mmol, 2.5 eq) and $CH_3CN$ (1 mL). The reaction mixture was stirred for 2 hours at 25° C. The crude product was purified by Prep-HPLC using the following conditions: Column, XBridge Shield RP18 OBD Column, 5 μm, 19*150 mm; mobile phase, water (0.05% $NH_3 \cdot H_2O$) and $CH_3CN$ (68% Phase B up to 75% in 7 min); Detector, UV 254/220 nm. Finally, (2'S,3S,4'S,5'R)-6-chloro-4'-(3-chloro-2-fluorophenyl)-2'-(2,2-dimethylpropyl)-N-[4-(8-{2-[2-(2,6-dioxopiperidin-3-yl)-1-oxo-3H-isoindol-4-yl]ethynyl}-2,3-dihydro-1,4-benzoxazine-4-carbonyl)-2-methoxyphenyl]-1,2-dihydrospiro[indole-3,3'-pyrrolidine]-5'-carboxamide (15 mg, 13.8%) was obtained as a white solid. LC-MS (ESI, m/z) M+1: 982/984. $^1$HNMR (400 MHz, DMSO-$d_6$) δ 11.01 (s, 1H), 10.70 (s, 1H), 8.32 (d, −8.4 Hz, 1H), 7.82-7.75 (m, 2H), 7.60 (t, J=7.6 Hz, 1H), 7.46-7.24 (m, 6H), 7.20 (t, J=8.0 Hz, 1H), 7.12 (dd, J=8.4, 1.8 Hz, 1H), 6.80 (t, J=8.0 Hz, 1H), 6.52 (dd, J=8.0, 2.0 Hz, 1H), 6.31 (d, −2.0 Hz, 1H), 5.52 (s, 1H), 5.18 (dd, J=13.2, 5.2 Hz, 1H), 4.57 (d, J=18.0 Hz, 1H), 4.51-4.38 (m, 3H), 4.31 (t, −9.8 Hz, 1H), 4.12 (d, −9.6 Hz, 1H), 4.02-3.89 (m, 2H), 3.84 (s, 3H), 3.72 (t, J=11.2 Hz, 1H), 3.53 (d, J=10.6 Hz, 1H), 3.31 (s, 1H), 3.22-3.12 (m, 2H), 3.0-2.87 (m, 1H), 2.61 (d, J=17.2 Hz, 1H), 2.10-2.02 (m, 1H), 1.35 (dd, J=14.2, 9.4 Hz, 1H), 1.20 (d, J=14.0 Hz, 1H), 0.91 (s, 9H).

Example 58: Preparation of (2'S,3S,4'S,5'R)-6-chloro-4'-(3-chloro-2-fluorophenyl)-2'-(2,2-dimethylpropyl)-N-{4-[(1S)-1-(2-{2-[(3S)-2,6-dioxopiperidin-3-yl]-1-oxo-3H-isoindol-4-yl}ethynyl)-6-azaspiro[2.5]octane-6-carbonyl]-2-methoxyphenyl}-1,2-dihydrospiro[indole-3,3'-pyrrolidine]-5'-carboxamide Synthesis of tert-butyl (S)-5-amino-4-(4-(((S)-6-(4-amino-3-methoxybenzoyl)-6-azaspiro[2.5]octan-1-yl)ethynyl)isoindolin-2-yl)-5-oxopentanoate: Into a 100 mL round-bottom flask purged and maintained under an inert atmosphere of nitrogen, were placed (S)-(4-amino-3-methoxyphenyl)(1-ethynyl-6-azaspiro[2.5]octan-6-yl)methanone (1.3 g, 4.5 mmol, 1.0 eq), tert-butyl (4S)-4-carbamoyl-4-(4-iodo-1-oxo-3H-isoindol-2-yl)butanoate (2.0 g, 6.8 mmol, 1.5 eq), $Pd(PPh_3)_4$(528 mg, 0.5 mmol, 0.1 eq), CuI (87 mg, 0.5 mmol, 0.1 eq), triethylamine (1.4 g, 13.7 mmol, 3.0 eq) and N,N-dimethylformamide (20 mL). The reaction mixture was stirred for 2 hours at 70° C. The resulting mixture was diluted with water (60 mL) and then extracted with ethyl acetate (2×60 mL). The combined organic phase was washed with brine (2×60 mL), dried over anhydrous sodium sulfate. After filtration, the filtrate was concentrated under vacuum. The crude residue was purified by a flash column (silica gel, ethyl acetate/petroleum ether=1:0) to give tert-butyl (S)-5-amino-4-(4-(((S)-6-(4-amino-3-methoxybenzoyl)-6-azaspiro[2.5]octan-1-yl)ethynyl)isoindolin-2-yl)-5-oxopentanoate (2.0 g, 74.0%) as light yellow solid.

Synthesis of tert-butyl (S)-5-amino-4-(4-(((S)-6-(4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxybenzoyl)-6-azaspiro[2.5]octan-1-yl)ethynyl)-1-oxoisoindolin-2-yl)-5-oxopentanoate: Into a 40 mL sealed tube, were placed tert-butyl (S)-5-amino-4-(4-(((S)-6-(4-amino-3-methoxybenzoyl)-6-azaspiro[2.5]octan-1-yl)ethynyl)-1-oxoisoindolin-2-yl)-5-oxopentanoate (1.2 g, 2.0 mmol, 1.0 eq), (2'S,3S,4'S,5'R)-6-chloro-4'-(3-chloro-2-fluorophenyl)-2'-neopentylspiro[indoline-3,3'-pyrrolidine]-5'-carboxylic acid (1.0 g, 2.2 mmol, 1.1 eq), TCFH (840 mg, 3.8 mmol, 1.5 eq), NMI (410 mg, 5.0 mmol, 2.5 eq) and $CH_3CN$ (15 mL). The reaction mixture was stirred for 6 hours at 25° C. The resulting mixture was diluted with water (40 mL) and then extracted with ethyl acetate (2×40 mL). The combined organic phase was washed with brine (2×40 mL), dried over anhydrous sodium sulfate. After filtration, the filtrate was concentrated under vacuum. The crude residue was purified by a flash column (silica gel, ethyl acetate/petroleum ether=1:0) to give tert-butyl (S)-5-amino-4-(4-(((S)-6-(4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxybenzoyl)-6-azaspiro[2.5]octan-1-yl)ethynyl)-1-oxoisoindolin-2-yl)-5-oxopentanoate (1.5 g, 72.8%) as light yellow solid. LC-MS (ESI, m/z) M+1: 1033/1035.

Synthesis of (2'S,3S,4'S,5'R)-6-chloro-4'-(3-chloro-2-fluorophenyl)-2'-(2,2-dimethylpropyl)-N-{4-[(1S)-1-(2-{2-[(3S)-2,6-dioxopiperidin-3-yl]-1-oxo-3H-isoindol-4-yl}ethynyl)-6-azaspiro[2.5]octane-6-carbonyl]-2-methoxyphenyl}-1,2-dihydrospiro[indole-3,3'-pyrrolidine]-5'-carboxamide: Into a 100 mL round-bottom flask were placed tert-butyl (S)-5-amino-4-(4-(((S)-6-(4-((2'S,3S,4'S,5'R)-6-chloro-4'-(3-chloro-2-fluorophenyl)-2'-neopentylspiro[indoline-3,3'-pyrrolidine]-5'-carboxamido)-3-methoxybenzoyl)-6-azaspiro[2.5]octan-1-yl)ethynyl)-1-oxoisoindolin-2-yl)-5-oxopentanoate (1.4 g, 1.4 mmol, 1.0 eq), benzenesulfonic acid (643 mg, 4.2 mmol, 3.0 eq) and $CH_3CN$ (40 mL). The reaction mixture was stirred for 4 hours at 80° C. The resulting mixture was diluted with ethyl acetate (100 mL), and then washed by saturated $NaHCO_3$ (30 mL), brine (30 mL), dried over anhydrous sodium sulfate. After filtration, the filtrate was concentrated under vacuum. The crude residue was purified by a flash column (silica gel, DCM/MeOH=10:1) and Prep-TLC (DCM/ethyl acetate=1:5). Finally, (2'S,3S,4'S,5'R)-6-chloro-4'-(3-chloro-2-fluorophenyl)-2'-(2,2-dimethylpropyl)-N-{4-[(1S)-1-(2-{2-[(3S)-2,6-dioxopiperidin-3-yl]-1-oxo-3H-isoindol-4-yl}ethynyl)-6-azaspiro[2.5]octane-6-carbonyl]-2-methoxyphenyl}-1,2-dihydrospiro[indole-3,3'-pyrrolidine]-5'-carboxamide (270 mg, 20.7%) was obtained as a white solid. LC-MS (ESI, m/z) M+1: 959/961. $^1$HNMR (300 MHz, Methanol-$d_4$) δ 8.38 (d, J=8.4 Hz, 1H), 7.75 (d, J=7.5 Hz, 1H), 7.62 (d, J=7.5 Hz, 1H), 7.51 (t, J=7.8 Hz, 1H), 7.38-7.25 (m, 2H), 7.19 (d, J=8.1 Hz, 1H), 7.16-7.06 (m, 2H), 7.04 (dd, J=8.1, 1.8 Hz, 1H), 6.63 (dd, J=8.1, 1.8 Hz, 1H), 6.43 (d, J=1.8 Hz, 1H), 5.21-5.11 (m, 1H), 4.58-4.33 (m, 3H), 4.27-4.07 (m, 2H), 3.95 (s, 3H), 3.80-3.48 (m, 4H), 3.45-3.35 (m, 2H), 3.06-2.70 (m, 2H), 2.30-2.15 (m, 1H), 1.93-1.60 (m, 4H), 1.42-1.28 (m, 4H), 1.17-1.08 (m, 1H), 1.0 (s, 9H), 0.92-0.83 (m, 1H). $T_R$=2.675 min in CHIRAL-HPLC, Column: YMC Cellulose-SC, 100*4.6 mm, 3 μm 109HA90115. mobile phase A: MTBE (0.2% DEA); mobile phase B: MeOH, Start Conc. of Pump B: 30.0%, Oven Temperature: 25° C.

Example 59: Preparation of (2'S,3S,4'S,5'R)-6-chloro-4'-(3-chloro-2-fluorophenyl)-2'-(2,2-dimethylpropyl)-N-{4-[(3S)-3-(3-{2-[(3S)-2,6-dioxopiperidin-3-yl]-1-oxo-3H-isoindol-4-yl}prop-2-yn-1-yl)piperidine-1-carbonyl]-2-methoxyphenyl}-1,2-dihydrospiro[indole-3,3'-pyrrolidine]-5'-carboxamide hydrochloride Synthesis of tert-butyl (3S)-3-(2-methoxyethenyl)piperidine-1-carboxylate: Into a 100 mL round-bottom flask purged and maintained under an inert atmosphere of nitrogen, were placed (methoxymethyl)triphenylphosphonium chloride (3.9 g, 11.3 mmol, 1.5 eq), tetrahydrofuran (20 mL). After that, t-BuOK (1.3 g, 11.3 mmol, 1.5 eq) was added at 0° C., followed by the addition of tert-butyl (3R)-3-formylpiperidine-1-carboxylate (1.6 g, 7.5 mmol, 1.0 eq) in tetrahydrofuran at −20° C. The resulting solution was stirred for 4 hours at 25° C. The resulting mixture was quenched by the addition of $NH_4Cl$ (aq.) (30 mL) and then extracted with ethyl acetate (2×50 mL). The combined organic phase was washed with brine (2×50 mL), dried over anhydrous sodium sulfate. After filtration, the filtrate was concentrated under vacuum. The crude residue was purified by a flash column (silica gel, ethyl acetate/petroleum ether=1:5) to give tert-butyl (3S)-3-(2-methoxyethenyl)piperidine-1-carboxylate (1.2 g, 66.3%) as light yellow oil. LC-MS (ESI, m/z) M+1: 242. $^1$HNMR (300 MHz, DMSO-$d_6$) δ 6.43 (d, J=12.9 Hz, 1H), 4.60 (dd, J=12.9, 8.1 Hz, 1H), 3.82-3.71 (m, 3H), 3.43 (s, 3H), 2.78-2.66 (m, 1H), 2.02-1.94 (m, 1H), 1.73-1.69 (m, 1H), 1.66-1.51 (m, 1H), 1.39 (s, 9H), 1.37-1.13 (m, 2H).

Synthesis of tert-butyl (3S)-3-(2-oxoethyl)piperidine-1-carboxylate: Into a 50-mL round-bottom flask were placed tert-butyl (3S)-3-(2-methoxyethenyl)piperidine-1-carboxylate (1.2 g, 4.9 mmol, 1.0 eq) and formic acid (3 mL). The reaction mixture was stirred for 1 hour at 25° C. The mixture was neutralized to pH=7-8 with $NaHCO_3$ (aq.) and then extracted with ethyl acetate (2×50 mL). The combined organic phase was washed with brine (2×50 mL) and dried over anhydrous sodium sulfate. After filtration, the filtrate was concentrated under vacuum. The crude residue was purified by a flash column (silica gel, ethyl acetate/petroleum ether=1:4) to give tert-butyl (3S)-3-(2-oxoethyl)piperidine-1-carboxylate (800 mg, 70.8%) as light yellow oil. LC-MS (ESI, m/z) M+1: 228. $^1$HNMR (400 MHz, DMSO-$d_6$) δ 9.66 (d, J=1.8 Hz, 1H), 3.76-3.66 (m, 2H), 2.83 (ddd, J=13.6, 10.8, 3.2 Hz, 1H), 2.44-2.26 (m, 3H), 1.94 (ddt, J=14.2, 7.4, 4.0 Hz, 1H), 1.73 (dd, J=13.4, 4.4 Hz, 1H), 1.57 (dt, J=13.0, 4.0 Hz, 1H), 1.39 (s, 9H), 1.36-1.29 (m, 1H), 1.20-1.12 (m, 1H).

Synthesis of tert-butyl (3S)-3-(prop-2-yn-1-yl)piperidine-1-carboxylate: Into a 50-mL round-bottom flask were placed tert-butyl (3S)-3-(2-oxoethyl)piperidine-1-carboxylate (800 mg, 3.5 mmol, 1.0 eq), MeOH (8 mL), $K_2CO_3$ (973 mg, 7.0 mmol, 2.0 eq) and seyferth-gilbert homologation (1.1 g, 5.3 mmol, 1.5 eq). The reaction mixture was stirred for 2 hours at 25° C. The resulting mixture was quenched by the addition of water (50 mL) and then extracted with ethyl acetate (2×50 mL). The combined organic phase was washed with brine (2×50 mL) and dried over anhydrous sodium sulfate. After filtration, the filtrate was concentrated under vacuum. The crude residue was purified by a flash column (silica gel, ethyl acetate/petroleum ether=1:4) to give tert-butyl (3S)-3-(prop-2-yn-1-yl)piperidine-1-carboxylate (700 mg, 89.1%) as light yellow oil. LC-MS (ESI, m/z) M+1: M-(t-Bu)+41+1: 209. $^{1}$HNMR (400 MHz, DMSO-$d_6$) δ 3.92 (s, 1H), 3.76 (d, J=13.0 Hz, 2H), 2.83 (t, J=2.8 Hz, 1H), 2.74 (ddd, J=13.8, 11.4, 3.2 Hz, 1H), 2.11 (dt, J=7.2, 2.8 Hz, 2H), 1.83-1.75 (m, 1H), 1.61-1.49 (m, 2H), 1.40 (s, 9H), 1.37-1.07 (m, 2H).

Synthesis of (3S)-3-(prop-2-yn-1-yl)piperidine hydrochloride: Into a 50-mL round-bottom flask were placed tert-butyl (3S)-3-(prop-2-yn-1-yl)piperidine-1-carboxylate (650 mg, 2.9 mmol, 1.0 eq), dichloromethane (6 mL), HCl (gas) in 1,4-dioxane (6 mL). The reaction mixture was stirred for 1 hour at 25° C. The resulting mixture was concentrated under vacuum to give (3S)-3-(prop-2-yn-1-yl) piperidine hydrochloride (450 mg crude) as off white solid. LC-MS (ESI, m/z) M+1: 124.

Synthesis of (3S)-1-(3-methoxy-4-nitrobenzoyl)-3-(prop-2-yn-1-yl)piperidine: Into a 20 mL sealed tube, were placed (3S)-3-(prop-2-yn-1-yl)piperidine hydrochloride (400 mg, 2.5 mmol, 1.0 eq), 3-methoxy-4-nitrobenzoic acid (494 mg, 2.5 mmol, 1.0 eq), HATU (1.1 g, 2.8 mmol, 1.1 eq), DIEA (971 mg, 7.5 mmol, 3.0 eq), N,N-dimethylformamide (4 mL). The reaction mixture was stirred for 2 hours at 25° C. The resulting mixture was quenched by the addition of water (50 mL) and then extracted with ethyl acetate (2×50 mL). The combined organic phase was washed with brine (2×50 mL) and dried over anhydrous sodium sulfate. After filtration, the filtrate was concentrated under vacuum. The crude residue was purified by a flash column (silica gel, ethyl acetate/petroleum ether=1:1) to give (3S)-1-(3-methoxy-4-nitrobenzoyl)-3-(prop-2-yn-1-yl)piperidine (650 mg, 85.8%) as light yellow oil. LC-MS (ESI, m/z) M+1: 303. $^{1}$HNMR (300 MHz, DMSO-$d_6$) δ 7.93 (d, J=8.1 Hz, 1H), 7.35 (d, J=1.5 Hz, 1H), 7.09 (dd, J=8.1, 1.5 Hz, 1H), 4.48-4.27 (m, 1H), 3.95 (s, 3H), 3.59-3.34 (m, 2H), 3.07-2.57 (m, 3H), 2.22 (d, J=6.6 Hz, 1H), 2.06 (s, 1H), 1.89-1.86 (m, 1H), 1.72 (br, 2H), 1.50-1.43 (m, 1H).

Synthesis of 2-methoxy-4-[(3S)-3-(prop-2-yn-1-yl)piperidine-1-carbonyl]aniline: Into a 40 mL sealed tube were placed (3S)-1-(3-methoxy-4-nitrobenzoyl)-3-(prop-2-yn-1-yl)piperidine (600 mg, 2.0 mmol, 1.0 eq), Fe (443 mg, 7.9 mmol, 4.0 eq), $NH_4Cl$ (849 mg, 15.9 mmol, 8.0 eq), EtOH (9 mL) and water (3 mL). The reaction mixture was stirred for 2 hours at 50° C. The resulting mixture was filtered, the filtrate was concentrated under vacuum. The crude residue was purified by a flash column (silica gel, ethyl acetate/petroleum ether=1:0) to give 2-methoxy-4-[(3S)-3-(prop-2-yn-1-yl)piperidine-1-carbonyl]aniline (450 mg, 83.3%) as light yellow oil. LC-MS (ESI, m/z) M+1: 273. $^{1}$HNMR (400 MHz, DMSO-$d_6$) δ 6.83 (d, J=1.8 Hz, 1H), 6.78 (dd, J=8.0, 1.8 Hz, 1H), 6.62 (d, J=8.0 Hz, 1H), 5.14 (s, 2H), 4.16 (s, 1H), 3.98 (s, 1H), 3.78 (s, 3H), 2.89-2.78 (m, 2H), 2.64 (t, J=11.8 Hz, 1H), 2.13 (td, J=6.8, 2.8 Hz, 2H), 1.92-1.83 (m, 1H), 1.69-1.62 (m, 2H), 1.50-1.36 (m, 1H), 1.33-1.24 (m, 1H).

Synthesis of tert-butyl (4S)-4-(4-{3-[(3S)-1-(4-amino-3-methoxybenzoyl)piperidin-3-yl]prop-1-yn-1-yl}-1-oxo-3H-isoindol-2-yl)-4-carbamoylbutanoate: Into a 20 mL sealed-tube purged and maintained under an inert atmosphere of nitrogen, were placed 2-methoxy-4-[(3S)-3-(prop-2-yn-1-yl)piperidine-1-carbonyl]aniline (280 mg, 1.0 mmol, 1.0 eq), tert-butyl (4S)-4-carbamoyl-4-(4-iodo-1-oxo-3H-isoindol-2-yl)butanoate (685 mg, 1.5 mmol, 1.5 eq), $Pd(PPh_3)_4$ (119 mg, 0.1 mmol, 0.1 eq), CuI (20 mg, 0.1 mmol, 0.1 eq), triethylamine (312 mg, 3.1 mmol, 3.0 eq) and N,N-dimethylformamide (4 mL). The reaction mixture was stirred for 2 hours at 70° C. The resulting mixture was diluted with water (60 mL) and then extracted with ethyl acetate (2×60 mL). The combined organic phase was washed with brine (2×60 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-(4-{3-[(3S)-1-(4-amino-3-methoxybenzoyl)piperidin-3-yl]prop-1-yn-1-yl}-1-oxo-3H-isoindol-2-yl)-4-carbamoylbutanoate (400 mg, 66.1%) as light yellow solid. LC-MS (ESI, m/z) M+1: 589.

Synthesis of tert-butyl (4S)-4-carbamoyl-4-(4-{3-[(3S)-1-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}piperidin-3-yl]prop-1-yn-1-yl}-1-oxo-3H-isoindol-2-yl)butanoate: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (100 mg, 0.2 mmol, 1.0 eq), tert-butyl (4S)-4-(4-{3-[(3S)-1-(4-amino-3-methoxybenzoyl)piperidin-3-yl]prop-1-yn-1-yl}-1-oxo-3H-isoindol-2-yl)-4-carbamoylbutanoate (196 mg, 0.3 mmol, 1.5 eq), TCFH (93 mg, 0.3 mmol, 1.5 eq), NMI (45 mg, 0.6 mmol, 2.5 eq), $CH_3CN$ (1 mL). The reaction mixture was stirred for 2 hours at 25° C. The resulting mixture was diluted with water (40 mL) and then extracted with ethyl acetate (2×40 mL). The combined organic phase was washed with brine (2×40 mL), dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{3-[(3S)-1-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}piperidin-3-yl]prop-1-yn-1-yl}-1-oxo-3H-isoindol-2-yl)butanoate (120 mg, 52.9%) as light yellow solid. LC-MS (ESI, m/z) M+1: 1021/1023.

Synthesis of (2'S,3S,4'S,5'R)-6-chloro-4'-(3-chloro-2-fluorophenyl)-2'-(2,2-dimethylpropyl)-N-{4-[(3S)-3-(3-{2-[(3S)-2,6-dioxopiperidin-3-yl]-1-oxo-3H-isoindol-4-yl}prop-2-yn-1-yl)piperidine-1-carbonyl]-2-methoxyphenyl}-1,2-dihydrospiro[indole-3,3'-pyrrolidine]-5'-carboxamide hydrochloride: Into an 8 mL sealed tube, were placed tert-butyl (4S)-4-carbamoyl-4-(4-{3-[(3S)-1-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}piperidin-3-yl]prop-1-yn-1-yl}-1-oxo-3H-isoindol-2-yl)butanoate (100 mg, 0.1 mmol, 1.0 eq), benzenesulfonic acid (23 mg, 0.1 mmol, 1.5 eq) and $CH_3CN$ (2 mL). The reaction mixture was stirred for 16 hours at 80° C. The crude product was purified by Prep-HPLC using the following conditions: Column, SunFire Prep C18 OBD Column, 50*250 mm 5 μm 10 nm; mobile phase, water (0.05% HCl) and $CH_3CN$ (45% Phase B up to 55% in 7 min); Detector, UV 254/220 nm. Finally, (2'S,3S,4'S,5'R)-6-chloro-4'-(3-chloro-2-fluorophenyl)-2'-(2,2-dimethylpropyl)-N-{4-[(3S)-3-(3-{2-[(3S)-2,6-dioxopiperidin-3-yl]-1-oxo-3H-isoindol-4-yl}prop-2-yn-1-yl) piperidine-1-carbonyl]-2-methoxyphenyl}-1,2-dihydrospiro [indole-3,3'-pyrrolidine]-5'-carboxamide hydrochloride (20 mg, 20.8%) was obtained as light yellow solid. LC-MS (ESI, m/z) M+1: 947/949. $^{1}$HNMR (400 MHz, DMSO-$d_6$) δ 10.97

(s, 1H), 7.91 (s, 1H), 7.74-7.64 (m, 3H), 7.53-7.27 (m, 6H), 7.05 (s, 1H), 6.97 (d, J=8.2 Hz, 1H), 6.66 (s, 1H), 6.41 (s, 1H), 5.13 (d, J=13.6 Hz, 2H), 4.59-4.35 (m, 5H), 4.04 (s, 1H), 3.77 (s, 4H), 3.39-3.30 (m, 1H), 2.90 (t, J=14.8 Hz, 3H), 2.61-2.56 (m, 1H), 2.02-1.91 (m, 4H), 1.82 (br, 1H), 1.51-1.35 (m, 4H), 0.82 (s, 11H).

Example 60: Preparation of tert-butyl(2'S,3S,4'S,5'R)-6-chloro-4'-(3-chloro-2-fluorophenyl)-2'-(2,2-dimethylpropyl)-N-{4-[(1S)-1-(2-{2-[(3S)-2,6-dioxopiperidin-3-yl]-1,3-dioxoisoindol-4-yl}ethynyl)-6-azaspiro[2.5]octane-6-carbonyl]-2-methoxyphenyl}-1,2-dihydrospiro[indole-3,3'-pyrrolidine]-5'-carboxamide Synthesis of tert-butyl (4S)-4-(4-{2-[(1S)-6-(4-amino-3-methoxybenzoyl)-6-azaspiro[2.5]octan-1-yl]ethynyl}-1,3-dioxoisoindol-2-yl)-4-carbamoylbutanoate: Into an 8 mL sealed tube purged and maintained under an inert atmosphere of nitrogen, were placed 4-[(1S)-1-ethynyl-6-azaspiro[2.5]octane-6-carbonyl]-2-methoxyaniline (160 mg, 0.6 mmol, 1.2 eq), tert-butyl (4S)-4-carbamoyl-4-(4-iodo-1,3-dioxoisoindol-2-yl)butanoate (215 mg, 0.5 mmol, 1.0 eq), CuI (9 mg, 0.1 mmol, 0.1 eq), triethylamine (142 mg, 1.4 mmol, 3.0 eq), $Pd(PPh_3)_4$(54 mg, 0.1 mmol, 0.1 eq) and N,N-dimethylformamide (2 mL). The reaction mixture was stirred for 2 hours at 70° C. The resulting mixture was diluted with water (40 mL) and extracted with ethyl acetate (2×40 mL). The combined organic phase was washed with brine (2×40 mL) and dried over anhydrous sodium sulfate. After filtration, the filtrate was concentrated under vacuum. The crude residue was purified by a flash column (silica gel, ethyl acetate/petroleum ether=1:0) to give (4S)-4-(4-{2-[(1S)-6-(4-amino-3-methoxybenzoyl)-6-azaspiro[2.5]octan-1-yl]ethynyl}-1,3-dioxoisoindol-2-yl)-4-carbamoylbutanoate (150 mg, 52.0%) as light yellow oil. LC-MS (ESI, m/z) M+1: 615.

Synthesis of tert-butyl (4S)-4-carbamoyl-4-(4-{2-[(1S)-6-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-6-azaspiro[2.5]octan-1-yl]ethynyl}-1,3-dioxoisoindol-2-yl)butanoate: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (74 mg, 0.2 mmol, 1.0 eq), tert-butyl (4S)-4-(4-{2-[(1S)-6-(4-amino-3-methoxybenzoyl)-6-azaspiro[2.5]octan-1-yl]ethynyl}-1,3-dioxoisoindol-2-yl)-4-carbamoylbutanoate (121 mg, 0.2 mmol, 1.2 eq), TCFH (69 mg, 0.2 mmol, 1.5 eq), NMI (34 mg, 0.4 mmol, 2.5 eq) and $CH_3CN$ (2 mL). The reaction mixture was stirred for 2 hours at 25° C. The resulting mixture was diluted with water (40 mL) and then extracted with ethyl acetate (2×40 mL). The combined organic phase was washed with brine (2×40 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1S)-6-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-6-azaspiro[2.5]octan-1-yl]ethynyl}-1,3-dioxoisoindol-2-yl)butanoate (130 mg, 75.7%) as light yellow oil. LC-MS (ESI, m/z) M+1: 1047/1049.

Synthesis of tert-butyl(2'S,3S,4'S,5'R)-6-chloro-4'-(3-chloro-2-fluorophenyl)-2'-(2,2-dimethylpropyl)-N-{4-[(1S)-1-(2-{2-[(3S)-2,6-dioxopiperidin-3-yl]-1,3-dioxoisoindol-4-yl}ethynyl)-6-azaspiro[2.5]octane-6-carbonyl]-2-methoxyphenyl}-1,2-dihydrospiro[indole-3,3'-pyrrolidine]-5'-carboxamide: Into an 8 mL sealed tube were placed tert-butyl (4S)-4-carbamoyl-4-(4-{2-[(1S)-6-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-6-azaspiro[2.5]octan-1-yl]ethynyl}-1,3-dioxoisoindol-2-yl)butanoate (100 mg, 0.1 mmol, 1.0 eq), $CH_3CN$ (2 mL) and benzenesulfonic acid (30 mg, 0.2 mmol, 2.0 eq). The reaction mixture was stirred for 16 hours at 80° C. The crude product was purified by Prep-HPLC using the following conditions: Column, XBridge Shield RP18 OBD Column, 5 μm, 19*150 mm; mobile phase, water (0.05% HCl) and $CH_3CN$ (45% Phase B up to 60% in 7 min); Detector, UV 254/220 nm. Finally, (2'S,3S,4'S,5'R)-6-chloro-4'-(3-chloro-2-fluorophenyl)-2'-(2,2-dimethylpropyl)-N-{4-[(1S)-1-(2-{2-[(3S)-2,6-dioxopiperidin-3-yl]-1,3-dioxoisoindol-4-yl}ethynyl)-6-azaspiro[2.5]octane-6-carbonyl]-2-methoxyphenyl}-1,2-dihydrospiro[indole-3,3'-pyrrolidine]-5'-carboxamide (1.8 mg, 1.9%) was obtained as off white solid. LC-MS (ESI, m/z) M+1: 972/973. $^1$HNMR (300 MHz, DMSO-$d_6$) δ 11.12 (s, 1H), 7.82 (d, J=3.2 Hz, 3H), 7.61-7.29 (m, 4H), 7.08 (br, 2H), 7.02-6.94 (m, 1H), 6.64 (br, 1H), 6.39 (br, 1H), 5.18-5.10 (m, 1H), 4.42-4.33 (m, 1H), 3.88-3.74 (m, 6H), 2.96-2.81 (m, 2H), 2.64-2.59 (m, 2H), 2.05 (br, 1H), 1.86-1.70 (m, 4H), 1.62-1.32 (m, 4H), 1.24 (s, 2H), 1.17-1.11 (m, 1H), 0.84 (br, 11H).

Example 61: Preparation of (2'S,3S,4'S,5'R)-6-chloro-4'-(3-chloro-2-fluorophenyl)-2'-(2,2-dimethylpropyl)-N-{4-[(1S,3S)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide Synthesis of tert-butyl (3E)-3-(2-ethoxy-2-oxoethylidene)piperidine-1-carboxylate: To a stirred mixture of triethyl phosphonoacetate (43.4 g, 195.7 mmol, 1.3 eq) in tetrahydrofuran (300 mL) was added t-BuOK (22.0 g, 195.7 mmol, 1.3 eq) in portions at 0° C. The reaction mixture was stirred for 1 hour at 0° C. To the above mixture was added tert-butyl 3-oxopiperidine-1-carboxylate (30.0 g, 150.6 mmol, 1.0 eq) at −50° C. The reaction mixture was stirred for additional 3 hours at 25° C. The resulting mixture was diluted with water (200 mL) and then extracted with ethyl acetate (2×200 mL). The combined organic layers were washed with brine (200 mL), dried over anhydrous sodium sulfate. After filtration, the filtrate was concentrated under vacuum. The crude residue was purified by a flash column (silica gel, ethyl acetate/petroleum ether=1:5) to give tert-butyl (3E)-3-(2-ethoxy-2-oxoethylidene)piperidine-1-carboxylate (26 g, 64.1%) as brown oil. LC-MS (ESI, m/z) M-(t-Bu)+41+1: 255. $^1$HNMR (400 MHz, DMSO-$d_6$) δ 5.74-5.71 (m, 1H), 4.54 (s, 1H), 4.15-3.99 (m, 2H), 3.92 (d, J=1.2 Hz, 1H), 3.44-3.37 (m, 2H), 2.86 (td, J=6.4, 1.6 Hz, 1H), 2.35 (td, J=6.3, 1.2 Hz, 1H), 1.66-1.53 (m, 2H), 1.38 (d, J=6.8, 9H), 1.23-1.18 (m, 3H).

Synthesis of 5-tert-butyl 1-ethyl 5-azaspiro[2.5]octane-1,5-dicarboxylate: To a stirred mixture of trimethyl(oxo)-lambda6-sulfanylium iodide (32.7 g, 148.5 mmol, 2.0 eq) in DMSO (200 mL) was added t-BuOK (16.7 g, 148.5 mmol, 2.0 eq) in portions at 25° C. The reaction mixture was stirred for 30 minutes at 25° C. After that, to the above mixture was added tert-butyl (3E)-3-(2-ethoxy-2-oxoethylidene)piperidine-1-carboxylate (20.0 g, 74.3 mmol, 1.0 eq) at 25° C. The reaction mixture was stirred for 16 hours at 25° C. The resulting mixture was diluted with water (400 mL) and then extracted with ethyl acetate (2×400 mL). The combined organic layers were washed with water (2×400 mL) and brine (2×400 mL), dried over anhydrous sodium sulfate. After filtration, the filtrate was concentrated under vacuum. The crude residue was purified by a flash column (silica gel, ethyl acetate/petroleum ether=1:5) to give 5-tert-butyl 1-ethyl 5-azaspiro[2.5]octane-1,5-dicarboxylate (6.5 g, 31.0%) as light yellow oil. LC-MS (ESI, m/z) M+1: 269. $^{1}$HNMR (300 MHz, DMSO-$d_6$) δ 4.11-4.03 (m, 2H), 3.44-3.39 (m, 2H), 3.17 (s, 1H), 3.0 (s, 1H), 1.96 (t, J=6.3 Hz, 1H), 1.80-1.67 (m, 2H), 1.42 (d, J=8.4 Hz, 9H), 1.37-1.23 (m, 1H), 1.18 (td, J=7.2, 5.4 Hz, 4H), 1.04 (dd, J=8.1, 4.5 Hz, 1H), 0.98-0.87 (m, 1H).

Synthesis of tert-butyl 1-(hydroxymethyl)-5-azaspiro[2.5]octane-5-carboxylate: Into a 500-mL 3-necked round-bottom flask, were placed 5-tert-butyl 1-ethyl 5-azaspiro[2.5]octane-1,5-dicarboxylate (6.5 g, 22.9 mmol, 1.0 eq), tetrahydrofuran (70 mL). After that, $LiAlH_4$ (2.0 g, 45.9 mmol, 2.0 eq) was added at 0° C. The reaction mixture was stirred for 1 hour at 0° C. The resulting mixture was quenched by the addition of water (2 mL), 15% NaOH (2 mL), water (6 mL). After filtration, the filtrate was concentrated under vacuum to give tert-butyl 1-(hydroxymethyl)-5-azaspiro[2.5]octane-5-carboxylate (5.5 g crude) as light yellow oil. LC-MS (ESI, m/z) M-(t-Bu)+41+1: 227. $^{1}$HNMR (400 MHz, DMSO-$d_6$) δ 4.40 (s, 1H), 3.45 (t, J=7.0 Hz, 2H), 3.40 (d, J=6.4 Hz, 2H), 3.34-3.19 (m, 2H), 2.10-2.06 (d, J=6.2 Hz, 1H), 1.94 (t, J=6.4 Hz, 1H), 1.74-1.68 (m, 1H), 1.63-1.54 (m, 1H), 1.41 (d, J=17.2 Hz, 9H), 1.01-0.76 (m, 1H), 0.57-0.37 (m, 1H), 0.09 (t, J=5.0 Hz, 1H).

Synthesis of tert-butyl 1-formyl-5-azaspiro[2.5]octane-5-carboxylate: Into a 250-mL round flask, were placed tert-butyl 1-(hydroxymethyl)-5-azaspiro[2.5]octane-5-carboxylate (5.5 g, 22.8 mmol, 1.0 eq), dichloromethane (60 mL). After that, PCC (9.8 g, 45.6 mmol, 2.0 eq) was added at 0° C. The reaction mixture was stirred for 2 hours at 25° C. The resulting mixture was then quenched by the addition of water (100 mL) and extracted with dichloromethane (2×100 mL). The combined organic phase was washed with brine (2×100 mL), dried over anhydrous sodium sulfate. After filtration, the filtrate was concentrated under vacuum. The crude residue was purified by a flash column (silica gel, ethyl acetate/petroleum ether=1:3) to give tert-butyl 1-formyl-5-azaspiro[2.5]octane-5-carboxylate (2.8 g, 51.3%) as light yellow oil. LC-MS (ESI, m/z) M-(t-Bu)+41+1: 225. $^{1}$HNMR (300 MHz, DMSO-$d_6$) δ 9.31 (d, J=5.4 Hz, 1H), 3.56-3.45 (m, 1H), 3.26-3.04 (m, 2H), 1.90-1.64 (m, 3H), 1.54 (ddd, J=13.5, 7.2, 3.6 Hz, 1H), 1.40 (s, 9H), 1.41-1.33 (m, 2H), 1.16-0.77 (m, 2H).

Synthesis of tert-butyl 1-ethynyl-5-azaspiro[2.5]octane-5-carboxylate: Into a 100 mL round-bottom flask were placed tert-butyl 1-formyl-5-azaspiro[2.5]octane-5-carboxylate (2.8 g, 11.7 mmol, 1.0 eq), MeOH (30 mL), $K_2CO_3$ (3.0 g, 23.4 mmol, 2.0 eq) and seyferth-gilbert homologation (3.4 g, 17.6 mmol, 1.5 eq). The reaction mixture was stirred for 2 hours at 25° C. The resulting mixture was then quenched by the addition of water (60 mL) and extracted with ethyl acetate (2×60 mL). The combined organic phase was washed with brine (2×60 mL), dried over anhydrous sodium sulfate. After filtration, the filtrate was concentrated under vacuum. The crude residue was purified by a flash column (silica gel, ethyl acetate/petroleum ether=1:3) to give tert-butyl 1-ethynyl-5-azaspiro[2.5]octane-5-carboxylate (1.2 g, 43.6%) as light yellow oil. LC-MS (ESI, m/z) M-(t-Bu)+41+1: 221. $^{1}$HNMR (300 MHz, DMSO-$d_6$) δ 3.55-3.47 (m, 1H), 3.20-3.09 (m, 3H), 2.70 (d, J=2.1 Hz, 1H), 1.68-1.50 (m, 4H), 1.39 (s, 9H), 1.39-1.30 (m, 1H), 0.97-0.82 (m, 1H), 0.51 (t, J=4.8 Hz, 1H).

Synthesis of 1-ethynyl-5-azaspiro[2.5]octane: To a stirred mixture of tert-butyl 1-ethynyl-5-azaspiro[2.5]octane-5-carboxylate (1.2 g, 5.1 mmol, 1.0 eq) and 2,6-dimethylpyridine (1.6 g, 15.3 mmol, 3.0 eq) in dichloromethane (15 mL) was added TMSI (2.0 g, 10.2 mmol, 2.0 eq) dropwise at 0° C. The reaction mixture was stirred for 1 hour at 0° C. The resulting mixture was concentrated under vacuum to give 1-ethynyl-5-azaspiro[2.5]octane (900 mg crude) as light yellow solid. LC-MS (ESI, m/z) M+1: 136.

Synthesis of 1-ethynyl-5-(3-methoxy-4-nitrobenzoyl)-5-azaspiro[2.5]octane: To a stirred mixture of 1-ethynyl-5-azaspiro[2.5]octane (900 mg crude, 6.6 mmol, 1.0 eq), 3-methoxy-4-nitrobenzoic acid (1.4 g, 7.3 mmol, 1.1 eq), DIEA (4.4 g, 34.0 mmol, 2.0 eq) in N,N-dimethylformamide (9 mL) was added HATU (2.8 g, 7.3 mmol, 1.1 eq) in portions at 25° C. The reaction mixture was stirred for 2 hours at 25° C. The resulting mixture was diluted with water (100 mL) and extracted with ethyl acetate (2×100 mL). The combined organic layers were washed with water (2×100 mL), dried over anhydrous sodium sulfate. After filtration, the filtrate was concentrated under vacuum. The crude residue was purified by a flash column (silica gel, ethyl acetate/petroleum ether=1:0) to give 1-ethynyl-5-(3-methoxy-4-nitrobenzoyl)-5-azaspiro[2.5]octane (1.5 g, 71.7%) as yellow oil. LC-MS (ESI, m/z) M+1: 315. $^{1}$HNMR (400 MHz, DMSO-$d_6$) δ 7.93 (dd, J=12.8, 8.0 Hz, 1H), 7.28 (d, J=11.8 Hz, 1H), 7.05 (dd, J=17.2, 8.2 Hz, 1H), 3.95 (d, J=5.0 Hz, 3H), 3.86-3.78 (m, 1H), 3.60-3.38 (m, 1H), 3.17-2.98 (m, 1H), 2.74 (d, J=5.6 Hz, 1H), 1.68 (s, 2H), 1.60 (s, 1H), 1.48 (s, 1H), 1.30-1.21 (m, 1H), 1.07-0.99 (m, 1H), 0.78-0.73 (m, 1H), 0.55 (d, J=38.1 Hz, 1H).

Synthesis of (1S,3S)-1-ethynyl-5-(3-methoxy-4-nitrobenzoyl)-5-azaspiro[2.5]octane and (1R,3S)-1-ethynyl-5-(3-methoxy-4-nitrobenzoyl)-5-azaspiro[2.5]octane and (1S,3R)-1-ethynyl-5-(3-methoxy-4-nitrobenzoyl)-5-azaspiro[2.5]octane and (1R,3R)-1-ethynyl-5-(3-methoxy-4-nitrobenzoyl)-5-azaspiro[2.5]octane: 1.5 g of 1-ethynyl-5-(3-methoxy-4-nitrobenzoyl)-5-azaspiro[2.5]octane was purified by Chiral-Prep-HPLC using the following conditions: (R, R)-WHELK-O1-Kromasil, 2.11*25 cm, 5 μm; Mobile Phase A: $CO_2$, Mobile Phase B: IPA (0.5%2M $NH_3$-MeOH); Flow rate: 55 mL/min; Gradient: isocratic 20% B; Detector, 220 nm. Finally, (1S,3S)-1-ethynyl-5-(3-methoxy-4-nitrobenzoyl)-5-azaspiro[2.5]octane (90 mg) was obtained as light yellow solid. And (1R,3S)-1-ethynyl-5-(3-methoxy-4-nitrobenzoyl)-5-azaspiro[2.5]octane (500 mg) was obtained as light yellow solid. (1S,3R)-1-ethynyl-5-(3-methoxy-4-nitrobenzoyl)-5-azaspiro[2.5]octane (520 mg) was obtained as light yellow solid. (1R,3R)-1-ethynyl-5-(3-methoxy-4-nitrobenzoyl)-5-azaspiro[2.5]octane (110 mg) was obtained as light yellow solid. LC-MS (ESI, m/z) M+1: 315. A, $T_R$=11.450 min in CHIRAL-HPLC, Column: CHIRALPAK IG-3, 100*4.6 mm, 3 um IG3000-BM008. mobile phase A: n-Hexane (0.1% DEA); mobile phase B: Isopropanol, Start Conc. of Pump B: 30.0% in 4 min, Oven Temperature: 25° C. B, $T_R$=7.693 min in CHIRAL-HPLC, Column: CHIRALPAK IG-3, 100*4.6 mm, 3 um IG3000-BM008. mobile phase A: n-Hexane (0.1% DEA); mobile phase B: Isopropanol, Start Conc. of Pump B: 30.0% in 4 min, Oven Temperature: 25° C. C, $T_R$=9.212 min in CHIRAL-HPLC, Column: CHIRALPAK IG-3, 100*4.6 mm, 3 um IG3000-BM008. mobile phase A: n-Hexane (0.1% DEA); mobile phase B: Isopropanol, Start Conc. of Pump B: 30.0% in 4 min, Oven Temperature: 25° C. D, $T_R$=10.343 min in CHIRAL-HPLC, Column: CHIRALPAK IG-3, 100*4.6 mm, 3 um IG3000-BM008. mobile phase A: n-Hexane (0.1% DEA); mobile phase B: Isopropanol, Start Conc. of Pump B: 30.0% in 4 min, Oven Temperature: 25° C.

Synthesis of tert-butyl (4S)-4-carbamoyl-4-(4-{2-[(1S,3S)-5-(3-methoxy-4-nitrobenzoyl)-5-azaspiro[2.5]octan-1-yl]ethynyl}-1-oxo-3H-isoindol-2-yl)butanoate: Into an 8 mL sealed tube purged and maintained under an inert atmosphere of nitrogen, were placed (1S,3S)-1-ethynyl-5-(3-methoxy-4-nitrobenzoyl)-5-azaspiro[2.5]octane (90 mg, 0.3 mmol, 1.0 eq), tert-butyl (4S)-4-carbamoyl-4-(4-iodo-1-oxo-3H-isoindol-2-yl)butanoate (191 mg, 0.4 mmol, 1.5 eq), CuI (6 mg, 0.1 mmol, 0.1 eq), triethylamine (87 mg, 0.9 mmol, 3.0 eq), $Pd(PPh_3)_4$ (33 mg, 0.1 mmol, 0.1 eq) and N,N-dimethylformamide (1 mL). The reaction mixture was stirred for 2 hours at 70° C. The resulting mixture was diluted with water (20 mL) and then extracted with ethyl acetate (2×20 mL). The combined organic phase was washed with brine (2×20 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1S,3S)-5-(3-methoxy-4-nitrobenzoyl)-5-azaspiro[2.5]octan-1-yl]ethynyl}-1-oxo-3H-isoindol-2-yl)butanoate (200 mg crude) as light yellow solid. LC-MS (ESI, m/z) M+1: 631.

Synthesis of tert-butyl (4S)-4-(4-{2-[(1S,3S)-5-(4-amino-3-methoxybenzoyl)-5-azaspiro[2.5]octan-1-yl]ethynyl}-1-oxo-3H-isoindol-2-yl)-4-carbamoylbutanoate: Into a 40 mL sealed tube were placed tert-butyl (4S)-4-carbamoyl-4-(4-{2-[(1S,3S)-5-(3-methoxy-4-nitrobenzoyl)-5-azaspiro[2.5]octan-1-yl]ethynyl}-1-oxo-3H-isoindol-2-yl)butanoate (180 mg, 0.3 mmol, 1.0 eq), Fe (64 mg, 1.1 mmol, 4.0 eq), $NH_4Cl$ (122 mg, 2.3 mmol, 8.0 eq), EtOH (6 mL), water (2 mL). The reaction mixture was stirred for 2 hours at 60° C. The resulting mixture was filtered, the filtrate was concentrated under vacuum. The crude residue was purified by a flash column (silica gel, dichloromethane/methanol=10:1) to give tert-butyl (4S)-4-(4-{2-[(1S,3S)-5-(4-amino-3-methoxybenzoyl)-5-azaspiro[2.5]octan-1-yl]ethynyl}-1-oxo-3H-isoindol-2-yl)-4-carbamoylbutanoate (160 mg, 93.3%) as light yellow solid. LC-MS (ESI, m/z) M+1: 601.

Synthesis of tert-butyl (4S)-4-carbamoyl-4-(4-{2-[(1S,3S)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (88 mg, 0.2 mmol, 1.0 eq), tert-butyl (4S)-4-(4-{2-[(1S,3S)-5-(4-amino-3-methoxybenzoyl)-5-azaspiro[2.5]octan-1-yl]ethynyl}-1-oxo-3H-isoindol-2-yl)-4-carbamoylbutanoate (141 mg, 0.2 mmol, 1.2 eq), TCFH (82 mg, 0.3 mmol, 1.5 eq), NMI (40 mg, 0.5 mmol, 2.5 eq), $CH_3CN$ (2 mL). The reaction mixture was stirred for 2 hours at 25° C. The resulting mixture was diluted with water (40 mL) and extracted with ethyl acetate (2×40 mL). The combined organic phase was washed with brine (2×40 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1S,3S)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (120 mg, 59.5%) as light yellow solid. LC-MS (ESI, m/z) M+1: 1033/1035.

Synthesis of (2'S,3S,4'S,5'R)-6-chloro-4'-(3-chloro-2-fluorophenyl)-2'-(2,2-dimethylpropyl)-N-{4-[(1S,3S)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide: Into an 8 mL sealed tube were placed tert-butyl (4S)-4-carbamoyl-4-(4-{2-[(1S,3S)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (100 mg, 0.1 mmol, 1.0 eq), $CH_3CN$ (3 mL) and benzenesulfonic acid (31 mg, 0.2 mmol, 2.0 eq). The reaction mixture was stirred for 16 hours at 80° C. The crude product was purified by Prep-HPLC using the following conditions: Column, XBridge Shield RP18 OBD Column, 5 μm, 19*150 mm; mobile phase, water (0.05% HCl) and $CH_3CN$ (40% Phase B up to 55% in 7 min); Detector, UV 254/220 nm. Finally, (2'S,3S,4'S,5'R)-6-chloro-4'-(3-chloro-2-fluorophenyl)-2'-(2,2-dimethylpropyl)-N-{4-[(1S,3S)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide (4.3 mg, 4.6%) was obtained as off white solid. LC-MS (ESI, m/z) M+1: 958/960. $^1$HNMR (400 MHz, DMSO-$d_6$) δ 10.97 (s, 1H), 9.82 (br, 1H), 9.10 (br, 1H), 7.88 (br, 1H), 7.70-7.57 (m, 2H), 7.52-7.39 (m, 5H), 7.29-7.24 (m, 1H), 6.95-6.90 (m, 2H), 6.64 (d, J=5.8 Hz 1H), 6.39 (s, 1H), 5.13-5.02 (m, 2H), 4.39-4.17 (m, 4H), 4.10-3.84 (m, 5H), 3.37-3.32 (m, 4H), 2.88-2.82 (m, 1H), 1.98-1.88 (m, 2H), 1.91 (m, 1H), 1.65-1.59 (m, 6H), 1.06-1.01 (m, 1H), 0.84 (br, 11H).

Example 62: Preparation of Synthesis of (2'S,3S,4'S,5'R)-6-chloro-4'-(3-chloro-2-fluorophenyl)-2'-(2,2-dimethylpropyl)-N-{4-[(1R,3S)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide Synthesis of tert-butyl (4S)-4-carbamoyl-4-(4-{2-[(1R,3S)-5-(3-methoxy-4-nitrobenzoyl)-5-azaspiro[2.5]octan-1-yl]ethynyl}-1-oxo-3H-isoindol-2-yl)butanoate: Into a 20 mL sealed tube purged and maintained under an inert atmosphere of nitrogen, were placed (1R,3S)-1-ethynyl-5-(3-methoxy-4-nitrobenzoyl)-5-azaspiro[2.5]octane (500 mg, 1.6 mmol, 1.0 eq), tert-butyl (4S)-4-carbamoyl-4-(4-iodo-1-oxo-3H-isoindol-2-yl)butanoate (1.0 g, 2.4 mmol, 1.5 eq), CuI (30 mg, 0.2 mmol, 0.1 eq), triethylamine (483 mg, 4.8 mmol, 3.0 eq), $Pd(PPh_3)_4$ (184 mg, 0.2 mmol, 0.1 eq) and N,N-dimethylformamide (5 mL). The reaction mixture was stirred for 2 hours at 70° C. The resulting mixture was diluted with water (100 mL) and then extracted with ethyl acetate (2×100 mL). The combined organic phase was washed with brine (2×100 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1R,3S)-5-(3-methoxy-4-nitrobenzoyl)-5-azaspiro[2.5]octan-1-yl]ethynyl}-1-oxo-3H-isoindol-2-yl)butanoate (600 mg, 59.8%) as light yellow solid. LC-MS (ESI, m/z) M+1: 631.

Synthesis of tert-butyl (4S)-4-(4-{2-[(1R,3S)-5-(4-amino-3-methoxybenzoyl)-5-azaspiro[2.5]octan-1-yl]ethynyl}-1- oxo-3H-isoindol-2-yl)-4-carbamoylbutanoate: Into a 40 mL sealed tube were placed tert-butyl (4S)-4-carbamoyl-4-(4-{2-[(1R,3S)-5-(3-methoxy-4-nitrobenzoyl)-5-azaspiro[2.5]octan-1-yl]ethynyl}-1-oxo-3H-isoindol-2-yl)butanoate (500 mg, 0.8 mmol, 1.0 eq), Fe (177 mg, 3.2 mmol, 4.0 eq), $NH_4Cl$ (339 mg, 6.3 mmol, 8.0 eq), EtOH (15 mL) and water (5 mL). The reaction mixture was stirred for 2 hours at 60° C. The resulting mixture was filtered, the filtrate was concentrated under vacuum. The crude residue was purified by a flash column (silica gel, dichloromethane/methanol=10:1) to give tert-butyl (4S)-4-(4-{2-[(1R,3S)-5-(4-amino-3-methoxybenzoyl)-5-azaspiro[2.5]octan-1-yl]ethynyl}-1-oxo-3H-isoindol-2-yl)-4-carbamoylbutanoate (450 mg, 94.5%) as light yellow solid. LC-MS (ESI, m/z) M+1: 601.

Synthesis of tert-butyl (4S)-4-carbamoyl-4-(4-{2-[(1R,3S)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (113 mg, 0.3 mmol, 1.0 eq), tert-butyl (4S)-4-(4-{2-[(1R,3S)-5-(4-amino-3-methoxybenzoyl)-5-azaspiro[2.5]octan-1-yl]ethynyl}-1-oxo-3H-isoindol-2-yl)-4-carbamoylbutanoate (181 mg, 0.3 mmol, 1.2 eq), TCFH (105 mg, 0.4 mmol, 1.5 eq), NMI (51 mg, 0.6 mmol, 2.5 eq) and $CH_3CN$ (2 mL). The reaction mixture was stirred for 2 hours at 25° C. The resulting mixture was diluted with water (40 mL) and extracted with ethyl acetate (2×40 mL). The combined organic phase was washed with brine (2×40 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1R,3S)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (170 mg, 65.7%) as light yellow solid. LC-MS (ESI, m/z) M+1: 1033/1035.

Synthesis of (2'S,3S,4'S,5'R)-6-chloro-4'-(3-chloro-2-fluorophenyl)-2'-(2,2-dimethylpropyl)-N-{4-[(1R,3S)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide: Into an 8 mL sealed tube were placed tert-butyl (4S)-4-carbamoyl-4-(4-{2-[(1R,3S)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (150 mg, 0.1 mmol, 1.0 eq), $CH_3CN$ (3 mL) and benzenesulfonic acid (46 mg, 0.3 mmol, 2.0 eq). The reaction mixture was stirred for 16 hours at 80° C. The crude product was purified by Prep-HPLC using the following conditions: Column, XBridge Shield RP18 OBD Column, 5 μm, 19*150 mm; mobile phase, water (0.05% HCl) and $CH_3CN$ (40% Phase B up to 55% in 7 min); Detector, UV 254/220 nm. Finally, (2'S,3S,4'S,5'R)-6-chloro-4'-(3-chloro-2-fluorophenyl)-2'-(2,2-dimethylpropyl)-N-{4-[(1R,3S)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide (3.9 mg, 2.8%) was obtained as off white solid. LC-MS (ESI, m/z) M+1: 958/960. $^1$HNMR (300 MHz, DMSO-$d_6$) δ 10.98 (s, 1H), 9.87 (br, 1H), 7.97 (br, 1H), 7.71 (dd, J=7.5, 1.2 Hz, 1H), 7.63 (d, J=7.5 Hz, 1H), 7.52 (t, J=7.6 Hz, 2H), 7.39-7.33 (m, 1H), 7.30-7.25 (m, 1H), 7.03 (s, 1H), 6.95 (d, J=8.1 Hz, 1H), 6.68-6.61 (m, 1H), 6.40 (s, 1H), 5.13 (dd, J=13.2, 5.1 Hz, 1H), 4.42 (d, J=17.7 Hz, 2H), 4.30 (d, J=17.6 Hz, 2H), 3.79 (br, 4H), 3.51-3.31 (m, 5H), 3.01-2.83 (m, 1H), 2.61 (d, J=16.5 Hz, 1H), 2.49-2.34 (m, 1H), 2.07-1.96 (m, 1H), 1.78 (br, 3H), 1.67 (br, 3H), 1.48 (br, 2H), 0.83 (s, 11H).

Example 63: Preparation of (2'S,3S,4'S,5'R)-6-chloro-4'-(3-chloro-2-fluorophenyl)-2'-(2,2-dimethylpropyl)-N-{4-[(1S,3R)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide Synthesis of tert-butyl (4S)-4-carbamoyl-4-(4-{2-[(1S,3R)-5-(3-methoxy-4-nitrobenzoyl)-5-azaspiro[2.5]octan-1-yl]ethynyl}-1-oxo-3H-isoindol-2-yl)butanoate: Into a 40 mL sealed tube purged and maintained under an inert atmosphere of nitrogen, were placed (1S,3R)-1-ethynyl-5-(3-methoxy-4-nitrobenzoyl)-5-azaspiro[2.5]octane (520 mg, 1.7 mmol, 1.0 eq), tert-butyl (4S)-4-carbamoyl-4-(4-iodo-1-oxo-3H-isoindol-2-yl)butanoate (1.1 g, 2.5 mmol, 1.5 eq), CuI (11 mg, 0.2 mmol, 0.1 eq), triethylamine (502 mg, 4.9 mmol, 3.0 eq), $Pd(PPh_3)_4$ (191 mg, 0.2 mmol, 0.1 eq) and N,N-dimethylformamide (6 mL). The reaction mixture was stirred for 2 hours at 70° C. The resulting mixture was diluted with water (120 mL) and extracted with ethyl acetate (2×120 mL). The combined organic phase was washed with brine (2×120 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1S,3R)-5-(3-methoxy-4-nitrobenzoyl)-5-azaspiro[2.5]octan-1-yl]ethynyl}-1-oxo-3H-isoindol-2-yl)butanoate (850 mg, 81.5%) as light yellow solid. LC-MS (ESI, m/z) M+1: 631.

Synthesis of tert-butyl (4S)-4-(4-{2-[(1S,3R)-5-(4-amino-3-methoxybenzoyl)-5-azaspiro[2.5]octan-1-yl]ethynyl}-1-oxo-3H-isoindol-2-yl)-4-carbamoylbutanoate: Into a 40 mL sealed tube were placed tert-butyl (4S)-4-carbamoyl-4-(4-{2-[(1S,3R)-5-(3-methoxy-4-nitrobenzoyl)-5-azaspiro[2.5]octan-1-yl]ethynyl}-1-oxo-3H-isoindol-2-yl)butanoate (500 mg, 0.8 mmol, 1.0 eq), Fe (177 mg, 3.2 mmol, 4.0 eq), $NH_4Cl$ (339 mg, 6.3 mmol, 8.0 eq), EtOH (15 mL), water (5 mL). The reaction mixture was stirred for 2 hours at 60° C. The resulting mixture was filtered, the filtrate was concentrated under vacuum. The crude residue was purified by a flash column (silica gel, dichloromethane/methanol=10:1) to give tert-butyl (4S)-4-(4-{2-[(1S,3R)-5-(4-amino-3-methoxybenzoyl)-5-azaspiro[2.5]octan-1-yl]ethynyl}-1-oxo-3H-isoindol-2-yl)-4-carbamoylbutanoate (410 mg, 86.1%) as light yellow solid. LC-MS (ESI, m/z) M+1: 601.

Synthesis of tert-butyl (4S)-4-carbamoyl-4-(4-{2-[(1S,3R)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (100 mg, 0.2 mmol, 1.0 eq), tert-butyl (4S)-4-(4-{2-[(1S,3R)-5-(4-amino-3-methoxybenzoyl)-5-azaspiro[2.5]octan-1-yl]ethynyl}-1-oxo-3H-isoindol-2-yl)-4-carbamoylbutanoate (160 mg, 0.3 mmol, 1.2 eq), TCFH (93 mg, 0.3 mmol, 1.5 eq), NMI (46 mg, 0.6 mmol, 2.5 eq) and $CH_3CN$ (2 mL). The resulting mixture was diluted with water (40 mL) and then extracted with ethyl acetate (2×40 mL). The combined organic phase was washed with brine (2×40 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1S,3R)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (140 mg, 61.1%) as light yellow solid. LC-MS (ESI, m/z) M+1: 1033/1035.

Synthesis of (2'S,3S,4'S,5'R)-6-chloro-4'-(3-chloro-2-fluorophenyl)-2'-(2,2-dimethylpropyl)-N-{4-[(1S,3R)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide: Into an 8 mL sealed tube were placed tert-butyl (4S)-4-carbamoyl-4-(4-{2-[(1S,3R)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (120 mg, 0.1 mmol, 1.0 eq), $CH_3CN$ (3 mL) and benzenesulfonic acid (37 mg, 0.2 mmol, 2.0 eq). The reaction mixture was stirred for 16 hours at 80° C. The crude product was purified by Prep-HPLC using the following conditions: Column, XBridge Shield RP18 OBD Column, 5 μm, 19*150 mm; mobile phase, water (0.05% HCl) and $CH_3CN$ (40% Phase B up to 55% in 7 min); Detector, UV 254/220 nm. Finally, (2'S,3S,4'S,5'R)-6-chloro-4'-(3-chloro-2-fluorophenyl)-2'-(2,2-dimethylpropyl)-N-{4-[(1S,3R)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide (3.9 mg, 3.5%) was obtained as off white solid. LC-MS (ESI, m/z) M+1: 958/960. $^1$HNMR (300 MHz, DMSO-$d_6$) δ 10.99 (s, 1H), 7.71 (d, J=7.5 Hz, 1H), 7.64 (d, J=7.5 Hz, 1H), 7.52 (t, J=7.5 Hz, 1H), 7.42-7.36 (m, 1H), 7.31-7.24 (m, 2H), 7.04 (br, 2H), 6.95 (d, J=9.0 Hz, 2H), 6.65 (s, 1H), 6.41 (s, 1H), 5.13 (dd, J=13.2, 5.1 Hz, 1H), 4.45 (d, J=17.7 Hz, 2H), 4.28 (d, J=17.7 Hz, 4H), 3.98-3.75 (m, 8H), 2.95-2.86 (m, 2H), 2.73 (s, 1H), 2.44-2.33 (m, 1H), 2.03 (br, 2H), 1.80-1.61 (m, 5H), 0.83 (s, 11H).

Example 64: Preparation of (2'S,3S,4'S,5'R)-6-chloro-4'-(3-chloro-2-fluorophenyl)-2'-(2,2-dimethylpropyl)-N-{4-[(1R,3R)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide Synthesis of tert-butyl (4S)-4-carbamoyl-4-(4-{2-[(1R,3R)-5-(3-methoxy-4-nitrobenzoyl)-5-azaspiro[2.5]octan-1-yl]ethynyl}-1-oxo-3H-isoindol-2-yl)butanoate: Into an 8 mL sealed tube purged and maintained under an inert atmosphere of nitrogen, were placed (1R,3R)-1-ethynyl-5-(3-methoxy-4-nitrobenzoyl)-5-azaspiro[2.5]octane (110 mg, 0.4 mmol, 1.0 eq), tert-butyl (4S)-4-carbamoyl-4-(4-iodo-1-oxo-3H-isoindol-2-yl)butanoate (233 mg, 0.5 mmol, 1.5 eq), CuI (7 mg, 0.1 mmol, 0.1 eq), triethylamine (106 mg, 1.1 mmol, 3.0 eq), $Pd(PPh_3)_4$(40 mg, 0.1 mmol, 0.1 eq) and N,N-dimethylformamide (2 mL). The reaction mixture was stirred for 2 hours at 70° C. The resulting mixture was diluted with water (30 mL) and then extracted with ethyl acetate (2×30 mL). The combined organic phase was washed with brine (2×30 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1R,3R)-5-(3-methoxy-4-nitrobenzoyl)-5-azaspiro[2.5]octan-1-yl]ethynyl}-1-oxo-3H-isoindol-2-yl)butanoate (300 mg crude) as light yellow solid. LC-MS (ESI, m/z) M+1: 631.

Synthesis of tert-butyl (4S)-4-(4-{2-[(1R,3R)-5-(4-amino-3-methoxybenzoyl)-5-azaspiro[2.5]octan-1-yl]ethynyl}-1-oxo-3H-isoindol-2-yl)-4-carbamoylbutanoate: Into a 40 mL sealed tube were placed tert-butyl (4S)-4-carbamoyl-4-(4-{2-[(1R,3R)-5-(3-methoxy-4-nitrobenzoyl)-5-azaspiro[2.5]octan-1-yl]ethynyl}-1-oxo-3H-isoindol-2-yl)butanoate (280 mg, 0.4 mmol, 1.0 eq), Fe (99 mg, 1.8 mmol, 4.0 eq), $NH_4Cl$ (190 mg, 3.6 mmol, 8.0 eq), EtOH (9 mL), water (3 mL). The reaction mixture was stirred for 2 hours at 60° C. The resulting mixture was filtered, the filtrate was concentrated under vacuum. The crude residue was purified by a flash column (silica gel, dichloromethane/methanol=10:1) to give tert-butyl (4S)-4-(4-{2-[(1R,3R)-5-(4-amino-3-methoxybenzoyl)-5-azaspiro[2.5]octan-1-yl]ethynyl}-1-oxo-3H-isoindol-2-yl)-4-carbamoylbutanoate (200 mg, 75.0%) as light yellow solid. LC-MS (ESI, m/z) M+1: 601.

Synthesis of tert-butyl (4S)-4-carbamoyl-4-(4-{2-[(1R,3R)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate: Into an 8 mL sealed tube, were placed (2'S,3S,4'S,5'R)-6-chloro-4'-(3-chloro-2-fluorophenyl)-2'-(2,2-dimethylpropyl)-1,2-dihydrospiro[indole-3,3'-pyrrolidine]-5'-carboxylic acid (113 mg, 0.3 mmol, 1.0 eq), tert-butyl (4S)-4-(4-{2-[(1R,3R)-5-(4-amino-3-methoxybenzoyl)-5-azaspiro[2.5]octan-1-yl]ethynyl}-1-oxo-3H-isoindol-2-yl)-4-carbamoylbutanoate (181 mg, 0.3 mmol, 1.2 eq), TCFH (105 mg, 0.4 mmol, 1.5 eq), NMI (51 mg, 0.6 mmol, 2.5 eq) and $CH_3CN$ (2 mL). The reaction mixture was stirred for 2 hours at 25° C. The resulting mixture was diluted with water (40 mL) and then extracted with ethyl acetate (2×40 mL). The combined organic phase was washed with brine (2×40 mL) and dried over anhydrous sodium sulfate. After filtration, the filtrate was concentrated under vacuum. The crude residue was purified by a flash column (silica gel, ethyl acetate/petroleum ether=1:0) to give tert-butyl (4S)-4-carbamoyl-4-(4-{2-[(1R,3R)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (120 mg, 46.4%) as light yellow solid. LC-MS (ESI, m/z) M+1: 1033/1035.

Synthesis of (2'S,3S,4'S,5'R)-6-chloro-4'-(3-chloro-2-fluorophenyl)-2'-(2,2-dimethylpropyl)-N-{4-[(1R,3R)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide: Into an 8 mL sealed tube were placed tert-butyl (4S)-4-carbamoyl-4-(4-{2-[(1R,3R)-5-{4-[(2'S,3S,4'S,5'R)-6-chloro-4'-(3-chloro-2-fluorophenyl)-2'-(2,2-dimethylpropyl)-1,2-dihydrospiro[indole-3,3'-pyrrolidin]-5'-ylamido]-3-methoxybenzoyl}-5-azaspiro[2.5]octan-1-yl]ethynyl}-1-oxo-3H-isoindol-2-yl)butanoate (100 mg, 0.1 mmol, 1.0 eq), $CH_3CN$ (3 mL) and benzenesulfonic acid (31 mg, 0.2 mmol, 2.0 eq). The reaction mixture was stirred for 16 hours at 80° C. The crude product was purified by Prep-HPLC using the following conditions: Column, XBridge Shield RP18 OBD Column, 5 μm, 19*150 mm; mobile phase, water (0.05% HCl) and $CH_3CN$ (40% Phase B up to 55% in 7 min); Detector, UV 254/220 nm. Finally, (2'S,3S,4'S,5'R)-6-chloro-4'-(3-chloro-2-fluorophenyl)-2'-(2,2-dimethylpropyl)-N-{4-[(1R,3R)-1-(2-{2-[(3S)-2,6-dioxopiperidin-3-yl]-1-oxo-3H-isoindol-4-yl}ethynyl)-5-azaspiro[2.5]octane-5-carbonyl]-2-methoxyphenyl}-1,2-dihydrospiro[indole-3,3'-pyrrolidine]-5'-carboxamide (4.3 mg, 4.6%) was obtained as off white solid. LC-MS (ESI, m/z) M+1: 958/960. $^1$HNMR (400 MHz, DMSO-$d_6$) δ 10.93 (s, 2H), 10.66 (br, 1H), 9.08 (br, 1H), 7.96 (br, 1H), 7.66-7.25 (m, 7H), 7.0-6.96 (m, 2H), 6.64 (s, 1H), 6.40 (s, 1H), 5.12-5.04 (m, 2H), 4.43-4.32 (m, 2H), 3.77-3.61 (m, 7H), 3.33 (br, 3H), 2.92-2.83 (m, 1H), 1.91 (br, 2H), 1.65-1.49 (m, 7H), 1.07-0.99 (m, 2H), 0.83 (s, 11H).

Example 67: Preparation of (2S,3S,4S,5R)-4-(3-chloro-2-fluorophenyl)-2-(2,2-dimethylpropyl)-N-{4-[(1S)-1-(2-{2-[(3S)-2,6-dioxopiperidin-3-yl]-1-oxo-3H-isoindol-4-yl}ethynyl)-6-azaspiro[2.5]octan-6-ylsulfonyl]-2-methoxyphenyl}-6'-(trifluoromethyl)-1',2'-dihydrospiro[pyrrolidine-3,3'-pyrrolo[3,2-c]pyridine]-5-carboxamide hydrochloride Synthesis of 1-ethynyl-6-azaspiro[2.5]octane: Into a 100-mL round-bottom flask, were placed tert-butyl 1-ethynyl-6-azaspiro[2.5]octane-6-carboxylate (1.2 g, 5.1 mmol, 1.0 eq), 2,6-dimethylpyridine (1.6 g, 15.3 mmol, 3.0 eq), dichloromethane (20 mL). After that, TMSI (2.0 g, 10.2 mmol, 2.0 eq) was added at 0° C. The reaction mixture was stirred for 2 hours at 0° C. The resulting mixture was concentrated under vacuum to give 1-ethynyl-6-azaspiro[2.5]octane as a brown solid (2.3 g crude).

Synthesis of 3-methoxy-4-nitrobenzenethiol: Into a 1000-mL 3-necked round-bottom flask, were placed 4-fluoro-2-methoxy-1-nitrobenzene (20.0 g, 116.9 mmol, 1.0 eq), EtOH (200 mL), $Na_2S·9H_2O$ (19.7 g, 81.8 mmol, 0.7 eq), sulfur (2.6 g, 81.8 mmol, 0.7 eq), NaOH (4.7 g, 116.9 mmol, 1.0 eq). The resulting solution was stirred for 2 hours at 90° C. The mixture was neutralized to pH=7-8 with HCl (1 M). The resulting mixture was concentrated under vacuum, diluted with water (200 mL) and then extracted with ethyl acetate (2×200 mL). The combined organics were washed with brine (2×200 mL) and dried over anhydrous $Na_2SO_4$. After filtration, the filtrate was concentrated under vacuum to give 3-methoxy-4-nitrobenzenethiol as a light yellow oil (10.0 g crude). LC-MS (ESI, m/z) M+1: 186.

Synthesis of 3-methoxy-4-nitrobenzenesulfonyl chloride: Into a 100-mL 3-necked round-bottom flask, were placed 3-methoxy-4-nitrobenzenethiol (3.0 g, 16.2 mmol, 1.0 eq), dichloromethane (30 mL), i-PrOH (2.0 g, 32.4 mmol, 2.0 eq). After that, NCS (7.6 g, 56.7 mmol, 3.5 eq) was added at 0° C. Then the resulting solution was stirred for 1 hour at 25° C. The reaction mixture was used for the next step without further purification.

Synthesis of 1-ethynyl-6-(3-methoxy-4-nitrobenzenesulfonyl)-6-azaspiro[2.5]octane: Into a 100-mL 3-necked round-bottom flask, were placed 1-ethynyl-6-azaspiro[2.5]octane (800 mg, 5.9 mmol, 1.0 eq), dichloromethane (10 mL), triethylamine (3.0 g, 29.6 mmol, 5.0 eq). After that, 3-methoxy-4-nitrobenzenesulfonyl chloride was added at 0° C. Then the resulting solution was stirred for 1 hour at 25° C. The resulting mixture was quenched with water (50 mL) and then extracted with dichloromethane (2×50 mL). The combined organics were washed with brine (2×50 mL) and dried over anhydrous $Na_2SO_4$. After filtration, the filtrate was concentrated under vacuum. The crude residue was applied onto a silica gel column and eluted with ethyl acetate/petroleum ether=1:3 to give 1-ethynyl-6-(3-methoxy-4-nitrobenzenesulfonyl)-6-azaspiro[2.5]octane as a light yellow oil (550 mg, 26.5%). LC-MS (ESI, m/z) M+1: 351. $^1$HNMR (400 MHz, DMSO-$d_6$) δ 8.13 (d, J=8.4 Hz, 1H), 7.56 (d, J=1.6 Hz, 1H), 7.50 (dd, J=8.4, 1.6 Hz, 1H), 3.82 (s, 3H), 3.26-3.10 (m, 2H), 3.03-2.95 (m, 2H), 2.69 (d, J=2.2 Hz, 1H), 1.71-1.56 (m, 2H), 1.52 (ddd, J=12.4, 8.0, 3.8 Hz, 1H), 1.43-1.25 (m, 2H), 0.81 (dd, J=8.6, 4.4 Hz, 1H), 0.52 (t, J=4.8 Hz, 1H).

Synthesis of (1S)-1-ethynyl-6-(3-methoxy-4-nitrobenzenesulfonyl)-6-azaspiro[2.5]octane & (1R)-1-ethynyl-6-(3-methoxy-4-nitrobenzenesulfonyl)-6-azaspiro[2.5]octane: 550 mg of 1-ethynyl-6-(3-methoxy-4-nitrobenzenesulfonyl)-6-azaspiro[2.5]octane was purified by Chiral-Prep-SFC using the following conditions: Column: CHIRALPAK IH, 3*25 cm, 5 μm; Mobile Phase A: $CO_2$, Mobile Phase B: IPA: HEX=1:1; Flow rate: 80 mL/min; Gradient: isocratic 35% B; Detector, 220 nm. Finally, (1S)-1-ethynyl-6-(3-methoxy-4-nitrobenzenesulfonyl)-6-azaspiro[2.5]octane was obtained as a light yellow oil (240 mg, 43.6%) and (1R)-1-ethynyl-6-(3-methoxy-4-nitrobenzenesulfonyl)-6-azaspiro[2.5]octane was obtained as a light yellow oil (260 mg, 47.3%).5A, $T_R$=1.905 min in CHIRAL-SFC, Column: IH 100×4.6 mm 3.0 um. mobile phase A: $CO_2$; mobile phase B: IPA (50% Hex), Start Conc. of Pump B: 10.0% in 4 min, Oven Temperature: 35° C. 5B, $T_R$=2.080 min in CHIRAL-SFC, Column: IH 100×4.6 mm 3.0 um. mobile phase A: $CO_2$; mobile phase B: IPA (50% Hex), Start Conc. of Pump B: 10.0% in 4 min, Oven Temperature: 35° C.

Synthesis of 4-[(1S)-1-ethynyl-6-azaspiro[2.5]octan-6-ylsulfonyl]-2-methoxyaniline: Into a 40-mL sealed tube, were placed (1S)-1-ethynyl-6-(3-methoxy-4-nitrobenzenesulfonyl)-6-azaspiro[2.5]octane (220 mg, 0.6 mmol, 1.0 eq), Fe (140 mg, 2.5 mmol, 4.0 eq), $NH_4Cl$ (269 mg, 5.0 mmol, 8.0 eq), EtOH (6 mL) and water (2 mL). The resulting solution was stirred for 2 hours at 50° C. The resulting mixture was filtered, the filtrate was concentrated under vacuum. The crude residue was applied onto a silica gel column and eluted with ethyl acetate/petroleum ether=1:1 to give 4-[(1S)-1-ethynyl-6-azaspiro[2.5]octan-6-ylsulfonyl]-2-methoxyaniline as a light yellow oil (170 mg, 84.5%). LC-MS (ESI, m/z) M+1: 321. $^1$HNMR (400 MHz, DMSO-$d_6$) δ 7.10 (dd, J=8.2, 2.0 Hz, 1H), 7.00 (d, J=2.0 Hz, 1H), 6.74 (d, J=8.4 Hz, 1H), 5.69 (s, 2H), 3.83 (s, 3H), 3.10-2.95 (m, 2H), 2.85-2.73 (m, 3H), 2.66 (d, J=2.2 Hz, 1H), 1.68-1.45 (m, 2H), 1.38-1.24 (m, 1H), 1.28-1.21 (m, 1H), 0.77 (dd, J=8.6, 4.4 Hz, 1H), 0.49 (t, J=4.8 Hz, 1H).

Synthesis of tert-butyl (4S)-4-(4-{2-[(1S)-6-(4-amino-3-methoxybenzenesulfonyl)-6-azaspiro[2.5]octan-1-yl]ethynyl}-1-oxo-3H-isoindol-2-yl)-4-carbamoylbutanoate: Into a 20-mL sealed-tube purged and maintained with an inert atmosphere of nitrogen, were placed 4-[(1S)-1-ethynyl-6-azaspiro[2.5]octan-6-ylsulfonyl]-2-methoxyaniline (150 mg, 0.5 mmol, 1.0 eq), tert-butyl (4S)-4-carbamoyl-4-(4-iodo-1-oxo-3H-isoindol-2-yl)butanoate (250 mg, 0.6 mmol, 1.2 eq), CuI (9 mg, 0.1 mmol, 0.1 eq), $Pd(PPh_3)_4$(54 mg, 0.1 mmol, 0.1 eq), triethylamine (142 mg, 1.4 mmol, 3.0 eq) and N,N-Dimethylformamide (3 mL). The resulting solution was stirred for 2 hours at 70° C. The resulting mixture was quenched by the addition of water (50 mL) and then extracted with ethyl acetate (2×50 mL). The combined organics were washed with brine (2×50 mL), dried over anhydrous $Na_2SO_4$. After filtration, the filtrate was concentrated under vacuum. The crude residue was applied onto a silica gel column and eluted with ethyl acetate/petroleum ether=4:1 to give tert-butyl (4S)-4-(4-{2-[(1S)-6-(4-amino-3-methoxybenzenesulfonyl)-6-azaspiro[2.5]octan-1-yl]ethynyl}-1-oxo-3H-isoindol-2-yl)-4-carbamoylbutanoate as a light yellow solid (230 mg, 77.2%). LC-MS (ESI, m/z) M+1: 637.

Synthesis of tert-butyl (4S)-4-carbamoyl-4-(4-{2-[(1S)-6-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzenesulfonyl}-6-azaspiro[2.5]octan-1-yl]ethynyl}-1-oxo-3H-isoindol-2-yl)butanoate: Into an 8-mL sealed tube, were placed (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (100 mg, 0.2 mmol, 1.0 eq), tert-butyl (4S)-4-(4-{2-[(1S)-6-(4-amino-3-methoxybenzenesulfonyl)-6-azaspiro[2.5]octan-1-yl]ethynyl}-1-oxo-3H-isoindol-2-yl)-4-carbamoylbutanoate (131 mg, 0.2 mmol, 1.0 eq), TCFH (87 mg, 0.3 mmol, 1.5 eq), NMI (42 mg, 0.5 mmol, 2.5 eq), $CH_3CN$ (2 mL). The resulting solution was stirred for 2 hours at 25° C. The resulting mixture was then quenched by the addition of water (30 mL) and then extracted with ethyl acetate (2×30 mL). The combined organics were washed with brine (2×30 ml) and then dried over anhydrous $Na_2SO_4$. After filtration, the filtrate was concentrated under vacuum. The crude residue was applied onto a silica gel column and eluted with ethyl acetate/petroleum ether=4:1 to give tert-butyl (4S)-4-carbamoyl-4-(4-{2-[(1S)-6-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzenesulfonyl}-6-azaspiro[2.5]octan-1-yl]ethynyl}-1-oxo-3H-isoindol-2-yl)butanoate as a light yellow solid (70 mg, 30.8%). LC-MS (ESI, m/z) M+1: 1104/1106.

Synthesis of (2S,3S,4S,5R)-4-(3-chloro-2-fluorophenyl)-2-(2,2-dimethylpropyl)-N-{4-[(1S)-1-(2-{2-[(3S)-2,6-dioxopiperidin-3-yl]-1-oxo-3H-isoindol-4-yl}ethynyl)-6-azaspiro[2.5]octan-6-ylsulfonyl]-2-methoxyphenyl}-6'-(trifluoromethyl)-1',2'-dihydrospiro[pyrrolidine-3,3'-pyrrolo[3,2-c]pyridine]-5-carboxamide hydrochloride: Into an 8-mL sealed tube, were placed tert-butyl (4S)-4-carbamoyl-4-(4-{2-[(1S)-6-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzenesulfonyl}-6-azaspiro[2.5]octan-1-yl]ethynyl}-1-oxo-3H-isoindol-2-yl)butanoate (65 mg, 0.1 mmol, 1.0 eq), benzenesulfonic acid (19 mg, 0.1 mmol, 2.0 eq), $CH_3CN$ (2 mL). The resulting solution was stirred for 16 hours at 80° C. The crude product was purified by Prep-HPLC using the following conditions: Column, SunFire Prep C18 OBD Column, 50*250 mm 5 μm 10 nm; mobile phase, water (0.05% HCl) and $CH_3CN$ (40% Phase B up to 50% in 7 min). Finally, (2S,3S,4S,5R)-4-(3-chloro-2-fluorophenyl)-2-(2,2-dimethylpropyl)-N-{4-[(1S)-1-(2-{2-[(3S)-2,6-dioxopiperidin-3-yl]-1-oxo-3H-isoindol-4-yl}ethynyl)-6-azaspiro[2.5]octan-6-ylsulfonyl]-2-methoxyphenyl}-6'-(trifluoromethyl)-1',2'-dihydrospiro[pyrrolidine-3,3'-pyrrolo[3,2-c]pyridine]-5-carboxamide hydrochloride was obtained as an off-white solid (5 mg, 8.0%). LC-MS (ESI, m/z) M+1: 1030/1032. $^1$HNMR (400 MHz, DMSO-$d_6$) δ 11.01 (s, 1H), 8.54 (s, 1H), 8.42-8.13 (m, 1H), 7.69 (d, J=7.6 Hz, 1H), 7.57 (d, J=7.6 Hz, 1H), 7.49 (t, J=7.6 Hz, 2H), 7.37 (dd, J=8.4, 2.0 Hz, 1H), 7.32-7.23 (m, 3H), 6.74 (s, 1H), 5.12 (dd, J=13.4, 5.2 Hz, 1H), 4.43 (d, J=17.8 Hz, 2H), 4.24 (d, J=17.6 Hz, 2H), 3.78-3.64 (m, 6H), 3.47 (br, 1H), 3.13-2.87 (m, 5H), 2.61 (d, J=18.0 Hz, 1H), 2.45-2.41 (m, 1H), 2.05-1.96 (m, 1H), 1.78-1.68 (m, 2H), 1.59 (dd, J=8.4, 5.2 Hz, 1H), 1.55-1.46 (m, 2H), 0.97 (dd, J=8.6, 4.2 Hz, 1H), 0.88 (s, 10H), 0.72 (t, J=4.8 Hz, 1H).

Example 68: Preparation of (2S,3S,4S,5R)-4-(3-chloro-2-fluorophenyl)-2-(2,2-dimethylpropyl)-N-{4-[(1R)-1-(2-{2-[(3S)-2,6-dioxopiperidin-3-yl]-1-oxo-3H-isoindol-4-yl}ethynyl)-6-azaspiro[2.5]octan-6-ylsulfonyl]-2-methoxyphenyl}-6'-(trifluoromethyl)-1',2'-dihydrospiro[pyrrolidine-3,3'-pyrrolo[3,2-c]pyridine]-5-carboxamide hydrochloride Synthesis of 4-[(1R)-1-ethynyl-6-azaspiro[2.5]octan-6-ylsulfonyl]-2-methoxyaniline: Into a 40-mL sealed tube, were placed (1R)-1-ethynyl-6-(3-methoxy-4-nitrobenzenesulfonyl)-6-azaspiro[2.5]octane (240 mg, 0.7 mmol, 1.0 eq), Fe (153 mg, 2.7 mmol, 4.0 eq), $NH_4Cl$ (293 mg, 5.5 mmol, 8.0 eq), EtOH (6 mL), water (2 mL). The resulting solution was stirred for 2 hours at 50° C. The resulting mixture was filtered, the filtrate was concentrated under vacuum. The crude residue was applied onto a silica gel column and eluted with ethyl acetate/petroleum ether=1:1 to give 4-[(1R)-1-ethynyl-6-azaspiro[2.5]octan-6-ylsulfonyl]-2-methoxyaniline as a light yellow oil (180 mg, 82.0%). LC-MS (ESI, m/z) M+1: 321. $^1$HNMR (400 MHz, DMSO-$d_6$) δ 7.10 (dd, J=8.2, 2.0 Hz, 1H), 7.00 (d, J=2.0 Hz, 1H), 6.74 (d, J=8.4 Hz, 1H), 5.69 (s, 2H), 3.83 (s, 3H), 3.10-2.95 (m, 2H), 2.85-2.73 (m, 3H), 2.66 (d, J=2.2 Hz, 1H), 1.68-1.45 (m, 2H), 1.38-1.24 (m, 1H), 1.28-1.21 (m, 1H), 0.77 (dd, J=8.6, 4.4 Hz, 1H), 0.49 (t, J=4.8 Hz, 1H).

Synthesis of tert-butyl (4S)-4-(4-{2-[(1R)-6-(4-amino-3-methoxybenzenesulfonyl)-6-azaspiro[2.5]octan-1-yl]ethynyl}-1-oxo-3H-isoindol-2-yl)-4-carbamoylbutanoate: Into a 20-mL sealed-tube purged and maintained with an inert atmosphere of nitrogen, were placed 4-[(1R)-1-ethynyl-6-azaspiro[2.5]octan-6-ylsulfonyl]-2-methoxyaniline (160 mg, 0.5 mmol, 1.0 eq), tert-butyl (4S)-4-carbamoyl-4-(4-iodo-1-oxo-3H-isoindol-2-yl)butanoate (266 mg, 0.6 mmol, 1.2 eq), triethylamine (152 mg, 1.5 mmol, 3.0 eq), CuI (10 mg, 0.1 mmol, 0.1 eq), $Pd(PPh_3)_4$(58 mg, 0.1 mmol, 0.1 eq) and N,N-Dimethylformamide (3 mL). The resulting solution was stirred for 2 hours at 70° C. The resulting mixture was then quenched by the addition of water (50 mL) and extracted with ethyl acetate (2×50 mL). The combined organics were washed with brine (2×50 mL) and dried over anhydrous $Na_2SO_4$. After filtration, the filtrate was concentrated under vacuum. The crude residue was applied onto a silica gel column and eluted with ethyl acetate/petroleum ether=4:1 to give tert-butyl (4S)-4-(4-{2-[(1R)-6-(4-amino-3-methoxybenzenesulfonyl)-6-azaspiro[2.5]octan-1-yl]ethynyl}-1-oxo-3H-isoindol-2-yl)-4-carbamoylbutanoate as a light yellow solid (250 mg, 78.6%). LC-MS (ESI, m/z) M+1: 637.

Synthesis of tert-butyl (4S)-4-carbamoyl-4-(4-{2-[(1R)-6-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzenesulfonyl}-6-azaspiro[2.5]octan-1-yl]ethynyl}-1-oxo-3H-isoindol-2-yl)butanoate: Into an 8-mL sealed tube, were placed (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (100 mg, 0.2 mmol, 1.0 eq), tert-butyl (4S)-4-(4-{2-[(1R)-6-(4-amino-3-methoxybenzenesulfonyl)-6-azaspiro[2.5]octan-1-yl]ethynyl}-1-oxo-3H-isoindol-2-yl)-

4-carbamoylbutanoate (assumed) (131 mg, 0.2 mmol, 1.0 eq), TCFH (87 mg, 0.3 mmol, 1.5 eq), NMI (42 mg, 0.5 mmol, 2.5 eq) and $CH_3CN$ (2 mL). The resulting solution was stirred for 2 hours at 25° C. The resulting mixture was then quenched by the addition of water (30 mL) and extracted with ethyl acetate (2×30 mL). The combined organics were washed with brine (2×30 ml) and dried over anhydrous $Na_2SO_4$. After filtration, the filtrate was concentrated under vacuum. The crude residue was applied onto a silica gel column and eluted with ethyl acetate/petroleum ether=4:1 to give tert-butyl (4S)-4-carbamoyl-4-(4-{2-[(1R)-6-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzenesulfonyl}-6-azaspiro[2.5]octan-1-yl]ethynyl}-1-oxo-3H-isoindol-2-yl)butanoate as a light yellow solid (90 mg, 39.6%). LC-MS (ESI, m/z) M+1: 1104/1106.

Synthesis of (2S,3S,4S,5R)-4-(3-chloro-2-fluorophenyl)-2-(2,2-dimethylpropyl)-N-{4-[(1R)-1-(2-{2-[(3S)-2,6-dioxopiperidin-3-yl]-1-oxo-3H-isoindol-4-yl}ethynyl)-6-azaspiro[2.5]octan-6-ylsulfonyl]-2-methoxyphenyl}-6'-(trifluoromethyl)-1',2'-dihydrospiro[pyrrolidine-3,3'-pyrrolo[3,2-c]pyridine]-5-carboxamide hydrochloride: Into an 8-mL sealed tube, were placed tert-butyl (4S)-4-carbamoyl-4-(4-{2-[(1R)-6-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzenesulfonyl}-6-azaspiro[2.5]octan-1-yl]ethynyl}-1-oxo-3H-isoindol-2-yl)butanoate (80 mg, 0.1 mmol, 1.0 eq), benzenesulfonic acid (23 mg, 0.1 mmol, 2.0 eq), $CH_3CN$ (2 mL). The resulting solution was stirred for 16 hours at 80° C. The crude product was purified by Prep-HPLC using the following conditions: Column, SunFire Prep C18 OBD Column, 50*250 mm 5 μm 10 nm; mobile phase, water (0.05% HCl) and $CH_3CN$ (40% Phase B up to 50% in 7 min). Finally, (2S,3S,4S,5R)-4-(3-chloro-2-fluorophenyl)-2-(2,2-dimethylpropyl)-N-{4-[(1R)-1-(2-{2-[(3S)-2,6-dioxopiperidin-3-yl]-1-oxo-3H-isoindol-4-yl}ethynyl)-6-azaspiro[2.5]octan-6-ylsulfonyl]-2-methoxyphenyl}-6'-(trifluoromethyl)-1',2'-dihydrospiro[pyrrolidine-3,3'-pyrrolo[3,2-c]pyridine]-5-carboxamide hydrochloride was obtained as an off-white solid (15 mg, 19.4%). LC-MS (ESI, m/z) M+1: 1030/1032. $^1$HNMR (400 MHz, DMSO-$d_6$) δ 10.99 (s, 1H), 8.53 (s, 1H), 8.45-8.26 (m, 1H), 7.72-7.66 (m, 1H), 7.57 (dd, J=7.6, 1.2 Hz, 1H), 7.52-7.48 (m, 2H), 7.36 (dd, J=8.4, 1.8 Hz, 1H), 7.33-7.22 (m, 3H), 6.74 (s, 1H), 5.11 (dd, J=13.2, 5.2 Hz, 1H), 4.36 (d, J=17.8 Hz, 2H), 4.29 (d, J=17.6 Hz, 2H), 3.89 (s, 4H), 3.81 (br, 1H), 3.46 (br, 1H), 3.07-2.86 (m, 5H), 2.60 (d, J=16.6 Hz, 1H), 2.50-2.40 (m, 1H), 2.05-1.98 (m, 1H), 1.78-1.65 (m, 2H), 1.60 (dd, J=8.4, 5.4 Hz, 1H), 1.53-1.48 (m, 3H), 0.96 (dd, J=8.6, 4.2 Hz, 1H), 0.90 (s, 10H), 0.72 (t, J=4.8 Hz, 1H).

Example 69: Preparation of (2S,3S,4S,5R)-4-(3-chloro-2-fluorophenyl)-2-(2,2-dimethylpropyl)-N-{4-[(2S)-2-(3-{2-[(3S)-2,6-dioxopiperidin-3-yl]-1-oxo-3H-isoindol-4-yl}prop-2-yn-1-yl)morpholine-4-carbonyl]-2-methoxyphenyl}-6'-(trifluoromethyl)-1',2'-dihydrospiro[pyrrolidine-3,3'-pyrrolo[3,2-c]pyridine]-5-carboxamide hydrochloride hydrogen Synthesis of 2-methoxy-4-[(2S)-2-(prop-2-yn-1-yl)morpholine-4-carbonyl]aniline: Into a 40-mL sealed tube, were placed (2S)-4-(3-methoxy-4-nitrobenzoyl)-2-(prop-2-yn-1-yl)morpholine (assumed) (290 mg, 1.0 mmol, 1.0 eq), Fe (213 mg, 3.8 mmol, 4.0 eq), $NH_4Cl$ (408 mg, 7.6 mmol, 8.0 eq), EtOH (9 mL), water (3 mL). The resulting solution was stirred for 2 hours at 70° C. The resulting mixture was filtered, the filtrate was concentrated under vacuum. The crude residue was applied onto a silica gel column and eluted with dichloromethane/methanol=10:1 to give 2-methoxy-4-[(2S)-2-(prop-2-yn-1-yl)morpholine-4-carbonyl]aniline as a light yellow oil (240 mg, 91.8%). LC-MS (ESI, m/z) M+1: 275. $^1$HNMR (300 MHz, DMSO-$d_6$) δ 6.87 (s, 1H), 6.82 (d, J=7.5 Hz, 1H), 6.62 (d, J=8.1 Hz, 1H), 5.18 (s, 2H), 4.17 (d, J=12.9 Hz, 1H), 3.93 (s, 1H), 3.97-3.84 (m, 1H), 3.80 (d, J=9.3 Hz, 3H), 3.52 (s, 2H), 3.03 (t, J=12.6 Hz, 1H), 2.87 (t, J=2.7 Hz, 1H), 2.78 (d, J=12.3 Hz, 1H), 2.45-2.29 (m, 2H).

Synthesis of tert-butyl (4S)-4-(4-{3-[(2S)-4-(4-amino-3-methoxybenzoyl)morpholin-2-yl]prop-1-yn-1-yl}-1-oxo-3H-isoindol-2-yl)-4-carbamoylbutanoate: Into an 8-mL sealed tube purged and maintained with an inert atmosphere of nitrogen, were placed 2-methoxy-4-[(2S)-2-(prop-2-yn-1-yl)morpholine-4-carbonyl]aniline (200 mg, 0.7 mmol, 1.0 eq), tert-butyl (4S)-4-carbamoyl-4-(4-iodo-1-oxo-3H-isoindol-2-yl)butanoate (486 mg, 1.1 mmol, 1.5 eq), CuI (14 mg, 0.1 mmol, 0.1 eq), TEA (221 mg, 2.2 mmol, 3.0 eq), $Pd(PPh_3)_4$(84 mg, 0.1 mmol, 0.1 eq) and DMF (2 mL). The resulting solution was stirred for 2 hours at 7° C.

The resulting mixture was then quenched by the addition of water (100 mL) and extracted with ethyl acetate (2×30 mL). The combined organics were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl (4S)-4-(4-{3-[(2S)-4-(4-amino-3-methoxybenzoyl)morpholin-2-yl]prop-1-yn-1-yl}-1-oxo-3H-isoindol-2-yl)-4-carbamoylbutanoate as a light yellow solid (400 mg, 92.9%). LC-MS (ESI, m/z) M+1: 591.

Synthesis of tert-butyl (4S)-4-carbamoyl-4-(4-{3-[(2S)-4-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzoyl}morpholin-2-yl]prop-1-yn-1-yl}-1-oxo-3H-isoindol-2-yl)butanoate: Into an 8-mL sealed tube, were placed tert-butyl (4S)-4-(4-{3-[(2S)-4-(4-amino-3-methoxybenzoyl)morpholin-2-yl]prop-1-yn-1-yl}-1-oxo-3H-isoindol-2-yl)-4-carbamoylbutanoate (150 mg, 0.3 mmol, 1.2 eq), (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (103 mg, 0.2 mmol, 1.0 eq), TCFH (89 mg, 0.3 mmol, 1.5 eq), NMI (44 mg, 0.5 mmol, 2.5 eq) and $CH_3CN$ (2 mL). The resulting solution was stirred for 2 hours at 25° C. and then quenched by the addition of water (50 mL). The resulting solution was extracted with ethyl acetate (2×40 mL). The combined organics were washed with brine (2×40 mL), dried over anhydrous $Na_2SO_4$. After filtration, the filtrate was concentrated under vacuum. The crude residue was applied onto a silica gel column and eluted with ethyl acetate/petroleum ether=1:0 to give tert-butyl (4S)-4-carbamoyl-4-(4-{3-[(2S)-4-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzoyl}morpholin-2-yl]prop-1-yn-1-yl}-1-oxo-3H-isoindol-2-yl)butanoate as a light yellow solid (90 mg, 40.1%). LC-MS (ESI, m/z) M+1: 1057/1059.

Synthesis of (2S,3S,4S,5R)-4-(3-chloro-2-fluorophenyl)-2-(2,2-dimethylpropyl)-N-{4-[(2S)-2-(3-{2-[(3S)-2,6-dioxopiperidin-3-yl]-1-oxo-3H-isoindol-4-yl}prop-2-yn-1-yl)

morpholine-4-carbonyl]-2-methoxyphenyl}-6'-(trifluoromethyl)-1',2'-dihydrospiro[pyrrolidine-3,3'-pyrrolo[3,2-c]pyridine]-5-carboxamide hydrochloride hydrogen: Into an 8 mL sealed tube, were placed tert-butyl (4S)-4-carbamoyl-4-(4-{3-[(2S)-4-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzoyl}morpholin-2-yl]prop-1-yn-1-yl}-1-oxo-3H-isoindol-2-yl)butanoate (80 mg, 0.1 mmol, 1.0 eq), $CH_3CN$ (1 mL), benzenesulfonic acid (24 mg, 0.2 mmol, 2.0 eq). The resulting solution was stirred for 16 hours at 80° C. The crude product was purified by Flash-Prep-HPLC using the following conditions: Column, C18 reversed phase column; mobile phase, water (0.05% HCl) and $CH_3CN$ (45% Phase B up to 60% in 7 min); Flow rate: 60 mL/min; Detector, 254/220 nm. Finally, (2S,3S,4S,5R)-4-(3-chloro-2-fluorophenyl)-2-(2,2-dimethylpropyl)-N-{4-[(2S)-2-(3-{2-[(3S)-2,6-dioxopiperidin-3-yl]-1-oxo-3H-isoindol-4-yl}prop-2-yn-1-yl)morpholine-4-carbonyl]-2-methoxyphenyl}-6'-(trifluoromethyl)-1',2'-dihydrospiro[pyrrolidine-3,3'-pyrrolo[3,2-c]pyridine]-5-carboxamide hydrochloride hydrogen was obtained as an off white solid (5.1 mg, 6.6%). LC-MS (ESI, m/z) M+1: 983/985. $^1$HNMR (300 MHz, DMSO-$d_6$) δ 10.97 (s, 1H), 8.54 (s, 1H), 8.10 (br, 1H), 7.72 (d, J=7.4 Hz, 1H), 7.54-7.47 (m, 3H), 7.29 (t, J=8.5 Hz, 1H), 7.10 (s, 1H), 7.05-6.95 (m, 1H), 6.72 (s, 1H), 5.14 (dd, J=13.2, 5.1 Hz, 1H), 4.45-4.24 (m, 7H), 3.84-3.76 (m, 6H), 3.74-3.65 (m, 1H), 3.62-3.43 (m, 2H), 2.92-2.59 (m, 6H), 2.04-1.96 (m, 1H), 1.34-1.29 (m, 1H), 0.89 (s, 9H).

Example 70: Preparation of (2S,3S,4S,5R)-4-(3-chloro-2-fluorophenyl)-2-(2,2-dimethylpropyl)-N-{4-[(2R)-2-(3-{2-[(3S)-2,6-dioxopiperidin-3-yl]-1-oxo-3H-isoindol-4-yl}prop-2-yn-1-yl)morpholine-4-carbonyl]-2-methoxyphenyl}-6'-(trifluoromethyl)-1',2'-dihydrospiro[pyrrolidine-3,3'-pyrrolo[3,2-c]pyridine]-5-carboxamide hydrochloride hydrogen Synthesis of 2-methoxy-4-[(2R)-2-(prop-2-yn-1-yl)morpholine-4-carbonyl]aniline: Into a 40-mL sealed tube, were placed (2R)-4-(3-methoxy-4-nitrobenzoyl)-2-(prop-2-yn-1-yl)morpholine (300 mg, 1.0 mmol, 1.0 eq), Fe (220 mg, 3.9 mmol, 4.0 eq), $NH_4Cl$ (422 mg, 7.9 mmol, 8.0 eq), EtOH (9 mL), water (3 mL). The resulting solution was stirred for 2 hours at 70° C. The resulting mixture was filtered, the filtrate was concentrated under vacuum. The crude residue was applied onto a silica gel column and eluted with dichloromethane/methanol=10:1 to give 2-methoxy-4-[(2R)-2-(prop-2-yn-1-yl)morpholine-4-carbonyl]aniline as a light yellow oil (250 mg, 92.4%). LC-MS (ESI, m/z) M+1: 275. $^1$HNMR (300 MHz, DMSO-$d_6$) δ 6.87 (s, 1H), 6.82 (d, J=7.5 Hz, 1H), 6.62 (d, J=8.1 Hz, 1H), 5.18 (s, 2H), 4.17 (d, J=12.9 Hz, 1H), 3.93 (s, 1H), 3.97-3.84 (m, 1H), 3.80 (d, J=9.3 Hz, 3H), 3.52 (s, 2H), 3.03 (t, J=12.6 Hz, 1H), 2.87 (t, J=2.7 Hz, 1H), 2.78 (d, J=12.3 Hz, 1H), 2.45-2.29 (m, 2H).

Synthesis of tert-butyl (4S)-4-(4-{3-[(2R)-4-(4-amino-3-methoxybenzoyl)morpholin-2-yl]prop-1-yn-1-yl}-1-oxo-3H-isoindol-2-yl)-4-carbamoylbutanoate: Into an 8-mL sealed tube purged and maintained with an inert atmosphere of nitrogen, were placed 2-methoxy-4-[(2R)-2-(prop-2-yn-1-yl)morpholine-4-carbonyl]aniline (200 mg, 0.7 mmol, 1.0 eq), tert-butyl (4S)-4-carbamoyl-4-(4-iodo-1-oxo-3H-isoindol-2-yl)butanoate (486 mg, 1.1 mmol, 1.5 eq), CuI (14 mg, 0.1 mmol, 0.1 eq), triethylamine (221 mg, 2.2 mmol, 3.0 eq), $Pd(PPh_3)_4$(84 mg, 0.1 mmol, 0.1 eq) and DMF (2 mL). The resulting solution was stirred for 2 hours at 70° C. The resulting mixture was then quenched by the addition of water (50 mL) and then extracted with ethyl acetate (2×30 mL). The combined organics were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl (4S)-4-(4-{3-[(2R)-4-(4-amino-3-methoxybenzoyl)morpholin-2-yl]prop-1-yn-1-yl}-1-oxo-3H-isoindol-2-yl)-4-carbamoylbutanoate (assumed) as a light yellow solid (420 mg, 97.5%). LC-MS (ESI, m/z) M+1: 591.

Synthesis of tert-butyl (4S)-4-carbamoyl-4-(4-{3-[(2R)-4-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzoyl}morpholin-2-yl]prop-1-yn-1-yl}-1-oxo-3H-isoindol-2-yl)butanoate: Into an 8-mL sealed tube, were placed tert-butyl (4S)-4-(4-{3-[(2R)-4-(4-amino-3-methoxybenzoyl)morpholin-2-yl]prop-1-yn-1-yl}-1-oxo-3H-isoindol-2-yl)-4-carbamoylbutanoate (150 mg, 0.3 mmol, 1.2 eq), (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (103 mg, 0.2 mmol, 1.0 eq), TCFH (89 mg, 0.3 mmol, 1.5 eq), NMI (44 mg, 0.5 mmol, 2.5 eq) and $CH_3CN$ (2 mL). The resulting solution was stirred for 2 hours at 25° C. The resulting mixture was then quenched by the addition of water (50 mL) and extracted with ethyl acetate (2×40 mL). The combined organics were washed with brine (2×40 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl (4S)-4-carbamoyl-4-(4-{3-[(2R)-4-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzoyl}morpholin-2-yl]prop-1-yn-1-yl}-1-oxo-3H-isoindol-2-yl)butanoate as a light yellow solid (100 mg, 44.6%). LC-MS (ESI, m/z) M+1: 1057/1059.

Synthesis of (2S,3S,4S,5R)-4-(3-chloro-2-fluorophenyl)-2-(2,2-dimethylpropyl)-N-{4-[(2R)-2-(3-{2-[(3S)-2,6-dioxopiperidin-3-yl]-1-oxo-3H-isoindol-4-yl}prop-2-yn-1-yl)morpholine-4-carbonyl]-2-methoxyphenyl}-6'-(trifluoromethyl)-1',2'-dihydrospiro[pyrrolidine-3,3'-pyrrolo[3,2-c]pyridine]-5-carboxamide hydrochloride hydrogen: Into an 8 mL sealed tube, were placed tert-butyl (4S)-4-carbamoyl-4-(4-{3-[(2R)-4-{4-[(2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridin]-5-ylamido]-3-methoxybenzoyl}morpholin-2-yl]prop-1-yn-1-yl}-1-oxo-3H-isoindol-2-yl)butanoate (95 mg, 0.1 mmol, 1.0 eq), $CH_3CN$ (1 mL), benzenesulfonic acid (28 mg, 0.2 mmol, 2.0 eq). The resulting solution was stirred for 16 hours at 80° C. The crude product was purified by Flash-Prep-HPLC using the following conditions: Column, C18 reversed phase column; mobile phase, water (0.05% $NH_3 \cdot H_2O$) and $CH_3CN$ (5% $CH_3CN$ up to 30% in 15 min); Flow rate: 60 mL/min; Detector, 254/220 nm. Finally, (2S,3S,4S,5R)-4-(3-chloro-2-fluorophenyl)-2-(2,2-dimethylpropyl)-N-{4-[(2R)-2-(3-{2-[(3S)-2,6-dioxopiperidin-3-yl]-1-oxo-3H-isoindol-4-yl}prop-2-yn-1-yl)morpholine-4-carbonyl]-2-methoxyphenyl}-6'-(trifluoromethyl)-1',2'-dihydrospiro[pyrrolidine-3,3'-pyrrolo[3,2-c]pyridine]-5-carboxamide hydrochloride hydrogen was obtained as an off white solid (5.4 mg, 5.9%). LC-MS (ESI, m/z) M+1: 983/985. $^1$HNMR (300 MHz, DMSO-$d_6$) δ 10.97 (s, 1H), 8.55 (s, 1H), 7.72 (d, J=7.7 Hz, 1H), 7.54-7.48 (m, 4H), 7.32-7.26 (m, 1H), 7.10 (s, 1H), 7.01 (d, J=8.6 Hz, 1H), 6.73 (s, 1H), 5.14 (d, J=10.7 Hz, 1H), 4.46-4.30 (m, 4H), 3.93-3.77 (m, 5H), 3.73-3.65 (m, 3H), 3.60-3.48 (m, 3H), 2.93-2.68 (m, 6H), 2.03-1.98 (m, 1H), 1.50-1.32 (m, 1H), 0.89 (s, 9H).

Example 71: Preparation of ((2S,3S,4S,5R)-4-(3-chloro-2-fluorophenyl)-2-(2,2-dimethylpropyl)-N-(4-{4-[2-(2,6-dioxopiperidin-3-yl)-1-oxo-3H-isoindol-5-yl]piperazine-1-carbonyl}-2-methoxyphenyl)-6'-(trifluoromethyl)-1',2'-dihydrospiro[pyrrolidine-3,3'-pyrrolo[3,2-c]pyridine]-5-carboxamide Synthesis of tert-butyl 4-[2-(2,6-dioxopiperidin-3-yl)-1-oxo-3H-isoindol-5-yl]piperazine-1-carboxylate: Into a 40-mL sealed-tube purged and maintained with an inert atmosphere of nitrogen, were placed 3-(5-iodo-1-oxo-3H-isoindol-2-yl)piperidine-2,6-dione (1.0 g, 2.7 mmol, 1.0 eq), tert-butyl piperazine-1-carboxylate (600 mg, 3.2 mmol, 1.2 eq), $Cs_2CO_3$ (1.8 g, 5.4 mmol, 2.0 eq), DMF (10 mL), 3rd Generation RuPhos precatalyst (230 mg, 0.3 mmol, 0.1 eq). The resulting solution was stirred for 14 hours at 110° C. The resulting mixture was then quenched by the addition of water (40 mL) and then extracted with ethyl acetate (2×40 mL). The combined organics were washed with brine (2×40 mL) and dried over anhydrous $Na_2SO_4$. After filtration, the filtrate was concentrated under vacuum. The crude residue was applied onto a silica gel column and eluted with ethyl acetate/petroleum ether=1:1 to give tert-butyl 4-[2-(2,6-dioxopiperidin-3-yl)-1-oxo-3H-isoindol-5-yl]piperazine-1-carboxylate as a light yellow solid (400 mg, 34.6%). LC-MS (ESI, m/z) M+1: 429. $^1$HNMR (400 MHz, DMSO-$d_6$) δ 10.95 (s, 1H), 7.54 (d, J=8.4 Hz, 1H), 7.07 (d, J=11.2 Hz, 2H), 5.06 (dd, J=13.4, 5.2 Hz, 1H), 4.34 (d, J=16.8 Hz, 1H), 4.22 (d, J=16.8 Hz, 1H), 3.49-3.46 (m, 4H), 3.30-3.27 (m, 4H), 2.98-2.84 (m, 1H), 2.64-2.55 (m, 1H), 2.43-2.32 (m, 1H), 2.01-1.89 (m, 1H), 1.43 (s, 9H).

Synthesis of 3-[1-oxo-5-(piperazin-1-yl)-3H-isoindol-2-yl]piperidine-2,6-dione hydrochloride: Into a 50-mL round-bottom flask, were placed tert-butyl 4-[2-(2,6-dioxopiperidin-3-yl)-1-oxo-3H-isoindol-5-yl]piperazine-1-carboxylate (380 mg, 0.9 mmol, 1.0 eq), $CH_2Cl_2$ (4 mL), HCl(gas) in 1,4-dioxane (4 mL). The resulting mixture was stirred for 1 hour at 25° C. The resulting mixture was concentrated under vacuum to give 3-[1-oxo-5-(piperazin-1-yl)-3H-isoindol-2-yl]piperidine-2,6-dione hydrochloride as a brown solid (350 mg crude). LC-MS (ESI, m/z) M+1: 329.

Synthesis of 3-{5-[4-(3-methoxy-4-nitrobenzoyl)piperazin-1-yl]-1-oxo-3H-isoindol-2-yl}piperidine-2,6-dione: Into a 20-mL sealed tube, were placed 3-[1-oxo-5-(piperazin-1-yl)-3H-isoindol-2-yl]piperidine-2,6-dione hydrochloride (150 mg, 0.4 mmol, 1.0 eq), 3-methoxy-4-nitrobenzoic acid (89 mg, 0.5 mmol, 1.1 eq), HATU (172 mg, 0.5 mmol, 1.1 eq), DIEA (159 mg, 1.2 mmol, 3.0 eq), DMF (3 mL). The resulting solution was stirred for 2 hours at 25° C. The resulting mixture was then quenched by the addition of water (30 mL) and then extracted with ethyl acetate (2×30 mL). The combined organics were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give 3-{5-[4-(3-methoxy-4-nitrobenzoyl)piperazin-1-yl]-1-oxo-3H-isoindol-2-yl}piperidine-2,6-dione as a light yellow solid (160 mg, 76.7%). LC-MS (ESI, m/z) M+1: 508.

Synthesis of 3-{5-[4-(4-amino-3-methoxybenzoyl)piperazin-1-yl]-1-oxo-3H-isoindol-2-yl}piperidine-2,6-dione: Into a 20-mL sealed tube, were placed 3-{5-[4-(3-methoxy-4-nitrobenzoyl)piperazin-1-yl]-1-oxo-3H-isoindol-2-yl}piperidine-2,6-dione (140 mg, 0.3 mmol, 1.0 eq), Fe (62 mg, 1.1 mmol, 4.0 eq), $NH_4Cl$ (118 mg, 2.2 mmol, 8.0 eq), EtOH (3 mL), $H_2O$ (1 mL). The resulting solution was stirred for 2 hours at 50° C. The resulting mixture was filtered, the filtrate was concentrated under vacuum. The crude residue was applied onto a silica gel column and eluted with ethyl acetate/petroleum ether=1:0 to give 3-{5-[4-(4-amino-3-methoxybenzoyl)piperazin-1-yl]-1-oxo-3H-isoindol-2-yl}piperidine-2,6-dione as a light yellow solid (110 mg, 83.5%). LC-MS (ESI, m/z) M+1: 478.

Synthesis of ((2S,3S,4S,5R)-4-(3-chloro-2-fluorophenyl)-2-(2,2-dimethylpropyl)-N-(4-{4-[2-(2,6-dioxopiperidin-3-yl)-1-oxo-3H-isoindol-5-yl]piperazine-1-carbonyl}-2-methoxyphenyl)-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1,2'-dihydrospiro[pyrrolidine-3,3'-pyrrolo[3,2-c]pyridine]-5-carboxylic acid (30 mg, 0.1 mmol, 1.0 eq), 3-{5-[4-(4-amino-3-methoxybenzoyl)piperazin-1-yl]-1-oxo-3H-isoindol-2-yl}piperidine-2,6-dione (35 mg, 0.1 mmol, 1.2 eq), TCFH (26 mg, 0.1 mmol, 1.5 eq), NMI (13 mg, 0.1 mmol, 2.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3 \cdot H_2O$) and $CH_3CN$ (55% Phase B up to 65% in 7 min); Detector, UV 254/220 nm. Finally, ((2S,3S,4S,5R)-4-(3-chloro-2-fluorophenyl)-2-(2,2-dimethylpropyl)-N-(4-{4-[2-(2,6-dioxopiperidin-3-yl)-1-oxo-3H-isoindol-5-yl]piperazine-1-carbonyl}-2-methoxyphenyl)-6'-(trifluoromethyl)-1,2'-dihydrospiro[pyrrolidine-3,3'-pyrrolo[3,2-c]pyridine]-5-carboxamide was obtained as a white solid (10 mg, 17.1%). LC-MS (ESI, m/z) M+1: 945/947. $^1$HNMR (400 MHz, DMSO-$d_6$) δ 10.95 (s, 1H), 10.66 (s, 1H), 8.42 (d, J=1.6 Hz, 1H), 8.37 (d, J=8.2 Hz, 1H), 7.56 (d, J=8.4 Hz, 1H), 7.49-7.39 (m, 2H), 7.23 (t, J=8.0 Hz, 1H), 7.16 (d, J=1.8 Hz, 1H), 7.13-7.06 (m, 2H), 7.03 (dd, J=8.2, 1.8 Hz, 1H), 6.62 (d, J=2.4 Hz, 2H), 5.06 (dd, J=13.2, 5.2 Hz, 1H), 4.41-4.31 (m, 2H), 4.29-4.18 (m, 2H), 3.89 (s, 3H), 3.78 (t, J=11.2 Hz, 1H), 3.72-3.63 (m, 4H), 3.36 (d, J=11.4 Hz, 5H), 2.91 (ddd, J=17.4, 13.4, 5.4 Hz, 1H), 2.64-2.55 (m, 1H), 2.39 (td, J=13.2, 4.5 Hz, 1H), 1.97 (d, J=12.8 Hz, 1H), 1.38 (dd, J=14.2, 9.4 Hz, 1H), 1.13 (d, J=13.8 Hz, 1H), 0.94 (s, 9H).

Example 72: Preparation of (2S,3S,4S,5R)-4-(3-chloro-2-fluorophenyl)-2-(2,2-dimethylpropyl)-N-{3-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[1.1.1]pentan-1-yl}-6'-(trifluoromethyl)-1',2'-dihydrospiro[pyrrolidine-3,3'-pyrrolo[3,2-c]pyridine]-5-carboxamide Synthesis of methyl 3-[(tert-butoxycarbonyl)amino]bicyclo[1.1.1]pentane-1-carboxylate: Into a 50-mL round-bottom flask, were placed 3-(methoxycarbonyl)bicyclo[1.1.1]pentane-1-carboxylic acid (3.0 g, 17.6 mmol, 1.0 eq), t-BuOH (60 mL), $Et_3N$ (7.1 g, 70.5 mmol, 4.0 eq), DPPA (7.3 g, 26.4 mmol, 1.5 eq). The resulting solution was stirred for 16 hours at 85° C. The resulting mixture was concentrated under vacuum. The resulting solution was diluted with water (50 mL) and then extracted with ethyl acetate (2×50 mL). The combined organics were washed with brine (2×50 mL) and dried over anhydrous $Na_2SO_4$. After filtration, the filtrate was concentrated under vacuum. The crude residue was applied onto a silica gel column and eluted with ethyl acetate/petroleum ether=1:4 to give methyl 3-[(tert-butoxycarbonyl)amino]bicyclo[1.1.1]pentane-1-carboxylate as a white solid (1.5 g, 35.3%). LC-MS (ESI, m/z) M+1-tBu: 227. $^1$HNMR (300 MHz, DMSO-$d_6$) δ 7.62 (s, 1H), 3.60 (s, 3H), 2.14 (s, 6H), 1.38 (s, 9H).

Synthesis of 3-[(tert-butoxycarbonyl)amino]bicyclo[1.1.1]pentane-1-carboxylic acid: Into a 50-mL round-bottom flask, were placed methyl 3-[(tert-butoxycarbonyl)amino]bicyclo[1.1.1]pentane-1-carboxylate (600 mg, 2.5 mmol, 1.0 eq), tetrahydrofuran (6 mL), $H_2O$ (6 mL), LiOH (119 mg, 5.0 mmol, 2.0 eq). The resulting mixture was stirred for 2 hours at 25° C. The resulting mixture was concentrated under vacuum and diluted with water (10 mL). The mixture was acidified to pH=3-4 with HCl (1 M). The precipitated solids were collected by filtration and washed with water (2×10 mL), and dried on rotary evaporator. Finally, 3-[(tert-butoxycarbonyl)amino]bicyclo[1.1.1]pentane-1-carboxylic acid was obtained as a white solid (450 mg, 79.6%). LC-MS (ESI, m/z) M+1: 228. $^1$HNMR (400 MHz, DMSO-$d_6$) δ 12.35 (s, 1H), 7.57 (s, 1H), 2.09 (s, 6H), 1.38 (s, 9H).

Synthesis of tert-butyl N-{3-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[1.1.1]pentan-1-yl}carbamate: Into an 8-mL sealed tube, were placed 3-[(tert-butoxycarbonyl)amino]bicyclo[1.1.1]pentane-1-carboxylic acid (200 mg, 0.9 mmol, 1.0 eq), 3-(4-{2-[(1S)-6-azaspiro[2.5]octan-1-yl]ethynyl}-1-oxo-3H-isoindol-2-yl)piperidine-2,6-dione (399 mg, 1.1 mmol, 1.2 eq), TCFH (370 mg, 1.3 mmol, 1.5 eq), NMI (181 mg, 2.2 mmol, 2.5 eq), $CH_3CN$ (3 mL). The resulting solution was stirred for 2 hours at 25° C. The resulting mixture was then quenched by the addition of water (30 mL) and then extracted with ethyl acetate (2×30 mL). The combined organics were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl N-{3-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[1.1.1]pentan-1-yl}carbamate (assumed) as a yellow solid (360 mg, 69.7%). LC-MS (ESI, m/z) M+1: 587.

Synthesis of 3-(4-{2-[(1S)-6-{3-aminobicyclo[1.1.1]pentane-1-carbonyl}-6-azaspiro[2.5]octan-1-yl]ethynyl}-1-oxo-3H-isoindol-2-yl)piperidine-2,6-dione hydrochloride: Into a 50-mL round-bottom flask, were placed tert-butyl N-{3-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[1.1.1]pentan-1-yl}carbamate (150 mg, 0.2 mmol, 1 eq), $CH_2Cl_2$ (2 mL), HCl(gas) in 1,4-dioxane (2 mL). The resulting mixture was stirred for 2 hours at 25° C. The resulting mixture was concentrated under vacuum to give 3-(4-{2-[(1S)-6-{3-aminobicyclo[1.1.1]pentane-1-carbonyl}-6-azaspiro[2.5]octan-1-yl]ethynyl}-1-oxo-3H-isoindol-2-yl)piperidine-2,6-dione hydrochloride as a yellow solid (120 mg crude). LC-MS (ESI, m/z) M+1: 487.

Synthesis of (2S,3S,4S,5R)-4-(3-chloro-2-fluorophenyl)-2-(2,2-dimethylpropyl)-N-{3-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[1.1.1]pentan-1-yl}-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (30 mg, 0.1 mmol, 1.0 eq), 3-(4-{2-[(1S)-6-{3-aminobicyclo[1.1.1]pentane-1-carbonyl}-6-azaspiro[2.5]octan-1-yl]ethynyl}-1-oxo-3H-isoindol-2-yl)piperidine-2,6-dione hydrochloride (48 mg, 0.1 mmol, 1.5 eq), TCFH (26 mg, 0.1 mmol, 1.5 eq), NMI (18 mg, 0.2 mmol, 3.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3 \cdot H_2O$) and $CH_3CN$ (52% Phase B up to 62% in 7 min); Detector, UV 254/220 nm. Finally, (2S,3S,4S,5R)-4-(3-chloro-2-fluorophenyl)-2-(2,2-dimethylpropyl)-N-{3-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[1.1.1]pentan-1-yl}-6'-(trifluoromethyl)-1',2'-dihydrospiro[pyrrolidine-3,3'-pyrrolo[3,2-c]pyridine]-5-carboxamide was obtained as a white solid (10 mg, 17.0%). LC-MS (ESI, m/z) M+1: 953/955. $^1$HNMR (400 MHz, DMSO-$d_6$) δ 10.99 (s, 1H), 8.36 (s, 1H), 8.30 (s, 1H), 7.69 (d, J=6.8 Hz, 1H), 7.64 (t, J=6.8 Hz, 1H), 7.54-7.49 (m, 1H), 7.43-7.34 (m, 2H), 7.19 (t, J=7.6 Hz, 1H), 6.60 (s, 2H), 5.20-5.08 (m, 1H), 4.52-4.37 (m, 1H), 4.35-4.25 (m, 1H), 4.17 (dd, J=19.2, 9.4 Hz, 1H), 4.07 (d, J=6.2 Hz, 1H), 3.76-3.65 (m, 1H), 3.63 (t, J=13.6 Hz, 2H), 3.53-3.46 (m, 1H), 3.29-3.24 (m, 3H), 2.96-2.86 (m, 1H), 2.67-2.57 (m, 1H), 2.47-2.41 (m, 1H), 2.29 (s, 6H), 2.05-2.00 (m, 1H), 1.67-1.62 (m, 2H), 1.58 (br, 1H), 1.47 (br, 1H), 1.31-1.22 (m, 2H), 1.11 (d, J=14.0 Hz, 1H), 1.07-1.02 (m, 1H), 0.82 (s, 10H).

Example 73: Preparation of (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[2.2.2]octan-1-yl}-6'-(trifluoromethyl)-1',2'-dihydrospiro[pyrrolidine-3,3'-pyrrolo[3,2-c]pyridine]-5-carboxamide Synthesis of tert-butyl N-{4-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[2.2.2]octan-1-yl}carbamate: Into a 20-mL sealed tube, were placed 4-[(tert-butoxycarbonyl)amino]bicyclo[2.2.2]octane-1-carboxylic acid (200 mg, 0.7 mmol, 1.0 eq), 3-(4-{2-[(1S)-6-azaspiro[2.5]octan-1-yl]ethynyl}-1-oxo-3H-isoindol-2-yl)piperidine-2,6-dione (336 mg, 0.9 mmol, 1.2 eq), TCFH (313 mg, 1.1 mmol, 1.5 eq), NMI (152 mg, 1.9 mmol, 2.5 eq), $CH_3CN$ (3 mL). The resulting solution was stirred for 2 hours at 25° C. The resulting mixture was then quenched by the addition of water (30 mL) and then extracted with ethyl acetate (2×30 mL). The combined organics were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl N-{4-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[2.2.2]octan-1-yl}carbamate as a light yellow solid (370 mg, 79.3%). LC-MS (ESI, m/z) M+1: 629.

Synthesis of 3-(4-{2-[(1S)-6-{4-aminobicyclo[2.2.2]octane-1-carbonyl}-6-azaspiro[2.5]octan-1-yl]ethynyl}-1-oxo-3H-isoindol-2-yl)piperidine-2,6-dione hydrochloride: Into a 50-mL round-bottom flask, were placed tert-butyl N-{4-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[2.2.2]octan-1-yl}carbamate (150 mg, 0.2 mmol, 1.0 eq), $CH_2Cl_2$ (2 mL), HCl(gas) in 1,4-dioxane (2 mL). The resulting mixture was stirred for 2 hours at 25° C. The resulting mixture was concentrated under vacuum to give 3-(4-{2-[(1S)-6-{4-aminobicyclo[2.2.2]octane-1-carbonyl}-6-azaspiro[2.5]octan-1-yl]ethynyl}-1-oxo-3H-isoindol-2-yl)piperidine-2,6-dione hydrochloride as a yellow solid (110 mg, crude).

Synthesis of (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[2.2.2]octan-1-yl}-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1,2'-dihydrospiro[pyrrolidine-3,3'-pyrrolo[3,2-c]pyridine]-5-carboxylic acid (30 mg, 0.1 mmol, 1.0 eq), 3-(4-{2-[(1S)-6-{4-aminobicyclo[2.2.2]octane-1-carbonyl}-6-azaspiro[2.5]octan-1-yl]ethynyl}-1-oxo-3H-isoindol-2-yl)piperidine-2,6-dione hydrochloride (52 mg, 0.1 mmol, 1.5 eq), TCFH (26 mg, 0.1 mmol, 1.5 eq), NMI (18 mg, 0.2 mmol, 3.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3 \cdot H_2O$) and $CH_3CN$ (50% Phase B up to 60% in 7 min); Detector, UV 254/220 nm. Finally, (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]bicyclo[2.2.2]octan-1-yl}-6'-(trifluoromethyl)-1',2'-dihydrospiro[pyrrolidine-3,3'-pyrrolo[3,2-c]pyridine]-5-carboxamide was obtained as a white solid (10 mg, 16.3%). LC-MS (ESI, m/z) M+1: 996/998. $^1$HNMR (400 MHz, DMSO-$d_6$) δ 10.99 (d, J=7.8 Hz, 1H), 8.25 (d, J=4.8 Hz, 1H), 7.74-7.67 (m, 2H), 7.67-7.61 (m, 1H), 7.51 (t, J=7.6 Hz, 1H), 7.43-7.35 (m, 2H), 7.19 (t, J=7.8 Hz, 1H), 6.62 (s, 2H), 5.17-5.10 (m, 1H), 4.45 (t, J=17.4 Hz, 1H), 4.32 (dd, J=17.6, 3.6 Hz, 1H), 4.10-3.94 (m, 2H), 3.88-3.66 (m, 2H), 3.60 (d, J=11.1 Hz, 1H), 3.51-3.41 (m, 3H), 3.23 (d, J=11.2 Hz, 1H), 3.10 (br, 1H), 2.99-2.86 (m, 1H), 2.61 (d, J=17.2 Hz, 1H), 2.45 (d, J=12.2 Hz, 1H), 2.10-1.99 (m, 1H), 1.86 (d, J=7.9 Hz, 12H), 1.68-1.55 (m, 3H), 1.45 (d, J=9.9 Hz, 1H), 1.29 (dd, −13.9, 8.8 Hz, 2H), 1.15-1.03 (m, 2H), 0.83 (s, 10H).

Example 74: Preparation of (2S,3S,4S,5R)-4-(3-chloro-2-fluorophenyl)-2-(2,2-dimethylpropyl)-N-[(1r,4r)-4-[(1S)-1-{2-[2-(2,6-dioxopiperidin-3-yl)-1-oxo-3H-isoindol-4-yl]ethynyl}-6-azaspiro[2.5]octane-6-carbonyl]cyclohexyl]-6'-(trifluoromethyl)-1',2'-dihydrospiro[pyrrolidine-3,3'-pyrrolo[3,2-c]pyridine]-5-carboxamide Synthesis of tert-butyl N-[(1r,4r)-4-[(1S)-1-{2-[2-(2,6-dioxopiperidin-3-yl)-1-oxo-3H-isoindol-4-yl]ethynyl}-6-azaspiro[2.5]octane-6-carbonyl]cyclohexyl]carbamate: Into an 8-mL sealed tube, were placed (1r,4r)-4-[(tert-butoxycarbonyl)amino]cyclohexane-1-carboxylic acid (200 mg, 0.8 mmol, 1.0 eq), 3-(4-{2-[(1S)-6-azaspiro[2.5]octan-1-yl]ethynyl}-1-oxo-3H-isoindol-2-yl)piperidine-2,6-dione (372 mg, 1.0 mmol, 1.2 eq), TCFH (346 mg, 1.2 mmol, 1.5 eq), NMI (169 mg, 2.1 mmol, 2.5 eq), $CH_3CN$ (3 mL). The resulting solution was stirred for 2 hours at 25° C. The resulting mixture was quenched by the addition of water (20 mL) and then extracted with ethyl acetate (2×20 mL). The combined organics were washed with brine (2×20 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl N-[(1r,4r)-4-[(1S)-1-{2-[2-(2,6-dioxopiperidin-3-yl)-1-oxo-3H-isoindol-4-yl]ethynyl}-6-azaspiro[2.5]octane-6-carbonyl]cyclohexyl]carbamate as a yellow solid (400 mg, 80.7%). LC-MS (ESI, m/z) M+1: 603.

Synthesis of 3-(1-oxo-4-{2-[(1S)-6-[(1r,4r)-4-aminocyclohexanecarbonyl]-6-azaspiro[2.5]octan-1-yl]ethynyl}-3H-isoindol-2-yl)piperidine-2,6-dione: Into a 100-mL round-bottom flask, were placed tert-butyl N-[(1r,4r)-4-[(1S)-1-{2-[2-(2,6-dioxopiperidin-3-yl)-1-oxo-3H-isoindol-4-yl]ethynyl}-6-azaspiro[2.5]octane-6-carbonyl]cyclohexyl]carbamate (150 mg, 0.2 mmol, 1.0 eq), $CH_2Cl_2$ (5 mL), 2,6-dimethylpyridine (108 mg, 1.0 mmol, 4.0 eq). After that, TMSI (149 mg, 0.7 mmol, 3.0 eq) was added at 0° C. The resulting mixture was stirred for 2 hours at 25° C. The resulting mixture was concentrated under vacuum to give 3-(1-oxo-4-{2-[(1S)-6-[(1r,4r)-4-aminocyclohexanecarbonyl]-6-azaspiro[2.5]octan-1-yl]ethynyl}-3H-isoindol-2-yl)piperidine-2,6-dione as a brown yellow solid (170 mg crude). LC-MS (ESI, m/z) M+1: 503.

Synthesis of (2S,3S,4S,5R)-4-(3-chloro-2-fluorophenyl)-2-(2,2-dimethylpropyl)-N-[(1r,4r)-4-[(1S)-1-{2-[2-(2,6-dioxopiperidin-3-yl)-1-oxo-3H-isoindol-4-yl]ethynyl}-6-azaspiro[2.5]octane-6-carbonyl]cyclohexyl]-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1,2'-dihydrospiro[pyrrolidine-3,3'-pyrrolo[3,2-c]pyridine]-5-carboxylic acid (30 mg, 0.1 mmol, 1.0 eq), 3-(1-oxo-4-{2-[(1S)-6-[(1r,4r)-4-aminocyclohexanecarbonyl]-6-azaspiro[2.5]octan-1-yl]ethynyl}-3H-isoindol-2-yl)piperidine-2,6-dione (47 mg, 0.1 mmol, 1.5 eq), TCFH (26 mg, 0.1 mmol, 1.5 eq), NMI (13 mg, 0.1 mmol, 2.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3 \cdot H_2O$) and $CH_3CN$ (53% Phase B up to 63% in 7 min); Detector, UV 254/220 nm. Finally, (2S,3S,4S,5R)-4-(3-chloro-2-fluorophenyl)-2-(2,2-dimethylpropyl)-N-[(1r,4r)-4-[(1S)-1-{2-[2-(2,6-dioxopiperidin-3-yl)-1-oxo-3H-isoindol-4-yl]ethynyl}-6-azaspiro[2.5]octane-6-carbonyl]cyclohexyl]-6'-(trifluoromethyl)-1,2'-dihydrospiro[pyrrolidine-3,3'-pyrrolo[3,2-c]pyridine]-5-carboxamide was obtained as a white solid (10 mg, 16.7%). LC-MS (ESI, m/z) M+1: 970/972. $^1$HNMR (400 MHz, DMSO-$d_6$) δ 11.00 (s, 1H), 8.29 (s, 1H), 7.76 (d, J=8.2 Hz, 1H), 7.70 (d, J=7.6 Hz, 1H), 7.64 (d, J=7.6 Hz, 1H), 7.51 (t, J=7.6 Hz, 1H), 7.43-7.36 (m, 2H), 7.20 (t, J=7.8 Hz, 1H), 6.61 (d, J=3.2 Hz, 2H), 5.17-5.09 (m, 1H), 4.42 (d, J=9.8 Hz, 1H), 4.35-4.30 (m, 1H), 4.11 (d, J=8.8 Hz, 1H), 4.04 (d, J=8.8 Hz, 1H), 3.70 (br, 2H), 3.60 (d, J=11.2 Hz, 1H), 3.47 (br, 3H), 3.25 (d, J=11.0 Hz, 1H), 3.16 (d, J=9.0 Hz, 1H), 2.90 (d, J=15.0 Hz, 1H), 2.60 (d, J=15.8 Hz, 2H), 2.47-2.42 (m, 1H), 2.13-1.89 (m, 2H), 1.82-1.64 (m, 5H), 1.58-1.41 (m, 5H), 1.32-1.16 (m, 4H), 1.10 (d, J=14.2 Hz, 2H), 0.83 (s, 10H).

Example 75: Preparation of (2S,3S,4S,5R)-4-(3-chloro-2-fluorophenyl)-2-(2,2-dimethylpropyl)-N-[(3R,6S)-6-[(1S)-1-{2-[2-(2,6-dioxopiperidin-3-yl)-1-oxo-3H-isoindol-4-yl]ethynyl}-6-azaspiro[2.5]octane-6-carbonyl]oxan-3-yl]-6'-(trifluoromethyl)-1',2'-dihydrospiro[pyrrolidine-3,3'-pyrrolo[3,2-c]pyridine]-5-carboxamide Synthesis of tert-butyl N-[(3R,6S)-6-[(1S)-1-{2-[2-(2,6-dioxopiperidin-3-yl)-1-oxo-3H-isoindol-4-yl]ethynyl}-6- azaspiro[2.5]octane-6-carbonyl]oxan-3-yl]carbamate: Into a 20-mL sealed tube, were placed (2S,5R)-5-[(tert-butoxycarbonyl)amino]oxane-2-carboxylic acid (200 mg, 0.8 mmol, 1.0 eq), 3-(4-{2-[(1S)-6-azaspiro[2.5]octan-1-yl]ethynyl}-1-oxo-3H-isoindol-2-yl)piperidine-2,6-dione (369 mg, 1.0 mmol, 1.2 eq), TCFH (343 mg, 1.2 mmol, 1.5 eq), NMI (167 mg, 2.0 mmol, 2.5 eq), $CH_3CN$ (3 mL). The resulting solution was stirred for 2 hours at 25° C. The resulting mixture was then quenched by the addition of water (30 mL) and then extracted with ethyl acetate (2×30 mL). The combined organics were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl N-[(3R,6S)-6-[(1S)-1-{2-[2-(2,6-dioxopiperidin-3-yl)-1-oxo-3H-isoindol-4-yl]ethynyl}-6-azaspiro[2.5]octane-6-carbonyl]oxan-3-yl]carbamate as a yellow solid (400 mg, 81.1%). LC-MS (ESI, m/z) M+1: 605.

Synthesis of 3-(4-{2-[(1S)-6-[(2S,5R)-5-aminooxane-2-carbonyl]-6-azaspiro[2.5]octan-1-yl]ethynyl}-1-oxo-3H-isoindol-2-yl)piperidine-2,6-dione: Into a 50-mL round-bottom flask, were placed tert-butyl N-[(3R,6S)-6-[(1S)-1-{2-[2-(2,6-dioxopiperidin-3-yl)-1-oxo-3H-isoindol-4-yl]ethynyl}-6-azaspiro[2.5]octane-6-carbonyl]oxan-3-yl]carbamate (150 mg, 0.2 mmol, 1.0 eq), $CH_2Cl_2$ (5 mL), 2,6-dimethylpyridine (106 mg, 1.0 mmol, 4.0 eq). After that, TMSI (149 mg, 0.7 mmol, 3.0 eq) was added at 0° C. The resulting mixture was stirred for 2 hours at 25° C. The resulting mixture was concentrated under vacuum to give 3-(4-{2-[(1S)-6-[(2S,5R)-5-aminooxane-2-carbonyl]-6-azaspiro[2.5]octan-1-yl]ethynyl}-1-oxo-3H-isoindol-2-yl)piperidine-2,6-dione as a light yellow solid (170 mg crude). LC-MS (ESI, m/z) M+1: 505.

Synthesis of (2S,3S,4S,5R)-4-(3-chloro-2-fluorophenyl)-2-(2,2-dimethylpropyl)-N-[(3R,6S)-6. [(1S)-1-{2-[2-(2,6-dioxopiperidin-3-yl)-1-oxo-3H-isoindol-4-yl]ethynyl}-6-azaspiro[2.5]octane-6-carbonyl]oxan-3-yl]-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1,2'-dihydrospiro[pyrrolidine-3,3'-pyrrolo[3,2-c]pyridine]-5-carboxylic acid (30 mg, 0.1 mmol, 1.0 eq), 3-(4-{2-[(1S)-6-[(2S,5R)-5-aminooxane-2-carbonyl]-6-azaspiro[2.5]octan-1-yl]ethynyl}-1-oxo-3H-isoindol-2-yl)piperidine-2,6-dione (47 mg, 0.1 mmol, 1.5 eq), TCFH (26 mg, 0.1 mmol, 1.5 eq), NMI (13 mg, 0.1 mmol, 2.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3{\cdot}H_2O$) and $CH_3CN$ (57% Phase B up to 67% in 7 min); Detector, UV 254/220 nm. Finally, (2S,3S,4S,5R)-4-(3-chloro-2-fluorophenyl)-2-(2,2-dimethylpropyl)-N-[(3R,6S)-6-[(1S)-1-{2-[2-(2,6-dioxopiperidin-3-yl)-1-oxo-3H-isoindol-4-yl]ethynyl}-6-azaspiro[2.5]octane-6-carbonyl]oxan-3-yl]-6'-(trifluoromethyl)-1,2'-dihydrospiro[pyrrolidine-3,3'-pyrrolo[3,2-c]pyridine]-5-carboxamide was obtained as a white solid (10 mg, 16.7%). LC-MS (ESI, m/z) M+1: 972/974. $^1$HNMR (400 MHz, DMSO-$d_6$) δ 10.99 (s, 1H), 8.32 (s, 1H), 7.82 (d, J=8.0 Hz, 1H), 7.70 (d, J=7.6 Hz, 1H), 7.64 (d, J=7.6 Hz, 1H), 7.51 (t, J=7.6 Hz, 1H), 7.43-7.35 (m, 2H), 7.22-7.18 (m, 1H), 6.61 (d, J=4.6 Hz, 2H), 5.12 (d, J=13.8 Hz, 1H), 4.50-4.37 (m, 1H), 4.33-4.28 (m, 1H), 4.19 (t, J=6.4 Hz, 1H), 4.14 (d, J=8.8 Hz, 1H), 4.06 (d, J=9.2 Hz, 1H), 3.78 (s, 1H), 3.67-3.57 (m, 4H), 3.26-3.13 (m, 3H), 2.95-2.88 (m, 1H), 2.67-2.56 (m, 1H), 2.44-2.36 (m, 1H), 2.07-1.98 (m, 3H), 1.78-1.73 (m, 2H), 1.68-1.63 (m, 2H), 1.62-1.39 (m, 3H), 1.37-1.24 (m, 2H), 1.14-1.02 (m, 2H), 0.83 (s, 10H).

Example 76: Preparation of (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-5-yl]ethynyl}-6-azaspiro[2.5]octane-6-carbonyl]-2-methoxyphenyl}-6'-(trifluoromethyl)-1',2'-dihydrospiro[pyrrolidine-3,3'-pyrrolo[3,2-c]pyridine]-5-carboxamide Synthesis of 3-(5-{2-[(1S)-6-(4-amino-3-methoxybenzoyl)-6-azaspiro[2.5]octan-1-yl]ethynyl}-1-oxo-3H-isoindol-2-yl)piperidine-2,6-dione: Into an 8-mL sealed tube purged and maintained with an inert atmosphere of nitrogen, were placed 4-[(1S)-1-ethynyl-6-azaspiro[2.5]octane-6-carbonyl]-2-methoxyaniline (50 mg, 0.2 mmol, 1.0 eq), 3-(5-iodo-1-oxo-3H-isoindol-2-yl)piperidine-2,6-dione (78 mg, 0.2 mmol, 1.2 eq), CuI (1 mg, 0.02 mmol, 0.1 eq), $Et_3N$ (53 mg, 0.5 mmol, 3.0 eq), $Pd(PPh_3)_4$ (20 mg, 0.02 mmol, 0.1 eq), DMF (5 mL).

The resulting solution was stirred for 2 hours at 70° C. in an oil bath. The resulting mixture was then quenched by the addition of water (100 mL) and then extracted with ethyl acetate (2×30 mL). The combined organics were washed with brine (2×30 mL) and then dried over anhydrous $Na_2SO_4$. After filtration, the filtrate was concentrated under vacuum. The crude residue was applied onto a silica gel column and eluted with ethyl acetate/petroleum ether=1:0 to give 3-(5-{2-[(1S)-6-(4-amino-3-methoxybenzoyl)-6-azaspiro[2.5]octan-1-yl]ethynyl}-1-oxo-3H-isoindol-2-yl)piperidine-2,6-dione as a light yellow solid (60 mg, 64.8%). LC-MS (ESI, m/z) M+1: 527.

Synthesis of (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-5-yl]ethynyl}-6-azaspiro[2.5]octane-6-carbonyl]-2-methoxyphenyl}-6'-(trifluoromethyl)-1',2'-dihydrospiro[pyrrolidine-3,3'-pyrrolo[3,2-c]pyridine]-5-carboxamide: Into an 8-mL sealed tube, were placed 3-(5-{2-[(1S)-6-(4-amino-3-methoxybenzoyl)-6-azaspiro[2.5]octan-1-yl]ethynyl}-1-oxo-3H-isoindol-2-yl)piperidine-2,6-dione (50 mg, 0.1 mmol, 1.0 eq), (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (46 mg, 0.1 mmol, 1.0 eq), TCFH (40 mg, 0.1 mmol, 1.5 eq), NMI (20 mg, 0.2 mmol, 2.5 eq), $CH_3CN$ (2 mL). The resulting solution was stirred for 2 hours at 25° C. The crude product was purified by Flash-Prep-HPLC using the following conditions: Column, C18 reversed phase column; mobile phase, water (0.05% $NH_3{\cdot}H_2O$) and $CH_3CN$ (5% $CH_3CN$ up to 30% in 15 min); Flow rate: 60 mL/min; Detector, 254/220 nm. Finally, (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-5-yl]ethynyl}-6-azaspiro[2.5]octane-6-carbonyl]-2-methoxyphenyl}-6'-(trifluoromethyl)-1',2'-dihydrospiro[pyrrolidine-3,3'-pyrrolo[3,2-c]pyridine]-5-carboxamide was obtained as an off-white solid (2.5 mg, 2.7%). LC-MS (ESI, m/z) M+1: 994/996. $^1$HNMR (300 MHz, DMSO-$d_6$) δ 10.99 (s, 1H), 10.63 (s, 1H), 8.40 (s, 1H), 8.34 (d, J=8.1 Hz, 1H), 7.67 (d, J=7.8 Hz, 1H), 7.61 (s, 1H), 7.46 (dd, J=15.9, 7.8 Hz, 3H), 7.23 (t, J=7.8 Hz, 1H), 7.12 (d, J=1.8 Hz, 1H), 6.99 (d, J=8.7 Hz, 1H), 6.61 (s, 1H), 5.11 (dd, J=13.2, 5.0 Hz, 1H), 4.52-4.17 (m, 4H), 3.88 (s, 3H), 3.78 (t, J=11.1 Hz, 1H), 3.67 (d, J=11.1 Hz, 1H), 3.58-3.41 (m, 2H), 3.41-3.35 (m, 2H), 2.89 (d, J=12.6 Hz, 1H), 2.68-2.55 (m, 2H), 2.40-2.30 (m, 1H), 2.04-1.95 (m, 1H), 1.68 (d, J=7.8 Hz, 3H), 1.58-1.49 (m, 1H), 1.38 (dd, J=14.1, 9.5 Hz, 2H), 1.27-1.12 (m, 1H), 1.08 (d, J=5.7 Hz, 2H), 0.93 (s, 9H), 0.81 (s, 1H).

Example 77: Preparation of (2S,3S,4S,5R)-4-(3-chloro-2-fluorophenyl)-2-(2,2-dimethylpropyl)-N-{4-[(1R)-1-{2-[2-(2,6-dioxopiperidin-3-yl)-1-oxo-3H-isoindol-5-yl]ethynyl}-6-azaspiro[2.5]octane-6-carbonyl]-2-methoxyphenyl}-6'-(trifluoromethyl)-1',2'-dihydrospiro[pyrrolidine-3,3'-pyrrolo[3,2-c]pyridine]-5-carboxamide Synthesis of 3-(5-{2-[(1R)-6-(4-amino-3-methoxybenzoyl)-6-azaspiro[2.5]octan-1-yl]ethynyl}-1-oxo-3H-isoindol-2-yl)piperidine-2,6-dione: Into an 8-mL sealed tube purged and maintained with an inert atmosphere of nitrogen, were placed 4-[(1R)-1-ethynyl-6-azaspiro[2.5]octane-6-carbonyl]-2-methoxyaniline (50 mg, 0.2 mmol, 1.0 eq), 3-(5-iodo-1-oxo-3H-isoindol-2-yl)piperidine-2,6-dione (78 mg, 0.2 mmol, 1.2 eq), CuI (3 mg, 0.02 mmol, 0.1 eq), $Et_3N$ (53 mg, 0.5 mmol, 3.0 eq), $Pd(PPh_3)_4$ (20 mg, 0.02 mmol, 0.1 eq), DMF (5 mL).

The resulting solution was stirred for 2 hours at 70° C. The resulting mixture was then quenched by the addition of water (100 mL) and extracted with ethyl acetate (2×30 mL). The combined organics were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give 3-(5-{2-[(1R)-6-(4-amino-3-methoxybenzoyl)-6-azaspiro[2.5]octan-1-yl]ethynyl}-1-oxo-3H-isoindol-2-yl)piperidine-2,6-dione as a light-yellow solid (60 mg, 64.8%). LC-MS (ESI, m/z) M+1: 527.

Synthesis of (2S,3S,4S,5R)-4-(3-chloro-2-fluorophenyl)-2-(2,2-dimethylpropyl)-N-{4-[(1R)-1-{2-[2-(2,6-dioxopiperidin-3-yl)-1-oxo-3H-isoindol-5-yl]ethynyl}-6-azaspiro[2.5]octane-6-carbonyl]-2-methoxyphenyl}-6'-(trifluoromethyl)-1',2'-dihydrospiro[pyrrolidine-3,3'-pyrrolo[3,2-c]pyridine]-5-carboxamide: Into an 8-mL sealed tube, were placed 3-(5-{2-[(1R)-6-(4-amino-3-methoxybenzoyl)-6-azaspiro[2.5]octan-1-yl]ethynyl}-1-oxo-3H-isoindol-2-yl)piperidine-2,6-dione (assumed) (50 mg, 0.1 mmol, 1.0 eq), (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (46 mg, 0.1 mmol, 1.0 eq), TCFH (40 mg, 0.1 mmol, 1.5 eq), NMI (20 mg, 0.2 mmol, 2.5 eq), $CH_3CN$ (2 mL). The resulting solution was stirred for 2 hours at 25° C. The crude product was purified by Flash-Prep-HPLC using the following conditions: Column, C18 reversed phase column; mobile phase, water (0.05% $NH_3 \cdot H_2O$) and $CH_3CN$ (5% $CH_3CN$ up to 30% in 15 min); Flow rate: 60 mL/min; Detector, 254/220 nm. Finally, (2S,3S,4S,5R)-4-(3-chloro-2-fluorophenyl)-2-(2,2-dimethylpropyl)-N-{4-[(1R)-1-{2-[2-(2,6-dioxopiperidin-3-yl)-1-oxo-3H-isoindol-5-yl]ethynyl}-6-azaspiro[2.5]octane-6-carbonyl]-2-methoxyphenyl}-6'-(trifluoromethyl)-1',2'-dihydrospiro[pyrrolidine-3,3'-pyrrolo[3,2-c]pyridine]-5-carboxamide was obtained as an off-white solid (4.8 mg, 5.1%). LC-MS (ESI, m/z) M+1: 994/996. $^1$HNMR (300 MHz, DMSO-$d_6$) δ 11.00 (s, 1H), 10.63 (s, 1H), 8.40 (s, 1H), 8.34 (d, J=8.1 Hz, 1H), 7.67 (d, J=7.8 Hz, 1H), 7.61 (s, 1H), 7.45 (dt, J=12.6, 7.2 Hz, 3H), 7.23 (t, J=7.8 Hz, 1H), 7.12 (s, 1H), 7.03-6.93 (m, 1H), 6.61 (s, 2H), 5.11 (dd, J=13.2, 5.1 Hz, 1H), 4.52-4.18 (m, 4H), 3.88 (s, 3H), 3.77 (t, J=10.8 Hz, 1H), 3.66 (d, J=11.4 Hz, 1H), 3.46 (d, J=27.6 Hz, 5H), 3.01-2.83 (m, 1H), 2.67-2.56 (m, 2H), 2.40 (d, J=13.2 Hz, 1H), 2.05-1.96 (m, 1H), 1.72 (d, J=22.2 Hz, 3H), 1.61-1.48 (m, 1H), 1.38 (dd, J=14.1, 9.3 Hz, 2H), 1.18-1.03 (m, 2H), 0.93 (s, 9H), 0.81 (d, J=4.2 Hz, 1H).

Example 78: Preparation of (2S,3S,4S,5R)-4-(3-chloro-2-fluorophenyl)-2-(2,2-dimethylpropyl)-N-{4-[(7R)-7-{2-[2-(2,6-dioxopiperidin-3-yl)-1-oxo-3H-isoindol-4-yl]ethynyl}-1,4-oxazepane-4-carbonyl]-2-methoxyphenyl}-6'-(trifluoromethyl)-1',2'-dihydrospiro[pyrrolidine-3,3'-pyrrolo[3,2-c]pyridine]-5-carboxamide Synthesis of 3-(4-{2-[(7R)-4-(3-methoxy-4-nitrobenzoyl)-1,4-oxazepan-7-yl]ethynyl}-1-oxo-3H-isoindol-2-yl)piperidine-2,6-dione: Into an 8-mL sealed-tube purged and maintained with an inert atmosphere of nitrogen, were placed (7R)-7-ethynyl-4-(3-methoxy-4-nitrobenzoyl)-1,4-oxazepane (20 mg, 0.1 mmol, 1.0 eq), 3-(4-iodo-1-oxo-3H-isoindol-2-yl)piperidine-2,6-dione (27 mg, 0.1 mmol, 1.1 eq), CuI (1. mg, 0.01 mmol, 0.1 eq), $Pd(PPh_3)_4$ (8 mg, 0.01 mmol, 0.1 eq), TEA (20 mg, 0.2 mmol, 3.0 eq), DMF (1 mL). The reaction mixture was stirred for 2 hours at 70° C. The resulting mixture was then quenched by the addition of water (30 mL) and then extracted with ethyl acetate (2×30 mL). The combined organic layers were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give 3-(4-{2-[(7R)-4-(3-methoxy-4-nitrobenzoyl)-1,4-oxazepan-7-yl]ethynyl}-1-oxo-3H-isoindol-2-yl)piperidine-2,6-dione as a light yellow solid (40 mg crude). LC-MS (ESI, m/z) M+1: 547.

Synthesis of 3-(4-{2-[(7R)-4-(4-amino-3-methoxybenzoyl)-1,4-oxazepan-7-yl]ethynyl}-1-oxo-3H-isoindol-2-yl)piperidine-2,6-dione: Into an 8-mL sealed tube, were placed 3-(4-{2-[(7R)-4-(3-methoxy-4-nitrobenzoyl)-1,4-oxazepan-7-yl]ethynyl}-1-oxo-3H-isoindol-2-yl)piperidine-2,6-dione (35 mg, 0.1 mmol, 1.0 eq), Fe (14 mg, 0.3 mmol, 4.0 eq), $NH_4Cl$ (27 mg, 0.5 mmol, 8.0 eq), EtOH (3 mL), water (1 mL). The resulting solution was stirred for 4 hours at 50° C. in an oil bath. The resulting mixture was filtered, the filtrate was concentrated under vacuum. The crude residue was applied onto a silica gel column and eluted with dichloromethane/methanol=10:1 to give 3-(4-{2-[(7R)-4-(4-amino-3-methoxybenzoyl)-1,4-oxazepan-7-yl]ethynyl}-1-oxo-3H-isoindol-2-yl)piperidine-2,6-dione as a light yellow solid (22 mg, 66.5%). LC-MS (ESI, m/z) M+1: 517.

Synthesis of (2S,3S,4S,5R)-4-(3-chloro-2-fluorophenyl)-2-(2,2-dimethylpropyl)-N-{4-[(7R)-7-{2-[2-(2,6-dioxopiperidin-3-yl)-1-oxo-3H-isoindol-4-yl]ethynyl}-1,4-oxazepane-4-carbonyl]-2-methoxyphenyl}-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (30 mg, 0.1 mmol, 1.0 eq), 3-(4-{2-[(7R)-4-(4-amino-3-methoxybenzoyl)-1,4-oxazepan-7-yl]ethynyl}-1-oxo-3H-isoindol-2-yl)piperidine-2,6-dione (35 mg, 0.1 mmol, 1.1 eq), TCFH (26 mg, 0.1 mmol, 1.5 eq), NMI (13 mg, 0.1 mmol, 2.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3 \cdot H_2O$) and $CH_3CN$ (45%

Phase B up to 55% in 7 min); Detector, UV 254/220 nm. Finally, (2S,3S,4S,5R)-4-(3-chloro-2-fluorophenyl)-2-(2,2-dimethylpropyl)-N-{4-[(7R)-7-{2-[2-(2,6-dioxopiperidin-3-yl)-1-oxo-3H-isoindol-4-yl]ethynyl}-1,4-oxazepane-4-carbonyl]-2-methoxyphenyl}-6'-(trifluoromethyl)-1',2'-dihydrospiro[pyrrolidine-3,3'-pyrrolo[3,2-c]pyridine]-5-carboxamide was obtained as a white solid (10 mg, 16.4%). LC-MS (ESI, m/z) M+1: 984/986. $^1$HNMR (400 MHz, DMSO-$d_6$) δ 10.99 (s, 1H), 10.61 (s, 1H), 8.41 (s, 1H), 8.30 (s, 1H), 7.78 (d, J=7.6 Hz, 1H), 7.75-7.65 (m, 1H), 7.57 (t, J=7.6 Hz, 1H), 7.43 (q, J=7.8 Hz, 2H), 7.23 (t, J=7.8 Hz, 1H), 7.12-6.88 (m, 2H), 6.61 (s, 2H), 5.13 (d, J=12.8 Hz, 1H), 4.93 (s, 1H), 4.52-4.47 (m, 1H), 4.39-4.30 (m, 2H), 4.26 (d, J=9.6 Hz, 1H), 3.96-3.47 (m, 10H), 3.41-3.37 (m, 1H), 3.29 (s, 1H), 2.93-2.84 (m, 1H), 2.62-2.58 (m, 1H), 2.23-2.05 (m, 2H), 2.04-1.99 (m, 1H), 1.40-1.34 (m, 1H), 1.24 (s, 1H), 1.12 (d, J=13.8 Hz, 1H), 0.92 (s, 9H).

Example 79: Preparation of (2S,3S,4S,5R)-4-(3-chloro-2-fluorophenyl)-2-(2,2-dimethylpropyl)-N-{4-[(7S)-7-{2-[2-(2,6-dioxopiperidin-3-yl)-1-oxo-3H-isoindol-4-yl]ethynyl}-1,4-oxazepane-4-carbonyl]-2-methoxyphenyl}-6'-(trifluoromethyl)-1',2'-dihydrospiro[pyrrolidine-3,3'-pyrrolo[3,2-c]pyridine]-5-carboxamide Synthesis of 3-(4-{2-[(7S)-4-(3-methoxy-4-nitrobenzoyl)-1,4-oxazepan-7-yl]ethynyl}-1-oxo-3H-isoindol-2-yl)piperidine-2,6-dione: Into an 8-mL sealed-tube, were placed (7S)-7-ethynyl-4-(3-methoxy-4-nitrobenzoyl)-1,4-oxazepane (20 mg, 0.1 mmol, 1.0 eq), 3-(4-iodo-1-oxo-3H-isoindol-2-yl)piperidine-2,6-dione (27 mg, 0.1 mmol, 1.1 eq), CuI (1 mg, 0.01 mmol, 0.1 eq), $Pd(PPh_3)_4$ (8 mg, 0.01 mmol, 0.1 eq), TEA (20 mg, 0.2 mmol, 3.0 eq), DMF (1 mL). The resulting solution was stirred for 2 hours at 70° C. The resulting mixture was quenched by the addition of water (30 mL) and then extracted with ethyl acetate (2×30 mL). The combined organic layers were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give 3-(4-{2-[(7S)-4-(3-methoxy-4-nitrobenzoyl)-1,4-oxazepan-7-yl]ethynyl}-1-oxo-3H-isoindol-2-yl)piperidine-2,6-dione as a light yellow solid (42 mg crude). LC-MS (ESI, m/z) M+1: 547.

Synthesis of 3-(4-{2-[(7S)-4-(4-amino-3-methoxybenzoyl)-1,4-oxazepan-7-yl]ethynyl}-1-oxo-3H-isoindol-2-yl)piperidine-2,6-dione: Into an 8-mL sealed tube was placed 3-(4-{2-[(7S)-4-(3-methoxy-4-nitrobenzoyl)-1,4-oxazepan-7-yl]ethynyl}-1-oxo-3H-isoindol-2-yl)piperidine-2,6-dione (40 mg, 0.1 mmol, 1.0 eq), Fe (16 mg, 0.3 mmol, 4.0 eq), $NH_4Cl$ (31 mg, 0.6 mmol, 8.0 eq), EtOH (3 mL), water (1 mL). The reaction mixture was stirred for 4 hours at 50° C. The resulting mixture was filtered, the filtrate was concentrated under vacuum. The crude residue was applied onto a silica gel column and eluted with dichloromethane/methanol=10:1 to give 3-(4-{2-[(7S)-4-(4-amino-3-methoxybenzoyl)-1,4-oxazepan-7-yl]ethynyl}-1-oxo-3H-isoindol-2-yl)piperidine-2,6-dione as a light yellow solid (25 mg, 66.1%). LC-MS (ESI, m/z) M+1: 517.

Synthesis of (2S,3S,4S,5R)-4-(3-chloro-2-fluorophenyl)-2-(2,2-dimethylpropyl)-N-{4-[(7S)-7-{2-[2-(2,6-dioxopiperidin-3-yl)-1-oxo-3H-isoindol-4-yl]ethynyl}-1,4-oxazepane-4-carbonyl]-2-methoxyphenyl}-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (24 mg, 0.05 mmol, 1.0 eq), 3-(4-{2-[(7S)-4-(4-amino-3-methoxybenzoyl)-1,4-oxazepan-7-yl]ethynyl}-1-oxo-3H-isoindol-2-yl)piperidine-2,6-dione (26 mg, 0.05 mmol, 1.00 eq), TCFH (21 mg, 0.1 mmol, 1.5 eq), NMI (10 mg, 0.1 mmol, 2.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3 \cdot H_2O$) and $CH_3CN$ (45% Phase B up to 55% in 7 min); Detector, UV 254/220 nm. Finally, (2S,3S,4S,5R)-4-(3-chloro-2-fluorophenyl)-2-(2,2-dimethylpropyl)-N-{4-[(7S)-7-{2-[2-(2,6-dioxopiperidin-3-yl)-1-oxo-3H-isoindol-4-yl]ethynyl}-1,4-oxazepane-4-carbonyl]-2-methoxyphenyl}-6'-(trifluoromethyl)-1',2'-dihydrospiro[pyrrolidine-3,3'-pyrrolo[3,2-c]pyridine]-5-carboxamide was obtained as a white solid (10 mg, 20.6%). LC-MS (ESI, m/z) M+1: 984/986. $^1$HNMR (400 MHz, DMSO-$d_6$) δ 10.99 (s, 1H), 10.59 (d, J=17.4 Hz, 1H), 8.55-8.41 (m, 1H), 8.30-8.18 (m, 1H), 7.82-7.62 (m, 2H), 7.62-7.53 (m, 1H), 7.43 (d, J=7.8 Hz, 2H), 7.23 (t, J=8.0 Hz, 1H), 7.11-6.80 (m, 2H), 6.61 (s, 2H), 5.21-4.81 (m, 2H), 4.52-4.48 (m, 1H), 4.42-4.19 (m, 3H), 4.08-3.44 (m, 12H), 3.36 (d, J=12.8 Hz, 1H), 2.95-2.86 (m, 1H), 2.62-2.56 (m, 1H), 2.41-1.90 (m, 4H), 1.40-1.34 (m, 1H), 1.16-1.18 (m, 1H), 0.94 (d, J=11.0 Hz, 9H).

Example 80: Preparation of (2S,3S,4S,5R)-4-(3-chloro-2-fluorophenyl)-N-(4-(4-(2-(2,6-dioxopiperidin-3-yl)-1-oxoisoindolin-5-yl)piperazine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide hydrochloride Synthesis of tert-butyl 4-[2-(2,6-dioxopiperidin-3-yl)-1-oxo-3H-isoindol-5-yl]piperazine-1-carboxylate: Into a 40-mL sealed-tube purged and maintained with an inert atmosphere of nitrogen, were placed 3-(5-iodo-1-oxo-3H-isoindol-2-yl)piperidine-2,6-dione (1.0 g, 2.7 mmol, 1.0 eq), tert-butyl piperazine-1-carboxylate (600 mg, 3.2 mmol, 1.2 eq), $Cs_2CO_3$ (1.8 g, 5.4 mmol, 2.0 eq), DMF (10 mL), 3rd Generation RuPhos precatalyst (230 mg, 0.3 mmol, 0.1 eq). The resulting solution was stirred for 14 hours at 110° C. The resulting mixture was quenched by the addition of water (40 mL) and then extracted with ethyl acetate (2×40 mL). The combined organic layers were washed with brine (2×40 mL) and dried over anhydrous $Na_2SO_4$. After filtration, the filtrate was concentrated under vacuum. The crude residue was applied onto a silica gel column and eluted with ethyl acetate/petroleum ether=1:1 to give tert-butyl 4-[2-(2,6-dioxopiperidin-3-yl)-1-oxo-3H-isoindol-5-yl]piperazine-1-carboxylate as a light yellow solid (400 mg, 34.6%). LC-MS (ESI, m/z) M+1: 429. $^1$HNMR (400 MHz, DMSO-$d_6$) δ 10.95 (s, 1H), 7.54 (d, J=8.4 Hz, 1H), 7.07 (d, J=11.2 Hz, 2H), 5.06 (dd, J=13.4, 5.2 Hz, 1H), 4.34 (d, J=16.8 Hz, 1H), 4.22 (d, J=16.8 Hz, 1H), 3.49-3.46 (m, 4H), 3.30-3.27 (m, 4H), 2.98-2.84 (m, 1H), 2.64-2.55 (m, 1H), 2.43-2.32 (m, 1H), 2.01-1.89 (m, 1H), 1.43 (s, 9H).

Synthesis of 3-[1-oxo-5-(piperazin-1-yl)-3H-isoindol-2-yl]piperidine-2,6-dione hydrochloride: Into a 50-mL round-bottom flask, were placed tert-butyl 4-[2-(2,6-dioxopiperidin-3-yl)-1-oxo-3H-isoindol-5-yl]piperazine-1-carboxylate (380 mg, 0.9 mmol, 1.0 eq), $CH_2Cl_2$ (4 mL), HCl(gas) in 1,4-dioxane (4 mL). The reaction mixture was stirred for 1 hour at 25° C. The resulting mixture was concentrated under vacuum to give 3-[1-oxo-5-(piperazin-1-yl)-3H-isoindol-2-yl]piperidine-2,6-dione hydrochloride as a brown solid (350 mg crude). LC-MS (ESI, m/z) M+1: 329.

Synthesis of tert-butyl N-(4-{4-[2-(2,6-dioxopiperidin-3-yl)-1-oxo-3H-isoindol-5-yl]piperazine-1-carbonyl}bicyclo[2.2.2]octan-1-yl)carbamate: Into a 20-mL sealed tube, were placed 3-[1-oxo-5-(piperazin-1-yl)-3H-isoindol-2-yl]piperidine-2,6-dione hydrochloride (130 mg, 0.3 mmol, 1.2 eq), 4-[(tert-butoxycarbonyl)amino]bicyclo[2.2.2]octane-1-carboxylic acid (80 mg, 0.3 mmol, 1.0 eq), HATU (124 mg, 0.3 mmol, 1.1 eq), DIEA (115 mg, 0.9 mmol, 3.0 eq), DMF (2 mL). The reaction mixture was stirred for 2 hours at 25° C. The resulting mixture was quenched by the addition of water (30 mL) and then extracted with ethyl acetate (2×30 mL). The combined organic layers were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give tert-butyl N-(4-{4-[2-(2,6-dioxopiperidin-3-yl)-1-oxo-3H-isoindol-5-yl]piperazine-1-carbonyl}bicyclo[2.2.2]octan-1-yl)carbamate as a light yellow solid (150 mg, 87.1%). LC-MS (ESI, m/z) M+1: 580.

Synthesis of 3-[5-(4-{4-aminobicyclo[2.2.2]octane-1-carbonyl}piperazin-1-yl)-1-oxo-3H-isoindol-2-yl]piperidine-2,6-dione hydrochloride: Into a 50-mL round-bottom flask, were placed tert-butyl N-(4-{4-[2-(2,6-dioxopiperidin-3-yl)-1-oxo-3H-isoindol-5-yl]piperazine-1-carbonyl}bicyclo[2.2.2]octan-1-yl)carbamate (120 mg, 0.2 mmol, 1.0 eq), $CH_2Cl_2$ (2 mL), HCl (gas) in 1,4-dioxane (2 mL). The reaction mixture was stirred for 1 hour at 25° C. The resulting mixture was concentrated under vacuum to give 3-[5-(4-{4-aminobicyclo[2.2.2]octane-1-carbonyl}piperazin-1-yl)-1-oxo-3H-isoindol-2-yl]piperidine-2,6-dione hydrochloride as a light yellow solid (100 mg crude). LC-MS (ESI, m/z) M+1: 480.

Synthesis of (2S,3S,4S,5R)-4-(3-chloro-2-fluorophenyl)-N-(4-(4-(2-(2,6-dioxopiperidin-3-yl)-1-oxoisoindolin-5-yl)piperazine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide hydrochloride: Into an 8-mL sealed tube, were placed (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (50 mg, 0.1 mmol, 1.0 eq), 3-[5-(4-{4-aminobicyclo[2.2.2]octane-1-carbonyl}piperazin-1-yl)-1-oxo-3H-isoindol-2-yl]piperidine-2,6-dione hydrochloride (58 mg, 0.1 mmol, 1.1 eq), HATU (43 mg, 0.1 mmol, 1.1 eq), DIEA (40 mg, 0.3 mmol, 3.0 eq), DMF (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% HCl) and $CH_3CN$ (45% Phase B up to 55% in 7 min); Detector, UV 254/220 nm. Finally, (2S,3S,4S,5R)-4-(3-chloro-2-fluorophenyl)-N-(4-(4-(2-(2,6-dioxopiperidin-3-yl)-1-oxoisoindolin-5-yl)piperazine-1-carbonyl)bicyclo[2.2.2]octan-1-yl)-2-neopentyl-6'-(trifluoromethyl)-1',2'-dihydrospiro[pyrrolidine-3,3'-pyrrolo[3,2-c]pyridine]-5-carboxamide hydrochloride was obtained as a white solid (10 mg, 10.3%). LC-MS (ESI, m/z) M+1: 947/949. $^1$HNMR (400 MHz, DMSO-$d_6$) δ 10.94 (s, 1H), 10.46 (br, 1H), 8.97 (s, 1H), 8.48 (d, J=2.2 Hz, 1H), 8.11 (s, 1H), 7.69 (t, J=7.2 Hz, 1H), 7.56 (dd, J=8.2, 6.0 Hz, 2H), 7.32-7.23 (m, 1H), 7.06-7.04 (m, 2H), 6.87 (s, 1H), 6.70 (s, 1H), 5.05 (dd, J=13.2, 5.2 Hz, 1H), 4.60-4.58 (m, 1H), 4.34 (d, J=16.8 Hz, 1H), 4.28-4.17 (m, 3H), 3.80 (d, J=11.8 Hz, 1H), 3.69 (s, 4H), 3.49 (d, J=11.8 Hz, 1H), 3.24 (t, J=5.0 Hz, 4H), 2.98-2.84 (m, 1H), 2.60-2.56 (m, 1H), 2.40-2.33 (m, 1H), 1.99-1.93 (m, 1H), 1.85-1.82 (m, 6H), 1.73-1.69 (m, 6H), 1.42 (d, J=15.2 Hz, 1H), 0.83 (s, 9H).

Example 81: Preparation of (2S,3S,4S,5R)-4-(3-chloro-2-fluorophenyl)-2-(2,2-dimethylpropyl)-N-{4-[(1S,3S)-1-{2-[2-(2,6-dioxopiperidin-3-yl)-1-oxo-3H-isoindol-4-yl]ethynyl}-5-azaspiro[2.5]octane-5-carbonyl]-2-methoxyphenyl}-6'-(trifluoromethyl)-1',2'-dihydrospiro[pyrrolidine-3,3'-pyrrolo[3,2-c]pyridine]-5-carboxamide Synthesis of (1S,3S)-1-ethynyl-5-(3-methoxy-4-nitrobenzoyl)-5-azaspiro[2.5]octane and (1R,3R)-1-ethynyl-5-(3-methoxy-4-nitrobenzoyl)-5-azaspiro[2.5]octane: 200 mg of (1S,3S)-1-ethynyl-5-(3-methoxy-4-nitrobenzoyl)-5-azaspiro[2.5]octane was purified by Chiral-SFC using the following conditions: Column: CHIRAL ART Cellulose-SB, 3*25 cm, 5 μm; mobile phase A: $CO_2$; mobile phase B: EtOH—Preparative; Flow rate: 50 mL/min; Gradient: isocratic 40% B; Detect 220 nm. Finally, (1S,3S)-1-ethynyl-5-(3-methoxy-4-nitrobenzoyl)-5-azaspiro[2.5]octane was obtained as an off-white solid (90 mg) and (1R,3R)-1-ethynyl-5-(3-methoxy-4-nitrobenzoyl)-5-azaspiro[2.5]octane was obtained as an off-white solid (95 mg). A, $T_R$=10.910 min in CHIRAL-HPLC, Column: XA-CHIRALPAK IG-3; 4.6*100 mm, 3 um; mobile Phase A: n-Hexane (0.1% DEA)/IPA=70/30; mobile phase B: Isopropanol, Flow rate: 1 mL/min; Gradient: 0% B to 0% B; Injection Volume: 5 ul mL. Start Conc. of Pump B: 10% to 30% in 2.0 min, hold 1.0 min at 30%, Oven Temperature: 25° C. B, $T_R$=10.050 min in CHIRAL-HPLC, Column: XA-CHIRALPAK IG-3; 4.6*100 mm, 3 um; mobile Phase A: n-Hexane (0.1% DEA)/IPA=70/30; mobile phase B: Isopropanol, Flow rate: 1 mL/min; Gradient: 0% B to 0% B; Injection Volume: 5 ul mL. Start Conc. of Pump B: 10% to 30% in 2.0 min, hold 1.0 min at 30%, Oven Temperature: 25° C.

Synthesis of 3-(4-{2-[(1S,3S)-5-(3-methoxy-4-nitrobenzoyl)-5-azaspiro[2.5]octan-1-yl]ethynyl}-1-oxo-3H-isoindol-2-yl)piperidine-2,6-dione: Into an 8-mL sealed tube purged and maintained with an inert atmosphere of nitrogen, were placed (1S,3S)-1-ethynyl-5-(3-methoxy-4-nitrobenzoyl)-5-azaspiro[2.5]octane (50 mg, 0.2 mmol, 1.0 eq), 3-(4-iodo-1-oxo-3H-isoindol-2-yl)piperidine-2,6-dione (71 mg, 0.2 mmol, 1.2 eq), CuI (3 mg, 0.02 mmol, 0.1 eq), $Et_3N$ (48 mg, 0.5 mmol, 3.0 eq), $Pd(PPh_3)_4$ (18 mg, 0.02 mmol, 0.1 eq), DMF (2 mL). The reaction mixture was stirred for 2 hours at 70° C. The resulting mixture was quenched by the addition of water (30 mL) and then extracted with ethyl acetate (2×30 mL). The combined organic layers were washed with brine (2×30 mL) and dried over anhydrous $Na_2SO_4$. After filtration, the filtrate was concentrated under vacuum. The crude residue was applied onto a silica gel column and eluted with ethyl acetate/petroleum ether=1:0 to give 3-(4-{2-[(1S,3S)-5-(3-methoxy-4-nitrobenzoyl)-5-azaspiro[2.5]octan-1-yl]ethynyl}-1-oxo-3H-isoindol-2-yl)piperidine-2,6-dione as a light yellow solid (50 mg, 56.5%). LC-MS (ESI, m/z) M+1: 557.

Synthesis of 3-(4-{2-[(1S,3S)-5-(4-amino-3-methoxybenzoyl)-5-azaspiro[2.5]octan-1-yl]ethynyl}-1-oxo-3H-isoindol-2-yl)piperidine-2,6-dione: Into an 8-mL sealed tube, were placed 3-(4-{2-[(1S,3S)-5-(3-methoxy-4-nitrobenzoyl)-5-azaspiro[2.5]octan-1-yl]ethynyl}-1-oxo-3H-isoindol-2-yl)piperidine-2,6-dione (45 mg, 0.08 mmol, 1.0 eq), Fe (18 mg, 0.3 mmol, 4.0 eq), $NH_4Cl$ (35 mg, 0.6 mmol, 8.0 eq), EtOH (3 mL), water (1 mL). The resulting solution was stirred for 2 hours at 50° C. The resulting mixture was filtered, the filtrate was concentrated under vacuum. The crude residue was applied onto a silica gel column and eluted with dichloromethane/methanol=10:1 to give 3-(4-{2-[(1S,3S)-5-(4-amino-3-methoxybenzoyl)-5-azaspiro[2.5]octan-1-yl]ethynyl}-1-oxo-3H-isoindol-2-yl)piperidine-2,6-dione as a light yellow solid (40 mg, 94.0%). LC-MS (ESI, m/z) M+1: 527.

Synthesis of (2S,3S,4S,5R)-4-(3-chloro-2-fluorophenyl)-2-(2,2-dimethylpropyl)-N-{4-[(1S,3S)-1-{2-[2-(2,6-dioxopiperidin-3-yl)-1-oxo-3H-isoindol-4-yl]ethynyl}-5-azaspiro[2.5]octane-5-carbonyl]-2-methoxyphenyl}-6'-(trifluoromethyl)-1',2'-dihydrospiro[pyrrolidine-3,3'-pyrrolo[3,2-c]pyridine]-5-carboxamide: Into an 8-mL sealed tube, were placed 3-(4-{2-[(1S,3S)-5-(4-amino-3-methoxybenzoyl)-5-azaspiro[2.5]octan-1-yl]ethynyl}-1-oxo-3H-isoindol-2-yl)piperidine-2,6-dione (35 mg, 0.1 mmol, 1.0 eq), (2S,3S,4S,5R)-4-(3-chloro-2-fluorophenyl)-2-(2,2-dimethylpropyl)-6'-(trifluoromethyl)-1',2'-dihydrospiro[pyrrolidine-3,3'-pyrrolo[3,2-c]pyridine]-5-carboxylic acid (42 mg, 0.1 mmol, 1.3 eq), TCFH (28 mg, 0.1 mmol, 1.5 eq), NMI (14 mg, 0.2 mmol, 2.5 eq), $CH_3CN$ (3 mL). The resulting solution was stirred for 2 hours at 25° C. The crude product was purified by Flash-Prep-HPLC using the following conditions: Column, C18 reversed phase column; mobile phase, water (0.05% $NH_3{\cdot}H_2O$) and $CH_3CN$ (5% $CH_3CN$ up to 30% in 15 min); Flow rate: 60 mL/min; Detector, 254/220 nm. Finally, (2S,3S,4S,5R)-4-(3-chloro-2-fluorophenyl)-2-(2,2-dimethylpropyl)-N-{4-[(1S,3S)-1-{2-[2-(2,6-dioxopiperidin-3-yl)-1-oxo-3H-isoindol-4-yl]ethynyl}-5-azaspiro[2.5]octane-5-carbonyl]-2-methoxyphenyl}-6'-(trifluoromethyl)-1',2'-dihydrospiro[pyrrolidine-3,3'-pyrrolo[3,2-c]pyridine]-5-carboxamide was obtained as an off-white solid (3.1 mg, 4.7%). LC-MS (ESI, m/z) M+1: 994/996. $^1$HNMR (300 MHz, DMSO-$d_6$) δ 11.00 (s, 1H), 10.92-10.89 (m, 1H), 8.46 (s, 1H), 7.62 (d, J=9.0 Hz, 2H), 7.48-7.44 (m, 4H), 7.24 (q, J=7.5, 7.2 Hz, 2H), 7.01-6.86 (m, 2H), 6.62 (d, J=1.8 Hz, 2H), 5.04 (d, J=12.6 Hz, 1H), 4.78-4.33 (m, 4H), 3.78-3.65 (m, 8H), 3.98-3.82 (m, 1H), 1.68-1.55 (m, 5H), 1.45-1.35 (m, 1H), 1.21-1.15 (m, 2H), 1.06-0.93 (m, 14H).

Example 82: Preparation of (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]phenyl}-6'-(trifluoromethyl)-1',2'-dihydrospiro[pyrrolidine-3,3'-pyrrolo[3,2-c]pyridine]-5-carboxamide Synthesis of 3-(4-{2-[(1S)-6-(4-nitrobenzoyl)-6-azaspiro[2.5]octan-1-yl]ethynyl}-1-oxo-3H-isoindol-2-yl)piperidine-2,6-dione: Into a 20-mL sealed tube, were placed 3-(4-{2-[(1S)-6-azaspiro[2.5]octan-1-yl]ethynyl}-1-oxo-3H-isoindol-2-yl)piperidine-2,6-dione (150 mg, 0.4 mmol, 1.0 eq), p-nitrobenzoic acid (66 mg, 0.4 mmol, 1.0 eq), HATU (166 mg, 0.4 mmol, 1.1 eq), DIEA (128 mg, 1.0 mmol, 2.5 eq), DMF (3 mL). The resulting solution was stirred for 2 hours at 25° C. The resulting mixture was quenched by the addition of water (50 mL) and then extracted with ethyl acetate (2×50 mL). The combined organic layers were washed with brine (2×50 mL) and dried over anhydrous $Na_2SO_4$. After filtration, the filtrate was concentrated under vacuum. The crude residue was applied onto a silica gel column and eluted with ethyl acetate/petroleum ether=1:0 to give 3-(4-{2-[(1S)-6-(4-nitrobenzoyl)-6-azaspiro[2.5]octan-1-yl]ethynyl}-1-oxo-3H-isoindol-2-yl)piperidine-2,6-dione as a light yellow solid (160 mg, 76.4%). LC-MS (ESI, m/z) M+1: 527.

Synthesis of 3-(4-{2-[(1S)-6-(4-aminobenzoyl)-6-azaspiro[2.5]octan-1-yl]ethynyl}-1-oxo-3H-isoindol-2-yl)piperidine-2,6-dione: Into a 20-mL sealed tube, were placed 3-(4-{2-[(1S)-6-(4-nitrobenzoyl)-6-azaspiro[2.5]octan-1-yl]ethynyl}-1-oxo-3H-isoindol-2-yl)piperidine-2,6-dione (130 mg, 0.2 mmol, 1.0 eq), Fe (55 mg, 1.0 mmol, 4.0 eq), $NH_4Cl$ (106 mg, 2.0 mmol, 8.0 eq), EtOH (3 mL), water (1 mL). The resulting solution was stirred for 2 hours at 50° C. The resulting mixture was filtered, the filtrate was concentrated under vacuum. The crude residue was applied onto a silica gel column and eluted with dichloromethane/methanol=10:1 to give 3-(4-{2-[(1S)-6-(4-aminobenzoyl)-6-azaspiro[2.5]octan-1-yl]ethynyl}-1-oxo-3H-isoindol-2-yl)piperidine-2,6-dione as a light yellow solid (100 mg, 81.6%). LC-MS (ESI, m/z) M+1: 497.

Synthesis of (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]phenyl}-6'-(trifluoromethyl)-1',2'-dihydrospiro[pyrrolidine-3,3'-pyrrolo[3,2-c]pyridine]-5-carboxamide: Into an 8-mL sealed tube, were placed (2S,3S,4S,5R)-4-(3-chloro-2-fluorophenyl)-2-(2,2-dimethylpropyl)-6'-(trifluoromethyl)-1,2'-dihydrospiro[pyrrolidine-3,3'-pyrrolo[3,2-c]pyridine]-5-carboxylic acid (40 mg, 0.1 mmol, 1.0 eq), 3-(4-{2-[(1S)-6-(4-aminobenzoyl)-6-azaspiro[2.5]octan-1-yl]ethynyl}-1-oxo-3H-isoindol-2-yl)piperidine-2,6-dione (41 mg, 0.1 mmol, 1.0 eq), TCFH (35 mg, 0.1 mmol, 1.5 eq), NMI (17 mg, 0.2 mmol, 2.5 eq), $CH_3CN$ (1 mL). The resulting solution was stirred for 2 hours at 25° C. The crude product was purified by Prep-HPLC using the following conditions: Column, SunFire Prep C18 OBD Column, 50*250 mm 5 μm 10 nm; mobile phase, Water (0.05% $NH_3{\cdot}H_2O$) and $CH_3CN$ (50% Phase B up to 60% in 7 min); Detector, UV 254/220 nm. Finally, (2S,3S,4S,5R)-4-(3-chloro-2-fluorophenyl)-2-(2,2-dimethylpropyl)-N-{4-[(1S)-1-{2-[2-(2,6-dioxopiperidin-3-yl)-1-oxo-3H-isoindol-4-yl]ethynyl}-6-azaspiro[2.5]octane-6-carbonyl]phenyl}-6'-(trifluoromethyl)-1',2'-dihydrospiro[pyrrolidine-3,3'-pyrrolo[3,2-c]pyridine]-5-carboxamide was obtained as a white solid (10 mg, 12.6%). LC-MS (ESI, m/z) M+1: 964/966. $^1$HNMR (400 MHz, DMSO-$d_6$) δ 10.98 (s, 1H), 10.19 (s, 1H), 8.38 (s, 1H), 7.69 (d, J=7.6 Hz, 1H), 7.61 (d, J=8.0 Hz, 3H), 7.51 (t, J=7.6 Hz, 1H), 7.47-7.38 (m, 4H), 7.23 (t, J=8.0 Hz, 1H), 6.62 (d, J=2.8 Hz, 2H), 5.12 (dd, J=13.2, 5.2 Hz, 1H), 4.45-4.38 (m, 1H), 4.32 (s, 3H), 3.63-3.44 (m, 6H), 3.35 (s, 1H), 3.29 (s, 1H), 2.96-2.87 (m, 1H), 2.61-2.56 (m, 1H), 2.44-2.37 (m, 1H), 2.01 (br, 1H), 1.72-1.65 (m, 3H), 1.55 (br, 1H), 1.41-1.29 (m, 2H), 1.16 (d, J=14.0 Hz, 1H), 1.09-1.05 (m, 1H), 0.88 (s, 9H), 0.84-0.81 (m, 1H).

Biological Example 1: In Vitro MDM2 Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al). Binding of GST-MDM2 protein and p53-peptide (biotinyated on its N-terminal) is registered by the FRET (fluorescence resonance energy transfer) between Europium (Eu)-labeled anti-GST antibody and streptavidin-conjugated Allophycocyanin (APC). Test is performed in black flat-bottom 384-well plates (Costar) in a total volume of 40 uL containing:90 nM biotinylate peptide, 160 ng/ml GST- MDM2, 20 nM streptavidin-APC (PerkinElmer Wallac), 2 nM Eu-labeled anti-GST-antibody (PerkmElmerWallac), 0.02% bovine serum albumin (BSA), 1 mM dithiothreitol (DTT) and 20 mM Tris-borate saline (TBS) buffer as follows: Add 10 ul. of GST-MDM2 (640 ng/ml working solution) in reaction buffer to each well. Add 10 uL diluted compounds (1:5 dilution in reaction buffer) to each well, mix by shaking. Add 20 uL biotinyiated p53 peptide (180 nM working solution) in reaction buffer to each well and mix on shaker. Incubate at 37° C. for 1 h. Add 20 11 L streptavidin-APC and Eii-anti-GST antibody mixture (6 nM Eu-anti-GST and 60 nM streptavidin-APC working solution) in TBS buffer with 0.02% BSA, shake at room temperature for 30 minutes and read using a TRF-capable plate reader at 665 and 615 nm (Victor 5, Perk in ElmcrWallac). If not specified, the reagents were purchased from Sigma Chemical Co. Such assays, carried out with a range of doses of test compounds, allowed the determination of the MDM2 $IC_{50}$ of the compounds of the present invention.

The following table lists the $IC_{50}$ values of certain compounds of the invention.

| Example ID | MDM2 $IC_{50}$ (nM) |
|---|---|
| AMG-232 | 0.7 |
| RG7388 | 0.4 |
| Example 1 | 0.37 |
| Example 7 | 97.60 |
| Example 8 | 0.77 |
| Example 9 | 0.58 |
| Example 10 | 276 |
| Example 11 | 0.18 |
| Example 12 | 103 |
| Example 14 | 114 |
| Example 15 | 638 |
| Example 16 | 1.54 |
| Example 17 | 1.36 |
| Example 18 | 1.30 |
| Example 19 | 2.03 |
| Example 20 | 3.67 |
| Example 21 | 3.45 |
| Example 22 | 272 |
| Example 23 | 169 |
| Example 24 | 2.97 |
| Example 25 | 3.72 |
| Example 26 | 46.8 |
| Example 27 | 16.5 |
| Example 28 | 10.8 |
| Example 29 | 12 |
| Example 30 | 13.2 |
| Example 31 | 6.1 |
| Example 32 | 2.59 |
| Example 33 | 2.29 |
| Example 34 | 2.00 |
| Example 35 | 3.74 |
| Example 36 | 2.03 |
| Example 37 | 1.95 |
| Example 38 | 3.82 |
| Example 39 | 2.67 |
| Example 42 | 4.51 |
| Example 43 | 4.67 |
| Example 44 | 1.83 |
| Example 48 | 1.21 |
| Example 49 | 1.05 |
| Example 50 | 1.59 |
| Example 51 | 1.42 |
| Example 58 | 1.65 |
| Example 56 | 23.4 |
| Example 58 | 3.38 |

Biological Example 2: In vitro Anti-proliferation Assay in BCL-2-dependent acute lymphoblastic leukemia (ALL) cell line RS4; 11 overexpressing Bcl-2 G101V Cell antiproliferation was assayed by PerkinElmer ATPlite™ Luminescence Assay System. Briefly, the various test cancer cell lines were plated at a density of about $1\times10^4$ cells per well in Costar 96-well plates, and were incubated with different concentrations of compounds for about 72 hours in medium supplemented with 5% FBS or 10% normal human serum (NHS). One lyophilized substrate solution vial was then reconstituted by adding 5 mL of substrate buffer solution, and was agitated gently until the solution was homogeneous. About 50 μL of mammalian cell lysis solution was added to 100 μL of cell suspension per well of a microplate, and the plate was shaken for about five minutes in an orbital shaker at −700 rpm. This procedure was used to lyse the cells and to stabilize the ATP. Next, 50 μL substrate solution was added to the wells and microplate was shaken for five minutes in an orbital shaker at −700 rpm. Finally, the luminescence was measured by a PerkinElmer TopCount® Microplate Scintillation Counter. Such assays, carried out with a range of doses of test compounds, allowed the determination of the cellular anti-antiproliferative $IC_{50}$ of the compounds of the present invention.

The following table lists the $IC_{50}$ values of certain compounds of the invention.

| Example ID | RS4;11-G101V $IC_{50}$ (nM) |
|---|---|
| RG7388 | 110 |
| Example 1 | 33.0 |
| Example 8 | 127 |
| Example 9 | 11 |
| Example 11 | 44.7 |
| Example 14 | >1000 |
| Example 15 | >1000 |
| Example 16 | 10.10 |
| Example 17 | 3.82 |
| Example 18 | 5.91 |
| Example 20 | 31.9 |
| Example 21 | 448 |
| Example 22 | >1000 |
| Example 23 | >1000 |
| Example 24 | 21.1 |
| Example 25 | 21.6 |
| Example 26 | 448 |
| Example 27 | >1000 |
| Example 32 | 83.20 |
| Example 33 | 104 |
| Example 34 | 122 |
| Example 35 | 82.70 |
| Example 36 | 35.35 |
| Example 37 | 34.40 |
| Example 38 | 67.90 |
| Example 39 | 127.00 |
| Example 40 | 11.40 |
| Example 41 | 54.30 |
| Example 42 | 99.1 |
| Example 43 | 28.30 |
| Example 44 | 13.1 |
| Example 46 | >1000 |
| Example 47 | >1000 |
| Example 48 | 12.40 |
| Example 49 | 14.10 |
| Example 50 | 23.5 |
| Example 51 | 18.3 |
| Example 55 | 11.20 |
| Example 56 | 1.09 |

-continued

| Example ID | RS4;11-G101V $IC_{50}$ (nM) |
|---|---|
| Example 58 | 7.71 |
| Example 61 | 5.75 |
| Example 62 | 40.2 |
| Example 63 | 41.6 |
| Example 64 | 188.0 |

Biological Example 3 Western Blot Assay

Western blotting is a technique that uses specific antibodies to identify proteins that have been separated based on size by gel electrophoresis. The immunoassay uses a membrane made of nitrocellulose or PVDF (polyvinylidene fluoride). The gel is placed next to the membrane and the application of an electrical current induces the proteins to migrate from the gel to the membrane. The membrane can then be further processed with antibodies specific for the target of interest and visualized using secondary antibodies and detection reagents.

In this study, RS4; 11 cells overexpressing Bcl2 G101V were plated in the 12-well plate and treated with compounds for 4 hrs at 37 C. After removal of media, cells were washed with PBS one time. The cells were then lysed directly in RIPA buffer (500 ul) by pipetting and collected into Eppendorf tubes. The lysates were clarified at 13000 rpm for 15 min. The protein concentration in the supernatants was determined using the Pierce BCA protein Assay kit. The protein concentration was normalized (20 ug of protein) and the samples were reduced in Laemmli's SDS-sample buffer at 70° C. in a heated block for 20 min. An equal amount of protein samples (20 ul) were resolved using precast Bolt PAA gels. The protein gels were transferred onto 0.45-μm pore size nitrocellulose membranes. The membranes were blocked with non-fat dry milk (5% wt/vol) in 1×Tris-buffered saline-Tween-20 for 1 h at room temperature, and were probed with: Recombinant rabbit Anti-MDM2 antibody [EPR22256-98](ab259265) from Abcam (dilution 1:1000), Mouse monoclonal Anti-p53 antibody [DO-1]-(ab1101) from Abcam (dilution 1:2500), Recombinant rabbit monoclonal Anti-p21 antibody [EPR362](ab109520) from Abcam (dilution 1:1000), Rabbit polyclonal Anti-PUMA antibody (ab9643), Abcam (dilution 1:1000), and Mouse monoclonal Anti-GAPDH antibody [$6C_5$](ab8245), Abcam. (1; 20,000). All antibodies were diluted in milk (5% wt/vol in TBST) and incubated overnight at 4° C. The membranes were washed three times (10 min each) in non-fat dry milk (5% wt/vol) in 1×Tris-buffered saline-Tween-20 and incubated with horse radish peroxidase (HRP)-conjugated anti-rabbit or anti-mouse secondary antibodies for 1 h (1:20000) at room temperature. Following sufficient washing with TBST (twice with milk and once with only TBST), the membranes were exposed with chemiluminescent HRP substrate, and the signal was detected using FluoroChem imager (Protein Simple).

Biological Example 4: Mice PK Study

The pharmacokinetics of compounds were evaluated in CD-1 mouse via Intravenous and Oral Administration. The IV dose was administered as a slow bolus in the Jugular vein, and oral doses were administered by gavage. The formulation for IV dosing was 5% DMSO in 20% HPBCD in water, and the PO formulation was 2.5% DMSO, 10% EtOH, 20% Cremphor EL, 67.5% D5W. The PK time point for the IV arm was 5, 15, 30 min, 1, 2, 4, 6, 8, 12, 24 hours post dose, and for PO arm was 15, 30 min, 1, 2, 4, 6, 8, 12, 24 hours post dose. Approximately 0.03 mL blood was collected at each time point. Blood of each sample was transferred into plastic micro centrifuge tubes containing EDTA-K2 and collect plasma within 15 min by centrifugation at 4000 g for 5 minutes in a 4° C. centrifuge. Plasma samples were stored in polypropylene tubes. The samples were stored in a freezer at −75±15° C. prior to analysis. Concentrations of compounds in the plasma samples were analyzed using a LC-MS/MS method. WinNonlin (Phoenix™, version 6.1) or other similar software was used for pharmacokinetic calculations. The following pharmacokinetic parameters were calculated, whenever possible from the plasma concentration versus time data: IV administration: $C_0$, $C_L$, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data was described using descriptive statistics such as mean, standard deviation. Additional pharmacokinetic or statistical analysis was performed at the discretion of the contributing scientist, and was documented in the data summary.

The PK results of Example 58 is shown in the Table below. The data shows that Example 58 has good

| Example 58 | AUClas(h * ng/ml) |
|---|---|
| Oral, 25 mpk, | 49,431 |

Biological Example 5: In vivo Xenograft Studies

Typically, athymic nude mice (CD-1 nu/nu) or SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 $mm^3$, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant.

What is claimed is:

1. A compound of Formula (I), or an N-oxide thereof, or a pharmaceutically acceptable salt, solvate, polymorph, tautomer, stereoisomer, an isotopic form, or a prodrug of said compound of Formula (I) or N-oxide thereof:

Formula (I)

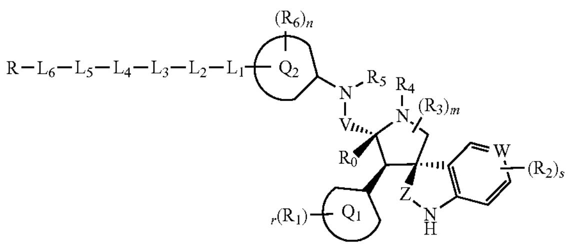

wherein

Z is $CH_2$, —$SO_2$—, or —$P(O)(R_a)$—; or Z is C(O) when $R_0$ is not H;

V is C(O);

W is $C(R_a)$ or N;

R is H or a small molecule E3 ubiquitin ligase binding moiety that binds an E3 ubiquitin ligase;

each of $L_1$, $L_2$, $L_3$, $L_4$, $L_5$, and $L_6$, independently, is absent, a bond, $(CR_aR_b)_p$, $N(R_a)$, O, S, C(O), $S(O_2)$, —$O(CR_aR_b)_p$—, —$N(R_a)(CR_aR_b)_p$—, OC(O), C(O)O, $OSO_2$, $S(O_2)O$, C(O)S, SC(O), C(O)C(O), $C(O)N(R_a)$, $N(R_a)C(O)$, $S(O_2)N(R_a)$, $N(R_a)S(O_2)$, OC(O)O, OC(O)S, $OC(O)N(R_a)$, $N(R_a)C(O)O$, $N(R_a)C(O)S$, $N(R_a)C(O)N(R_a)$, $(CR_aR_b)_pN(R_a)(CR_aR_b)_q$, $(CR_aR_b)_pN(R_a)C(O)(CR_aR_b)_q$, $OC(O)N(R_b)(CR_aR_b)_{p+1}N(R_b)(CR_aR_b)_q$, $(CR_aR_b)_pC(O)N(R_a)(CR_aR_b)_q$, bivalent alkyl, bivalent alkenyl, bivalent alkynyl, bivalent cycloalkyl, bivalent cycloalkenyl, bivalent heterocycloalkyl, bivalent heterocycloalkenyl, bivalent aryl, or bivalent heteroaryl, in which said bivalent alkyl, bivalent cycloalkyl, bivalent cycloalkenyl, bivalent heterocycloalkyl, bivalent spiro-heterocyclic, bivalent fused-heterocyclic, bivalent bridged-heterocyclic, bivalent heterocycloalkenyl, bivalent aryl, or bivalent heteroaryl is optionally substituted with one or more $R_d$;

each of $R_0$, $R_1$, $R_2$, $R_3$, $R_4$, $R_5$, and $R_6$, independently, H, D, alkyl, alkenyl, alkynyl, cycloalkyl, cycloalkenyl, heterocycloalkyl, spiroheterocycloalkyl, heterocycloalkenyl, aryl, heteroaryl, halo, cyano, —$OR_a$, —$SR_a$, -alkyl-$R_a$, -alkyl-O—$P(O)(R_a)(R_b)$, -alkyl-$OC(O)N(R_a)(R_b)$, —$NH(CH_2)_pR_a$, —$C(O)R_a$, —$S(O)R_a$, —$SO_2R_a$, —$C(O)OR_a$, —$OC(O)R_a$, —$NR_bR_c$, —$C(O)N(R_b)R_c$, —$N(R_b)C(O)R_c$, in which said alkyl, spiroalkyl, alkenyl, alkynyl, cycloalkyl, cycloalkenyl, heterocycloalkyl, heterocycloalkenyl, aryl, heteroaryl is optionally substituted with one or more $R_d$;

each of $Q_1$, and $Q_2$, independently, is cycloalkyl, cycloalkenyl, heterocycloalkyl, heterocycloalkenyl, spiroheterocyclyl, fused heterocyclyl, bridged heterocyclyl, aryl, or heteroaryl;

$R_a$, $R_b$, $R_c$ and $R_d$, independently, is H, D, alkyl, spiroalkyl, alkenyl, alkynyl, halo, cyano, amine, nitro, hydroxy, ═O, -alkyl-O—P(O)(OH)(OH), C(O)NHOH, C(O)OH, C (O)$NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, alkoxy, alkoxyalkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, ═O, -alkyl-O—P(O)(OH)(OH), C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, alkoxy, alkoxyalkyl, cycloalkyl, cycloalkenyl, heterocycloalkyl, heterocycloalkenyl, aryl, heteroaryl is optionally substituted with one or more $R_f$; and $R_f$ is H, D, alkyl, spiroalkyl, alkenyl, alkynyl, halo, cyano, amine, nitro, hydroxy, ═O, -alkyl-O—P(O)(OH)(OH), C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, two of $R_1$ groups, taken together with the atom to which they are attached, may optionally form a cycloalkyl or heterocycloalkyl optionally substituted with one or more $R_d$;

two of $R_2$ groups, taken together with the atom to which they are attached, may optionally form a cycloalkyl or heterocycloalkyl optionally substituted with one or more $R_d$;

two of $R_3$ groups, taken together with the atom to which they are attached, may optionally form a cycloalkyl or heterocycloalkyl optionally substituted with one or more $R_d$;

two of $R_6$ groups, taken together with the atom to which they are attached, may optionally form a cycloalkyl or heterocycloalkyl optionally substituted with one or more $R_d$;

$R_3$ and $R_4$ groups, taken together with the atom to which they are attached, may optionally form a cycloalkyl or heterocycloalkyl optionally substituted with one or more $R_d$;

$R_4$ and $R_5$ groups, taken together with the atom to which they are attached, may optionally form a cycloalkyl or heterocycloalkyl optionally substituted with one or more $R_d$;

$R_5$ and $R_6$ groups, taken together with the atom to which they are attached, may optionally form a cycloalkyl or heterocycloalkyl optionally substituted with one or more $R_d$;

two of $R_d$ groups, taken together with the atom to which they are attached, may optionally form a cycloalkyl or heterocycloalkyl optionally substituted with one or more $R_e$;

two of $R_e$ groups, taken together with the atom to which they are attached, may optionally form a cycloalkyl or heterocycloalkyl optionally substituted with one or more $R_f$; and each of m, n, r, and s, independently, is 0, 1, 2, or 3.

2. The compound according to claim 1 or an N-oxide thereof, or a pharmaceutically acceptable salt, solvate, polymorph, tautomer, stereoisomer, an isotopic form, or a prodrug thereof, wherein the compound is represented by Formula (II):

Formula (II)

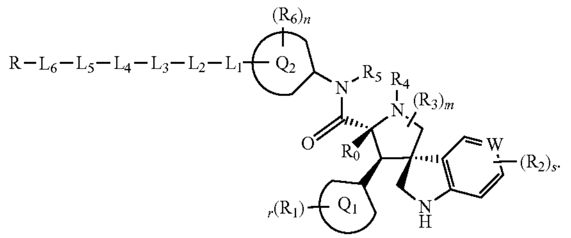

3. The compound according to claim 2 or an N-oxide thereof, or a pharmaceutically acceptable salt, solvate, polymorph, tautomer, stereoisomer, an isotopic form, or a prodrug thereof, wherein the compound is represented by Formula (III):

Formula (III)

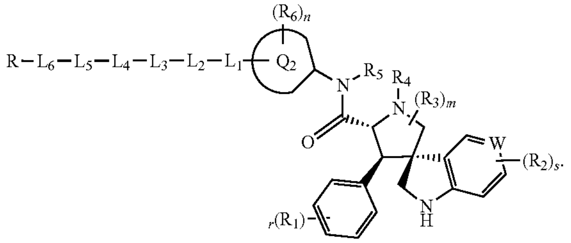

4. The compound according to claim 1, or an N-oxide thereof, or a pharmaceutically acceptable salt, solvate, polymorph, tautomer, stereoisomer, an isotopic form, or a prodrug thereof, wherein the compound is represented by Formula (VI):

Formula (IV)

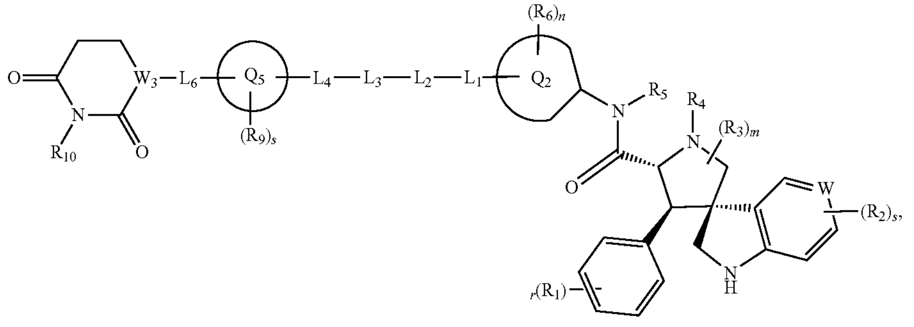

wherein $R_{10}$ is H, D, -alkyl-O—P(O)($R_a$)($R_b$), or -alkyl-OC(O)—$R_a$;

$W_3$ is N or CH;

$L_5$ is absent, NH, CONH, or O;

$Q_5$ is absent, cycloalkyl, cycloalkenyl, heterocycloalkyl, heterocycloalkenyl, spiro-heterocyclic, fused-heterocyclic, bridged-heterocyclic, heterocycloalkenyl, aryl, or heteroaryl;

$R_9$ is absent, H, D, alkyl, alkenyl, alkynyl, cycloalkyl, cycloalkenyl, heterocycloalkyl, spiroheterocycloalkyl, heterocycloalkenyl, aryl, heteroaryl, halo, oxo, cyano, —$OR_a$, —$SR_a$, -alkyl-$R_a$, -alkyl-O—P(O)($R_a$)($R_b$), -alkyl-OC(O)N($R_a$)($R_b$), —NH$(CH_2)_p$$R_a$, —C(O)$R_a$, —S(O)$R_a$, —$SO_2R_a$, —C(O)O$R_a$, —OC(O)$R_a$, —N$R_bR_c$, —C(O)N($R_b$)$R_c$, —N($R_b$)C(O)$R_c$, in which said alkyl, spiroalkyl, alkenyl, alkynyl, cycloalkyl, cycloalkenyl, heterocycloalkyl, heterocycloalkenyl, aryl, heteroaryl is optionally substituted with one or more $R_d$;

$R_9$ and $L_4$ groups, taken together with the atom to which they are attached, may optionally form a cycloalkyl or heterocycloalkyl optionally substituted with one or more $R_d$; and s is 0, 1, 2, 3, or 4.

5. The compound according to claim 1, or an N-oxide thereof, or a pharmaceutically acceptable salt, solvate, polymorph, tautomer, stereoisomer, an isotopic form, or a prodrug thereof, wherein the compound is represented by Formula (V):

Formula (V)

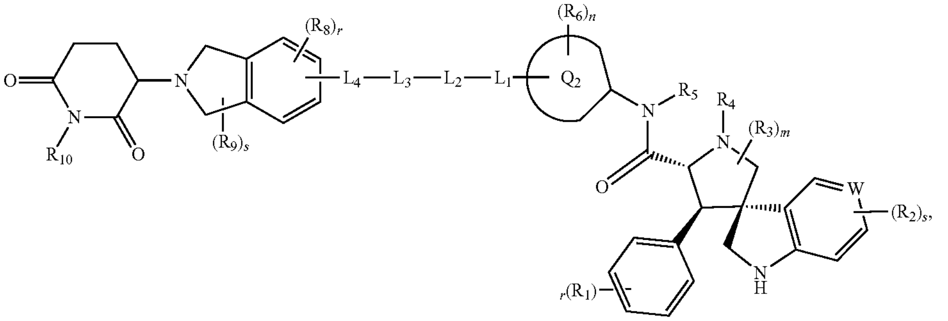

wherein $R_8$ is absent, H, D, alkyl, alkenyl, alkynyl, cycloalkyl, cycloalkenyl, heterocycloalkyl, spiroheterocycloalkyl, heterocycloalkenyl, aryl, heteroaryl, halo, oxo, cyano, —$OR_a$, —$SR_a$, -alkyl-$R_a$, -alkyl-O—P(O)($R_a$)($R_b$), -alkyl-OC(O)N($R_a$)($R_b$), —NH$(CH_2)_pR_a$, —C(O)$R_a$, —S(O)$R_a$, —$SO_2R_a$, —C(O)$OR_a$, —OC(O)$R_a$, —$NR_bR_c$, —C(O)N($R_b$)$R_c$, —N($R_b$)C(O)$R_c$, in which said alkyl, spiroalkyl, alkenyl, alkynyl, cycloalkyl, cycloalkenyl, heterocycloalkyl, heterocycloalkenyl, aryl, heteroaryl is optionally substituted with one or more $R_d$;

$R_8$ and $L_4$ groups, taken together with the atom to which they are attached, may optionally form a cycloalkyl or heterocycloalkyl optionally substituted with one or more $R_d$; and r is 0, 1, 2, 3, or 4.

6. A pharmaceutical composition comprising a compound of Formulae (I) or an N-oxide thereof, as defined in claim 1, or a pharmaceutically acceptable salt, solvate, polymorph, tautomer, stereoisomer, an isotopic form, or a prodrug of said compound of Formula (I) or an N-oxide thereof, and a pharmaceutically acceptable diluent or carrier.

7. A method of treating a neoplastic disease, autoimmune disease, and inflammatory disorder, comprising administering to a subject in need thereof an effective amount of a compound of Formula (I) or an N-oxide thereof, as defined in claim 1, or a pharmaceutically acceptable salt, solvate, polymorph, tautomer, stereoisomer, an isotopic form, or a prodrug of said compound of Formula (I) or an N-oxide thereof.

* * * * *